United States Patent
Takahashi et al.

(10) Patent No.: US 9,879,183 B2
(45) Date of Patent: Jan. 30, 2018

(54) LIQUID CRYSTAL COMPOUND HAVING CF$_2$O BONDING GROUP AND TOLAN SKELETON, LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Michiko Takahashi, Chiba (JP); Sayaka Fujimori, Chiba (JP); Yasuyuki Sasada, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

(21) Appl. No.: 15/317,412

(22) PCT Filed: Jun. 4, 2015

(86) PCT No.: PCT/JP2015/066246
§ 371 (c)(1),
(2) Date: Dec. 9, 2016

(87) PCT Pub. No.: WO2015/190399
PCT Pub. Date: Dec. 17, 2015

(65) Prior Publication Data
US 2017/0107427 A1    Apr. 20, 2017

(30) Foreign Application Priority Data

Jun. 11, 2014 (JP) ................. 2014-120566

(51) Int. Cl.
| | | |
|---|---|---|
| *G02F 1/1333* | (2006.01) | |
| *C09K 19/34* | (2006.01) | |
| *C09K 19/30* | (2006.01) | |
| *C07C 43/225* | (2006.01) | |
| *C07D 239/26* | (2006.01) | |
| *C07D 213/30* | (2006.01) | |
| *C07D 213/68* | (2006.01) | |
| *C07D 239/34* | (2006.01) | |

(Continued)

(52) U.S. Cl.
CPC ........ *C09K 19/3402* (2013.01); *C07C 43/225* (2013.01); *C07D 213/30* (2013.01); *C07D 213/68* (2013.01); *C07D 239/26* (2013.01); *C07D 239/34* (2013.01); *C09K 19/3001* (2013.01); *C09K 19/3003* (2013.01); *C09K 19/3066* (2013.01); *C09K 19/3068* (2013.01); *C09K 2019/0466* (2013.01); *C09K 2019/301* (2013.01); *C09K 2019/3004* (2013.01); *C09K 2019/3009* (2013.01); *C09K 2019/3071* (2013.01); *C09K 2019/3075* (2013.01); *C09K 2019/3077* (2013.01); *C09K 2019/3083* (2013.01); *C09K 2019/3422* (2013.01); *C09K 2019/3425* (2013.01); *G02F 1/29* (2013.01)

(58) Field of Classification Search
CPC ............ C09K 19/3402; C09K 19/3068; C09K 19/3003; C09K 19/3001; C09K 19/3066; C09K 2019/3075; C09K 2019/3071; C09K 2019/3077; C09K 2019/3083; C09K 2019/3004; C09K 2019/3009; C09K 2019/301; C09K 2019/3422; C09K 2019/3425; C09K 2019/0466; C07D 43/225; C07D 239/26; C07D 239/34; C07D 213/30; C07D 213/68; G02F 1/1333
USPC ...................................... 252/299.6
See application file for complete search history.

(56) References Cited

U.S. PATENT DOCUMENTS

| | | | |
|---|---|---|---|
| 5,728,319 A | 3/1998 | Matsui et al. | |
| 7,846,514 B2 * | 12/2010 | Shimada ................ | C09K 19/10 252/299.61 |

(Continued)

FOREIGN PATENT DOCUMENTS

| | | |
|---|---|---|
| WO | 9611897 | 4/1996 |
| WO | 2008090780 | 7/2008 |

(Continued)

OTHER PUBLICATIONS

Peng et al., "Fast response property of low-viscosity difluorooxymethylene-bridged liquid crystals", Liquid Crystals, Jan. 2013, pp. 91-96.

(Continued)

*Primary Examiner* — Geraldina Visconti
(74) *Attorney, Agent, or Firm* — JCIPRNET

(57) ABSTRACT

To show a liquid crystal compound satisfying at least one of physical properties such as high chemical stability, a high clearing point, a low minimum temperature of a liquid crystal phase, low viscosity, large optical anisotropy, large dielectric anisotropy, a suitable elastic constant and excellent compatibility with other liquid crystal compounds, a liquid crystal composition containing the compound and a liquid crystal display device including the composition.
A compound is represented by formula (1).

(1)

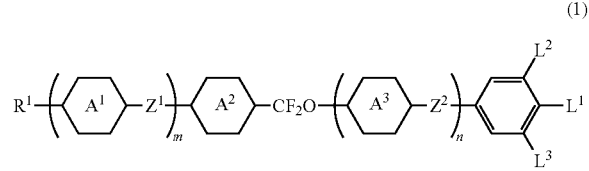

15 Claims, No Drawings

(51) Int. Cl.
C09K 19/04 (2006.01)
G02F 1/29 (2006.01)

(56) References Cited

U.S. PATENT DOCUMENTS 7,951,432 B2 * 5/2011 Tanaka .................. C07C 43/225
                                                    252/299.61
8,475,888 B2 * 7/2013 Tanaka .................. C07D 213/30
                                                    252/299.5

FOREIGN PATENT DOCUMENTS

| WO | 2008105286 | 9/2008 |
| WO | 2009150963 | 12/2009 |
| WO | 2010047260 | 4/2010 |

OTHER PUBLICATIONS

Martin Petrzilka, "New Liquid Crystals: The Synthesis and Mesomorphic Properties of Nematic Alkenylsubstituted Cyanophenylcyclohexanes", Mol. Cryst. Liq. Cryst., Jan. 1985, pp. 109-123.
Petrzilka et al, "New Liquid Crystals: The Synthesis and Mesomorphic Properties of Alkenylsubstituted Cyanophenylcyclohexanes and Cyanobiphenylylcyclohexanes", Mol. Cryst. Liq. Cryst., Jan. 1985, pp. 327-342.
"International Search Report (Form PCT/ISA/210) of PCT/JP2015/066246", with English translation thereof, dated Sep. 1, 2015, pp. 1-4.

* cited by examiner

//LIQUID CRYSTAL COMPOUND HAVING CF₂O BONDING GROUP AND TOLAN SKELETON, LIQUID CRYSTAL COMPOSITION AND LIQUID CRYSTAL DISPLAY DEVICE

CROSS-REFERENCE TO RELATED APPLICATION

This application is a 371 application of the international PCT application serial no. PCT/JP2015/066246, filed on Jun. 4, 2015, which claims the priority benefit of Japan application no. 2014-120566, filed on Jun. 11, 2014. The entirety of each of the above-mentioned patent applications is hereby incorporated by reference herein and made a part of this specification.

TECHNICAL FIELD

The invention relates to a liquid crystal compound, a liquid crystal composition and a liquid crystal display device. More specifically, the invention relates to a liquid crystal compound having a $CF_2O$ bonding group and a tolan skeleton, a liquid crystal composition that contains the compound and has a nematic phase, and a liquid crystal display device including the composition.

A liquid crystal display device has been widely used in a display of a personal computer, a television and so forth. The device utilizes physical properties such as optical anisotropy and dielectric anisotropy of a liquid crystal compound. Specific examples of an operating mode of the liquid crystal display device include a phase change (PC) mode, a twisted nematic (TN) mode, a super twisted nematic (STN) mode, a bistable twisted nematic (BTN) mode, an electrically controlled birefringence (ECB) mode, an optically compensated bend (OCE) mode, an in-plane switching (IPS) mode, avertical alignment (VA) mode, a fringe field switching (FFS) mode and a polymer sustained alignment (PSA) mode.

In such a liquid crystal display device, a liquid crystal composition having suitable physical properties is used. In order to further improve characteristics of the liquid crystal display device, the liquid crystal compound contained in the composition preferably has physical properties described in (1) to (8) below.
 (1) High stability to heat, light or the like,
 (2) a high clearing point,
 (3) a low minimum temperature of a liquid crystal phase,
 (4) small viscosity ($\eta$),
 (5) large optical anisotropy ($\Delta n$),
 (6) large dielectric anisotropy ($\Delta \epsilon$),
 (7) a suitable elastic constant (K), and
 (8) excellent compatibility with other liquid crystal compounds.

An effect of physical properties of the liquid crystal compound on the characteristics of the device is as described below. A compound having the high stability to heat, light and so forth as described in (1) increases a voltage holding ratio of the device. Thus, a service life of the device becomes longer. A compound having the high clearing point as described in (2) extends a temperature range in which the device can be used. A compound having the low minimum temperature of the liquid crystal phase such as a nematic phase and a smectic phase as described in (3), in particular, a compound having the low minimum temperature of the nematic phase, also extends a temperature range in which the device can be used. A compound having the small viscosity as described in (4) decreases a response time of the device.

A compound having the large optical anisotropy as described in (5) improves a contrast of the device. According to a design of the device, a compound having the large optical anisotropy or a small optical anisotropy, more specifically, a compound having a suitable optical anisotropy is required. When the response time is shortened by decreasing a cell gap of the device, a compound having the large optical anisotropy is suitable. A compound having the large dielectric anisotropy as described in (6) decreases a threshold voltage of the device. Thus, an electric power consumption of the device is reduced. On the other hand, a compound having a small dielectric anisotropy shortens the response time of the device by decreasing viscosity of the composition.

With regard to (7), a compound having the large elastic constant shortens the response time of the device. A compound having the small elastic constant decreases the threshold voltage of the device. Therefore, the suitable elastic constant is required according to the characteristics that are desirably improved. A compound having the excellent compatibility with other liquid crystal compounds as described in (8) is preferred. The reason is that the physical properties of the composition are adjusted by mixing liquid crystal compounds having different physical properties.

A variety of liquid crystal compounds having the large dielectric anisotropy have so far been prepared. A variety of liquid crystal compounds having the large optical anisotropy have been also prepared. The reason is that excellent physical properties that are not found in a conventional compound are expected from a new compound. The reason is because a suitable balance is expected to be obtained regarding at least two of physical properties by adding the new compound to a liquid crystal composition. In view of such a situation, with regard to physical properties (1) to (8) described above, a compound having excellent physical properties and a suitable balance, above all, a compound having both the large dielectric anisotropy ($\Delta \epsilon$) and the large optical anisotropy ($\Delta n$) has been desired.

In Patent literature No. 1, compound (S-1) having a $CF_2O$ group and a tolan skeleton is described.

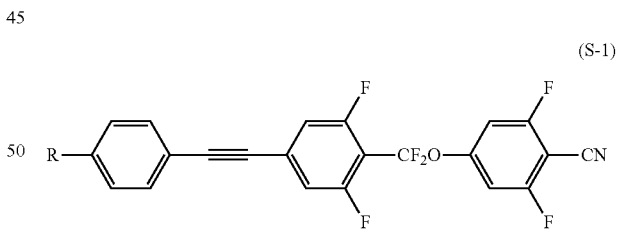

(S-1)

In Non-patent literature No. 2, compound (S-2) having a $CF_2O$ group and a tolan skeleton is described.

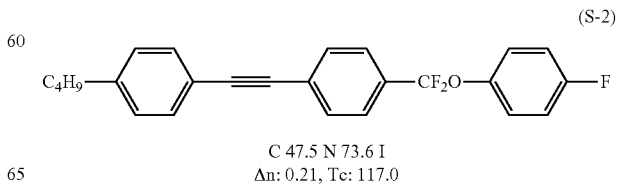

(S-2)

C 47.5 N 73.6 I
$\Delta n$: 0.21, Tc: 117.0

CITATION LIST

Patent Literature

Patent literature No. 1: WO 96/011897 A.

Non-Patent Literature

Non-patent literature No. 1: Liq. Cryst. 2013. 40. pp. 91-96.
Non-patent literature No. 2: Mol. Cryst. Liq. Cryst., 1985, 131, p. 109.
Non-patent literature No. 3: Mol. Cryst. Liq. Cryst., 1985, 131, p. 327.

SUMMARY OF INVENTION

Technical Problem

The invention provides a liquid crystal compound satisfying at least one of physical properties such as a high stability to heat and light, a high clearing point, a low minimum temperature of a liquid crystal phase, a small viscosity, a large optical anisotropy, a large dielectric anisotropy, a suitable elastic constant and an excellent compatibility with other liquid crystal compounds. The invention provides a compound having a larger optical anisotropy and a larger dielectric anisotropy in comparison with a similar compound. The invention further provides a liquid crystal composition that contains the compound and satisfies at least one of physical properties such as a high maximum temperature of a nematic phase, a low minimum temperature of the nematic phase, a small viscosity, a large optical anisotropy, a large dielectric anisotropy and a suitable elastic constant. The object invention provides a liquid crystal composition having a suitable balance regarding at least two of the physical properties. The invention also provides a liquid crystal display device that includes the composition, and has a wide temperature range in which the device can be used, a short response time, a large voltage holding ratio, a low threshold voltage, a large contrast ratio and a long service life.

Solution to Problem

The invention concerns a compound represented by formula (1), a liquid crystal composition containing the compound and a liquid crystal display device including the composition:

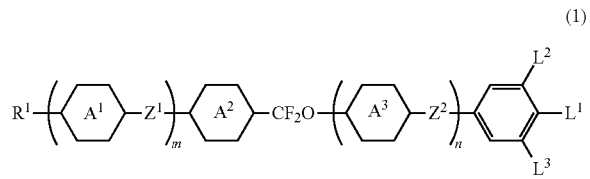

(1)

wherein, in formula (1),
$R^1$ is alkyl having 1 to 15 carbons, and in the alkyl, at least one piece of —$CH_2$— may be replaced by —O—, and at least one piece of —$CH_2CH_2$— may be replaced by —CH=CH—, and in the groups, at least one piece of hydrogen may be replaced by halogen;
ring $A^1$, ring $A^2$ and ring $A^3$ are independently 1,4-cyclohexylene, 1,4-cyclohexenylene, 1,4-phenylene, 2-halogeno-1,4-phenylene, 2,6-dihalogeno-1,4-phenylene, pyrimidine-2,5-diyl or pyridine-2,5-diyl;
$Z^1$ and $Z^2$ are independently a single bond or —C≡C—, but at least one is —C≡C—;
$L^1$ is halogen, —$OCF_3$ or —$CF_3$;
$L^2$ and $L^3$ are independently hydrogen or halogen, but at least one is halogen; and
m and n are independently 0, 1 or 2, and a sum of m and n is 1 or 2.

Advantageous Effects of Invention

A first advantage of the invention is to provide a liquid crystal compound satisfying at least one of physical properties such as a high stability to heat and light, a high clearing point, a low minimum temperature of a liquid crystal phase, a small viscosity, a large optical anisotropy, a large dielectric anisotropy, a suitable elastic constant and an excellent compatibility with other liquid crystal compounds. The advantage is to provide a compound having a larger optical anisotropy and a larger dielectric anisotropy in comparison with a similar compound (see Comparative Example 1). A second advantage is to provide a liquid crystal composition that contains the compound in the invention and satisfies at least one of physical properties such as a high maximum temperature of a nematic phase, a low minimum temperature of the nematic phase, a small viscosity, a large optical anisotropy, a large dielectric anisotropy and a suitable elastic constant. The advantage is to provide a liquid crystal composition having a suitable balance regarding at least two of the physical properties. A third advantage is to provide a liquid crystal display device that includes the composition in the invention, and has a wide temperature range in which the device can be used, a short response time, a large voltage holding ratio, a low threshold voltage, a large contrast ratio and a long service life.

DESCRIPTION OF EMBODIMENTS

Usage of terms herein is as described below. A liquid crystal compound is a generic term for a compound having a liquid crystal phase such as a nematic phase and a smectic phase, and a compound having no liquid crystal phase but to be added for the purpose of adjusting physical properties of a composition such as a maximum temperature, a minimum temperature, viscosity and dielectric anisotropy. The compounds have a six-membered ring such as 1,4-cyclohexylene and 1,4-phenylene, and have rod-like molecular structure. A liquid crystal composition is prepared by mixing such liquid crystal compounds. A proportion (content) of the liquid crystal compounds is expressed in terms of weight percent (% by weight) based on the weight of the liquid crystal composition. An additive such as a polymerizable compound, a polymerization initiator, an optically active compound, an antioxidant, an ultraviolet light absorber, a light stabilizer, a heat stabilizer, an antifoaming agent and a dye is added to the composition when necessary. A proportion (amount of addition) of the additive is expressed in terms of weight percent (% by weight) based on the weight of the liquid crystal composition in a manner identical to the proportion of the liquid crystal compounds. Weight parts per million (ppm) may be occasionally used.

A liquid crystal display device is a generic term for a liquid crystal display panel and a liquid crystal display module. The liquid crystal compound, the liquid crystal composition and the liquid crystal display device may be occasionally abbreviated as "compound," "composition"

and "device," respectively. A clearing point is a transition temperature between the liquid crystal phase and an isotropic phase in the liquid crystal compound. A minimum temperature of the liquid crystal phase is a transition temperature between a solid and the liquid crystal phase (the smectic phase, the nematic phase or the like) in the liquid crystal compound. A maximum temperature of the nematic phase is a transition temperature between the nematic phase and the isotropic phase in the liquid crystal composition, and may be occasionally abbreviated as "maximum temperature." A minimum temperature of the nematic phase may be occasionally abbreviated as "minimum temperature."

A compound represented by formula (1) may be occasionally abbreviated as "compound (1)." The abbreviation may occasionally apply also to a compound represented by formula (2) or the like. In formulas (1) to (15), a symbol $A^1$, $B^1$, $C^1$ or the like surrounded by a hexagonal shape corresponds to ring $A^1$, ring $B^1$ and ring $C^1$, respectively. A symbol of terminal group $R^{11}$ is used in a plurality of compounds. In the compounds, two groups represented by two pieces of arbitrary may be identical or different. For example, in one case, $R^{11}$ of compound (2) is ethyl and $R^{11}$ of compound (3) is ethyl. In another case, $R^{11}$ of compound (2) is ethyl and $R^{11}$ of compound (3) is propyl. A same rule applies also to a symbol such as any other terminal group and a ring. In formula (5), when i is 2, two of rings $C^1$ exists. In the compound, two groups represented by two of rings $C^1$ may be identical or different. A same rule applies also to arbitrary two when i is larger than 2. A same rule applies also to a symbol such as any other ring and a bonding group.

An expression "at least one piece of "A" may be replaced by "B"" means that, when the number of "A" is 1, a position of "A" is arbitrary, and also when the number of "A" is 2 or more, positions thereof can be selected without restriction. An expression "at least one piece of A may be replaced by B, C or D" means including a case where arbitrary A is replaced by B, a case where arbitrary A is replaced by C, and a case where arbitrary A is replaced by D, and also a case where a plurality of pieces A are replaced by at least two of B, C and D. For example, "alkyl in which at least one piece of —CH$_2$— may be replaced by —O— or —CH═CH—" includes alkyl, alkenyl, alkoxy, alkoxyalkyl, alkoxyalkenyl and alkenyloxyalkyl. In addition, a case where replacement of two consecutive pieces of —CH$_2$— by —O— results in forming —O—O— is not preferred. In the alkyl or the like, a case where replacement of —CH$_2$— of a methyl part (—CH$_2$—H) by —O— results in forming —O—H is not preferred, either.

Halogen means fluorine, chlorine, bromine and iodine. Preferred halogen is fluorine and chlorine. Further preferred halogen is fluorine. Alkyl of the liquid crystal compound is straight-chain alkyl or branched-chain alkyl, but includes no cyclic alkyl. In general, straight-chain alkyl is preferred to branched-chain alkyl. A same rule applies also to a terminal group such as alkoxy and alkenyl. With regard to a configuration of 1,4-cyclohexylene, trans is preferred to cis for increasing the maximum temperature. Then, 2-fluoro-1,4-phenylene means two divalent groups described below. In a chemical formula, fluorine may be leftward (L) or rightward (R). A same rule applies also to an asymmetrical divalent group formed by removing two pieces of hydrogen from a ring, such as tetrahydropyran-2,5-diyl.

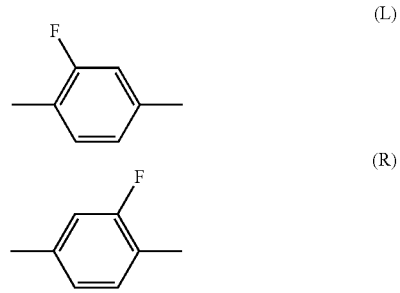

The invention includes items described below.
Item 1. A compound, represented by formula (1):

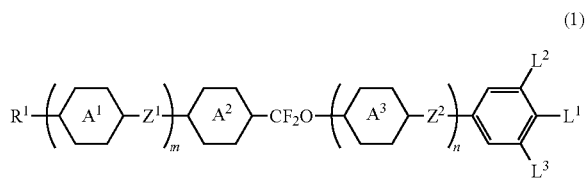

wherein, in formula (1),
$R^1$ is alkyl having 1 to 15 carbons, and in the alkyl, at least one piece of —CH$_2$— may be replaced by —O—, and at least one piece of —CH$_2$CH$_2$— may be replaced by —CH═CH—, and in the groups, at least one piece of hydrogen may be replaced by halogen;
ring $A^1$, ring $A^2$ and ring $A^3$ are independently 1,4-cyclohexylene, 1,4-cyclohexenylene, 1,4-phenylene, 2-halogeno-1,4-phenylene, 2,6-dihalogeno-1,4-phenylene, pyrimidine-2,5-diyl or pyridine-2,5-diyl;
$Z^1$ and $Z^2$ are independently a single bond or —C≡C—, but at least one is —C≡C—;
$L^1$ is halogen, —OCF$_3$ or —CF$_3$;
$L^2$ and $L^3$ are independently hydrogen or halogen, but at least one is halogen; and
m and n are independently 0, 1 or 2, and a sum of m and n is 1 or 2.

Item 2. The compound according to item 1, wherein in formula (1) described in item 1,
$R^1$ is alkyl having 1 to 15 carbons, alkenyl having 2 to 15 carbons, alkoxy having 2 to 15 carbons, alkyl having 1 to 15 carbons in which at least one piece of hydrogen is replaced by halogen, alkenyl having 2 to 15 carbons in which at least one piece of hydrogen is replaced by halogen, or alkoxy having 2 to 15 carbons in which at least one piece of hydrogen is replaced by halogen;
ring $A^1$, ring $A^2$ and ring $A^3$ are independently 1,4-cyclohexylene, 1,4- cyclohexenylene, 1,4-phenylene, 2-halogeno-1,4-phenylene, 2,6-dihalogeno-1,4-phenylene, pyrimidine-2,5-diyl or pyridine-2,5-diyl;
$Z^1$ and $Z^2$ are independently a single bond or —C≡C—, and at least one of m pieces of $Z^1$ and n pieces of $Z^2$ is —C≡C—;
$L^1$ is halogen, —OCF$_3$ or —CF$_3$;
$L^2$ and $L^3$ are independently hydrogen or halogen, but at least one is halogen; and
m and n are independently 0, 1 or 2, and a sum of m and n is 1 or 2.

Item 3. The compound according to item 1, represented by any one of formulas (1-1) to (1-3):

(1-1)
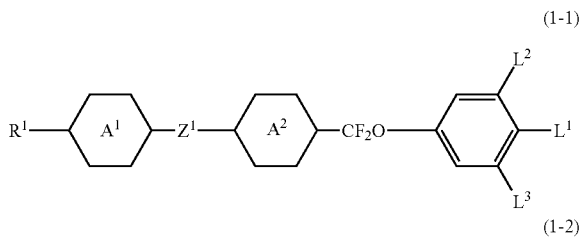

(1-2)
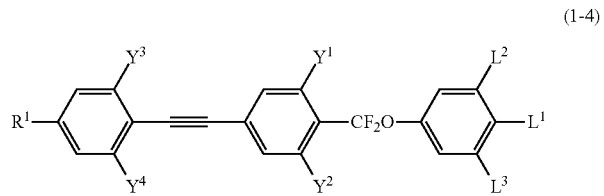

(1-3)
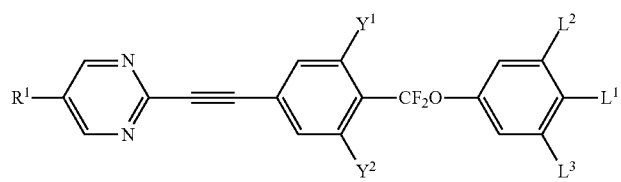

wherein, in formulas (1-1) to (1-3), $R^1$ is alkyl having 1 to 15 carbons, alkenyl having 2 to 15 carbons, alkoxy having 1 to 14 carbons or alkenyloxy having 2 to 14 carbons;

ring $A^1$, ring $A^2$ and ring $A^3$ are independently 1,4-cyclohexylene, 1,4-cyclohexenylene, 1,4-phenylene, 2-halogeno-1,4-phenylene, 2,6-dihalogeno-1,4-phenylene, pyrimidine-2,5-diyl or pyridine-2,5-diyl;

$Z^1$ and $Z^2$ are independently a single bond or —C≡C—, and at least one of m pieces of $Z^1$ and n pieces of $Z^2$ is —C≡C—;

$L^1$ is halogen, —OCF$_3$ or —CF$_3$; and $L^2$ and $L^3$ are independently hydrogen or fluorine, and at least one is fluorine.

Item 4. The compound according to item 3, wherein, in formulas (1-1) to (1-3), ring $A^1$, ring $A^2$ and ring $A^3$ are independently 1,4-phenylene, 2-halogeno-1,4-phenylene, 2,6-dihalogeno-1,4-phenylene, pyrimidine-2,5-diyl or pyridine-2,5-diyl; and $L^1$ is fluorine, —OCF$_3$ or —CF$_3$.

Item 5. The compound according to item 1, represented by any one of formulas (1-4) to (1-28):

(1-4)
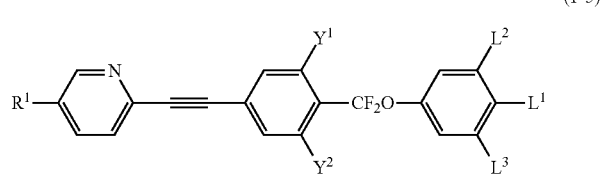

(1-5)

(1-6)
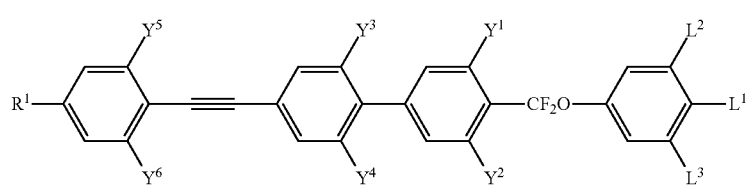

(1-7)
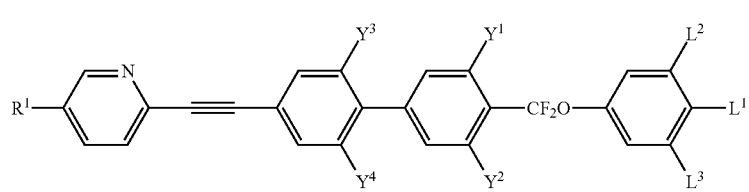

(1-8)
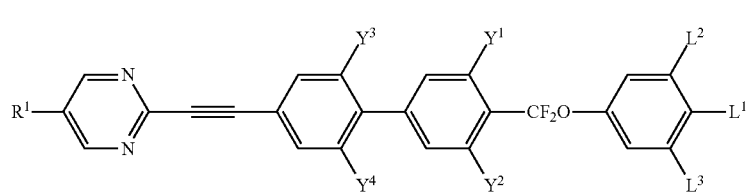

(1-9)

-continued
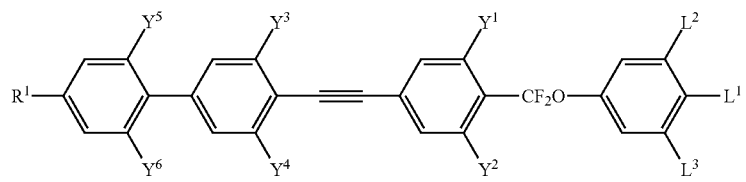
(1-10)

(1-11)
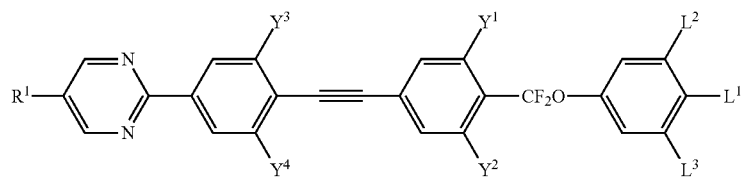
(1-12)
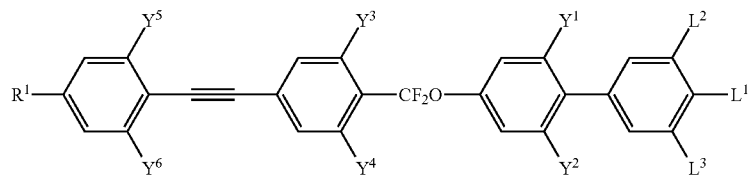
(1-13)
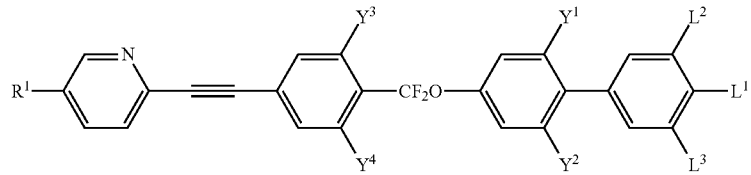
(1-14)
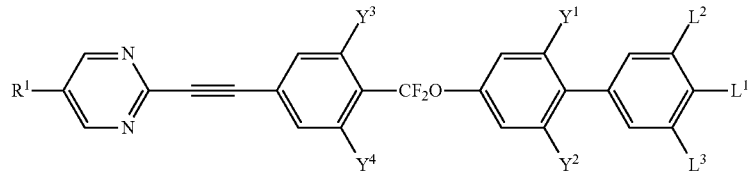
(1-15)

(1-16)

(1-17)

(1-18)
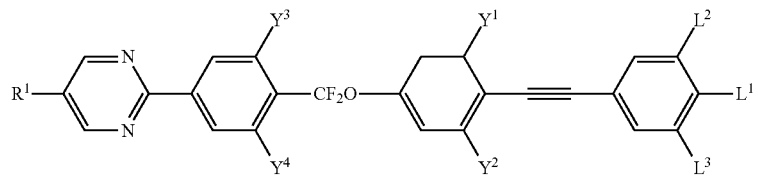
(1-19)
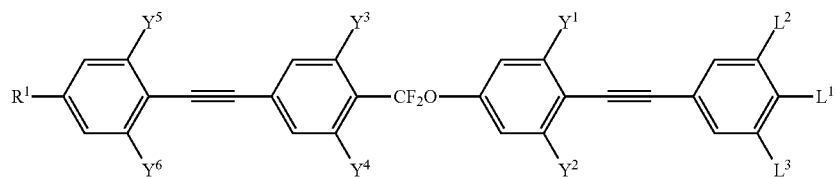
(1-20)
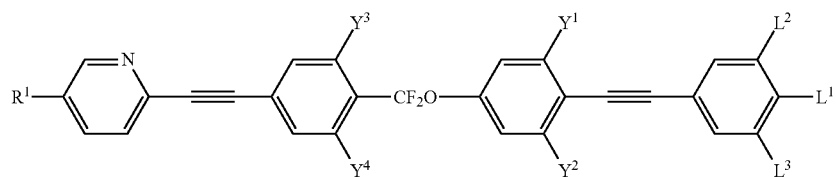
(1-21)
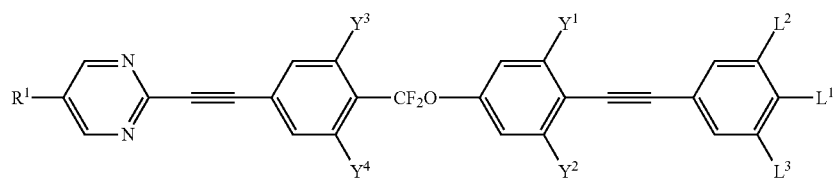
(1-22)
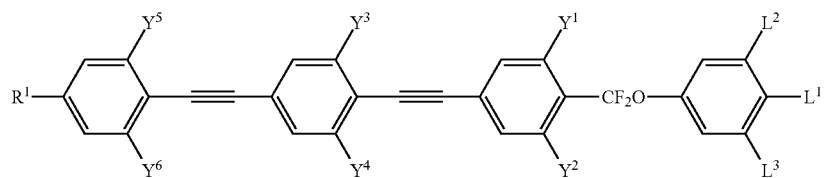
(1-23)
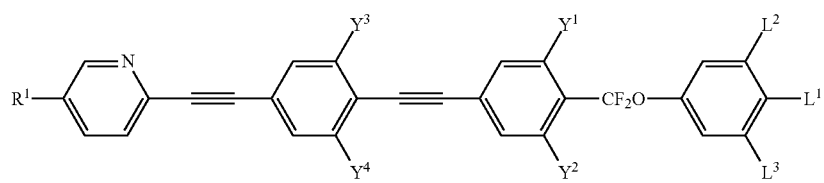
(1-24)
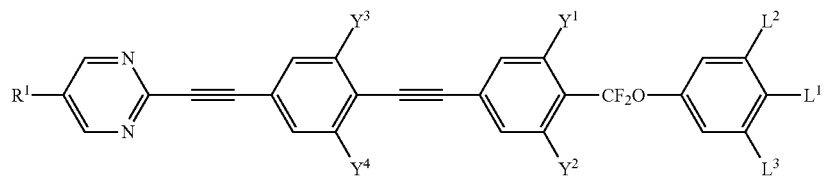
(1-25)
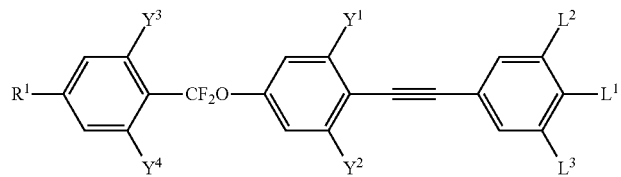

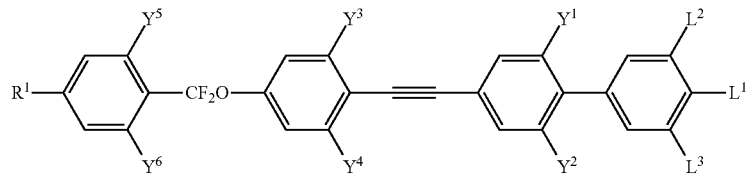
(1-26)

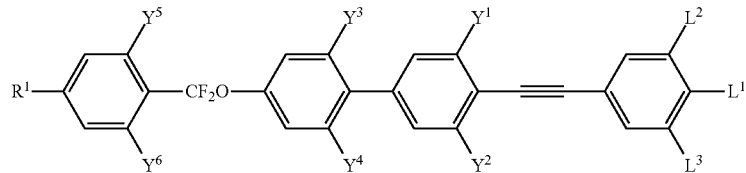
(1-27)

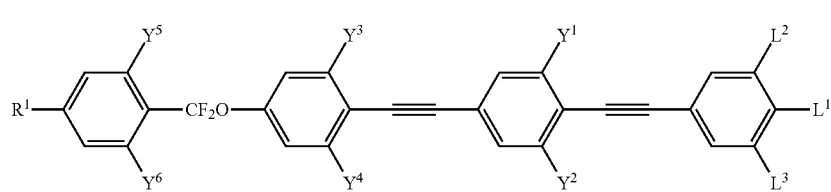
(1-28)

wherein, in formulas (1-4) to (1-28), $R^1$ is alkyl having 1 to 15 carbons, alkenyloxy having 2 to 15 carbons, alkoxy having 1 to 14 carbons or alkenyloxy having 2 to 14 carbons; $Y^1$, $Y^2$, $Y^3$, $Y^4$, $Y^5$ and $Y^6$ are independently hydrogen, fluorine or chlorine; $L^1$ is fluorine, chlorine, —$OCF_3$ or —$CF_3$; and $L^2$ and $L^3$ are independently hydrogen or fluorine, but at least one is fluorine.

Item 6. The compound according to item 5, wherein, in formulas (1-4) to (1-28), $L^1$ is fluorine or —$CF_3$.

Item 7. A liquid crystal composition, containing at least one compound according to any one of items 1 to 6.

Item 8. The liquid crystal composition according to item 7, further containing at least one compound selected from the group of compounds represented by formulas (2) to (4):

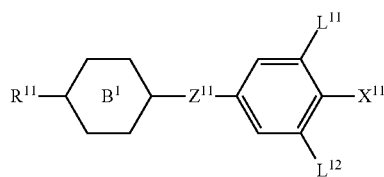
(2)

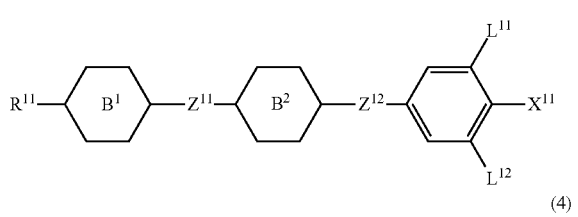
(3)

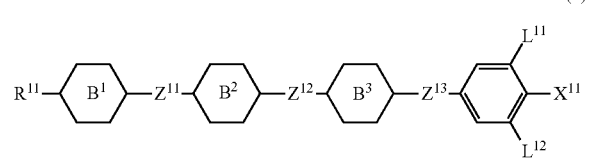
(4)

wherein, in formulas (2) to (4), $R^{11}$ is alkyl having 1 to 10 carbons or alkenyl having 2 to 10 carbons, and in the alkyl and the alkenyl, at least one piece of hydrogen may be replaced by fluorine, and at least one piece of —$CH_2$— may be replaced by —O—;

$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;

ring $R^1$, ring $B^2$ and ring $B^3$ are independently 1,4-cyclohexylene, 1,4-phenylene in which at least one piece of hydrogen may be replaced by fluorine, tetrahydropyran-2,5-diyl, 1,3-dioxane-2,5-diyl or pyrimidine-2,5-diyl;

$Z^{11}$, $Z^{12}$ and $Z^{13}$ are independently a single bond, —$CH_2CH_2$—, —CH=CH—, —C≡C—, —COO—, —$CF_2O$—, —$OCF_2$—, —$CH_2O$— or —$(CH_2)_4$—, and when any one of $Z^{11}$, $Z^{12}$ and $Z^{13}$ is —C≡C—, others are a single bond, —$CH_2CH_2$—, —CH=CH—, —C≡C—, —COO—, —$OCF_2$—, —$CH_2O$— or —$(CH_2)_4$ and when any one of $Z^{11}$, $Z^{12}$ and $Z^{13}$ is —$CF_2O$—, others are a single bond, —$CH_2CH_2$—, —CH=CH—, —COO—, —$CF_2O$—, —$OCF_2$—, —$CH_2O$— or —$(CH_2)_4$; and $L^{11}$ and $L^{12}$ are independently hydrogen or fluorine.

Item 9. The liquid crystal composition according to item 7 or 8, further containing at least one compound selected from the group of compounds represented by formula (5):

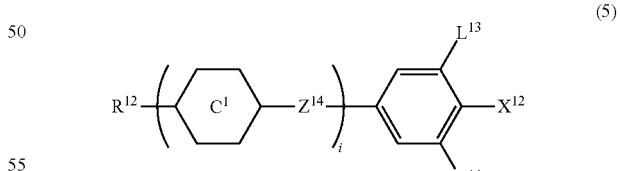
(5)

wherein, in formula (5), $R^{12}$ is alkyl having 1 to 10 carbons or alkenyl having 2 to 10 carbons, and in the alkyl and the alkenyl, at least one piece of hydrogen may be replaced by fluorine, and at least one piece of —$CH_2$— may be replaced by —O—;

$X^{12}$ is —C≡N or —C≡C—C≡N;

ring $C^1$ is 1,4-cyclohexylene, 1,4-phenylene in which at least one piece of hydrogen may be replaced by fluorine, tetrahydropyran-2,5-diyl, 1,3-dioxane-2,5-diyl or pyrimidine-2,5-diyl;

$Z^{14}$ is a single bond, —$CH_2CH_2$—, —COO—, —$CF_2O$—, —$OCF_2$— or —$CH_2O$—;

$L^u$ and $L^{14}$ are independently hydrogen or fluorine; and i is 1, 2, 3 or 4.

Item 10. The liquid crystal composition according to any one of items 7 to 9, further containing at least one compound selected from the group of compounds represented by formulas (6) to (12):

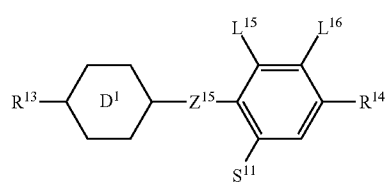
(6)

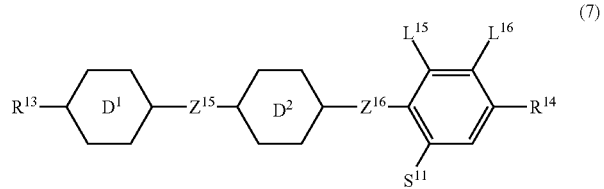
(7)

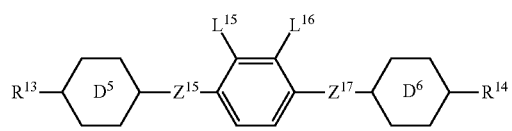
(8)

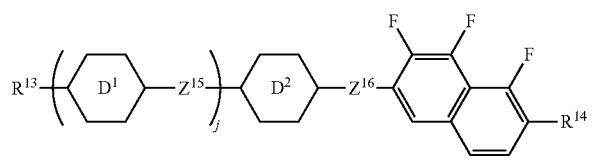
(9)

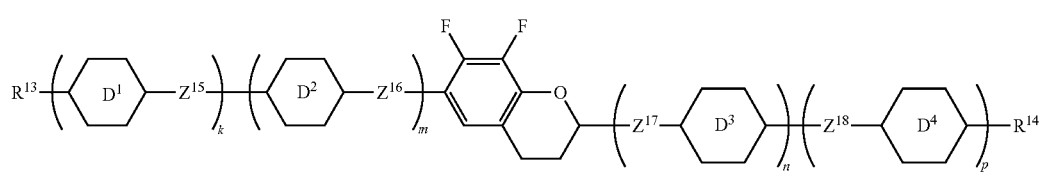
(10)

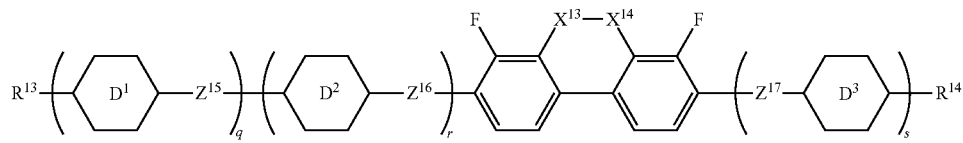
(11)

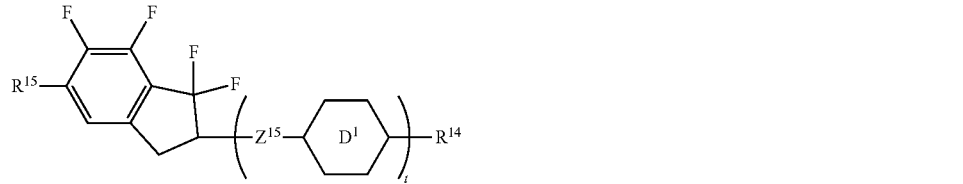
(12)

wherein, in formulas (6) to (12), $R^{13}$ and $R^{14}$ are independently alkyl having 1 to 10 carbons or alkenyl having 2 to 10 carbons, and in the alkyl and the alkenyl, at least one piece of —$CH_2$— may be replaced by —O—, and at least one piece of hydrogen may be replaced by fluorine;

$R^{15}$ is hydrogen, fluorine, alkyl having 1 to 10 carbons or alkenyl having 2 to 10 carbons, and in the alkyl and the alkenyl, at least one piece of —$CH_2$— may be replaced by —O—, and at least one piece of hydrogen may be replaced by fluorine;

$S^{11}$ is hydrogen or methyl;

$X^{13}$ and $X^{14}$ are independently —$CF_2$—, —O— or —CHF—;

ring $D^1$, ring $D^2$, ring $D^3$ and ring $D^4$ are independently 1,4-cyclohexylene, 1,4-cyclohexenylene, 1,4-phenylene in which at least one piece of hydrogen may be replaced by fluorine, tetrahydropyran-2,5-diyl or decahydronaphthalene-2,6-diyl;

ring $D^5$ and ring $D^6$ are independently 1,4-cyclohexylene, 1,4-cyclohexenylene, 1,4-phenylene, tetrahydropyran-2,5-diyl or decahydronaphthalene-2,6-diyl;

$Z^{15}$, $Z^{16}$, $Z^{17}$ and $Z^{18}$ are independently a single bond, —$CH_2CH_2$—, —COO—, —$CH_2O$—, —$OCF_2$— or —$OCF_2CH_2CH_2$—;

$L^{15}$ and $L^{16}$ are independently fluorine or chlorine; and j, k, m, n, p, q, r and s are independently 0 or 1, a sum of k, m, n and p is 1 or 2, a sum of q, r and s is 0, 1, 2 or 3, and t is 1, 2 or 3.

Item 11. The liquid crystal composition according to any one of items 7 to 10, further containing at least one compound selected from the group of compounds represented by formulas (13) to (15):

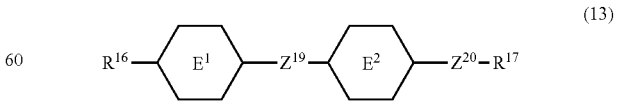
(13)

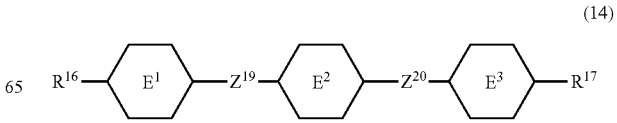
(14)

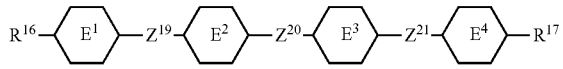

(15)

wherein, in formulas (13) to (15), $R^{16}$ and $R^{17}$ are independently alkyl having 1 to 10 carbons or alkenyl having 2 to 10 carbons, and in the alkyl or the alkenyl, at least one piece of —$CH_2$— may be replaced by —O—, and at least one piece of hydrogen may be replaced by fluorine;

ring $E^1$, ring $E^2$, ring $E^3$ and ring $E^4$ are independently 1,4-cyclohexylene, 1,4-phenylene, 2-fluoro-1,4-phenylene, 2,5-difluoro-1,4-phenylene or pyrimidine-2,5-diyl; and $Z^{19}$, $Z^{20}$ and $Z^{21}$ are independently a single bond, —$CH_2CH_2$—, —CH=CH—, —C≡C— or —COO—.

Item 12. The liquid crystal composition according to any one of items 7 to 11, further containing at least one of a polymerizable compound, an optically active compound, an antioxidant, an ultraviolet light absorber, a light stabilizer, a heat stabilizer and an antifoaming agent.

Item 13. A liquid crystal display device including the liquid crystal composition according to any one of items 7 to 12.

Item 14. The liquid crystal display device according to item 13, wherein the liquid crystal composition according to any one of items 7 to 12 is encapsulated.

Item 15. The liquid crystal display device according to item 13, wherein the liquid crystal composition according to any one of items 7 to 12 is used in a lens to be utilized for switching between 2D and 3D.

The compound, the liquid crystal composition and the liquid crystal display device according to the invention will be described in the order.

1. Compound (1) of the Invention
1-1. Preferred Example

Compound (1) of the invention has a feature of having —$CF_2O$— and —C≡C—. Compound (1) has a large dielectric anisotropy (Δε) and a large optical anisotropy (Δn) in comparison with a similar compound. Preferred examples of compound (1) will be described. Preferred examples of a terminal group, a ring structure, a bonding group and a substituent in compound (1) applies also to a subordinate formula of formula (1) for compound (1).

hydrogen is replaced by halogen, or alkoxy having 1 to 15 carbons in which at least one piece of hydrogen is replaced by halogen.

Specific examples of $R^1$ also include alkyl having 1 to 15 carbons, alkenyl having 2 to 15 carbons, alkoxy having 2 to 15 carbons, alkyl having 1 to 15 carbons in which at least one piece of hydrogen is replaced by halogen, alkenyl having 2 to 15 carbons in which at least one piece of hydrogen is replaced by halogen, or alkoxy having 2 to 15 carbons in which at least one piece of hydrogen is replaced by halogen.

Specific examples of such a left-terminal group $R^1$ include alkyl, alkoxy, alkoxyalkyl, alkoxyalkoxy, alkenyl, alkenyloxy, alkenyloxyalkyl and alkoxyalkenyl. In the groups, at least one piece of hydrogen may be replaced by halogen. Preferred halogen is fluorine or chlorine. Further preferred halogen is fluorine. The groups have a straight chain or a branched chain, but include no cyclic group such as cyclohexyl. In the groups, the straight chain is preferred to the branched chain.

A preferred configuration of —CH=CH— in the alkenyl depends on a position of a double bond. A trans configuration is preferred in alkenyl having the double bond in an odd-numbered position, such as —CH=CHCH$_3$, —CH=CHC$_2$H$_5$, —CH=CHC$_3$H$_7$, —CH=CHC$_4$H$_9$, —C$_2$H$_4$CH=CHCH$_3$ and —C$_2$H$_4$CH=CHC$_2$H$_5$. A cis configuration is preferred in alkenyl having the double bond in an even-numbered position, such as —CH$_2$CH=CHCH$_3$, —CH$_2$CH=CHC$_2$H$_5$ and —CH$_2$CH=CHC$_3$H$_7$. An alkenyl compound having a preferred configuration has a high clearing point or a wide temperature range of the liquid crystal phase. A detailed description is found in Mol. Cryst. Liq. Cryst., 1985, 131, 109 and Mol. Cryst. Liq. Cryst., 1985, 131, 327.

Specific examples of the alkyl include —CH$_3$, —C$_2$H$_5$, —C$_3$H$_7$, —C$_4$H$_9$, —C$_5$H$_{11}$, —C$_6$H$_{13}$ or —C$_7$H$_{15}$.

Specific examples of the alkoxy include —OCH$_3$, —OC$_2$H$_5$, —OC$_3$H$_7$, —OC$_4$H$_9$, —OC$_5$H$_{11}$, —OC$_6$H$_{13}$ or —OC$_7$H$_{15}$.

Specific examples of the alkoxyalkyl include —CH$_2$OCH$_3$, —CH$_2$OC$_2$H$_5$, —CH$_2$OC$_3$H$_7$, —(CH$_2$)$_2$—OCH$_3$, —(CH$_2$)$_2$—OC$_2$H$_5$, —(CH$_2$)$_2$—OC$_3$H$_7$, —(CH$_2$)$_3$—OCH$_3$, —(CH$_2$)$_4$—OCH$_3$ or —(CH$_2$)$_5$—OCH$_3$.

Specific examples of the alkenyl include —CH=CH$_2$, —CH=CHCH$_3$, —CH$_2$CH=CH$_2$, —CH=CHC$_2$H$_5$,

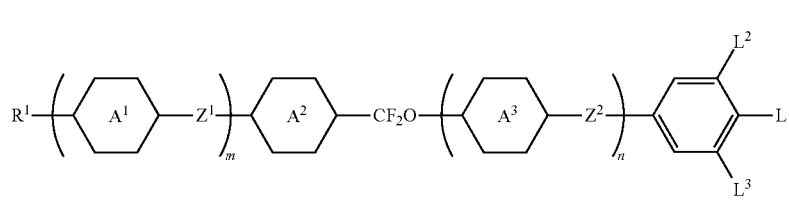

(1)

In formula (1), $R^1$ is alkyl having 1 to 15 carbons, and in the alkyl, at least one piece of —CH$_2$— may be replaced by —O—, and at least one piece of —CH$_2$CH$_2$— may be replaced by —CH=CH—, and in the groups, at least one piece of hydrogen may be replaced by halogen.

Specific examples of $R^1$ include alkyl having 1 to 15 carbons, alkenyl having 2 to 15 carbons, alkoxy having 1 to 15 carbons, alkyl having 1 to 15 carbons in which at least one piece of hydrogen is replaced by halogen, alkenyl having 2 to 15 carbons in which at least one piece of —CH$_2$CH=CHCH$_3$, —(CH$_2$)$_2$—CH=CH$_2$, —CH=CHC$_3$H$_7$, —CH$_2$CH=CHC$_2$H$_5$, —(CH$_2$)$_2$—CH=CHCH$_3$ or —(CH$_2$)$_3$—CH=CH$_2$.

Specific examples of the alkenyloxy include —OCH$_2$CH=CH$_2$, —OCH$_2$CH=CHCH$_3$ or —OCH$_2$CH=CHC$_2$H$_5$.

Specific examples of alkyl in which at least one piece of hydrogen is replaced by halogen include —CH$_2$F, —CHF$_2$, —CF$_3$, —(CH$_2$)$_2$—F, —CF$_2$CH$_2$F, —CF$_2$CHF$_2$, —CH$_2$CF$_3$, —CF$_2$CF$_3$, —(CH$_2$)$_3$—F, —(CF$_2$)$_3$—F, —CF$_2$CHFCF$_3$, —CHFCF$_2$CF$_3$, —(CH$_2$)$_4$—F, —(CF$_2$)$_4$—F, —(CH$_2$)$_5$—F, —(CF$_2$)$_5$—F, —CH$_2$Cl, —CHCl$_2$, —CCl$_3$, —(CH$_2$)$_2$—Cl, —CCl$_2$CH$_2$Cl, —CCl$_2$CHCl$_2$, —CH$_2$CCl$_3$, —CCl$_2$CCl$_3$, (CH$_2$)$_3$—Cl, —(CCl$_2$)$_3$—Cl, —CCl$_2$CHClCCl$_3$, —CHClCCl$_2$CCl$_3$, —(CH$_2$)$_4$—Cl, —(CCl$_2$)$_4$—Cl, —(CH$_2$)$_5$—Cl or —(CCl$_2$)$_5$—Cl.

Specific examples of alkoxy in which at least one piece of hydrogen is replaced by halogen —OCH$_2$F, —OCHF$_2$, —OCF$_3$, —O—(CH$_2$)$_2$—F, —OCF$_2$CH$_2$F, —OCF$_2$CHF$_2$, —OCH$_2$CF$_3$, —O—(CH$_2$)$_3$—F, —O—(CF$_2$)$_3$—F, —OCF$_2$CHFCF$_3$, —OCHFCF$_2$CF$_3$, —O(CH$_2$)$_4$—F, —O—(CF$_2$)$_4$—F, —O—(CH$_2$)$_5$—F, —O—(CF$_2$)$_5$—F, —OCH$_2$Cl, —OCHCl$_2$, —OCCl$_3$—O—(CH$_2$)$_2$—Cl, —OCCl$_2$CH$_2$Cl, —OCCl$_2$CHCl$_2$, —OCH$_2$CCl$_3$, —O—(CH$_2$)$_3$—, —O—(CCl$_2$)$_3$—Cl, —OCCl$_2$CHClCCl$_3$, —OCHClCCl$_2$CCl$_3$, —O(CH$_2$)$_4$—, —O—(CCl$_2$)$_4$—Cl, —O—(CH$_2$)$_5$—Cl or —O—(CCl$_2$)$_5$—Cl.

Specific examples of alkenyl in which at least one piece of hydrogen is replaced by halogen include —CH═CHF, —CH═CF$_2$, —CF═CHF, —CH═CHCH$_2$F, —CH═CHCF$_3$, —(CH$_2$)$_2$—CH═CF$_2$, —CH$_2$CH═CHCF$_3$, —CH═CHCF$_2$CF$_3$, —CH═CHCl, —CH═CCl$_2$, —CCl═CHCl, —CH═CHCH$_2$Cl, —CH═CHCCl$_3$, —(CH$_2$)$_2$—CH═CCl$_2$, —CH$_2$CH═CHCCl$_3$ or —CH═CHCCl$_2$CCl$_3$.

Specific preferred examples of R$^1$ include alkyl having 1 to 15 carbons, alkenyl having 2 to 15 carbons, alkoxy having 1 to 14 carbons or alkenyloxy having 1 to 14 carbons. Further preferred examples of R$^1$ include alkyl having 1 to 7 carbons, alkoxy having 1 to 7 carbons, alkenyl having 2 to 8 carbons or alkenyloxy having 2 to 8 carbons. Still further preferred examples of R$^1$ include —CH$_3$, —C$_2$H$_5$, —C$_3$H$_7$, —C$_4$H$_9$, —C$_5$H$_{11}$, —OCH$_3$, —OC$_2$H$_5$, —OC$_3$H$_7$, —OC$_4$H$_9$, —CO$_5$H$_{11}$, —CH═CH$_2$, —CH═CHCH$_3$, —(CH$_2$)$_2$—CH═CH$_2$—CH$_2$CH═CHC$_2$H$_5$, —(CH$_2$)$_2$—CH═CHCH$_3$, —OCH$_2$CH═CH$_2$, —OCH$_2$CH═CHCH$_3$ or —OCH$_2$CH═CHC$_2$H$_5$. Most preferred examples of R$^1$ include —C$_3$H$_7$, —C$_4$H$_9$, —C$_5$H$_{11}$, —C$_6$H$_{13}$, —OC$_2$H$_5$, —OC$_3$H$_7$, —OC$_4$H$_9$, —(CH$_2$)$_2$CH═CH$_2$, —(CH$_2$)$_2$—CH═CHCH$_3$ or —OCH$_2$CH═CH$_2$.

In formula (1), ring A$^1$, ring A$^2$ and ring A$^3$ are independently 1,4-cyclohexylene, 1,4-cyclohexenylene, 1,4-phenylene, 2-halogeno-1,4-phenylene, 2,6-dihalogeno-1,4-phenylene, pyrimidine-2,5-diyl or pyridine-2,5-diyl.

Specific preferred examples of ring A$^1$, ring A$^2$ and ring A$^3$ include 1,4-phenylene, 2-halogeno-1,4-phenylene, 2,6-dihalogeno-1,4-phenylene, pyrimidine-2,5-diyl or pyridine-2,5-diyl. Specific preferred examples of 1,4-phenylene in which at least one piece of hydrogen is replaced by halogen include formulas (A-1) to (A-5).

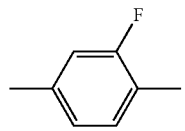
(A-1)

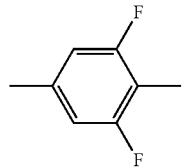
(A-2)

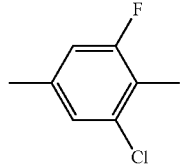
(A-3)

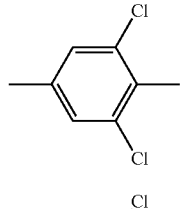
(A-4)

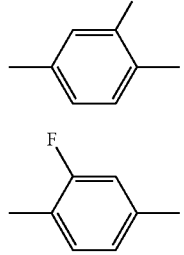
(A-5)

(A-6)

Then, 2-fluoro-1,4-phenylene is not left-right symmetric. In a chemical formula thereof, fluorine includes a case where the fluorine is located on a side of a left-terminal group (leftward; A-6) and a case where the fluorine is located on aside of a right-terminal group (rightward; A-1). Preferred 2-fluoro-1,4-phenylene is rightward (A-1) in order to increase the dielectric anisotropy. A same rule applies also to 2,6-difluoro-1,4-phenylene or the like. More specifically, formulas (A-1) to (A-5) are preferred as the case where the fluorine is located on the side of the right-terminal group.

Further preferred examples of 1, 4-phenylene in which at least one piece of hydrogen is replaced by halogen include 2-fluoro-1,4-phenylene, 2,6-difluoro-1,4-phenylene, 2-chloro-6-fluoro-1,4-phenylene, 2,6-dichloro-1,4-phenylene or 2-chloro-1,4-phenylene. Most preferred examples of 1,4-phenylene in which at least one piece of hydrogen is replaced by halogen include 2-fluoro-1,4-phenylene or 2,6-difluoro-1,4-phenylene.

Further preferred examples of ring A$^1$, ring A$^2$ or ring A$^3$ include: ring A$^1$ being 1,4-phenylene, 2-halogeno-1,4-phenylene, 2,6-dihalogeno-1,4-phenylene, pyrimidine-2,5-diyl or pyridine-2,5-diyl; and ring A$^2$ or ring A$^3$ being 1,4-phenylene, 2-halogeno-1,4-phenylene or 2,6-dihalogeno-1, 4-phenylene.

In formula (1), Z$^1$ and Z$^2$ are independently a single bond or —C≡C—, but at least one is —C≡C—. More specifically, compound (1) has —CF$_2$O— and —C≡C—. Compound (1) may have two pieces of —C≡C—. Preferred examples of compound (1) are described in item 5. In the compounds, further preferred examples include compound (1-4), compound (1-5), compound (1-6) and compound (1-16) to compound (1-24). Particularly preferred examples include compound (1-7) to compound (1-15).

In formula (1), L$^1$ is halogen, —OCF$_3$ or —CF$_3$; and L$^2$ and L$^3$ are independently hydrogen or halogen, but at least one is halogen. Specific preferred examples of L$^1$ include fluorine, chlorine, —OCF$_3$ or —CF$_3$, and specific preferred examples of L$^2$ and L$^3$ include fluorine or chlorine. Further preferred examples of L$^1$ include fluorine, —OCF$_3$ or —CF$_3$, and further preferred examples of L$^2$ and L$^3$ include fluorine. In a preferred combination of L$^2$ and L$^3$, one of L$^2$ and L$^3$ is hydrogen, and the other is fluorine, or both L$^2$ and L$^3$ are fluorine. In a further preferred combination of L$^2$ and L$^3$, both L$^2$ and L$^3$ are fluorine.

In formula (1), m and n are independently 0, 1 or 2, and a sum of m and n is 1 or 2. When a sum of m and n is 1, a compound thereof is a tricyclic compound. When a sum of m and n is 2, a compound thereof is a tetracyclic compound. From a viewpoint of a low viscosity, in a preferred combination, m is 1 and n is 0. From a viewpoint of a high maximum temperature, in a preferred combination, m is 1 and n is 1, or m is 2 and n is 0.

1-2. Physical Properties of Compound (1)

In compound (1), physical properties such as a clearing point, optical anisotropy and dielectric anisotropy can be arbitrarily adjusted by suitably combining kinds of R$^1$, ring A$^1$, ring A$^2$, ring A$^3$, Z$^1$, Z$^2$, L$^1$, L$^2$ and L$^3$. Compound (1) may contain an isotope such as $^2$H (deuterium) and $^{13}$C in an amount larger than an amount of natural abundance because no significant difference is caused in the physical properties of the compound. A main effect of kinds of or the like on the physical properties of compound (1) will be described below.

When a left-terminal group R$^1$ has the straight chain, a temperature range of the liquid crystal phase is wide and the viscosity is small. When R$^1$ has the branched chain, compatibility with other liquid crystal compounds is good. A compound in which R$^1$ is optically active is useful as a chiral dopant. A reverse twisted domain to be generated in the liquid crystal display device can be prevented by adding the compound to the composition. A compound in which R$^1$ is not optically active is useful as a component of the composition. When R$^1$ is alkenyl, a preferred configuration depends on a position of a double bond. An alkenyl compound having the preferred configuration has the small viscosity, the high maximum temperature or the wide temperature range of the liquid crystal phase.

When all of ring A$^1$, ring A$^2$ and ring A$^3$ are 1,4-cyclohexylene, the clearing point is high and the viscosity is small. When at least one of ring A$^1$, ring A$^2$ and ring A$^3$ is 1,4-phenylene, or 1,4-phenylene in which at least one piece of hydrogen is replaced by halogen, the optical anisotropy is comparatively large and an orientational order parameter is comparatively large. When all of ring A$^1$, ring A$^2$ and ring A$^3$ are 1,4-phenylene, 1,4-phenylene in which at least one piece of hydrogen is replaced by halogen, or a combination thereof, the optical anisotropy is particularly large. When at least one of ring A$^1$, ring A$^2$ and ring A$^3$ is 1,4-phenylene in which at least one piece of hydrogen is replaced by halogen, pyrimidine-2,5-diyl or pyridine-2,5-diyl, the dielectric anisotropy is large.

When a bonding group Z$^1$ is a single bond, chemical stability is high and the viscosity is small. When Z$^1$ is —C≡C—, the optical anisotropy and the dielectric anisotropy are large, and the maximum temperature is high.

When one of L$^2$ and L$^3$ is fluorine, the dielectric anisotropy is large. When both L$^2$ and L$^3$ are fluorine, the dielectric anisotropy is particularly large.

Specific preferred examples of compound (1) include compound (1-1), compound (1-2) and compound (1-3). Compound (1-1) is preferred from a viewpoint of a low minimum temperature. Compound (1-2) or compound (1-3) is preferred from a viewpoint of a high maximum temperature. Compound (1-2) is preferred from a viewpoint of a large optical anisotropy. Compound (1-3) is preferred from a viewpoint of an excellent compatibility at a low temperature. From a viewpoint of optical anisotropy or dielectric anisotropy, specific preferred examples of compound (1-1) to compound (1-3) include compound (1-4) to compound (1-28).

As described above, a compound having objective physical properties can be obtained by suitably selecting a kind of the ring structure, the terminal group, the bonding group or the like. Accordingly, compound (1) is useful as a component of a liquid crystal composition used in a liquid crystal display device having a mode such as the PC mode, the TN mode, the STN mode, the ECB mode, the OCB mode, the IPS mode and the VA mode.

1-3. Synthesis of Compound (1)

A synthesis method of compound (1) will be described. Compound (1) can be prepared by suitably combining synthesis methods in synthetic organic chemistry. Methods for introducing an objective terminal group, ring and bonding group into a starting material are described in books such as "Organic Syntheses" (John Wiley & Sons, Inc.), "Organic Reactions" (John Wiley & Sons, Inc.), "Comprehensive Organic Synthesis" (Pergamon Press) and "New Experimental Chemistry Course (Shin Jikken Kagaku Koza in Japanese)" (Maruzen Co., Ltd.).

1-3a. Formation of a Bonding Group

A method for forming a bonding group in compound (1) is as described in a scheme below. In the scheme, MSG$_1$ (or MSG$^2$) is a monovalent organic group having at least one ring. The monovalent organic groups represented by a plurality of MSG$^1$ (or MSG$^2$) may be identical or different. Compounds (1A) to (1J) correspond to compound (1).

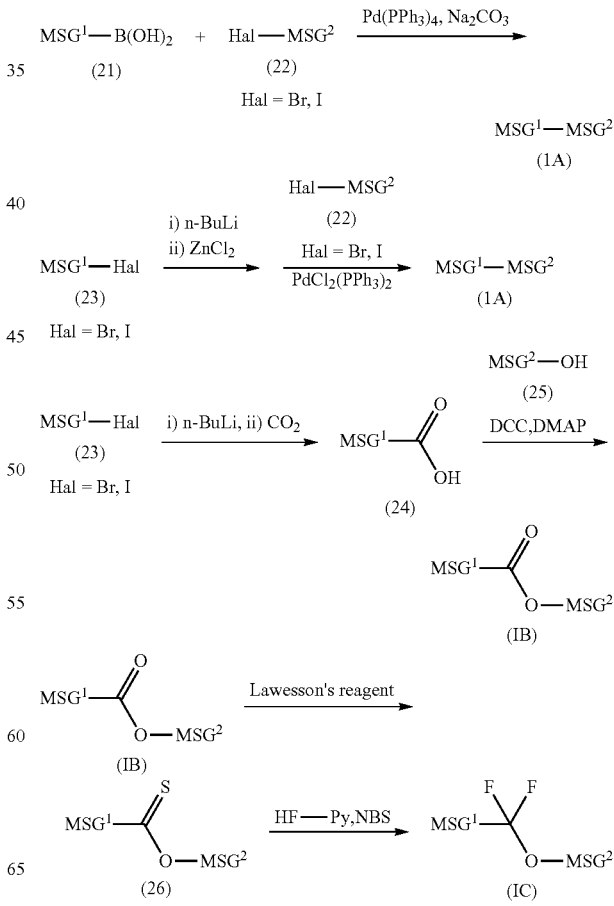

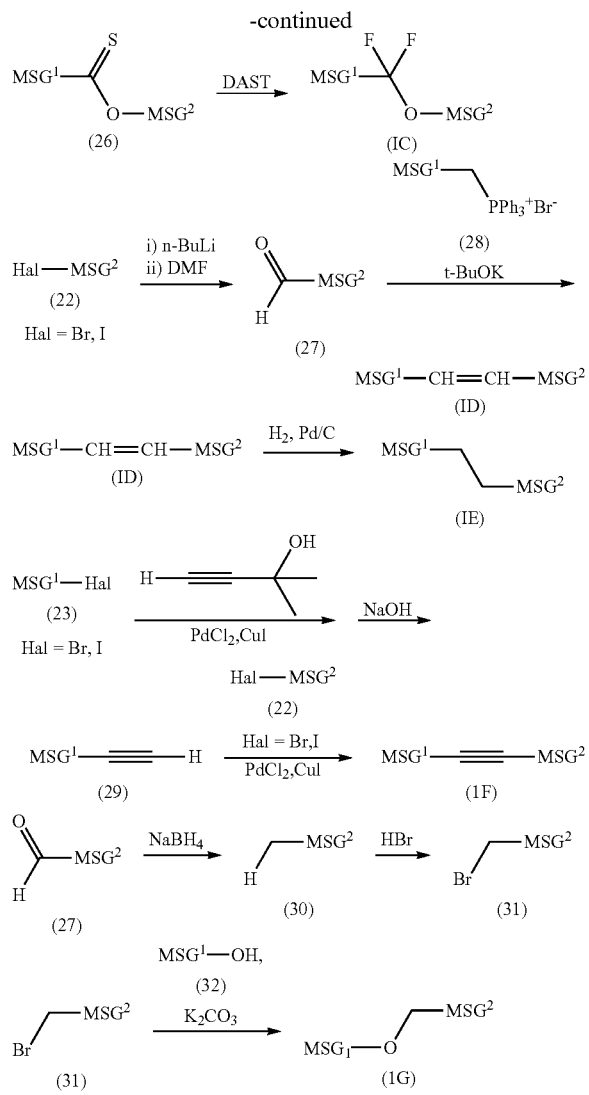

(I) Formation of a Single Bond

Compound (1A) is prepared by allowing arylboronic acid (21) to react with compound (22), in the presence of carbonate and a catalyst including tetrakis(triphenylphosphine)palladium. Compound (1A) is also prepared by allowing compound (23) to react with n-butyllithium and subsequently with zinc chloride, and further with compound (22) in the presence of a catalyst including dichlorobis(triphenylphosphine)palladium.

(II) Formation of —COO—

Carboxylic acid (24) is obtained by allowing compound (23) to react with n-butyllithium and subsequently with carbon dioxide. Compound (1B) having —COO— is prepared by dehydration of compound (24) and phenol (25) prepared according to a publicly known method from compound (21) in the presence of 1,3-dicyclohexylcarbodiimide (DCC) and 4-dimethylaminopyridine (DMAP).

(III) Formation of —CF$_2$O—

Compound (26) is obtained by sulfurating compound (1B) with a Lawesson's reagent. Compound (1C) is prepared by fluorinating compound (26) with a hydrogen fluoride-pyridine complex and N-bromosuccinimide (NBS). Refer to M. Kuroboshi et al., Chem. Lett., 1992, 827. Compound (1C) is also prepared by fluorinating compound (26) with (diethylamino)sulfur trifluoride (DAST). Refer to W. H. Bunnelle et al., J. Org. Chem. 1990, 55, 768.

(IV) Formation of —CH═CH—

Aldehyde (27) is obtained by allowing compound (22) to react with n-butyllithium and subsequently with N,N-dimethylformamide (DMF). Compound (1D) is prepared by allowing phosphorus ylide generated by allowing phosphonium salt (28) to react with potassium t-butoxide to react with aldehyde (27). A cis isomer may be generated depending on reaction conditions, and therefore the cis isomer is isomerized into a trans isomer according to a publicly known method when necessary.

(V) Formation of —CH$_2$CH$_2$—

Compound (1E) is prepared by hydrogenating compound (1D) in the presence of a catalyst including palladium on carbon.

(VI) Formation of —C≡C—

Compound (29) is obtained by allowing compound (23) to react with 2-methyl-3-butyn-2-ol in the presence of a catalyst including dichloropalladium and copper iodide, and then performing deprotection under basic conditions. Compound (1F) is prepared by allowing compound (29) to react with compound (22) in the presence of a catalyst including dichlorobis(triphenylphosphine)palladium and copper halide.

(VII) Formation of —CH$_2$O—

Compound (30) is obtained by reducing compound (27) with sodium borohydride. Compound (31) is obtained by brominating the obtained compound with hydrobromic acid. Compound (1G) is prepared by allowing compound (32) to react with compound (31) in the presence of potassium carbonate.

1-3b. Formation of Ring A$^1$, Ring A$^2$ and Ring A$^3$

A starting material is commercially available or a synthetic method is well known with regard to a ring such as 1,4-cyclohexylene, 1,4-phenylene, 2-fluoro-1,4-phenylene, 2,6-difluoro-1,4-phenylene, pyrimidine-2,5-diyl and pyridine-2,5-diyl.

1-3c. Synthesis Example

An example of a method for preparing compound (1-A) is as described below. Compound (33) is obtained by allowing compound (32) prepared according to an existing method to react with s-butyllithium and subsequently with iodine. Compound (34) is obtained by allowing compound (33) to react with ethynyltrimethylsilane in the presence of bis(triphenylphosphine)palladium(II) dichloride and copper(I) iodide. Compound (35) is obtained by performing desilylation of compound (34) in the presence of potassium carbonate. Compound (1-A) is prepared by allowing compound (36) prepared according to an existing method to react with compound (35) in the presence of PdCl$_2$(Amphos)$_2$ (Pd-132) and cesium carbonate.

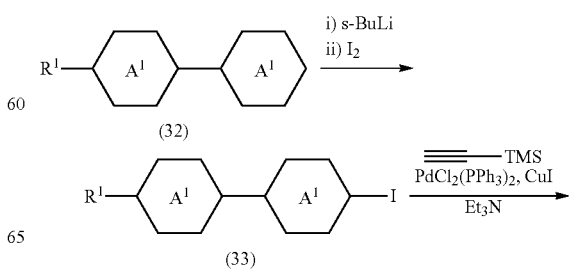

-continued

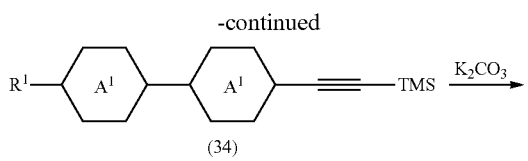

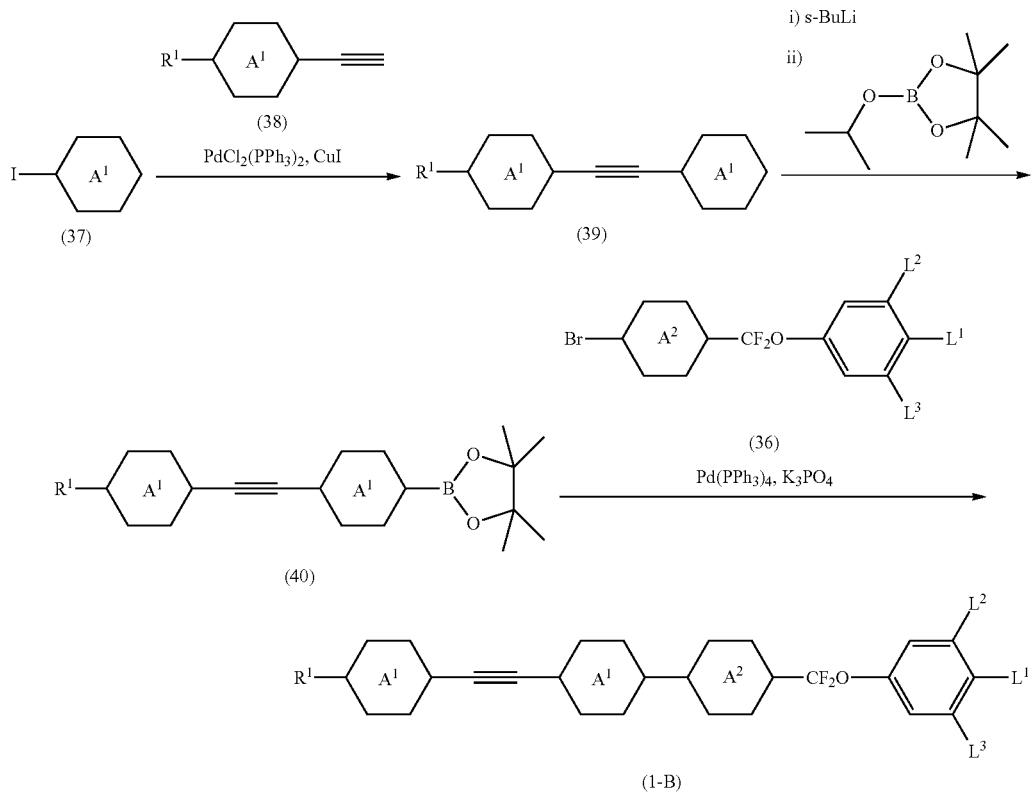

An example of a method for preparing compound (1-B) is as described below. Compound (39) is obtained by allowing compound (37) prepare according to an existing method to react with compound (38) in the presence of bis(triphenylphosphine)palladium(II) dichloride and copper (I) iodide. Compound (40) is obtained by allowing compound (39) to react with s-butyllithium and subsequently with isopropoxyboronic acid pinacol. Compound (1-B) is prepared by allowing compound (40) to react with compound (36) prepared according to an existing method in the presence of tetrakis(triphenylsphophine)palladium(0) and potassium phosphate.

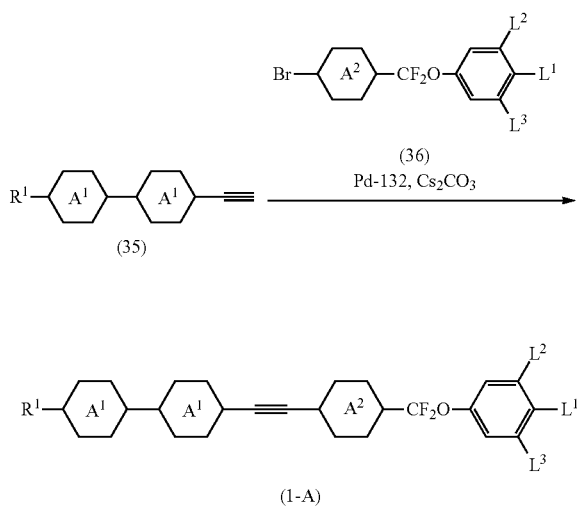

In the compounds, definitions of $R^1$, ring $A^1$, ring $A^2$, ring $A^3$, $L^1$, $L^2$ and $L^3$ are identical to definitions described above.

2. Liquid Crystal Composition 2-1. Compounds (2) to (15)

A liquid crystal composition of the invention will be described. The composition contains at least one compound (1) as component A. The composition may contain two, three or more compounds (1). A component in the composition may be only compound (1). In order to develop excellent physical properties, the composition preferably contains at least one of compounds (1) in the range of 1% by weight to 99% by weight. In a composition having a positive dielectric anisotropy, a preferred content of compound (1) is in the range of 5% by weight to 60% by weight. In a composition having a negative dielectric anisotropy, a preferred content of compound (1) is 30% by weight or less. The composition may also contain compound (1) and various liquid crystal compounds that are not described herein.

A preferred composition contains a compound selected from components B, C, D and E shown below. When the composition is prepared, components can also be selected, for example, by taking into account a dielectric anisotropy of compound (1). When a composition having the positive dielectric anisotropy is prepared for a mode such as the TFT mode, the IPS mode and the FFS mode, main components include components A, B and E. When a composition having the positive dielectric anisotropy is prepared for a mode such as the STN mode and the TN mode, main components include components A, C and E. When a composition having the negative dielectric anisotropy is prepared for a mode such as the VA mode and the PSA mode, main components include components D and E, and component A is added for the purpose of adjusting a voltage-transmittance curve of a device. A composition in which the components are suitably selected has a high maximum temperature, a low minimum temperature, a small viscosity, a suitable optical anisotropy, a large dielectric anisotropy and a suitable elastic constant.

Component B includes compounds (2) to (4). Component C includes compound (5). Component D includes compounds (6) to (12). Component E includes compounds (13) to (15). The components will be described in the order.

Component B is a compound having a halogen-containing group or a fluorine-containing group at a right terminal. Specific preferred examples of component B include compounds (2-1) to (2-16), compounds (3-1) to (3-113) or compounds (4-1) to (4-57). In the compounds, definitions of $R^{11}$ and $X^{11}$ are identical to definitions described in item 8.

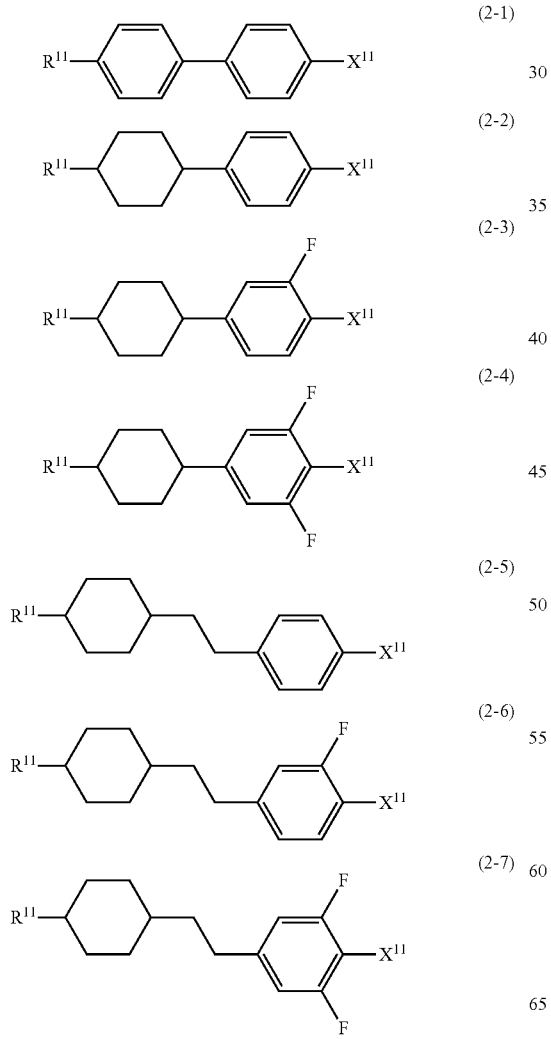
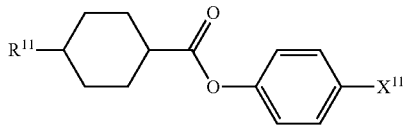
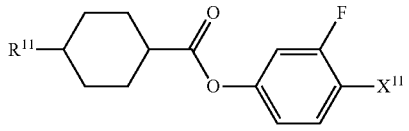
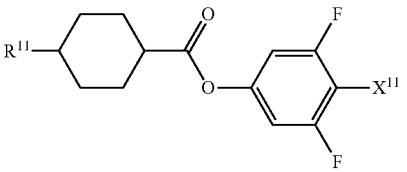
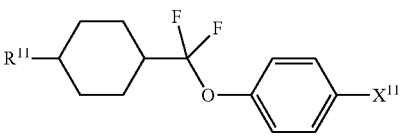
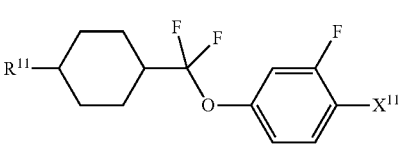
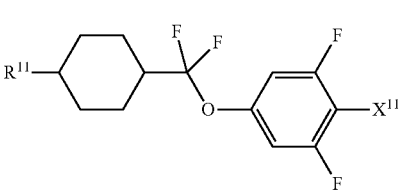
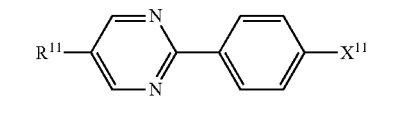
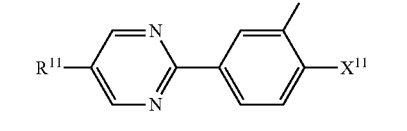
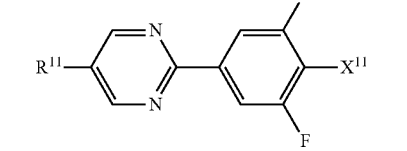
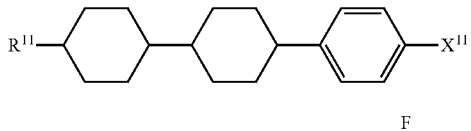

(3-3) 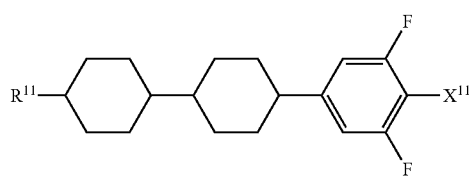
(3-4) 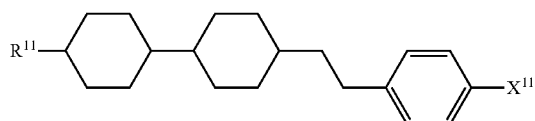
(3-5) 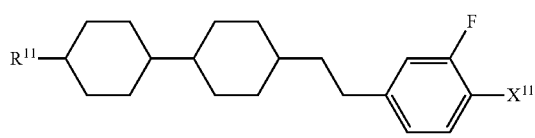
(3-6) 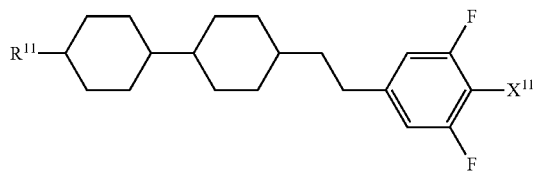
(3-7) 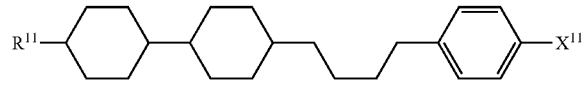
(3-8) 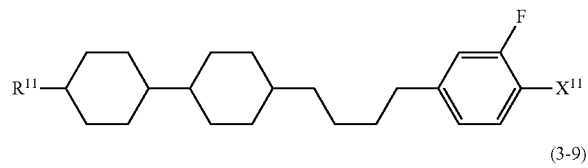
(3-9) 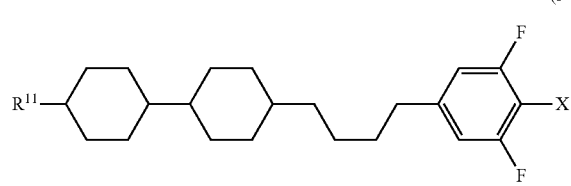
(3-10) 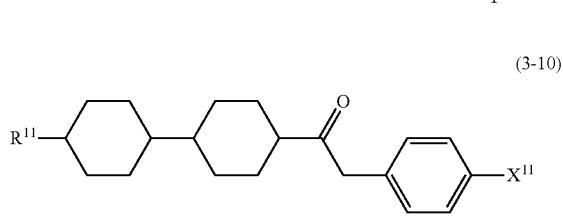
(3-11) 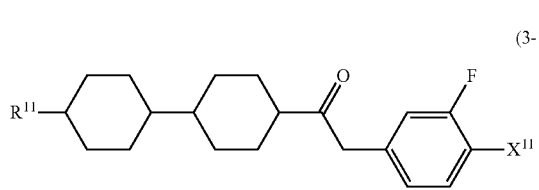
(3-12) 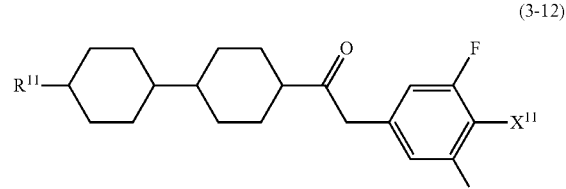
(3-13) 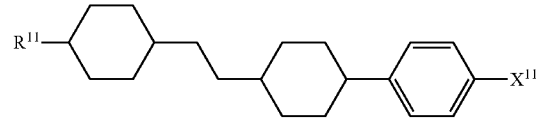
(3-14) 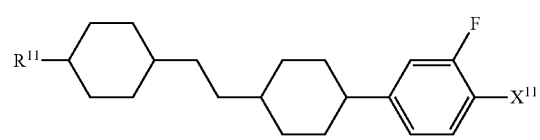
(3-15) 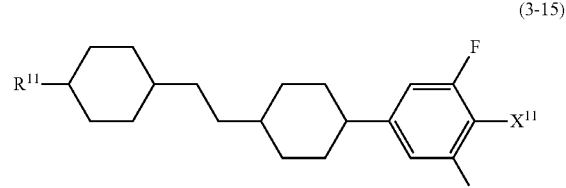
(3-16) 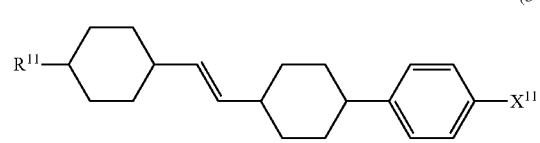
(3-17) 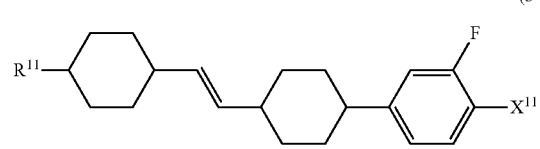
(3-18) 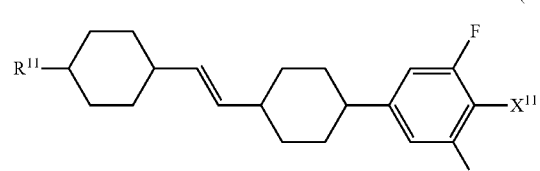
(3-19) 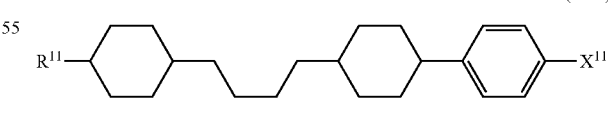
(3-20) 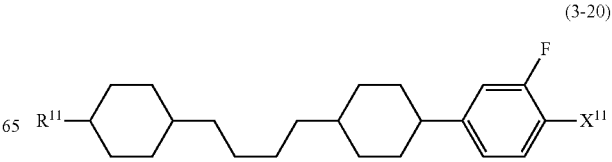

(3-21) 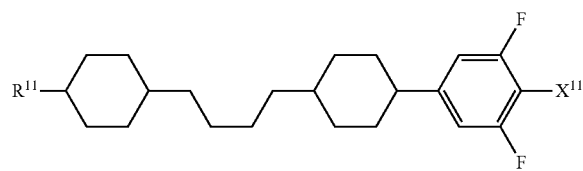
(3-22) 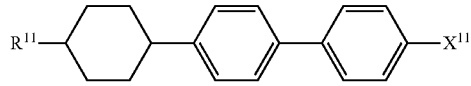
(3-23) 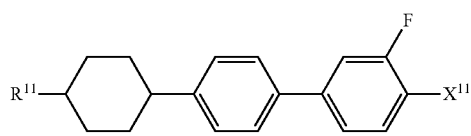
(3-24) 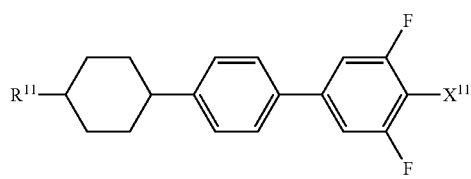
(3-25) 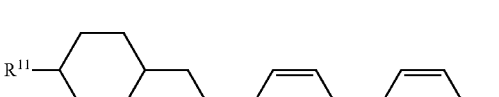
(3-26) 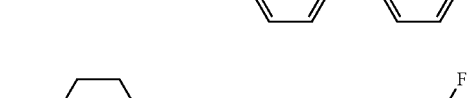
(3-27) 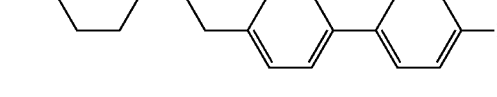
(3-28) 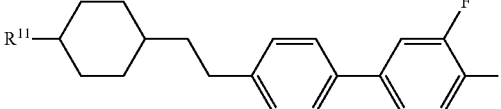
(3-29) 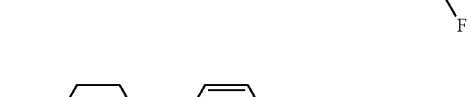
(3-30) 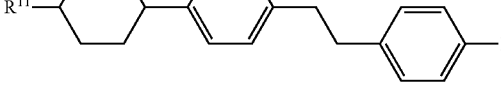
(3-31) 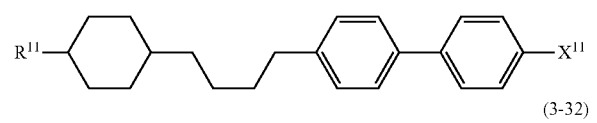
(3-32) 
(3-33) 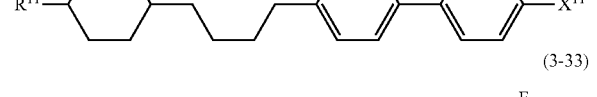
(3-34) 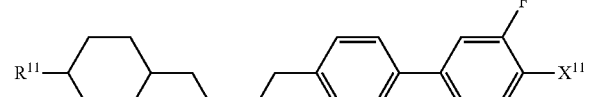
(3-35) 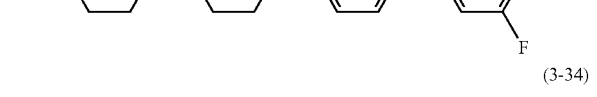
(3-36) 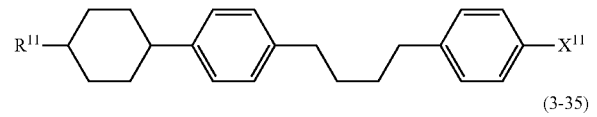
(3-37) 
(3-38) 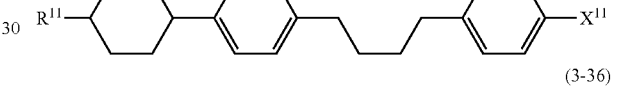
(3-39) 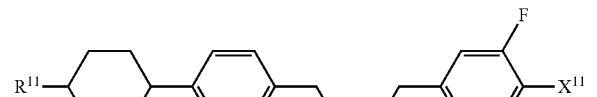
(3-40) 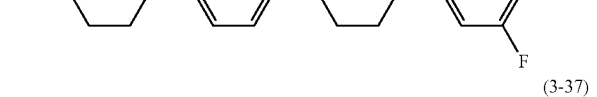

(3-41)
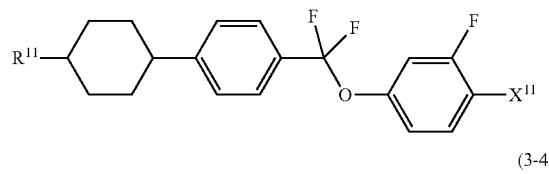
(3-42)
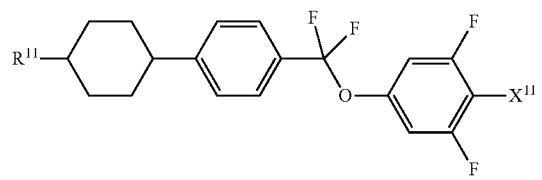
(3-43)
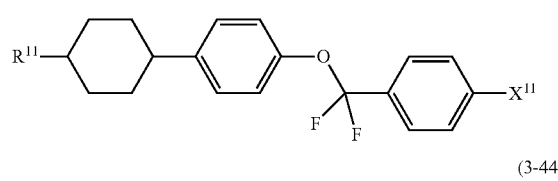
(3-44)
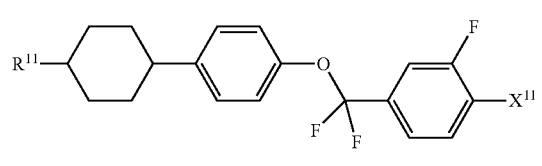
(3-45)
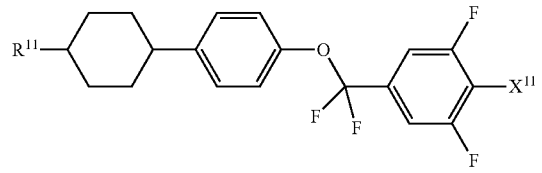
(3-46)
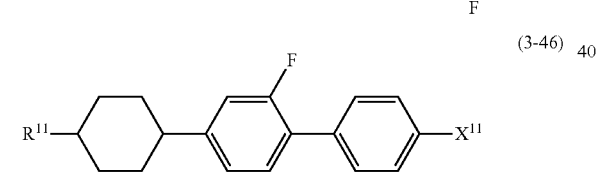
(3-47)
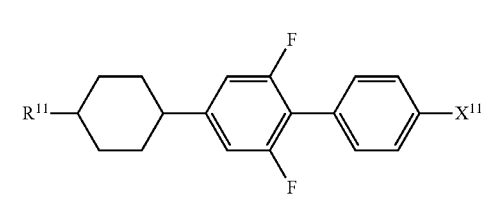
(3-48)
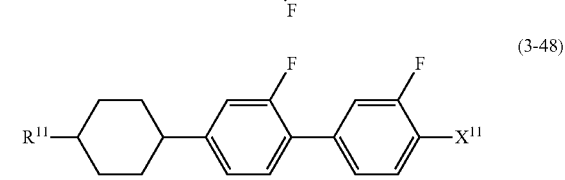
(3-49)
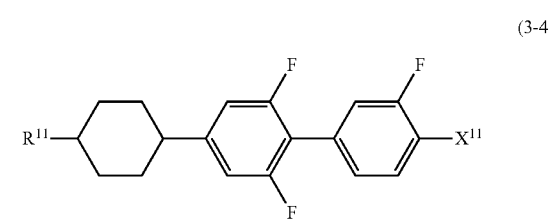
(3-50)
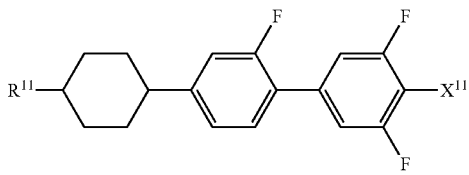
(3-51)
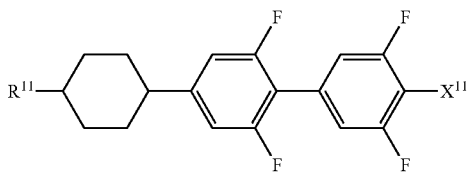
(3-52)
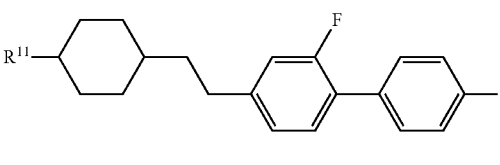
(3-53)
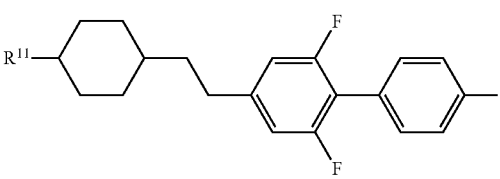
(3-54)
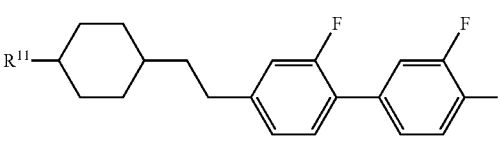
(3-55)
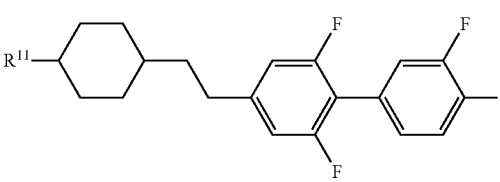
(3-56)
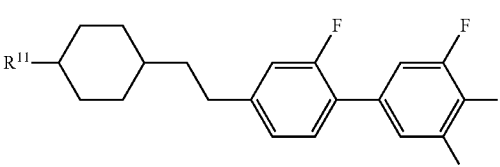
(3-57)
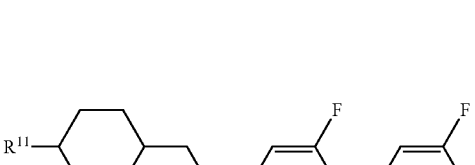

(3-58)
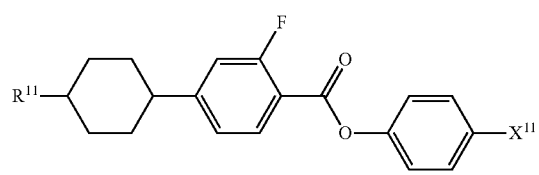
(3-59)
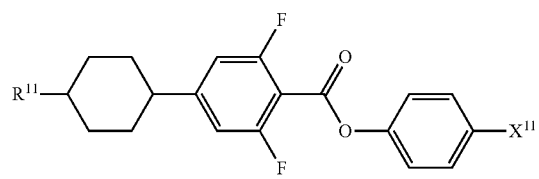
(3-60)
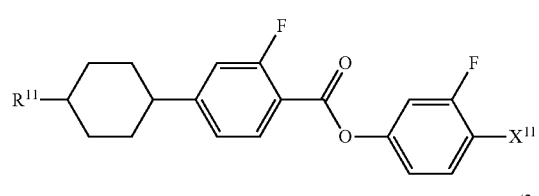
(3-61)
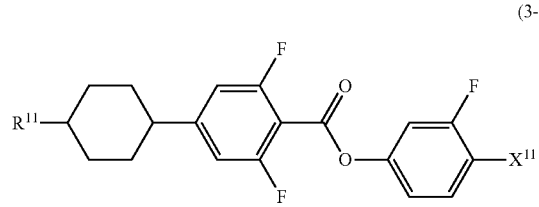
(3-62)
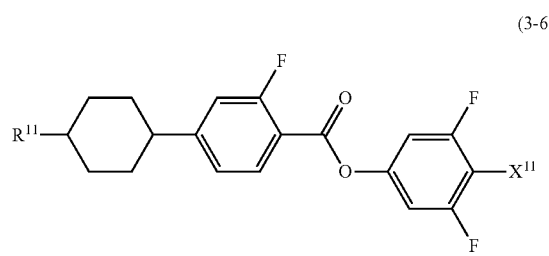
(3-63)
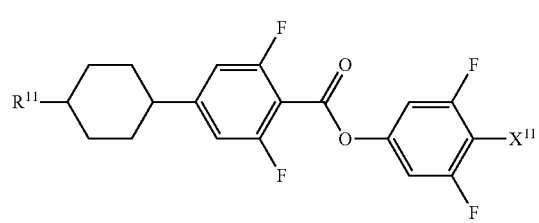
(3-64)
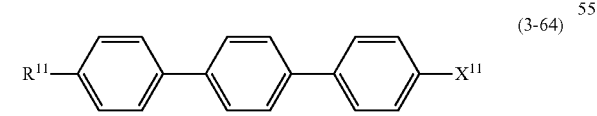
(3-65)
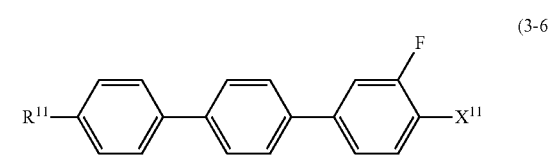
(3-66)
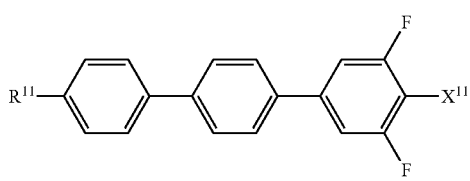
(3-67)
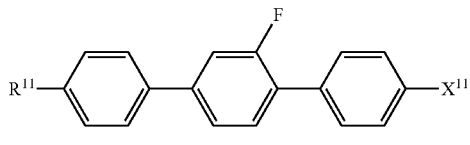
(3-68)
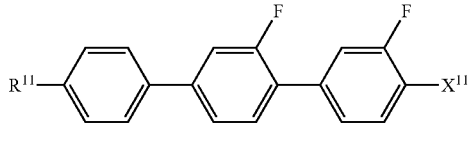
(3-69)
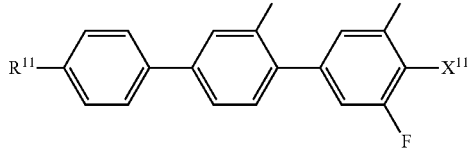
(3-70)
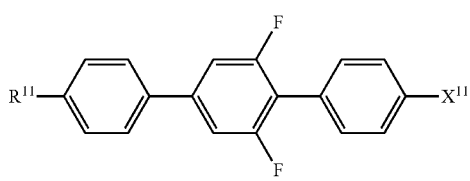
(3-71)
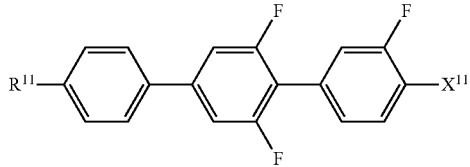
(3-72)
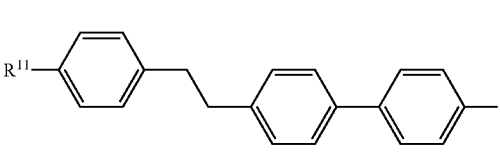
(3-73)
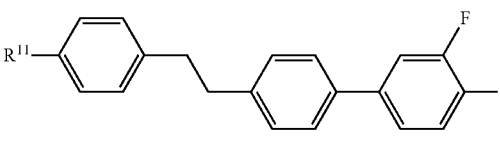
(3-74)
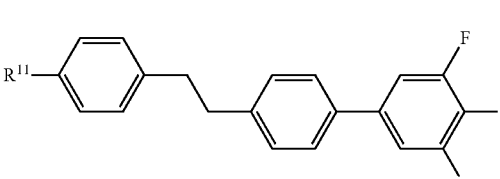

(3-75)
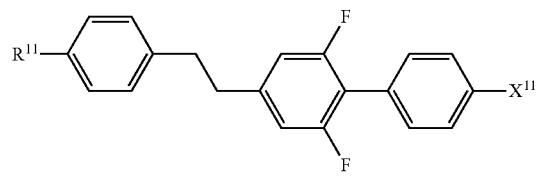
(3-76)
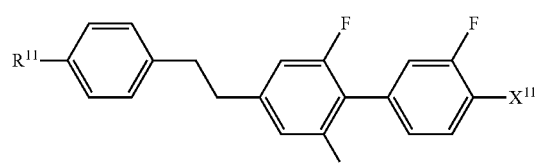
(3-77)
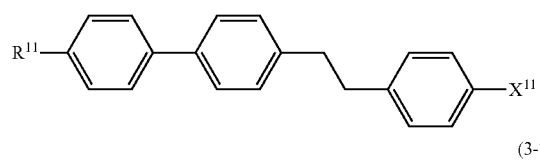
(3-78)
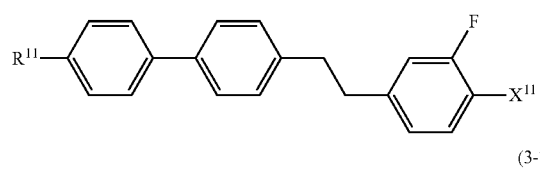
(3-79)
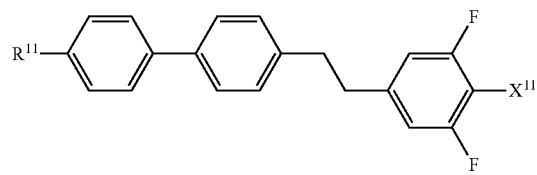
(3-80)
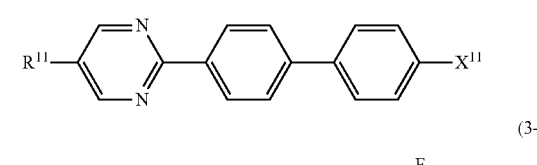
(3-81)
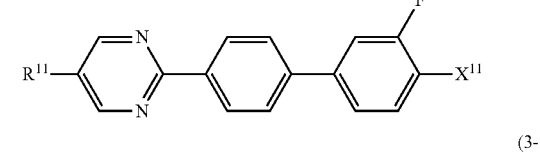
(3-82)
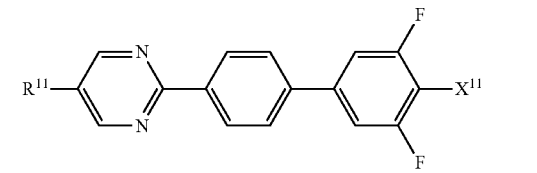
(3-83)
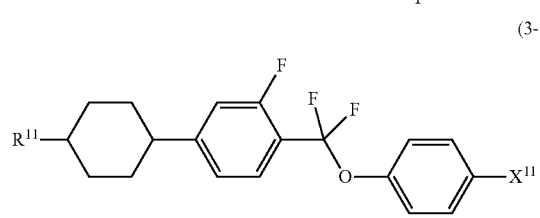
(3-84)
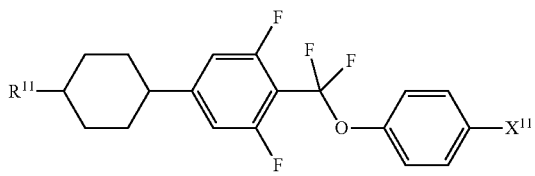
(3-85)
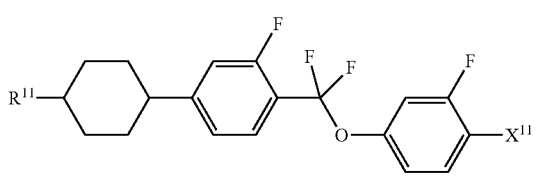
(3-86)
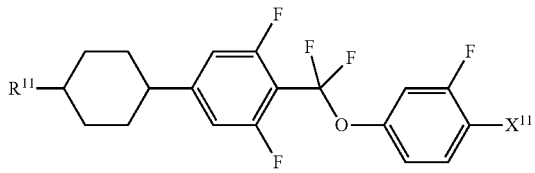
(3-87)
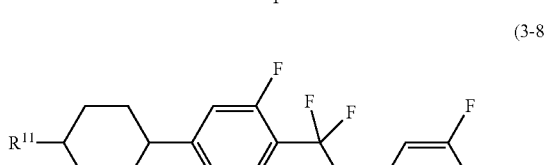
(3-88)
(3-89)
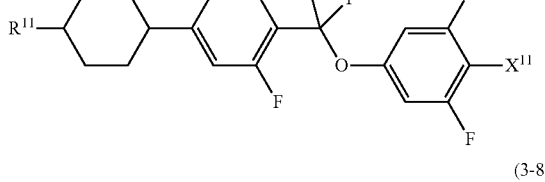
(3-90)
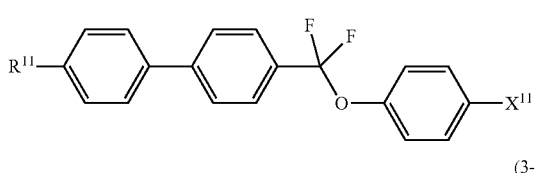
(3-91)
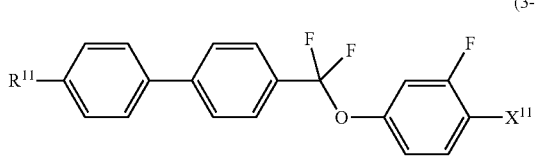

(3-92) 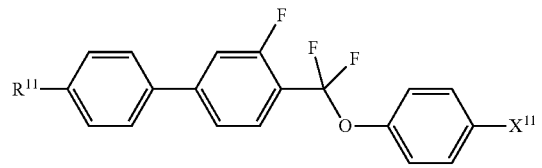
(3-93) 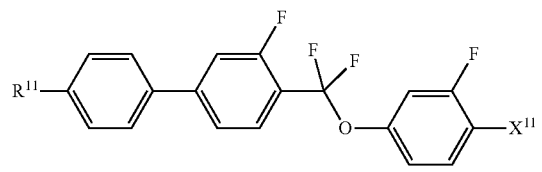
(3-94) 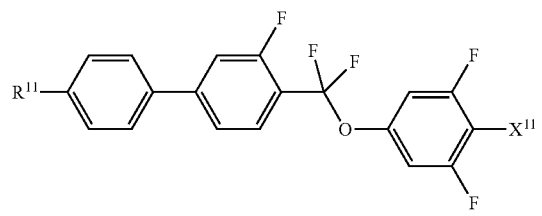
(3-95) 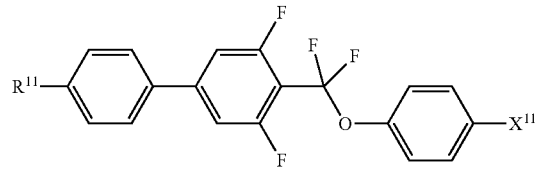
(3-96) 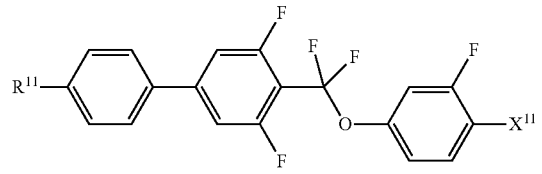
(3-97) 
(3-98) 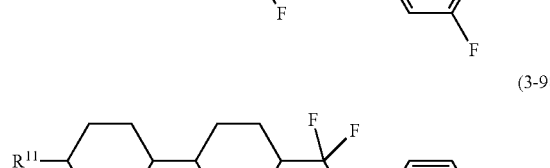
(3-99) 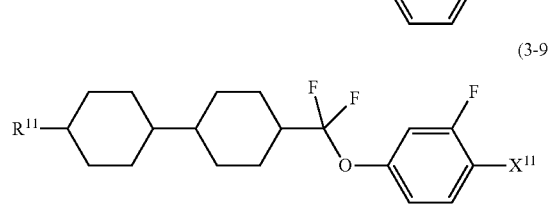
(3-100) 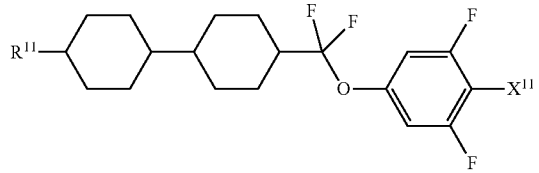
(3-101) 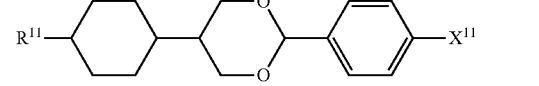
(3-102) 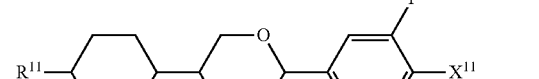
(3-103) 
(3-104) 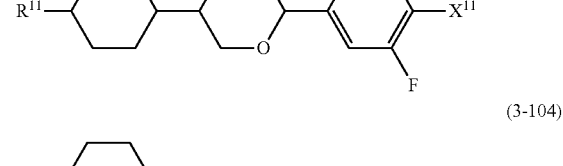
(3-105) 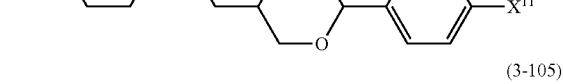
(3-106) 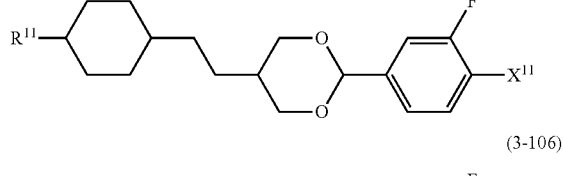
(3-107) 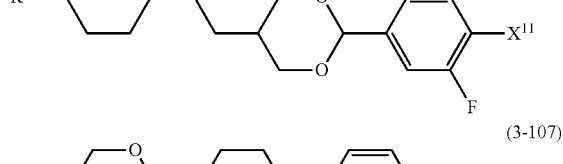
(3-108) 
(3-109) 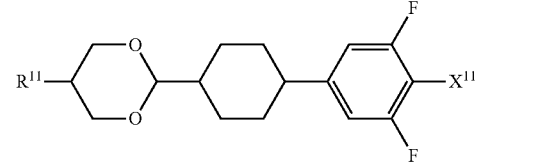

(3-110)
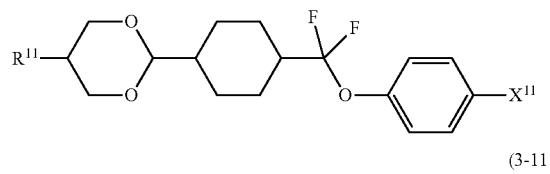
(3-111)
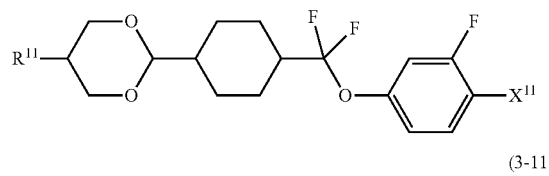
(3-112)
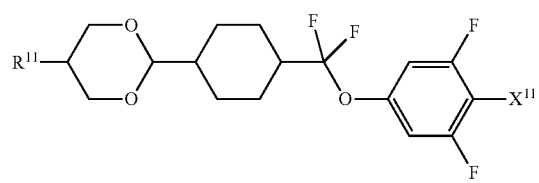
(3-113)
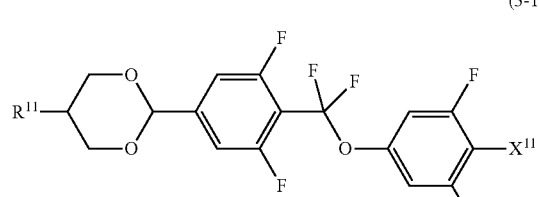
(4-1)
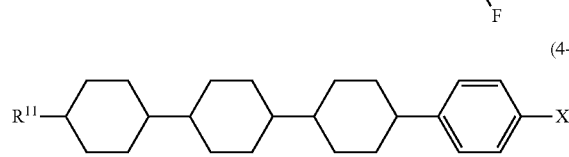
(4-2)
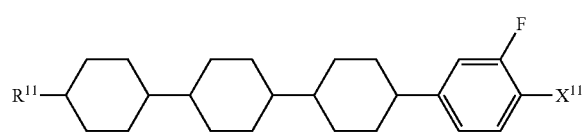
(4-3)
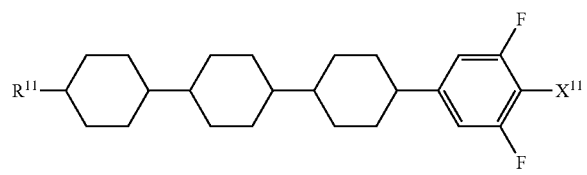
(4-4)
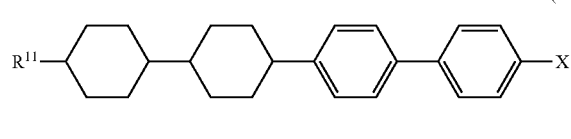
(4-5)
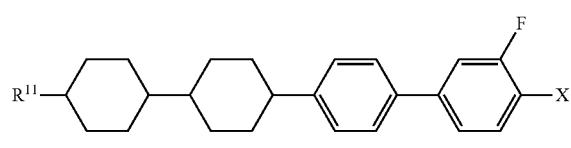
(4-6)
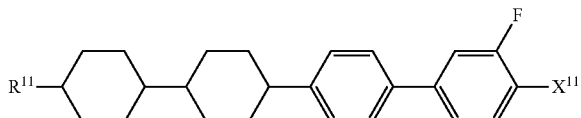
(4-7)
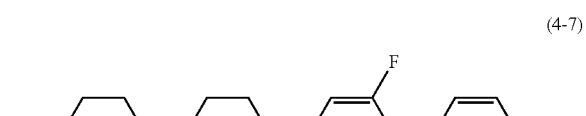
(4-8)
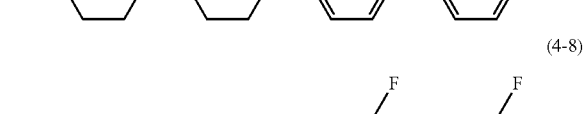
(4-9)
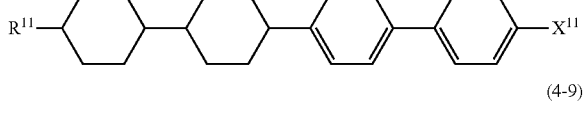
(4-10)
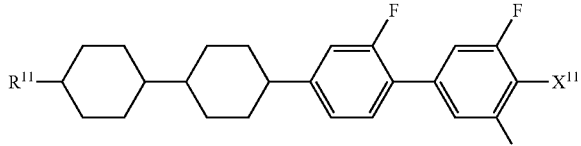
(4-11)
(4-12)
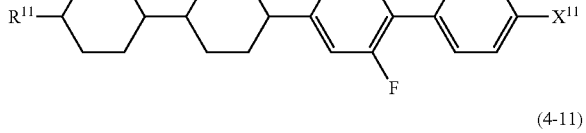
(4-13)
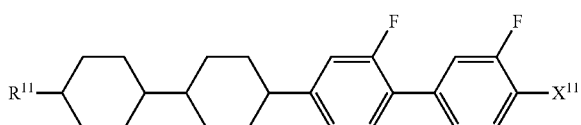
(4-14)

(4-15) 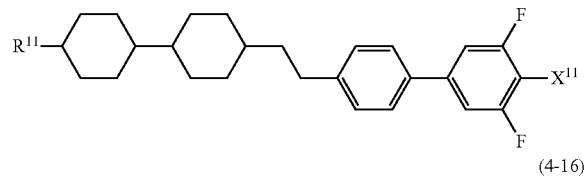
(4-16) 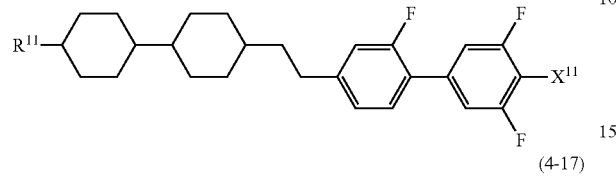
(4-17) 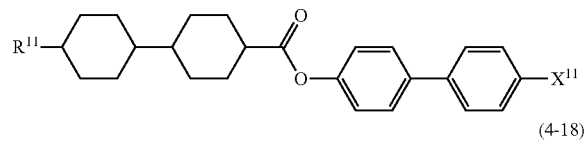
(4-18) 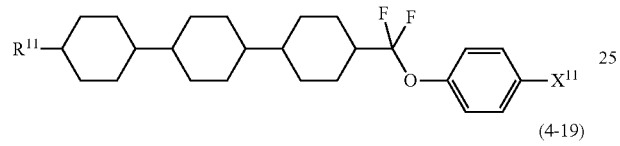
(4-19) 
(4-20) 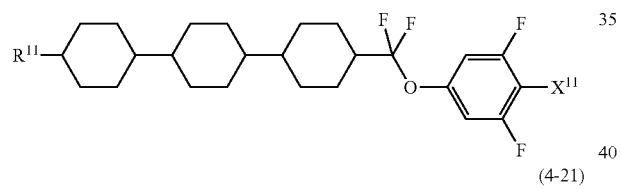
(4-21) 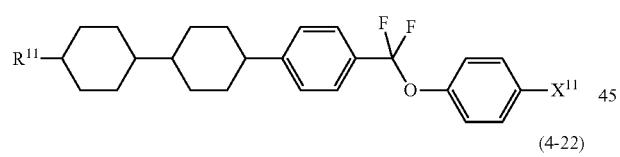
(4-22) 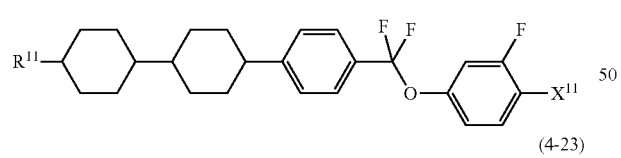
(4-23) 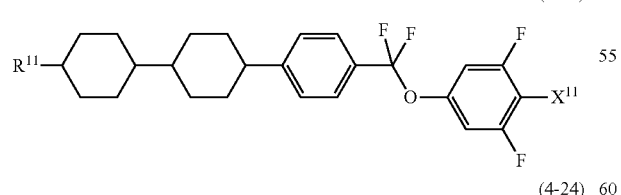
(4-24) 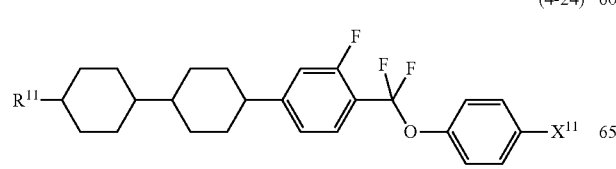
(4-25) 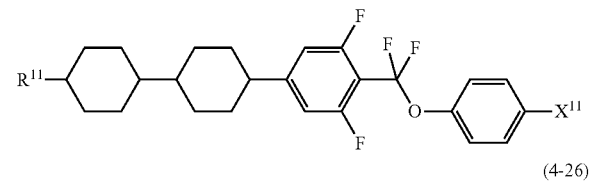
(4-26) 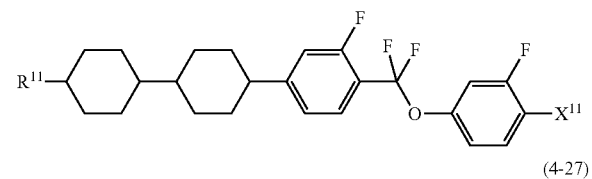
(4-27) 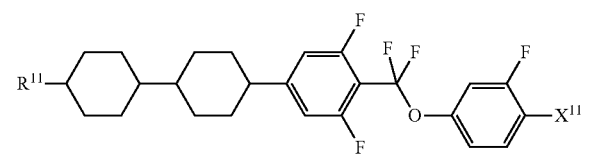
(4-28) 
(4-29) 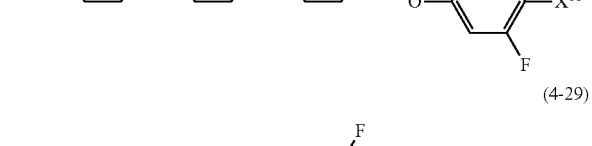
(4-30) 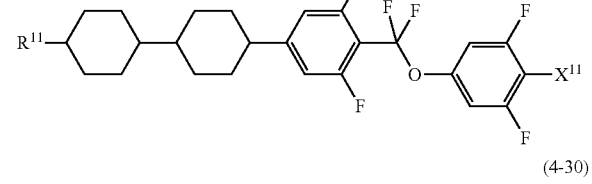
(4-31) 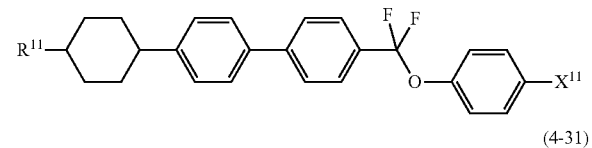
(4-32) 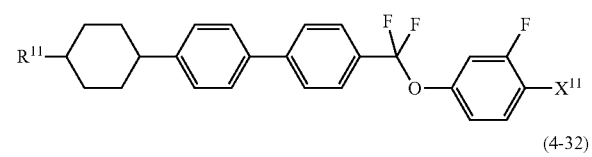
(4-33) 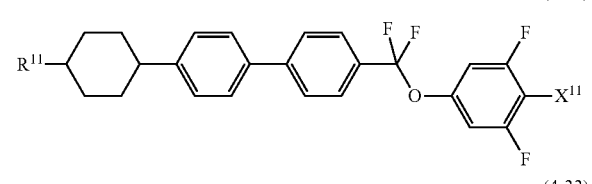
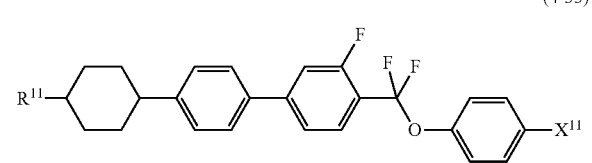

(4-34)
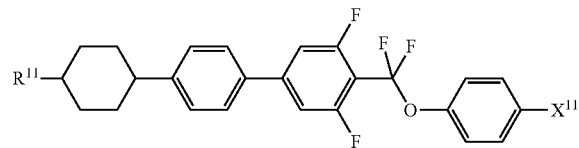
(4-35)
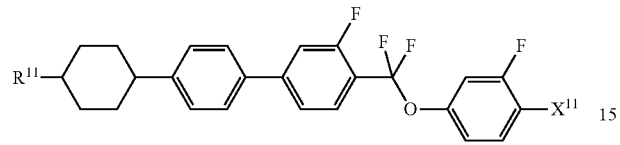
(4-36)
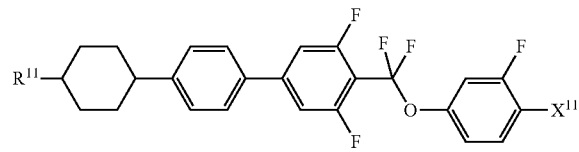
(4-37)
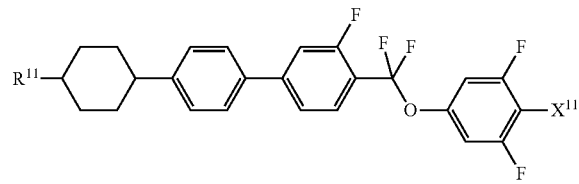
(4-38)
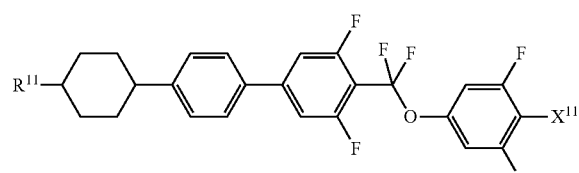
(4-39)
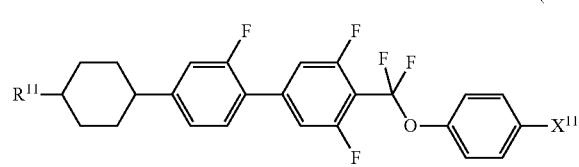
(4-40)
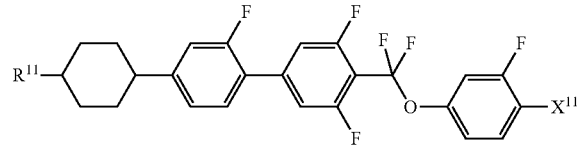
(4-41)
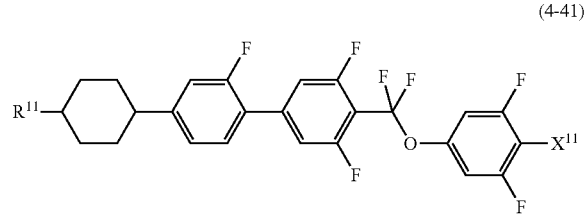
(4-42)
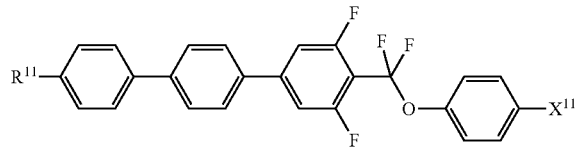
(4-43)
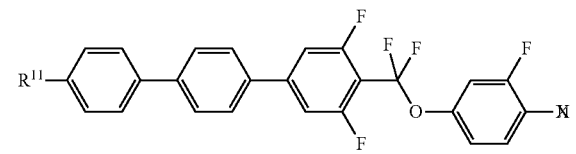
(4-44)
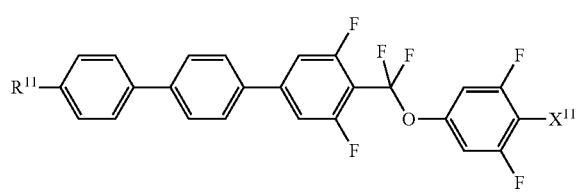
(4-45)
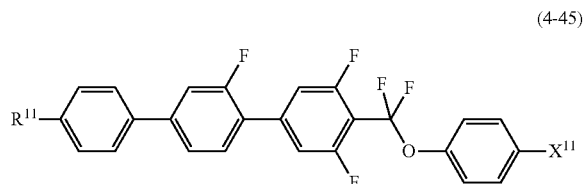
(4-46)
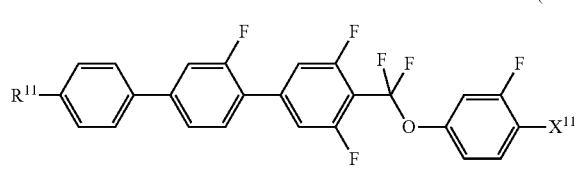
(4-47)
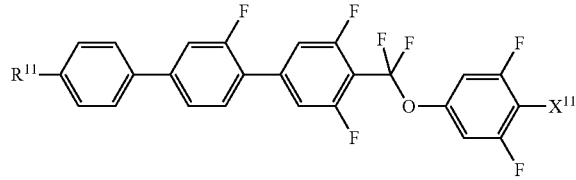
(4-48)
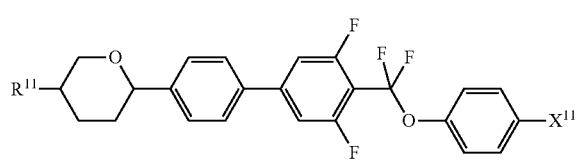
(4-49)
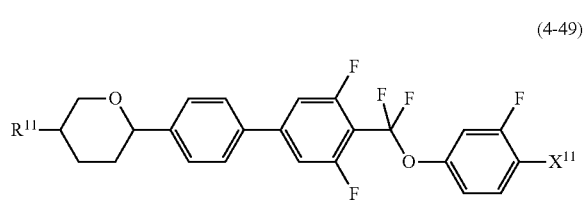

-continued

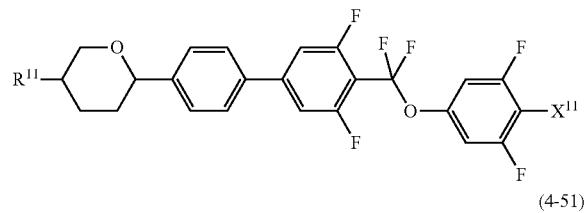
(4-50)

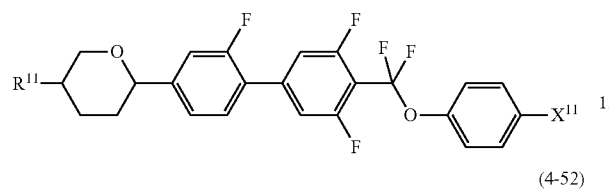
(4-51)

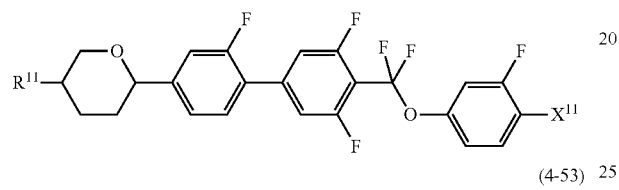
(4-52)

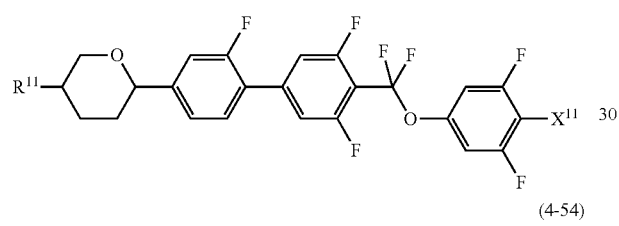
(4-53)

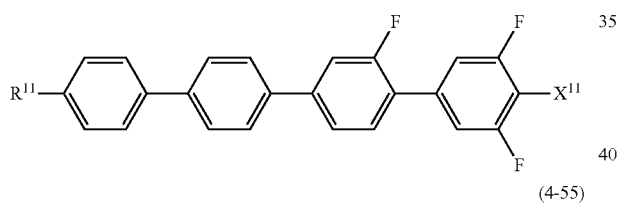
(4-54)

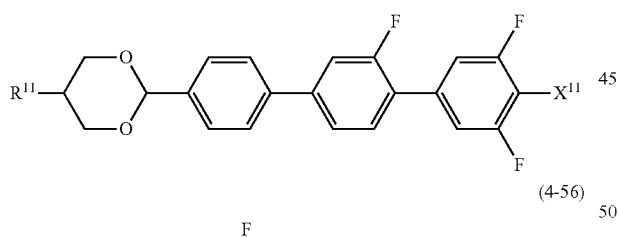
(4-55)

(4-56)

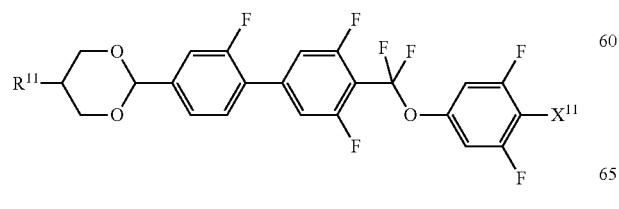
(4-57)

Component B has a positive dielectric anisotropy, and a superb stability to heat, light and so forth, and therefore is used for preparing a composition for the mode such as the TFT mode, the IPS mode and the FFS mode. A content of component B is suitably in the range of 1% by weight to 99% by weight, preferably in the range of 10% by weight to 97% by weight, and further preferably in the range of 40% by weight to 95% by weight, based on the weight of the composition. Further addition of compounds (13) to (15) (component E) allows adjustment of viscosity of the composition.

Component C is compound (5) in which a right-terminal group is —C≡N or —C≡C—C≡N. Specific preferred examples of component C include compounds (5-1) to (5-64). In the compounds (component C), definitions of $R^{12}$ and $X^{12}$ are identical to definitions described in item 9.

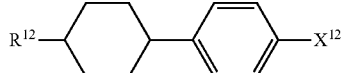
(5-1)

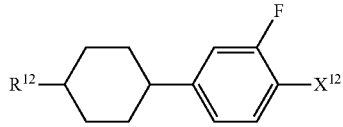
(5-2)

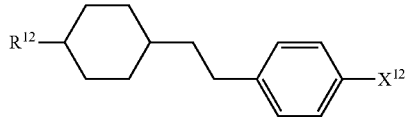
(5-3)

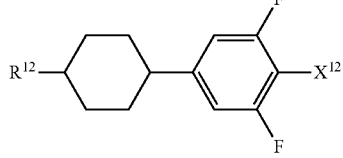
(5-4)

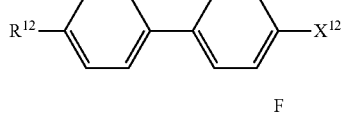
(5-5)

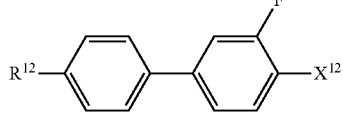
(5-6)

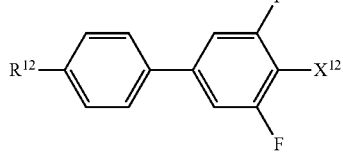
(5-7)

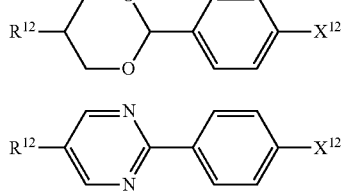
(5-8)

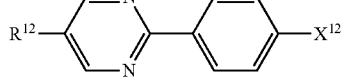
(5-9)

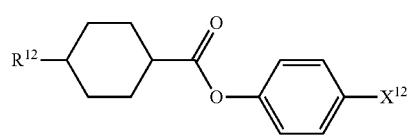 (5-10)
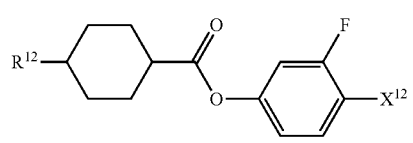 (5-11)
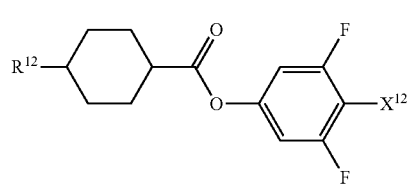 (5-12)
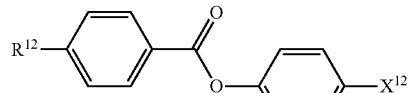 (5-13)
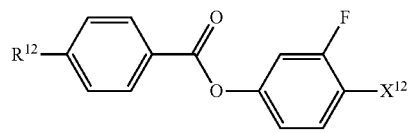 (5-14)
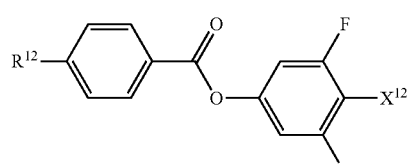 (5-15)
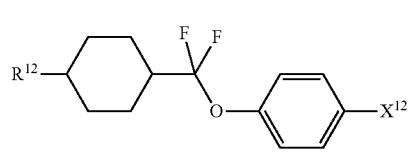 (5-16)
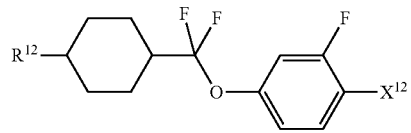 (5-17)
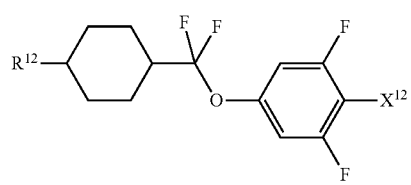 (5-18)
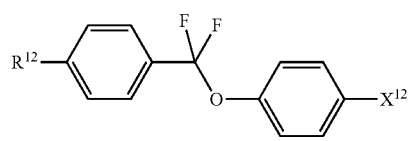 (5-19)
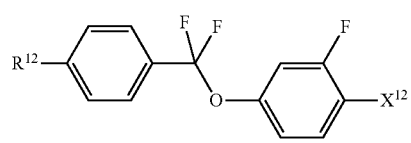 (5-20)
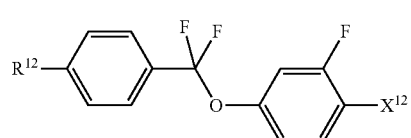 (5-21)
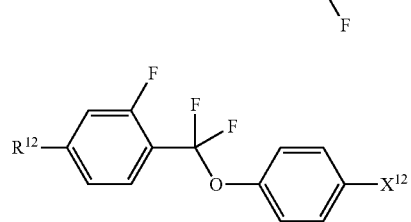 (5-22)
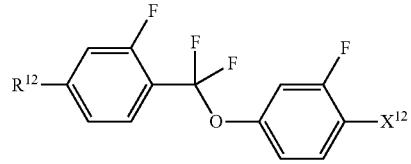 (5-23)
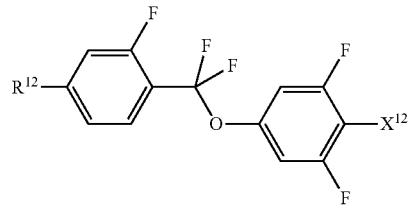 (5-24)
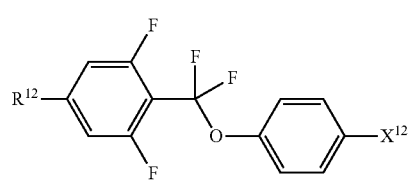 (5-25)
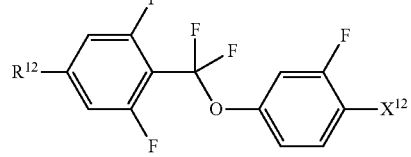 (5-26)
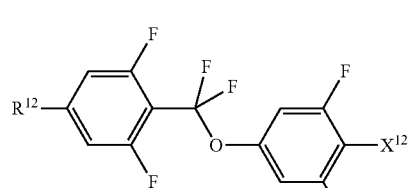 (5-27)
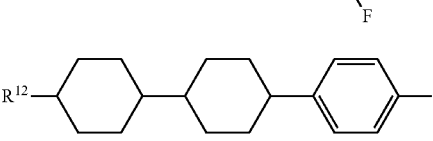 (5-28)

(5-29)
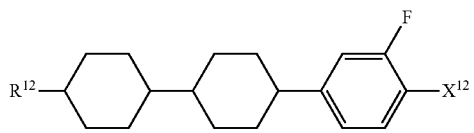
(5-30)
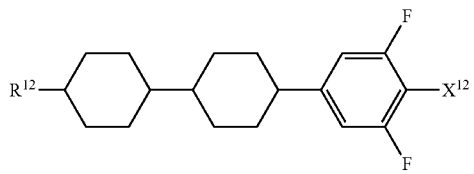
(5-31)
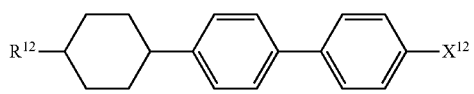
(5-32)
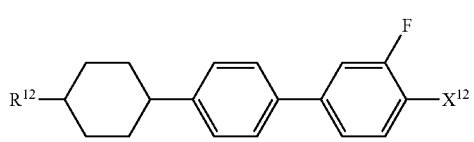
(5-33)
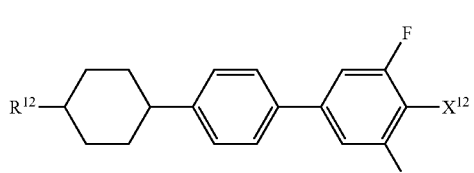
(5-34)
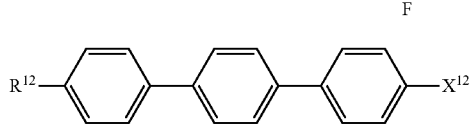
(5-35)
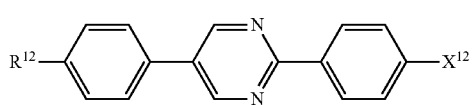
(5-36)
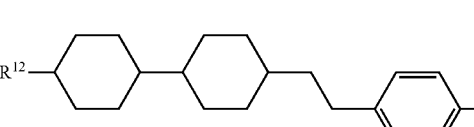
(5-37)
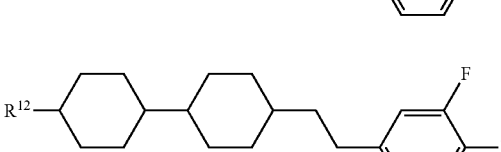
(5-38)
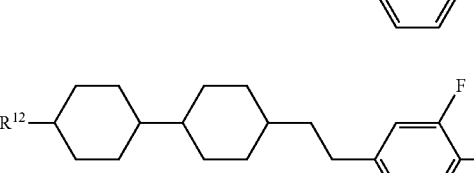
(5-39)
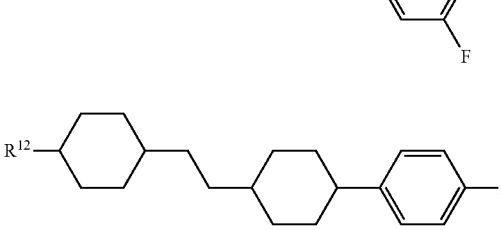
(5-40)
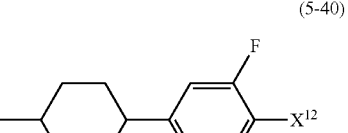
(5-41)
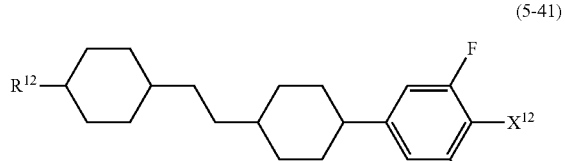
(5-42)
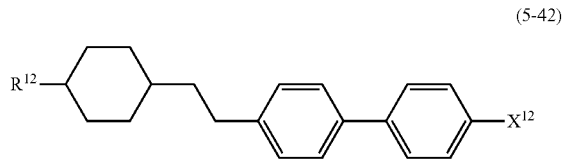
(5-43)
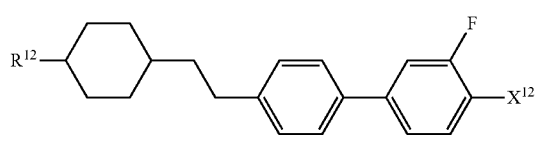
(5-44)
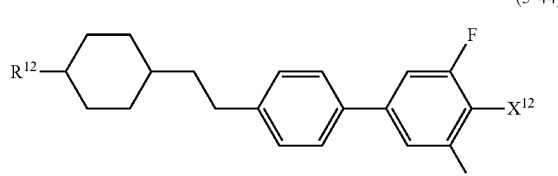
(5-45)
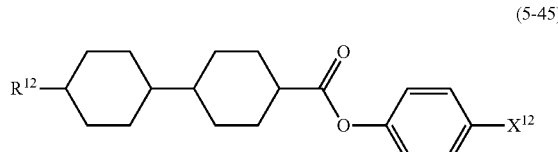
(5-46)
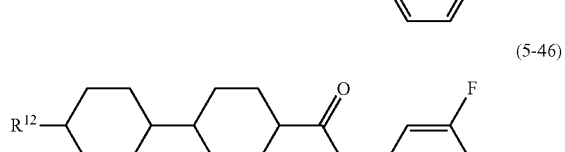
(5-47)
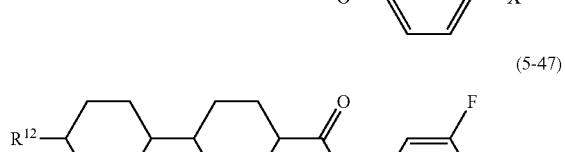
(5-48)
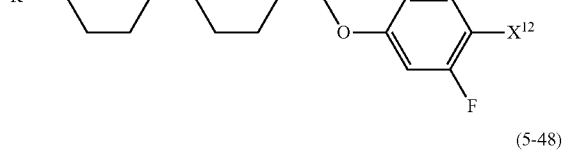

(5-49) 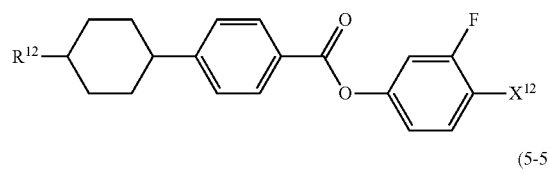

(5-50) 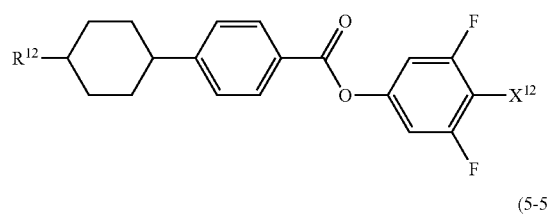

(5-51) 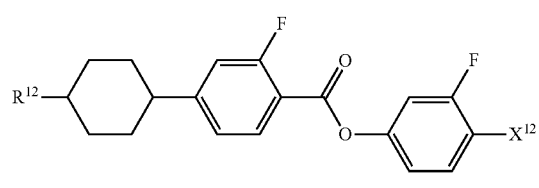

(5-52) 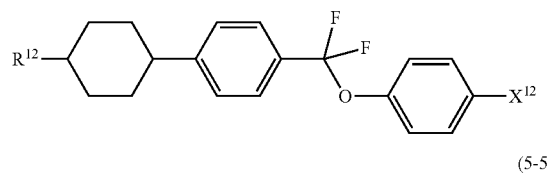

(5-53) 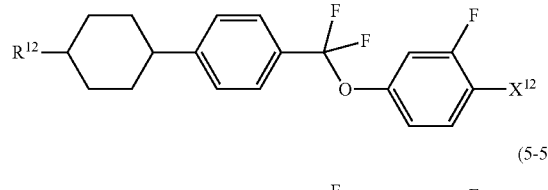

(5-54) 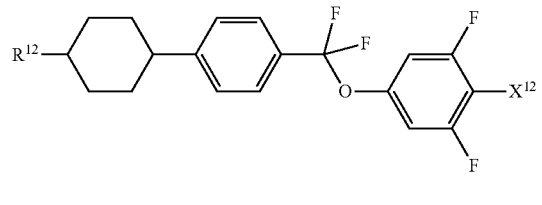

(5-55) 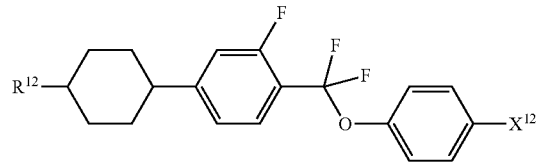

(5-56) 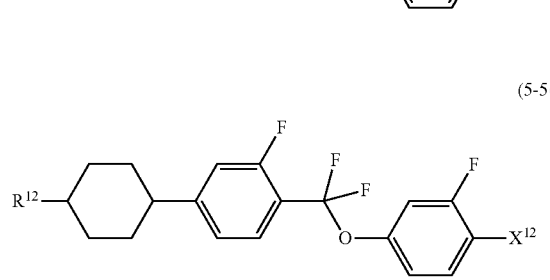

(5-57) 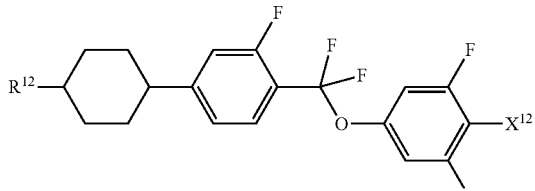

(5-58) 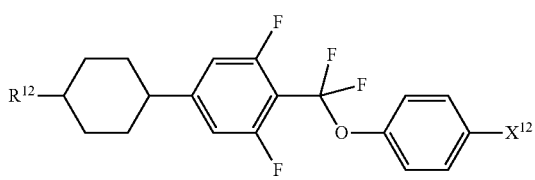

(5-59) 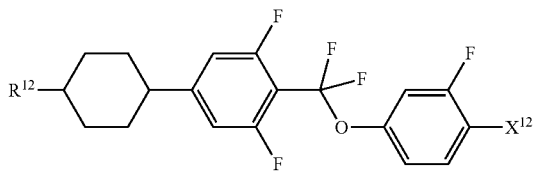

(5-60) 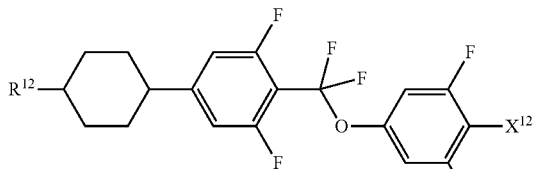

(5-61) 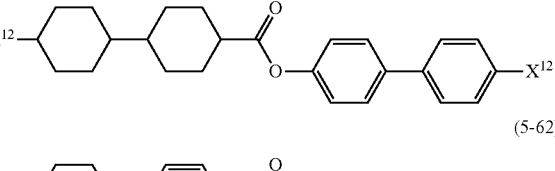

(5-62) 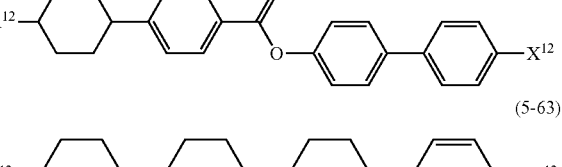

(5-63) 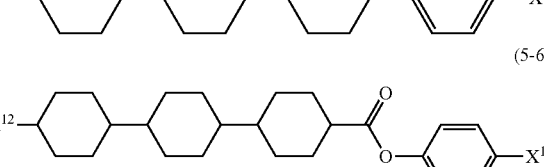

(5-64) 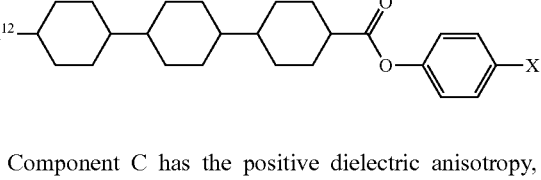

Component C has the positive dielectric anisotropy, a value of which is large, and therefore is mainly used for preparing a composition for a mode such as the STN mode, the TN mode and the PSA mode. Dielectric anisotropy of the composition can be increased by adding component C. Component C is effective in extending the temperature range of the liquid crystal phase, adjusting the viscosity or adjusting the optical anisotropy. Component C is also useful for adjustment of the voltage-transmittance curve of the device.

When a composition for a mode such as the STN mode and the TN mode is prepared, a content of component C is suitably in the range of 1% by weight to 99% by weight, preferably in the range of 10% by weight to 97% by weight, and further preferably in the range of 40% by weight to 95% by weight, based on the weight of the composition. In the composition, the temperature range of the liquid crystal phase, the viscosity, the optical anisotropy, the dielectric anisotropy or the like can be adjusted by adding component E.

Component D includes compounds (6) to (12). The compounds have a benzene ring in which hydrogen in lateral positions are replaced by two pieces of halogen, such as 2,3-difluoro-1,4-phenylene. Specific preferred examples of component D include compounds (6-1) to (6-8), compounds (7-1) to (7-17), compound (8-1), compounds (9-1) to (9-3), compounds (10-1) to (10-11), compounds (11-1) to (11-3) or compounds (12-1) to (12-3). In the compounds (components D), definitions of $R^{13}$, $R^{14}$ and $R^{15}$ are identical to definitions described in item 10.

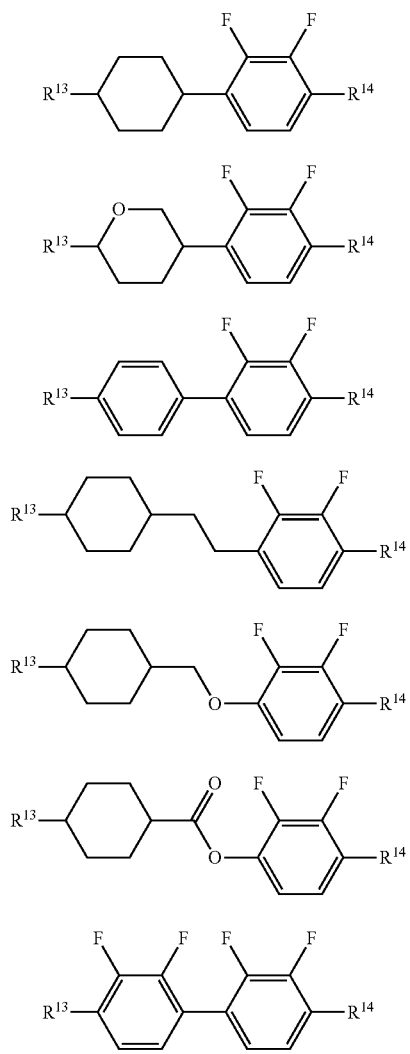

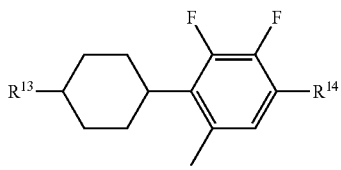
(6-8)

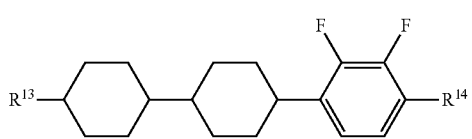
(7-1)

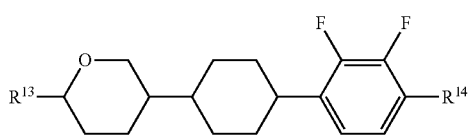
(7-2)

(7-3)

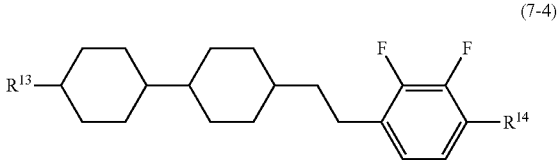
(7-4)

(7-5)

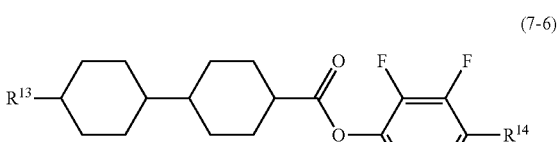
(7-6)

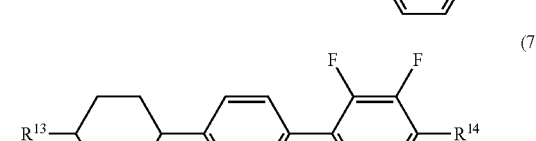
(7-7)

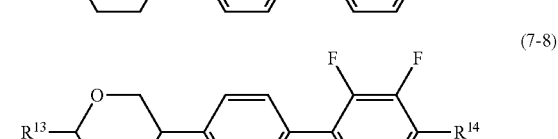
(7-8)

(7-9)

(7-10)
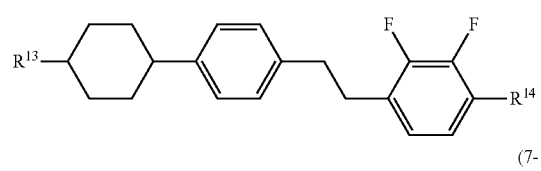
(7-11)
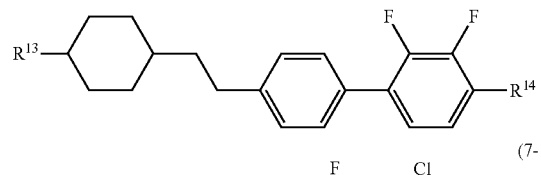
(7-12)
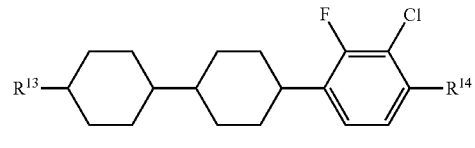
(7-13)
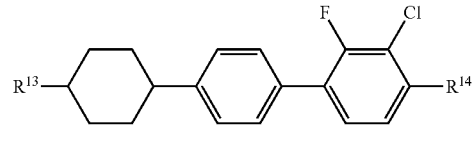
(7-14)
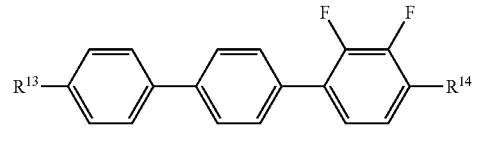
(7-15)
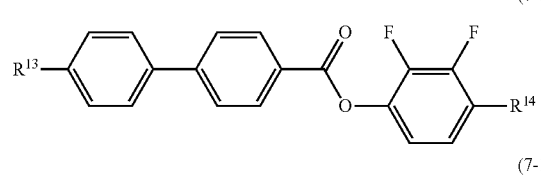
(7-16)
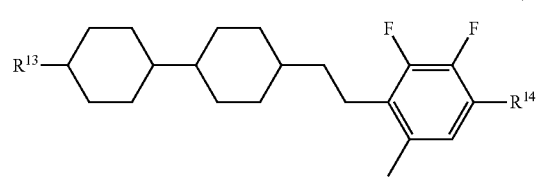
(7-17)
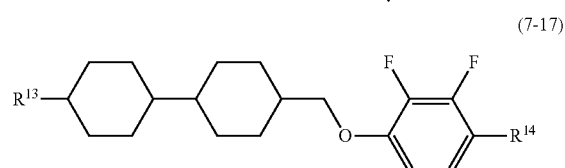
(8-1)
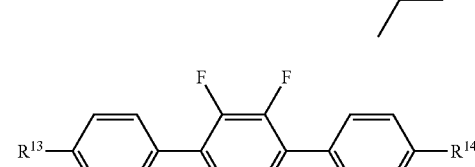
(9-1)
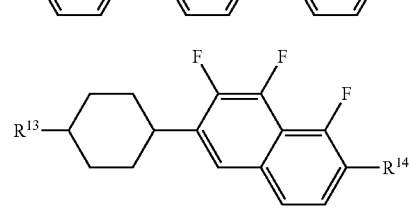
(9-2)
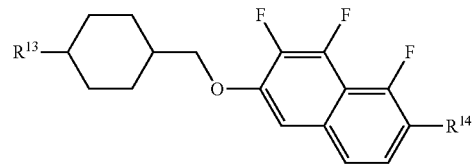
(9-3)
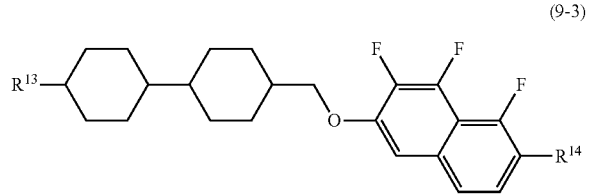
(10-1)
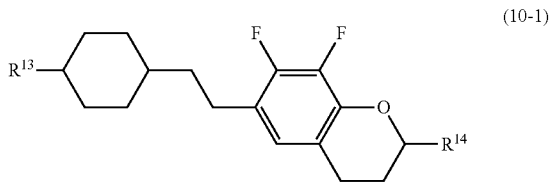
(10-2)
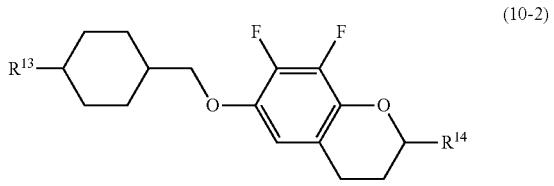
(10-3)
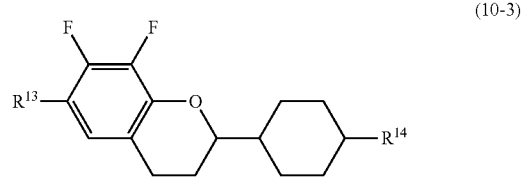
(10-4)
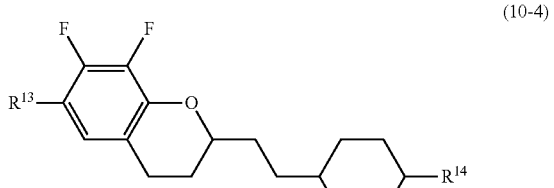
(10-5)

(10-6)
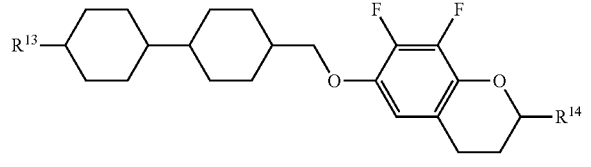

(10-7)
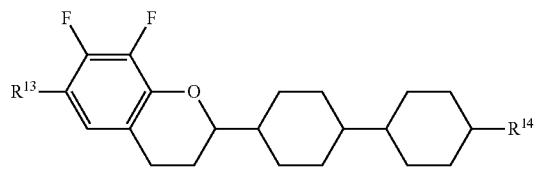

(10-8)
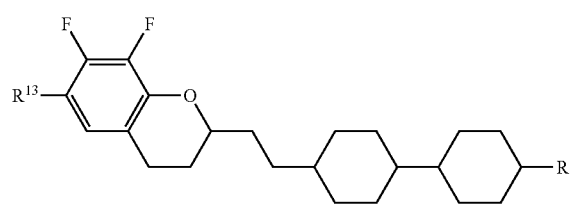

(10-9)
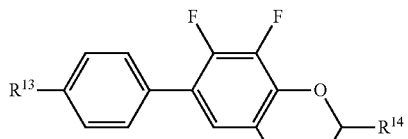

(10-10)
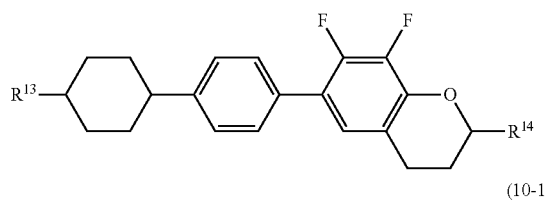

(10-11)
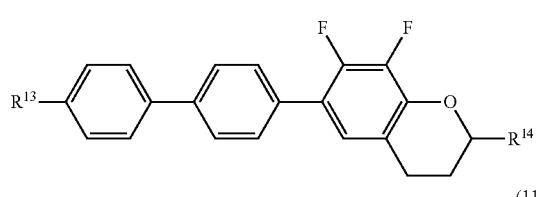

(11-1)
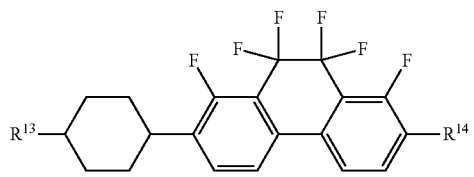

(11-2)
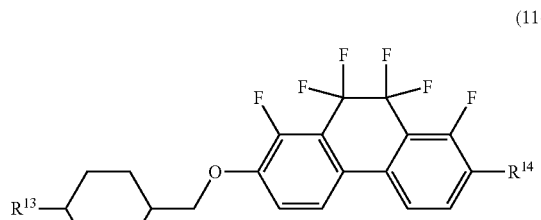

(11-3)
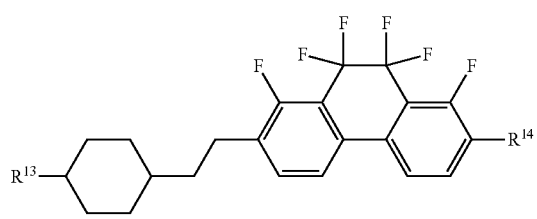

(12-1)
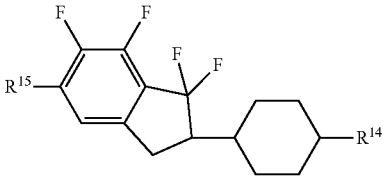

(12-2)
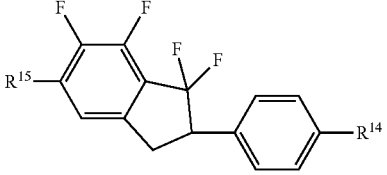

(12-3)
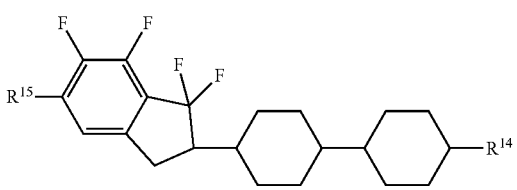

Component D is a compound having the negative dielectric anisotropy. Component D is mainly used for preparing a composition for the mode such as the VA mode and the PSA mode. Among types of component D, compound (6) is a bicyclic compound, and therefore is mainly effective in adjusting the viscosity, the optical anisotropy or the dielectric anisotropy. Compounds (7) and (8) are a tricyclic compound, and therefore are effective in increasing the maximum temperature, the optical anisotropy or the dielectric anisotropy. Compounds (9) to (12) are effective in increasing the dielectric anisotropy.

When a composition for the mode such as the VA mode and the PSA mode is prepared, a content of component D is preferably 40% by weight or more, and further preferably in the range of 50% by weight to 95% by weight, based on the weight of the composition. When component D is added to a composition having the positive dielectric anisotropy, the content of component D is preferably 30% by weight or less based on the weight of the composition. The voltage-transmittance curve of the device can be adjusted by adding component D.

Component E includes a compound in which two terminal groups are alkyl or the like. Specific preferred examples of component E include compounds (13-1) to (13-11), compounds (14-1) to (14-19) or compounds (15-1) (15-7). In the compounds (component E), definitions of $R^{16}$ and $R^{17}$ are identical to definitions described in item 11.

(13-1)
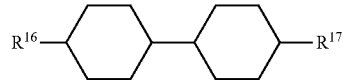

(13-2)
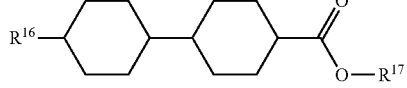

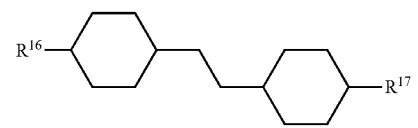 (13-3)
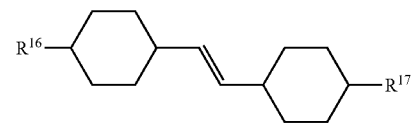 (13-4)
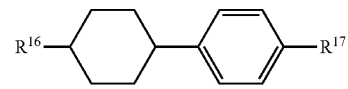 (13-5)
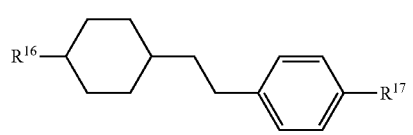 (13-6)
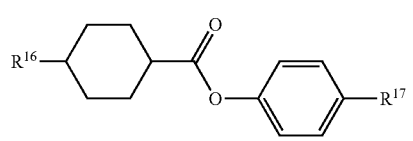 (13-7)
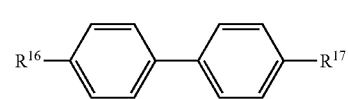 (13-8)
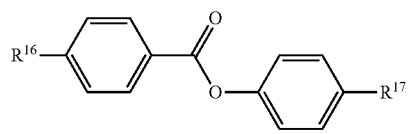 (13-9)
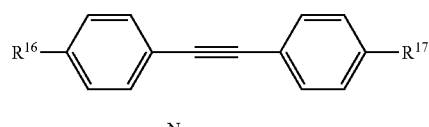 (13-10)
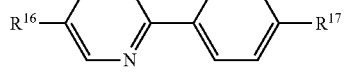 (13-11)
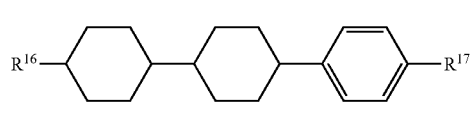 (14-1)
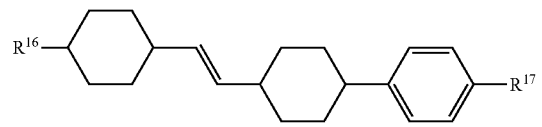 (14-2)
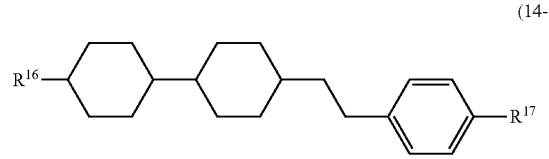 (14-3)
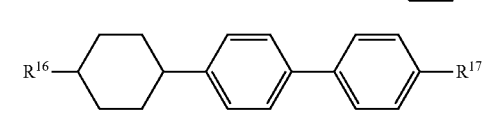 (14-4)
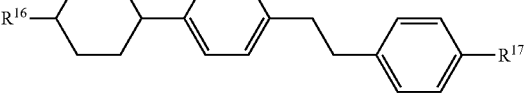 (14-5)
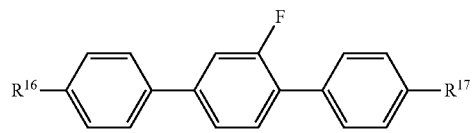 (14-6)
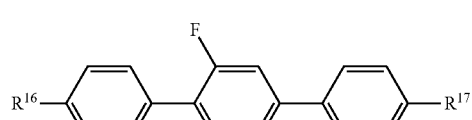 (14-7)
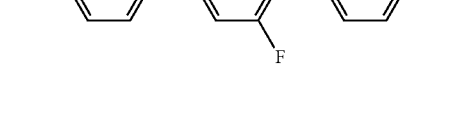 (14-8)
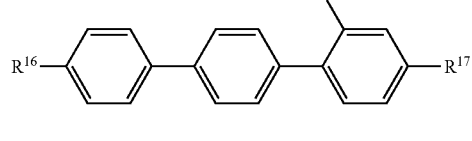 (14-9)
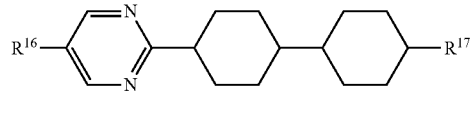 (14-10)
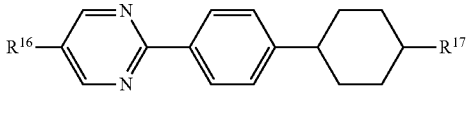 (14-11)
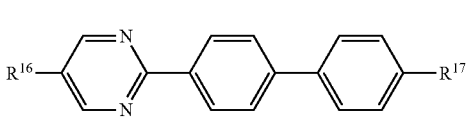 (14-12)
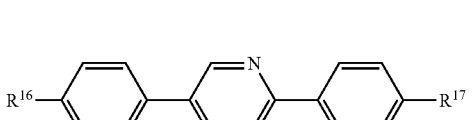 (14-13)
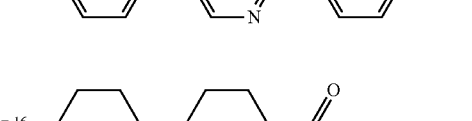 (14-14)

-continued

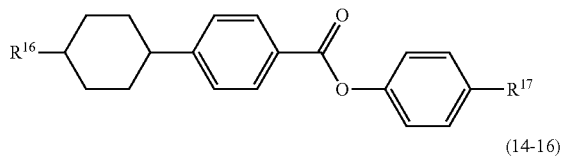
(14-15)

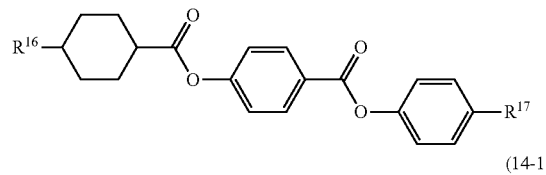
(14-16)

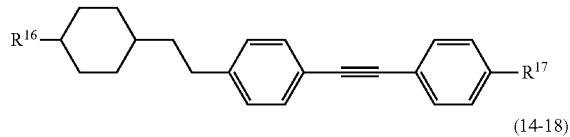
(14-17)

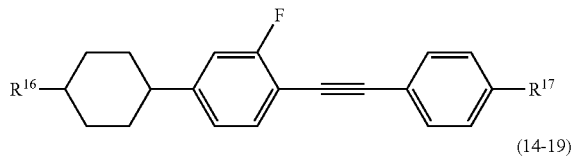
(14-18)

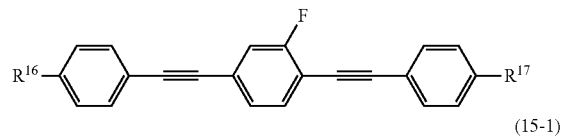
(14-19)

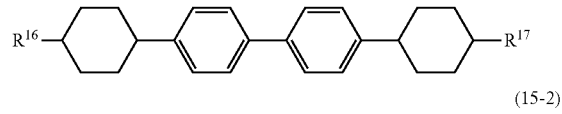
(15-1)

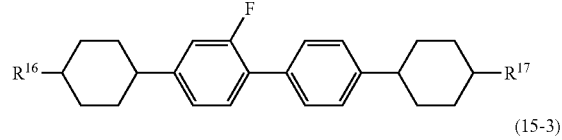
(15-2)

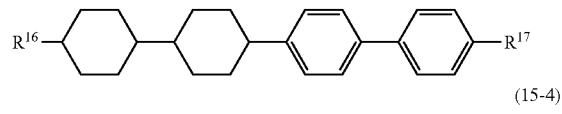
(15-3)

(15-4)

-continued

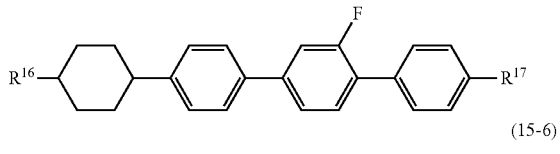
(15-5)

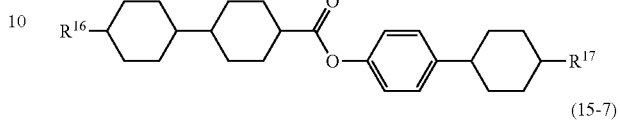
(15-6)

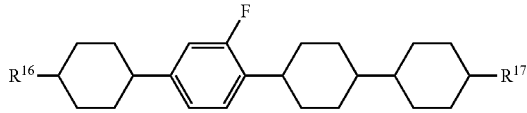
(15-7)

Component E has a small absolute value of dielectric anisotropy, and therefore is a compound close to neutrality. Compound (13) is mainly effective in adjusting the viscosity or adjusting the optical anisotropy. Compounds (14) and (15) are effective in extending the temperature range of the nematic phase by increasing the maximum temperature or effective in adjusting the optical anisotropy.

If a content of component E is increased, the dielectric anisotropy of the composition is decreased, but the viscosity is decreased. Thus, as long as a desired value of threshold voltage of the device is met, the content is preferably as large as possible. Accordingly, when the composition is prepared, the content of component E is preferably 30% by weight or more, and further preferably 40% by weight or more, based on the weight of the composition.

2-1. Additive

Preparation of a composition is performed by a method for dissolving required components at a high temperature, or the like. According to an application, an additive may be added to the composition. Specific examples of the additives include the optically active compound, the polymerizable compound, the polymerization initiator, the antioxidant, the ultraviolet light absorber, the light stabilizer, the heat stabilizer, the antifoaming agent and the dye. Such additives are well known to those skilled in the art, and described in literature.

The composition may further contain at least one optically active compound. The optically active compound is effective in inducing helical structure in liquid crystal molecules to give a required twist angle, and thereby preventing a reverse twist. Specific preferred examples of the optically active compounds include compounds (Op-1) to (Op-18) described below.

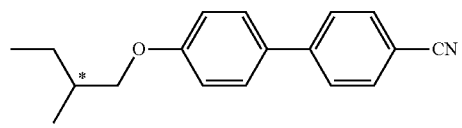
(Op-1)

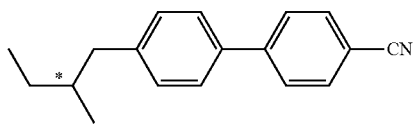
(Op-2)

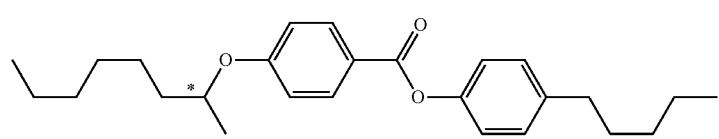
(Op-3)

(Op-4)
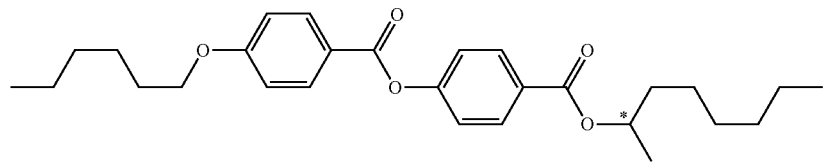
(Op-5)
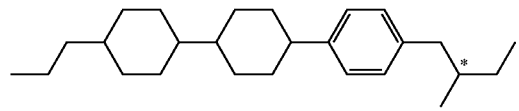
(Op-6)
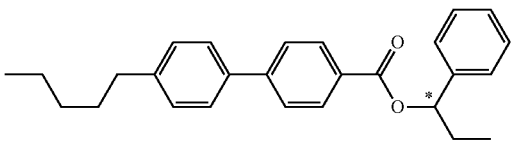
(Op-7)
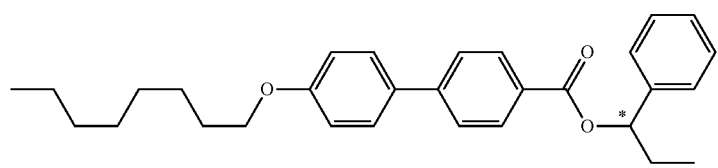
(Op-8)
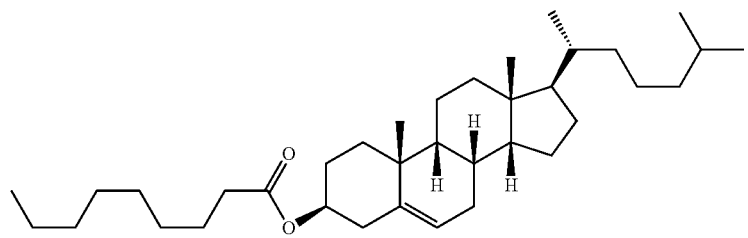
(Op-9)
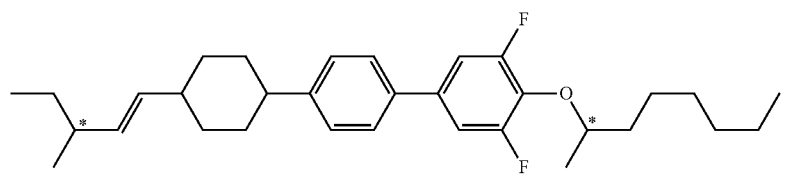
(Op-10)
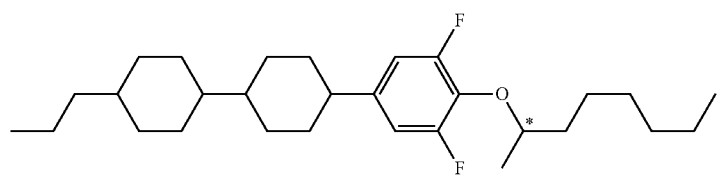
(Op-11)
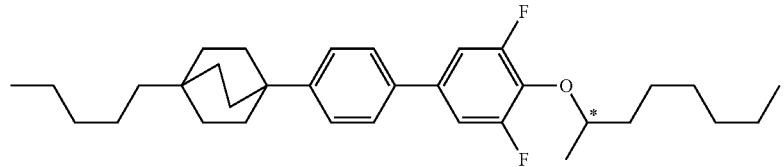
(Op-12)
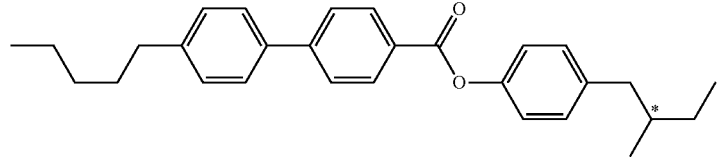

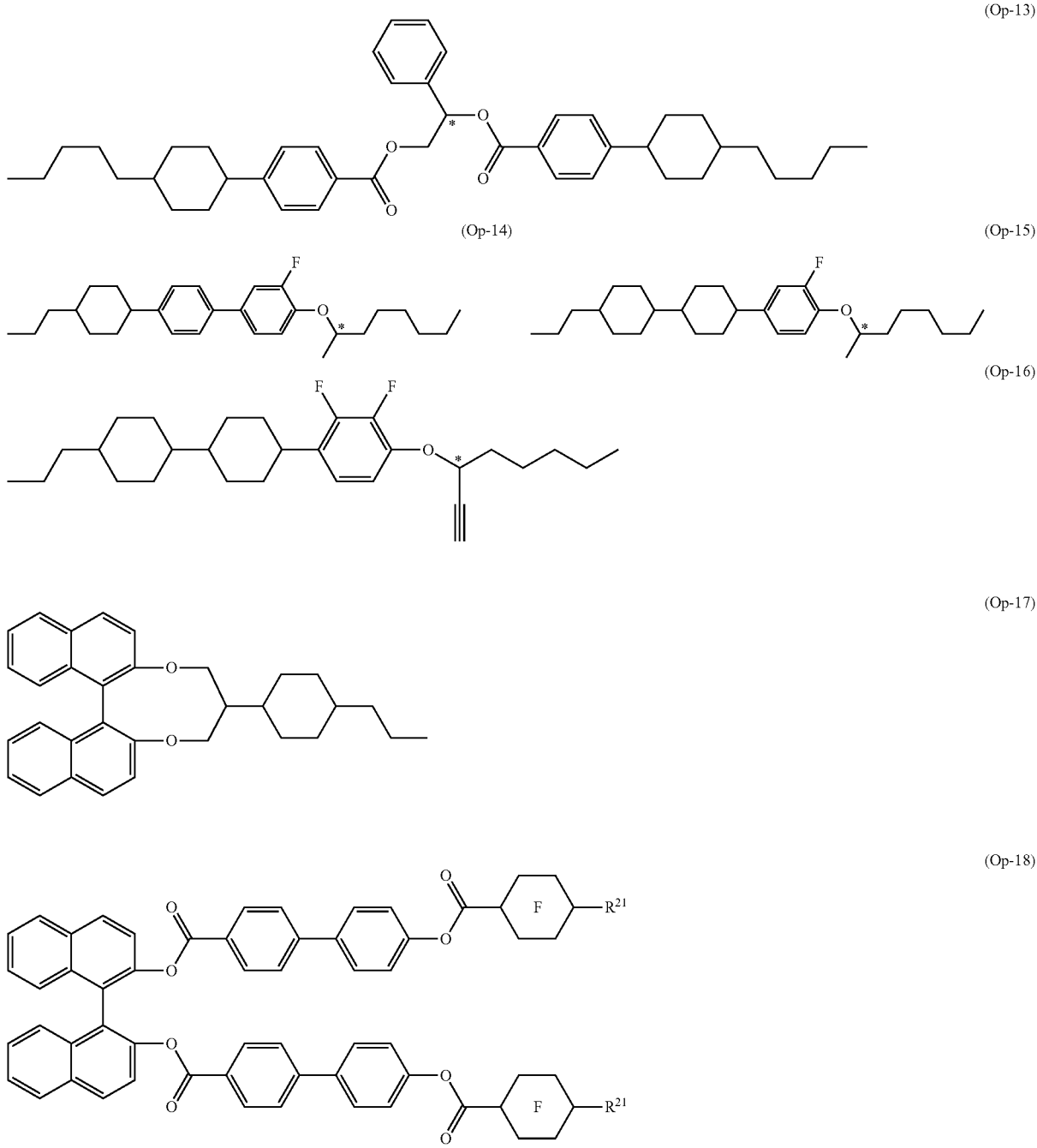

wherein, in compound (Op-18), ring F is 1,4-cyclohexylene or 1,4-phenylene, and $R^{21}$ is alkyl having 1 to 10 carbons.

In the composition, a helical pitch is adjusted by adding such an optically active compound. The helical pitch is preferably adjusted in the range of 40 micrometers to 200 micrometers in a composition for the TFT mode and the TN mode. In a composition for the STN mode, the helical pitch is preferably adjusted in the range of 6 micrometers to 20 micrometers. In the case of a composition for the BTN mode, the helical pitch is preferably adjusted in the range of 1.5 micrometers to 4 micrometers. Two or more optically active compounds may be added for the purpose of adjusting temperature dependence of the helical pitch.

The composition can also be used for the PSA mode by adding a polymerizable compound. Specific examples of the polymerizable compounds include acrylate, methacrylate, a vinyl compound, a vinyloxy compound, propenyl ether, an epoxy compound (oxirane, oxetane) and vinyl ketone. The polymerizable compound is polymerized by irradiation with ultraviolet light or the like. An initiator such as a photopolymerization initiator may be added. Suitable conditions for polymerization, suitable types of the initiator and suitable amounts thereof are known to those skilled in the art and are described in literature. Specific preferred examples of the polymerizable compounds include compounds (M-1) to (M-12).

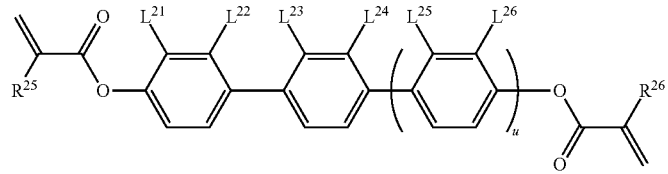
(M-1)
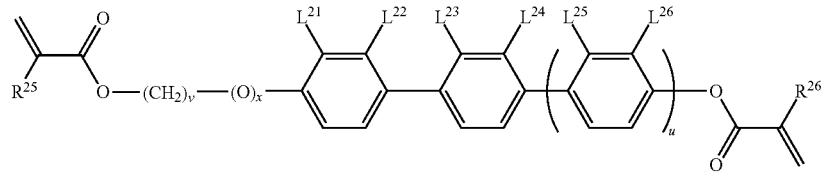
(M-2)
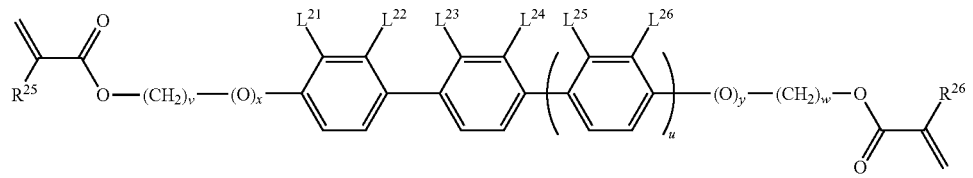
(M-3)
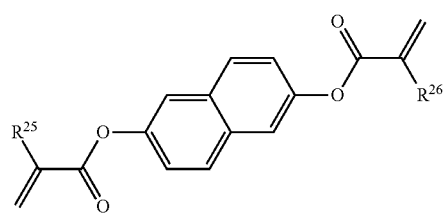
(M-4)
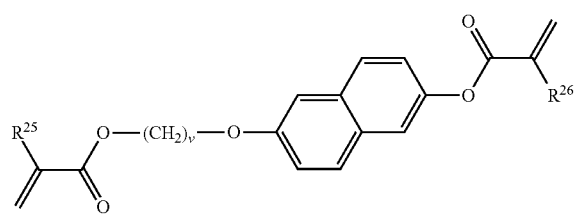
(M-5)
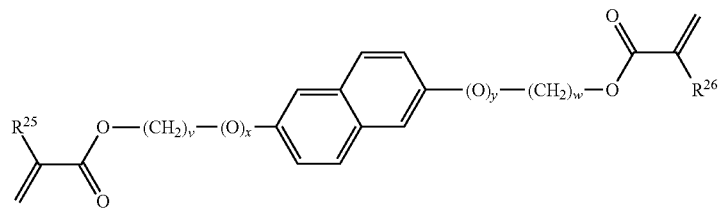
(M-6)
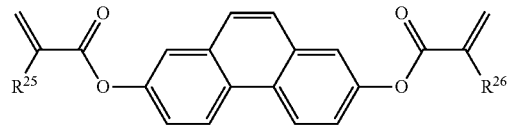
(M-7)
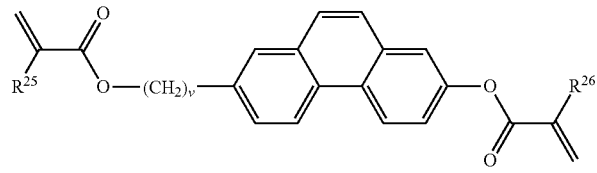
(M-8)
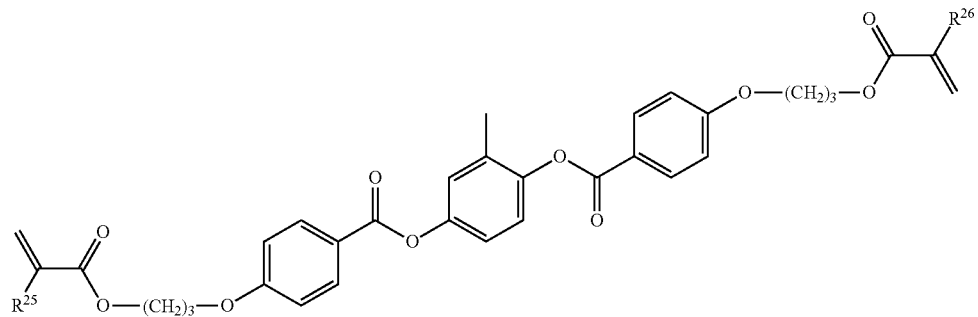
(M-9)

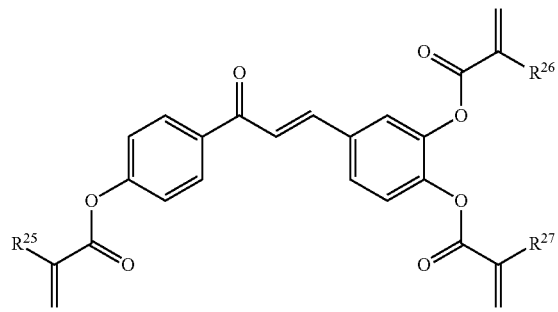

(M-10)

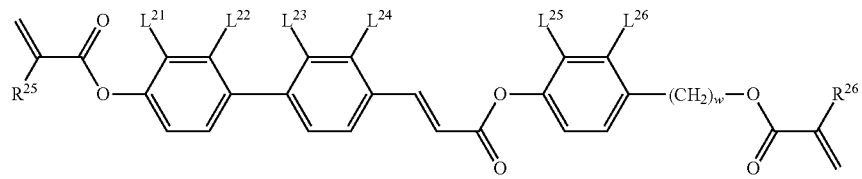

(M-11)

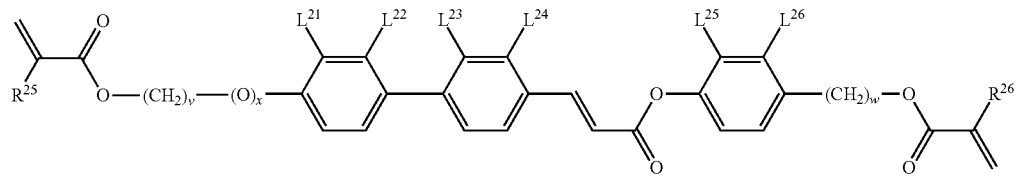

(M-12)

In compounds (M-1) to (M-12), $R^{25}$, $R^{26}$ and $R^{27}$ are independently hydrogen or methyl; u, x and y are independently 0 or 1; v and w are independently an integer from 1 to 10; and $L^{21}$, $L^{22}$, $L^{23}$, $L^{24}$, $L^{25}$ and $L^{26}$ are independently hydrogen or fluorine.

The antioxidant is effective for maintaining a large voltage holding ratio. Specific preferred examples of the antioxidants include compounds (AO-1) or (AO-2) described below; IRGANOX (registered trademark) 415, IRGANOX 565, IRGANOX 1010, IRGANOX 1035, IRGANOX 3114 or IRGANOX 1098. The ultraviolet light absorber is effective for preventing a decrease of the maximum temperature. Specific preferred examples of the ultraviolet light absorber include a benzophenone derivative, a benzoate derivative and a triazole derivative. Specific examples include compounds (AO-3) and (AO-4) described below; TINUVIN (registered trademark) 329, TINUVIN P, TINUVIN 326, TINUVIN 234, TINUVIN 213, TINUVIN 400, TINUVIN 328 and TINUVIN 99-2; or 1,4-diazabicyclo[2.2.2]octane (DABCO).

The light stabilizer such as an amine having steric hindrance is preferred for maintaining the large voltage holding ratio. Specific preferred examples of the light stabilizers include compounds (AO-5) or (AO-6) described below, TINUVIN 144, TINUVIN 765 or TINUVIN770DF. The heat stabilizer is also effective for maintaining the large voltage holding ratio, and preferred examples include IRGAFOS 168 (trade name: BASF SE). A dichroic dye such as an azo dye or an anthraquinone dye is added to the composition to be adapted for a device having a guest host (GH) mode. The antifoaming agent is effective for preventing foam formation. Specific preferred examples of the antifoaming agents include dimethyl silicone oil and methylphenyl silicone oil.

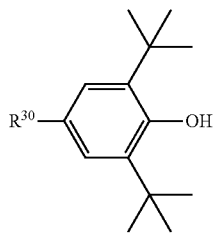

(AO-1)

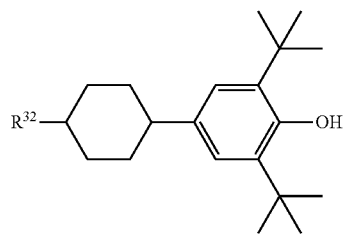

(AO-2)

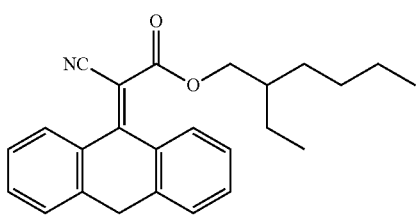

(AO-3)

-continued

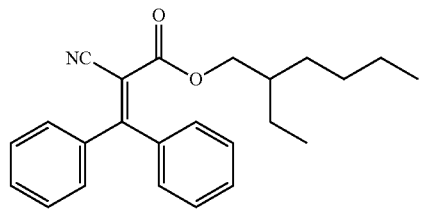
(AO-4)

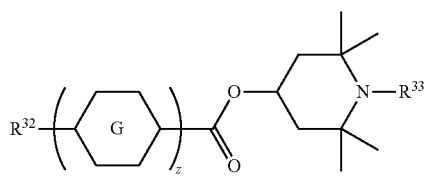
(AO-5)

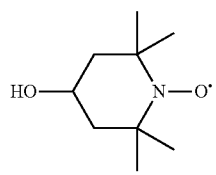
(AO-6)

In compound (AO-1), $R^{30}$ is alkyl having 1 to 20 carbons, alkoxy having 1 to 20 carbons, —COOR$^{31}$ or —CH$_2$CH$_2$COOR$^{31}$, in which $R^{31}$ is alkyl having 1 to 20 carbons. In compound (AO-2), $R^{32}$ is alkyl having 1 to 20 carbons. In compound (AO-5), $R^{32}$ is alkyl having 1 to 20 carbons; $R^{33}$ is hydrogen, methyl or O. (oxygen radical); ring G is 1,4-cyclohexylene or 1,4-phenylene; and Z is 1, 2 or 3.

The composition can also be used for a guest host (GH) mode by adding a dichroic dye such as a merocyanine type, a styryl type, an azo type, an azomethine type, an azoxy type, a quinophthalone type, an anthraquinone type and a tetrazine type.

3 Liquid crystal display device

The composition can be used in the liquid crystal display device having an operating mode such as the PC mode, the TN mode, the STN mode, the OCB mode and the PSA mode, and driven by an active matrix (AM). The composition can also be used in the liquid crystal display device having the operating mode such as the PC mode, the TN mode, the STN mode, the OCB mode, the VA mode and the IPS mode, and driven by a passive matrix (PM) mode. The AM mode and the PM mode devices can also be applied to any of a reflective type, a transmissive type and a transflective type.

The composition can also be used in a nematic curvilinear aligned phase (NCAP) device prepared by microencapsulating a nematic liquid crystal, a polymer dispersed liquid crystal display device (PDLCD) and a polymer network liquid crystal display device (PNLCD) in which a three-dimensional network-polymer is formed in the liquid crystal, and a nanocapsule dispersed liquid crystal display device. The composition can also be used in a three-dimensional image display device. In the device, a liquid crystal lens panel is combined with an ordinary liquid crystal display device. The panel can be adjusted into a lens state or a non-lens state by applying voltage to the panel and changing a refractive index of the liquid crystal. Thus, switching between 2D display and 3D display can be made. Compound (1) is also useful as a component of such a switch liquid crystal.

EXAMPLES

The invention will be described in greater detail by way of Examples (including Synthesis Examples and Use Examples). The invention is not limited by the Examples. The invention includes a mixture of a composition in Use Example 1 and a composition in Use Example 2. The invention also includes a composition prepared by mixing at least two of compositions in the Use Examples.

1. Example of Compound (1)

Compound (1) was prepared according to procedures described below. The prepared compound was identified by a method such as an NMR analysis. Physical properties of the compound and the composition and characteristics of a device were measured by methods described below.

NMR Analysis

For measurement, DRX-500 made by Bruker BioSpin Corporation was used. In $^1$H-NMR measurement, a sample was dissolved in a deuterated solvent such as CDCl$_3$, and measurement was carried out under conditions of room temperature, 500 MHz and 16 times of accumulation. Tetramethylsilane was used as an internal standard. In $^{19}$F-NMR measurement, CFCl$_3$ was used as an internal standard, and measurement was carried out under conditions of 24 times of accumulation. In explaining nuclear magnetic resonance spectra obtained, s, d, t, q, quin, sex and m stand for a singlet, a doublet, a triplet, a quartet, a quintet, a sextet and a multiplet, and br being broad, respectively.

Sample for Measurement

Upon measuring phase structure and transition temperature, a liquid crystal compound itself was used as a sample. Upon measuring physical properties such as a maximum temperature of a nematic phase, viscosity, optical anisotropy and dielectric anisotropy, a composition prepared by mixing the compound with a base liquid crystal was used as a sample.

When a sample in which the compound was mixed with the base liquid crystal was used, measurement was carried out as described below. The sample was prepared by mixing 15% by weight of the compound and 85% by weight of the base liquid crystal. From a measured value of the sample, an extrapolated value was calculated according to an extrapolation method represented by the following formula, and the calculated value was described:

[extrapolated value] =(100 ×[measured value of a sample] - [% by weight of a base liquid crystal] ×[measured value of the base liquid crystal]) / [% by weight of a compound].

When crystals (or a smectic phase) precipitated at 25° C. even at the ratio of the compound to the base liquid crystal, a ratio of the compound to the base liquid crystal was changed in the order of (10% by weight: 90% by weight), (5% by weight: 95% by weight) and (1% by weight: 99% by weight), and physical properties of the sample were measured at a ratio at which no crystal (or no smectic phase) precipitated at 25° C. In addition, unless otherwise noted, the ratio of the compound to the base liquid crystal was (15% by weight: 85% by weight).

As the base liquid crystal, base liquid crystal (i) described below was used. Proportions of components in base liquid crystal (i) were expressed in terms of % by weight.

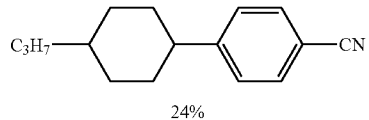

24%

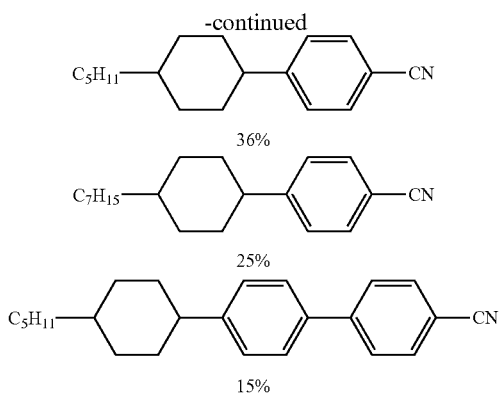

Measuring Method

Physical properties were measured according to methods described below. Most of the measuring methods are applied as described in the Standard of Japan Electronics and Information Technology Industries Association (hereinafter abbreviated as JEITA) (JEITA ED-2521B) discussed and established by JEITA, or modified thereon. No TFT was attached to a TN device used for measurement.

(1) Phase Structure

A sample was placed on a hot plate in a melting point apparatus (FP-52 Hot Stage made by Mettler-Toledo International Inc.) equipped with a polarizing microscope, and a state of phase and a change thereof were observed with the polarizing microscope while the sample was heated at a rate of 3° C. per minute, and a kind of the phase was specified.

(2) Transition Temperature (° C.)

For measurement, a differential scanning calorimeter, Diamond DSC System, made by PerkinElmer, Inc., or a high sensitivity differential scanning calorimeter, X-DSC7000, made by SII NanoTechnology Inc. was used. A sample was heated and then cooled at a rate of 3° C. per minute, and a starting point of an endothermic peak or an exothermic peak caused by a phase change of the sample was determined by extrapolation, and thus a transition temperature was determined. Temperature at which a compound undergoes transition from a solid to a liquid crystal phase such as the smectic phase and the nematic phase may be occasionally abbreviated as "minimum temperature of the liquid crystal phase." Temperature at which the compound undergoes transition from the liquid crystal phase to an isotropic liquid may be occasionally abbreviated as "clearing point."

A crystal was expressed as C. When kinds of the crystals were distinguishable, each of the crystals was expressed as $C_1$ or $C_2$. The smectic phase or the nematic phase was expressed as S or N. When smectic A phase, smectic B phase, smectic C phase or smectic F phase was distinguishable among the smectic phases, the phases were expressed as $S_A$, $S_B$, $S_C$ or $S_F$, respectively. A liquid (isotropic) was expressed as I. A transition temperature was expressed as "C 50.0 N 100.0 I," for example. The expression indicates that a transition temperature from the crystals to the nematic phase is 50.0° C., and a transition temperature from the nematic phase to the liquid is 100.0° C.

(3) Compatibility at Low Temperature

Samples in which the base liquid crystal and the compound were mixed for proportions of the compounds to be 20% by weight, 15% by weight, 10% by weight, 5% by weight, 3% by weight and 1% by weight were prepared, and put in glass vials. After the glass vials were kept in freezers at −10° C. or −20° C. for a predetermined period of time, whether or not crystals or a smectic phase precipitated was observed.

(4) Maximum Temperature of Nematic Phase ($T_{NI}$ or NI; ° C.)

A sample was placed on a hot plate in a melting point apparatus equipped with a polarizing microscope, and heated at a rate of 1° C. per minute. Temperature when part of the sample began to change from a nematic phase to an isotropic liquid was measured. When the sample was a mixture of a compound and the base liquid crystal, the maximum temperature was expressed in terms of a symbol $T_{NI}$. When the sample was a mixture of a compound and component B or the like, the maximum temperature was expressed in terms of a symbol NI. A maximum temperature of the nematic phase may be occasionally abbreviated as "maximum temperature."

(5) Minimum Temperature of Nematic Phase ($T_c$; ° C.)

Samples each having a nematic phase were kept in freezers at temperatures of 0° C., −10° C., −20° C., −30° C. and −40° C. for 10 days, and then liquid crystal phases were observed. For example, when the sample maintained the nematic phase at −20° C. and changed to crystals or a smectic phase at −30° C., $T_c$ was expressed as $T_c \leq -20°$ C. A minimum temperature of the nematic phase may be occasionally abbreviated as "minimum temperature."

(6) Viscosity (Bulk Viscosity; η; Measured at 20° C.; mPa·s)

For measurement, a cone-plate (E type) rotational viscometer made by Tokyo Keiki Inc. was used.

(7) Viscosity (Rotational Viscosity; γ1; Measured at 25° C.; mPa·s)

Measurement was carried out according to a method described in M. Imai et al., Molecular Crystals and Liquid Crystals, Vol. 259, 37 (1995). A sample was put in a TN device in which a twist angle was 0 degrees and a distance (cell gap) between two glass substrates was 5 micrometers. Voltage was applied stepwise to the device in the range of 16 V to 19.5 V at an increment of 0.5 V. After a period of 0.2 second with no voltage application, voltage was repeatedly applied under conditions of only one rectangular wave (rectangular pulse; 0.2 second) and no voltage application (2 seconds). A peak current and a peak time of transient current generated by the applied voltage were measured. A value of rotational viscosity was obtained from the measured values and calculation equation (8) on page 40 of the paper presented by M. Imai et al. A value of a dielectric anisotropy required for the calculation was determined using the device by which the rotational viscosity was measured and by a method described below.

(8) Optical Anisotropy (Refractive Index Anisotropy; Measured at 25° C.; Δn)

Measurement was carried out by an Abbe refractometer with a polarizing plate mounted on an ocular, using light at a wavelength of 589 nanometers. A surface of a main prism was rubbed in one direction, and then a sample was added dropwise onto the main prism. A refractive index (n∥) was measured when a direction of polarized light was parallel to a direction of rubbing. A refractive index (n⊥) was measured when the direction of polarized light was perpendicular to the direction of rubbing. A value of optical anisotropy (Δn) was calculated from an equation: Δn=n∥−n⊥.

(9) Dielectric Anisotropy (Δε; Measured at 25° C.)

A sample was put in a TN device in which a distance (cell gap) between two glass substrates was 9 micrometers and a twist angle was 80 degrees. Sine waves (10 V, 1 kHz) were applied to the device, and after 2 seconds, a dielectric constant (ε∥) of liquid crystal molecules in a major axis direction was measured. Sine waves (0.5 V, 1 kHz) were applied to the device, and after 2 seconds, a dielectric constant ($\epsilon\perp$) of the liquid crystal molecules in a minor axis direction was measured. A value of dielectric anisotropy was calculated from an equation: $\Delta\epsilon=\epsilon\|-\epsilon\perp$.

(10) Elastic Constant (K; Measured at 25° C.; pN)

For measurement, HP4284A LCR Meter made by Yokogawa-Hewlett-Packard Co. was used. A sample was put in a horizontal alignment device in which a distance (cell gap) between two glass substrates was 20 micrometers. An electric charge of 0 V to 20 V was applied to the device, and electrostatic capacity and applied voltage were measured. The measured values of electrostatic capacity (C) and applied voltage (V) were fitted to equation (2.98) and equation (2.101) on page 75 of "Liquid Crystal Device Handbook" (Ekisho Debaisu Handobukku in Japanese; The Nikkan Kogyo Shimbun, Ltd.) and values of $K_{11}$ and $K_{33}$ were obtained from equation (2.99). Next, $K_{22}$ was calculated using the previously determined values of $K_{11}$ and $K_{33}$ in equation (3.18) on page 171. Elastic constant K was expressed in terms of a mean value of the thus determined $K_{11}$, $K_{22}$ and $K_{33}$.

(11) Threshold Voltage (Vth; Measured at 25° C.; V)

For measurement, an LCD5100 luminance meter made by Otsuka Electronics Co., Ltd. was used. A light source was a halogen lamp. A sample was put in a normally white mode TN device in which a distance (cell gap) between two glass substrates was 0.45/Δn (μm) and a twist angle was 80 degrees. A voltage (32 Hz, rectangular waves) to be applied to the device was stepwise increased from 0 V to 10 V at an increment of 0.02 V. On the occasion, the device was irradiated with light from a direction perpendicular to the device, and an amount of light transmitted through the device was measured. A voltage-transmittance curve was prepared, in which the maximum amount of light corresponds to 100% transmittance and the minimum amount of light corresponds to 0% transmittance. A threshold voltage was expressed in terms of voltage at 90% transmittance.

(12) Voltage Holding Ratio (VHR-1; Measured at 25° C.; %)

A TN device used for measurement had a polyimide alignment film, and a distance (cell gap) between two glass substrates was 5 micrometers. A sample was put in the device, and the device was sealed with an ultraviolet-curable adhesive. The device was charged by applying a pulse voltage (60 microseconds at 5 V) at 25° C. A decaying voltage was measured for 16.7 milliseconds with a high-speed voltmeter, and area A between a voltage curve and a horizontal axis in a unit cycle was determined. Area B was an area without decay. A voltage holding ratio is expressed in terms of a percentage of area A to area B.

(13) Voltage Holding Ratio (VHR-2; Measured at 80° C.; %)

A voltage holding ratio (VHR-2) was determined according to a method identical with the method in VHR-1 except that measurement was carried out at 80° C. The results were expressed in terms of a symbol VHR-2.

Raw Material

Solmix (registered trade name) A-11 is a mixture of ethanol (85.5%), methanol (13.4%) and 2-propanol (1.1%), and was purchased from Japan Alcohol Trading Co., Ltd.

Synthesis Example 1

Synthesis of Compound (1-6-77)

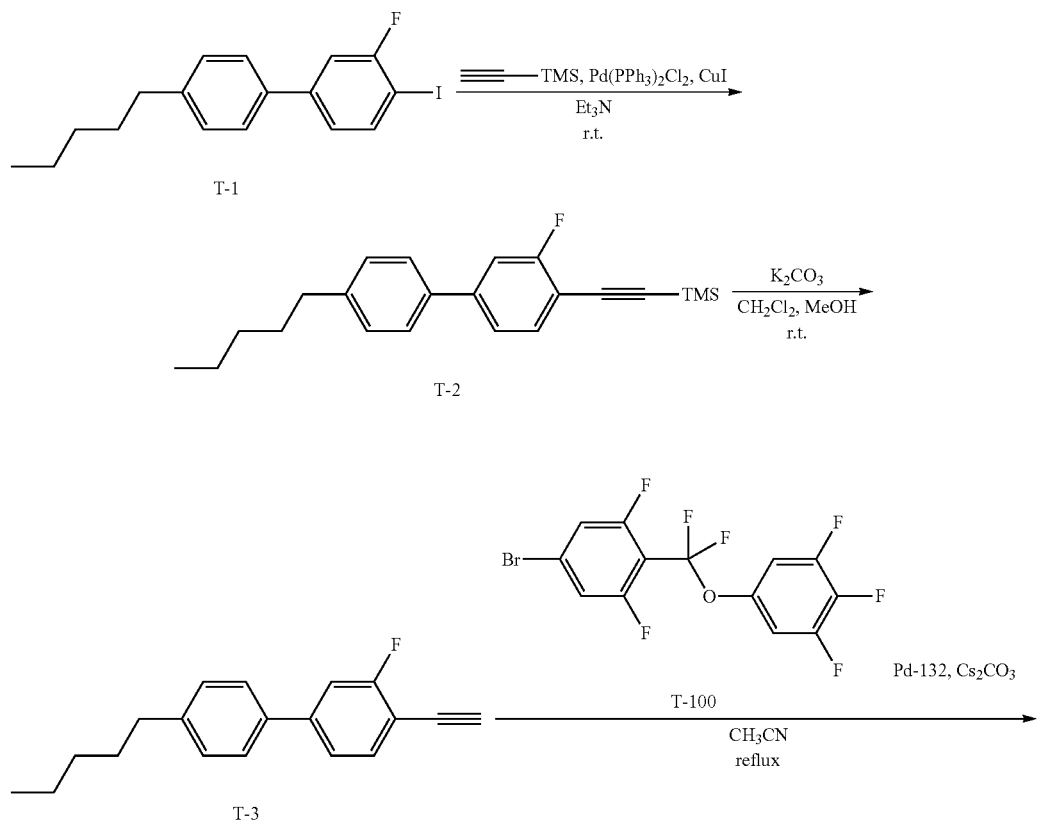

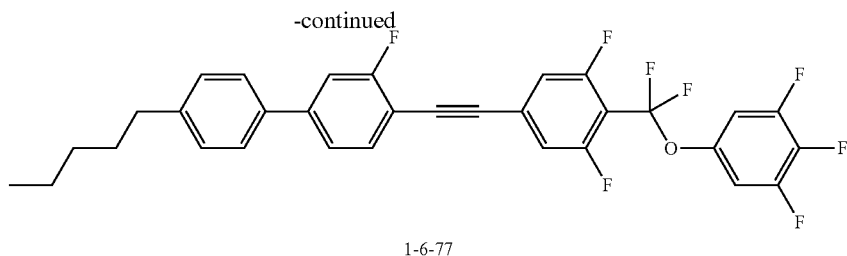

1-6-77

First Step:

Ethynyltrimethylsilane (3.34 g, 34.04 mmol) was added dropwise to compound (T-1) (11.4 g, 30.96 mmol) prepared according to a publicly known method, bis (triphenylphosphine) palladium (II) dichloride (2.17 g, 3.10 mmol) and a triethylamine (175 mL) solution of copper (I) iodide (0.59 g, 3.10 mmol), and the resulting mixture was stirred at room temperature for 2 hours. The resulting reaction mixture was subjected to filtration with a filter paper, a palladium residue was washed with toluene, and the mixed filtrate was concentrated. Water (250 mL) was added to the residue, and the resulting mixture was subjected to extraction with toluene (250 mL). An extracted solution was washed with water and saturated brine, dried over anhydrous magnesium sulfate, and concentrated under reduced pressure. The resulting residue was purified by column chromatography (heptane/ethyl acetate=20/1, volume ratio) to obtain compound (T-2) (9.59 g, 28.33 mmol, 91.5%).

Second Step:

Compound (T-2) (9.59 g, 28.33 mmol) obtained in the first step was dissolved in dichloromethane (55 mL) and methanol (55 mL). Potassium carbonate (5.28 g, 38.18 mol) was added thereto little by little in a solid state, and then the resulting mixture was stirred at room temperature for 2 hours. The resulting reaction mixture was poured into water (150 mL) and subjected to extraction with toluene. An extracted solution was washed with water and saturated brine, dried over anhydrous magnesium sulfate, and concentrated under reduced pressure. The resulting residue was purified by column chromatography (heptane) to obtain compound (T-3) (6.75 g, 25.34 mmol, 79.7%).

Third Step:

Compound (T-3) (2.22 g, 8.33 mmol) obtained in the second step and an acetonitrile (12 mL) solution of compound (T-100) (2.70 g, 6.94 mmol) prepared according to a publicly known method were mixed with $PdCl_2$ $(Amphos)_2$ (Pd-132; 0.0246 g, 0.03 mmol) and cesium carbonate (4.983 g, 15.29 mmol), and the resulting mixture was heated and refluxed for 2.5 hours. The resulting reaction mixture was left to cool down to room temperature, and then poured into water (50 mL) and subjected to extraction with toluene. An extracted solution was washed with water and saturated brine, dried over anhydrous magnesium sulfate, and concentrated under reduced pressure. The resulting residue was purified by column chromatography (heptane/ethyl acetate=100/1, volume ratio) and subsequently by recrystallization (ethyl acetate/2-propanol=1/10, volume ratio) to obtain compound (1-6-77) (2.22 g, 3.87 mmol, 55.7%).

$^1$H-NMR ($CDCl_3$; δ ppm): 7.55 (1H, t, J=7.6 Hz), 7.51 (2H, d, J =8.1 Hz), 7.40 (1H, dd, J=1.7 Hz, 8.1 Hz), 7.36 (1H, dd, J=1.3 Hz, 10.6 Hz), 7.27 (2H, t, J=8.1 Hz), 7.18 (2H, d, J=9.4 Hz), 6.98 (2H, dd, J=6.0 Hz, 7.4 Hz), 2.66 (2H, t, J=7.6 Hz), 1.65 (2H, quin, J=7.5 Hz), 1.36-1.34 (4H, m), 0.91 (3H, t, J=6.9 Hz).

Physical properties of compound (1-6-77) were as described below.

Phase transition temperature: C 60.3 $S_A$ 81.8 N 161.5 I.

Maximum temperature ($T_{NI}$)=125.7° C.; dielectric anisotropy (Δε) =39.5; optical anisotropy (Δn)=0.270.

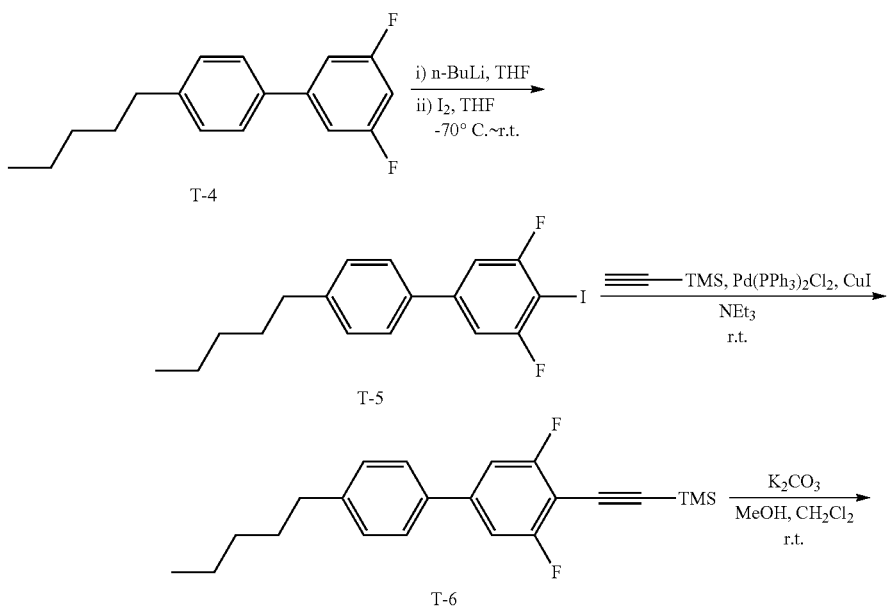

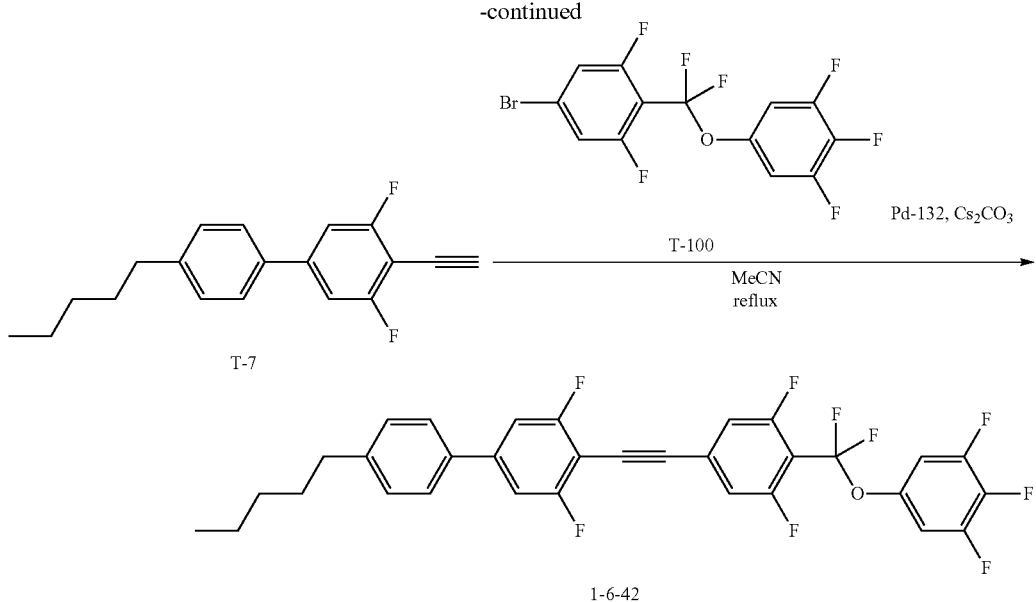

Synthesis Example 2

Synthesis of Compound (1-6-42)

First Step:

A THF (50 mL) solution of compound (T-4) (5.00 g, 19.21 mmol, ZIEBEN CHEMICALS CO., LTD.) was cooled down to −70° C., and n-BuLi was added dropwise thereto. The resulting mixture was stirred at −70° C. for 2.25 hours, and then a THF (50 mL) solution of iodine (5.85 g, 23.05 mmol) was added dropwise thereto. The resulting mixture was stirred at −70° C. for 2 hours, and then the resulting reaction mixture was returned to room temperature. The resulting mixture was poured into an aqueous solution of sodium thiosulfate (100 mL) and subjected to extraction with toluene. An extracted solution was washed with water and saturated brine, dried over anhydrous magnesium sulfate, and concentrated under reduced pressure. The resulting residue was purified by column chromatography (heptane) to obtain compound (T-5) (7.90 g, 19.21 mmol, quantitatively).

Second Step:

Ethynyltrimethylsilane (3.34 g, 34.04 mmol) was added dropwise to compound (T-5) (7.90 g, 19.21 mmol) obtained in the first step, bis(triphenylphosphine)palladium(II) dichloride (1.44 g, 2.05 mmol) and a triethylamine (120 mL) solution of copper(I) iodide (0.39 g, 2.05 mmol), and the resulting mixture was stirred at room temperature for 4 hours. The resulting reaction mixture was subjected to filtration with a filter paper, a palladium residue was washed with toluene, and the mixed filtrate was concentrated. Water (150 mL) was added to the residue, and the resulting mixture was subjected to extraction with toluene (150 mL). An extracted solution was washed with water and saturated brine, dried over anhydrous magnesium sulfate, and concentrated under reduced pressure. The resulting residue was purified by column chromatography (heptane/ethyl acetate=100/1, volume ratio) to obtain compound (T-6) (7.25 g, 20.34 mmol, 99.4%).

Third step:

Compound (T-6) (7.25 g, 20.34 mmol) obtained in the second step was dissolved in dichloromethane (40 mL) and methanol (40 mL). Potassium carbonate (3.37 g, 24.40 mol) was added thereto little by little in a solid state, and then the resulting mixture was stirred at room temperature for 1.5 hours. The resulting reaction mixture was poured into water (100 mL) and subjected to extraction with toluene. An extracted solution was washed with water and saturated brine, dried over anhydrous magnesium sulfate, and concentrated under reduced pressure. The resulting residue was purified by column chromatography (heptane/ethyl acetate =50/1, volume ratio) to obtain compound (T-7) (4.84 g, 17.02 mmol, 83.7%).

Fourth Step:

Compound (T-7) (2.5 g, 8.79 mmol) obtained in the third step and an acetonitrile (13 mL) solution of compound (T-100) (2.7 g, 6.94 mmol) prepared according to a publicly known method were mixed with $PdCl_2(Amphos)_2$ (Pd-132; 0.0311 g, 0.04 mmol) and cesium carbonate (5.729 g, 17.58 mmol), and the resulting mixture was heated and refluxed for 3 hours. The resulting reaction mixture was left to cool down to room temperature, and then poured into water (50 mL) and subjected to extraction with toluene. An extracted solution was washed with water and saturated brine, dried over anhydrous magnesium sulfate, and concentrated under reduced pressure. The resulting residue was purified by column chromatography (heptane/ethyl acetate=100/1, volume ratio) and subsequently by recrystallization (ethyl acetate/2-propanol=1/10, volume ratio) to obtain compound (1-6-42) (2.22 g, 3.87 mmol, 55.7%).

$^1$H-NMR (CDCl$_3$; δ ppm): 7.49 (2H, d, J=8.2 Hz), 7.28 (2H, t, J=8.1 Hz), 7.20 (4H, dd, J=2.4 Hz, 10.8 Hz), 6.98 (2H, dd, J=6.1 Hz, 7.4 Hz), 2.66 (2H, t, J=7.8 Hz), 1.65 (2H, quin, J=7.4 Hz), 1.35-1.34 (4H, m), 0.91 (3H, t, J=6.9 Hz).

Physical properties of compound (1-6-42) were as described below. In addition, for measurement of a maximum temperature, optical anisotropy and dielectric anisotropy, a sample in which a ratio of the compound to the base liquid crystal was (10% by weight: 90% by weight) was used.

Phase transition temperature: C 87.5 S$_A$ 109.1 N 163.1 I.

Maximum temperature (T$_{NI}$)=113.7° C.; dielectric anisotropy (Δε) =48.9; optical anisotropy (Δn)=0.257.

Synthesis Example 3

Synthesis of Compound (1-6-11)

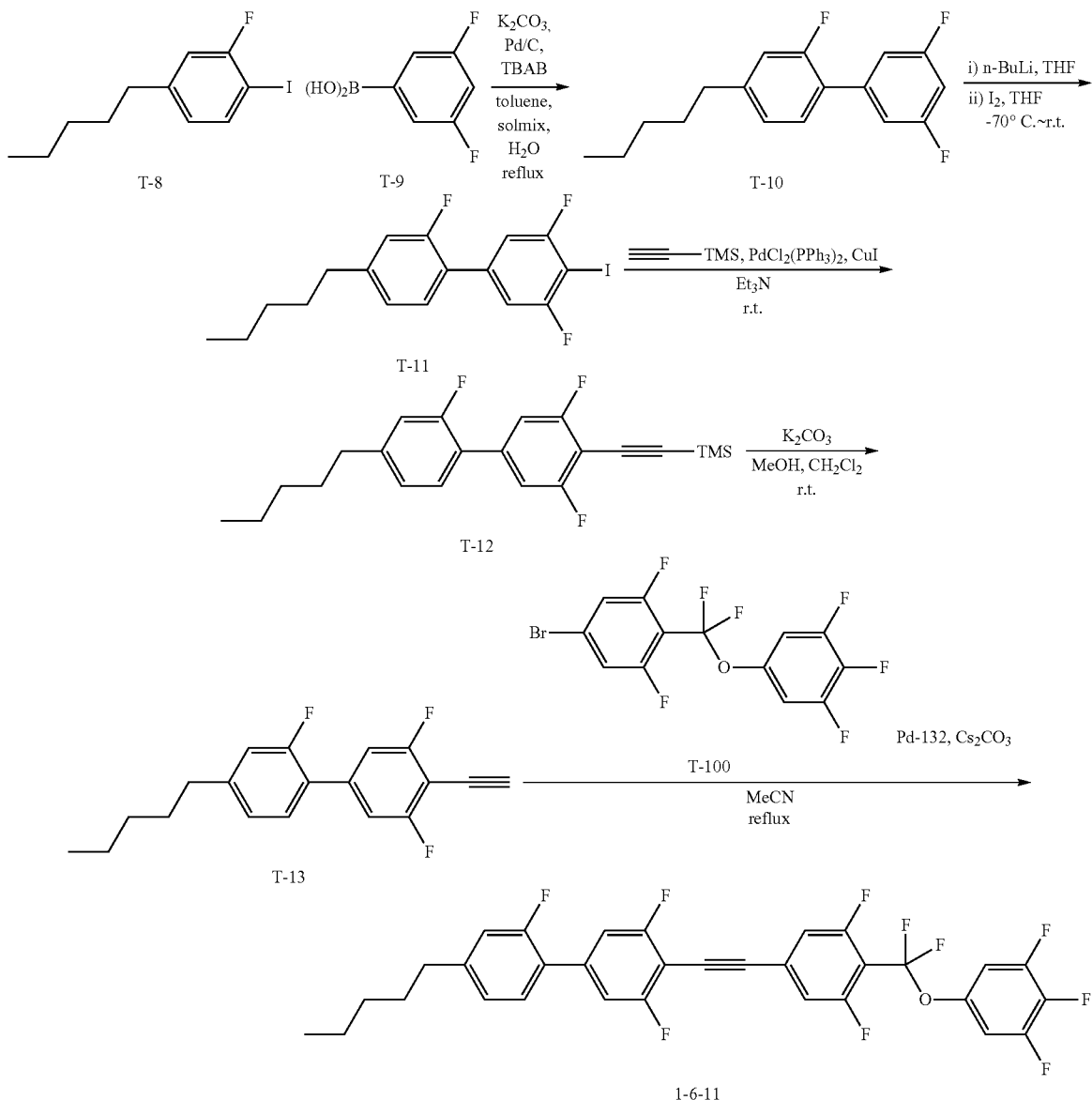

First Step:

Potassium carbonate (17.74 g, 128.4 mmol) and a solmix (63 mL) suspension of tetrabutylammonium bromide (2.76 g, 8.56 mmol) were added to compound (T-8) (12.50 g, 42.79 mmol) prepared according to a publicly known method and a toluene (63 mL) solution of (3,5-difluorophenyl)boronic acid (T-9) (7.43 g, 47.07 mmol). Palladium on carbon (0.277 g, 2.6 mmol) and water (63 mL) were added thereto and mixed therewith, and the resulting mixture was refluxed for 1.5 hours. The resulting reaction mixture was subjected to filtration with a filter paper, a palladium residue was washed with toluene, and the mixed filtrate was concentrated. Water (100 mL) was added to the residue, and the resulting mixture was subjected to extraction with toluene (100 mL). An extracted solution was washed with water and saturated brine, dried over anhydrous magnesium sulfate, and concentrated under reduced pressure. The resulting residue was purified by column chromatography (heptane) to obtain compound (T-10) (10.37 g, 37.26 mmol, 87.0%).

Second Step:

A THF (100 mL) solution of compound (T-10) (10.37 g, 37.26 mmol) obtained in the first step was cooled down to −70° C., and n-BuLi was added dropwise thereto. The resulting mixture was stirred at −70° C. for 2.5 hours, and then a THF (100 mL) solution of iodine (11.35 g, 44.71 mmol) was added dropwise thereto. The resulting mixture was stirred at −70° C. for 1 hour, and then the resulting reaction mixture was returned to room temperature. The resulting mixture was poured into an aqueous solution of sodium thiosulfate (100 mL) and subjected to extraction with toluene. An extracted solution was washed with water and saturated brine, dried over anhydrous magnesium sulfate, and concentrated under reduced pressure. The resulting residue was purified by column chromatography (heptane) to obtain compound (T-11) (13.44 g, 33.25 mmol, 89.2%).

Third Step:

Ethynyltrimethylsilane (2.14 g, 21.77 mmol) was added dropwise to compound (T-11) (8.00 g, 19.79 mmol) obtained in the second step, bis(triphenylphosphine)palladium(II) dichloride (1.39 g, 1.98 mmol) and a triethylamine (110 mL) solution of copper(I) iodide (0.38 g, 1.98 mmol), and the resulting mixture was stirred at room temperature for 2.5 hours. The resulting reaction mixture was subjected to filtration with a filter paper, a palladium residue was washed with toluene, and the mixed filtrate was concentrated. Water was added to the residue, and the resulting mixture was subjected to extraction with toluene. An extracted solution was washed with water and saturated brine, dried over anhydrous magnesium sulfate, and concentrated under reduced pressure. The resulting residue was purified by column chromatography (heptane) to obtain compound (T-12) (6.61 g, 17.67 mmol, 89.2%).

Fourth step:

Compound (T-12) (6.61 g, 17.67 mmol) obtained in the third step was dissolved in dichloromethane (40 mL) and methanol (40 mL). Potassium carbonate (2.92 g, 21.18 mol) was added thereto little by little in a solid state, and then the resulting mixture was stirred at room temperature for 1 hour. The resulting reaction mixture was poured into water (100 mL) and subjected to extraction with toluene. An extracted solution was washed with water and saturated brine, dried over anhydrous magnesium sulfate, and concentrated under reduced pressure. The resulting residue was purified by column chromatography (heptane/ethyl acetate =100/1, volume ratio) to obtain compound (T-13) (4.98 g, 16.47 mmol, 93.3%).

Fifth Step:

Compound (T-13) (2.50 g, 8.27 mmol) obtained in the fourth step and an acetonitrile (26 mL) solution of compound (T-100) (3.86 g, 9.92 mmol) prepared according to a publicly known method were mixed with PdCl$_2$(Amphos)$_2$ (Pd-132; 0.0293 g, 0.04 mmol) and cesium carbonate (5.39 g, 16.54 mmol), and the resulting mixture was heated and refluxed for 4.5 hours. The resulting reaction mixture was left to cool down to room temperature, and then poured into water (50 mL) and subjected to extraction with toluene. An extracted solution was washed with water and saturated brine, dried over anhydrous magnesium sulfate, and concentrated under reduced pressure. The resulting residue was purified by column chromatography (heptane/ethyl acetate=100/1, volume ratio) and subsequently by recrystallization (ethyl acetate/2-propanol=1/10, volume ratio) to obtain compound (1-6-11) (2.99 g, 4.90 mmol, 59.2%).

$^1$H-NMR (CDCl$_3$; δ ppm): 7.34 (1H, t, J=8.1 Hz), 7.22-7.19 (4H, m), 7.07-6.97 (4H, m), 2.65 (2H, t, J=7.9 Hz), 1.65 (2H, quin, J =7.5 Hz), 1.37-1.32 (4H, m), 0.91 (3H, t, J=6.9 Hz).

Physical properties of compound (1-6-11) were as described below.

Phase transition temperature: C 92.0 S$_A$ 156.3 I.

Maximum temperature (T$_{NI}$)=99.7° C.; dielectric anisotropy (Δε)=54.6; optical anisotropy (Δn)=0.250.

Synthesis Example 4

Synthesis of Compound (1-5-32)

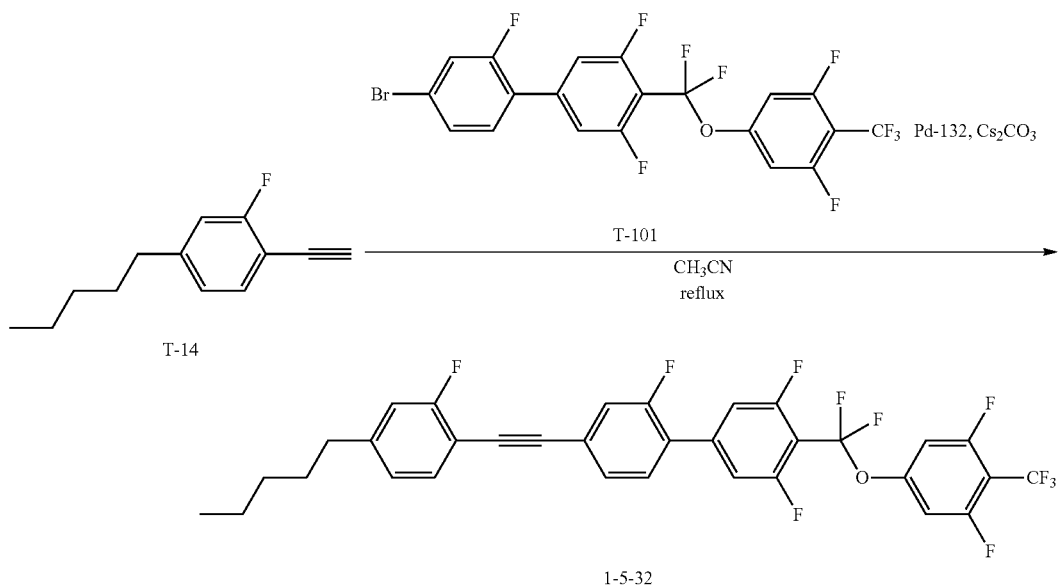

First Step:

Compound (T-14) (1.47 g, 7.50 mmol) prepared according to a publicly known method and an acetonitrile (100 mL) solution of compound (T-101) (4.0 g, 7.50 mmol) prepared according to a publicly known method were added to PdCl$_2$(Amphos)$_2$ (Pd-132; 0.0266 g, 0.04 mmol) and cesium carbonate (4.89 g, 17.58 mmol), and the resulting mixture was heated and refluxed for 4 hours. The resulting reaction mixture was left to cool down to room temperature, and then poured into water (50 mL) and subjected to extraction with toluene. An extracted solution was washed with water and saturated brine, dried over anhydrous magnesium sulfate, and concentrated under reduced pressure. The resulting residue was purified by column chromatography (heptane/toluene=4/1, volume ratio) and subsequently by recrystallization (heptane/solmix=1/4, volume ratio) to obtain compound (1-5-32) (1.1 g, 1.71 mmol, 22.8%).

$^1$H-NMR (CDCl$_3$; δ ppm): 7.44-7.36 (2H, m), 7.49 (2H, d, J=6.05 Hz), 7.25 (2H, d, J=9.65 Hz), 6.99 (2H, d, J=10.0 Hz), 6.95 (2H, d, J=9.7 Hz), 2.63 (2H, t, J=7.6 Hz), 1.63 (2H, quin, J=7.7 Hz), 1.37-1.29 (4H, m), 0.90 (3H, t, J=6.7 Hz).

Physical properties of compound (1-5-32) were as described below.

Phase transition temperature: C 79.2 $S_A$ 99.2 N 150.6 I.

Maximum temperature ($T_{NI}$)=103.7° C.; dielectric anisotropy (Δε) =57.4; optical anisotropy (Δn)=0.250.

Synthesis Example 5

Synthesis of Compound (1-6-84)

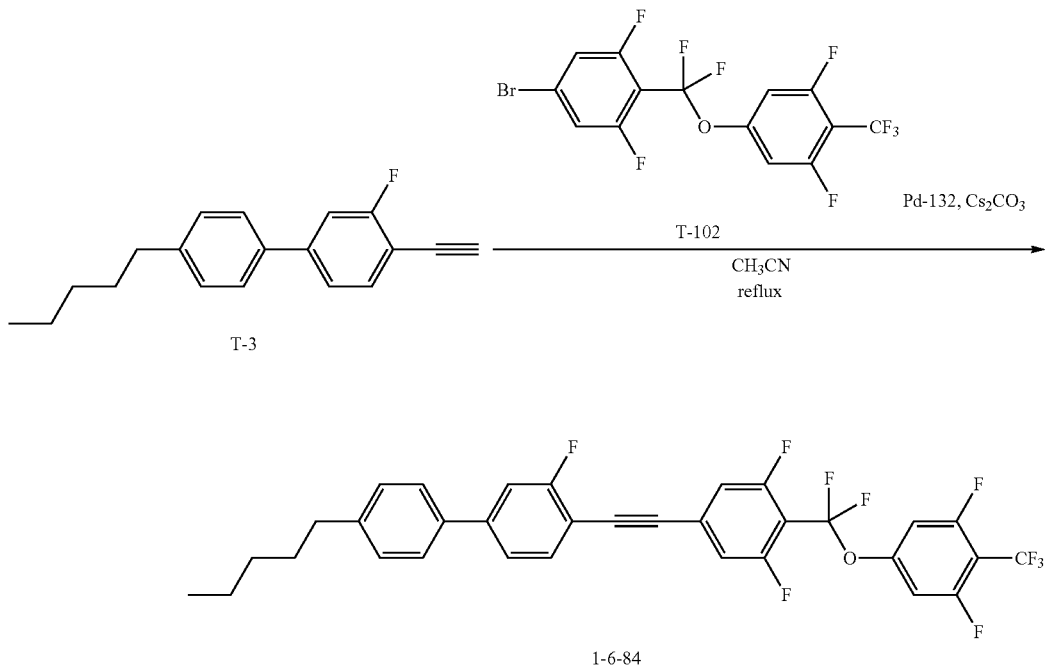

First Step:

Compound (T-3) (3.03 g, 11.4 mmol) prepared according to the previous section and an acetonitrile (150 mL) solution of compound (T-102) (5.0 g, 11.39 mmol) prepared according to a publicly known method were added to $PdCl_2$ (Amphos)$_2$ (Pd-132; 0.043 g, 0.06 mmol) and cesium carbonate (7.42 g, 22.78 mmol), and the resulting mixture was heated and refluxed for 4 hours. The resulting reaction mixture was left to cool down to room temperature, and then poured into water (50 mL) and subjected to extraction with toluene. An extracted solution was washed with water and saturated brine, dried over anhydrous magnesium sulfate, and concentrated under reduced pressure. The resulting residue was purified by column chromatography (heptane/toluene=4/1, volume ratio) and subsequently by recrystallization (heptane/solmix=1/4, volume ratio) to obtain compound (1-6-84) (1.52 g, 2.43 mmol, 21.4%).

$^1$H-NMR (CDCl$_3$; δ ppm): 7.55 (1H, t, J=7.70 Hz), 7.51 (2H, d, J =8.15 Hz), 7.38 (1H, dd, J=1.6 Hz, 8.0 Hz), 7.36 (1H, dd, J=1.0 Hz, 10.7 Hz), 7.28 (2H, d, J=8.10 Hz), 7.18 (2H, d, J=9.6 Hz), 6.97 (2H, d, J=9.9 Hz), 2.65 (2H, t, J=7.6 Hz), 1.65 (2H, quin, J=7.5 Hz), 1.38-1.32 (4H, m), 0.91 (3H, t, J=6.8 Hz).

Physical properties of compound (1-6-84) were as described below.

Phase transition temperature: C 92.9 N 156.4 I.

Maximum temperature ($T_{NI}$)=119.7° C.; dielectric anisotropy (Δε) =52.8; optical anisotropy (Δn)=0.264.

Synthesis Example 6

Synthesis of Compound (1-5-50)

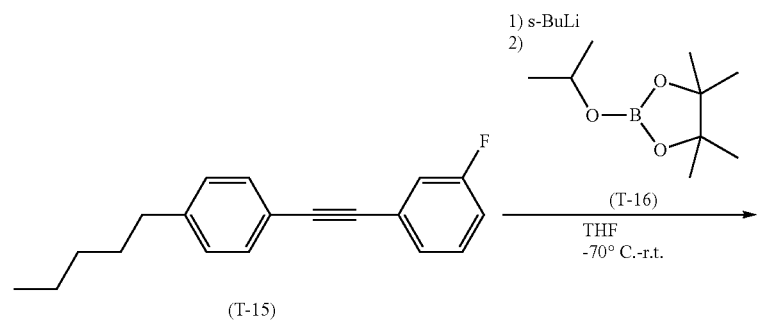

89 90

-continued

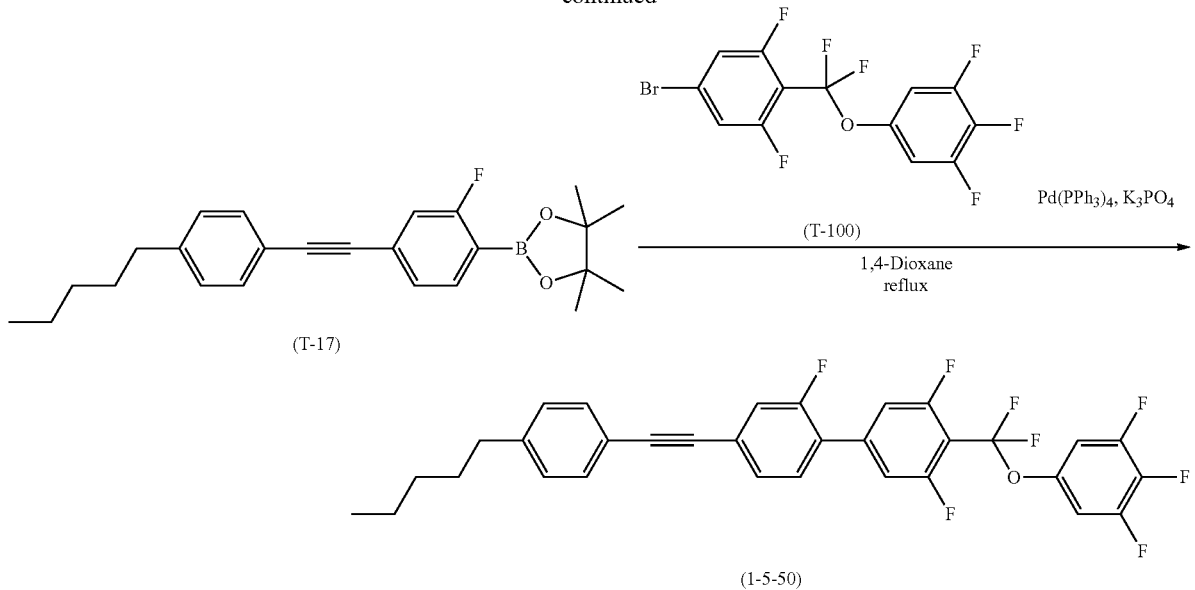

25

First Step:

A THF (40 mL) solution of compound (T-15) (5.00 g, 18.8 mmol) prepared according to a publicly known method was cooled down to −70° C., and s-BuLi (1.01 M; a cyclohexane solution, 22.3 mL) was added dropwise thereto. The resulting mixture was stirred at −70° C. for 2 hours, and then a THF (10 mL) solution of compound (T-16) (4.56 mL, 22.5 mmol) was added dropwise thereto, and the resulting mixture was returned to room temperature. The resulting reaction mixture was poured into a saturated aqueous solution of ammonium chloride (50 mL) and subjected to extraction with ethyl acetate. An extracted solution was washed with water and saturated brine, dried over anhydrous magnesium sulfate, and concentrated under reduced pressure. The resulting residue was purified by recrystallization (heptane) to obtain compound (T-17) (4.64 g, 11.8 mmol, 63%).

Second Step:

Compound (T-17) (3.63 g, 9.25 mmol) and a 1,4-dioxane (30 mL) solution of compound (T-100) (3.00 g, 7.71 mmol) prepared according to a publicly known method were mixed with tetrakis(triphenylphosphine)palladium(0) (0.267 g, 0.23 mmol) and potassium phosphate (4.91 g, 23.1 mmol), and the resulting mixture was heated and refluxed for 10 hours. The resulting reaction mixture was left to cool down to room temperature, and then poured into water (100 mL) and subjected to extraction with toluene. An extracted solution was washed with water and saturated brine, dried over anhydrous magnesium sulfate, and concentrated under reduced pressure. The resulting residue was purified by column chromatography (heptane/toluene=10/1, volume ratio) and subsequently by recrystallization (2-propanol) to obtain compound (1-5-50) (2.53 g, 4.40 mmol, 57%).

$^1$H-NMR (CDCl$_3$; δ ppm): 7.46 (2H, d, J=8.1 Hz), 7.42-7.39 (2H, m), 7.35 (1H, d, J=11.8 Hz), 7.24 (2H, d, J=10.6 Hz), 7.19 (2H, d, J=8.1 Hz), 7.02-6.97 (2H, m), 2.63 (2H, t, J=7.8 Hz), 1.63 (2H, quin, J=7.6 Hz), 1.37-1.29 (4H, m), 0.90 (3H, t, J=7.0 Hz).

Physical properties of compound (1-5-50) were as described below.

Phase transition temperature: C 63.3 N 149.3 I.

Maximum temperature (T$_{NI}$)=119° C.; dielectric anisotropy (Δε)=37.1; optical anisotropy (Δn)=0.257.

Synthesis Example 7

Synthesis of Compound (1-7-31)

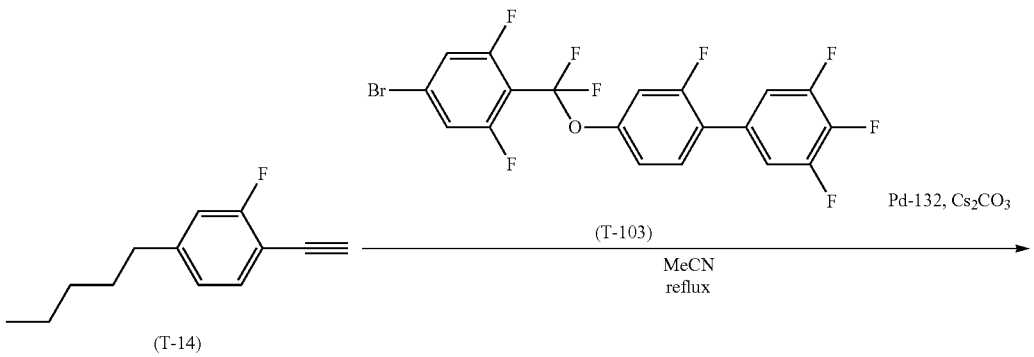

-continued

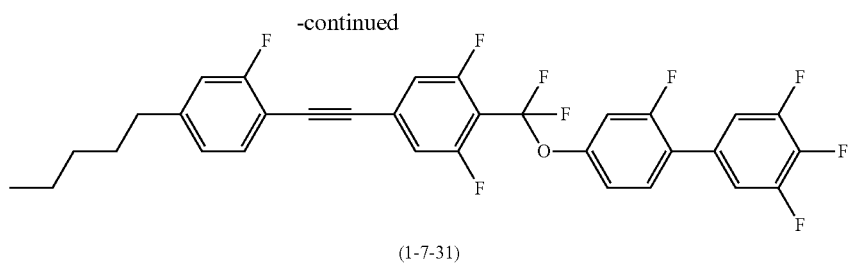

(1-7-31)

First Step:

Compound (T-14) (2.82 g, 14.8 mmol) and an acetonitrile (120 mL) solution of compound (T-103) (5.96 g, 12.3 mmol) prepared according to a publicly known method were mixed with $PdCl_2$ $(Amphos)_2$ (Pd-132; 46.2 mg, 0.0652 mmol) and cesium carbonate (8.04 g, 24.7 mmol), and the resulting mixture was heated and refluxed for 4 hours. The resulting reaction mixture was left to cool down to room temperature, and then poured into water (100 mL) and subjected to extraction with toluene. An extracted solution was washed with water (200 mL) and saturated brine (50 mL), dried over anhydrous magnesium sulfate, and concentrated under reduced pressure. The resulting residue was purified by column chromatography (heptane/toluene=10/1, volume ratio) and subsequently by recrystallization (2-propanol/ethyl acetate=5/1, volume ratio) to obtain compound (1-7-31) (3.49 g, 5.89 mmol, 48%).

$^1$H-NMR ($CDCl_3$; δ ppm): 7.43-7.34 (2H, m), 7.18-7.12 (6H, m), 6.99-6.93 (2H, m), 2.63 (2H, t, J=7.9 Hz), 1.62 (2H, quin, J=7.5 Hz), 1.38-1.26 (4H, m), 0.90 (3H, t, J=7.0 Hz).

Physical properties of compound (1-7-31) were as described below.

Phase transition temperature: C 74.7 N 126.4 I.

Maximum temperature ($T_{NI}$)=84.4° C.; dielectric anisotropy (Δε)=47.5; optical anisotropy (Δn)=0.230.

Synthesis Example 8

Synthesis of Compound (1-4-10)

First step:

Then, compound (T-14) (1.80 g, 9.46 mmol) and an acetonitrile (32 mL) solution of compound (T-100) (4.05 g, 10.41 mmol) prepared according to a publicly known method were mixed with $PdCl_2(Amphos)_2$ (Pd-132; 0.067 g, 0.09 mmol) and cesium carbonate (6.17 g, 18.92 mmol), and the resulting mixture was heated and refluxed for 8 hours. The resulting reaction mixture was left to cool down to room temperature, and then poured into water (50 mL) and subjected to extraction with toluene. An extracted solution was washed with water and saturated brine, dried over anhydrous magnesium sulfate, and concentrated under reduced pressure. The resulting residue was purified by column chromatography (heptane) and subsequently by recrystallization (ethyl acetate/2-propanol =1/10, volume ratio) to obtain compound (1-4-10) (1.39 g, 2.79 mmol, 29.5%).

$^1$H-NMR ($CDCl_3$; δ ppm): 7.41 (1H, t, J=7.4 Hz), 7.15 (2H, d, J =9.6), 6.99-6.95 (4H, m), 2.63 (2H, t, J=7.6 Hz), 1.62 (2H, quin, J=7.5 Hz), 1.35-1.30 (4H, m), 0.90 (3H, t, J=6.8 Hz).

Physical properties of compound (1-4-10) were as described below.

Phase transition temperature: C 4.4 N 16.2 I.

Maximum temperature ($T_{NI}$)=25.0° C.; dielectric anisotropy (Δε)=38.6; optical anisotropy (Δn)=0.164.

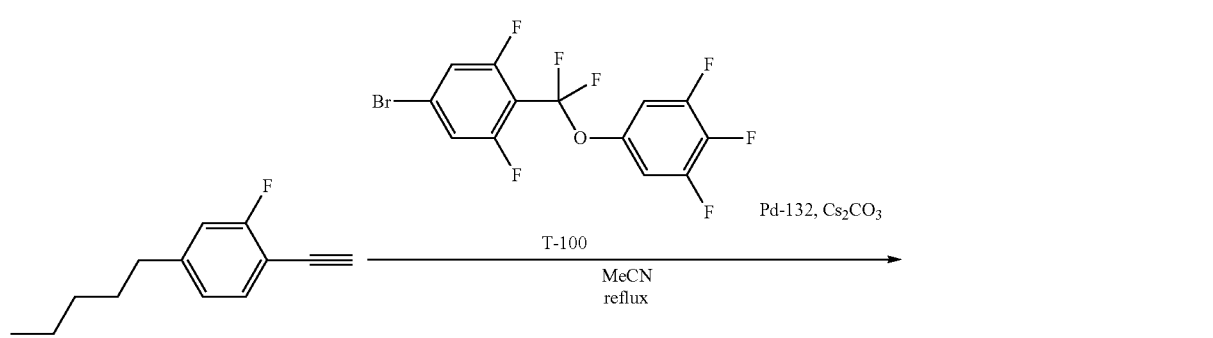

Synthesis Example 9

Synthesis of Compound (1-4-32)

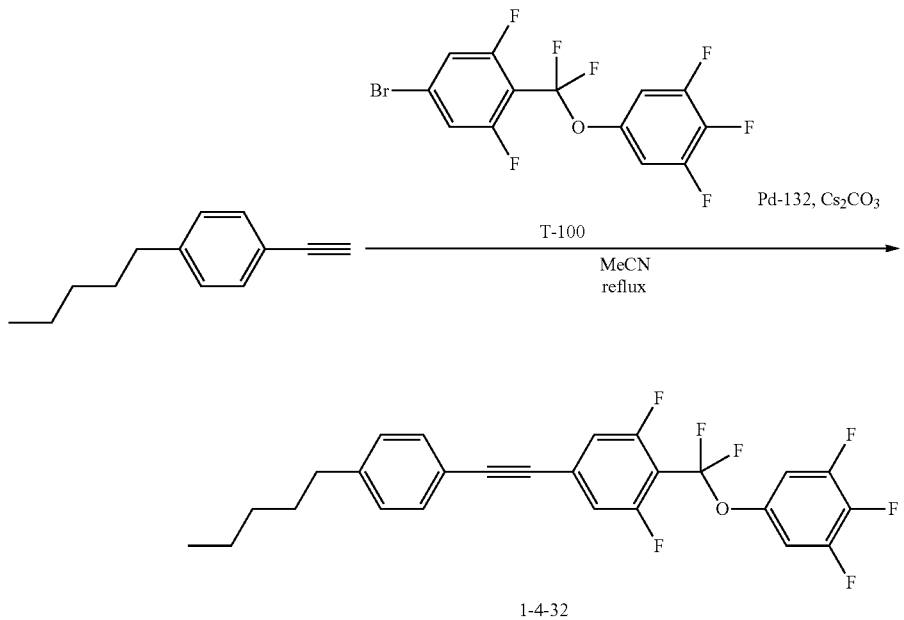

1-4-32

First Step:

Then, 1-ethynyl-4-pentylbenzene (1.80 g, 10.45 mmol, ZIEBEN CHEMICALS CO., LTD.) and an acetonitrile (32 mL) solution of compound (T-100) (4.88 g, 12.54 mmol) prepared according to a publicly known method were mixed with $PdCl_2(Amphos)_2$ (Pd-132; 0.074 g, 0.10 mmol) and cesium carbonate (6.80 g, 20.90 mmol), and the resulting mixture was heated and refluxed for 11.5 hours. The resulting reaction mixture was left to cool down to room temperature, and then poured into water (50 mL) and subjected to extraction with toluene. An extracted solution was washed with water and saturated brine, dried over anhydrous magnesium sulfate, and concentrated under reduced pressure. The resulting residue was purified by column chromatography (heptane) and subsequently by recrystallization (ethyl acetate/2-propanol=1/10, volume ratio) to obtain compound (1-4-32) (1.17 g, 2.44 mmol, 23.3%).

$^1$H-NMR (CDCl$_3$; δ ppm): 7.45 (2H, d, J=8.1 Hz), 7.19 (2H, d, J =8.1 Hz), 7.12 (2H, d, J=9.6 Hz), 6.97 (2H, dd, J=7.6 Hz, 6.1 Hz). 2.63 (2H, t, J=7.7 Hz), 1.62 (2H, quin, J=7.4 Hz), 1.35-1.30 (4H, m), 0.90 (3H, t, J=6.8 Hz).

Physical properties of compound (1-4-32) were as described below.

Phase transition temperature: C 30.6 I.

Maximum temperature $(T_{NI})$=33.0° C.; dielectric anisotropy (Δε)=32.6; optical anisotropy (Δn)=0.177.

Synthesis Example 10

Synthesis of Compound (1-5-23)

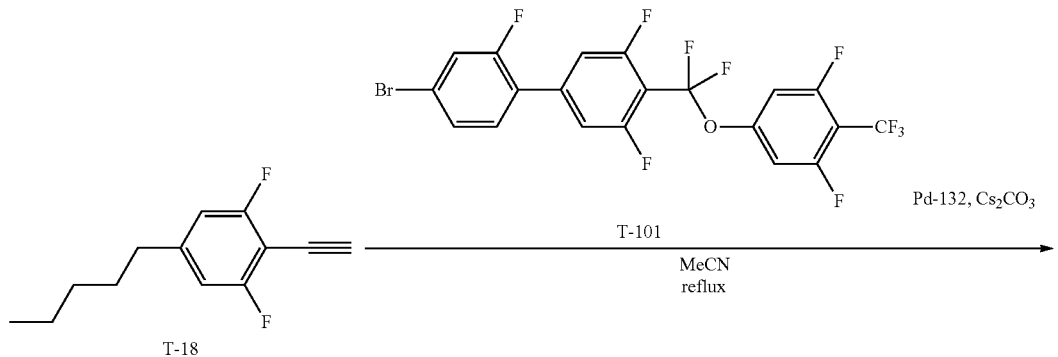

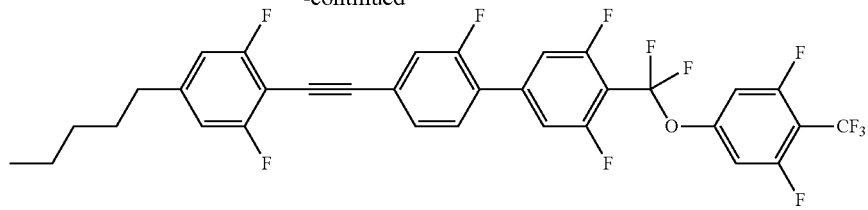

1-5-23

First Step:

Compound (T-18) (1.47 g, 7.50 mmol) prepared according to a publicly known method and compound (T-101) (4.0 g, 7.50 mmol) prepared according to a publicly known method with $PdCl_2(Amphos)_2$ (Pd-132; 0.0266 g, 0.04 mmol) and cesium carbonate (4.89 g, 17.58 mmol) were added to acetonitrile (100 mL), and the resulting mixture was heated and refluxed for 4 hours. The resulting reaction mixture was left to cool down to room temperature, and then poured into water (50 mL) and subjected to extraction with toluene. An extracted solution was washed with water (50 mL) and saturated brine (50 mL), dried over anhydrous magnesium sulfate, and concentrated under reduced pressure. The resulting residue was fractionated by column chromatography (eluate: heptane/toluene=4/1 (volume ratio)), and then purified by recrystallization (solvent: heptane/solmix=1/5) to obtain compound (1-5-23) (1.2 g, 1.82 mmol, 24.2%).

$^1$H-NMR ($CDCl_3$; δ ppm): 7.46-7.38 (3H, m), 7.49 (2H, d, J=10.4 Hz), 6.99 (2H, d, J=9.85 Hz), 6.78 (2H, d, J=8.10 Hz), 2.62 (2H, t, J=7.65 Hz), 1.62 (2H, quin, J=7.45 Hz), 1.37-1.29 (4H, m), 0.90 (3H, t, J=6.8 Hz).

Physical properties of compound (1-5-23) were as described below. In addition, for measurement of a maximum temperature, optical anisotropy and dielectric anisotropy, a sample in which a ratio of the compound to the base liquid crystal was (5% by weight: 95% by weight) was used.

Phase transition temperature: C 112.7 SmA 133.9 N 163.7 I.

Maximum temperature (NI)=97.7° C.; dielectric anisotropy (Δε)=62.1; optical anisotropy (Δn)=0.237.

Synthesis Example 11

Synthesis of Compound (1-5-28)

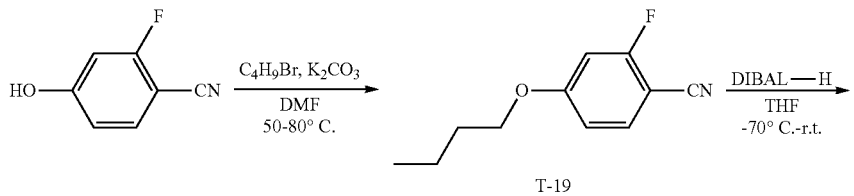

T-19

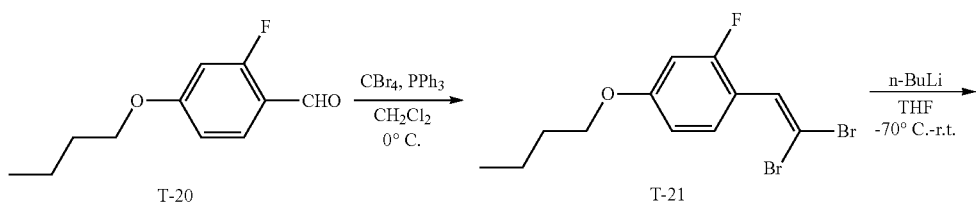

T-20      T-21

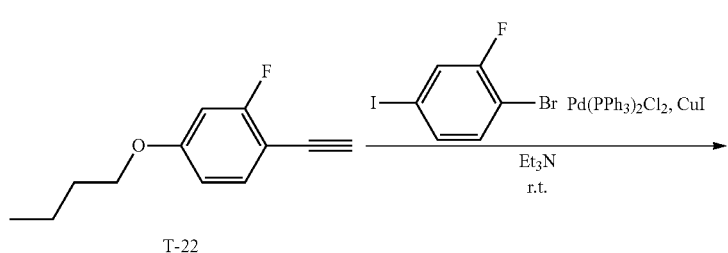

T-22

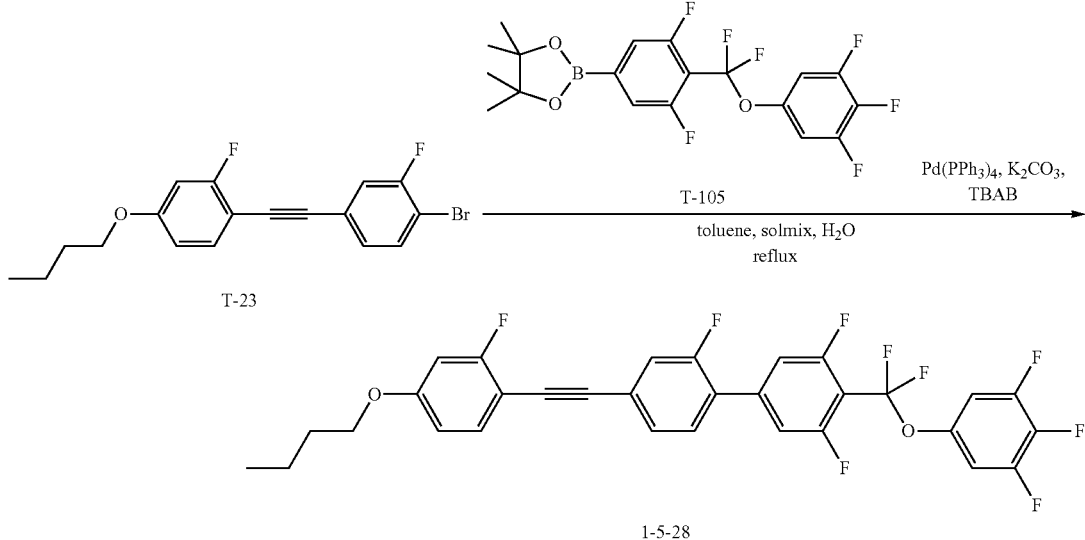

First Step:

Then, 2-fluoro-4-hydroxybenzonitrile (50.00 g, 364.7 mmol, TCI) and an N,N-dimethylformamide (200 mL) solution of potassium carbonate (50.42 g, 364.82 mmol) were heated at 50° C. for 1 hour, and then 1-bromobutane (50.01 g, 364.99 mmol) was added dropwise thereto. The resulting mixture was heated at 80° C. for 3 hours, and then the resulting reaction mixture was returned to room temperature. The resulting mixture was poured into water (300 mL) and subjected to extraction with toluene. An extracted solution was washed with water and saturated brine, dried over anhydrous magnesium sulfate, and concentrated under reduced pressure. The resulting residue was purified by column chromatography (toluene) to obtain compound (T-19) (64.67 g, 360.7 mmol, 98.9%).

Second Step:

A THF (350 mL) solution of compound (T-19) (33.18 g, 171.7 mmol) obtained in the first step was cooled down to −70° C., diisobutylammonium hydride (180 mL, 181.80 mmol) was added dropwise thereto, and the resulting mixture was stirred at −70° C. for 2 hours. The resulting mixture was returned to room temperature and stirred at room temperature for 15 hours, and then poured into 3N-HCl and subjected to extraction with ethyl acetate. An extracted solution was washed with water and saturated brine, dried over anhydrous magnesium sulfate, and concentrated under reduced pressure to obtain compound (T-20) (32.28 g, 164.8 mmol, 95.8%).

Third Step:

A dichloromethane (200 mL) solution of carbon tetrabromide (104.03 g, 396.6 mmol) was cooled down to 0° C., triphenylphosphine (65.71 g, 198.1 mmol) was added dropwise thereto, and the resulting mixture was stirred for 10 minutes. A dichloromethane solution (70 mL) of compound (T-20) (32.28 g, 164.5 mmol) obtained in the second step was added dropwise thereto, and the resulting mixture was stirred at 0° C. for 1 hour. The resulting reaction mixture was diluted with heptane and subjected to celite filtration, a solid residue was removed, and the resulting solution was concentrated under reduced pressure. The resulting residue was purified by column chromatography (toluene) to obtain compound (T-21) (62.03 g, 160.5 mmol, 97.6%).

Fourth Step:

A THF (300 mL) solution of compound (T-21) (56.49 g, 160.5 mmol) obtained in the third step was cooled down to −70° C., n-BuLi (205.6 mL, 329.0 mmol) was added dropwise thereto, and the resulting mixture was stirred at −70° C. for 1 hour. The resulting reaction mixture was returned to room temperature, poured into water (500 mL) and subjected to extraction with toluene. An extracted solution was washed with water and saturated brine, dried over anhydrous magnesium sulfate, and concentrated under reduced pressure. The resulting residue was purified by column chromatography (heptane) to obtain compound (T-22) (7.98 g, 41.51 mmol, 25.9%)

Fifth step:

Then, 1-bromo-2-fluoro-4-iodobenzene (10.87 g, 36.13 mmol, TCI), bis(triphenylphosphine)palladium(II) dichloride (0.367 g, 0.52 mmol) and a triethylamine (100 mL) solution of copper(I) iodide (0.075 g, 0.39 mmol) were mixed, compound (T-22) (7.48 g, 36.19 mmol) obtained in the fourth step was added dropwise thereto, and the resulting mixture was stirred at room temperature for 18 hours. The resulting reaction mixture was concentrated under reduced pressure, dissolved in toluene, washed with ammonium chloride, water and saturated brine, dried over anhydrous magnesium sulfate, and concentrated under reduced pressure. The resulting residue was purified by column chromatography (heptane/toluene =4/1, volume ratio) and subsequently by recrystallization (2-propanol) to obtain compound (T-23) (7.51 g, 20.56 mmol, 56.8%).

Sixth Step:

Compound (T-23) (3.91 g, 10.71 mmol) obtained in the fifth step, compound (T-105) (4.67 g, 10.71 mmol) prepared according to a publicly known method, tetrakis(triphenyl) palladium(0) (0.67 g, 0.58 mmol), tetrabutylammonium bromide (0.89 g, 2.76 mmol), toluene (7 mL) of potassium carbonate (2.21 g, 16.0 mmol), solmix (7 mL) and an aqueous (7 mL) solution were mixed, and the resulting mixture was heated and refluxed for 46 hours. The resulting reaction mixture was left to cool down to room temperature, and then poured into water and subjected to extraction with toluene. An extracted solution was washed with water and saturated brine, dried over anhydrous magnesium sulfate, and concentrated under reduced pressure. The resulting residue was purified by column chromatography (heptane/toluene=3/1, volume ratio) and subsequently by recrystallization (2-propanol) to obtain compound (1-5-28) (2.18 g, 3.67 mmol, 34.3%).

$^1$H-NMR (CDCl$_3$; δ ppm): 7.44-7.39 (3H, m), 7.35 (1H, d, J=11.3 Hz), 7.24 (2H, d, J=10.6 Hz), 7.00 (2H, dd, J=7.5 Hz, 6.0), 6.71-6.66 (2H, m), 3.98 (2H, t, J=6.6 Hz), 1.79 (2H, quin, J=6.5 Hz), 1.54-1.46 (2H, m), 0.99 (3H, t, J=7.5 Hz).

Physical properties of compound (1-5-28) were as described below.

Phase transition temperature: C 82.5 S$_A$124.9 N 184.3 I.

Maximum temperature (T$_{NI}$)=124.4° C.; dielectric anisotropy (Δε) =43.4; optical anisotropy (Δn)=0.264.

Synthesis Example 12

Synthesis of Compound (1-5-31)

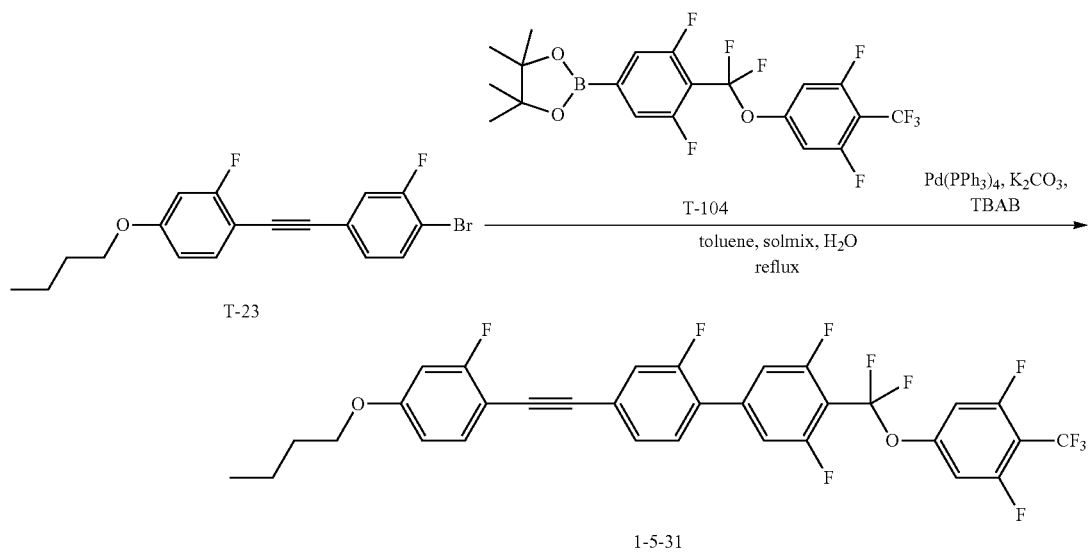

First Step:

Compound (T-23) (3.20 g, 8.76 mmol) prepared according to the previous section, compound (T-104) (4.27 g, 8.78 mmol) prepared according to a publicly known method, tetrakis(triphenyl)palladium(0) (0.61 g, 0.53 mmol), tetrabutylammonium bromide (0.71 g, 2.20 mmol), toluene (7 mL) of potassium carbonate (1.81 g, 13.10 mmol), solmix (7 mL) and an aqueous (7 mL) solution were mixed, and the resulting mixture was heated and refluxed for 28 hours. The resulting reaction mixture was left to cool down to room temperature, and then poured into water and subjected to extraction with toluene. An extracted solution was washed with water and saturated brine, dried over anhydrous magnesium sulfate, and concentrated under reduced pressure. The resulting residue was purified by column chromatography (heptane/toluene=3/1, volume ratio) and subsequently by recrystallization (2-propanol) to obtain compound (1-5-31) (2.90 g, 4.50 mmol, 51.4%).

$^1$H-NMR (CDCl$_3$; δ ppm): 7.42-7.39 (3H, m), 7.36 (1H, d, 11.4 Hz), 7.25 (2H, d, J=10.3), 6.99 (2H, d, J=9.9), 6.71-6.66 (2H, m), 3.98 (2H, t, J=6.7 Hz), 1.79 (2H, quin, J=6.5 Hz), 1.54-1.46 (2H, m), 0.99 (3H, t, J=7.3 Hz).

Physical properties of compound (1-5-31) were as described below.

Phase transition temperature: C 80.2 C 88.5 S$_A$148.3 N 182.8 I.

Maximum temperature (T$_{NI}$)=118.4° C.; dielectric anisotropy (Δε) =58.9; optical anisotropy (Δn)=0.257.

Synthesis Example 13

Synthesis of Compound (1-5-49)

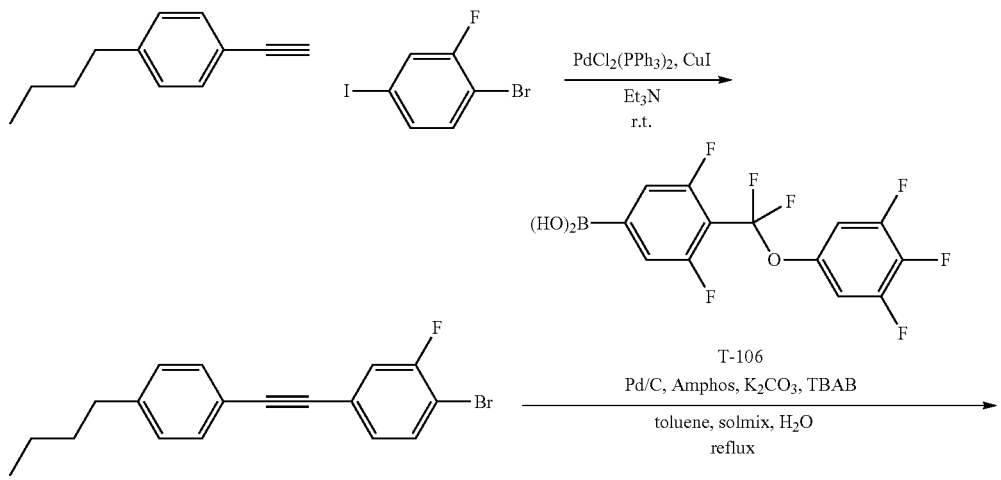

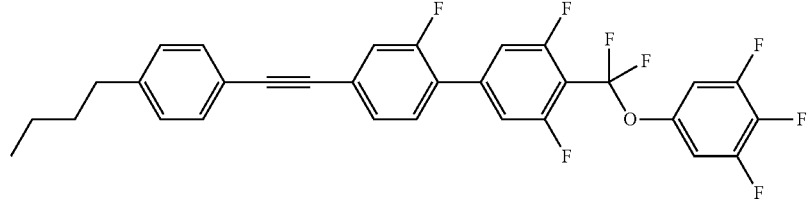

1-5-49

First step:

Then, 1-bromo-2-fluoro-4-iodobenzene (62.75 g, 208.5 mmol, TCI), bis(triphenylphosphine)palladium(II) dichloride (13.31 g, 18.96 mmol) and a triethylamine (500 mL) solution of copper(I) iodide (3.61 g, 18.96 mmol) were mixed, 1-butyl-4-ethynylbenzene (30.00 g, 189.6 mmol, ZIEBEN CHEMICALS CO., LTD.) was added dropwise thereto, and the resulting mixture was stirred at room temperature for 17 hours. The resulting reaction mixture was subjected to filtration with a filter paper, a palladium residue was washed with toluene, and the mixed filtrate was concentrated. Water was added to the residue, and the resulting mixture was subjected to extraction with toluene. An extracted solution was washed with water and saturated brine, dried over anhydrous magnesium sulfate, and concentrated under reduced pressure. The resulting residue was purified by column chromatography (heptane) to obtain compound (T-24) (59.99 g, 181.1 mmol, 95.5%).

Second Step:

Compound (T-24) (15.37 g, 46.40 mmol) obtained in the first step, compound (T-106) (17.25 g, 48.72 mmol) prepared according to a publicly known method, palladium on carbon (1.64 g, 0.769 mmol), Amphos (1.92 mg, 0.0072 mmol), potassium carbonate (12.83 g, 92.81 mmol), toluene (70 mL) of tetrabutylammonium bromide (2.99 g, 9.28 mmol), solmix (70 mL) and an aqueous (70 mL) solution were mixed, and the resulting mixture was heated and refluxed for 2 hours. The resulting reaction mixture was left to cool down to room temperature, and then poured into water and subjected to extraction with toluene. An extracted solution was washed with water and saturated brine, dried over anhydrous magnesium sulfate, and concentrated under reduced pressure. The resulting residue was purified by column chromatography (heptane/ethyl acetate =100/1, volume ratio) and subsequently by recrystallization (2-propanol/ethyl acetate=10/1) to obtain compound (1-5-49) (15.33 g, 27.35 mmol, 58.9%).

$^1$H-NMR (CDCl$_3$; δ ppm): 7.46 (2H, d, J=8.1 Hz), 7.42-7.39 (2H, m), 7.35 (2H, d, J=11.6), 7.24 (2H, d, J=10.7), 7.19 (2H, d, J=8.1), 7.00 (2H, t, J=6.2), 2.64 (2H, t, J=7.7 Hz), 1.61 (2H, quin, J=7.9 Hz), 1.36 (2H, sext, J=7.4), 0.94 (3H, t, J=7.4 Hz).

Physical properties of compound (1-5-49) were as described below.

Phase transition temperature: C 56.4 N 147.3 I.

Maximum temperature (T$_{NI}$)=113.7° C.; dielectric anisotropy (Δε) =36.9; optical anisotropy (Δn)=0.250.

Synthesis Example 14

Synthesis of Compound (1-5-54)

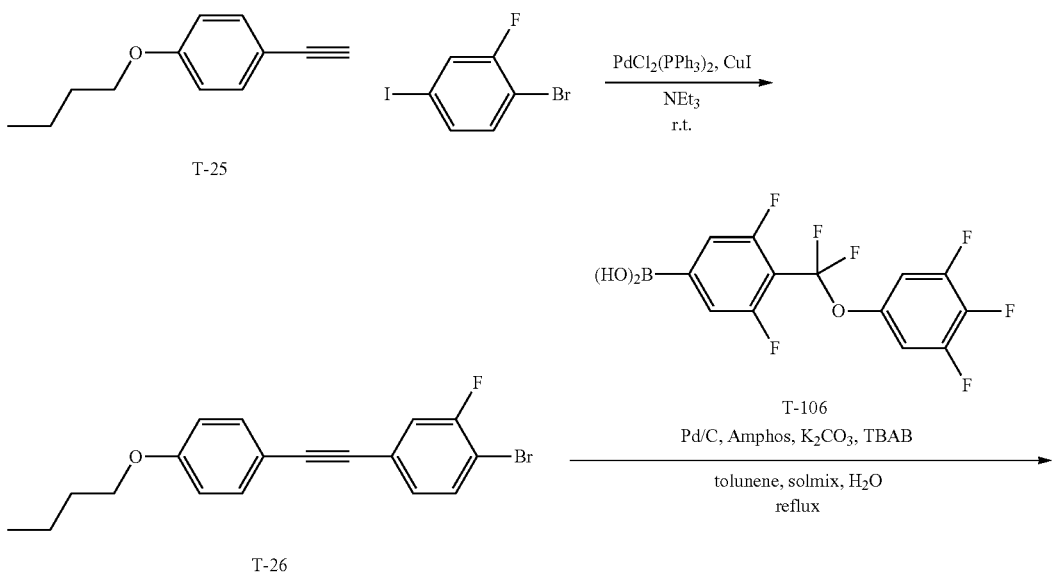

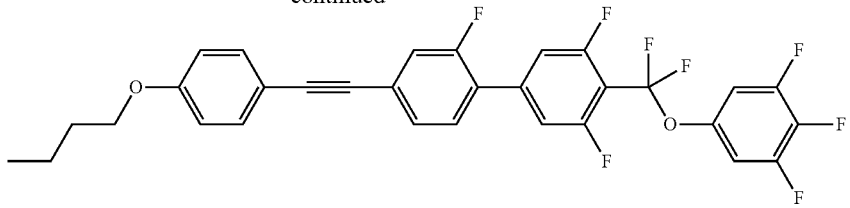

1-5-54

First Step:

Then, 1-bromo-2-fluoro-4-iodobenzene (4.71 g, 15.65 mmol, TCI), bis(triphenylphosphine)palladium(II) dichloride (0.549 g, 0.78 mmol) and a triethylamine (30 mL) solution of copper(I) iodide (0.298 g, 1.57 mmol) were mixed, compound (T-25) (3.00 g, 17.22 mmol) prepared according to a publicly known method was added dropwise thereto, and the resulting mixture was stirred at room temperature for 15 hours. The resulting reaction mixture was subjected to filtration with a filter paper, a palladium residue was washed with toluene, and the mixed filtrate was concentrated. Water was added to the residue, and the resulting mixture was subjected to extraction with toluene. An extracted solution was washed with water (50 mL) and saturated brine (50 mL), dried over anhydrous magnesium sulfate, and concentrated under reduced pressure. The resulting residue was purified by column chromatography (heptane) to obtain compound (T-26) (4.38 g, 13.01 mmol, 83.1).

Second Step:

Compound (T-26) (4.77 g, 13.74 mmol) obtained in the first step, compound (T-106) (5.11 g, 14.42 mmol) prepared according to a publicly known method, palladium on carbon (0.117 g, 0.05 mmol), Amphos (7.29 mg, 0.03 mmol), potassium carbonate (3.80 g, 27.48 mmol), toluene (20 mL) of tetrabutylammonium bromide (0.89 g, 2.75 mmol), sol-mix (20 mL) and an aqueous (20 mL) solution were mixed, and the resulting mixture was heated and refluxed for 9 hours. The resulting reaction mixture was left to cool down to room temperature, and then poured into water and subjected to extraction with toluene. An extracted solution was washed with water and saturated brine, dried over anhydrous magnesium sulfate, and concentrated under reduced pressure. The resulting residue was purified by column chromatography (heptane/ethyl acetate =100/1, volume ratio) and subsequently by recrystallization (2-propanol/ethyl acetate=10/1) to obtain compound (1-5-54) (5.63 g, 9.77 mmol, 71.1%).

$^1$H-NMR (CDCl$_3$; δ ppm): 7.48 (2H, d, J=8.7 Hz), 7.43-7.39 (2H, m), 7.33 (1H, d, J=11.7), 7.24 (2H, d, J=10.7 Hz), 7.00 (2H, t, J=7.4), 6.91 (2H, d, J=8.7), 4.00 (2H, t, J=6.5), 1.80 (2H, quin, J=8.0 Hz), 1.56-1.48 (2H, m), 1.00 (3H, t, J=7.4 Hz).

Physical properties of compound (1-5-54) were as described below.

Phase transition temperature: C 78.7 S$_A$ 92.1 N 183.8I.

Maximum temperature (T$_{NI}$)=136.4° C.; dielectric anisotropy (Δε) =38.8; optical anisotropy (Δn)=0.277.

Synthesis Example 15

Synthesis of Compound (1-5-56)

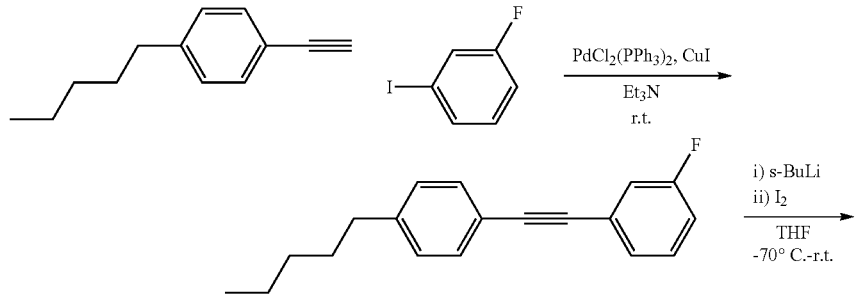

T-27

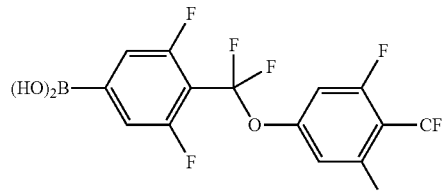

T-107

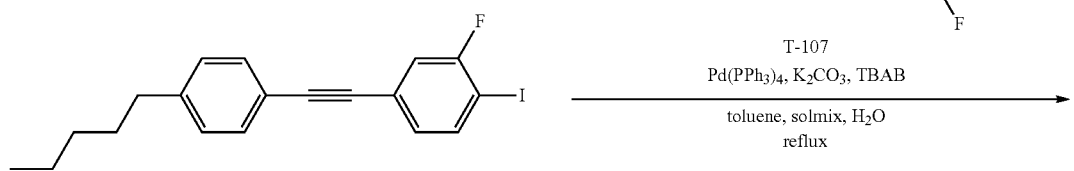

T-28

-continued

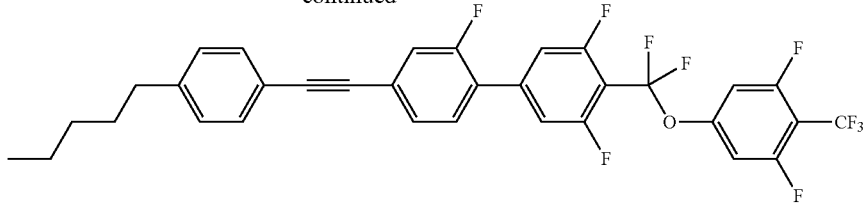

1-5-56

First Step:

Then, 1-fluoro-3-iodobenzene (10.00 g, 45.05 mmol, TCI), bis(triphenylphosphine)palladium(II) dichloride (3.16 g, 4.50 mmol) and a triethylamine (130 mL) solution of copper(I) iodide (0.858 g, 4.50 mmol) were mixed, 1-ethynyl-4-pentylbenzene (8.53 g, 49.55 mmol, ZIEBEN CHEMICALS CO., LTD.) was added dropwise thereto, and the resulting mixture was stirred at room temperature for 16 hours. The resulting reaction mixture was subjected to filtration with a filter paper, a palladium residue was washed with toluene, and the mixed filtrate was concentrated. Water was added to the residue, and the resulting mixture was subjected to extraction with toluene. An extracted solution was washed with water (100 mL) and saturated brine (100 mL), dried over anhydrous magnesium sulfate, and concentrated under reduced pressure. The resulting residue was purified by column chromatography (heptane) to obtain compound (T-27) (11.79 g, 44.26 mmol, 98.3%).

Second step

A THF (120 mL) solution of compound (T 27) (11.74 g, 44.08 mmol) obtained in the first step was cooled down to −70° C., and s-BuLi (48.97 mL, 52.89 mmol) was added dropwise thereto. The resulting mixture was stirred at -70° C. for 6 hours, and then a THF (220 mL) solution of iodine (15.66 g, 61.71 mmol) was added dropwise thereto. The resulting mixture was stirred at -70° C. for 2 hours, and then the resulting reaction mixture was returned to room temperature. The resulting mixture was poured into an aqueous solution of sodium thiosulfate (100 mL) and subjected to extraction with toluene. An extracted solution was washed with water (150 mL) and saturated brine (150 mL), dried over anhydrous magnesium sulfate, and concentrated under reduced pressure. The resulting residue was purified by column chromatography (heptane) to obtain compound (T-28) (16.34 g, 41.66 mmol, 94.5%).

Third Step:

Compound (T-28) (1.70 g, 4.34 mmol) obtained in the second step, compound (T-107) (1.46 g, 3.61 mmol) prepared according to a publicly known method, palladium on carbon (0.0319 g, 0.30 mmol), potassium carbonate (1.00 g, 7.23 mmol), toluene (9 mL) of tetrabutylammonium bromide (0.23 g, 0.72 mmol), solmix (9 mL) and an aqueous (9 mL) solution were mixed, and the resulting mixture was heated and refluxed for 8.5 hours. The resulting reaction mixture was left to cool down to room temperature, and then poured into water and subjected to extraction with toluene. An extracted solution was washed with water and saturated brine, dried over anhydrous magnesium sulfate, and concentrated under reduced pressure. The resulting residue was purified by column chromatography (heptane/ethyl acetate=100/1, volume ratio) and subsequently by recrystallization (2-propanol/ethyl acetate=10/1) to obtain compound (1-5-56) (0.86 g, 1.37 mmol, 37.9%).

$^1$H-NMR (CDCl$_3$; δ ppm): 7.46 (2H, d, J=8.0 Hz), 7.42-7.41 (2H, m), 7.35 (1H, d, J=11.7), 7.25 (2H, d, J=9.2 Hz), 7.19 (2H, d, J =8.1), 6.99 (2H, d, J=9.9), 2.63 (2H, t, J=4.9), 1.63 (2H, quin, J=7.3 Hz), 1.35-1.30 (4H, m), 0.90 (3H, t, J=7.0 Hz).

Physical properties of compound (1-5-56) were as described below.

Phase transition temperature: C 86.8 N 140.0 I.

Maximum temperature $(T_{NI})$=112.4° C.; dielectric anisotropy (Δε) =50.1; optical anisotropy (Δn)=0.244.

Synthesis Example 16

Synthesis of Compound (1-6-49)

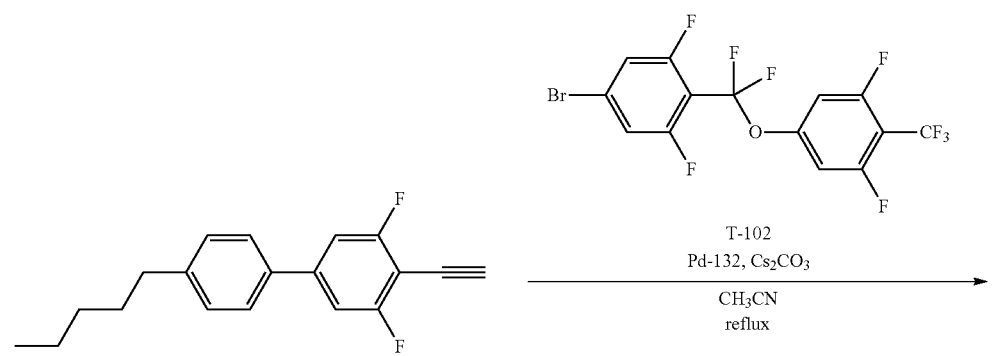

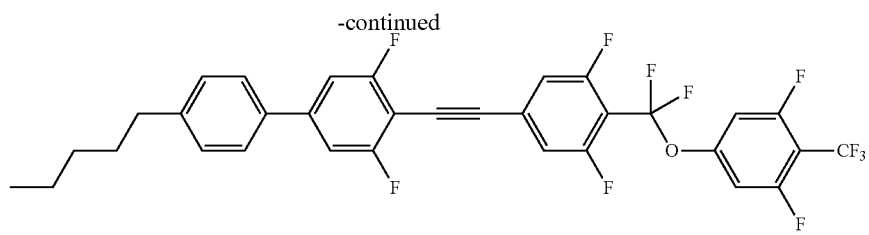

1-6-49

First Step:

Compound (T-29) (3.24 g, 11.4 mmol) prepared according to a publicly known method and compound (T-102) (5.0 g, 11.39 mmol) prepared according to a publicly known method with $PdCl_2(Amphos)_2$ (Pd-132; 0.040 g, 0.06 mmol) and cesium carbonate (7.42 g, 22.78 mmol) were added to acetonitrile (150 mL), and the resulting mixture was heated and refluxed for 4 hours. The resulting reaction mixture was left to cool down to room temperature, and then poured into water (50 mL) and subjected to extraction with toluene. An extracted solution was washed with water (50 mL) and saturated brine (50 mL), dried over anhydrous magnesium sulfate, and concentrated under reduced pressure. The resulting residue was fractionated by column chromatography (eluate: heptane/toluene=4/1 (volume ratio)), and then purified by recrystallization (solvent: heptane/solmix=1/4) to obtain compound (1-6-49) (3.86 g, 6.01 mmol, 52.8).

$^1$H-NMR ($CDCl_3$; δ ppm): 7.47 (2H, d, J=8.15 Hz), 7.27 (2H, d, J =8.15 Hz), 7.17 (2H, d, J=9.85 Hz), 6.96 (2H, d, J=9.75 Hz), 2.64 (2H, t, J=7.65 Hz), 1.64 (2H, quin, J=7.40 Hz), 1.39-1.30 (4H, m), 0.90 (3H, t, J=6.8 Hz).

Physical properties of compound (1-6-49) were as described below. In addition, for measurement of a maximum temperature, optical anisotropy and dielectric anisotropy, a sample in which a ratio of the compound to the base liquid crystal was (5% by weight: 95% by weight) was used.

Phase transition temperature: C1 5.4 C2 100 SmX 107.4 SmA 124.2 N 161.4 Iso.

Maximum temperature (NI)=105.7° C.; dielectric anisotropy (Δε)=60.1; optical anisotropy (Δn)=0.257.

Synthesis Example 17

Synthesis of Compound (1-6-62)

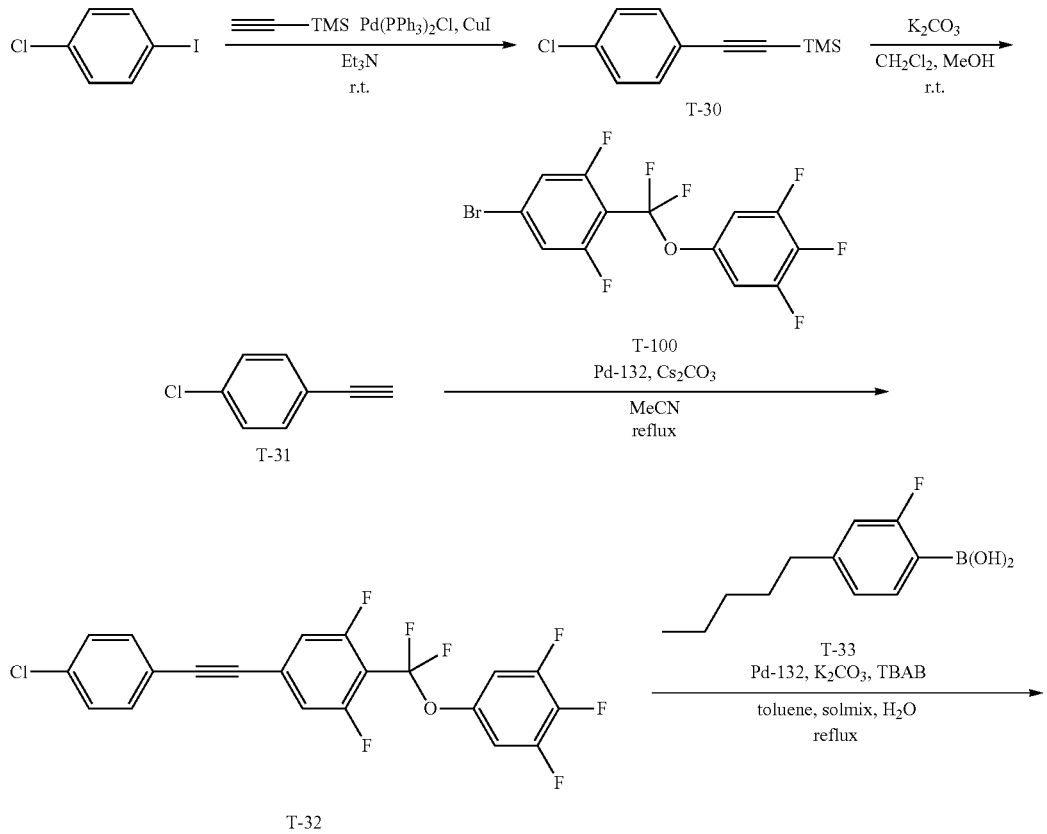

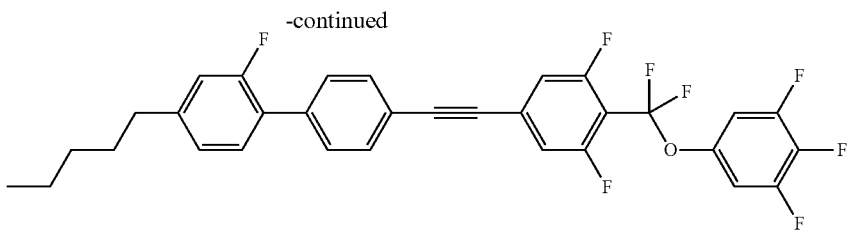

1-6-62

First Step:

Then, 1-chloro-4-iodobenzene (25.00 g, 41.94 mmol, TCI), bis(triphenylphosphine)palladium(II) dichloride (7.36 g, 4.19 mmol) and a triethylamine (250 mL) solution of copper(I) iodide (2.00 g, 4.19 mmol) were mixed, trimethylsilyl acetylene (11.33 g, 46.13 mmol) was added dropwise thereto, and the resulting mixture was stirred at room temperature for 16 hours. The resulting reaction mixture was subjected to filtration with a filter paper, a palladium residue was washed with toluene, and the mixed filtrate was concentrated. Water was added to the residue, and the resulting mixture was subjected to extraction with toluene. An extracted solution was washed with water (150 mL) and saturated brine (150 mL), dried over anhydrous magnesium sulfate, and concentrated under reduced pressure. The resulting residue was purified by column chromatography (heptane) to obtain compound (T-30) (18.87 g, 90.39 mmol, 86.2%).

Second step:,

Compound (T-30) (18.87 g, 90.39 mmol) obtained in the first step was dissolved in dichloromethane (150 mL) and methanol (150 mL). Potassium carbonate (14.99 g, 108.5 mol) was added thereto, and then the resulting mixture was stirred at room temperature for 16 hours. The resulting reaction mixture was poured into water (100 mL) and subjected to extraction with toluene. An extracted solution was washed with water (100 mL) and saturated brine (100 mL), dried over anhydrous magnesium sulfate, and concentrated under reduced pressure. The resulting residue was purified by column chromatography (hexane) to obtain compound (T-31) (9.63 g, 70.51 mmol, 78.0%).

Third step:

Compound (T-100) (11.73 g, 30.14 mmol) prepared according to a publicly known method, PdCl$_2$(Amphos)$_2$ (Pd-132; 0.43 g, 0.60 mmol) and an acetonitrile (120 mL) solution of cesium carbonate (19.64g, 60.28 mmol) were mixed, compound (T-31) (5.94 g, 43.49 mmol) obtained in the second step was added thereto, and the resulting mixture was heated and refluxed for 14 hours. The resulting reaction mixture was left to cool down to room temperature, and then poured into water and subjected to extraction with ethyl acetate. An extracted solution was washed with water and saturated brine, dried over anhydrous magnesium sulfate, and concentrated under reduced pressure. The resulting residue was purified by column chromatography (heptane/ ethyl acetate =100/1, volume ratio) to obtain compound (T-32) (12.20 g, 27.43 mmol, 91.0%).

Fourth Step:

Compound (T-32) (6.88 g, 15.47 mmol) obtained in the third step, compound (T-33) (3.90 g, 18.6 mmol) prepared according to a publicly known method, PdCl$_2$(Amphos)$_2$ (Pd-132; 0.11 g, 0.15 mmol), potassium carbonate (4.27 g, 30.94 mmol), toluene (20 mL) of tetrabutylammonium bromide (1.00 g, 3.09 mmol), solmix (20 mL) and an aqueous (20 mL) solution were mixed, and the resulting mixture was heated and refluxed for 9 hours. The resulting reaction mixture was left to cool down to room temperature, and then poured into water and subjected to extraction with toluene. An extracted solution was washed with water and saturated brine, dried over anhydrous magnesium sulfate, and concentrated under reduced pressure. The resulting residue was purified by column chromatography (heptane/ethyl acetate=100/1, volume ratio) and subsequently by recrystallization (2-propanol/ethyl acetate=10/1) to obtain compound (1-6-62) (4.48 g, 7.80 mmol, 50.4%).

$^1$H-NMR (CDCl$_3$; δ ppm): 7.59 (4H, dd, J=11.9 Hz, 3.2 Hz), 7.35 (1H, t, J=8.1), 7.15 (2H, d, J=9.6), 7.05 (1H, dd, J=9.1 Hz, 1.1 Hz), 7.01-6.97 (3H, m), 2.65 (2H, t, J=7.6 Hz), 1.65 (2H, quin, J=7.4 Hz), 1.37-1.32 (4H, m), 0.91 (3H, t, J=7.0 Hz).

Physical properties of compound (1-6-62) were as described below.

Phase transition temperature: C 84.3 N 145.3 I.

Maximum temperature (T$_{NI}$)=121.0° C.; dielectric anisotropy (Δε) =42.9; optical anisotropy (Δn)=0.257.

Synthesis Example 18

Synthesis of Compound (1-6-83)

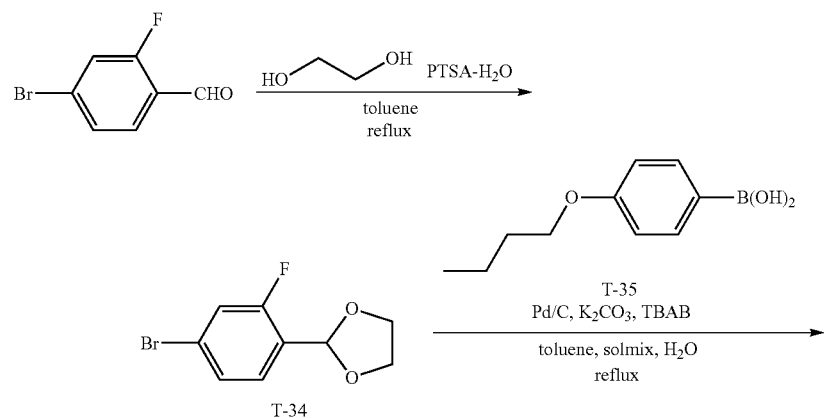

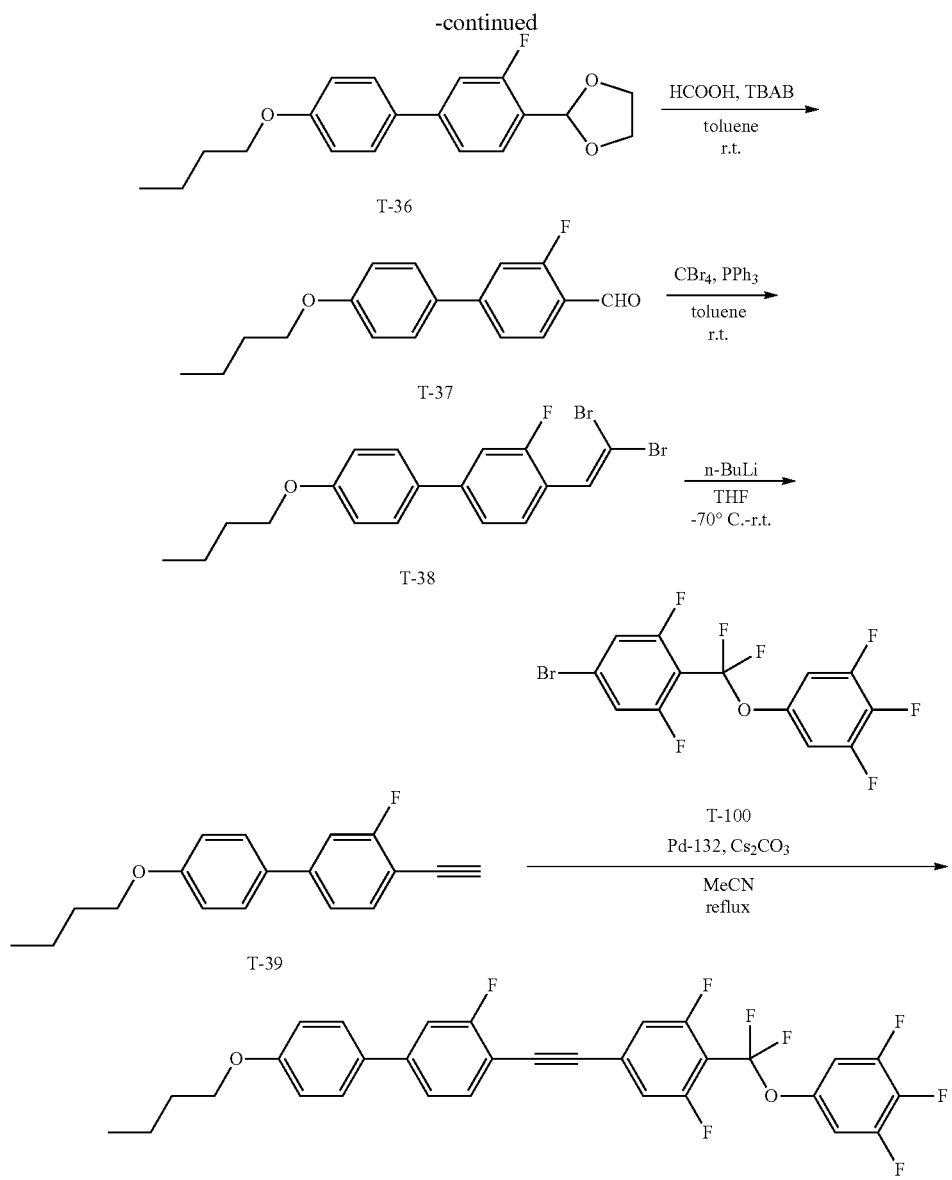

First Step:

Then, 4-bromo-2-fluorobenzaldehyde (10.00 g, 49.26 mmol), ethylene glycol (3.97 g, 64.04 mmol) and a toluene (200 mL) solution of p-toluenesulfonic acid monohydrate (0.47 g, 2.46 mmol) were heated and refluxed for 4 hours. The resulting reaction mixture was poured into saturated sodium hydrogencarbonate and subjected to extraction with ethyl acetate. An extracted solution was washed with water and saturated brine, dried over anhydrous magnesium sulfate, and concentrated under reduced pressure. The resulting residue was purified by column chromatography (heptane/ethyl acetate=20/1, volume ratio) to obtain compound (T-34) (11.49 g, 46.51 mmol, 94.4%).

Second step:

Compound (T-34) (11.49 g, 46.51 mmol) obtained in the first step, compound (T-35) (9.39 g, 48.39 mmol) prepared according to a publicly known method, palladium on carbon (0.41 g, 3.86 mmol), potassium carbonate (12.86 g, 93.01 mmol), toluene (40 mL) of tetrabutylammonium bromide (3.00 g, 9.30 mmol), solmix (40 mL) and an aqueous (40 mL) solution were mixed, and the resulting mixture was heated and refluxed for 9 hours. The resulting reaction mixture was left to cool down to room temperature, and then poured into water and subjected to extraction with toluene. An extracted solution was washed with water and saturated brine, dried over anhydrous magnesium sulfate, and concentrated under reduced pressure. The resulting residue was purified by column chromatography (heptane/ethyl acetate =8/1, volume ratio) to obtain compound (T-36) (12.52 g, 39.57 mmol, 85.1%).

Third Step:

Compound (T-36) (12.52 g, 39.57 mmol) obtained in the second step, formic acid (20.90 mL, 554.0 mmol) and a toluene (125 mL) solution of tetrabutylammonium bromide (0.29 g, 11.87 mmol) were stirred at room temperature for 17.5 hours. The resulting reaction mixture was poured into water and subjected to extraction with ethyl acetate. An extracted solution was washed with water and saturated brine, dried over anhydrous magnesium sulfate, and concentrated under reduced pressure. The resulting residue was purified by column chromatography (heptane/ethyl acetate=20/1, volume ratio) to obtain compound (T-37) (9.68 g, 35.6 mmol, 89.9%).

Fourth step:

Carbon tetrabromide (9.38 g, 28.28 mmol) was added to a toluene solution (70 mL) of triphenylphosphine (14.83 g, 56.55 mmol), and the resulting mixture was stirred at room temperature for 3.5 hours. A toluene (70 mL) solution of compound (T-37) (3.5 g, 12.85 mmol) obtained in the third step was added thereto, and the resulting mixture was stirred for 15 hours. The resulting reaction mixture was poured into water and subjected to extraction with toluene. An extracted solution was washed with water and saturated brine, dried over anhydrous magnesium sulfate, and concentrated under reduced pressure. The resulting residue was purified by column chromatography (heptane/ethyl acetate =10/1) to obtain compound (T-38) (5.36 g, 12.52 mmol, 97.4%).

Fifth Step:

A THF (115 mL) solution of compound (T-38) (11.45 g, 26.74 mmol) obtained in the fourth step was cooled down to −70° C., n-BuLi (33.43 mL, 53.40 mmol) was added dropwise thereto, and the resulting mixture was stirred at −70° C. for 2 hours. The resulting reaction mixture was returned to room temperature, poured into ice water (200 mL) and subjected to extraction with toluene. An extracted solution was washed with water and saturated brine, dried over anhydrous magnesium sulfate, and concentrated under reduced pressure. The resulting residue was purified by column chromatography (heptane/ethyl acetate=100/1) to obtain compound (T-39) (4.60 g, 17.14 mmol, 64.1%)

Sixth Step:

Compound (T-39) (1.50 g, 5.59 mmol) obtained in the fifth step and an acetonitrile (15 mL) solution of compound (T-100) (2.39 g, 6.15 mmol) prepared according to a publicly known method were mixed with $PdCl_2(Amphos)_2$ (Pd-132; 0.15 g, 0.28 mmol) and an acetonitrile (5 mL) solution of cesium carbonate (2.19 g, 6.71 mmol), and the resulting mixture was heated and refluxed for 7.5 hours. The resulting reaction mixture was left to cool down to room temperature, and then poured into water and subjected to extraction with toluene. An extracted solution was washed with water and saturated brine, dried over anhydrous magnesium sulfate, and concentrated under reduced pressure. The resulting residue was purified by column chromatography (heptane/ethyl acetate=40/1) and subsequently by recrystallization (ethyl acetate/2-propanol=1/10, volume ratio) to obtain compound (1-6-83) (0.79 g, 1.37 mmol, 24.5%).

$^1$H-NMR (CDCl$_3$; δ ppm): 7.55-7.52 (3H, m), 7.37 (1H, dd, J=8.1 Hz, 1.7 Hz), 7.33 (1H, dd, J=10.7, 1.2 Hz), 7.18 (2H, d, J=9.6 Hz), 6.99-6.96 (4H, m), 4.02 (2H, t, J=6.5 Hz), 1.80 (2H, quin, J=7.1 Hz), 1.56-1.48 (2H, m), 0.99 (3H, t, J=7.5 Hz).

Physical properties of compound (1-6-83) were as described below. In addition, for measurement of a maximum temperature, optical anisotropy and dielectric anisotropy, a sample in which a ratio of the compound to the base liquid crystal was (10% by weight: 90% by weight) was used.

Phase transition temperature: C 110.3 S$_A$ 144.1 N 196.2 I.

Maximum temperature (T$_{NI}$)=142.7° C.; dielectric anisotropy (Δε) =39.8; optical anisotropy (Δn)=0.287.

Synthesis Example 19

Synthesis of Compound (1-6-86)

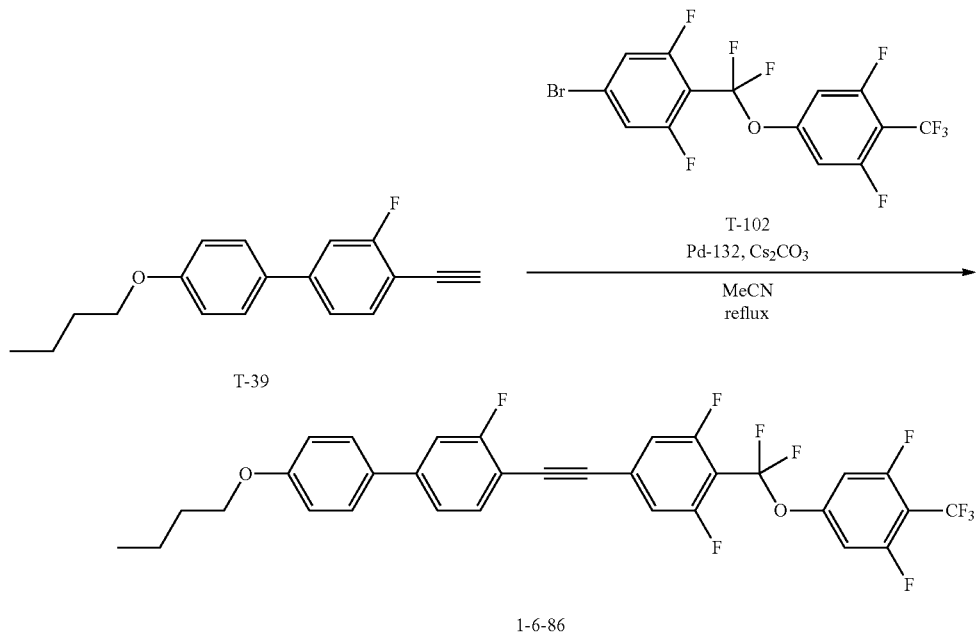

First Step:

Compound (T-39) (1.27 g, 4.73 mmol) prepared according to the previous section and an acetonitrile (10 mL) solution of compound (T-102) (2.18 g, 4.97 mmol) prepared according to a publicly known method were mixed with $PdCl_2(Amphos)_2$ (Pd-132; 0.13 g, 0.24 mmol) and an acetonitrile (5 mL) solution of cesium carbonate (1.85 g, 5.67 mmol), and the resulting mixture was heated and refluxed for 13 hours. The resulting reaction mixture was left to cool down to room temperature, and then poured into water and subjected to extraction with toluene. An extracted solution was washed with water and saturated brine, dried over anhydrous magnesium sulfate, and concentrated under reduced pressure. The resulting residue was purified by column chromatography (heptane/ethyl acetate=40/1) and subsequently by recrystallization (ethyl acetate/2-propanol=1/10, volume ratio) to obtain compound (1-6-86) (0.64 g, 1.02 mmol, 21.6%).

$^1$H-NMR (CDCl$_3$; δ ppm): 7.55-7.51 (3H, m), 7.37 (1H, dd, J=8.1 Hz, 1.7 Hz), 7.33 (1H, dd, J=10.7 Hz, 1.5 Hz), 7.19 (2H, d, J=9.6 Hz), 7.00-6.97 (4H, m), 4.02 (2H, t, J=6.6 Hz), 1.80 (2H, quin, J=7.5 Hz), 1.55-1.48 (2H, m), 1.00 (3H, t, J=7.5 Hz).

Physical properties of compound (1-6-86) were as described below. In addition, for measurement of a maximum temperature, optical anisotropy and dielectric anisotropy, a sample in which a ratio of the compound to the base liquid crystal was (3% by weight: 97% by weight) was used.

Phase transition temperature: C 70.8 C 135.0 N 190.7 I.

Maximum temperature (T$_{NI}$)=131.7° C.; dielectric anisotropy (Δε) =51.9; optical anisotropy (Δn)=0.304.

Synthesis Example 20

Synthesis of Compound (1-7-32)

was stirred at −70° C. for 2 hours, and then a THF (500 mL) solution of iodine (139.4 g, 549.2 mmol) was added dropwise thereto, and the resulting reaction mixture was returned to room temperature. The resulting mixture was poured into an aqueous solution of ammonium chloride (100 mL), an aqueous solution of sodium thiosulfate was added thereto, and the resulting mixture was subjected to extraction with hexane. An extracted solution was washed with water and saturated brine, dried over anhydrous magnesium sulfate, and concentrated under reduced pressure. The resulting residue was purified by column chromatography (hexane) to obtain compound (T-40) (100.6 g, 381.0 mmol, 73.0%).

Second step:

Compound (T-40) (60.00 g, 227.2 mmol) obtained in the first step, bis(triphenylphosphine)palladium(II) dichloride (1.629 g, 2.32 mmol) and a triethylamine (500 mL) solution of copper(I) iodide (0.441 g, 2.32 mmol) were mixed, trimethylsilylacetylene (24.88 g, 253.31 mmol) was added dropwise thereto, and the resulting mixture was stirred at room temperature for 3 hours. The resulting reaction mixture was subjected to filtration with a filter paper, a palladium residue was washed with toluene, and the mixed filtrate was

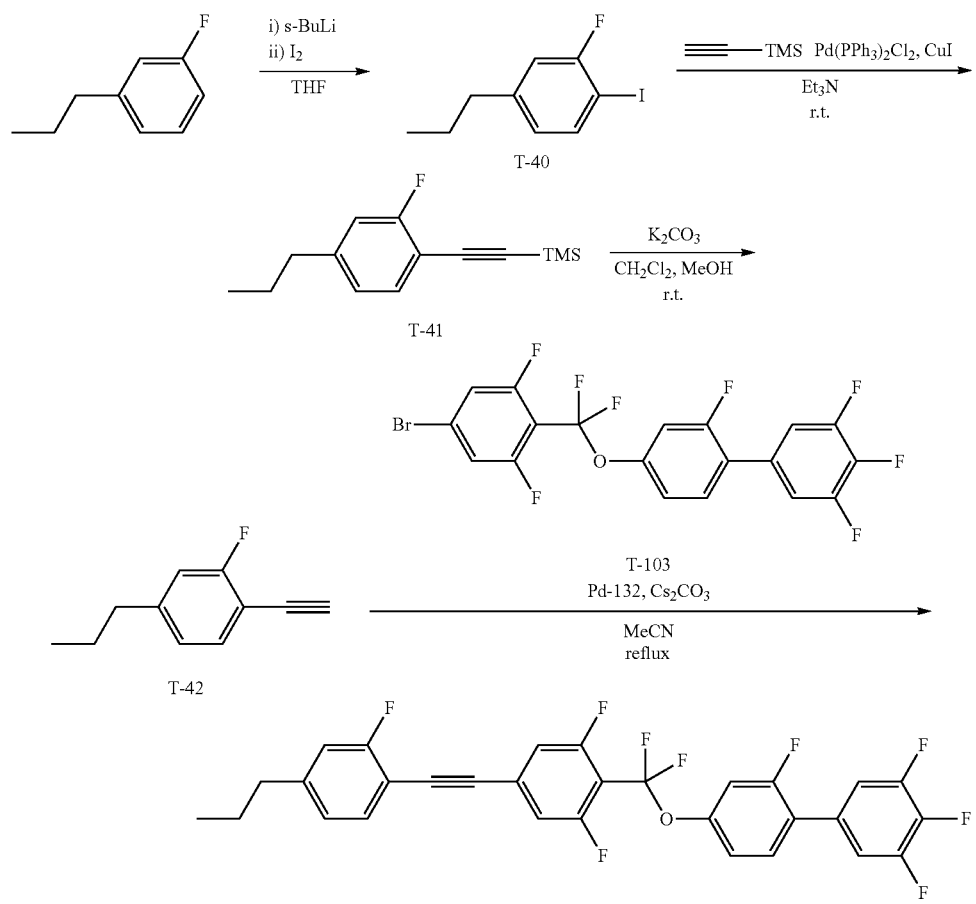

First step:

A THF (500 mL) solution of 1-fluoro-3-propylbenzene (90.91 g, 521.7 mmol, ZIEBEN CHEMICALS CO., LTD.) was cooled down to −70° C., and s-BuLi (500 mL, 540.00 mmol) was added dropwise thereto. The resulting mixture concentrated. Water was added to the residue, and the resulting mixture was subjected to extraction with toluene. An extracted solution was washed with water and saturated brine, dried over anhydrous magnesium sulfate, and concentrated under reduced pressure. The resulting residue was purified by column chromatography (heptane) to obtain compound (T-41) (46.84 g, 199.86 mrnol, 88.0%).

Third step:

Compound (T-41) (52.93 g, 225.83 mmol) obtained in the second step was dissolved in methanol (300 mL). Potassium carbonate (37.62 g, 272.2 mol) was added thereto, and then the resulting mixture was stirred at room temperature for 6 hours. The resulting reaction mixture was poured into water and subjected to extraction with toluene. An extracted solution was washed with water and saturated brine, dried over anhydrous magnesium sulfate, and concentrated under reduced pressure. The resulting residue was purified by column chromatography (heptane/toluene =9/1, volume ratio) to obtain compound (T-42) (36.63 g, 225.83 mmol, 92.6%).

Fourth Step:

Compound (T-42) (3.56 g, 21.95 mmol) obtained in the third step and an acetonitrile (80 mL) solution of compound (T-103) (10.00 g, 20.70 mmol) prepared according to a publicly known method were mixed with $PdCl_2(Amphos)_2$ (Pd-132; 0.076 g, 0.11 mmol) and cesium carbonate (13.56 g, 41.62 mmol), and the resulting mixture was heated and refluxed for 4 hours. The resulting reaction mixture was left to cool down to room temperature, and then poured into water and subjected to extraction with toluene. An extracted solution was washed with water and saturated brine, dried over anhydrous magnesium sulfate, and concentrated under reduced pressure. The resulting residue was purified by column chromatography (heptane/toluene=6/1, volume ratio) and subsequently by recrystallization (toluene) to obtain compound (1-7-32) (3.10 g, 5.49 mmol, 26.5%).

$^1$H-NMR (CDCl$_3$; δ ppm): 7.41 (1H, t, J=7.5 Hz), 7.37 (1H, t, J =8.6), 7.18-7.13 (6H, m), 6.98-6.94 (2H, m), 2.61 (2H, t, J=7.5 Hz), 1.62 (2H, sext, J=7.6 Hz), 0.95 (3H, t, J=7.4 Hz).

Physical properties of compound (1-7-32) were as described below. In addition, for measurement of a maximum temperature, optical anisotropy and dielectric anisotropy, a sample in which a ratio of the compound to the base liquid crystal was (3% by weight: 97% by weight) was used.

Phase transition temperature: C 118.8 N 132.5 I.

Maximum temperature ($T_{NI}$)=88.4° C.; dielectric anisotropy (Δε)=55.2; optical anisotropy (Δn)=0.237.

Synthesis Example 21

Synthesis of Compound (1-8-9)

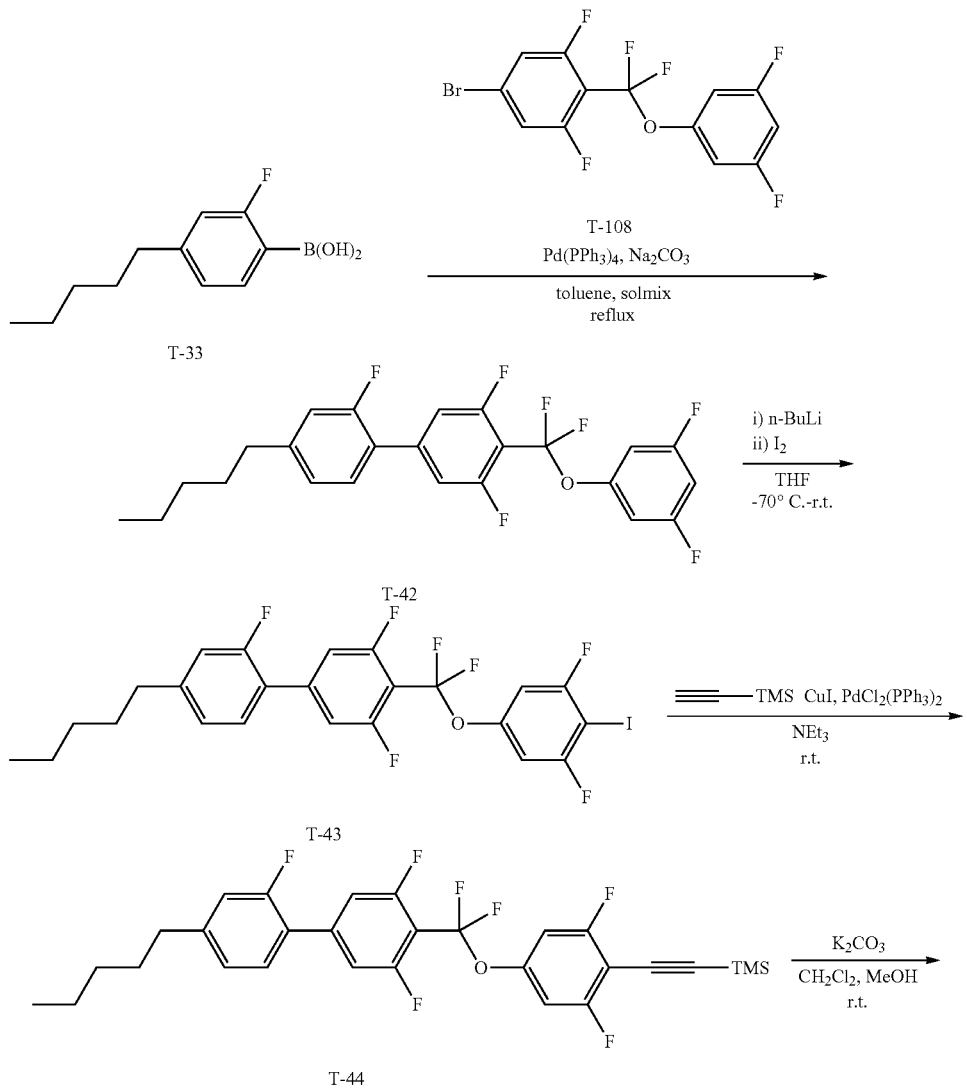

-continued

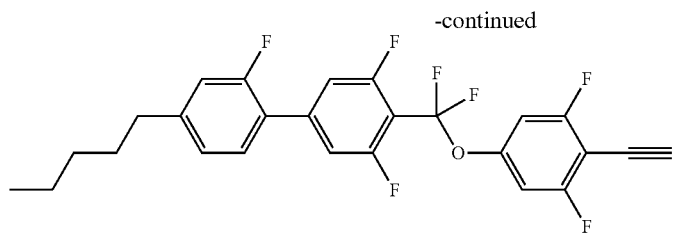

T-45

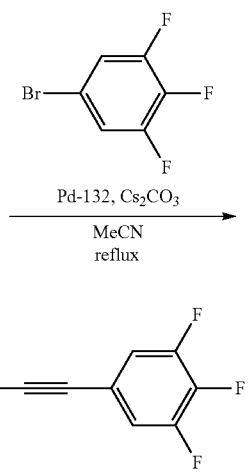

Pd-132, Cs₂CO₃
MeCN
reflux 1-8-9

First step:

Compound (T-108) (5.00 g, 13.47 mmol) prepared according to a publicly known method, toluene (35 mL) of tetrakis(triphenylphosphine)palladium(0) (0.78 g, 0.67 mmol) and a 2N-potassium carbonate aqueous solution (70 mL) were mixed, a solmix (35 mL) solution of compound (T-33) (3.11 g, 14.82 mmol) prepared according to a publicly known method was added thereto, and the resulting mixture was heated and refluxed for 5.5 hours. The resulting reaction mixture was left to cool down to room temperature, and then poured into water and subjected to extraction with toluene. An extracted solution was washed with water and saturated brine, dried over anhydrous magnesium sulfate, and concentrated under reduced pressure. The resulting residue was purified by column chromatography (heptane) to obtain compound (T-42) (5.81 g, 12.73 mmol, 94.5%).

Second Step:

A THF (80 mL) solution of compound (T-42) (5.89 g, 12.91 mmol) obtained in the first step was cooled down to −70° C., n-BuLi (8.87 mL, 14.20 mmol) was added dropwise thereto, the resulting mixture was stirred at −70° C. for 2 hours, and a THF (30 mL) solution of iodine (3.93 g, 15.49 mml) was added dropwise thereto. The resulting reaction mixture was returned to 0° C., poured into an aqueous solution of sodium sulfite and subjected to extraction with toluene. An extracted solution was washed with water and saturated brine, dried over anhydrous magnesium sulfate, and concentrated under reduced pressure. The resulting residue was purified by column chromatography (heptane) to obtain compound (T-43) (5.01 g, 11.89 mmol, 92.1%).

Third Step:

Compound (T-43) (5.44 g, 9.34 mmol) obtained in the second step, bis(triphenylphosphine)palladium(II) dichloride (0.656 g, 0.93 mmol) and a triethylamine (110 mL) solution of copper(I) iodide (0.178 g, 0.93 mmol) were mixed, trimethylsilylacetylene (1.44 mL, 10.28 mmol) was added dropwise thereto, and the resulting mixture was stirred at room temperature for 4 hours. The resulting reaction mixture was subjected to filtration with a filter paper, a palladium residue was washed with toluene, and the mixed filtrate was concentrated. Water was added to the residue, and the resulting mixture was subjected to extraction with toluene. An extracted solution was washed with water and saturated brine, dried over anhydrous magnesium sulfate, and concentrated under reduced pressure. The resulting residue was purified by column chromatography (heptane/ethyl acetate=100/1) to obtain compound (T-44) (4.90 g, 8.87 mmol, 95.0%).

Fourth Step:

Compound (T-44) (4.90 g, 8.87 mmol) obtained in the third step was dissolved in dichloromethane (25 mL) and methanol (25 mL). Potassium carbonate (1.47 g, 10.64 mol) was added thereto, and then the resulting mixture was stirred at room temperature for 2 hours. The resulting reaction mixture was poured into water and subjected to extraction with toluene. An extracted solution was washed with water and saturated brine, dried over anhydrous magnesium sulfate, and concentrated under reduced pressure. The resulting residue was purified by column chromatography (heptane) to obtain compound (T-45) (3.76 g, 7.83 mmol, 88.3%).

Fifth Step:

Compound (T-45) (3.67 g, 7.64 mmol) obtained in the fourth step and an acetonitrile (25 mL) solution of 1-bromo-3,4,5-trifluorobenzene (1.93 g, 9.17 mmol, ZIEBEN CHEMICALS CO., LTD.) were mixed with PdCl₂(Amphos)₂ (Pd-132; 0.027 g, 0.04 mmol) and cesium carbonate (4.98 g, 15.28 mmol), and the resulting mixture was heated and refluxed for 11 hours. The resulting reaction mixture was left to cool down to room temperature, and then poured into water and subjected to extraction with toluene. An extracted solution was washed with water and saturated brine, dried over anhydrous magnesium sulfate, and concentrated under reduced pressure. The resulting residue was purified by column chromatography (heptane) and subsequently by recrystallization (ethyl acetate/2-propanol=1/10, volume ratio) to obtain compound (1-8-9) (1.79 g, 2.93 mmol, 38.4%).

$^1$H-NMR (CDCl₃; δ ppm): 7.33 (1H, t, J=7.9 Hz), 7.23-7.18 (4H, m), 7.07 (1H, dd, J=7.8 Hz, 1.1 Hz), 7.02 (1H, dd, 12.0 Hz, 0.9 Hz), 6.95 (2H, d, J=7.6), 2.65 (2H, t, J=7.7 Hz), 1.65 (2H, quin, J=7.3 Hz), 1.38-1.31 (4H, m), 0.91 (3H, t, J=6.8 Hz).

Physical properties of compound (1-8-9) were as described below. In addition, for measurement of a maximum temperature, optical anisotropy and dielectric anisotropy, a sample in which a ratio of the compound to the base liquid crystal was (5% by weight: 95% by weight) was used.

Phase transition temperature: C 97.2 N 134.0 I.

Maximum temperature ($T_{NI}$)=83.7° C.; dielectric anisotropy (Δε)=52.1; optical anisotropy (Δn)=0.217.

Synthesis Example 22

Synthesis of Compound (1-10-24)

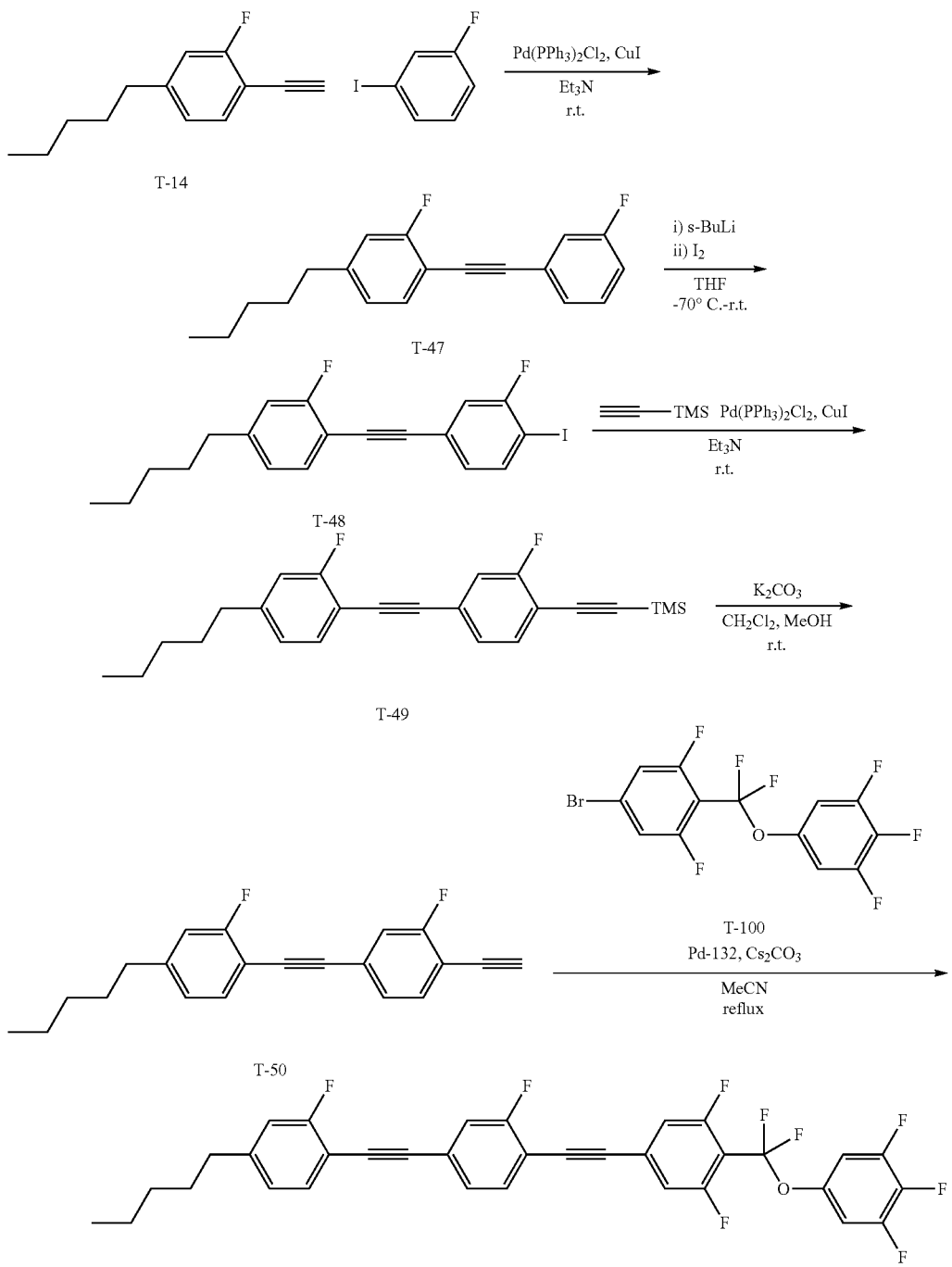

First step:

Then, 1-fluoro-3-iodobenzene (4.24 g, 22.30 mmol), bis(triphenylphosphine)palladium(II) dichloride (1.42 g, 2.03 mmol) and a triethylamine (67.5 mL) solution of copper(I) iodide (0.386 g, 2.03 mmol) were mixed, compound (T-14) (4.50 g, 20.27 mmol) was added dropwise thereto, and the resulting mixture was stirred at room temperature for 2 hours. The resulting reaction mixture was subjected to filtration with a filter paper, a palladium residue was washed with toluene, and the mixed filtrate was concentrated. Water was added to the residue, and the resulting mixture was subjected to extraction with toluene. An extracted solution was washed with water and saturated brine, dried over anhydrous magnesium sulfate, and concentrated under reduced pressure. The resulting residue was purified by column chromatography (heptane) to obtain compound (T-47) (5.12 g, 18.00 mmol, 88.8%).

Second step:

A THF (90 mL) solution of compound (T 47) (5.56 g, 19.55 mmol) obtained in the first step was cooled down to −70° C., and s-BuLi (22.78 mL, 23.78 mmol) was added dropwise thereto. The resulting mixture was stirred at −70° C. for 3 hours, and then a THF (20 mL) solution of iodine (6.20 g, 24.44 mmol) was added dropwise thereto, and the resulting reaction mixture was returned to room temperature. The resulting mixture was poured into an aqueous solution of sodium thiosulfate (100 mL) and subjected to extraction with toluene. An extracted solution was washed with water and saturated brine, dried over anhydrous magnesium sulfate, and concentrated under reduced pressure. The resulting residue was purified by column chromatography (heptane) to obtain compound (T-48) (7.93 g, 19.33 mmol, 98.9%).

Third step:

Compound (T-48) (6.32 g, 15.41 mmol) obtained in the second step, bis(triphenylphosphine)palladium(II) dichloride (1.08 g, 1.54 mmol) and a triethylamine (94.8 mL) solution of copper(I) iodide (0.293 g, 1.54 mmol) were mixed, trimethylsilylacetylene (1.66 g, 16.95 mmol) was added dropwise thereto, and the resulting mixture was stirred at room temperature for 6.5 hours. The resulting reaction mixture was subjected to filtration with a filter paper, a palladium residue was washed with toluene, and the mixed filtrate was concentrated. Water was added to the residue, and the resulting mixture was subjected to extraction with toluene. An extracted solution was washed with water and saturated brine, dried over anhydrous magnesium sulfate, and concentrated under reduced pressure. The resulting residue was purified by column chromatography (heptane) to obtain compound (T-49) (4.81 g, 12.64 mmol, 82.1%).

Fourth step:

Compound (T-49) (4.81 g, 12.64 mmol) obtained in the third step was dissolved in dichloromethane (20 mL) and methanol (20 mL). Potassium carbonate (2.10 g, 15.17 mol) was added thereto, and then the resulting mixture was stirred at room temperature for 4.5 hours. The resulting reaction mixture was poured into water and subjected to extraction with toluene. An extracted solution was washed with water and saturated brine, dried over anhydrous magnesium sulfate, and concentrated under reduced pressure. The resulting residue was purified by column chromatography (heptane) to obtain compound (T-50) (3.59 g, 11.64 mmol, 92.1%).

Fifth Step:

Compound (T-50) (2.69 g, 8.73 mmol) obtained in the fourth step and an acetonitrile (30 mL) solution of compound (T-100) (2.83 g, 7.27 mmol) prepared according to a publicly known method were mixed with $PdCl_2(Amphos)_2$ (Pd-132; 0.0258 g, 0.04 mmol) and an acetonitrile (20 mL) solution of cesium carbonate (4.74 g, 14.55 mmol), and the resulting mixture was heated and refluxed for 5 hours. The resulting reaction mixture was left to cool down to room temperature, and then poured into water and subjected to extraction with toluene. An extracted solution was washed with water and saturated brine, dried over anhydrous magnesium sulfate, and concentrated under reduced pressure. The resulting residue was purified by column chromatography (heptane) and subsequently by recrystallization (toluene/2-propanol=1/5, volume ratio) to obtain compound (1-10-24) (2.82 g, 4.58 mmol, 62.9%).

$^1$H-NMR ($CDCl_3$; δ ppm): 7.49 (1H, t, J=7.6 Hz), 7.41 (1H, t, J =7.6), 7.35-7.29 (2H, m), 7.17 (2H, d, J=9.3), 6.99-6.94 (4H, m), 2.62 (2H, t, J=7.7 Hz), 1.62 (2H, quin, J=7.5 Hz), 1.38-1.27 (4H, m), 0.90 (3H, t, J=6.8 Hz).

Physical properties of compound (1-10-24) were as described below.

Phase transition temperature: C 92.5 $S_A$ 112.5 N 187.4 I.

Maximum temperature ($T_{NI}$)=132.4° C.; dielectric anisotropy (Δε) =47.9; optical anisotropy (Δn)=0.324.

Synthesis Example 23

Synthesis of Compound (1-5-57)

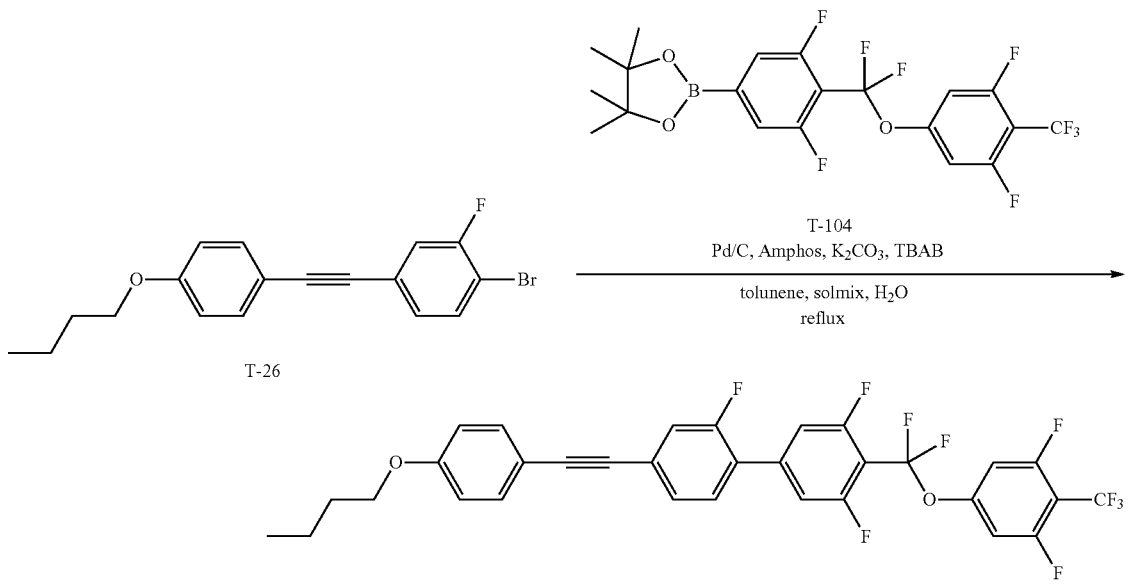

First Step:

Compound (T-26) (2.54 g, 7.33 mmol) prepared according to the previous section, compound (T-104) (3.74 g, 7.69 mmol) prepared according to a publicly known method, palladium on carbon (0.624 g, 0.03 mmol), Amphos (3.89 mg, 0.01 mmol), potassium carbonate (2.03 g, 14.65 mmol), toluene (10 mL) of tetrabutylammonium bromide (0.472 g, 1.47 mmol), solmix (10 mL) and an aqueous (10 mL) solution were mixed, and the resulting mixture was heated and refluxed for 11 hours. The resulting reaction mixture was left to cool down to room temperature, and then poured into water and subjected to extraction with toluene. An extracted solution was washed with water and saturated brine, dried over anhydrous magnesium sulfate, and concentrated under reduced pressure. The resulting residue was purified by column chromatography (heptane/ethyl acetate=100/1, volume ratio) and subsequently by recrystallization (2-propanol/ethyl acetate=10/1) to obtain compound (1-5-57) (3.19 g, 5.09 mmol, 69.5%).

$^1$H-NMR (CDCl$_3$; δ ppm): 7.48 (2H, d, J=4.9 Hz), 7.43-7.38 (2H, m)), 7.33 (1H, d, J=11.9 Hz), 7.28-7.24 (2H, m), 6.99 (2H, d, J =9.9 Hz), 6.89 (2H, d, J=7.0 Hz), 3.99 (2H, t, J=6.5 Hz), 1.79 (2H, quin, J=7.1 Hz), 1.50 (2H, sext, J=7.5 Hz), 0.98 (3H, t, J =7.5 Hz).

Physical properties of compound (1-5-57) were as described below. In addition, for measurement of a maximum temperature, optical anisotropy and dielectric anisotropy, a sample in which a ratio of the compound to the base liquid crystal was (10% by weight: 90% by weight) was used.

Phase transition temperature: C 109.9 N 177.2 I.

Maximum temperature (T$_{NI}$)=127.7° C.; dielectric anisotropy (Δε) =50.1; optical anisotropy (Δn)=0.267.

Synthesis Example 24

Synthesis of Compound (1-6-66)

First Step:
4-bromo-3-phenol (3.50 g, 18.32 mmol, TCI), 1-bromobutane (2.51 g, 18.32 mmol) and an acetone (70 mL) solution of potassium carbonate (5.07 g, 36.65 mmol) were heated and refluxed for 14.5 hours, and then the resulting reaction mixture was returned to room temperature. The resulting mixture was poured into water and subjected to extraction with ethyl acetate. An extracted solution was washed with water and saturated brine, dried over anhydrous magnesium sulfate, and concentrated under reduced pressure. The resulting residue was purified by column chromatography (heptane) to obtain compound (T-51) (4.13 g, 16.71 mmol, 91.2%).

Second Step:
Isopropylmagnesium chloride (9.19 mL, 18.38 mmol) was cooled down to −10° C., a THF solution (35 mL) of compound (T-51) (4.13 g, 16.71 mmol) obtained in the first step was added dropwise thereto, and the resulting mixture was stirred at −10° C. for 2 hours. A THF (5 mL) solution of trimethyl borate (1.91 g, 18.38 mmol) was added dropwise thereto, and the resulting mixture was stirred at −10° C. for 1 hour. The reaction mixture was returned to room temperature, poured into 1N-HCl, stirred for 1 hour, and subjected to extraction with ethyl acetate. An extracted solution was washed with water and saturated brine, dried over anhydrous magnesium sulfate, and concentrated under reduced pressure. Heptane was added to a residue, and the resulting mixture was filtered, and dried under reduced pressure to obtain compound (T-52) (1.32 g, 6.23 mmol, 37.3%).

Third step:
Compound (T-52) (1.32 g, 6.23 mmol) obtained in the second step, compound (T-31) (2.31 g, 5.19 mmol), PdCl$_2$

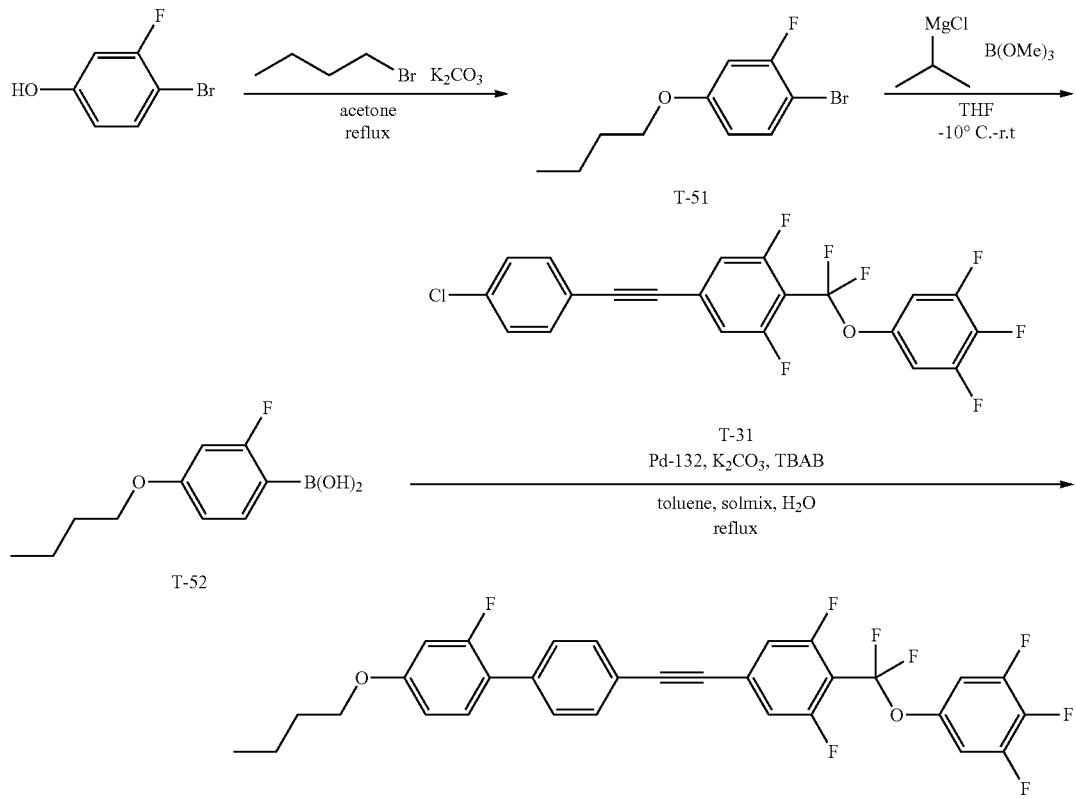

1-6-66

(Amphos)$_2$ (Pd-132; 0.0367 g, 0.05 mmol), potassium carbonate (1.43 g, 10.38 mmol), toluene (7 mL) of tetrabutylammonium bromide (0.334 g, 1.04 mmol), solmix (7 mL) and an aqueous (7 mL) solution were mixed, and the resulting mixture was heated and refluxed for 8.5 hours. The resulting reaction mixture was left to cool down to room temperature, and then poured into water and subjected to extraction with toluene. An extracted solution was washed with water and saturated brine, dried over anhydrous magnesium sulfate, and concentrated under reduced pressure. The resulting residue was purified by column chromatography (heptane/ethyl acetate =100/1, volume ratio) and subsequently by recrystallization (2-propanol/ethyl acetate =10/1) to obtain compound (1-6-66) (0.45 g, 0.78 mmol, 15.1%).

$^1$H-NMR (CDCl$_3$; δ ppm): 7.46 (2H, d, J=8.7 Hz), 7.37 (1H, t, J =8.7 Hz), 7.18-7.13 (4H, m), 7.10 (2H, d, J=9.6 Hz), 6.89 (2H, d, J=8.8 Hz), 3.99 (2H, t, J=6.5 Hz), 1.79 (2H, quin, J=7.1 Hz), 1.50 (2H, sext, J=7.5 Hz), 0.99 (3H, t, J=7.4 Hz).

Physical properties of compound (1-6-66) were as described below. In addition, for measurement of a maximum temperature, optical anisotropy and dielectric anisotropy, a sample in which a ratio of the compound to the base liquid crystal was (5% by weight: 95% by weight) was used.

Phase transition temperature: C 102.8 N 176.5 I.

Maximum temperature (T$_{NI}$)=139.7° C.; dielectric anisotropy (Δε) =40.1; optical anisotropy (Δn)=0.277.

Synthesis Example 25

Synthesis of Compound (1-7-90)

First Step:

Compound (T-25) (1.59 g, 9.15 mmol) prepared according to the previous section and an acetonitrile (35 mL) solution of compound (T-103) (4.02 g, 8.32 mmol) prepared according to a publicly known method were mixed with PdCl$_2$(Amphos)$_2$ (Pd-132; 0.12 g, 0.17 mmol) and an acetonitrile (5 mL) solution of cesium carbonate (1.85 g, 5.67 mmol), and the resulting mixture was heated and refluxed for 7.5 hours. The resulting reaction mixture was left to cool down to room temperature, and then poured into water and subjected to extraction with toluene. An extracted solution was washed with water and saturated brine, dried over anhydrous magnesium sulfate, and concentrated under reduced pressure. The resulting residue was purified by column chromatography (heptane/ethyl acetate=100/1) and subsequently by recrystallization (ethyl acetate/2-propanol=1/10, volume ratio) to obtain compound (1-7-90) (2.66 g, 4.61 mmol, 55.5%).

$^1$H-NMR (CDCl$_3$; δ ppm): 7.59-7.54 (4H, m), 7.36 (1H, t, J=8.8 Hz), 7.15 (2H, d, J=9.5 Hz), 6.98 (2H, dd, J=7.4 Hz, 6.4 Hz), 6.78 (1H, dd, J=8.6 Hz, 2.4 Hz), 6.72 (1H, dd, J=12.8, 2.4 Hz), 4.00 (2H, t, J=6.5 Hz), 1.80 (2H, quin, J=7.1 Hz), 1.51 (2H, sext, J =7.4 Hz), 1.00 (3H, t, J=7.4 Hz).

Physical properties of compound (1-7-90) were as described below.

Phase transition temperature: C 56.7 C 70.0N 151.9 I.

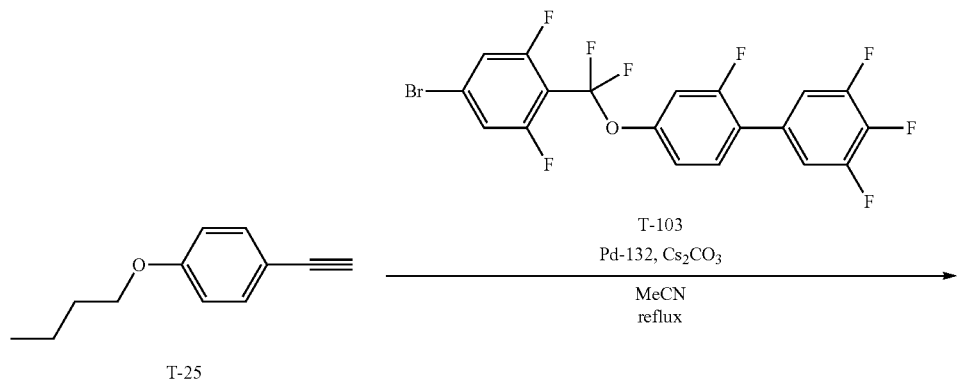

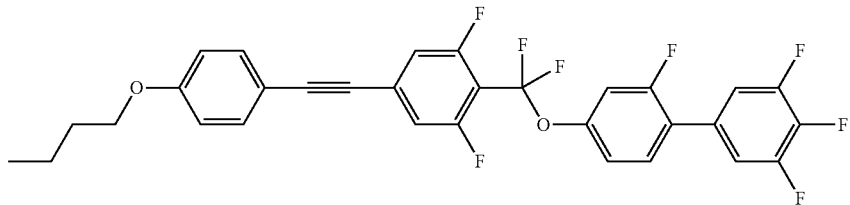

Synthesis Example 26

Synthesis of Compound (1-6-92)

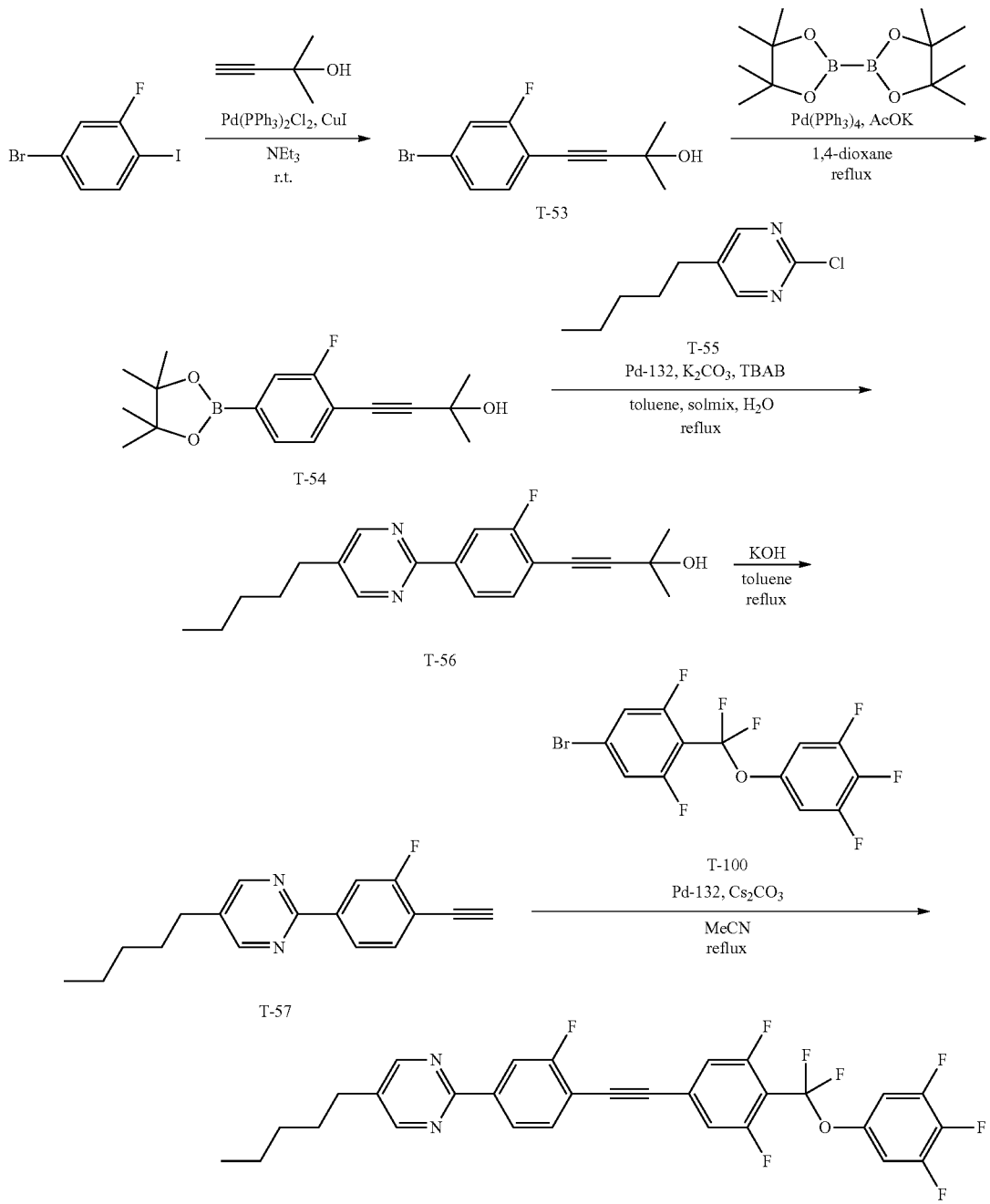

First Step:

Then, 1-bromo-3-fluoro-4-iodobenzene (20.00 g, 66.47 mmol, TCI), bis(triphenylphosphine)palladium(II) dichloride (4.67 g, 6.65 mmol) and a triethylamine (200 mL) solution of copper (I) iodide (1.27 g, 6.65 mmol) were mixed, 2-methyl-3-butyn-2-ol (6.15 g, 73.12 mmol) was added dropwise thereto, and the resulting mixture was stirred at room temperature for 16 hours. The resulting reaction mixture was subjected to filtration with a filter paper, a palladium residue was washed with toluene, and the mixed filtrate was concentrated. Water was added to the residue, and the resulting mixture was subjected to extraction with toluene. An extracted solution was washed with water and saturated brine, dried over anhydrous magnesium sulfate, and concentrated under reduced pressure. The resulting residue was purified by column chromatography (heptane/ethyl acetate=8/1) to obtain compound (T-53) (17.09 g, 66.47 mmol, quantitatively).

Second Step:

Compound (T-53) (17.36 g, 67.52 mmol) obtained in the first step, bis(pinacolate)diboron (18.00 g, 70.90 mmol), potassium acetate (19.88 g, 202.6 mmol) and a 1,4-dioxane (175 mL) solution of tetrakis (triphenylphosphine)palladium (0) (0.780 g, 0.68 mmol) were mixed, and the resulting mixture was heated and refluxed for 11.5 hours. The resulting reaction mixture was left to cool down to room temperature, and then poured into water and subjected to extraction with toluene. An extracted solution was washed with water and saturated brine, dried over anhydrous magnesium sulfate, and concentrated under reduced pressure. The resulting residue was purified by column chromatography (heptane/ethyl acetate=4/1, volume ratio) to obtain compound (T-54) (18.70 g, 61.48 mmol, 91.1%).

Third step:

Compound (T-54) (17.80 g, 59.84 mmol) obtained in the second step, compound (T-55) (9.82 g, 54.40 mmol), PdCl$_2$ (Amphos)$_2$ (Pd-132; 0.377 g, 0.54 mmol), potassium carbonate (14.71 g, 108.8 mmol), toluene (60 mL) of tetrabutylammonium bromide (3.43 g, 10.88 mmol), solmix (60 mL) and an aqueous (60 mL) solution were mixed, and the resulting mixture was heated and refluxed for 8.5 hours. The resulting reaction mixture was left to cool down to room temperature, and then poured into water and subjected to extraction with toluene. An extracted solution was washed with water and saturated brine, dried over anhydrous magnesium sulfate, and concentrated under reduced pressure. The resulting residue was purified by column chromatography (heptane/ethyl acetate =100/1, volume ratio) to obtain compound (T-56) (13.75 g, 42.12 mmol, 79.2%).

Fourth Step:

Compound (T-56) (9.98 g, 30.57 mmol) obtained in the third step and toluene (200 mL) of potassium hydroxide (1.87 g, 33.33 mmol) were mixed, and the resulting mixture was heated and refluxed for 3 hours. The resulting reaction mixture was left to cool down to room temperature, and then poured into an aqueous solution of ammonium chloride and subjected to extraction with toluene. An extracted solution was washed with water and saturated brine, dried over anhydrous magnesium sulfate, and concentrated under reduced pressure. The resulting residue was purified by column chromatography (toluene) to obtain compound (T-57) (8.04 g, 29.87 mmol, 97.7%).

Fifth step:

Compound (T-57) (8.04 g, 29.87 mmol) obtained in the fourth step and an acetonitrile (100 mL) solution of compound (T-100) (11.80 g, 30.33 mmol) prepared according to a publicly known method were mixed with PdCl$_2$(Amphos)2 (Pd-132; 0.107 g, 0.15 mmol) and cesium carbonate (19.56 g, 60.03 mmol), and the resulting mixture was heated and refluxed for 5 hours. The resulting reaction mixture was left to cool down to room temperature, and then poured into water and subjected to extraction with toluene. An extracted solution was washed with water and saturated brine, dried over anhydrous magnesium sulfate, and concentrated under reduced pressure. The resulting residue was purified by column chromatography (heptane/toluene =1/4, volume ratio) and subsequently by recrystallization (toluene/2-propanol =1/1) to obtain compound (1-6-92) (5.90 g, 10.23 mmol, 34.3%).

$^1$H-NMR (CDCl$_3$; δ ppm): 8.65 (2H, s), 8.25 (1H, dd, J =8.2, 1.2), 8.22 (1H, d, J =10.6), 7.62 (1H, t, 7.5 Hz), 7.19 (2H, d, J =9.4 Hz), 6.98 (2H, dd, J =7.2, 6.2 Hz), 2.65 (2H, t, J =7.6 Hz), 1.67 (2H, quin, J =7.5 Hz), 1.37 - 1.35 (4H, m), 0.91 (3H, t, J =6.8 Hz).

Physical properties of compound (1-6-92) were as described below.

Phase transition temperature: C 105.6 SA 153.0 N 181.2 I.

Maximum temperature (T$_{NI}$)=134.4° C.; dielectric anisotropy (Δε)=56.8; optical anisotropy (Δn)=0.270.

Comparative Example 1

For comparison, compound (A) was selected as described below. The reason is that the compound had —CF$_2$O— but had no —C≡C—. Compound (A) was prepared according to the description in WO 96/011897 A.

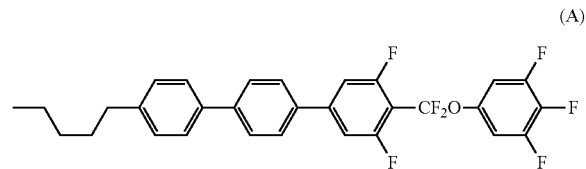

(A)

$^1$H-NMR (CDCl$_3$; δ ppm): 7.68 (2H, d, J=8.5 Hz), 7.63 (2H, d, J=8.5 Hz), 7.55 (2H, d, J=6.8 Hz), 7.30-7.25 (4H, m), 7.00 (2H, dd, J=6.0, 7.5 Hz), 2.65 (2H, t, J=7.5 Hz), 1.65 (2H, quin, J 7.7 Hz), 1.44-1.34 (4H, m), 0.96 (3H, t, J=7.5 Hz)

Physical properties of compound (A) were as described below.

Phase transition temperature: C, 108.6; N, 139.9; I. Maximum temperature (T$_{NI}$)=117.7° C.; dielectric anisotropy (Δε)=25.6; optical anisotropy (Δn)=0.204.

Physical properties of compounds prepared in Synthesis Examples 1 to 24 and 26 and Comparative Example 1 are summarized in Table 1. As a result, compound (1) were found to be excellent in having a larger dielectric anisotropy (Δε) and a larger optical anisotropy (Δn) in comparison with comparative compound (A).

TABLE 1

Physical properties of compound (1)

| Examples | Compounds | Maximum temperature (T$_{NI}$) | Dielectric anisotropy (Δε) | Optical anisotropy (Δn) |
| --- | --- | --- | --- | --- |
| Synthesis Example 1 | Compound (1-6-77) | 125.7° C. | 39.5 | 0.270 |
| Synthesis Example 2 | Compound (1-6-42) | 113.7° C. | 48.9 | 0.257 |
| Synthesis Example 3 | Compound (1-6-11) | 99.7° C. | 54.6 | 0.250 |
| Synthesis Example 4 | Compound (1-5-32) | 103.7° C. | 57.4 | 0.250 |
| Synthesis Example 5 | Compound (1-6-84) | 119.7° C. | 52.8 | 0.264 |
| Synthesis Example 6 | Compound (1-5-50) | 119.0° C. | 37.1 | 0.257 |
| Synthesis Example 7 | Compound (1-7-31) | 84.4° C. | 47.5 | 0.230 |
| Synthesis Example 8 | Compound (1-4-10) | 25.0° C. | 38.6 | 0.164 |
| Synthesis Example 9 | Compound (1-4-32) | 33.0° C. | 32.6 | 0.177 |
| Synthesis Example 10 | Compound (1-5-23) | 97.7° C. | 62.1 | 0.237 |

TABLE 1-continued

| | | Physical properties of compound (1) | | |
|---|---|---|---|---|
| Examples | Compounds | Maximum temperature ($T_{NI}$) | Dielectric anisotropy ($\Delta\epsilon$) | Optical anisotropy ($\Delta n$) |
| Synthesis Example 11 | Compound (1-5-28) | 124.4° C. | 43.4 | 0.264 |
| Synthesis Example 12 | Compound (1-5-31) | 118.4° C. | 58.9 | 0.257 |
| Synthesis Example 13 | Compound (1-5-49) | 113.7° C. | 36.9 | 0.250 |
| Synthesis Example 14 | Compound (1-5-54) | 136.4° C. | 38.8 | 0.277 |
| Synthesis Example 15 | Compound (1-5-56) | 112.4° C. | 50.1 | 0.244 |
| Synthesis Example 16 | Compound (1-6-49) | 105.7° C. | 60.1 | 0.257 |
| Synthesis Example 17 | Compound (1-6-62) | 121.0° C. | 42.9 | 0.257 |
| Synthesis Example 18 | Compound (1-6-83) | 142.7° C. | 39.8 | 0.287 |
| Synthesis Example 19 | Compound (1-6-86) | 131.7° C. | 51.9 | 0.304 |
| Synthesis Example 20 | Compound (1-7-32) | 88.4° C. | 55.2 | 0.237 |
| Synthesis Example 21 | Compound (1-8-9) | 83.7° C. | 52.1 | 0.217 |
| Synthesis Example 22 | Compound (1-10-24) | 132.4° C. | 47.9 | 0.342 |
| Synthesis Example 23 | Compound (1-5-57) | 127.7° C. | 50.1 | 0.267 |
| Synthesis Example 24 | Compound (1-6-66) | 139.7° C. | 40.1 | 0.277 |
| Synthesis Example 26 | Compound (1-6-92) | 134.4° C. | 56.8 | 0.270 |
| Comparative Example 1 | Compound (A) | 117.7° C. | 25.6 | 0.204 |

According to the synthesis method of compound (1) as already described, compounds (1-4-1) to (1-4-45), compounds (1-5-1) to (1-5-99), compounds (1-6-1) to (1-6-124), compounds (1-7-1) to (1-7-117), compounds (1-8-1) to (1-8-115), compounds (1-9-1) to (1-9-104), compounds (1-10-1) to (1-10-90), compounds (1-11-1) to (1-11-24), compounds (1-12-1) to (1-12-55), compounds (1-13-1) to (1-13-57) or compounds (1-14-1) to (1-14-60) are prepared as described below.

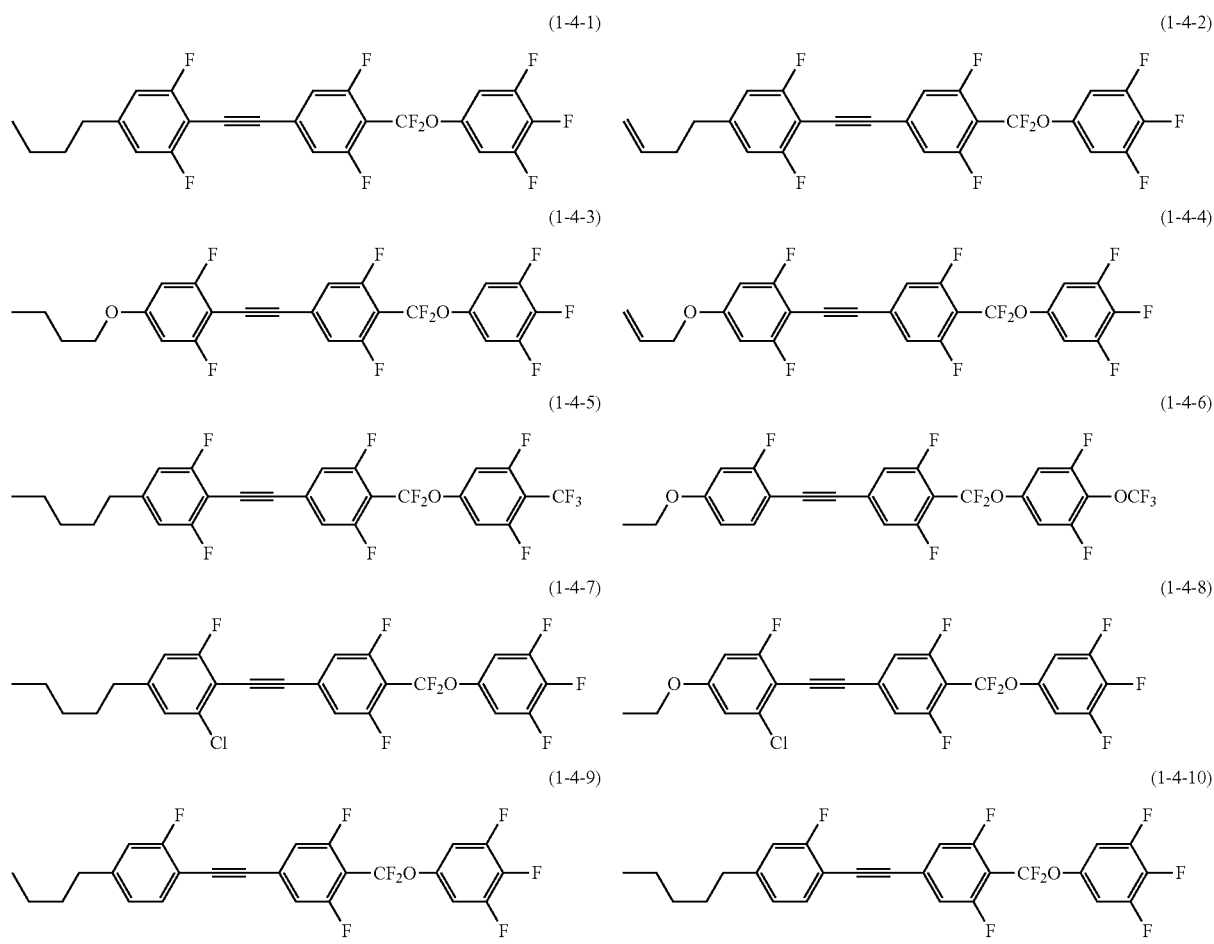

C 4.4 N 16.2 I
$T_{NI} = 25.0°$ C., $\Delta\epsilon = 38.6$, $\Delta n = 0.164$

-continued
(1-4-11)
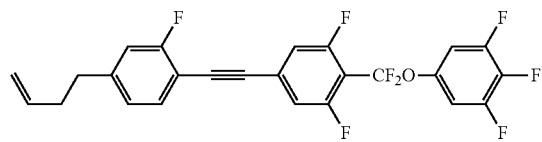
(1-4-12)
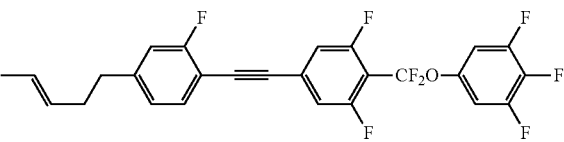
(1-4-13)
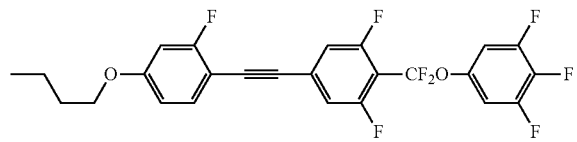
(1-4-14)
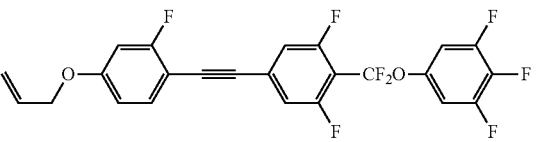
(1-4-15)
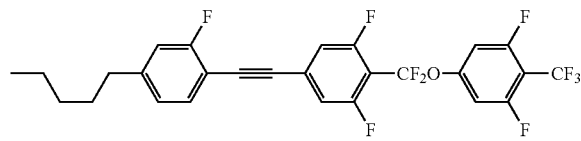
(1-4-16)
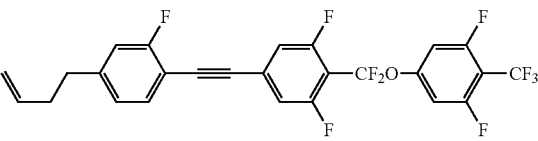
(1-4-17)
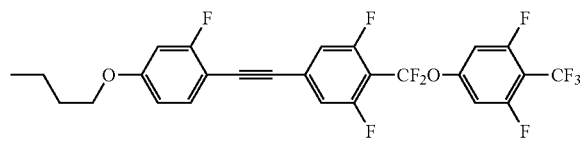
(1-4-18)
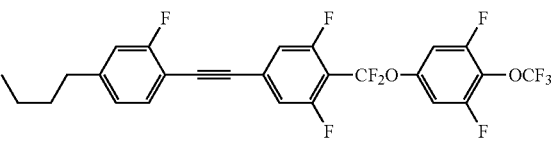
(1-4-19)
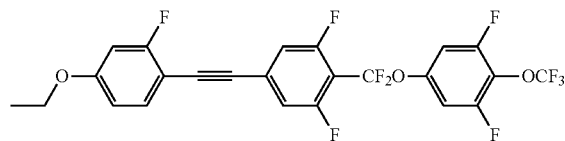
(1-4-20)
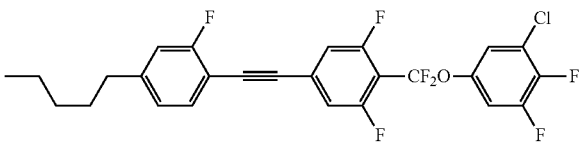
(1-4-21)
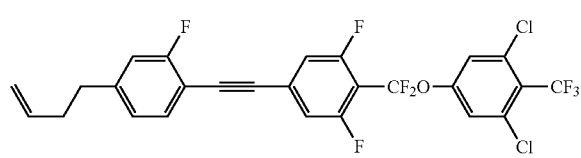
(1-4-22)
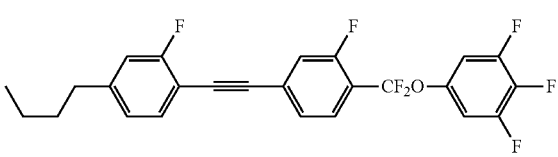
(1-4-23)
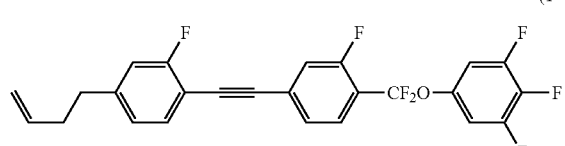
(1-4-24)
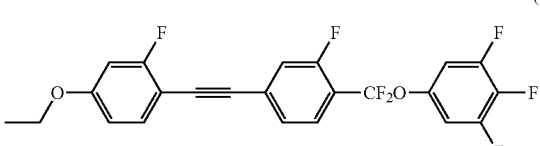
(1-4-25)
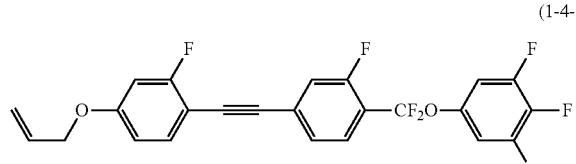
(1-4-26)
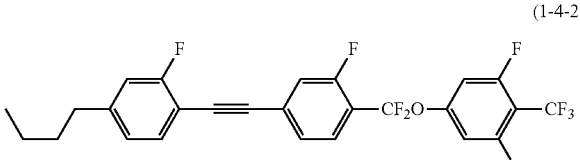
(1-4-27)
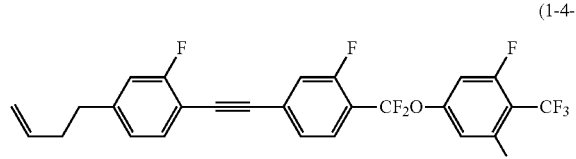
(1-4-28)
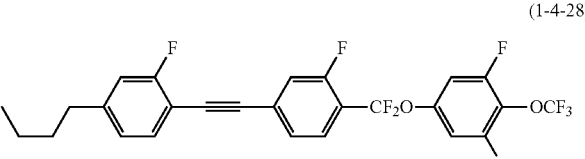

-continued
(1-4-29)
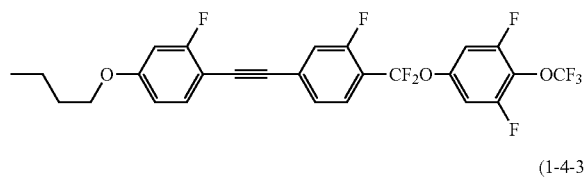
(1-4-30)
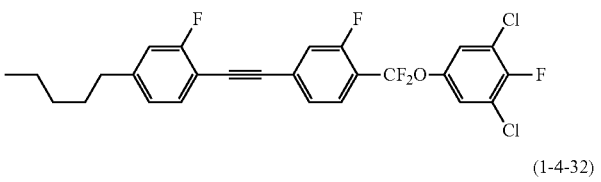
(1-4-31)
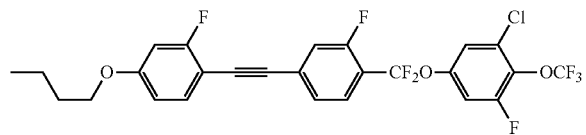
(1-4-32)
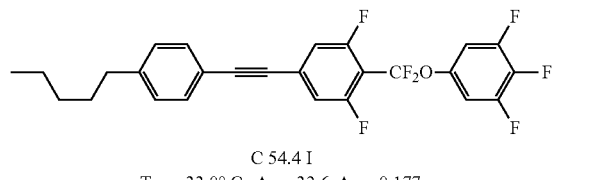
C 54.4 I
$T_{NI}$ = 33.0° C., Δε = 32.6, Δn = 0.177
(1-4-33)
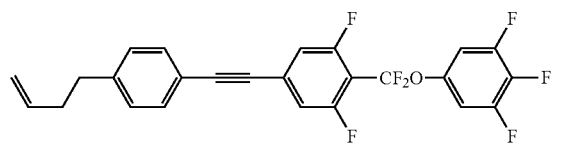
(1-4-34)
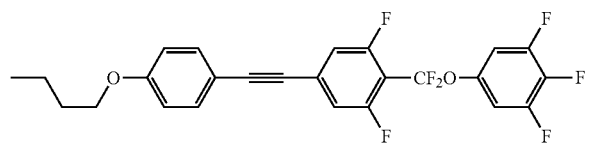
(1-4-35)
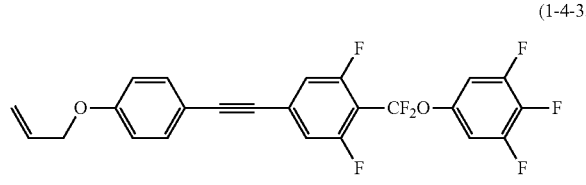
(1-4-36)
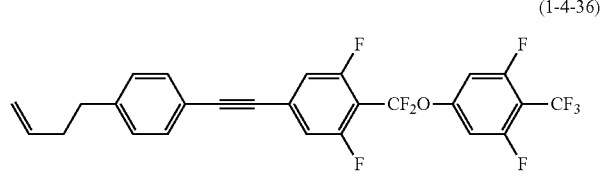
(1-4-37)
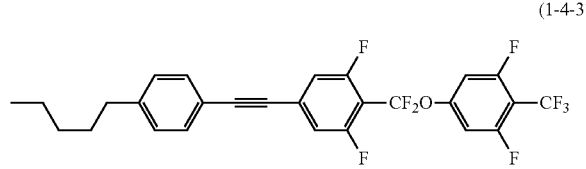
(1-4-38)
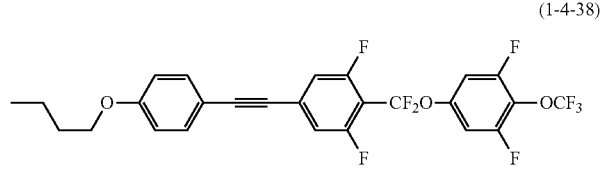
(1-4-39)
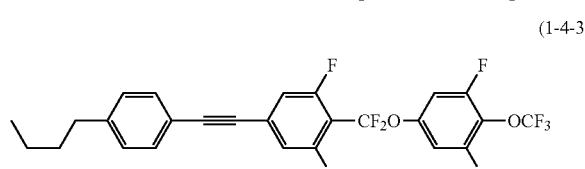
(1-4-40)
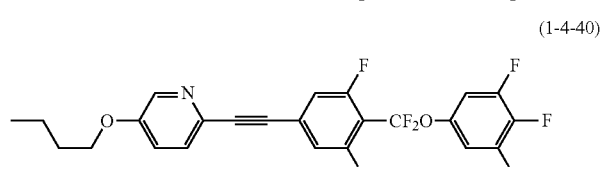
(1-4-41)
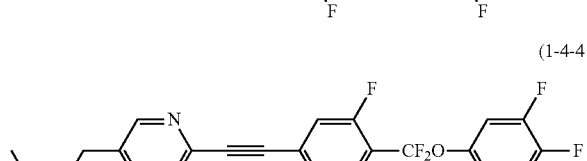
(1-4-42)
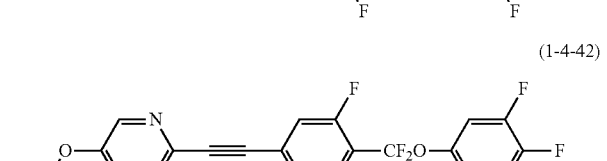
(1-4-43)
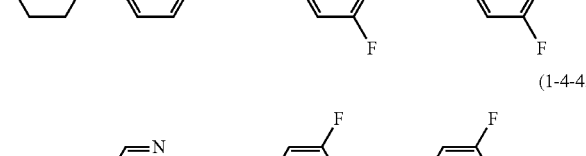
(1-4-44)
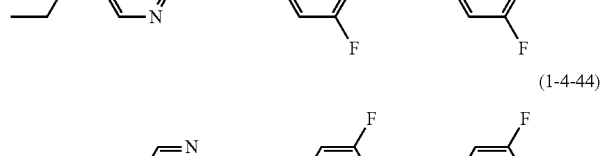
(1-4-45)
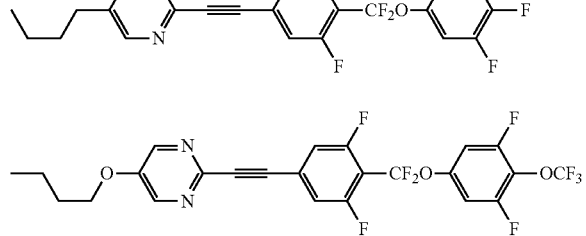

-continued
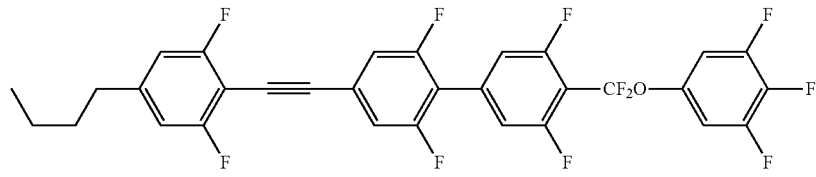
(1-5-1)
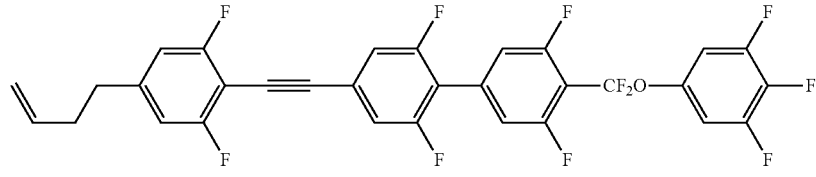
(1-5-2)
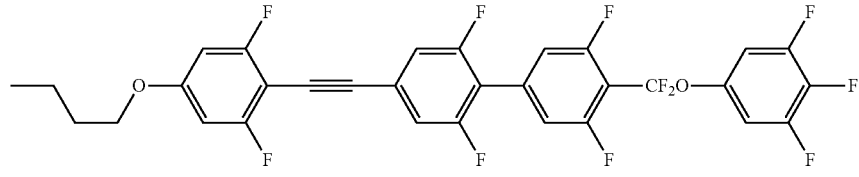
(1-5-3)
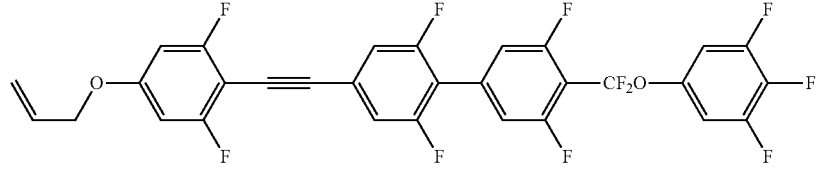
(1-5-4)
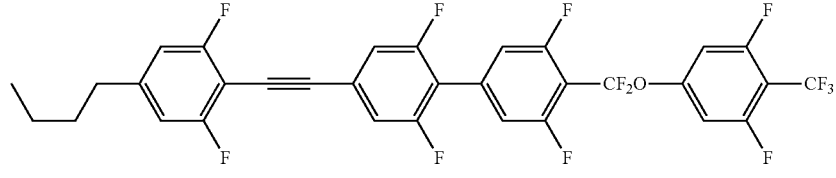
(1-5-5)
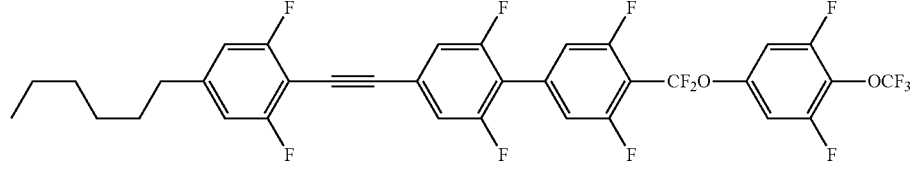
(1-5-6)
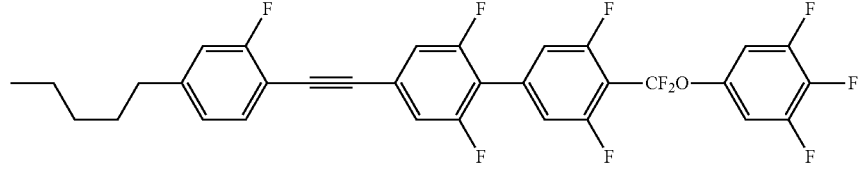
(1-5-7)
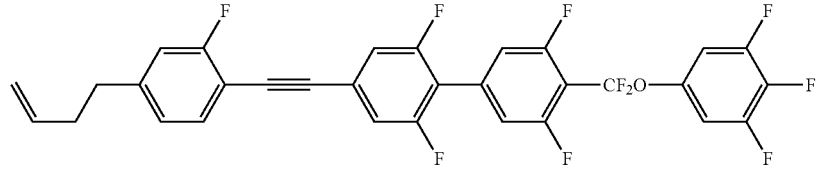
(1-5-8)
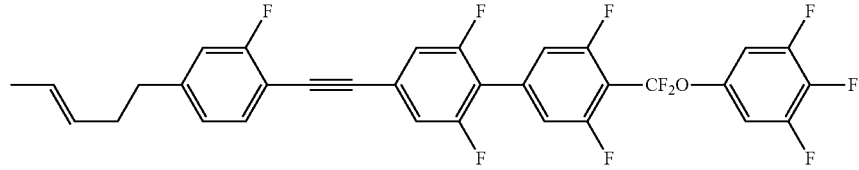
(1-5-9)

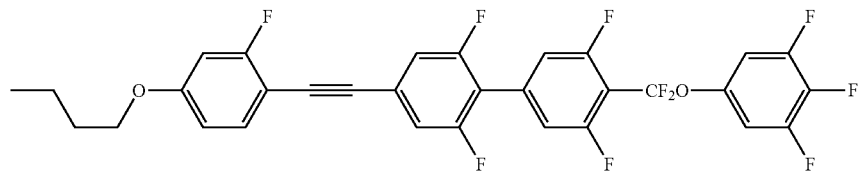
(1-5-10)
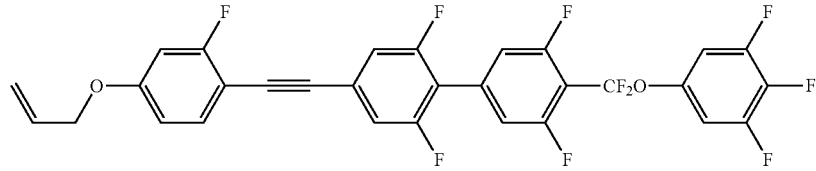
(1-5-11)
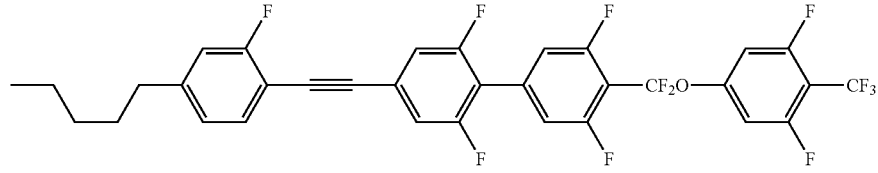
(1-5-12)
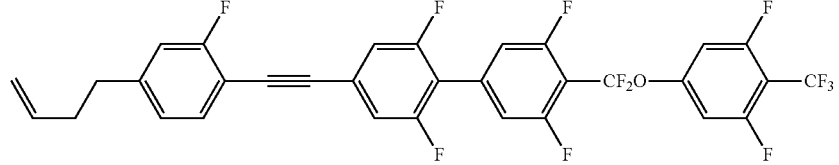
(1-5-13)
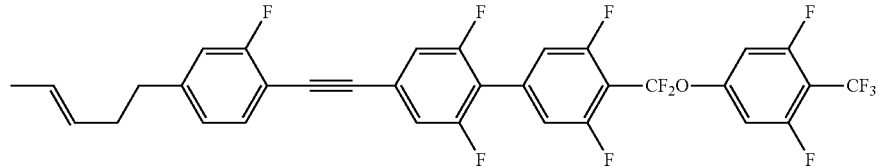
(1-5-14)
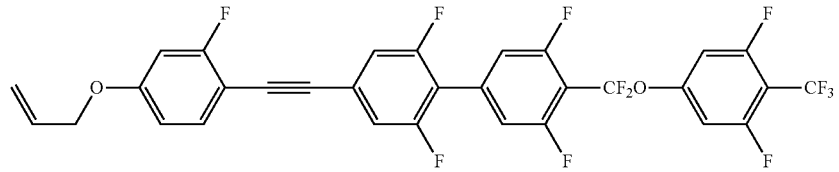
(1-5-15)
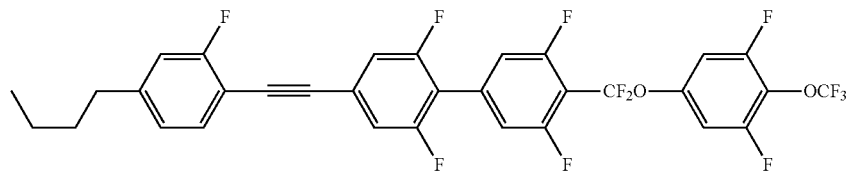
(1-5-16)
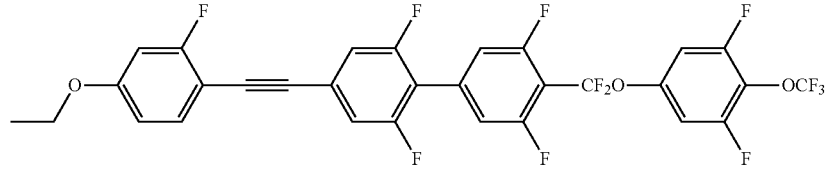
(1-5-17)
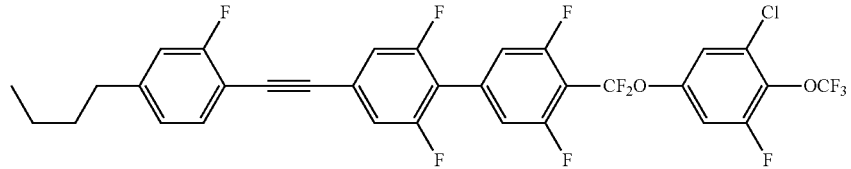
(1-5-18)

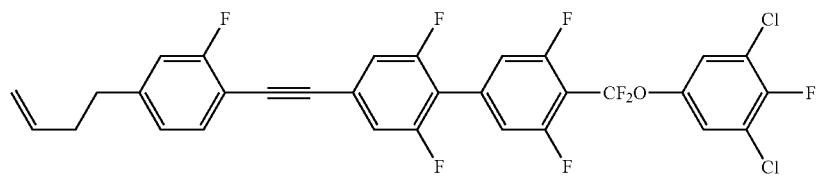
(1-5-19)
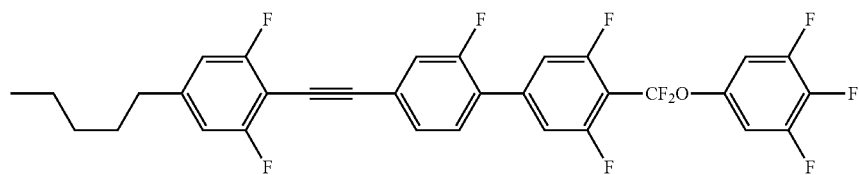
(1-5-20)
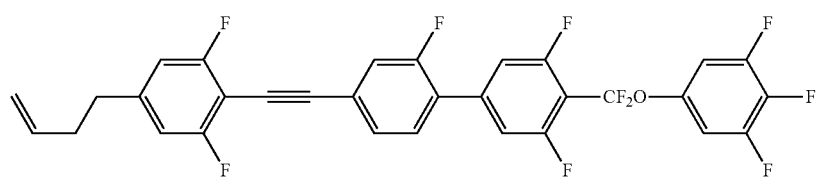
(1-5-21)
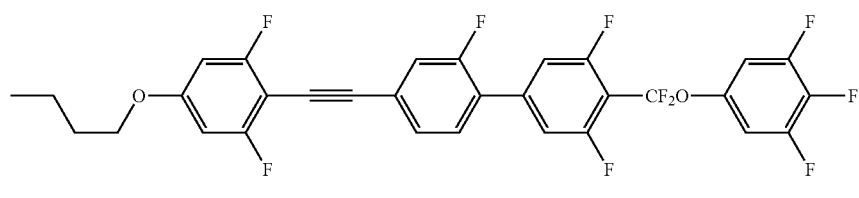
(1-5-22)
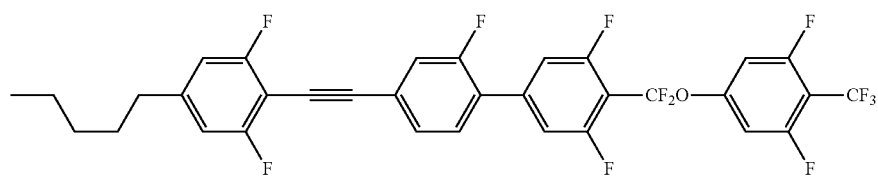
(1-5-23)
C 112.7 SA 133.9 N 163.7 I
$T_{NI}$ = 97.7° C., $\Delta\varepsilon$ = 62.1, $\Delta n$ = 0.237
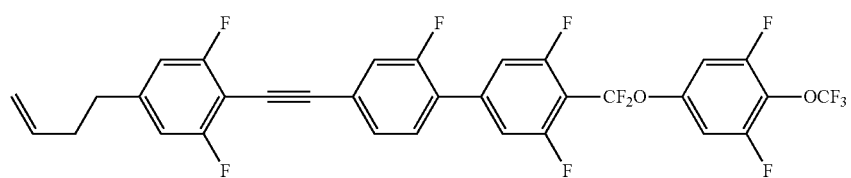
(1-5-24)
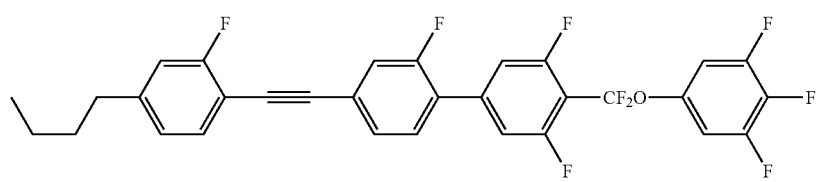
(1-5-25)
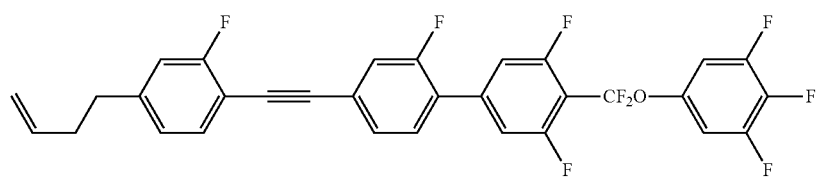
(1-5-26)

(1-5-27)
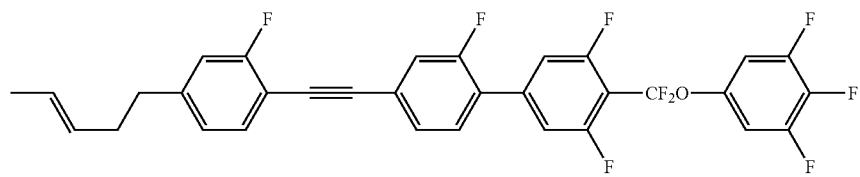
(1-5-28)
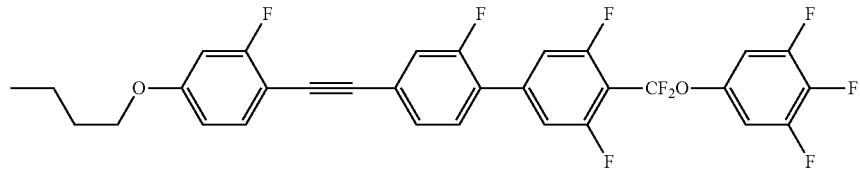
C 82.5 SA 124.9 N 184.3 I
$T_{NI}$ = 124.4° C., Δε = 43.4, Δn = 0.264
(1-5-29)
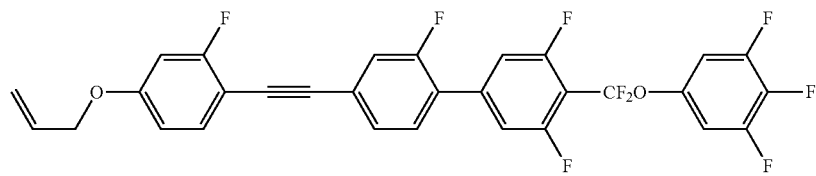
(1-5-30)
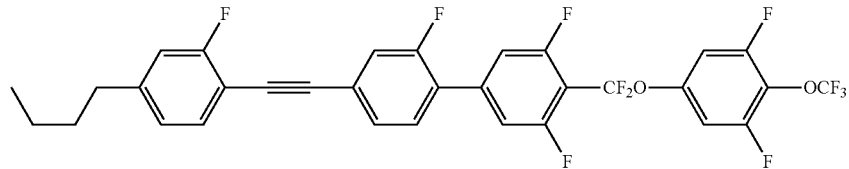
(1-5-31)
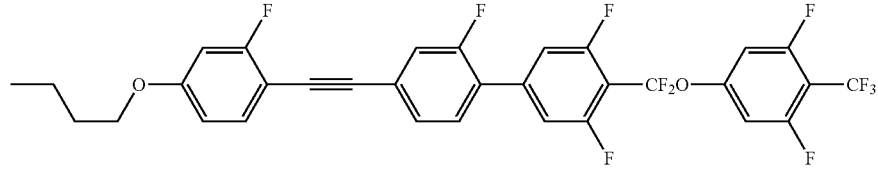
C 80.2 C 88.5 SA 148.3 N 182.8 I
$T_{NI}$ = 118.4° C., Δε = 58.9, Δn = 0.257
(1-5-32)
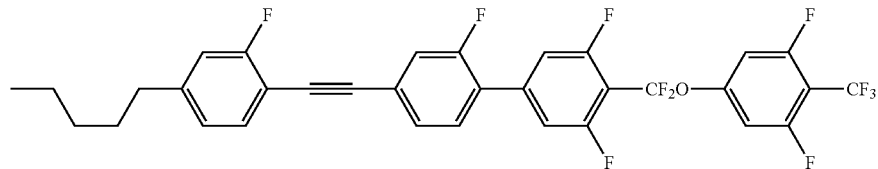
C 79.2 SA 99.2 N 150.6 I
$T_{NI}$ = 103.7° C., Δε = 57.4, Δn = 0.250
(1-5-33)
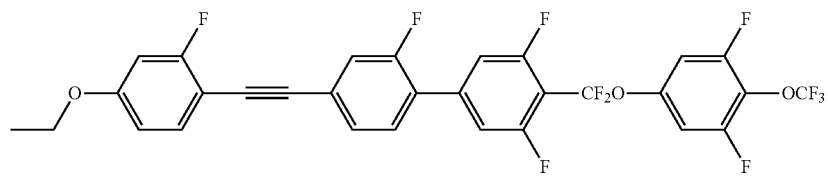
(1-5-34)
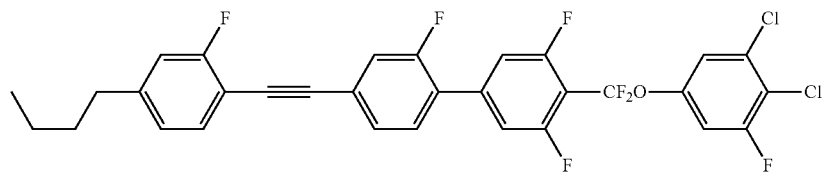

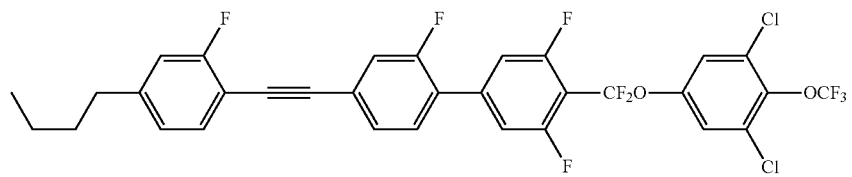 (1-5-35)
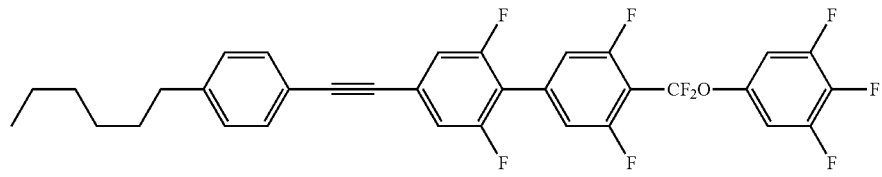 (1-5-36)
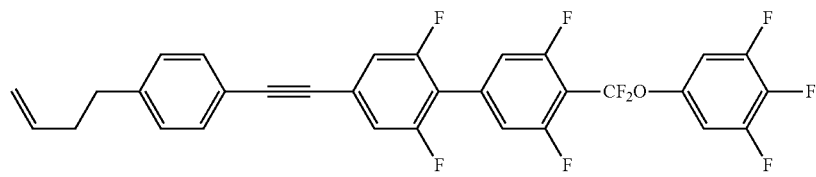 (1-5-37)
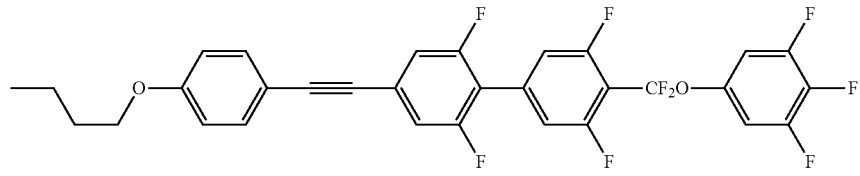 (1-5-38)
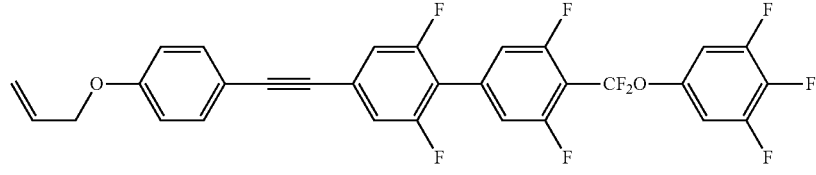 (1-5-39)
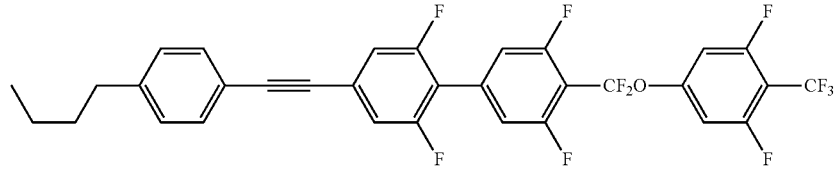 (1-5-40)
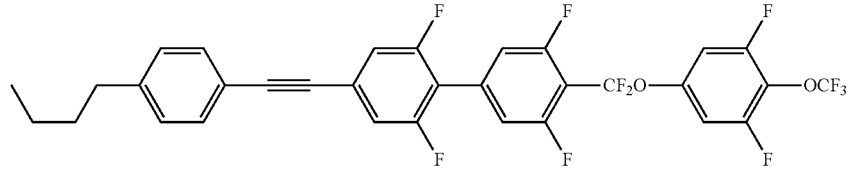 (1-5-41)
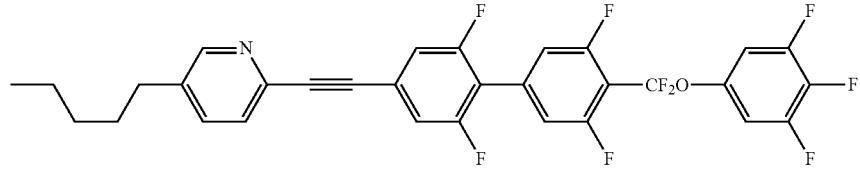 (1-5-42)
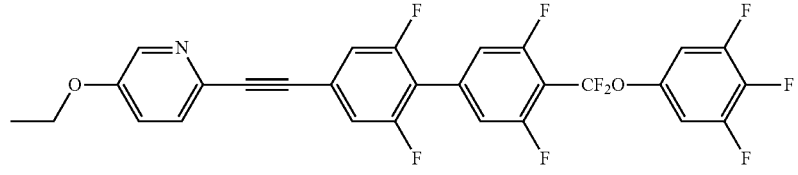 (1-5-43)

-continued
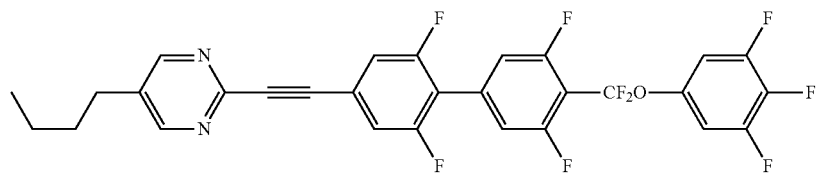
(1-5-44)
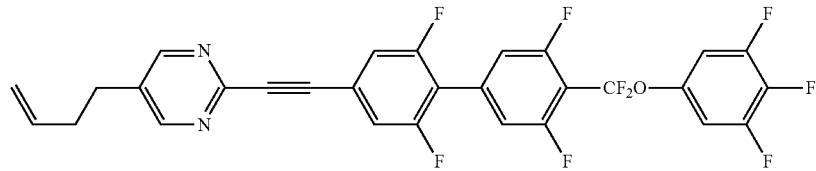
(1-5-45)
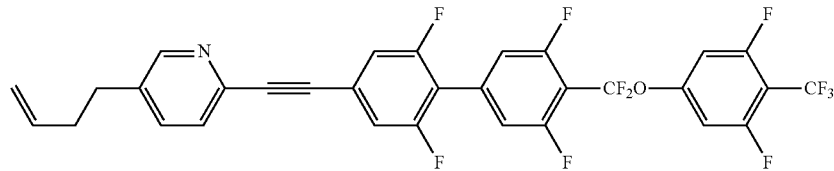
(1-5-46)
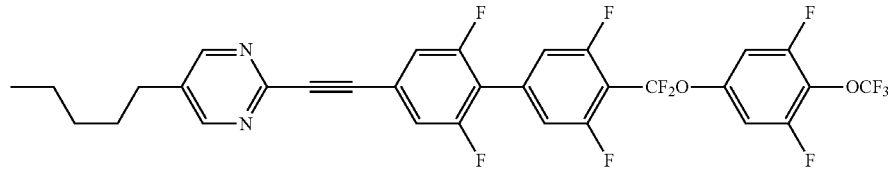
(1-5-47)
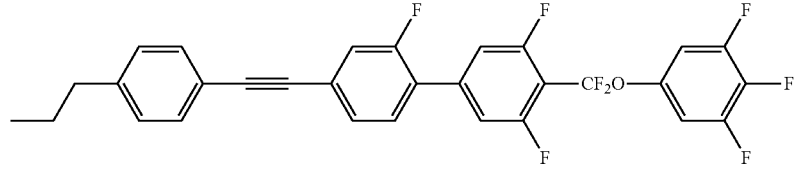
(1-5-48)
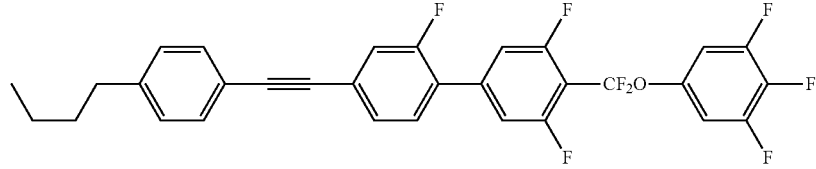
(1-5-49)
C 56.4 N 147.3 I
$T_{NI}$ = 113.7° C., Δε = 36.9, Δn = 0.203
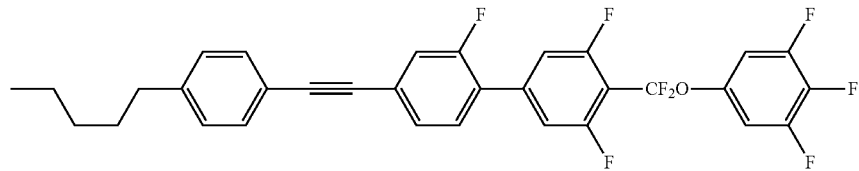
(1-5-50)
C 63.3 N 149.3 I
$T_{NI}$ = 119.0° C., Δε = 37.1, Δn = 0.257
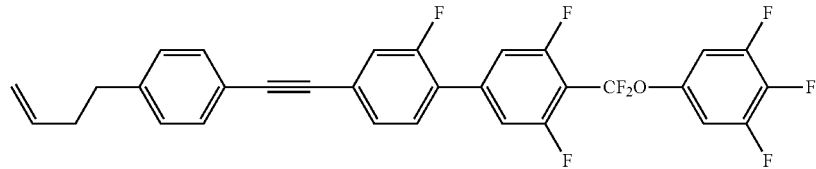
(1-5-51)

-continued
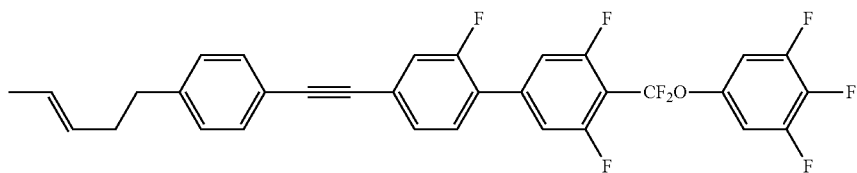
(1-5-52)
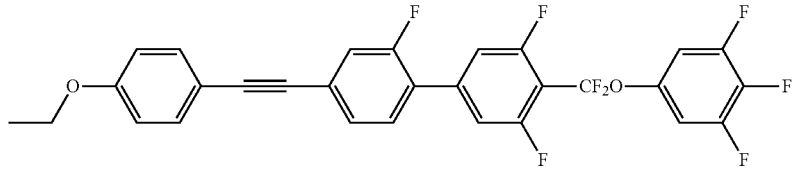
(1-5-53)
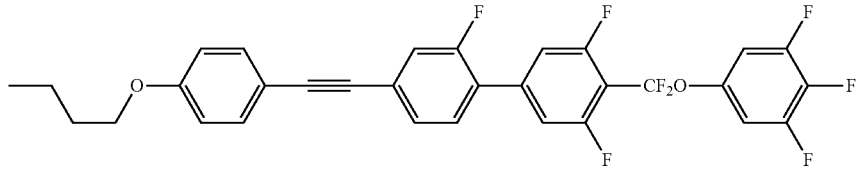
(1-5-54)
C 78.7 SA 92.1 N 183.8 I
$T_{NI}$ = 136.4° C., $\Delta\varepsilon$ = 38.8, $\Delta n$ = 0.277
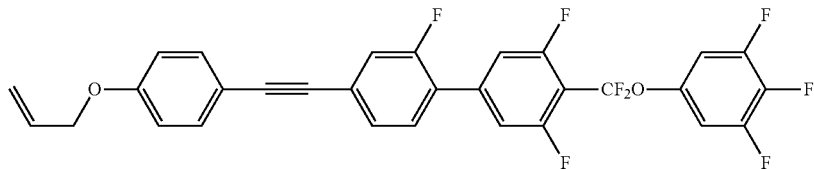
(1-5-55)
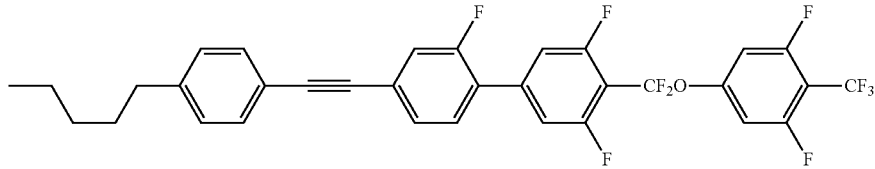
(1-5-56)
C 86.8 N 140 I
$T_{NI}$ = 112.4° C., $\Delta\varepsilon$ = 50.1, $\Delta n$ = 0.244
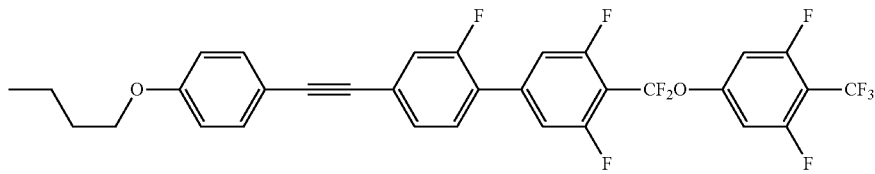
(1-5-57)
C 109.9 N 177.2 I
$T_{NI}$ = 127.7° C., $\Delta\varepsilon$ = 50.1, $\Delta n$ = 0.267
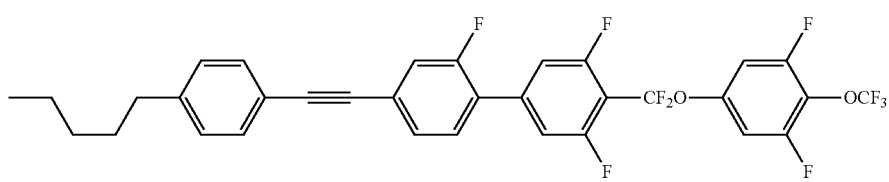
(1-5-58)
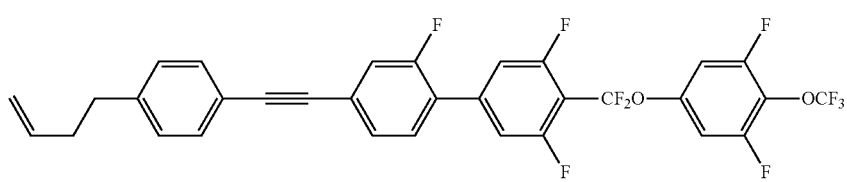
(1-5-59)

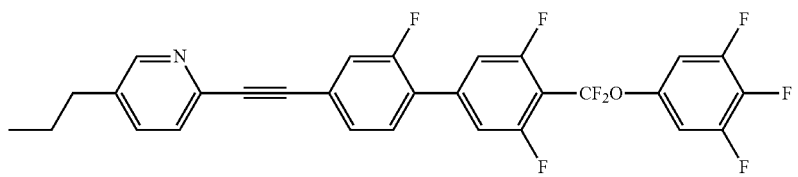
(1-5-60)
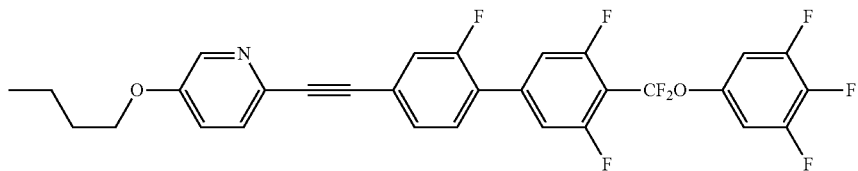
(1-5-61)
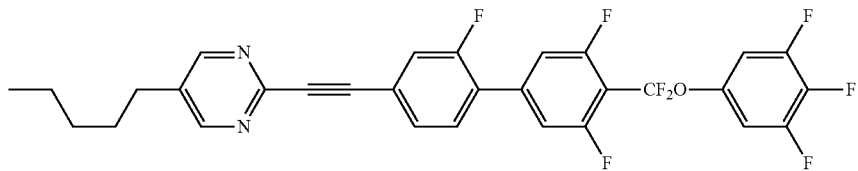
(1-5-62)
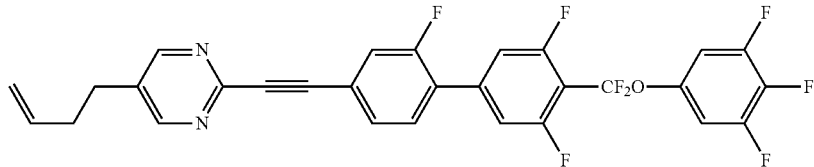
(1-5-63)
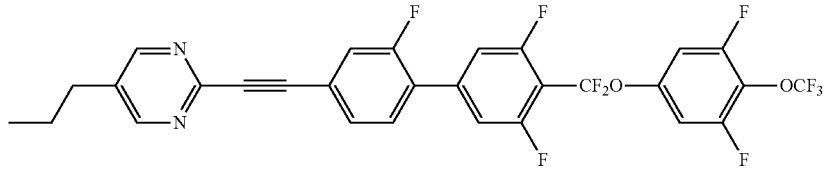
(1-5-64)
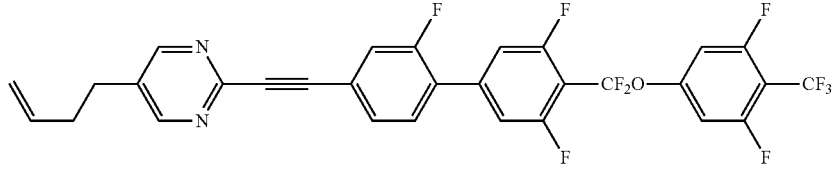
(1-5-65)
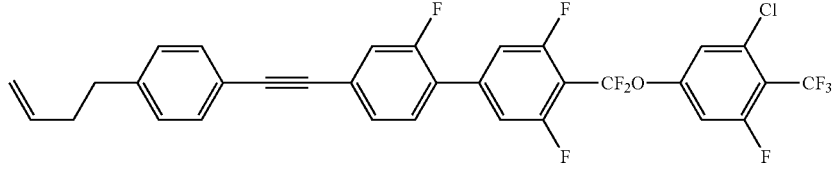
(1-5-66)
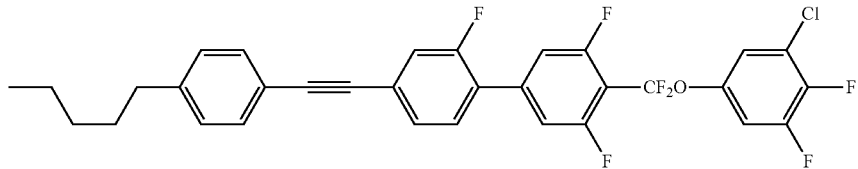
(1-5-67)
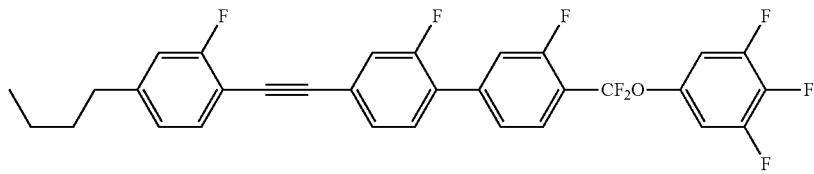
(1-5-68)

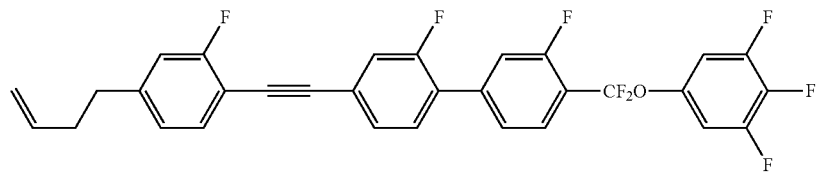 (1-5-69)
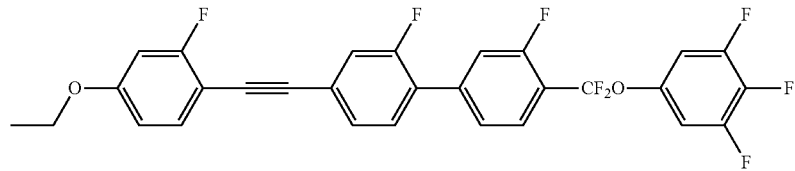 (1-5-70)
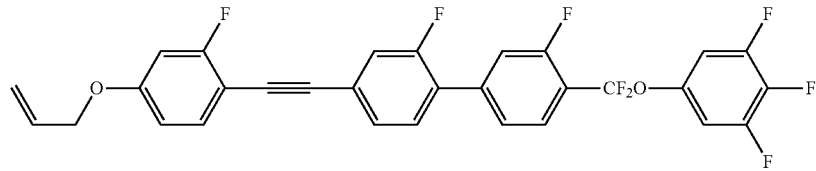 (1-5-71)
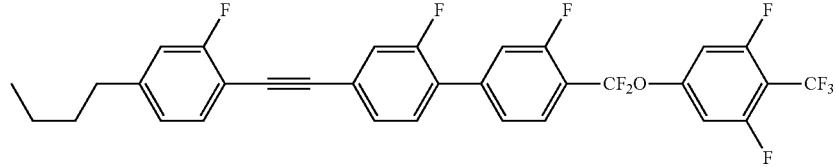 (1-5-72)
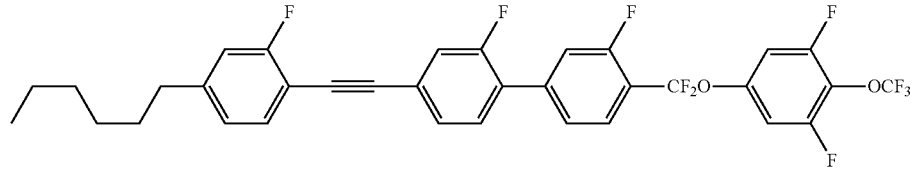 (1-5-73)
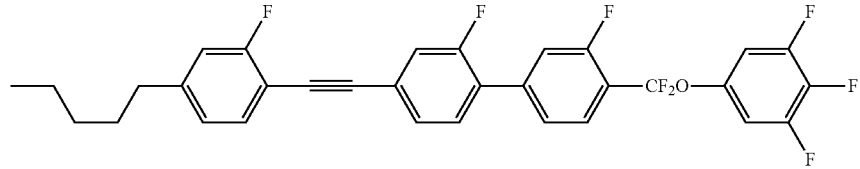 (1-5-74)
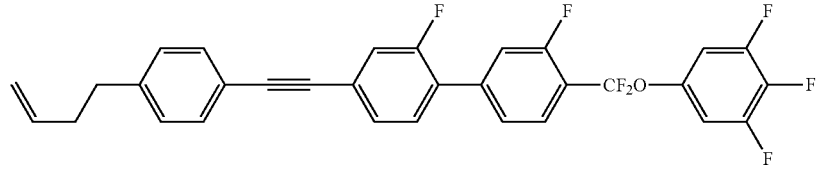 (1-5-75)
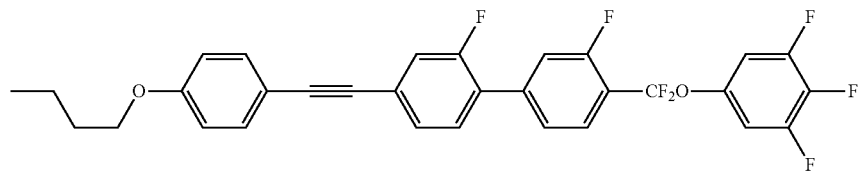 (1-5-76)
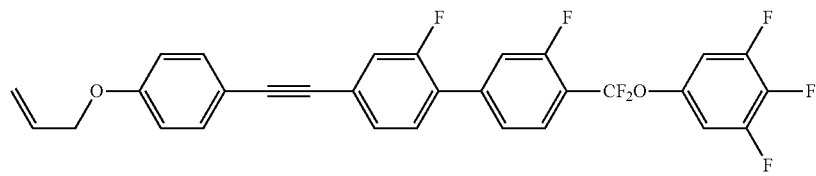 (1-5-77)

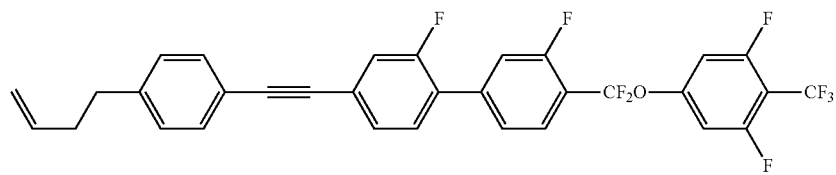
(1-5-78)
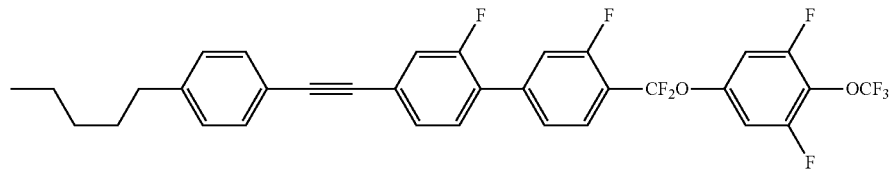
(1-5-79)
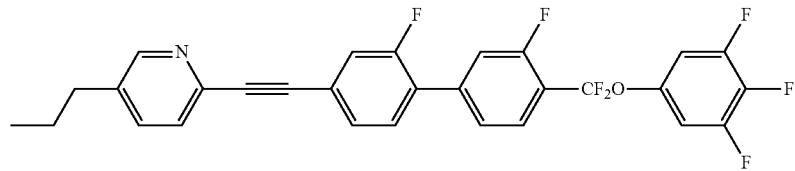
(1-5-80)
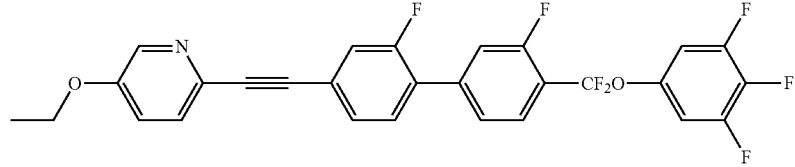
(1-5-81)
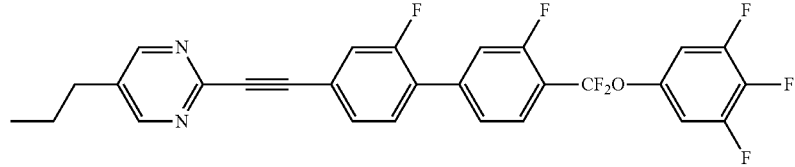
(1-5-82)
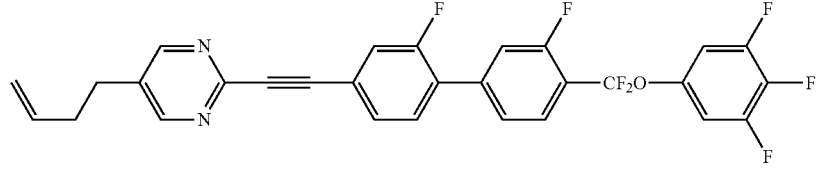
(1-5-83)
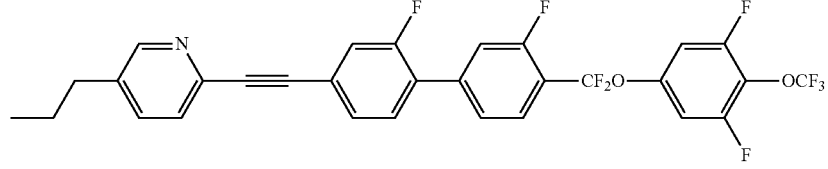
(1-5-84)
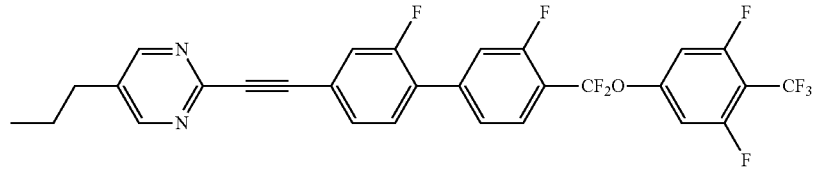
(1-5-85)
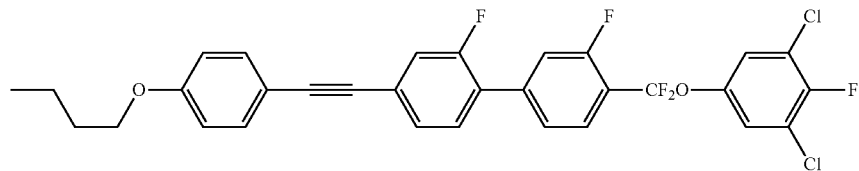
(1-5-86)

-continued
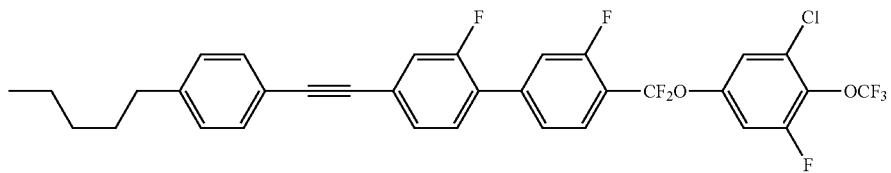
(1-5-87)
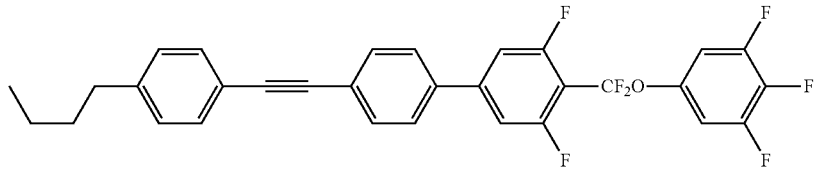
(1-5-88)
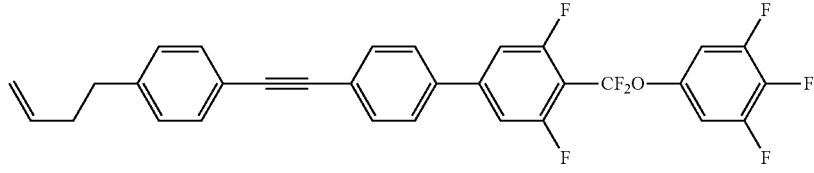
(1-5-89)
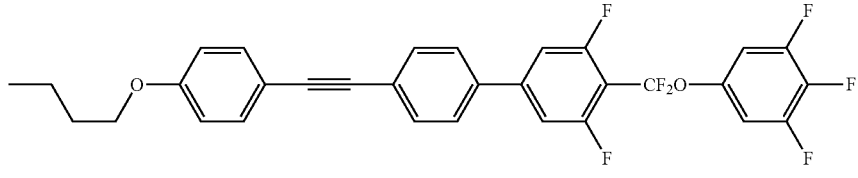
(1-5-90)
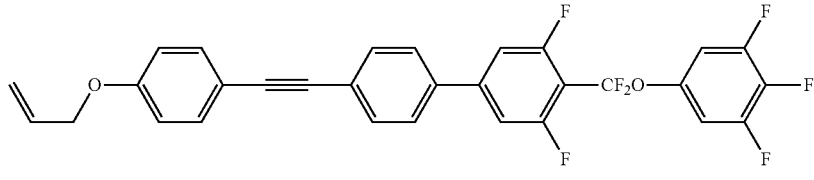
(1-5-91)
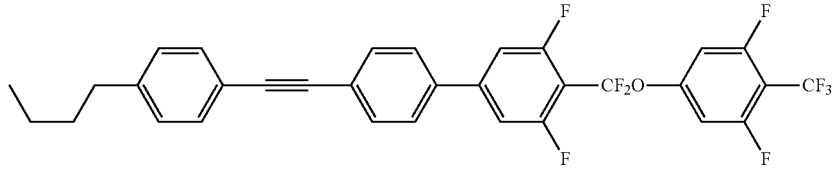
(1-5-92)
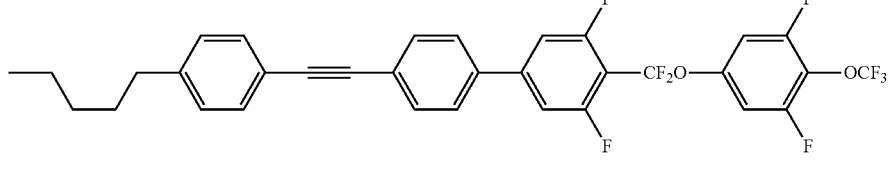
(1-5-93)
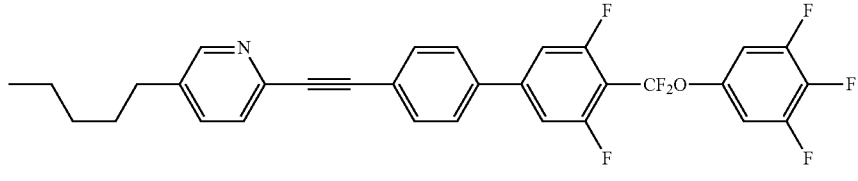
(1-5-94)
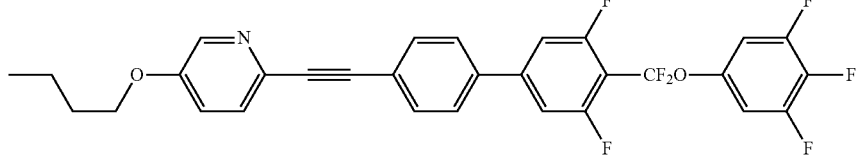
(1-5-95)

-continued
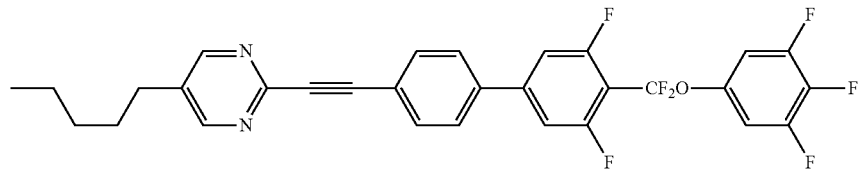
(1-5-96)
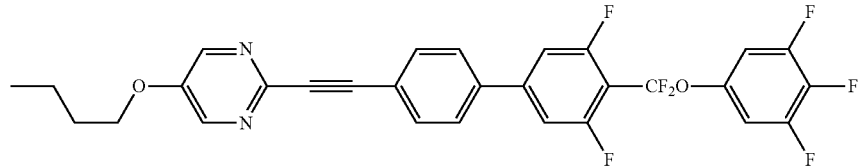
(1-5-97)
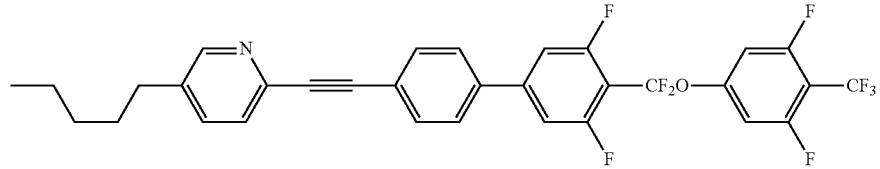
(1-5-98)
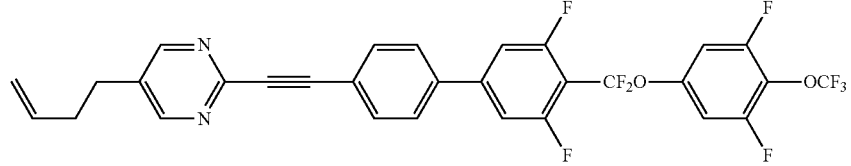
(1-5-99)
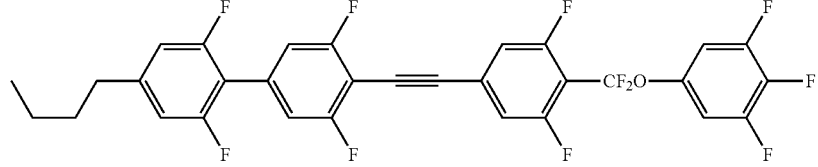
(1-6-1)
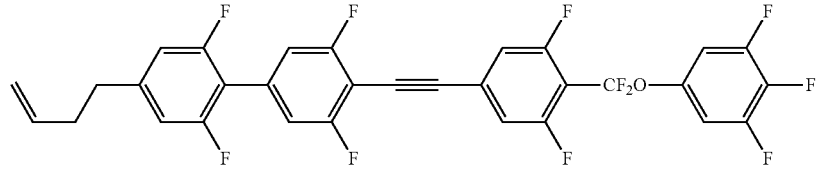
(1-6-2)
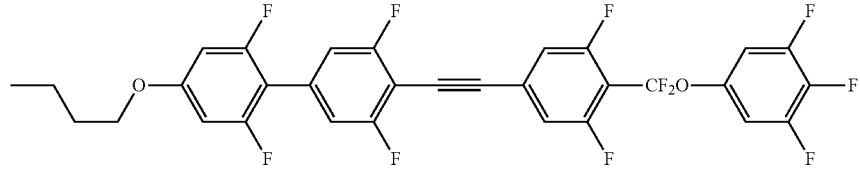
(1-6-3)
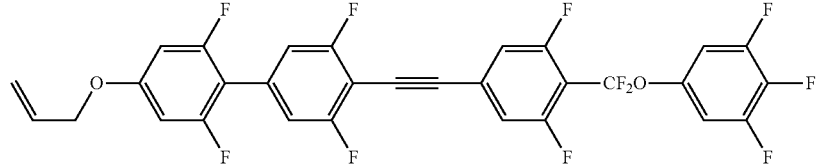
(1-6-4)
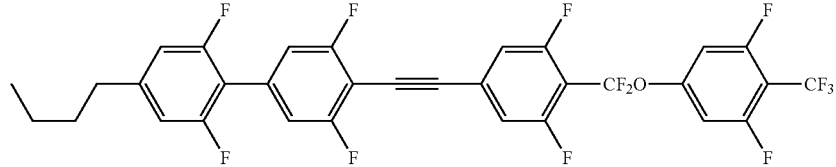
(1-6-5)

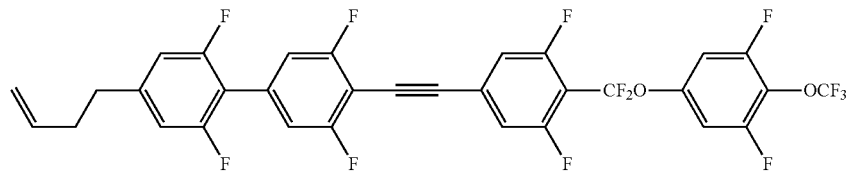
(1-6-6)
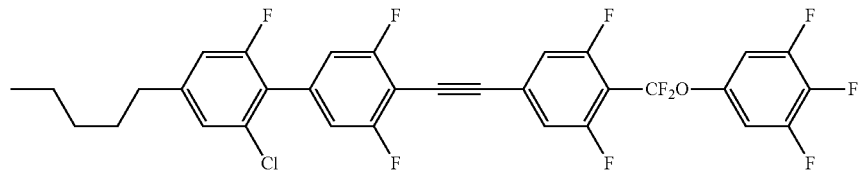
(1-6-7)
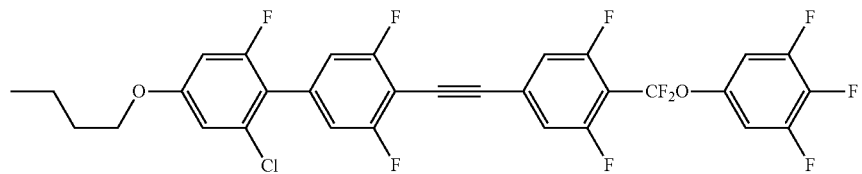
(1-6-8)
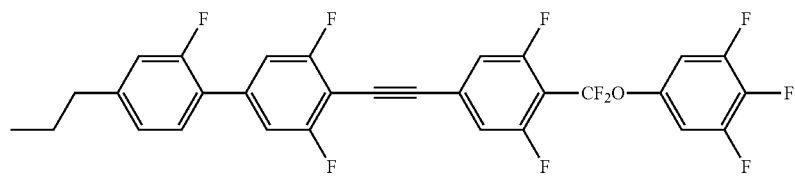
(1-6-9)
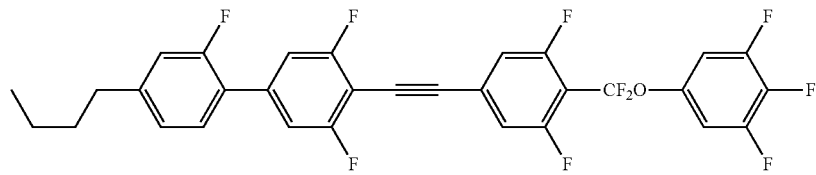
(1-6-10)
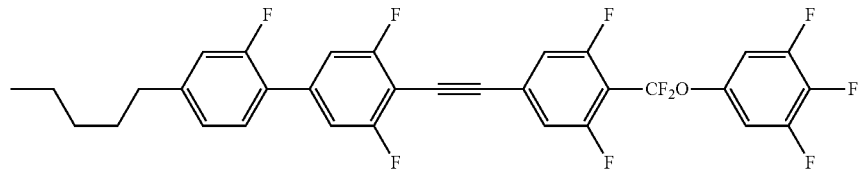
C 91.2 SA 156.1 I
$T_{NI}$ = 99.7° C., Δε = 54.6, Δn = 0.250
(1-6-11)
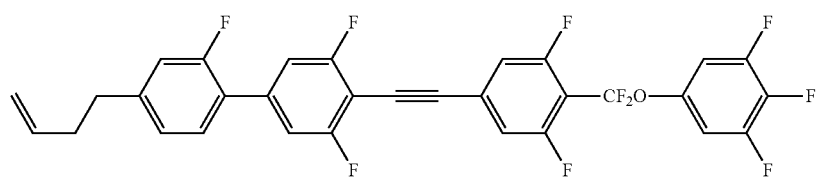
(1-6-12)
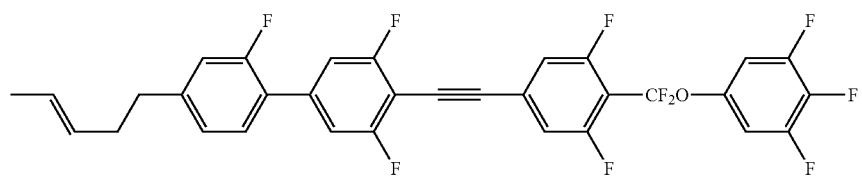
(1-6-13)

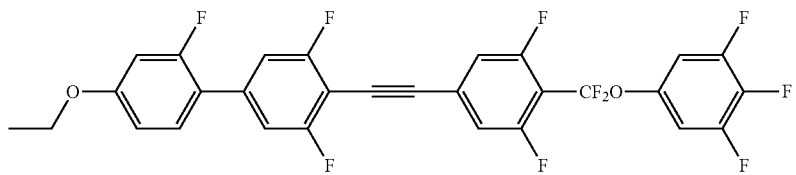
(1-6-14)
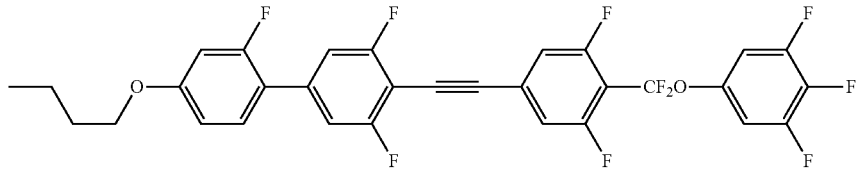
(1-6-15)
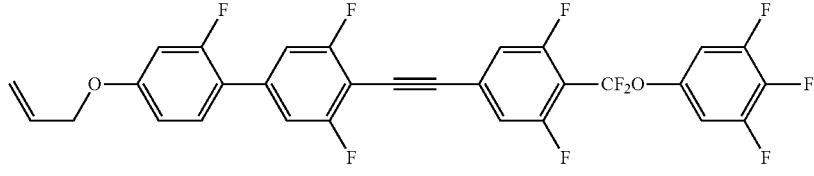
(1-6-16)
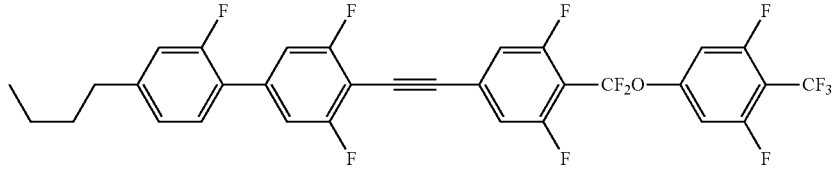
(1-6-17)
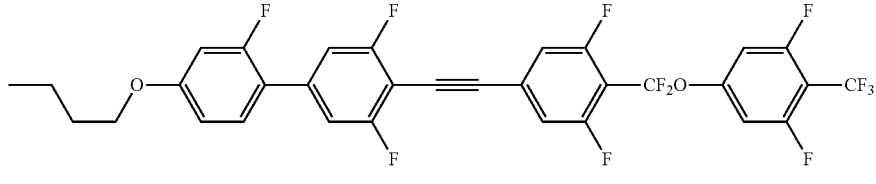
(1-6-18)
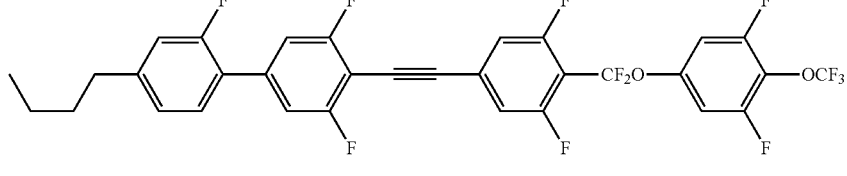
(1-6-19)
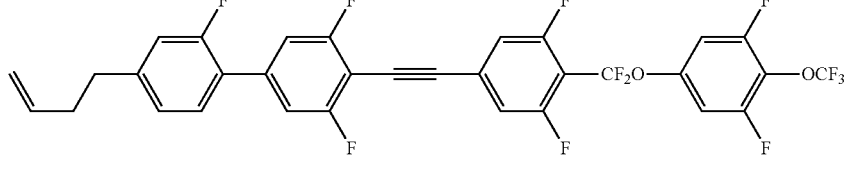
(1-6-20)
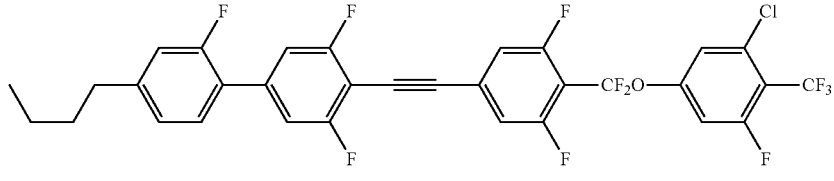
(1-6-21)
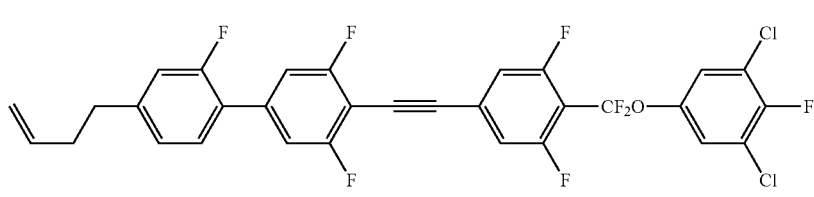
(1-6-22)

-continued
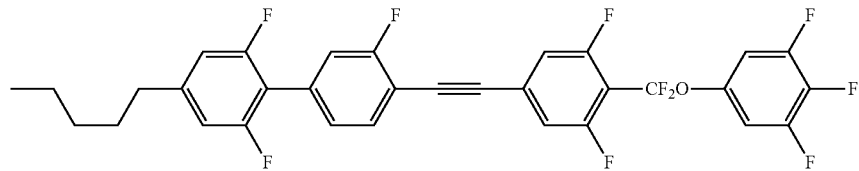
(1-6-23)
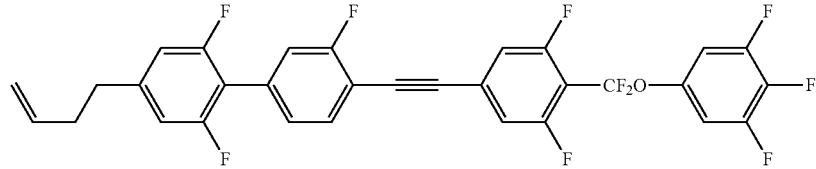
(1-6-24)
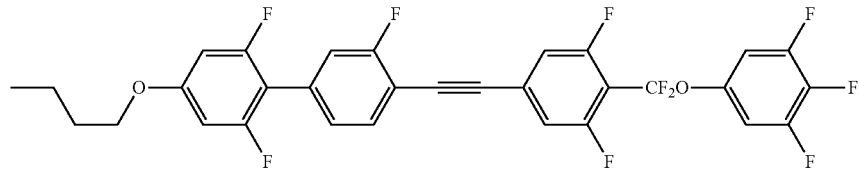
(1-6-25)
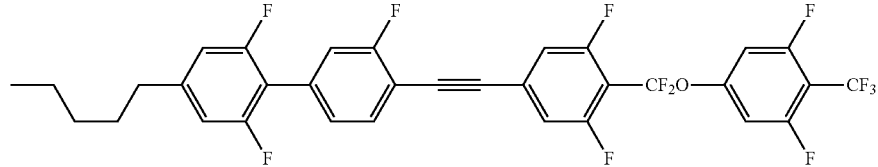
(1-6-26)
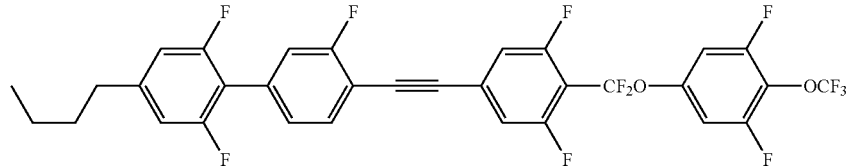
(1-6-27)
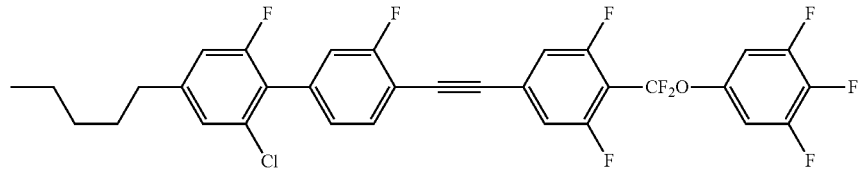
(1-6-28)
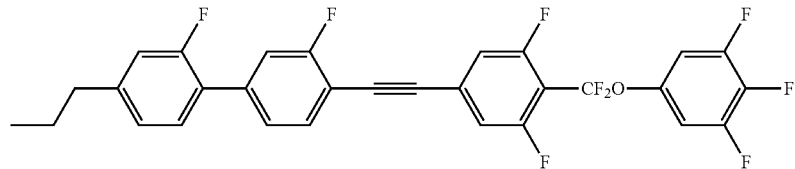
(1-6-29)
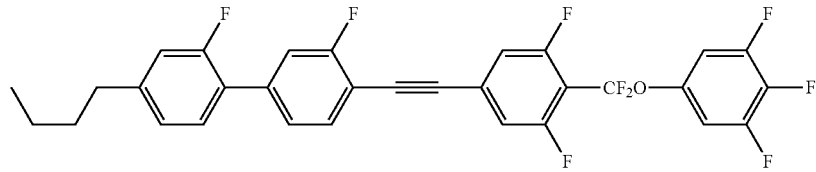
(1-6-30)
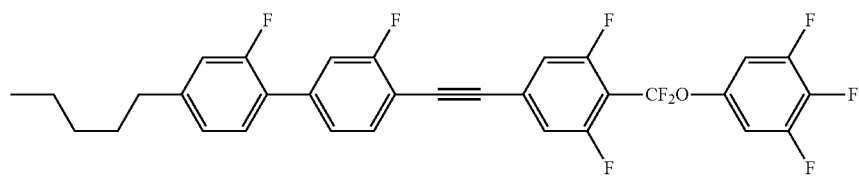
(1-6-31)

(1-6-32)
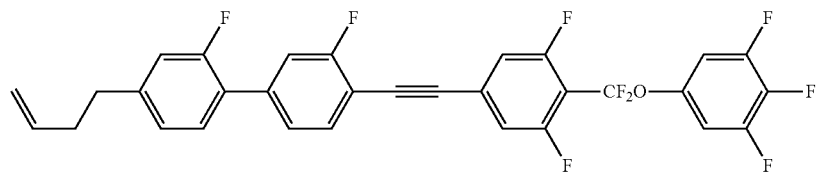
(1-6-33)
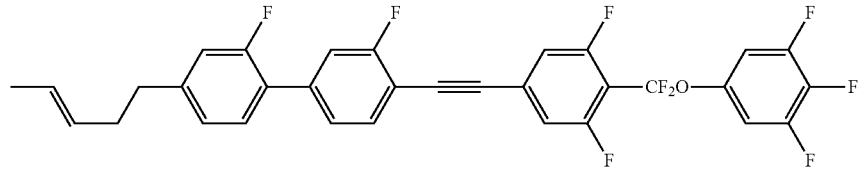
(1-6-34)
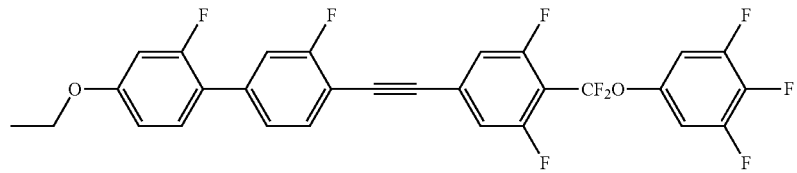
(1-6-35)
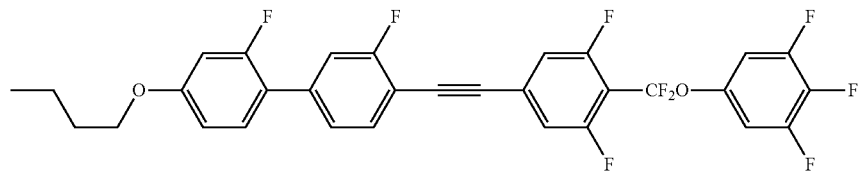
(1-6-36)
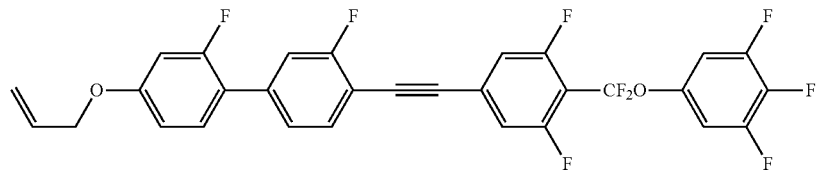
(1-6-37)
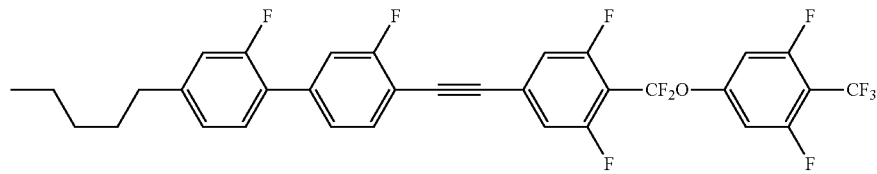
(1-6-38)
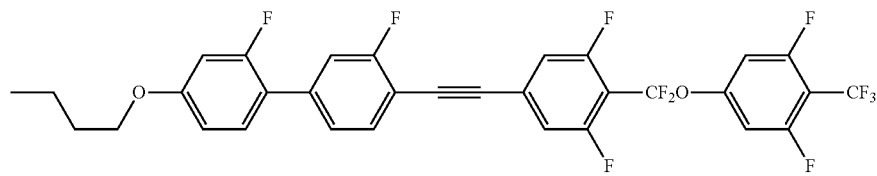
(1-6-39)
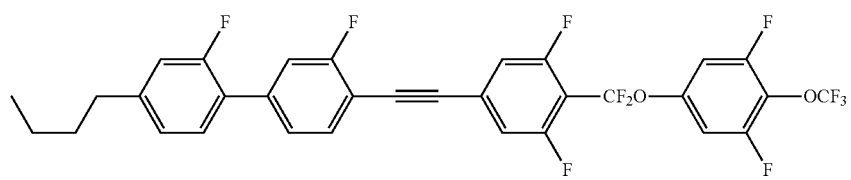
(1-6-40)
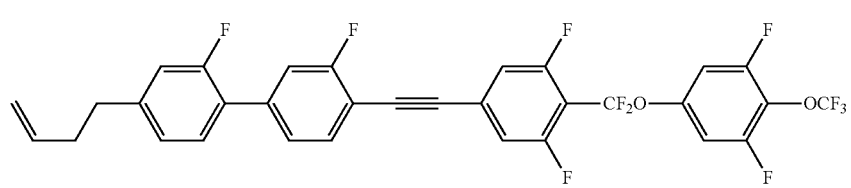

-continued
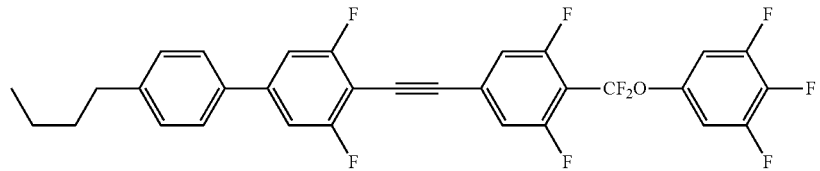
(1-6-41)
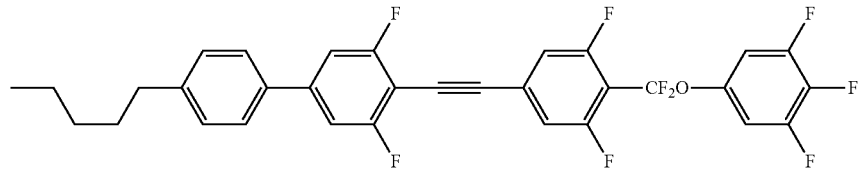
(1-6-42)
C 87.5 SA 109.1 N 163.1 I
$T_{NI}$ = 113.7° C., $\Delta\varepsilon$ = 48.9, $\Delta n$ = 0.257
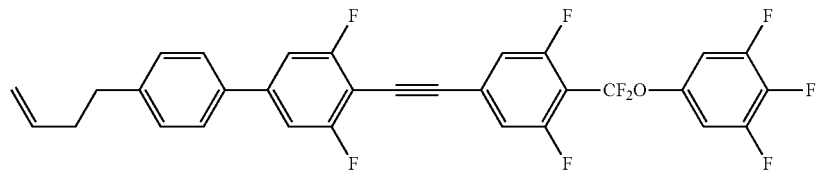
(1-6-43)
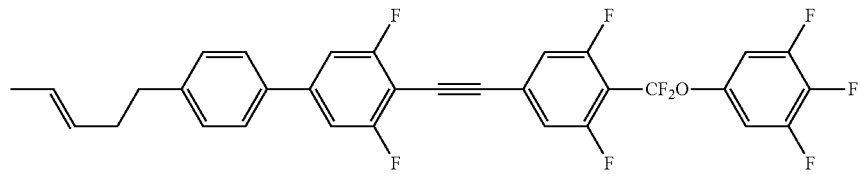
(1-6-44)
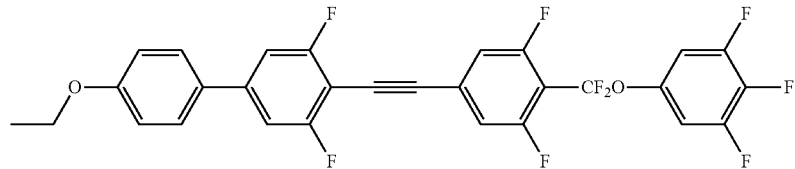
(1-6-45)
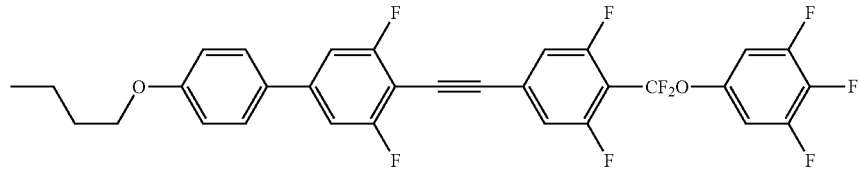
(1-6-46)
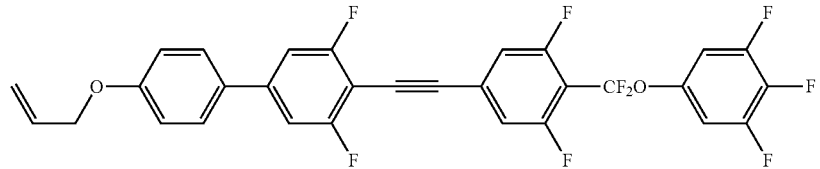
(1-6-47)
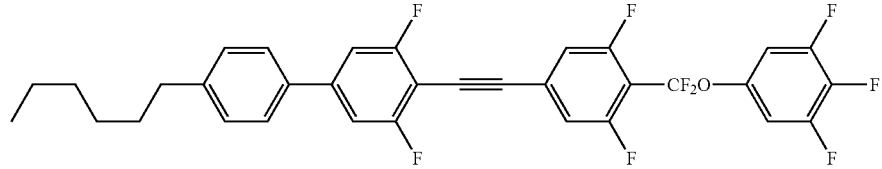
(1-6-48)

-continued
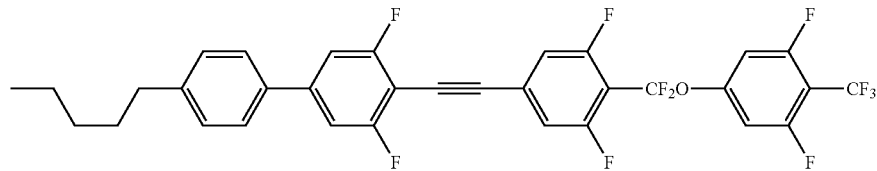
(1-6-49)
C 5.4 C 100 SX 107.4 SA 124.2 N 161.4 I
$T_{NI} = 105.7°$ C., $\Delta\varepsilon = 60.1$, $\Delta n = 0.257$
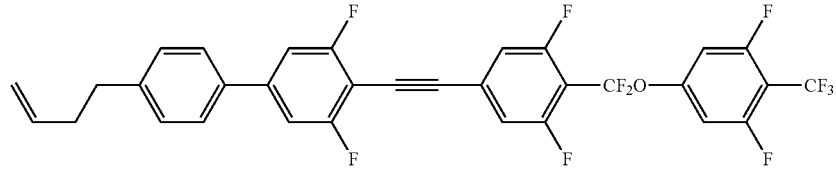
(1-6-50)
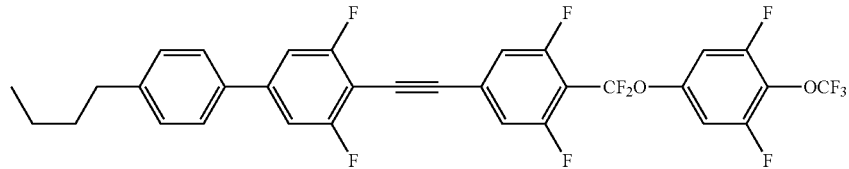
(1-6-51)
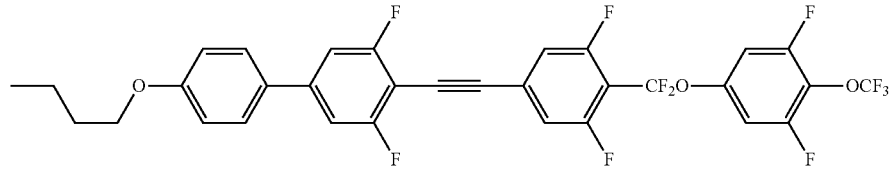
(1-6-52)
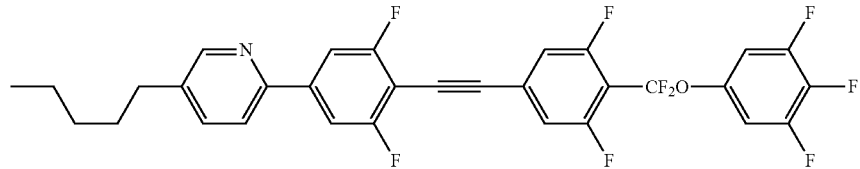
(1-6-53)
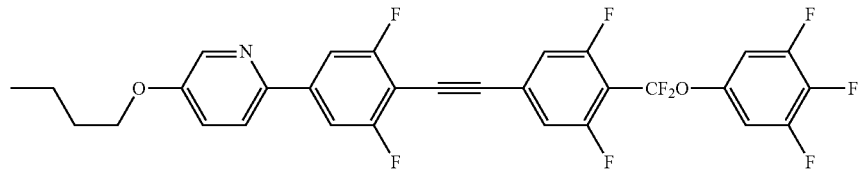
(1-6-54)
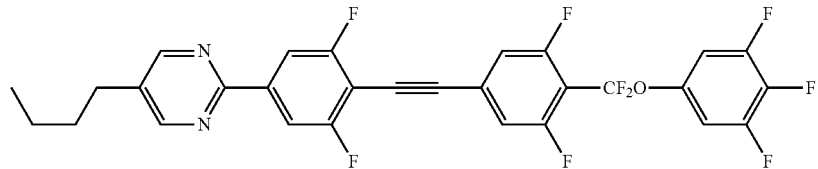
(1-6-55)
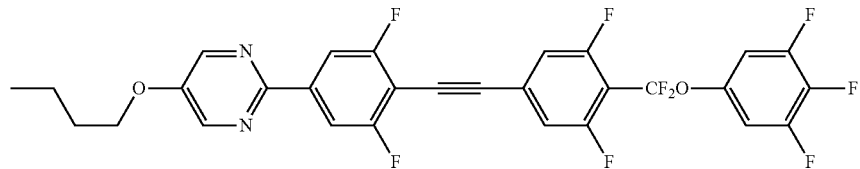
(1-6-56)

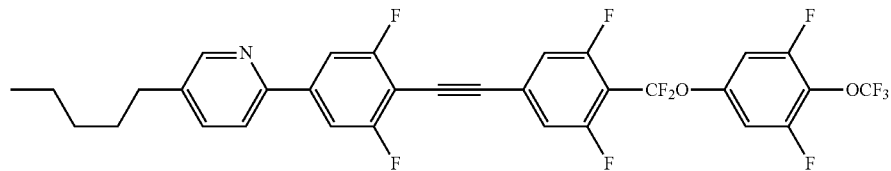
(1-6-57)
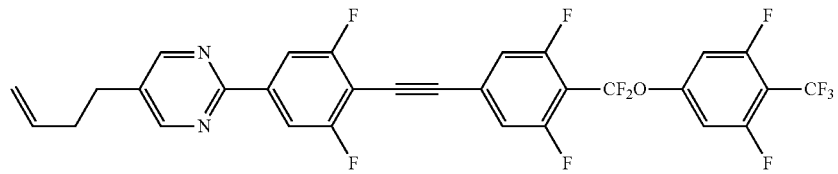
(1-6-58)
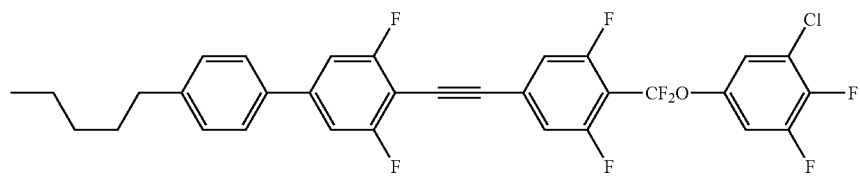
(1-6-59)
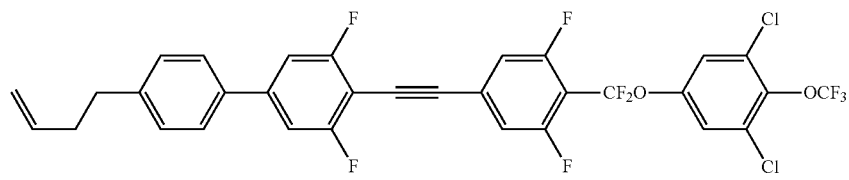
(1-6-60)
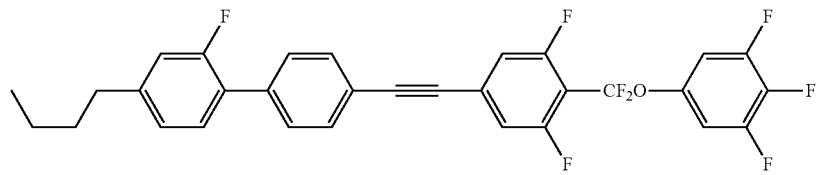
(1-6-61)
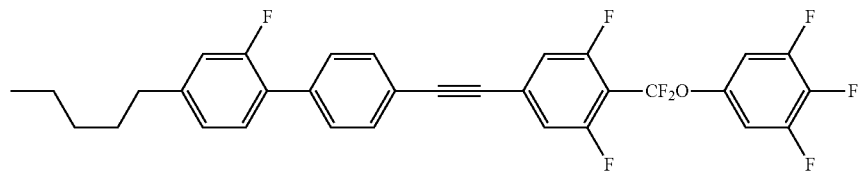
(1-6-62)
C 84.3 N 145.3 I
$T_{NI}$ = 121.0° C., Δε = 42.9, Δn = 0.257
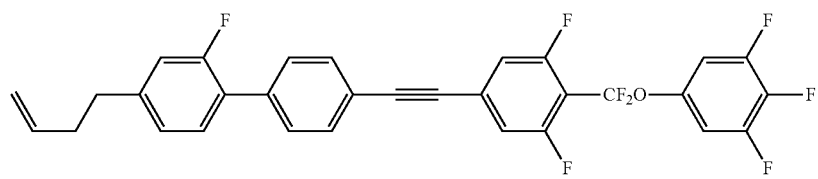
(1-6-63)
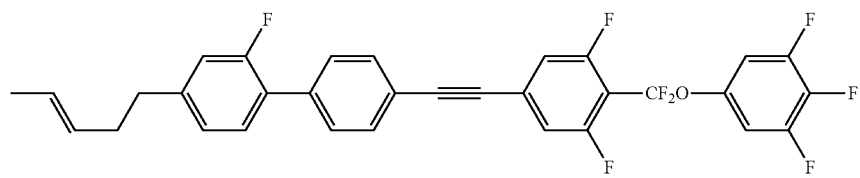
(1-6-64)

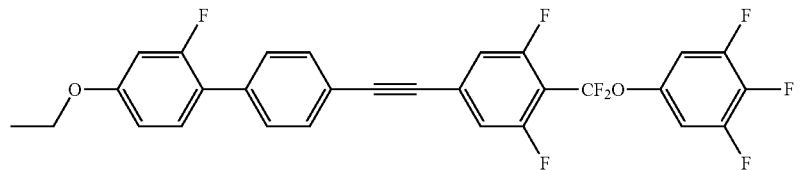
(1-6-65)
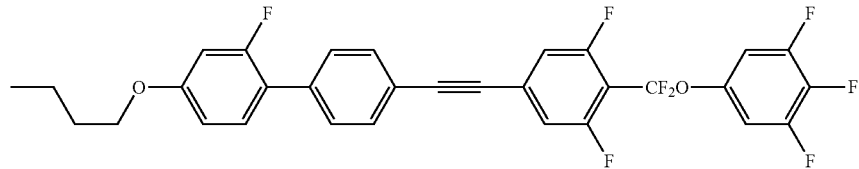
C 102.8 N 176.5 I
$T_{NI}$ = 139.7° C., Δε = 40.1, Δn = 0.277
(1-6-66)
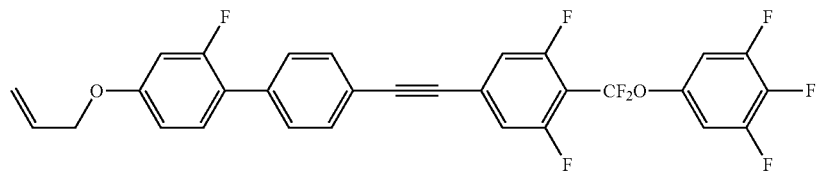
(1-6-67)
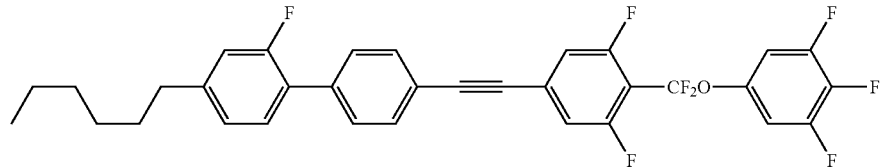
(1-6-68)
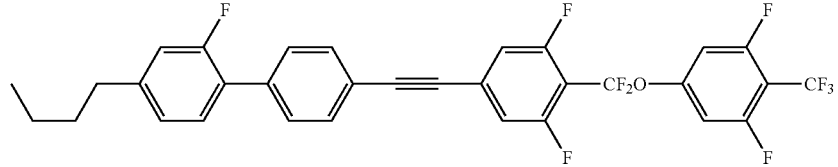
(1-6-69)
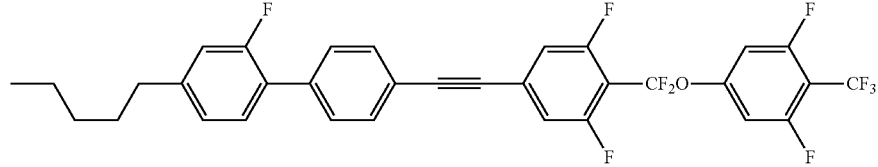
(1-6-70)
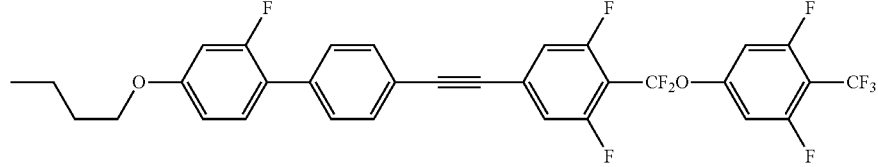
(1-6-71)
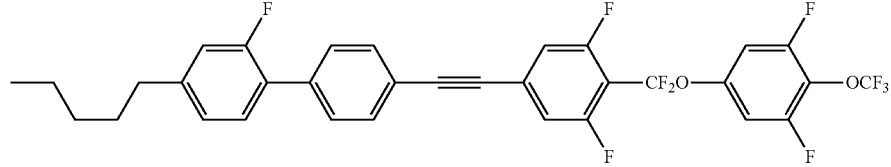
(1-6-72)

-continued
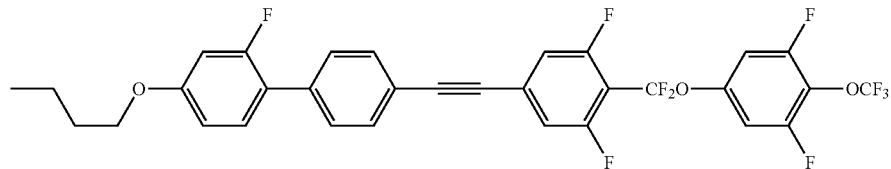
(1-6-73)
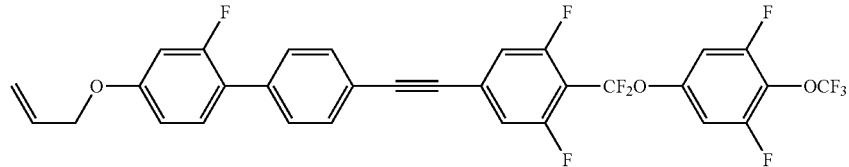
(1-6-74)
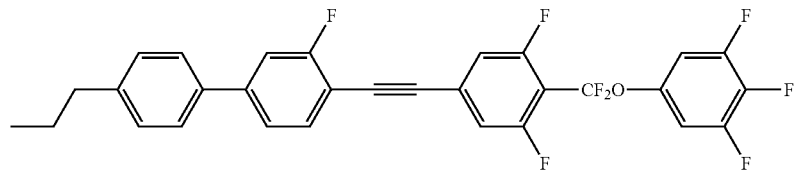
(1-6-75)
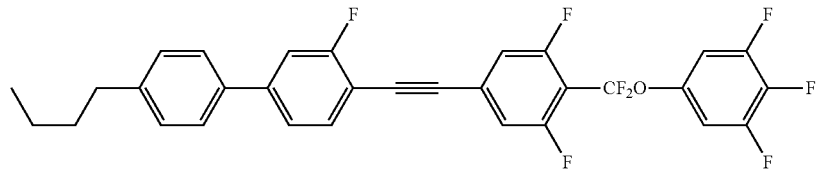
(1-6-76)
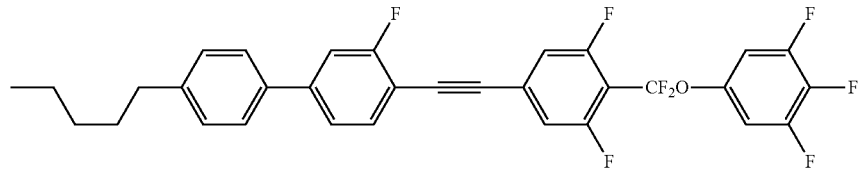
(1-6-77)
C 60.3 SA 81.8 N 161.5 I
$T_{NI}$ = 125.7° C., Δε = 39.5, Δn = 0.270
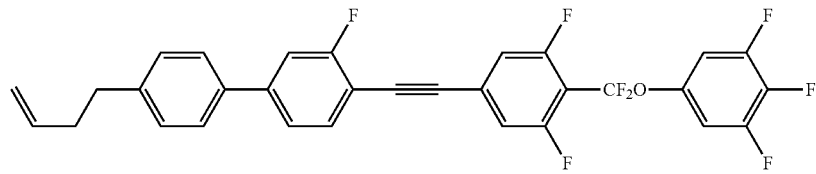
(1-6-78)
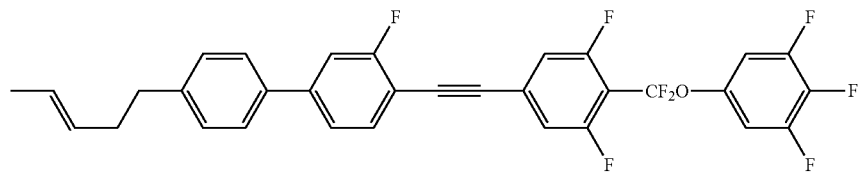
(1-6-79)
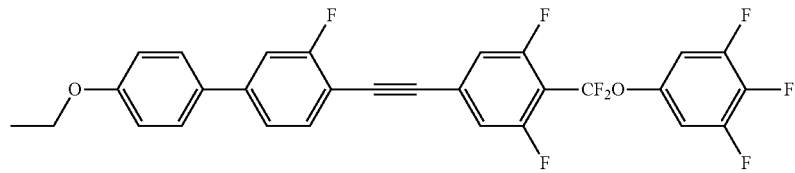
(1-6-80)

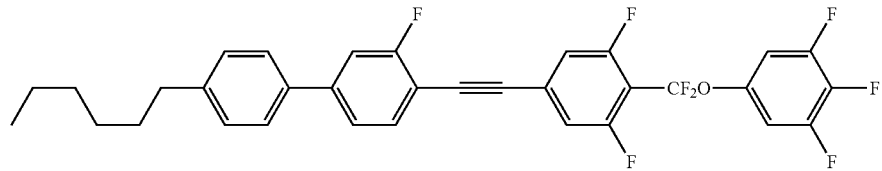
(1-6-81)
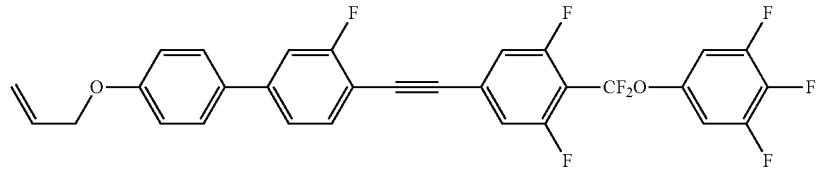
(1-6-82)
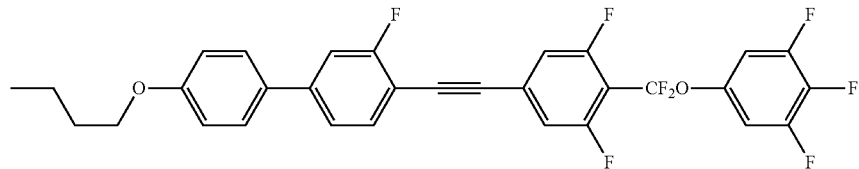
(1-6-83)
C 110.3 SA 144.1 N 196.2 I
$T_{NI}$ = 142.7° C., $\Delta\varepsilon$ = 39.8, $\Delta n$ = 0.287
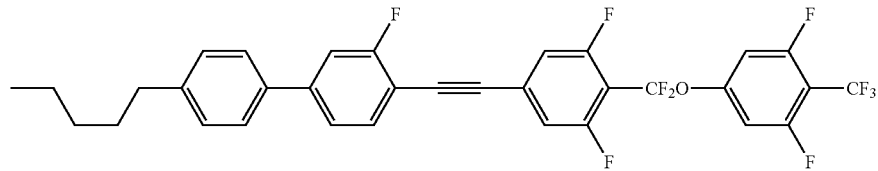
(1-6-84)
C 92.9 N 156.4 I
$T_{NI}$ = 119.7° C., $\Delta\varepsilon$ = 52.8, $\Delta n$ = 0.264
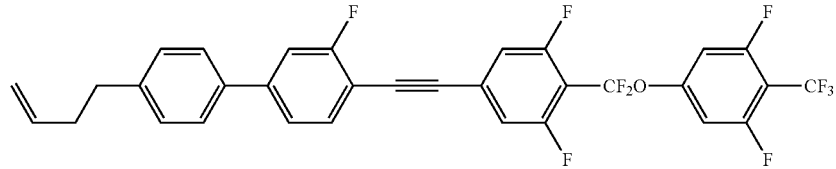
(1-6-85)
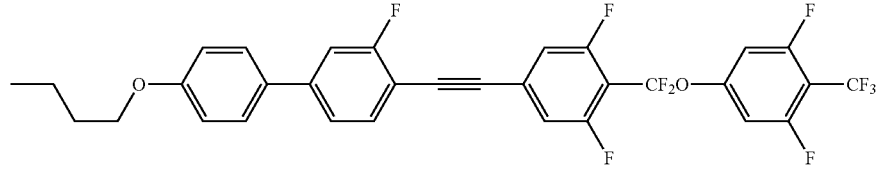
(1-6-86)
C 70.8 C 135 N 190.7 I
$T_{NI}$ = 131.7° C., $\Delta\varepsilon$ = 51.9, $\Delta n$ = 0.304
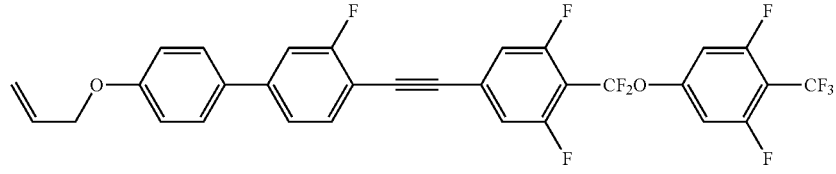
(1-6-87)

-continued
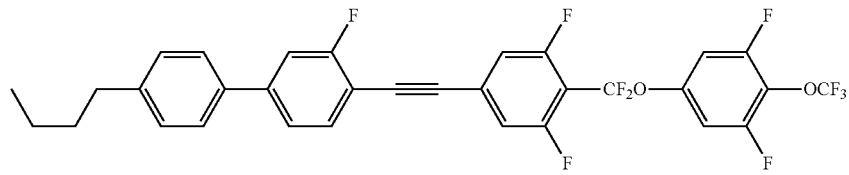
(1-6-88)
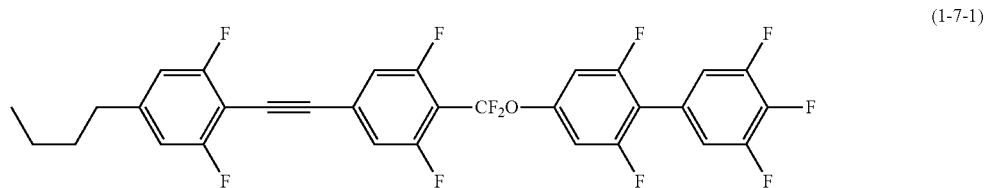
(1-7-1)
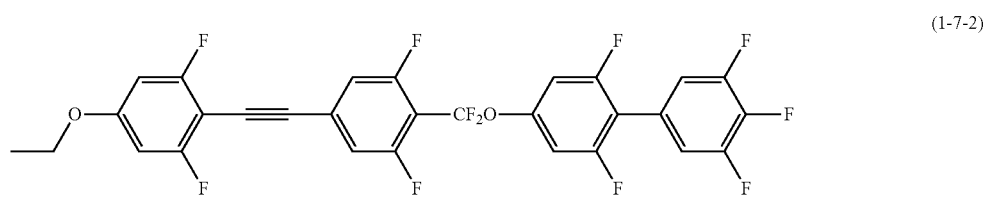
(1-7-2)
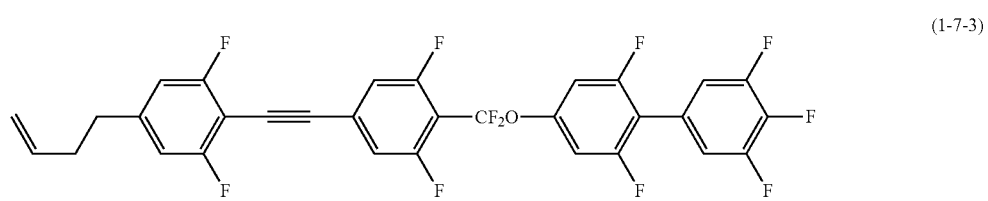
(1-7-3)
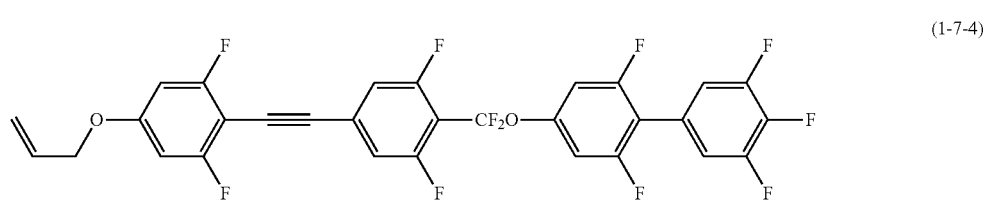
(1-7-4)
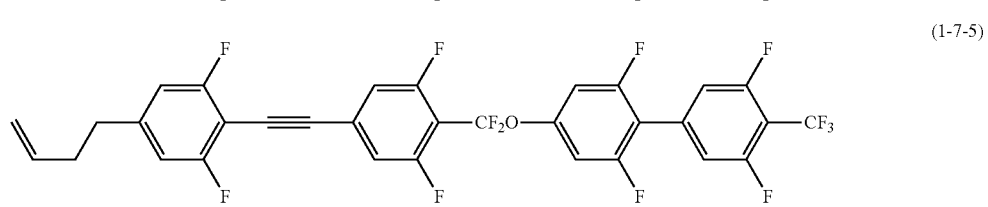
(1-7-5)
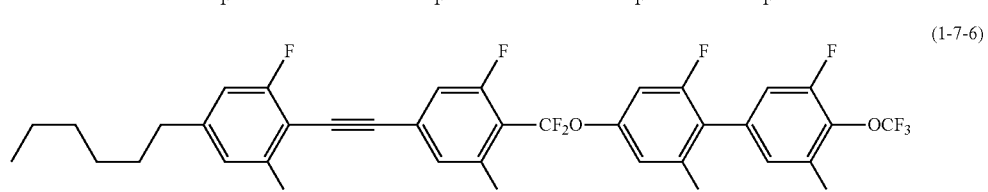
(1-7-6)
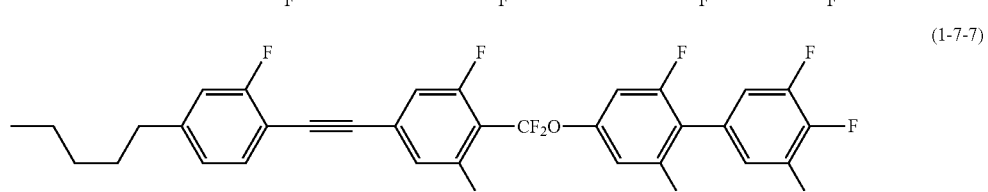
(1-7-7)

(1-7-8)
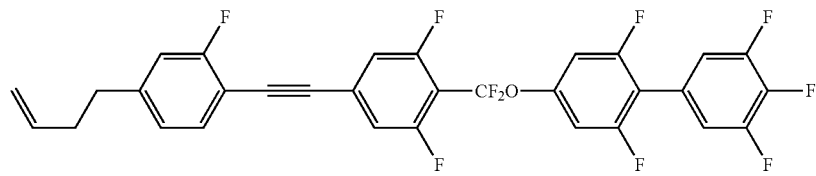
(1-7-9)
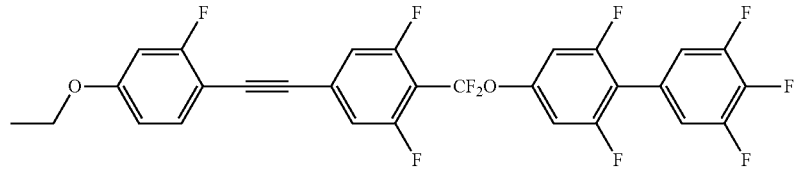
(1-7-10)
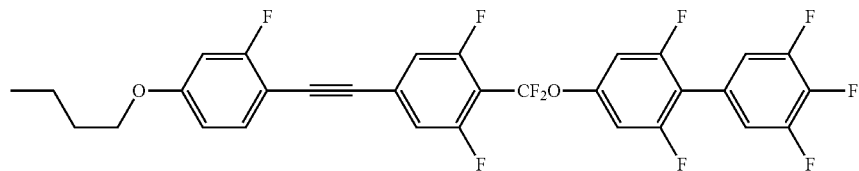
(1-7-11)
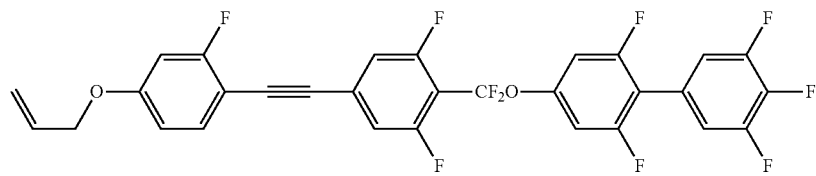
(1-7-12)
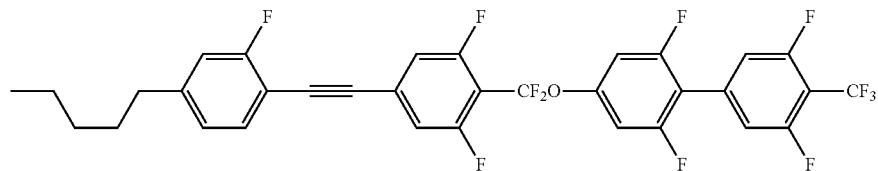
(1-7-13)
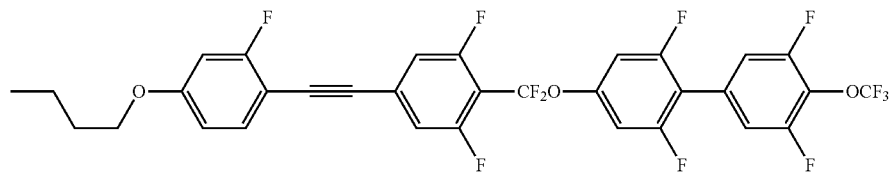
(1-7-14)
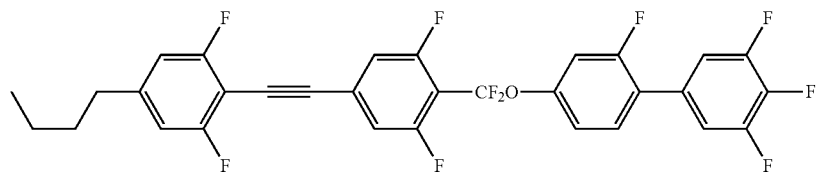
(1-7-15)
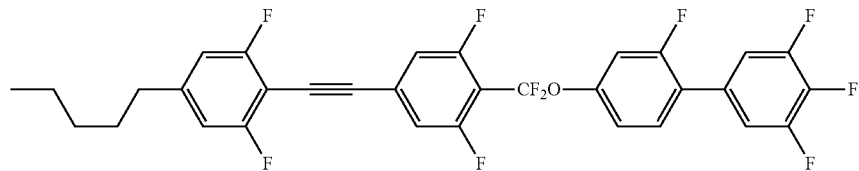
(1-7-16)
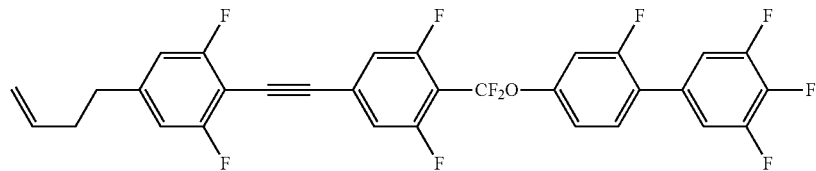

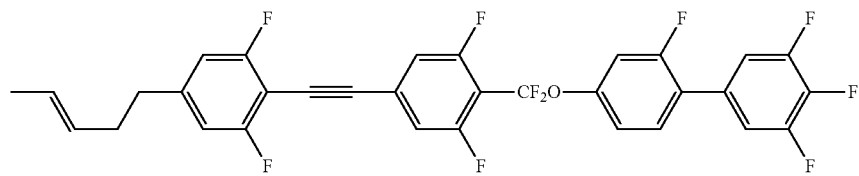
(1-7-17)
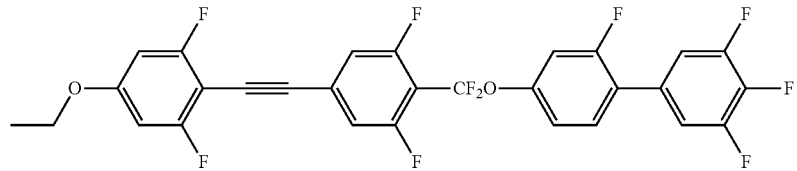
(1-7-18)
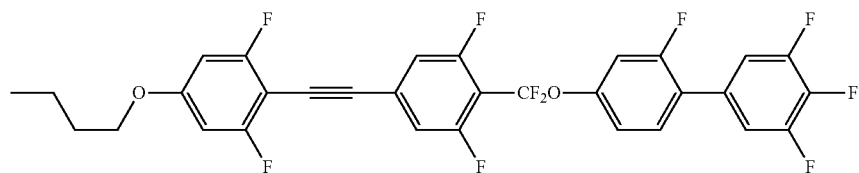
(1-7-19)
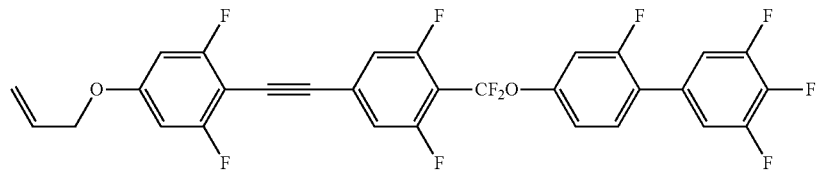
(1-7-20)
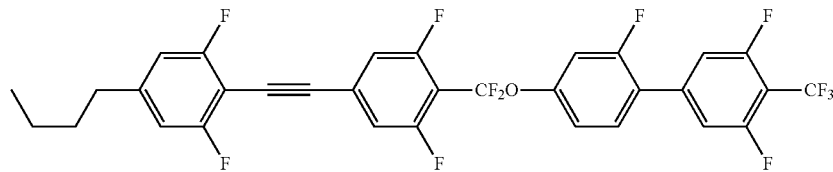
(1-7-21)
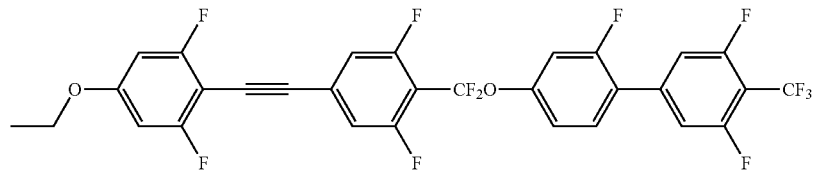
(1-7-22)
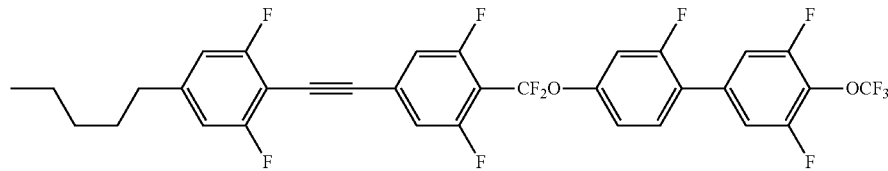
(1-7-23)
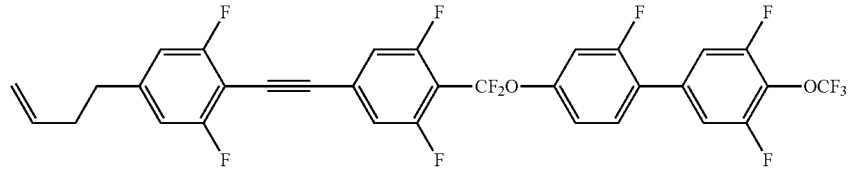
(1-7-24)
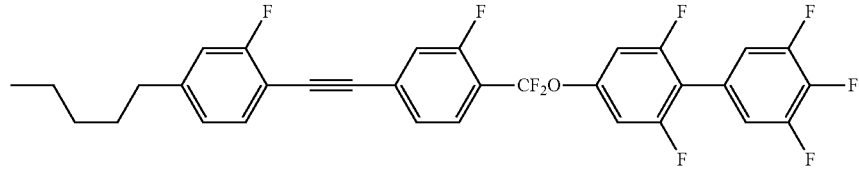
(1-7-25)

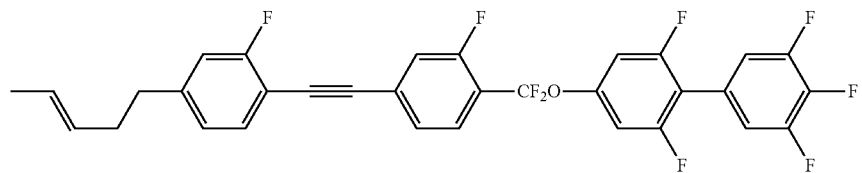
(1-7-26)
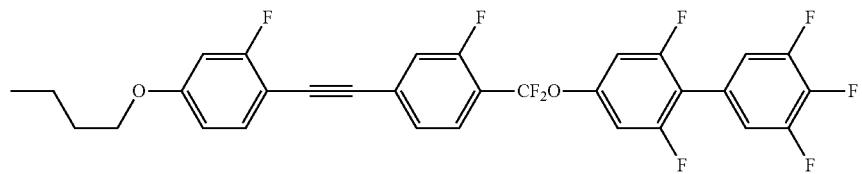
(1-7-27)
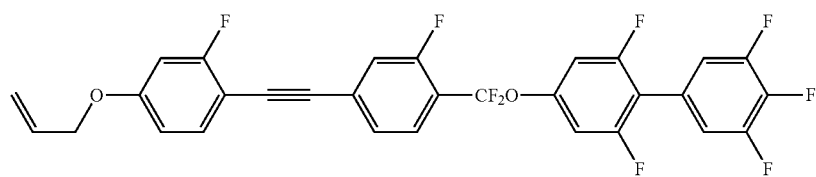
(1-7-28)
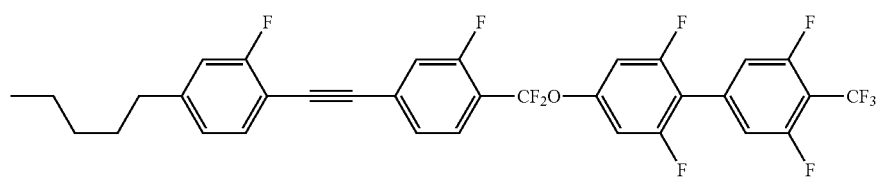
(1-7-29)
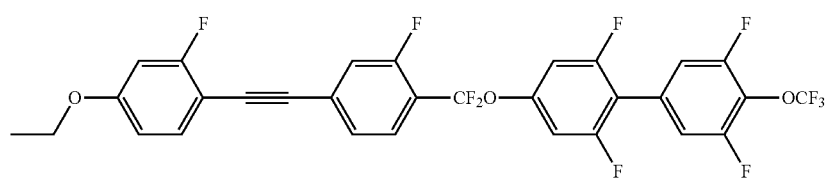
(1-7-30)
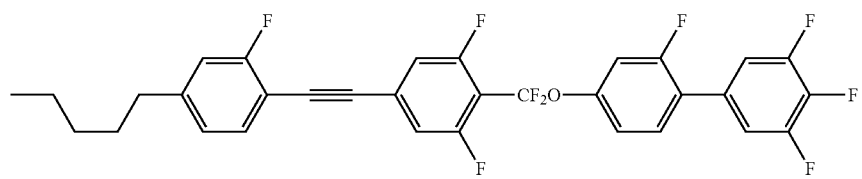
(1-7-31)
C 74.7 N 126.4 I
$T_{NI}$ = 84.4° C., Δε = 47.5, Δn = 0.230
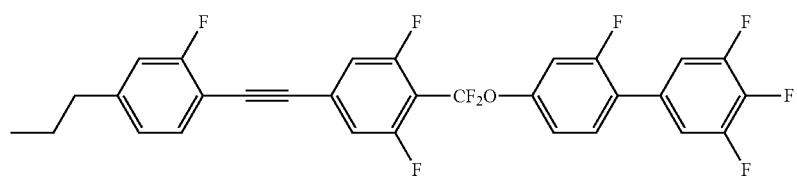
(1-7-32)
118.8 N 132.5 I
$T_{NI}$ = 88.4° C., Δε = 55.2, Δn = 0.237
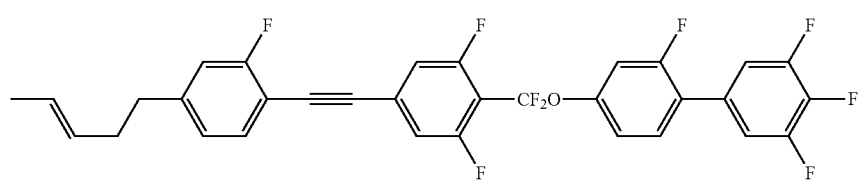
(1-7-33)

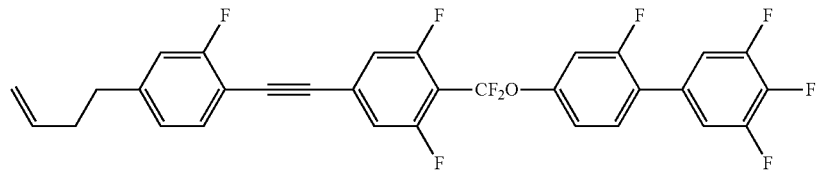
(1-7-34)
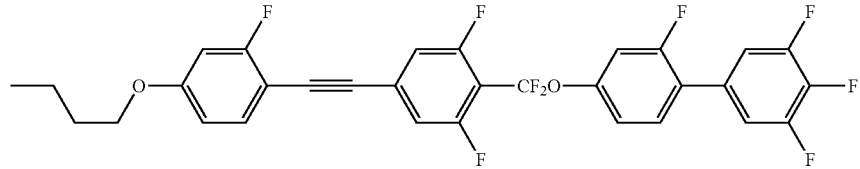
(1-7-35)
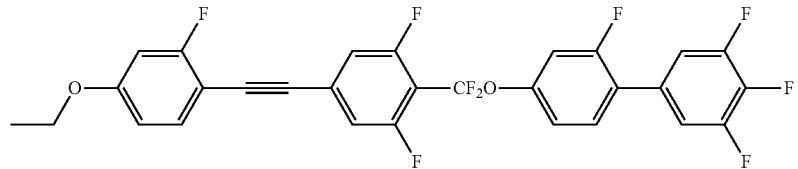
(1-7-36)
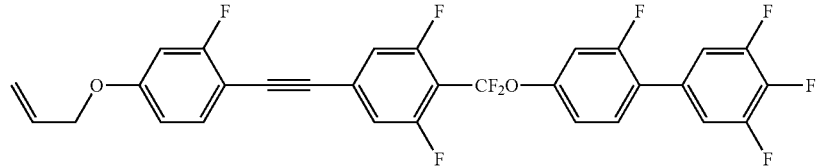
(1-7-37)
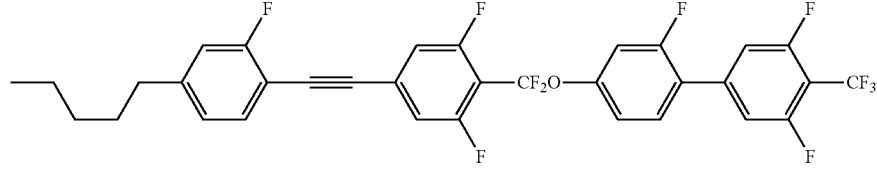
(1-7-38)
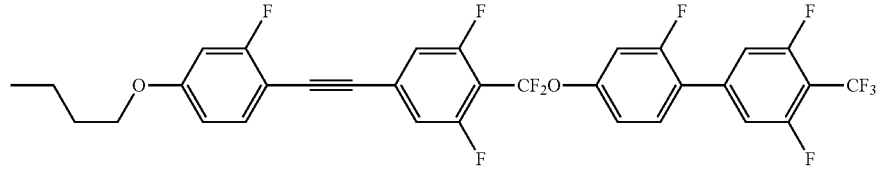
(1-7-39)
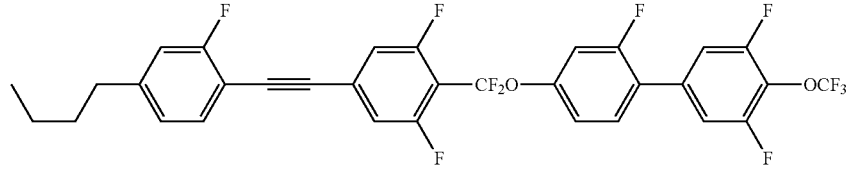
(1-7-40)
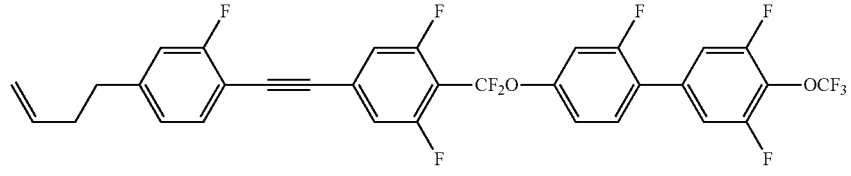
(1-7-41)
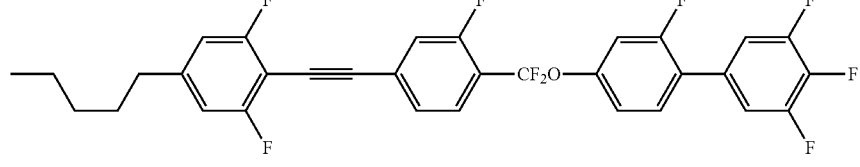
(1-7-42)

(1-7-43)
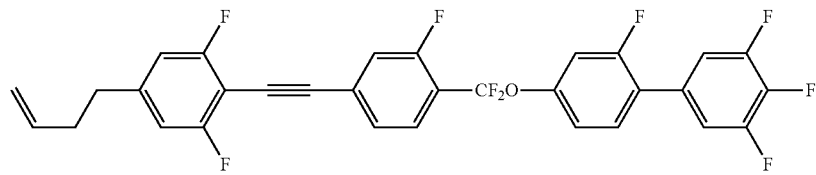
(1-7-44)
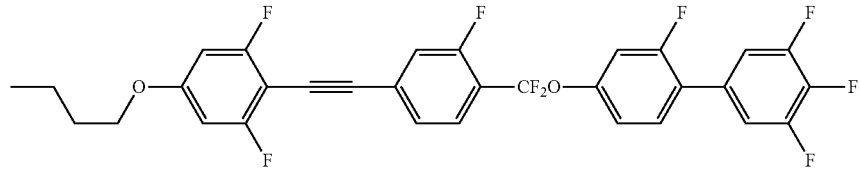
(1-7-45)
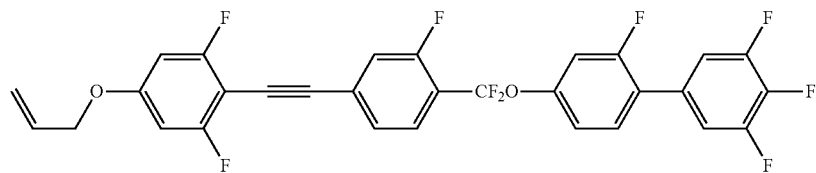
(1-7-46)
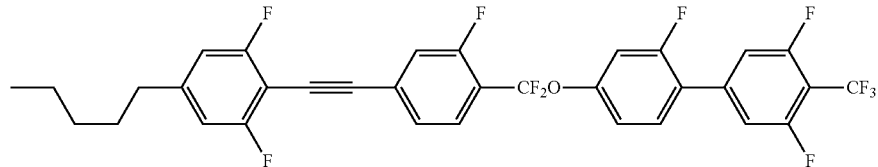
(1-7-47)
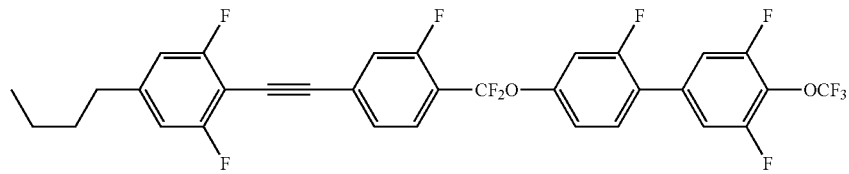
(1-7-48)
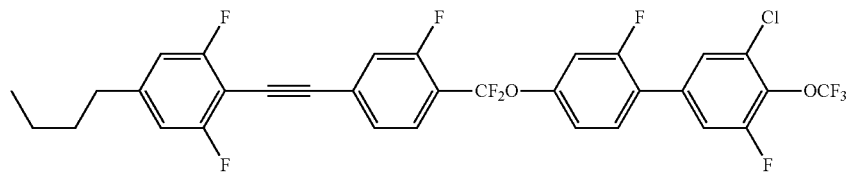
(1-7-49)
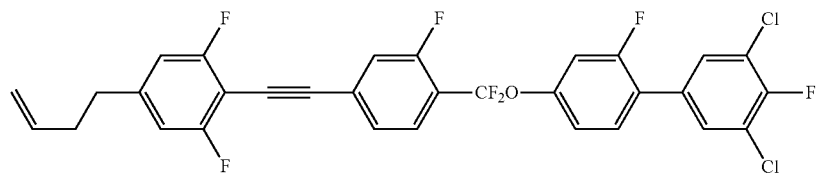
(1-7-50)
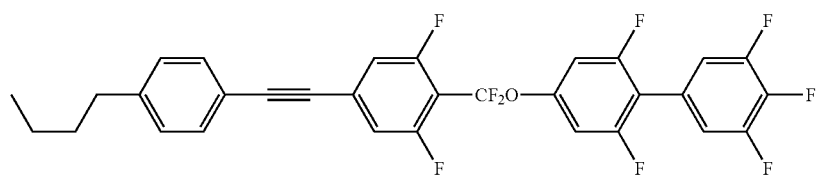
(1-7-51)
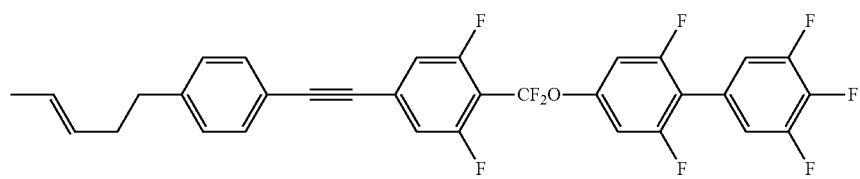

(1-7-52)
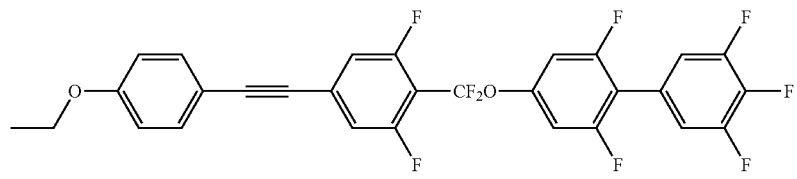
(1-7-53)
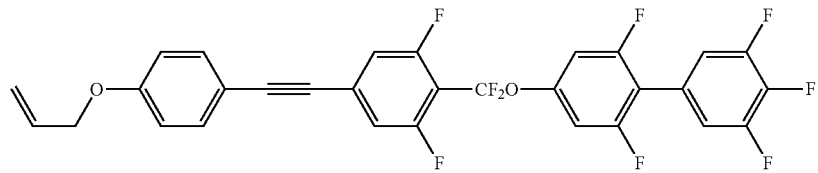
(1-7-54)
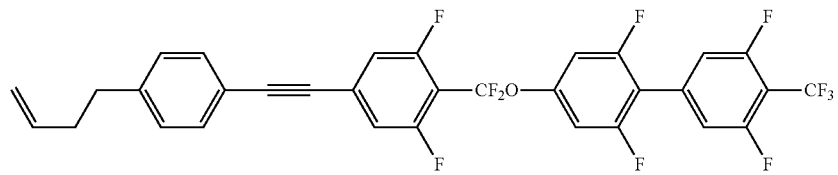
(1-7-55)
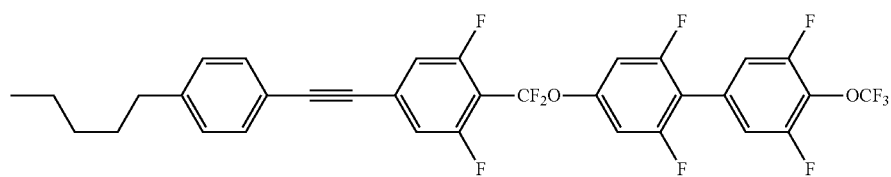
(1-7-56)
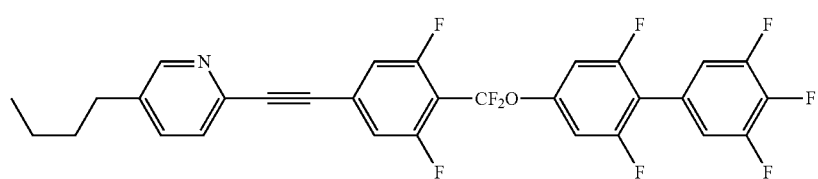
(1-7-57)
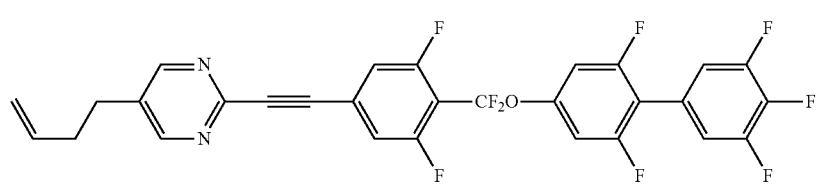
(1-7-58)
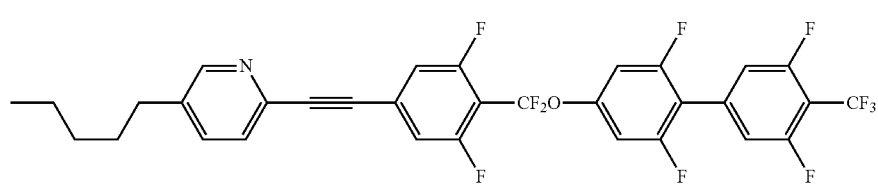
(1-7-59)
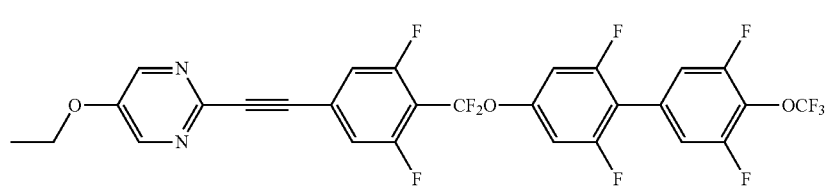
(1-7-60)
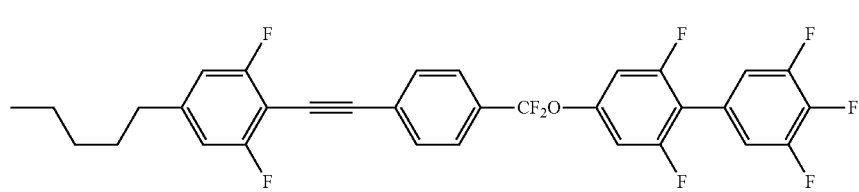

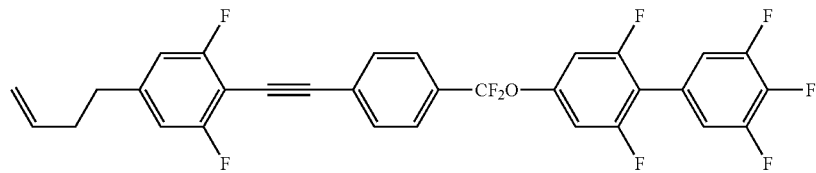
(1-7-61)
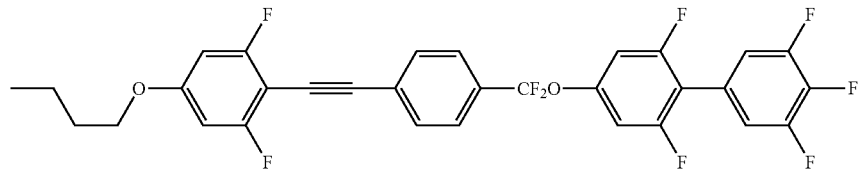
(1-7-62)
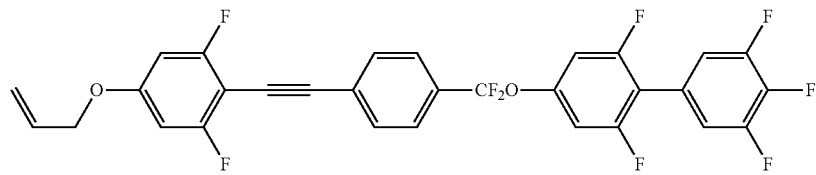
(1-7-63)
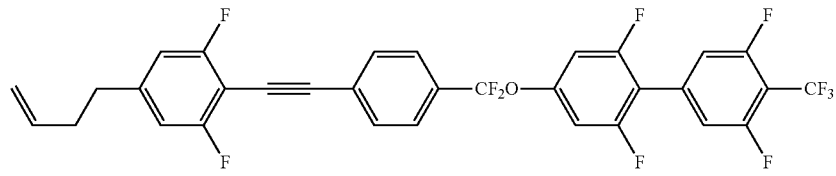
(1-7-64)
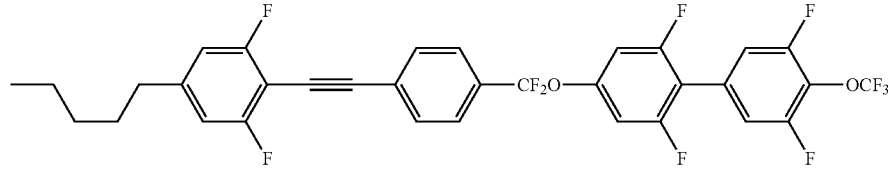
(1-7-65)
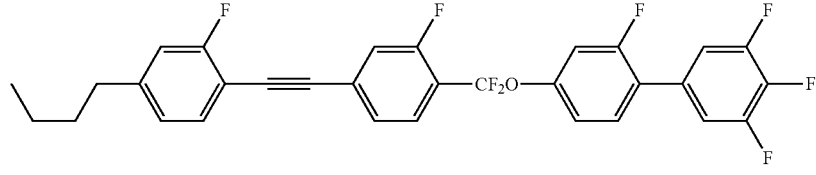
(1-7-66)
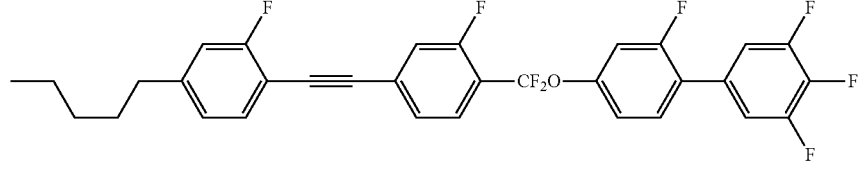
(1-7-67)
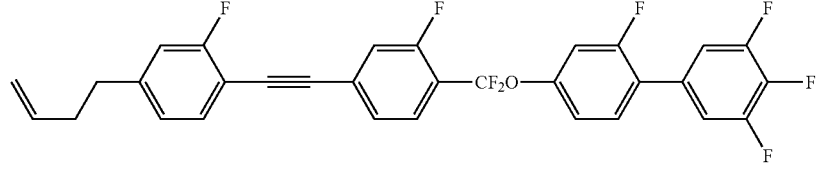
(1-7-68)
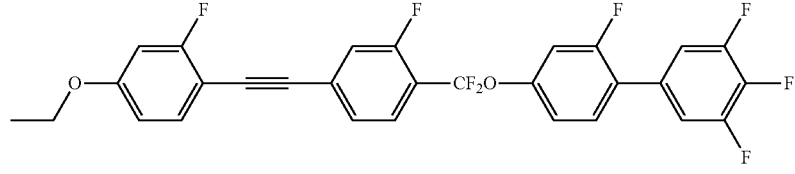
(1-7-69)

(1-7-70)
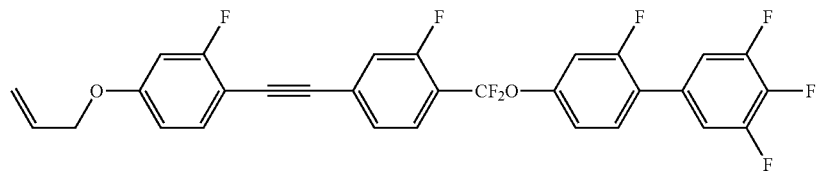
(1-7-71)
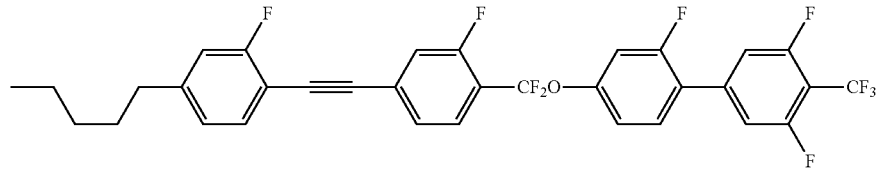
(1-7-72)
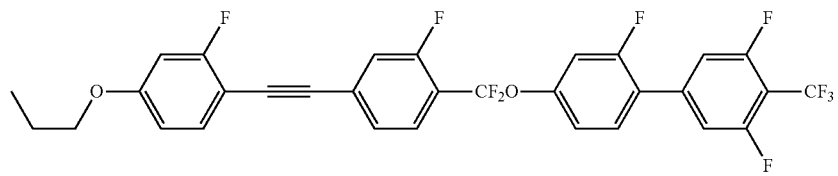
(1-7-73)
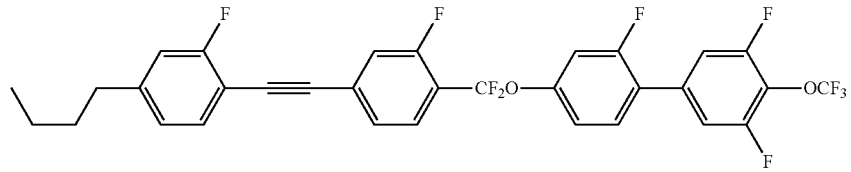
(1-7-74)
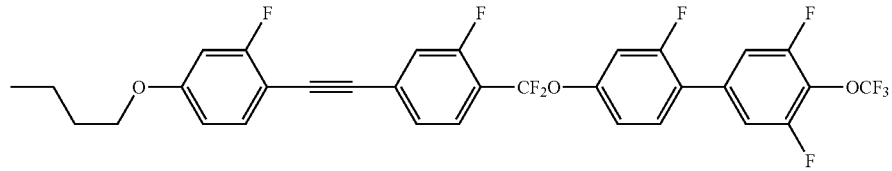
(1-7-75)
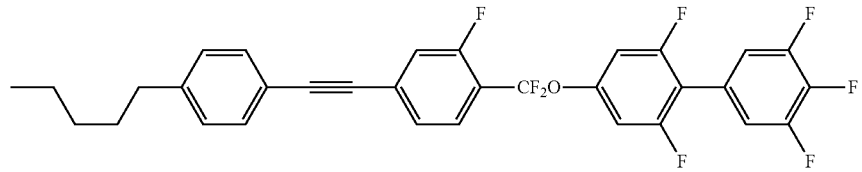
(1-7-76)
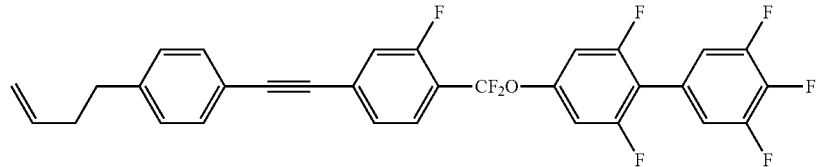
(1-7-77)
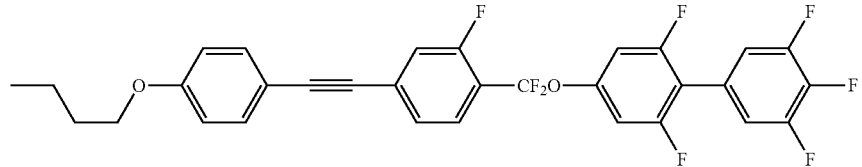
(1-7-78)
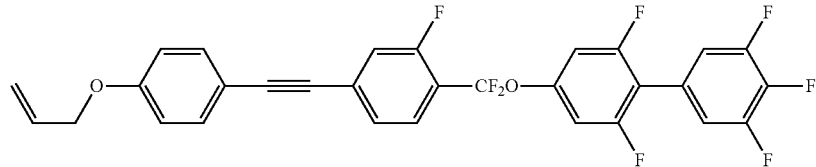

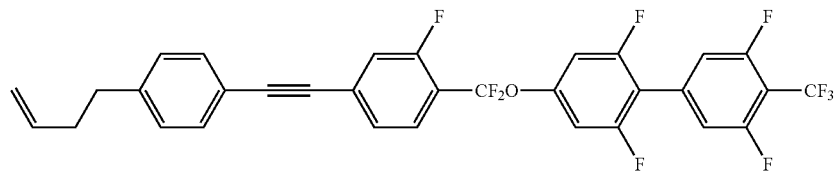 (1-7-79)
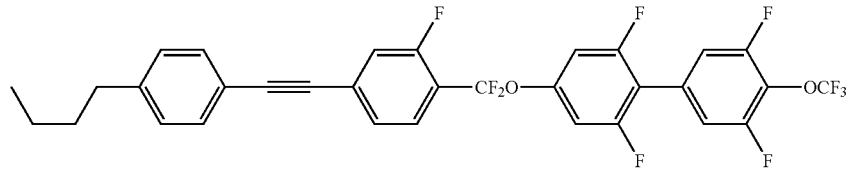 (1-7-80)
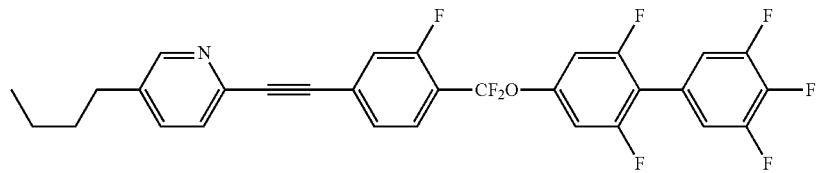 (1-7-81)
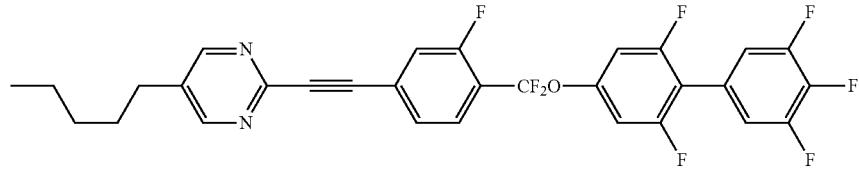 (1-7-82)
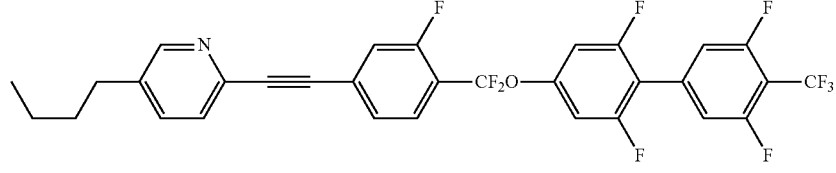 (1-7-83)
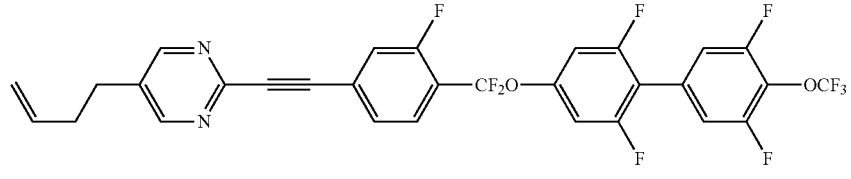 (1-7-84)
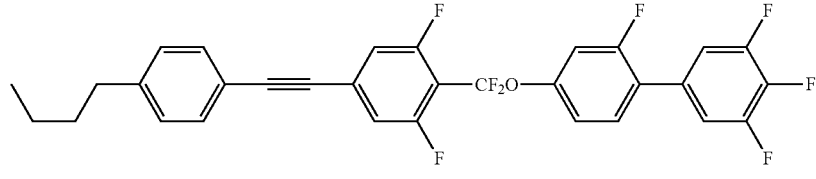 (1-7-85)
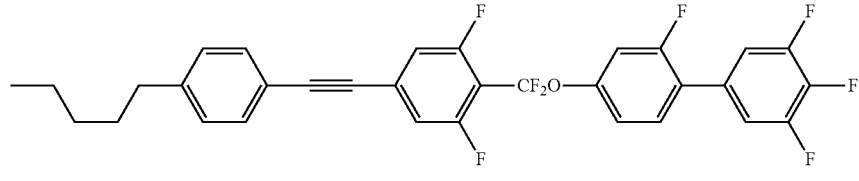 (1-7-86)
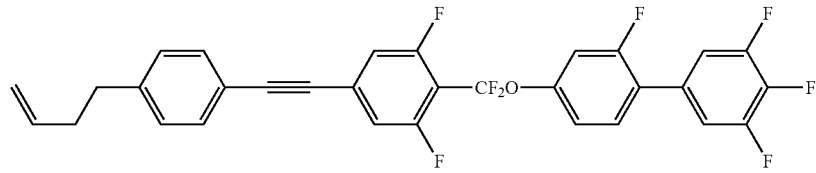 (1-7-87)

-continued
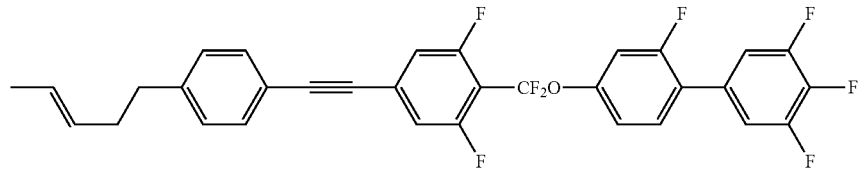
(1-7-88)
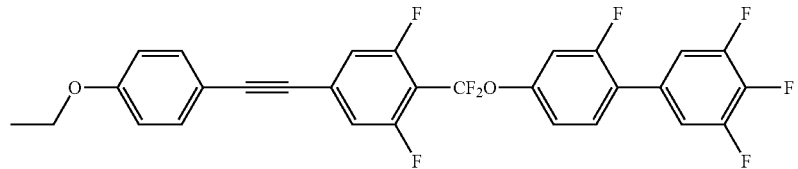
(1-7-89)
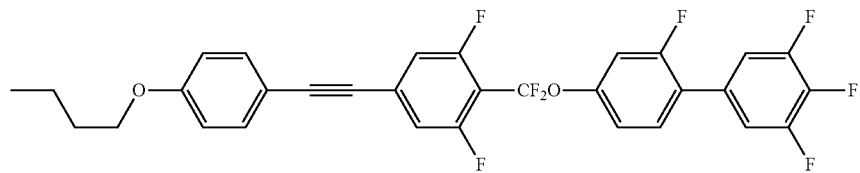
(1-7-90)
C 56.7 C 70 N 151.9 I
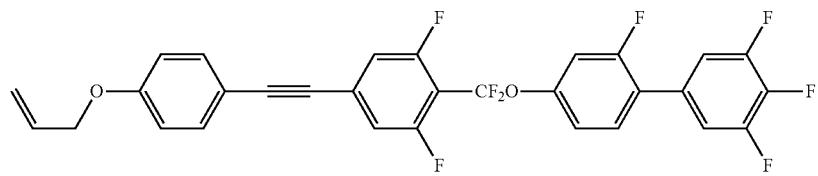
(1-7-91)
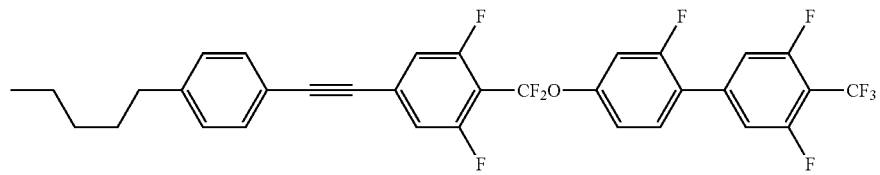
(1-7-92)
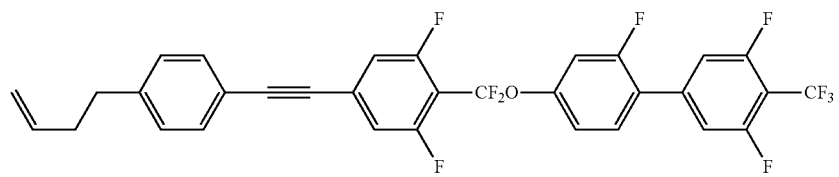
(1-7-93)
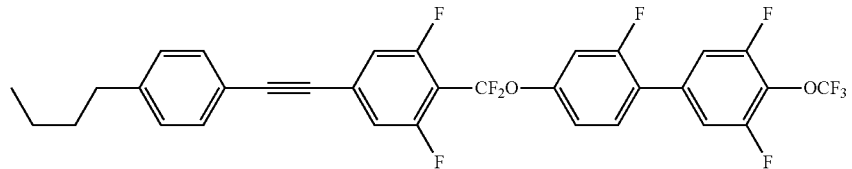
(1-7-94)
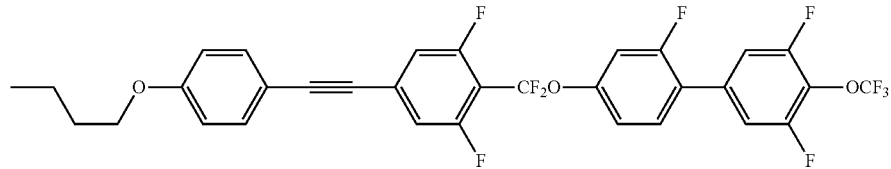
(1-7-95)

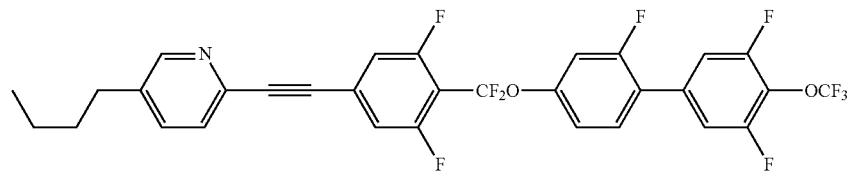
(1-7-96)
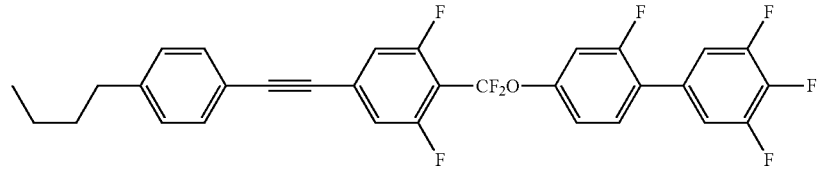
(1-7-97)
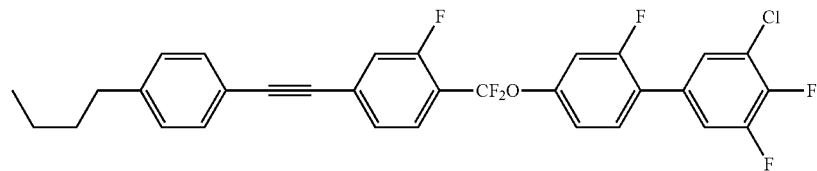
(1-7-98)
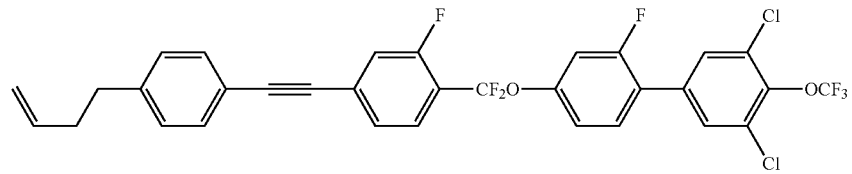
(1-7-99)
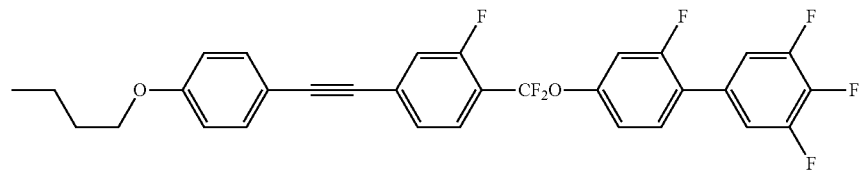
(1-7-100)
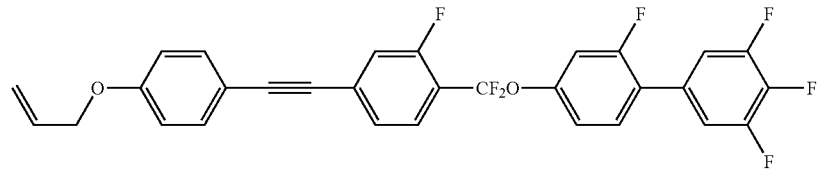
(1-7-101)
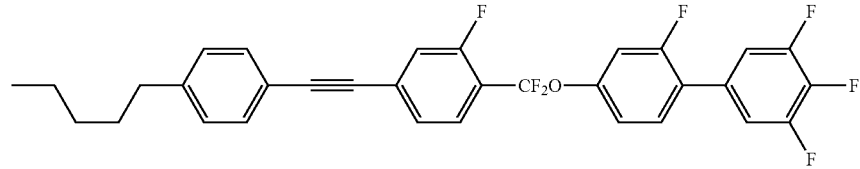
(1-7-102)
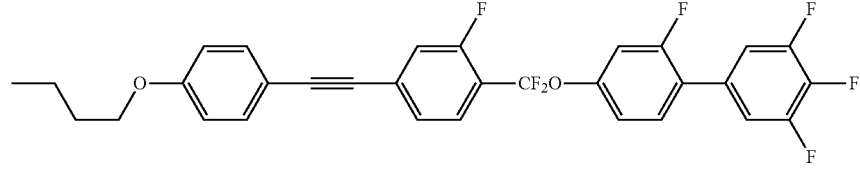
(1-7-103)
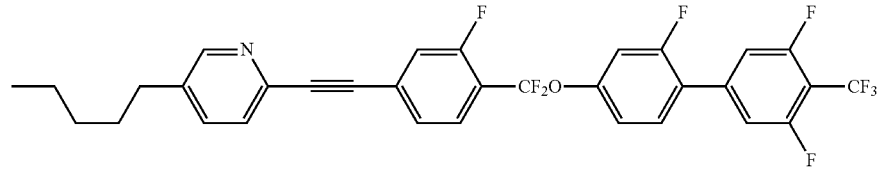
(1-7-104)

-continued
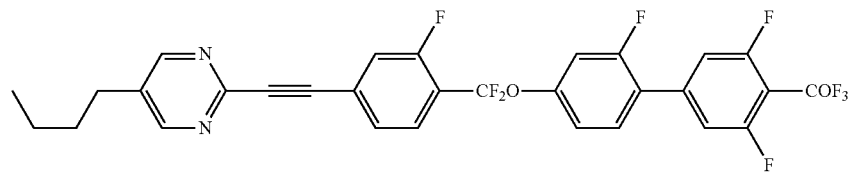
(1-7-105)
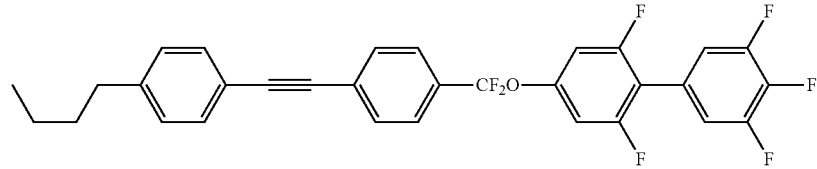
(1-7-106)
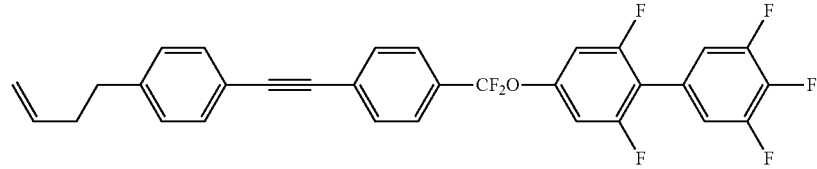
(1-7-107)
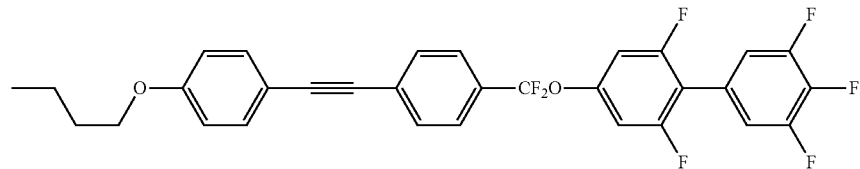
(1-7-108)
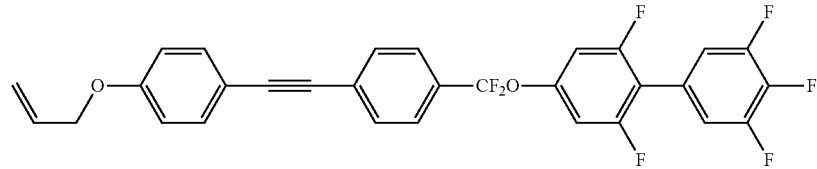
(1-7-109)
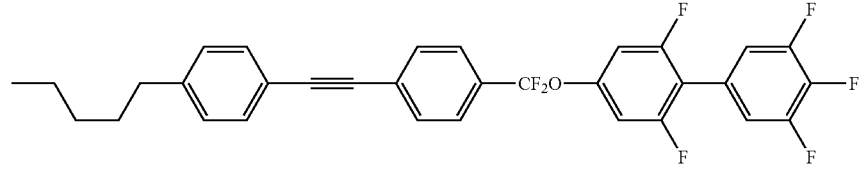
(1-7-110)
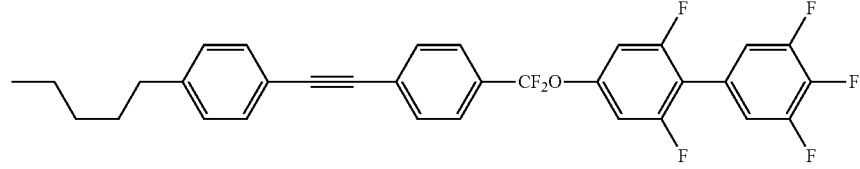
(1-7-111)
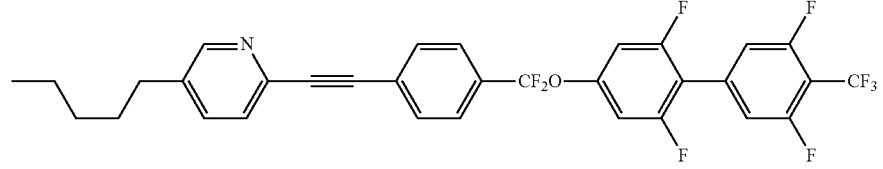
(1-7-112)
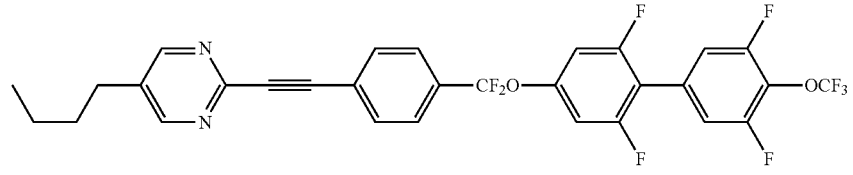
(1-7-113)

(1-7-114)
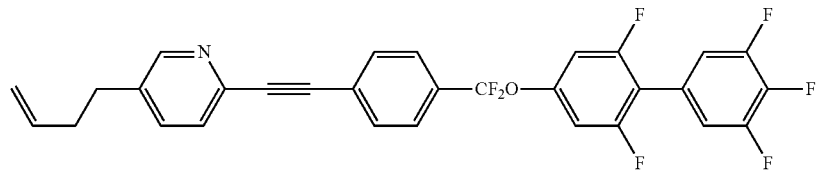
(1-7-115)
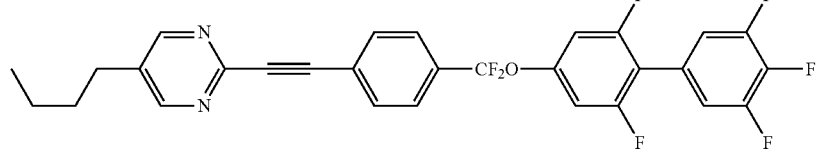
(1-7-116)
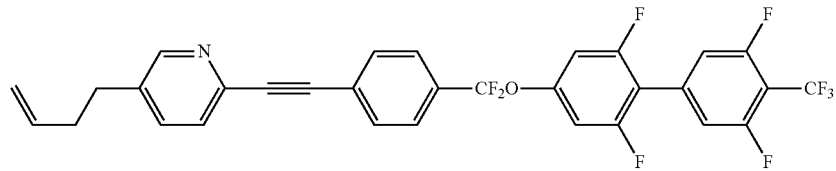
(1-7-117)
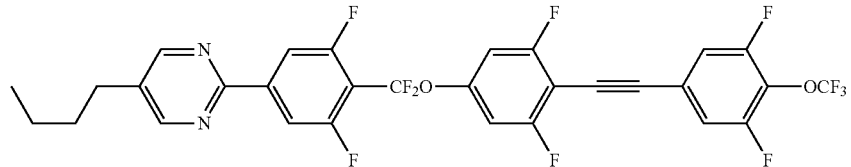
(1-8-1)
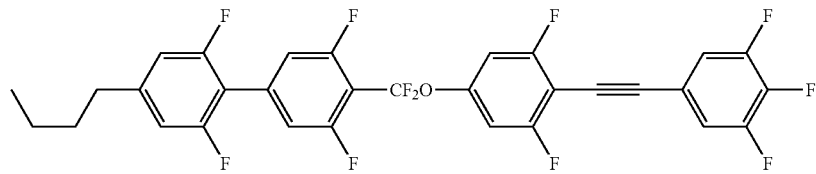
(1-8-2)
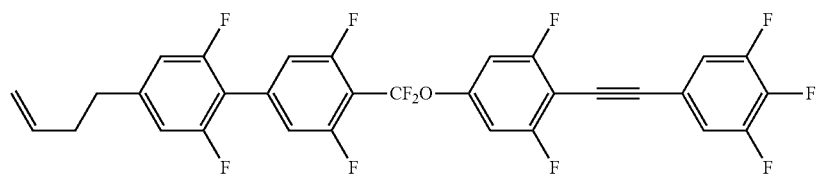
(1-8-3)
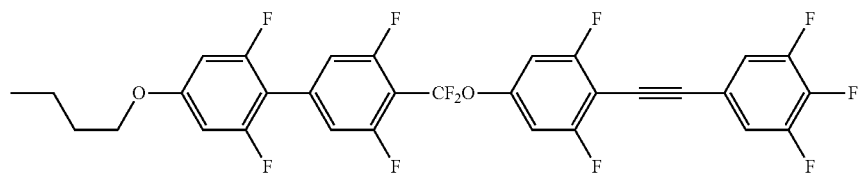
(1-8-4)
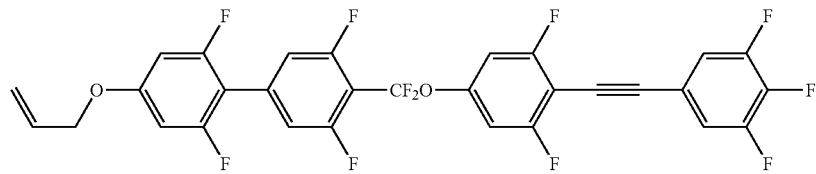
(1-8-5)
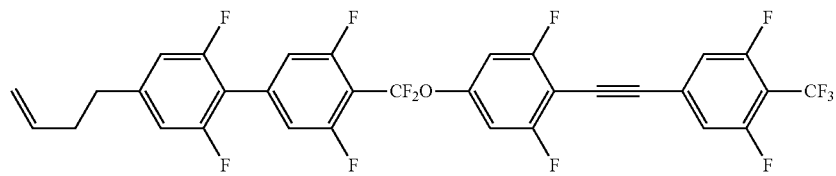

-continued
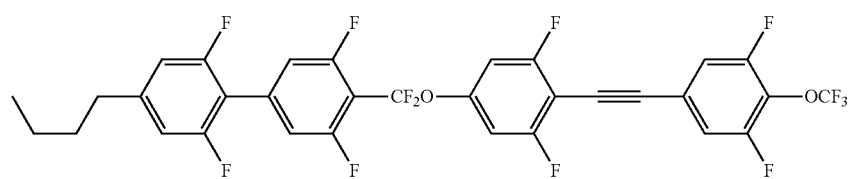
(1-8-6)
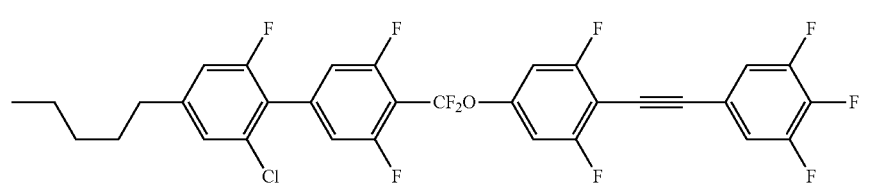
(1-8-7)
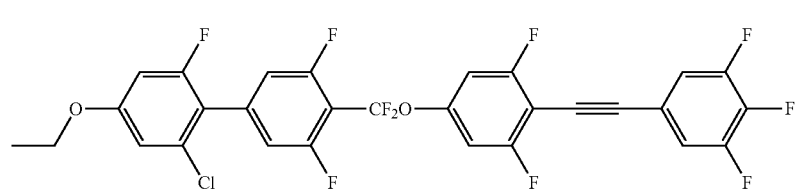
(1-8-8)
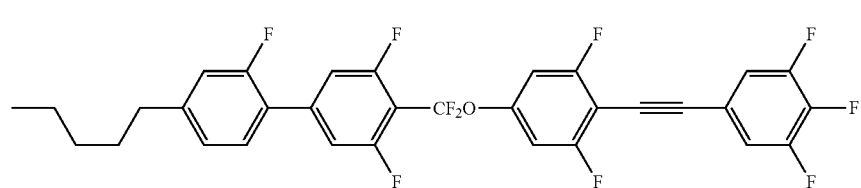
(1-8-9)
$^a$C 97.2 N 134 I
$T_{NI}$ = 83.7° C., Δε = 52.1, Δn = 0.217
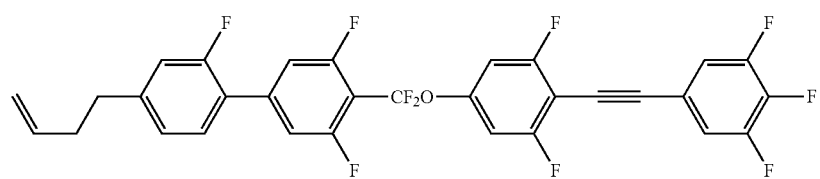
(1-8-10)
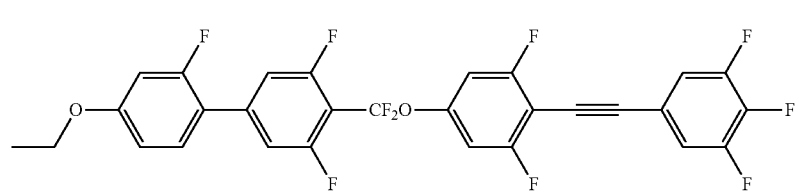
(1-8-11)
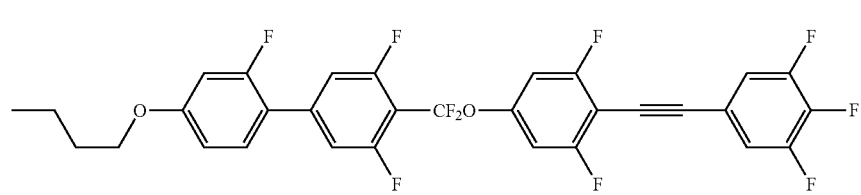
(1-8-12)
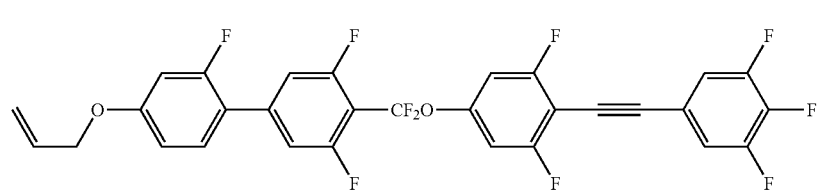
(1-8-13)

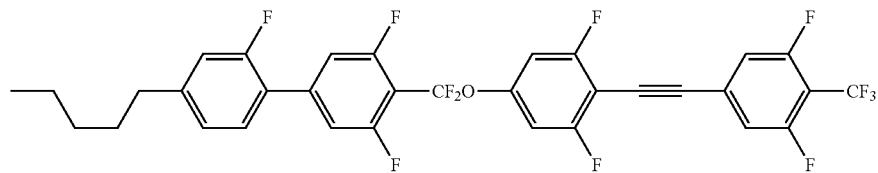
(1-8-14)
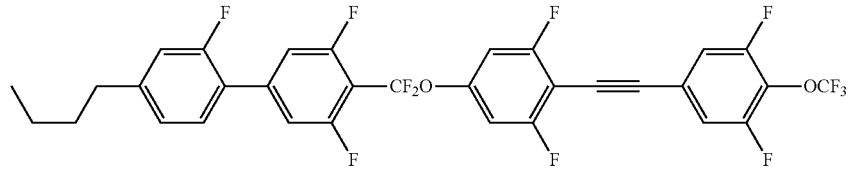
(1-8-15)
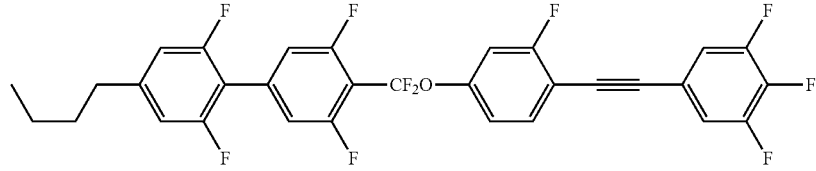
(1-8-16)
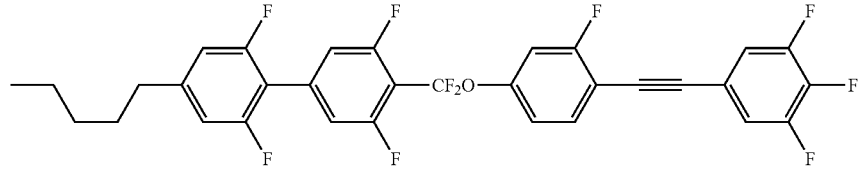
(1-8-17)
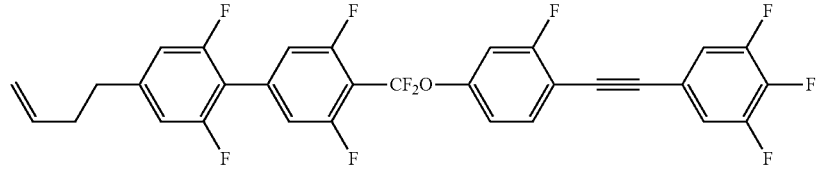
(1-8-18)
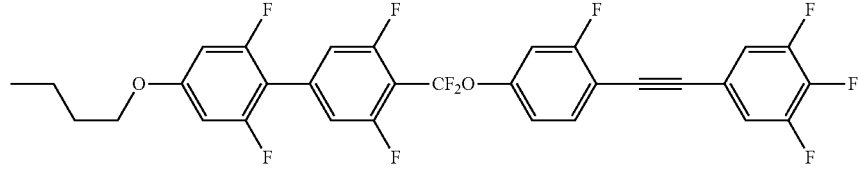
(1-8-19)
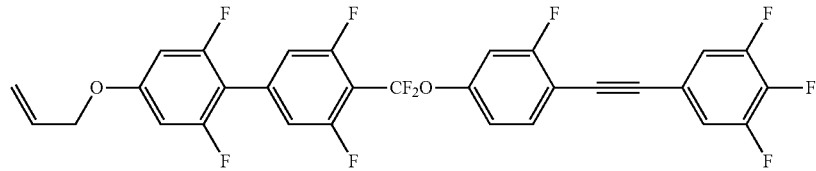
(1-8-20)
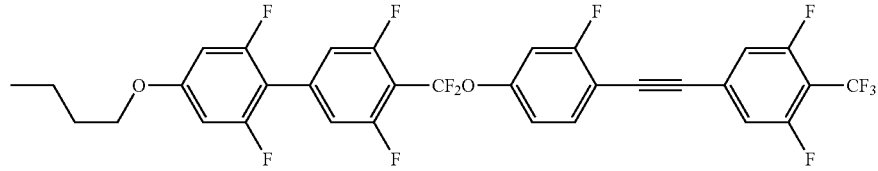
(1-8-21)
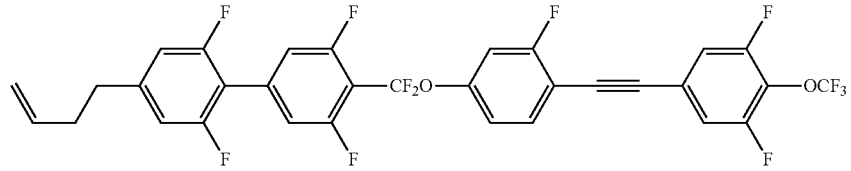
(1-8-22)

-continued
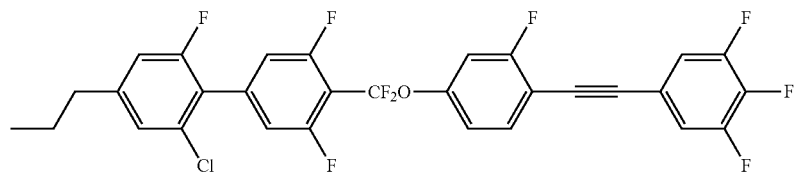
(1-8-23)
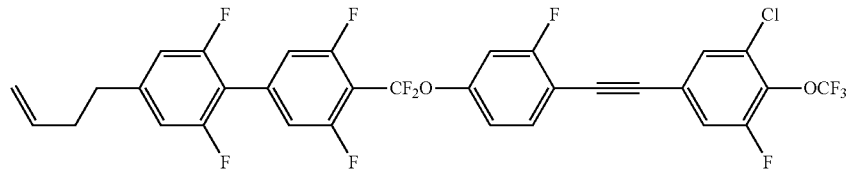
(1-8-24)
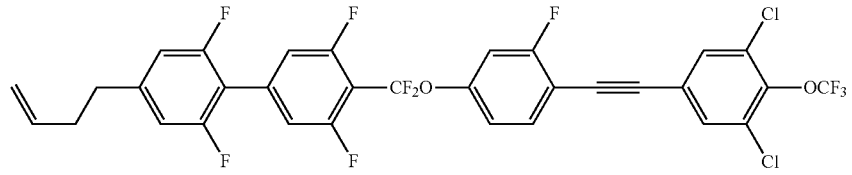
(1-8-25)
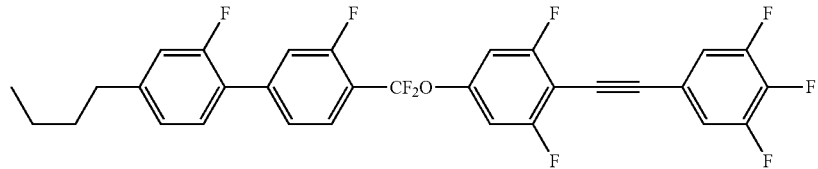
(1-8-26)
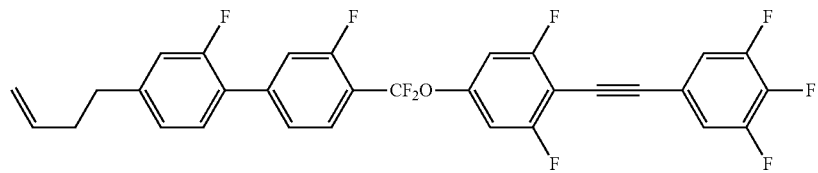
(1-8-27)
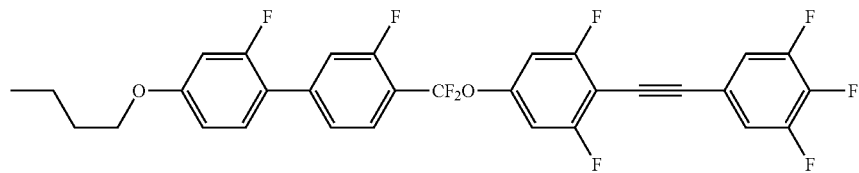
(1-8-28)
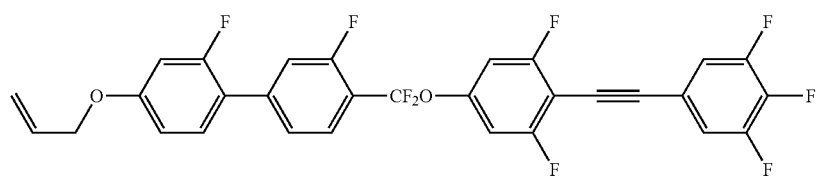
(1-8-29)
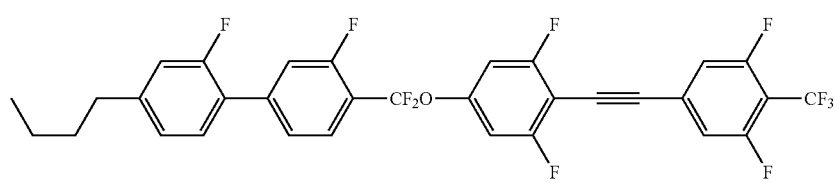
(1-8-30)
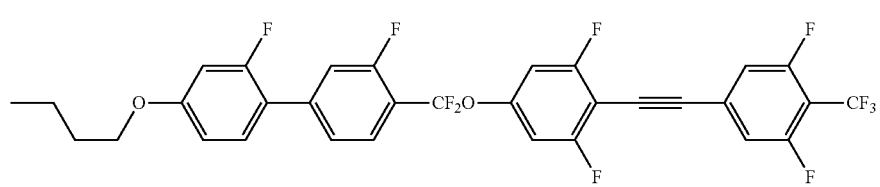
(1-8-31)

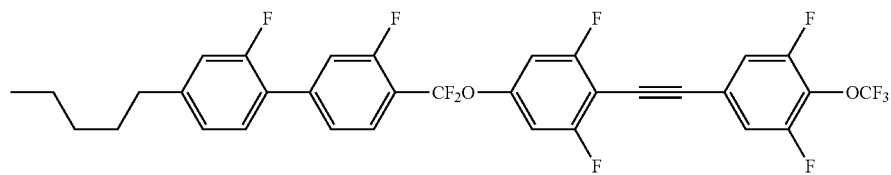
(1-8-32)
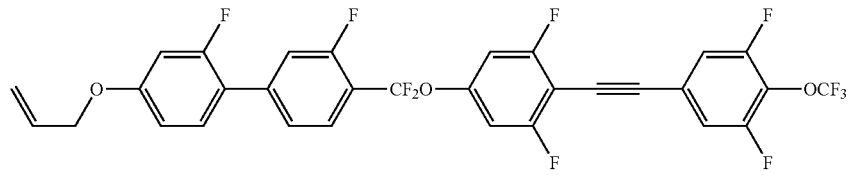
(1-8-33)
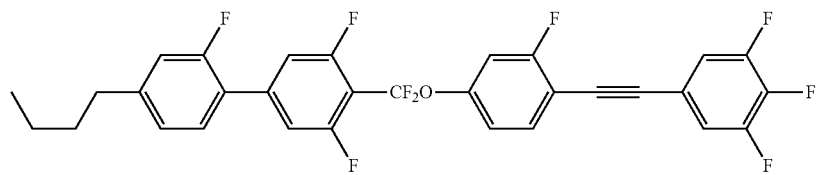
(1-8-34)
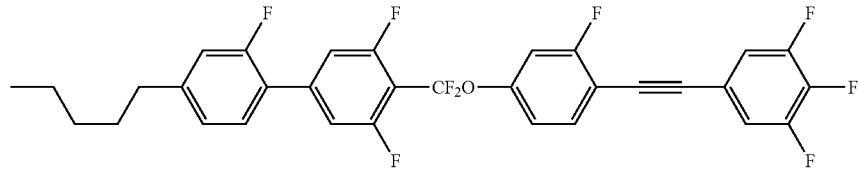
(1-8-35)
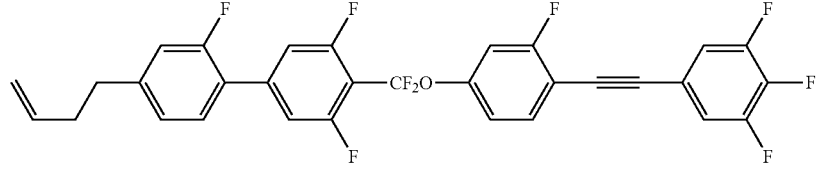
(1-8-36)
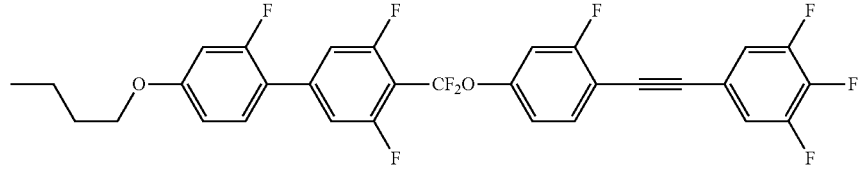
(1-8-37)
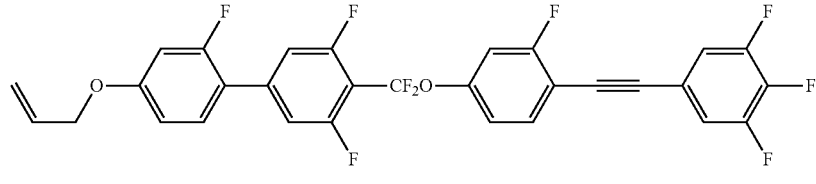
(1-8-38)
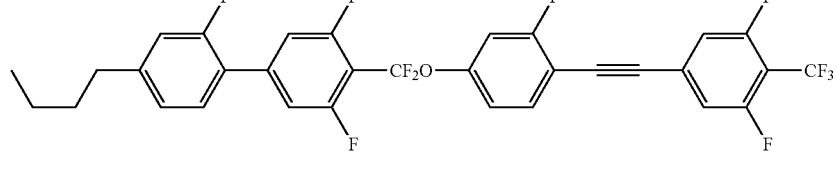
(1-8-39)
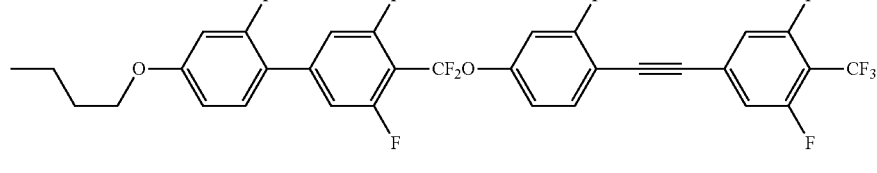
(1-8-40)

-continued
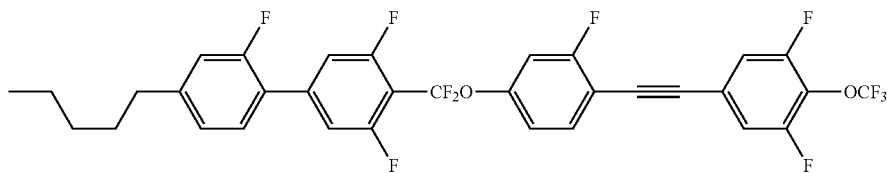
(1-8-41)
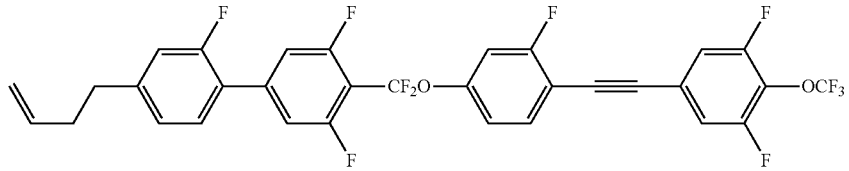
(1-8-42)
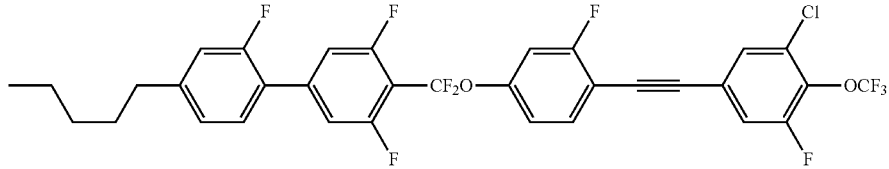
(1-8-43)
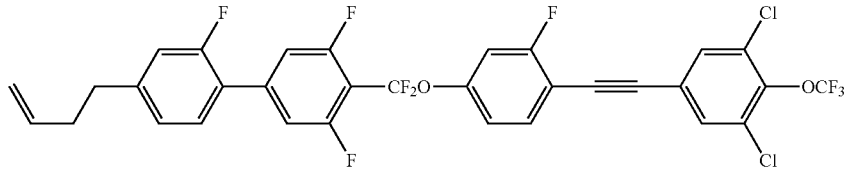
(1-8-44)
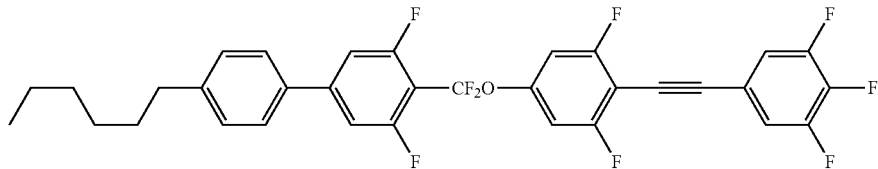
(1-8-45)
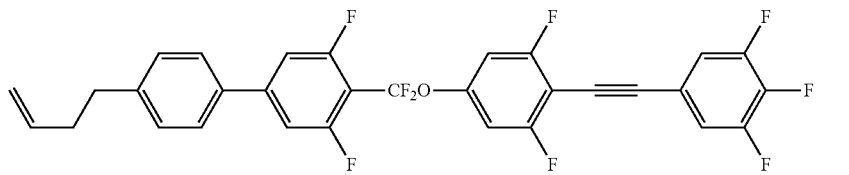
(1-8-46)
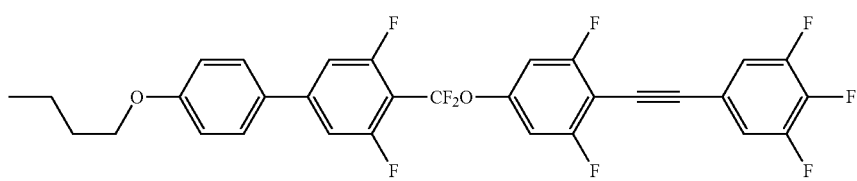
(1-8-47)
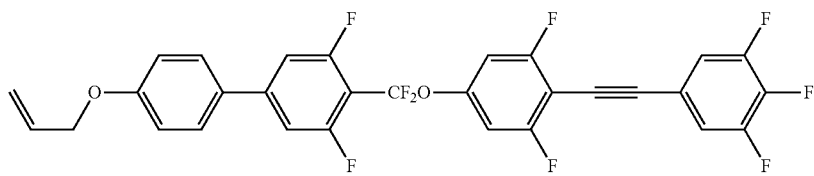
(1-8-48)
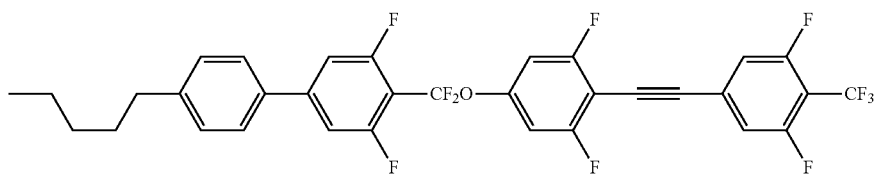
(1-8-49)

-continued
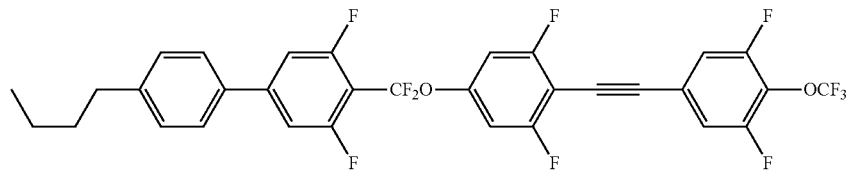
(1-8-50)
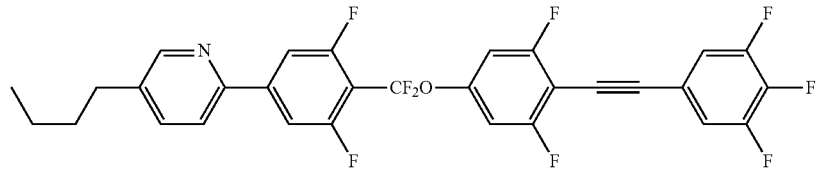
(1-8-51)
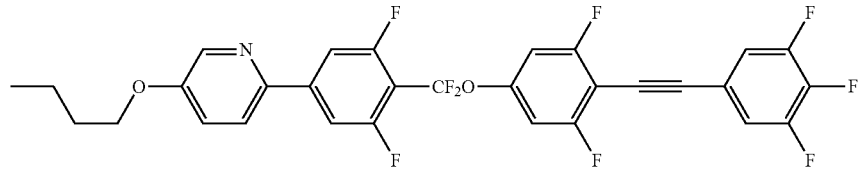
(1-8-52)
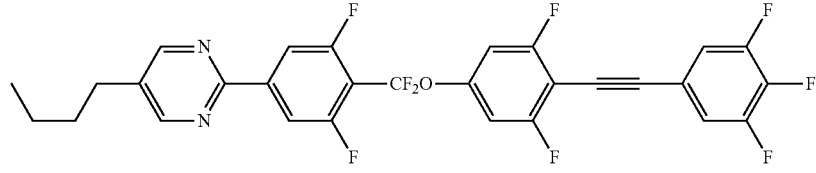
(1-8-53)
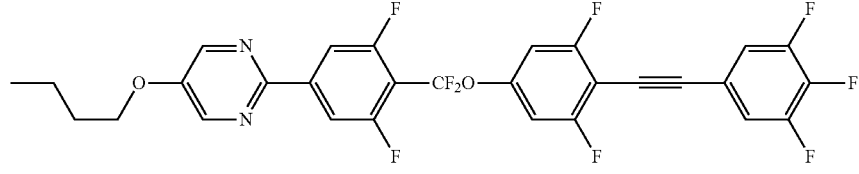
(1-8-54)
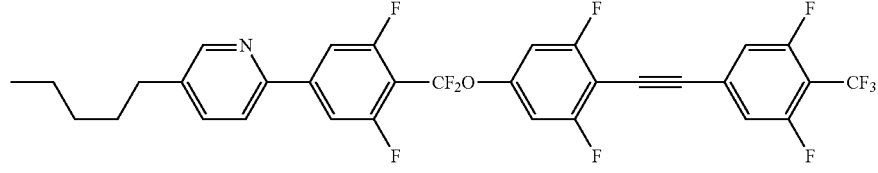
(1-8-55)
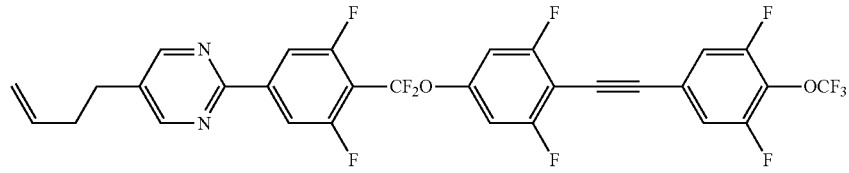
(1-8-56)
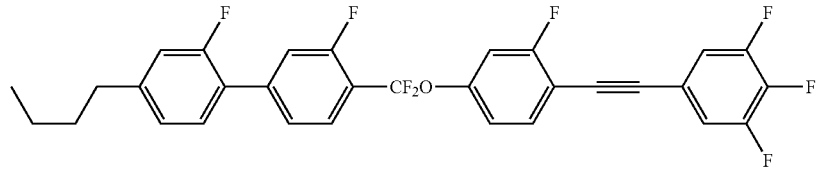
(1-8-57)
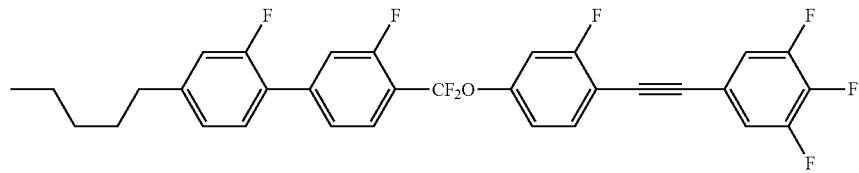
(1-8-58)

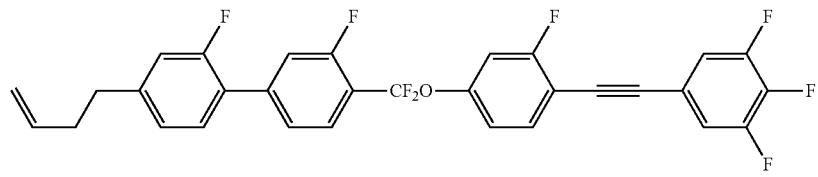
(1-8-59)
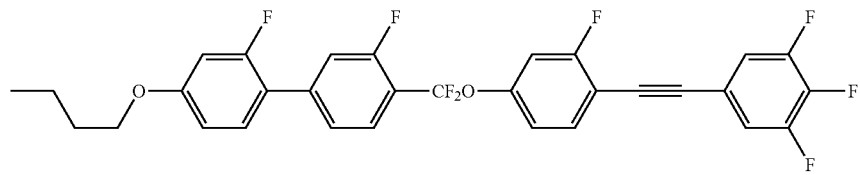
(1-8-60)
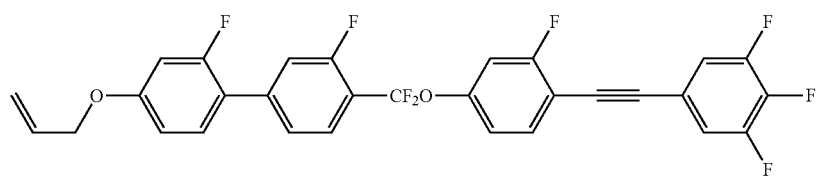
(1-8-61)
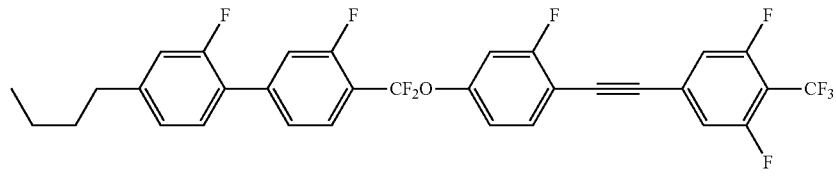
(1-8-62)
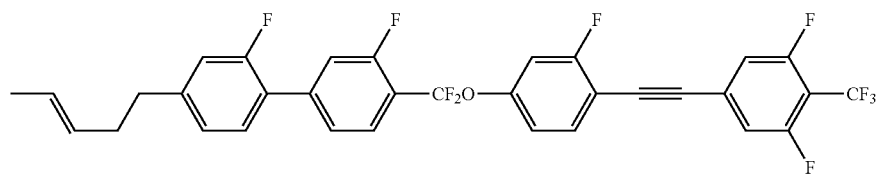
(1-8-63)
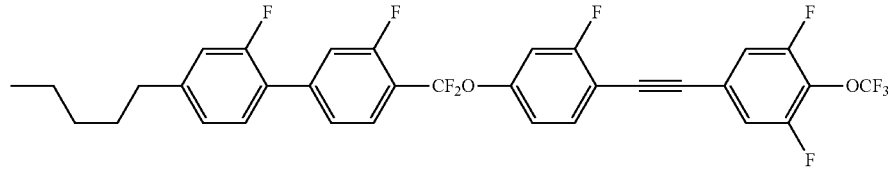
(1-8-64)
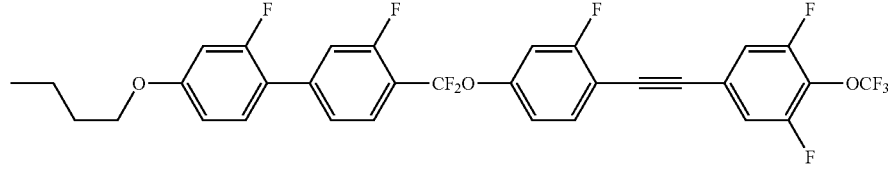
(1-8-65)
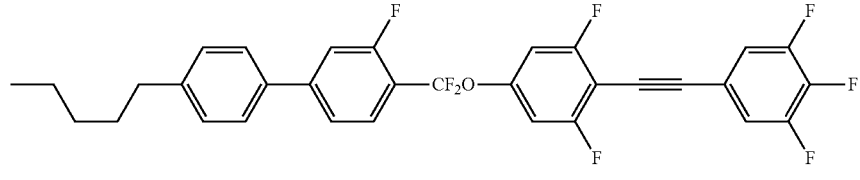
(1-8-66)
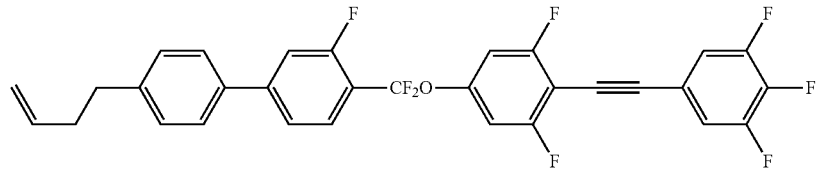
(1-8-67)

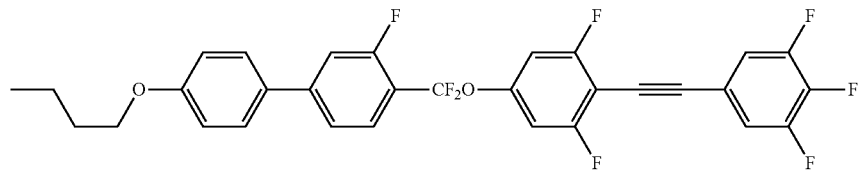
(1-8-68)
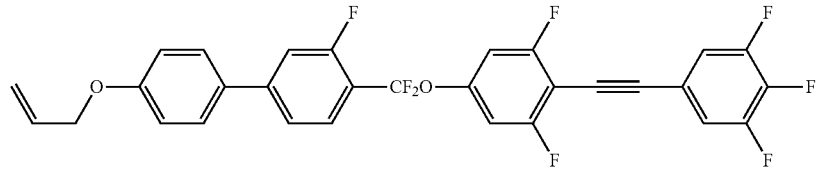
(1-8-69)
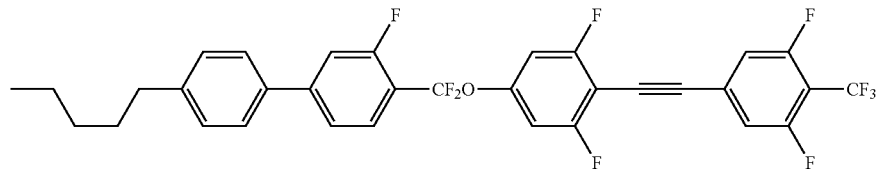
(1-8-70)
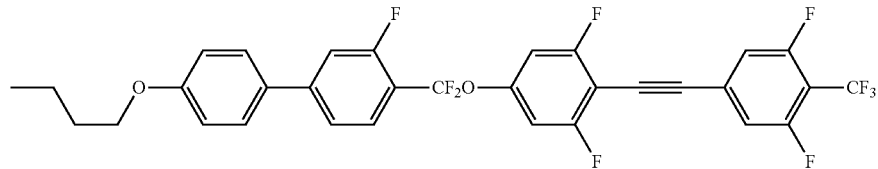
(1-8-71)
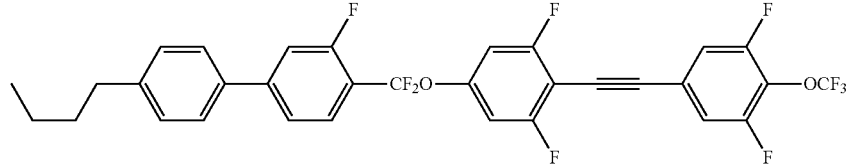
(1-8-72)
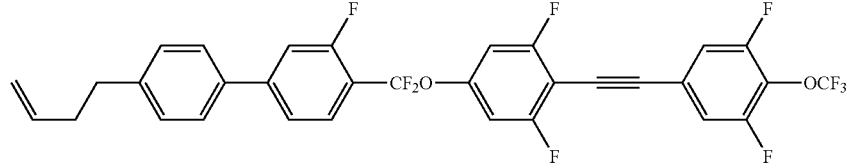
(1-8-73)
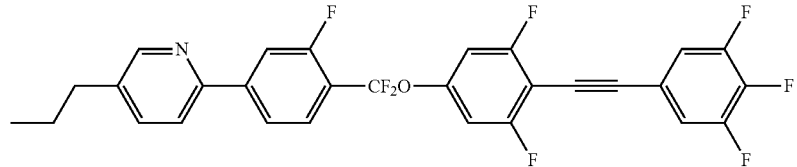
(1-8-74)
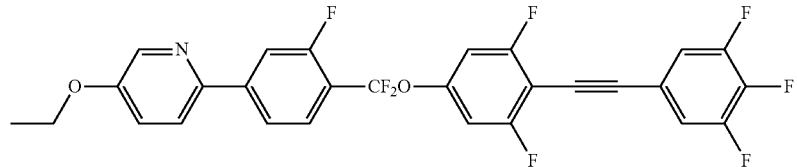
(1-8-75)
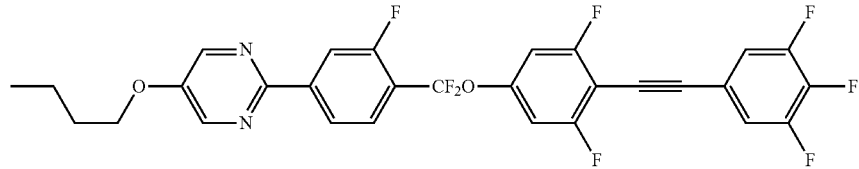
(1-8-76)

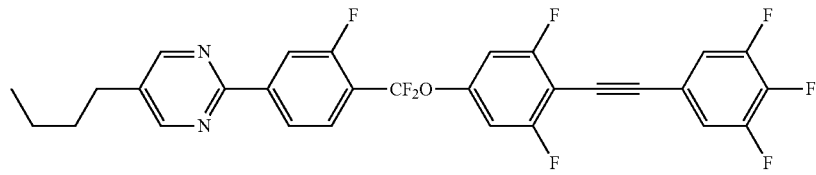
(1-8-77)
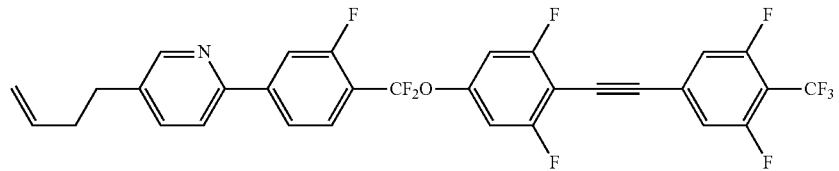
(1-8-78)
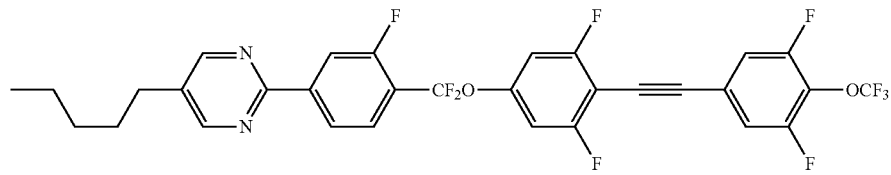
(1-8-79)
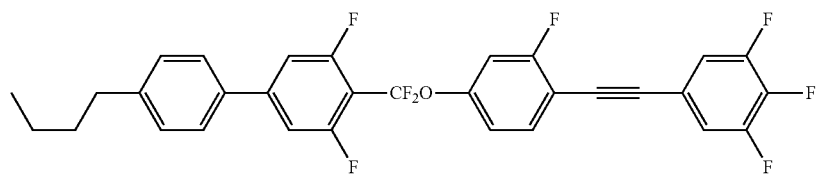
(1-8-80)
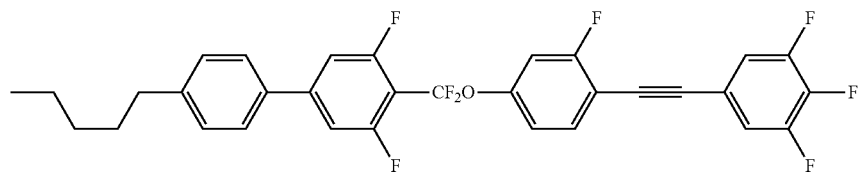
(1-8-81)
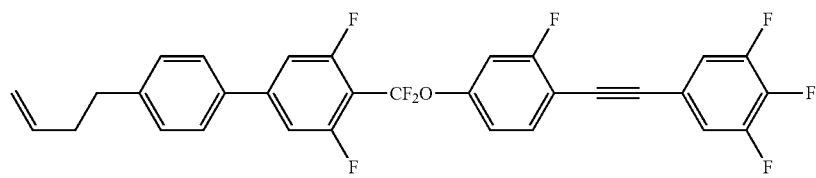
(1-8-82)
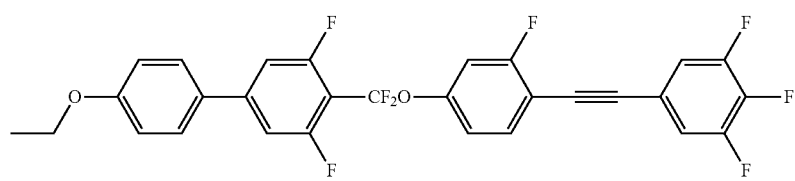
(1-8-83)
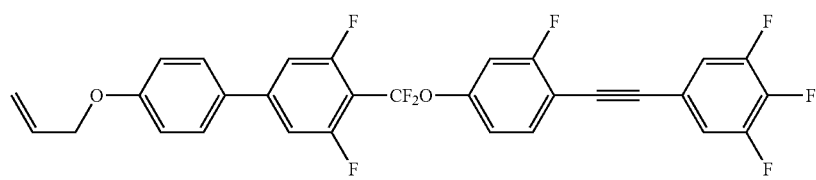
(1-8-84)
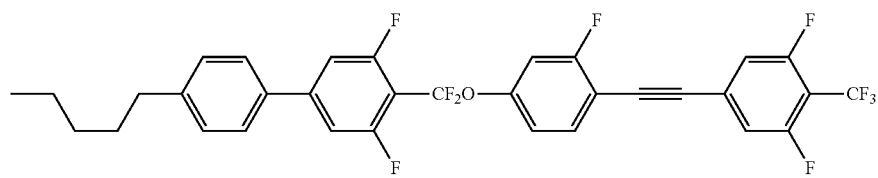
(1-8-85)

-continued
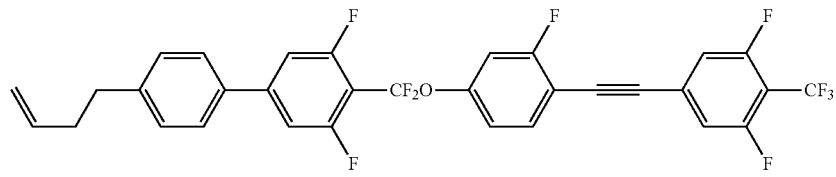
(1-8-86)
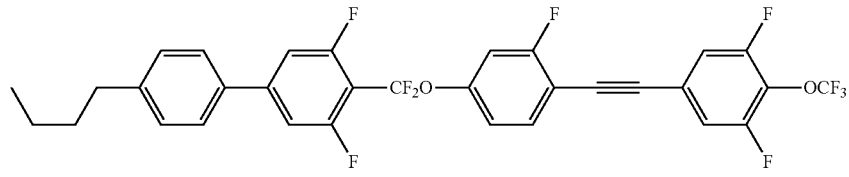
(1-8-87)
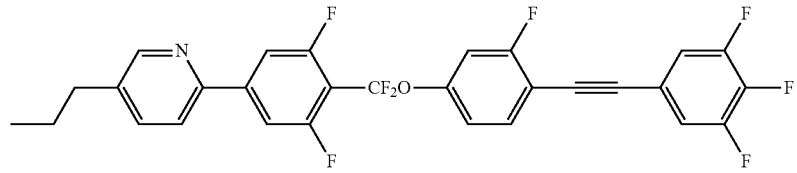
(1-8-88)
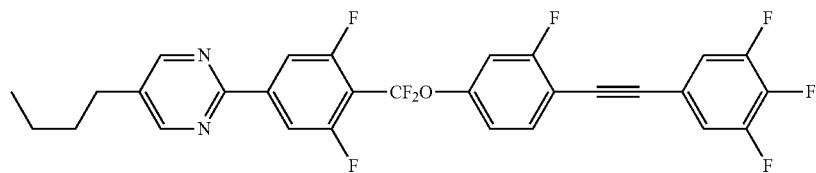
(1-8-89)
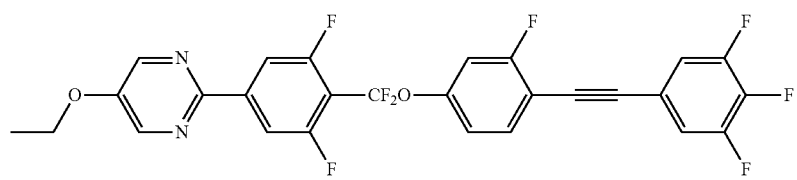
(1-8-90)
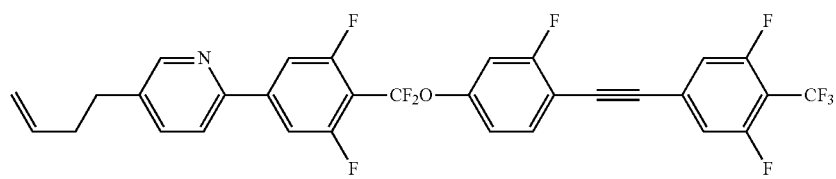
(1-8-91)
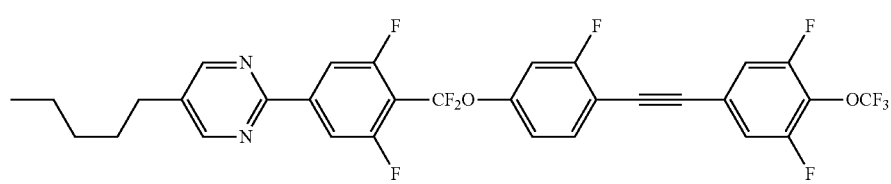
(1-8-92)
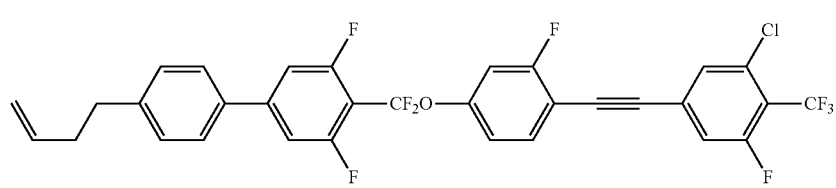
(1-8-93)
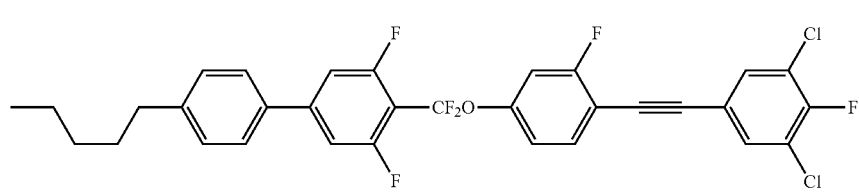
(1-8-94)

-continued
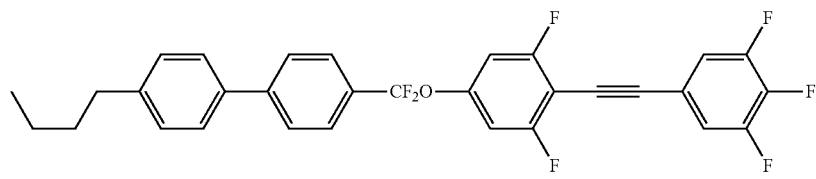
(1-8-95)
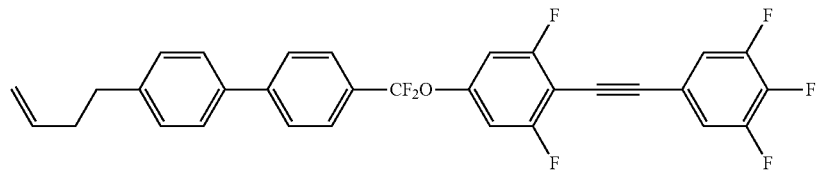
(1-8-96)
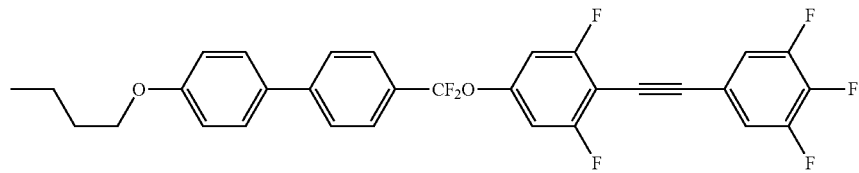
(1-8-97)
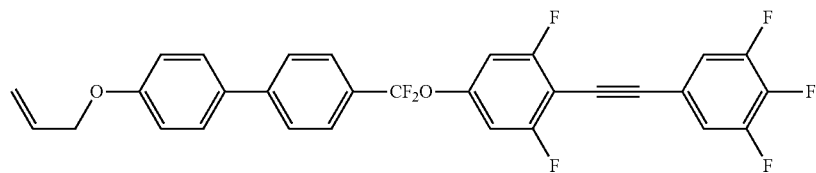
(1-8-98)
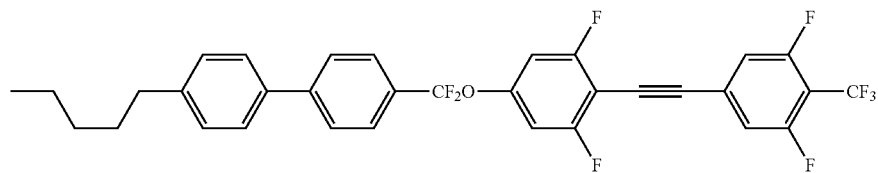
(1-8-99)
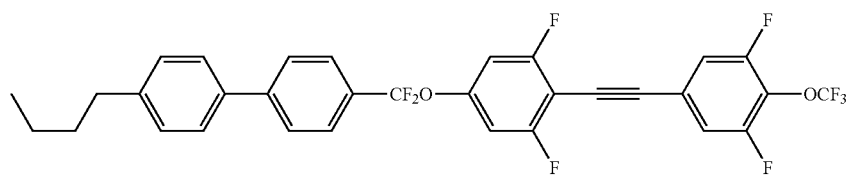
(1-8-100)
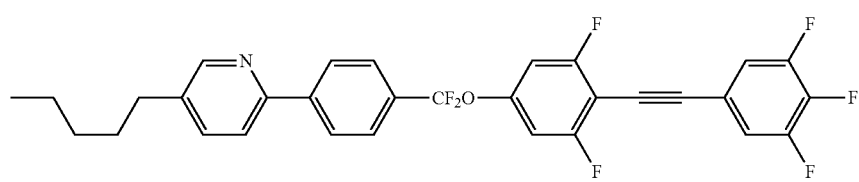
(1-8-101)
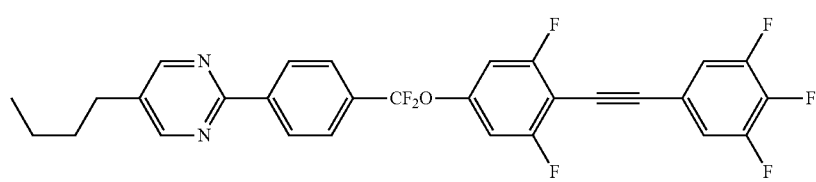
(1-8-102)
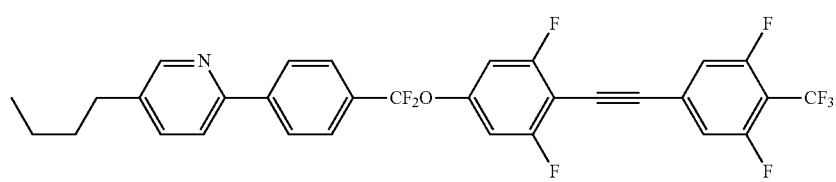
(1-8-103)

-continued
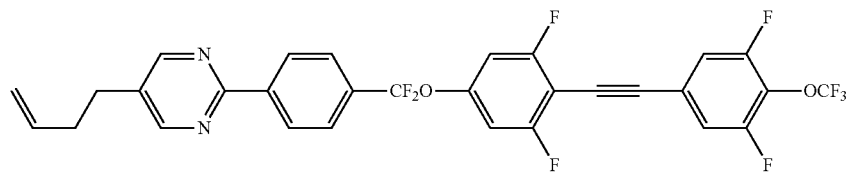 (1-8-104)
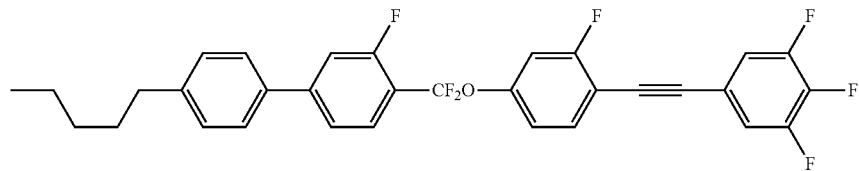 (1-8-105)
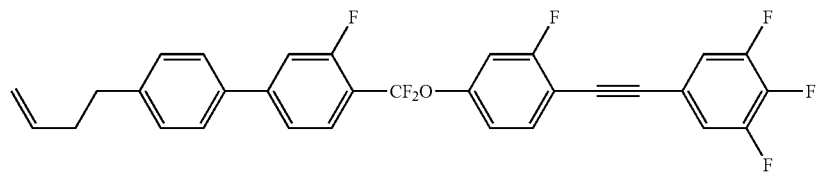 (1-8-106)
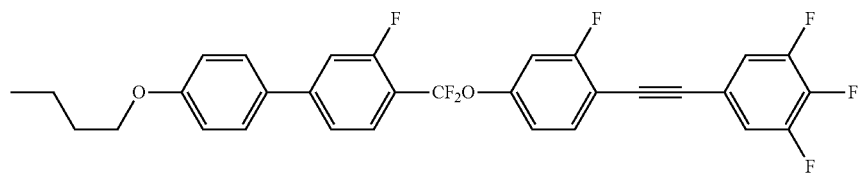 (1-8-107)
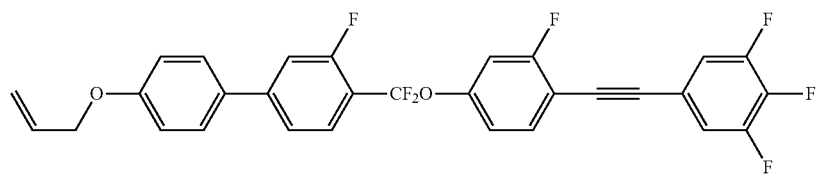 (1-8-108)
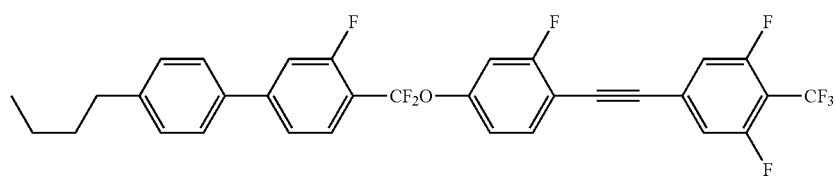 (1-8-109)
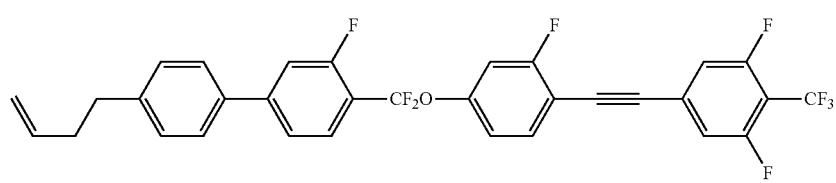 (1-8-110)
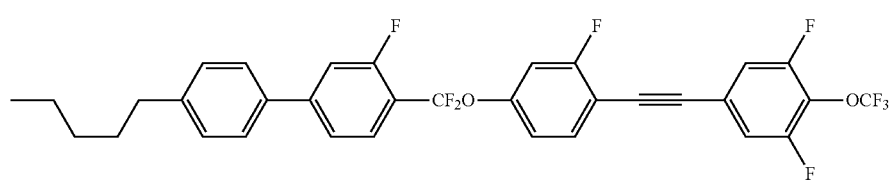 (1-8-111)
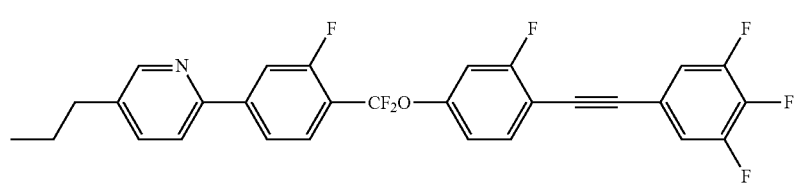 (1-8-112)

-continued
(1-8-113)
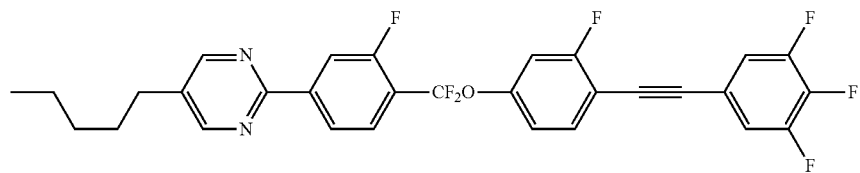
(1-8-114)
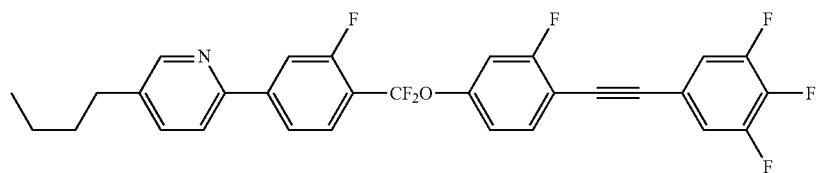
(1-8-115)
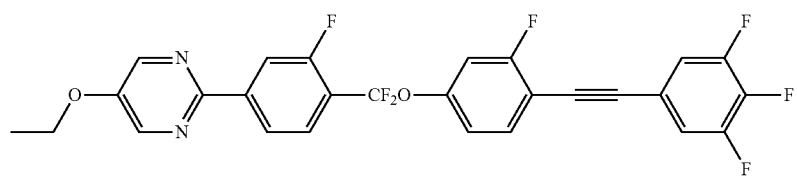
(1-9-1)
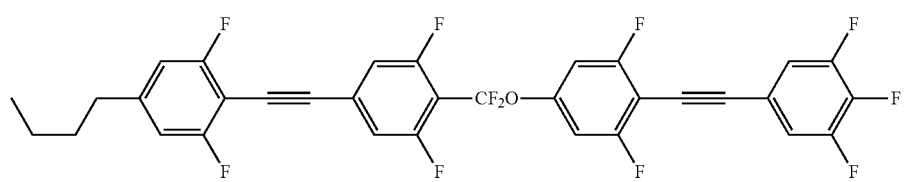
(1-9-2)
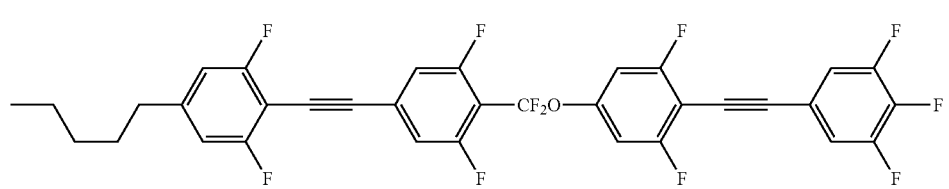
(1-9-3)
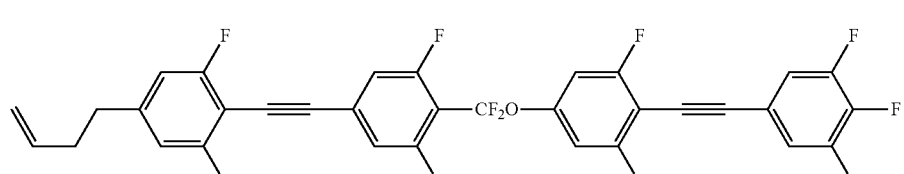
(1-9-4)
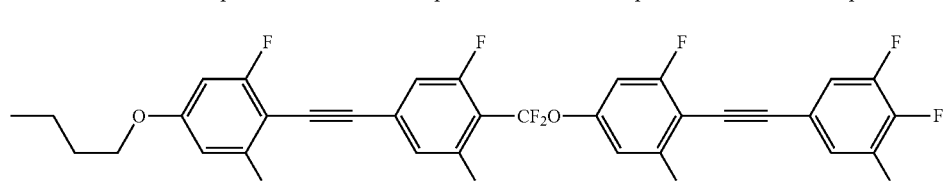
(1-9-5)
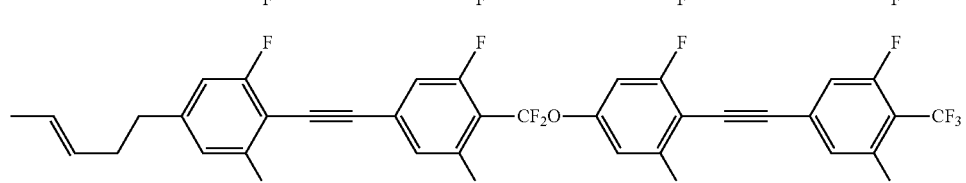
(1-9-6)
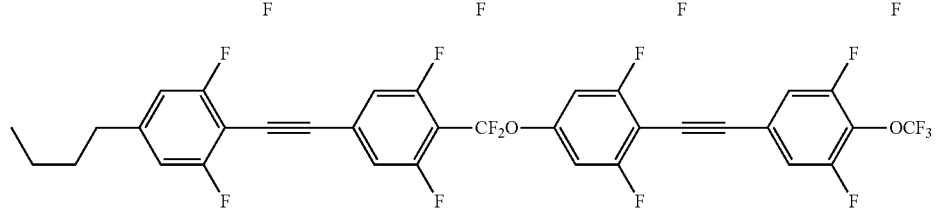

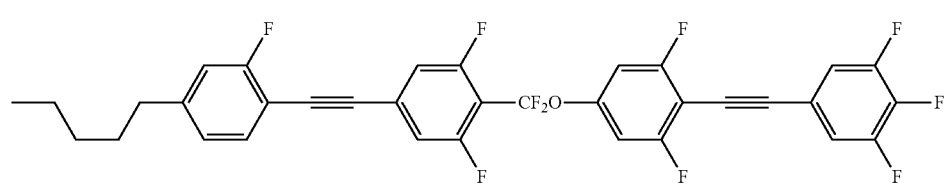
(1-9-7)
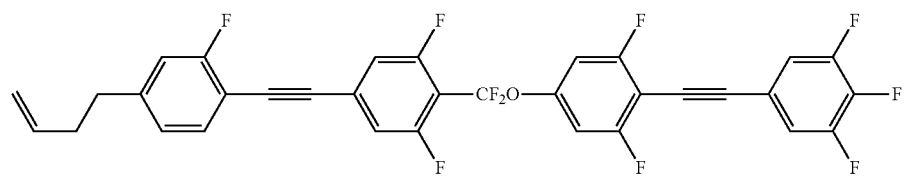
(1-9-8)
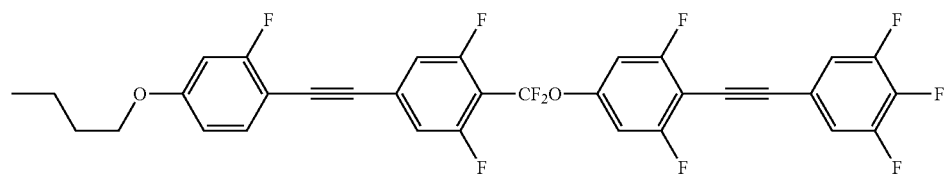
(1-9-9)
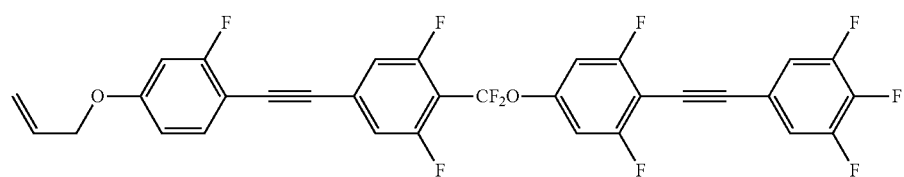
(1-9-10)
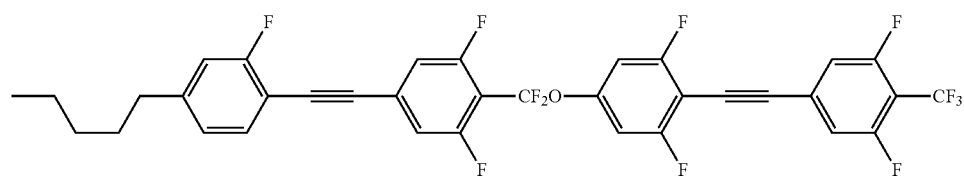
(1-9-11)
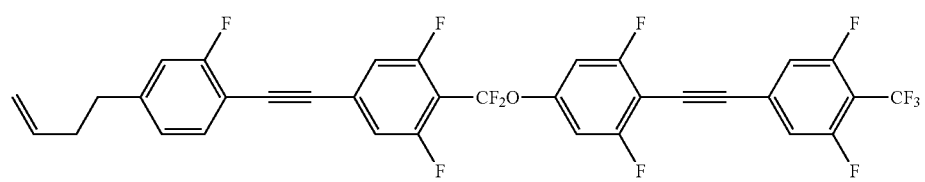
(1-9-12)
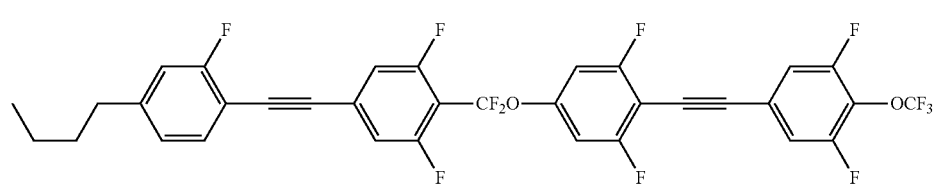
(1-9-13)
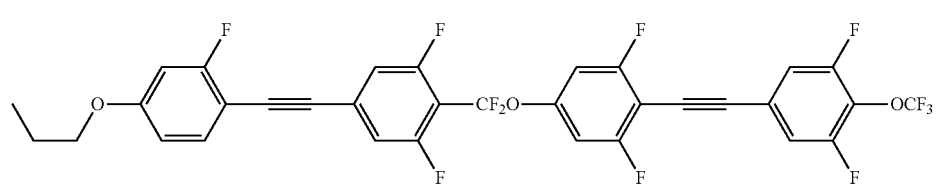
(1-9-14)
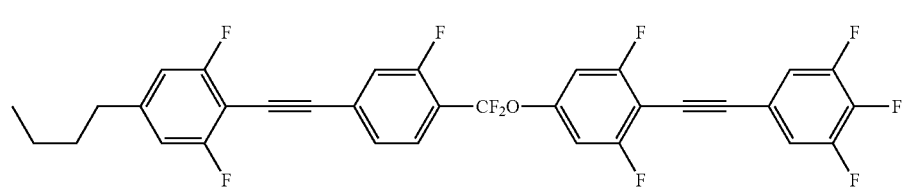
(1-9-15)

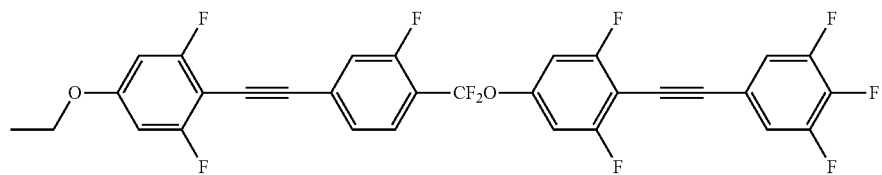
(1-9-16)
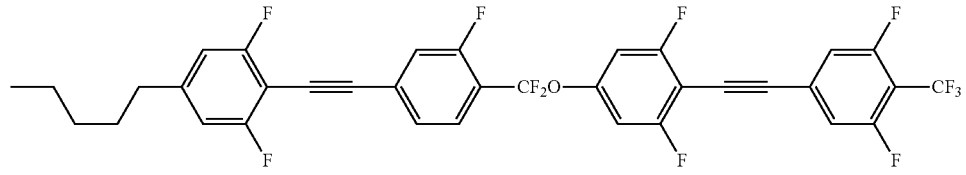
(1-9-17)
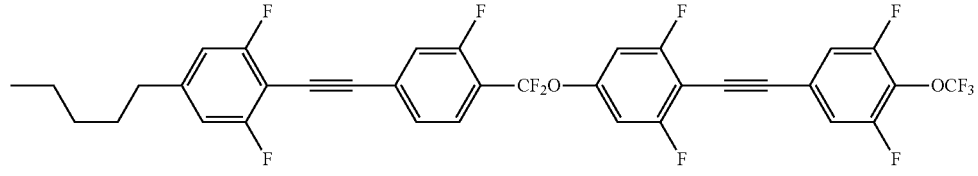
(1-9-18)
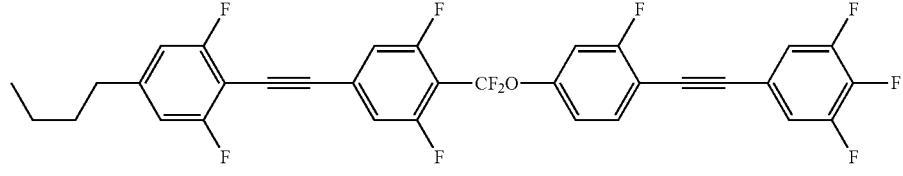
(1-9-19)
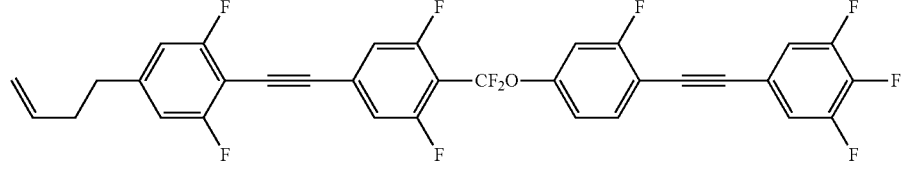
(1-9-20)
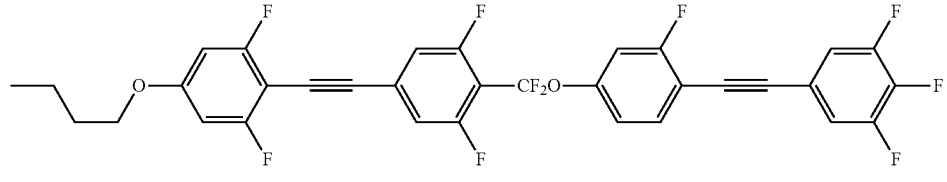
(1-9-21)
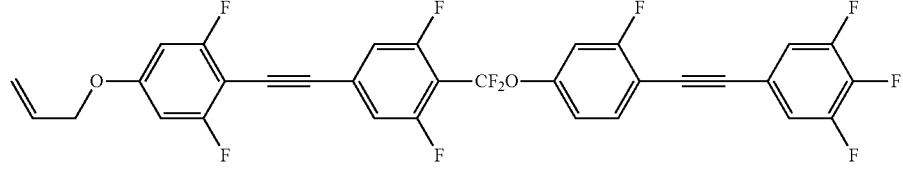
(1-9-22)
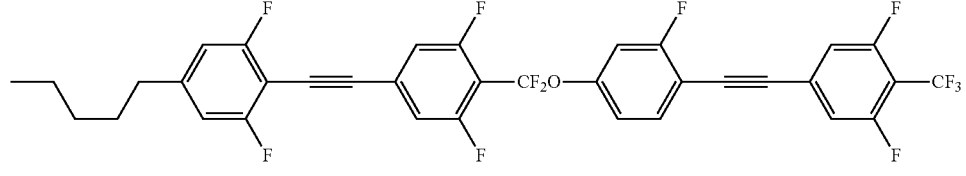
(1-9-23)
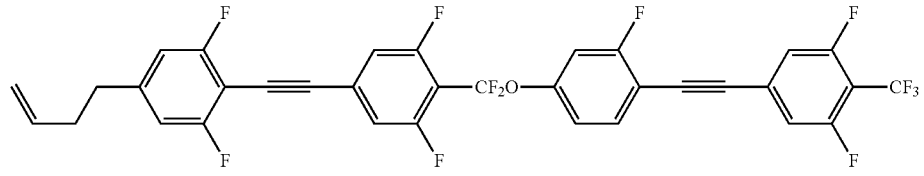
(1-9-24)

(1-9-25)
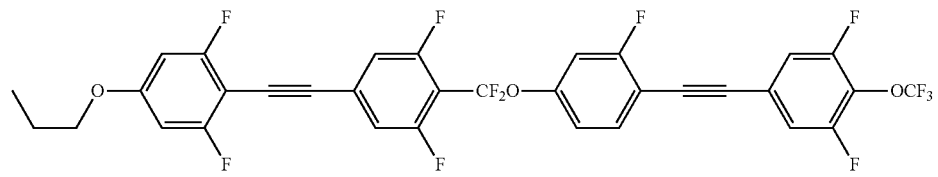
(1-9-26)
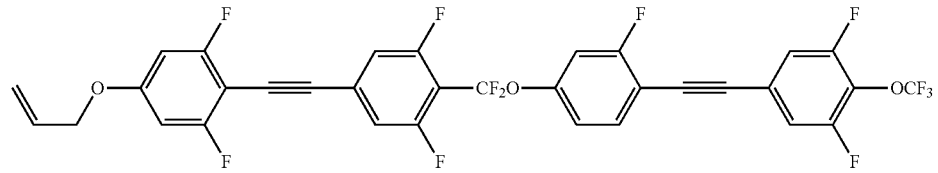
(1-9-27)
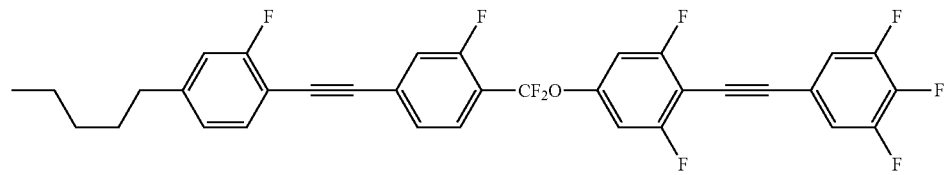
(1-9-28)
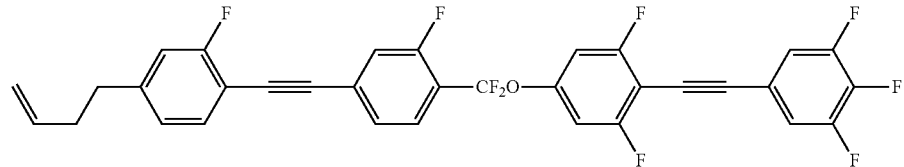
(1-9-29)
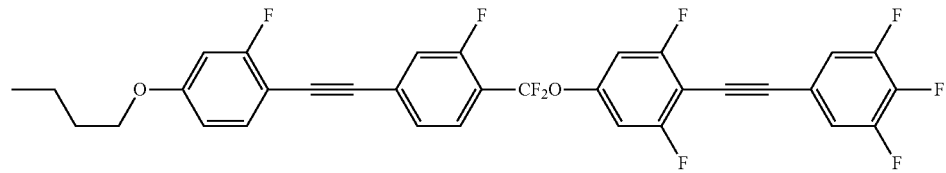
(1-9-30)
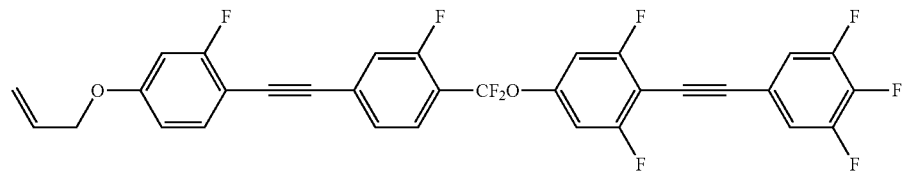
(1-9-31)
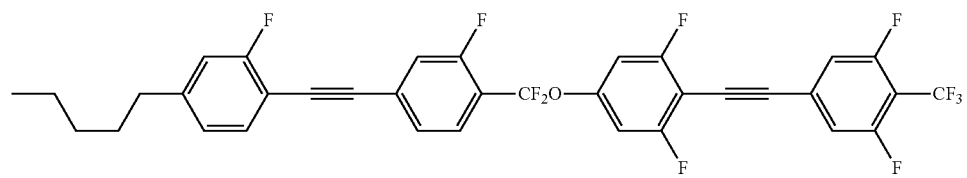
(1-9-32)
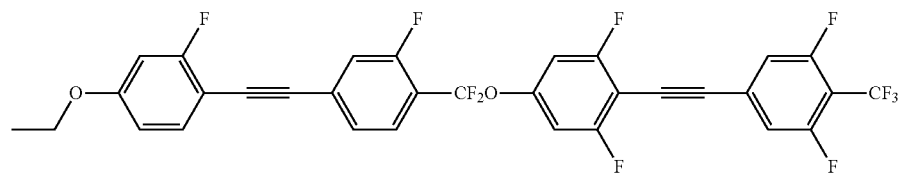
(1-9-33)
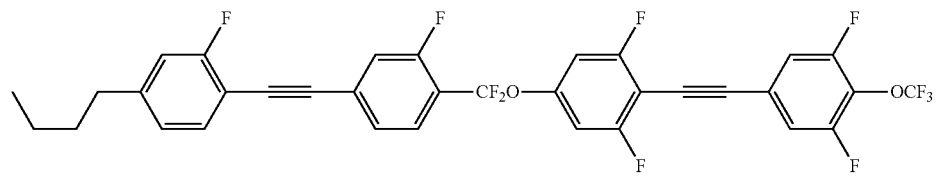

-continued
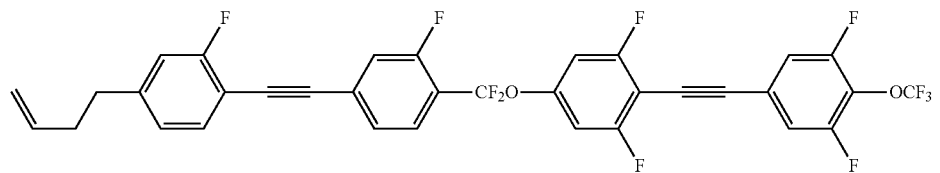
(1-9-34)
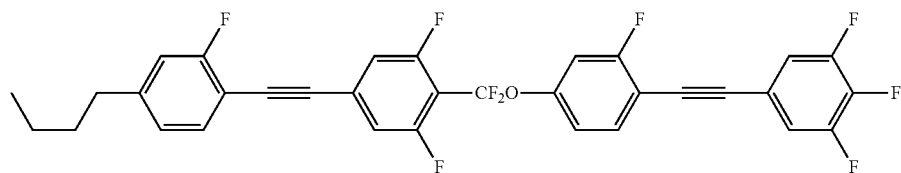
(1-9-35)
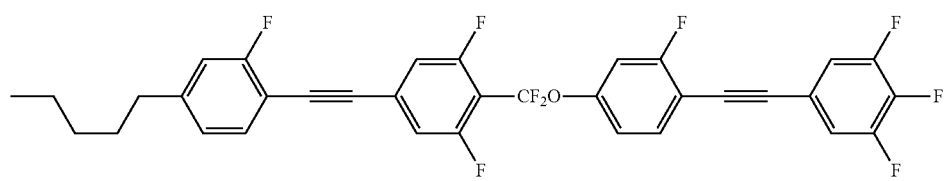
(1-9-36)
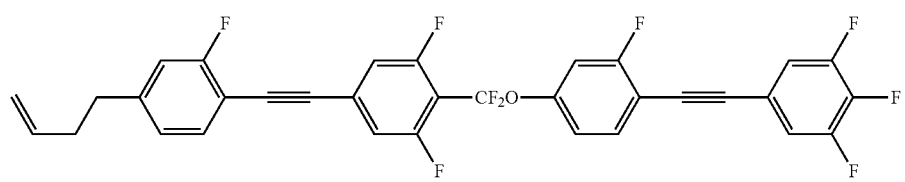
(1-9-3)
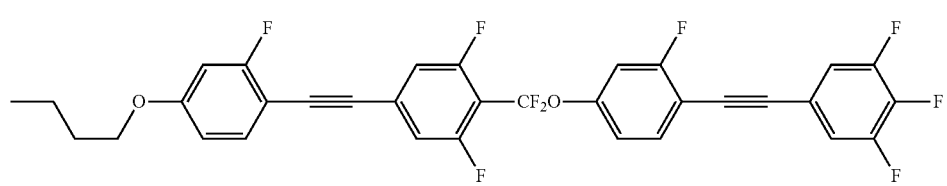
(1-9-38)
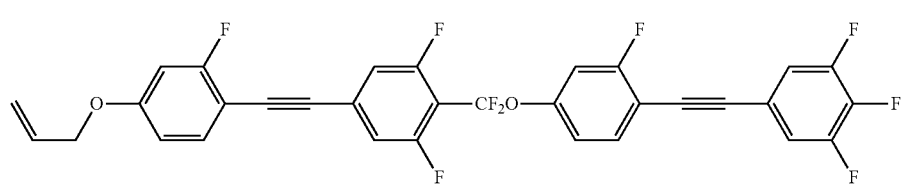
(1-9-39)
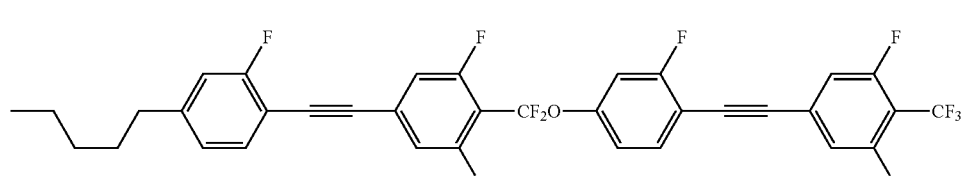
(1-9-40)
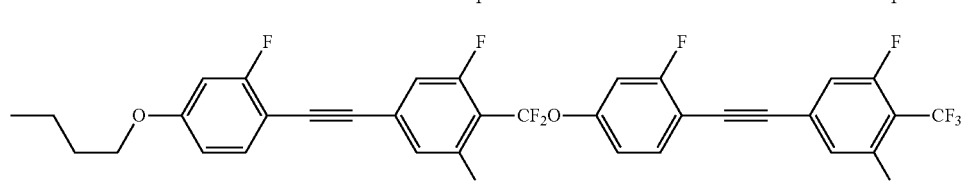
(1-9-41)
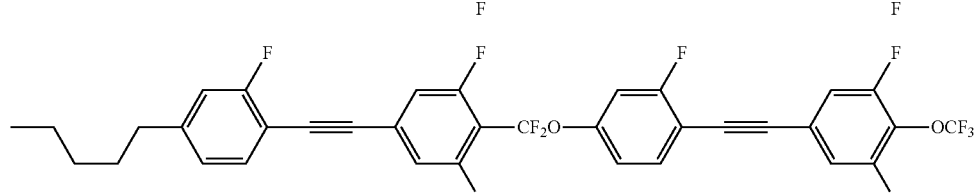
(1-9-42)

-continued
(1-9-43)
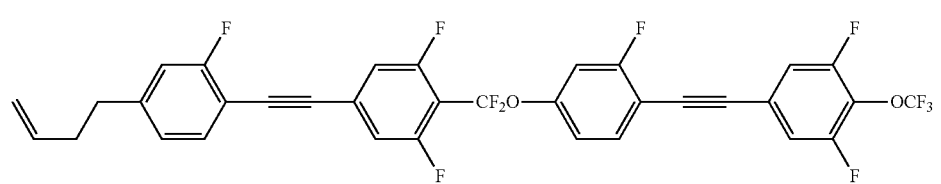
(1-9-44)
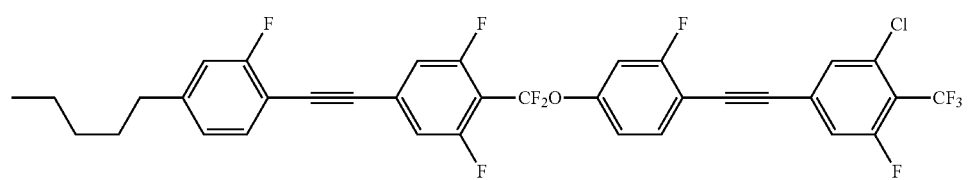
(1-9-45)
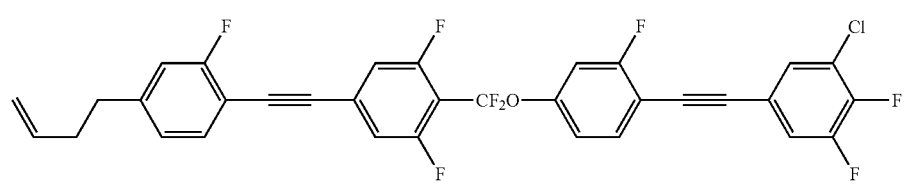
(1-9-46)
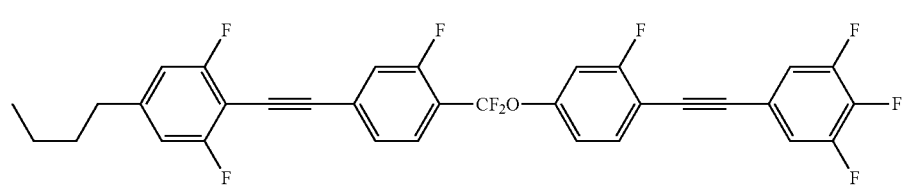
(1-9-47)
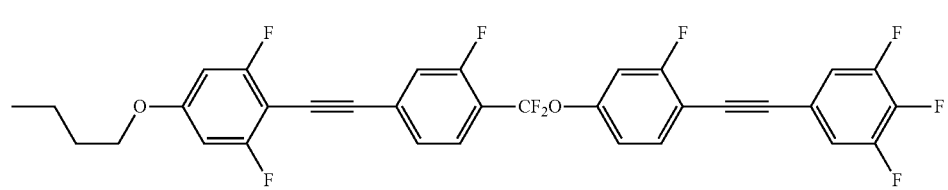
(1-9-48)
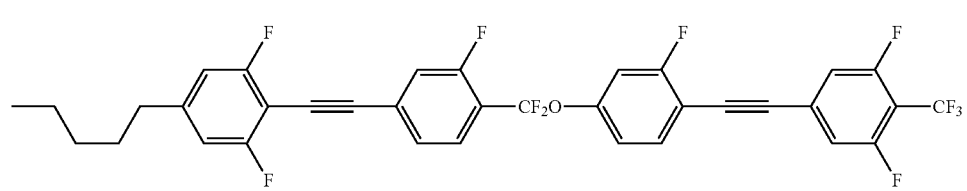
(1-9-49)
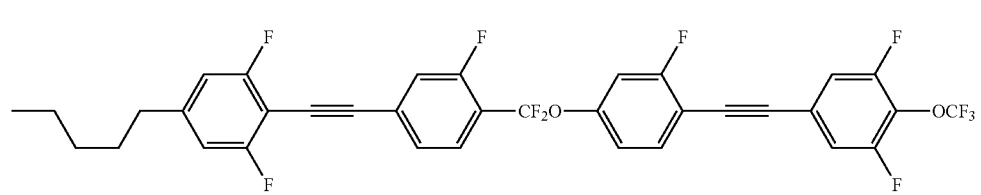
(1-9-50)
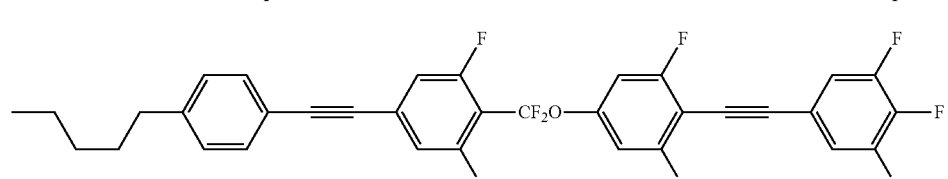
(1-9-51)
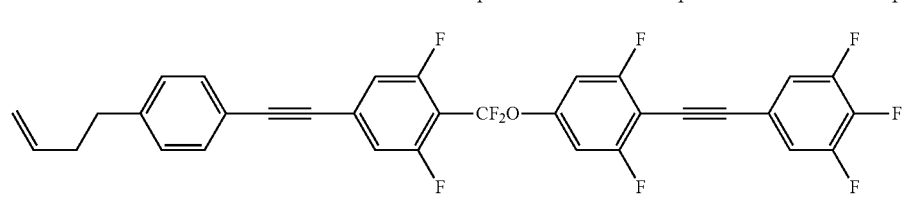

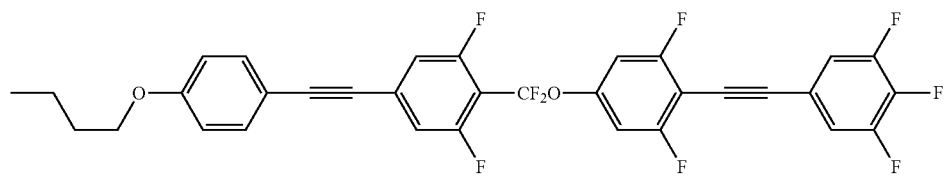
(1-9-52)
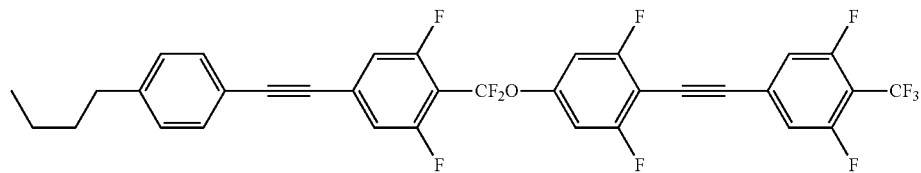
(1-9-53)
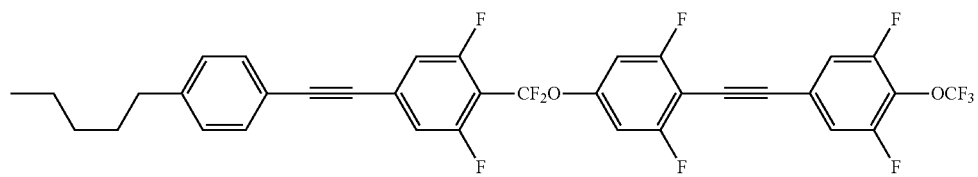
(1-9-54)
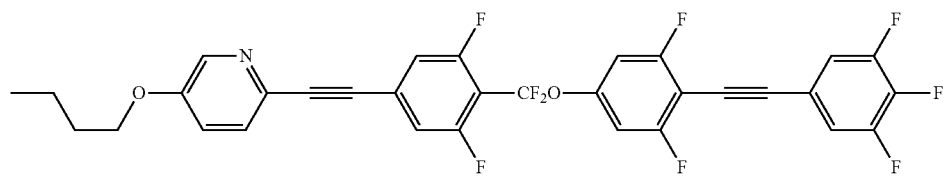
(1-9-55)
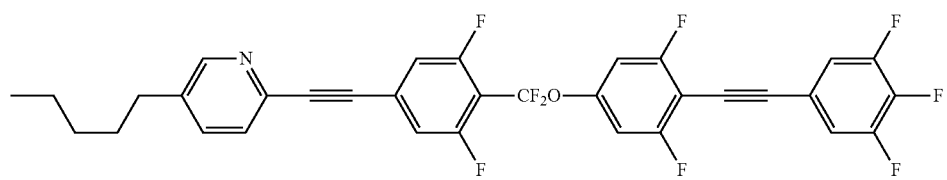
(1-9-56)
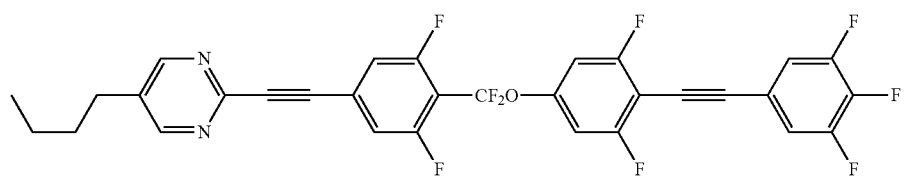
(1-9-57)
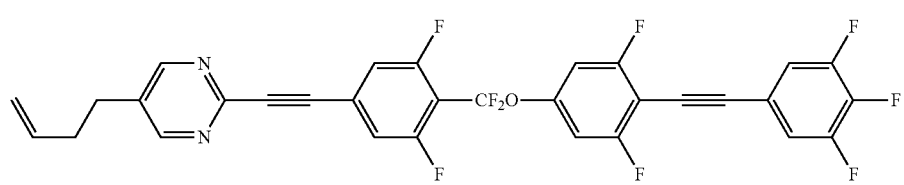
(1-9-58)
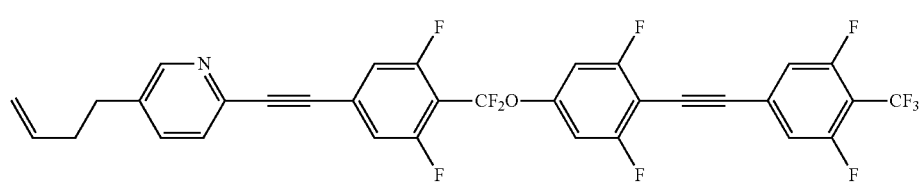
(1-9-59)
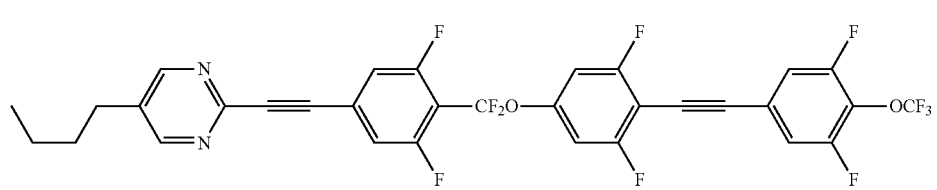
(1-9-60)

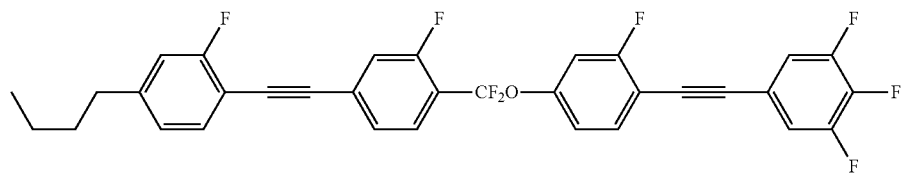
(1-9-61)
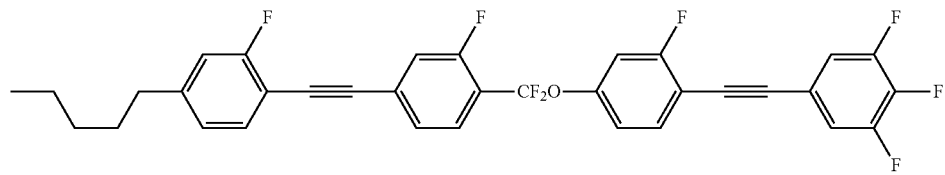
(1-9-62)
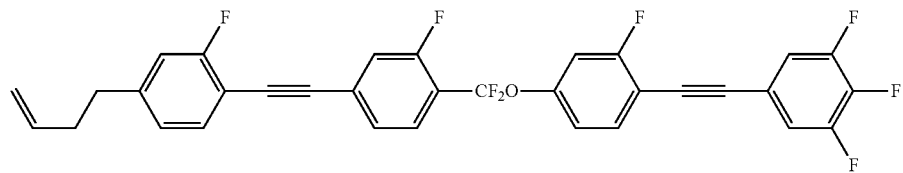
(1-9-63)
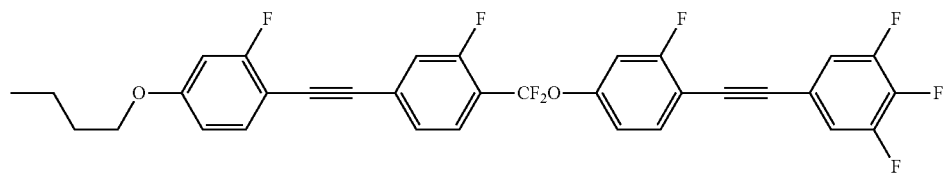
(1-9-64)
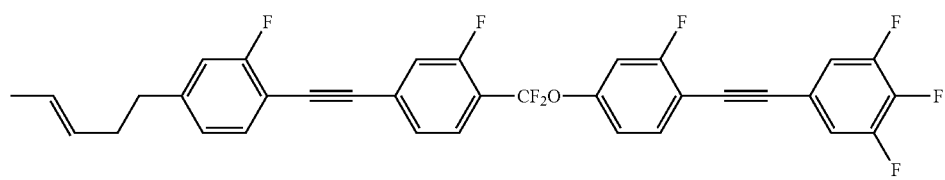
(1-9-65)
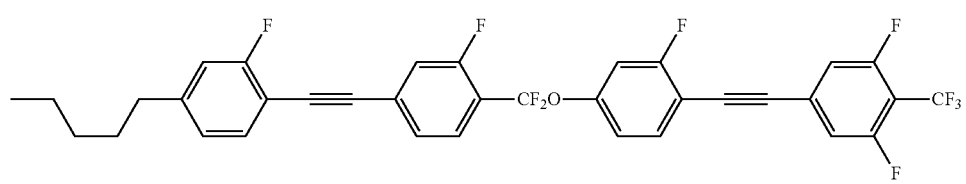
(1-9-66)
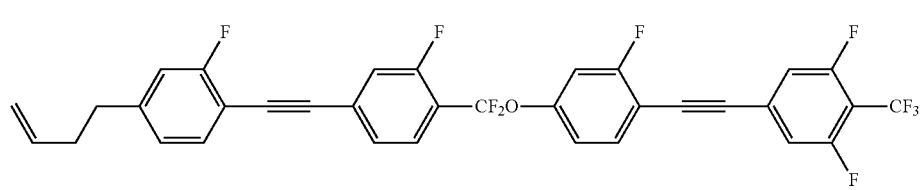
(1-9-67)
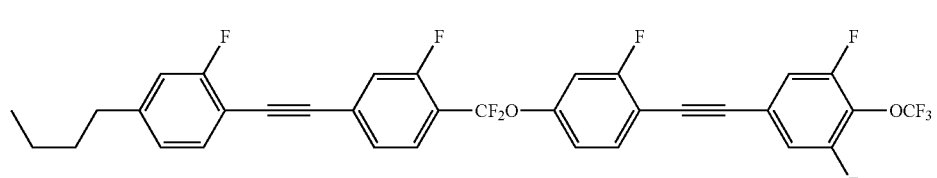
(1-9-68)
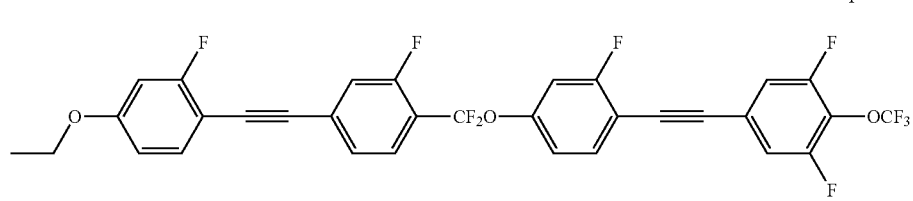
(1-9-69)

-continued
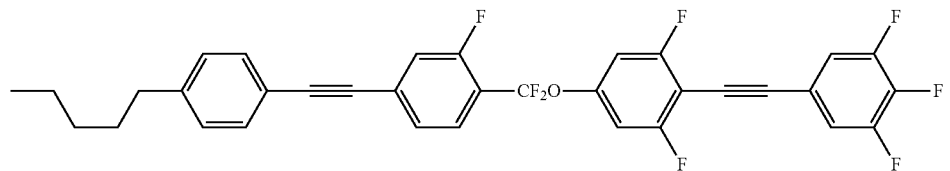 (1-9-70)
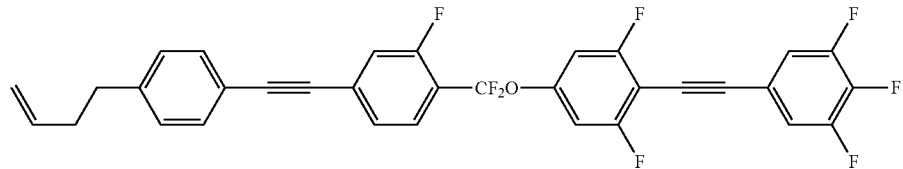 (1-9-71)
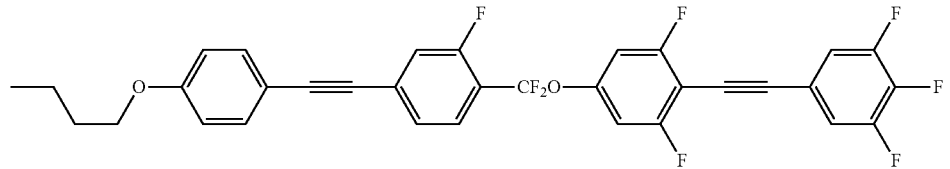 (1-9-72)
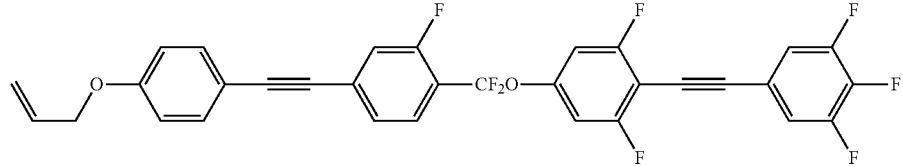 (1-9-73)
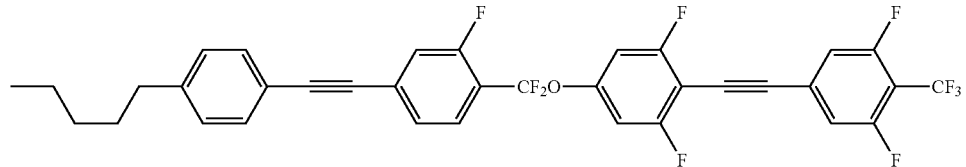 (1-9-74)
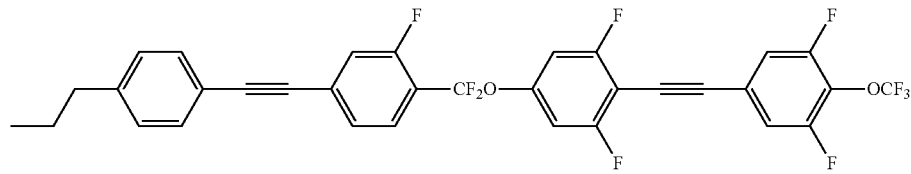 (1-9-75)
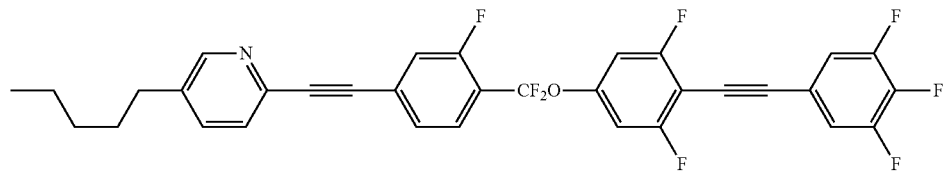 (1-9-76)
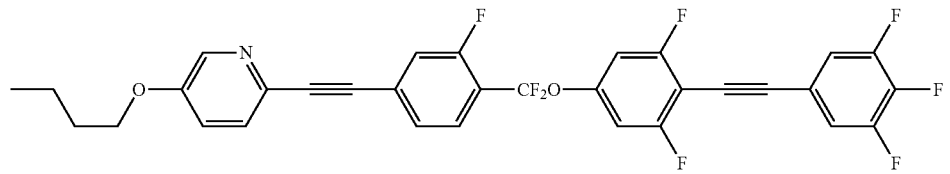 (1-9-77)
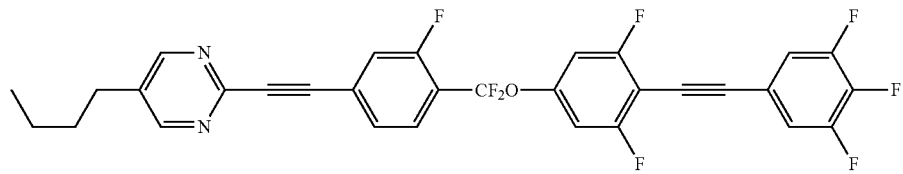 (1-9-78)

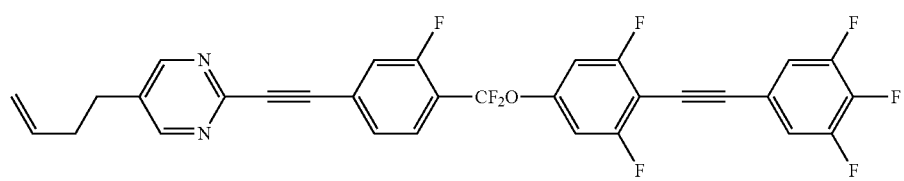
(1-9-79)
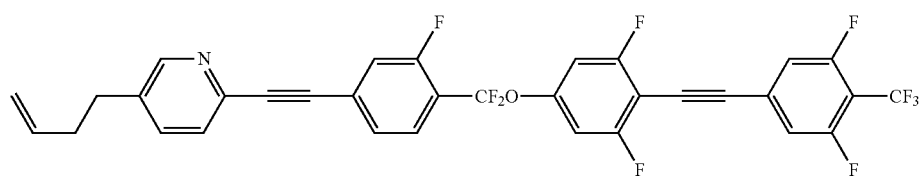
(1-9-80)
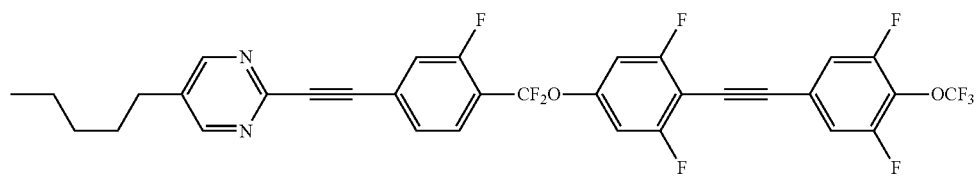
(1-9-81)
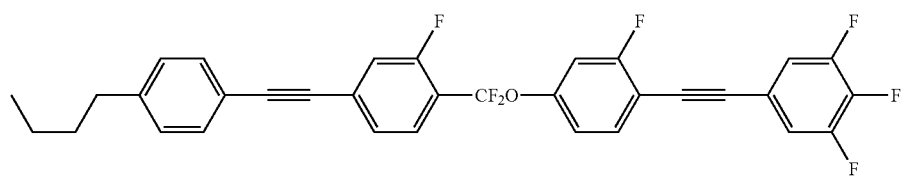
(1-9-82)
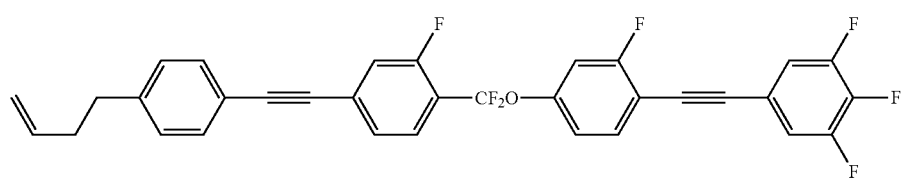
(1-9-83)
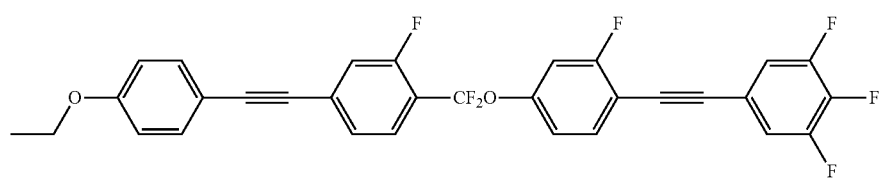
(1-9-84)
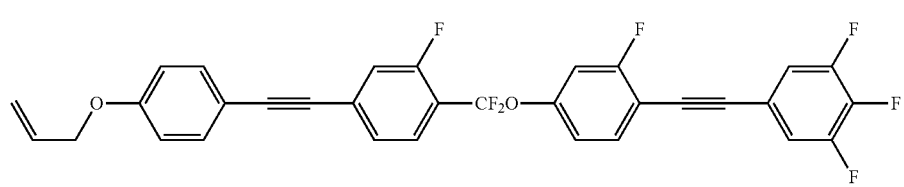
(1-9-85)
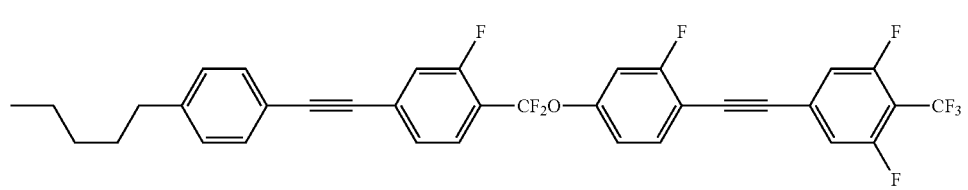
(1-9-86)
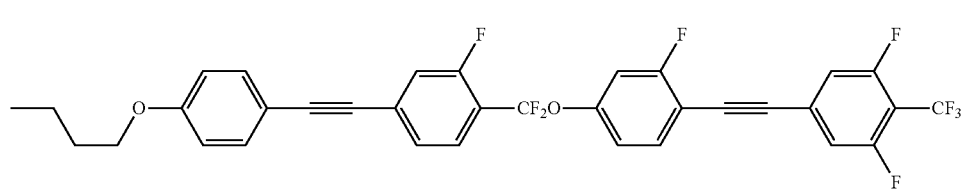
(1-9-87)

-continued
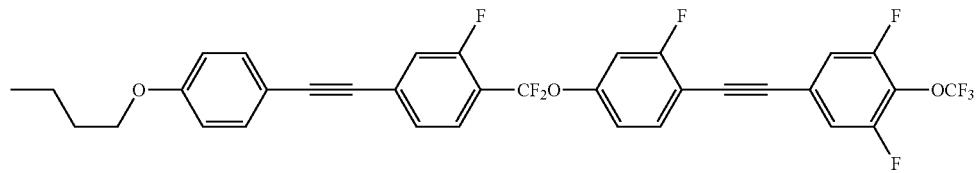
(1-9-88)
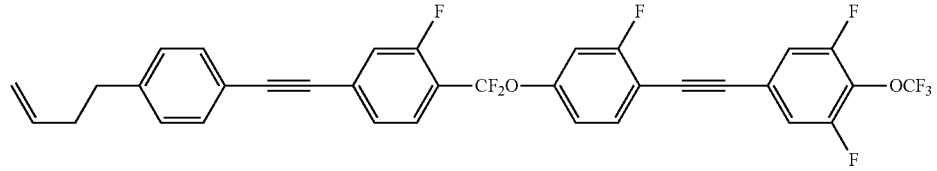
(1-9-89)
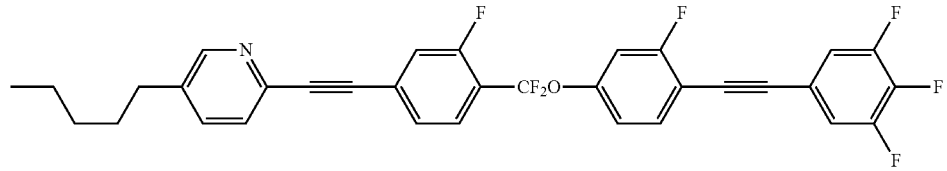
(1-9-90)
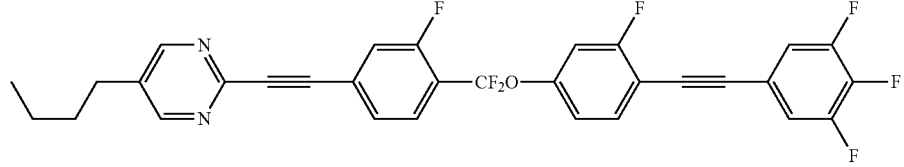
(1-9-91)
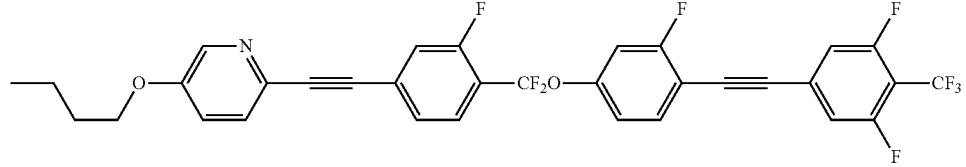
(1-9-92)
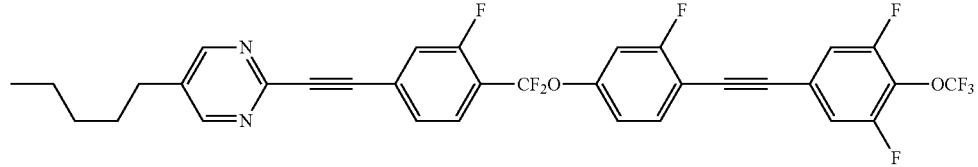
(1-9-93)
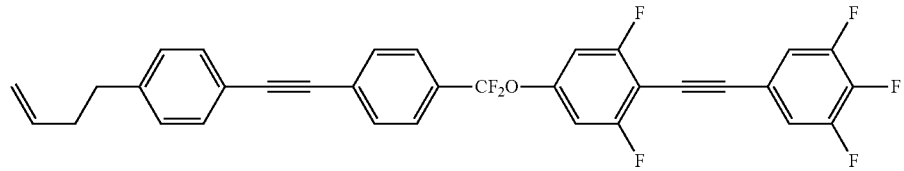
(1-9-97)
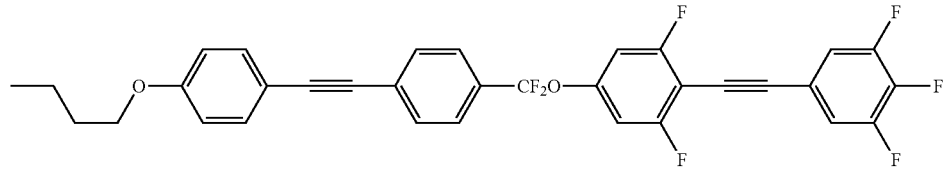
(1-9-98)

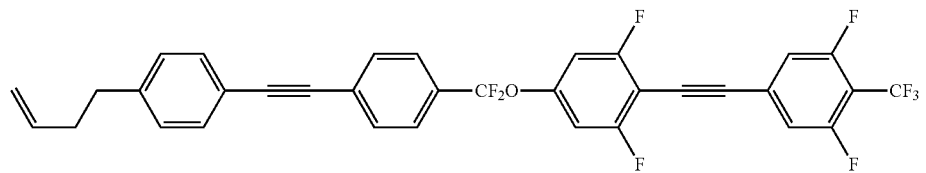 (1-9-99)
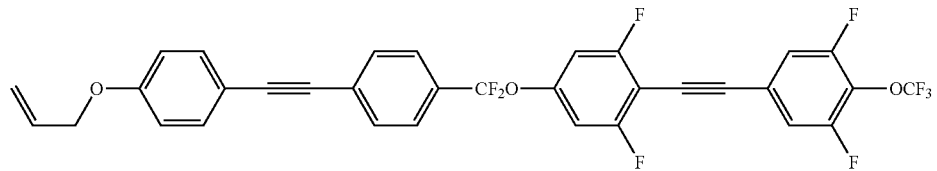 (1-9-100)
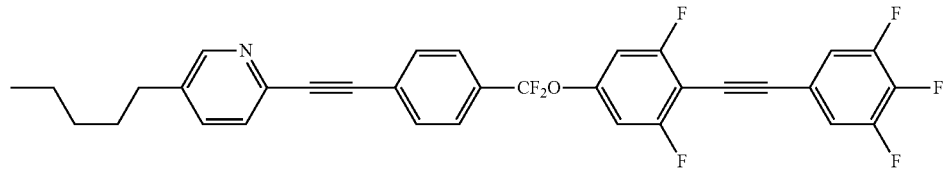 (1-9-101)
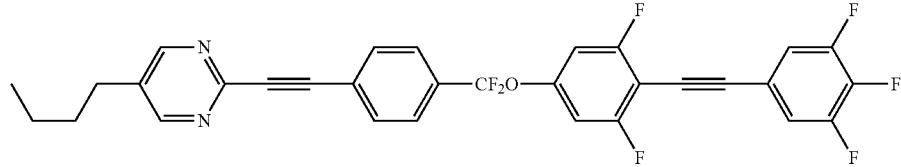 (1-9-102)
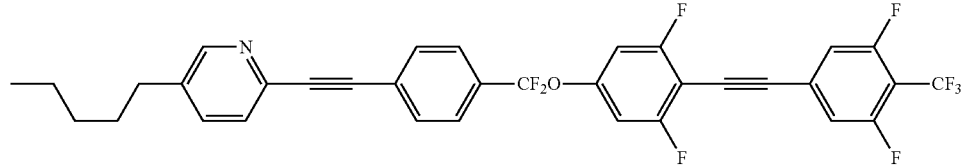 (1-9-103)
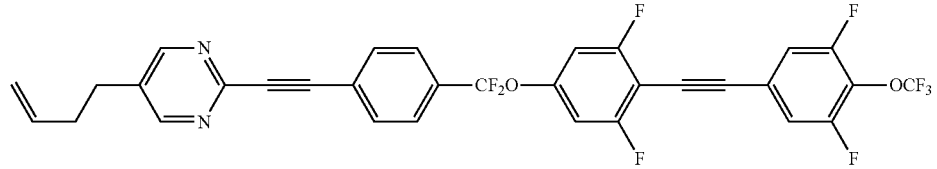 (1-9-104)
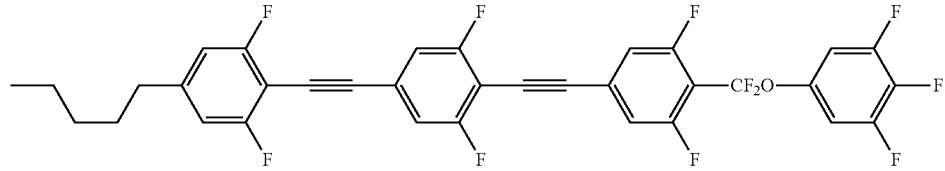 (1-10-1)
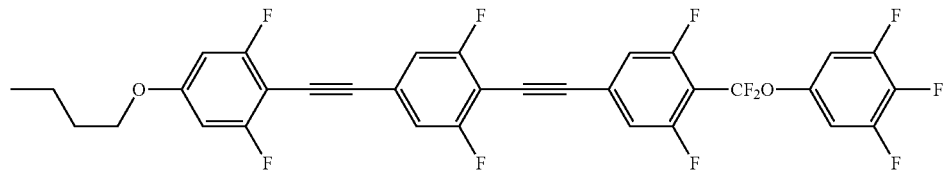 (1-10-2)
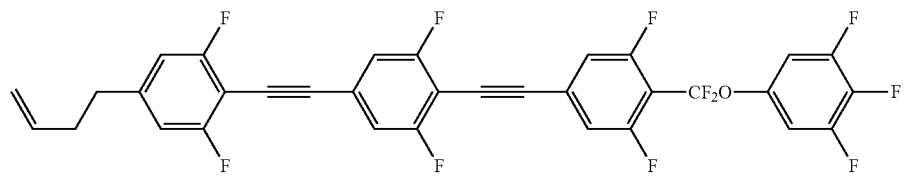 (1-10-3)

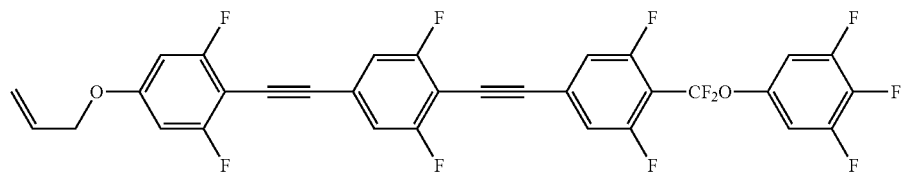
(1-10-4)
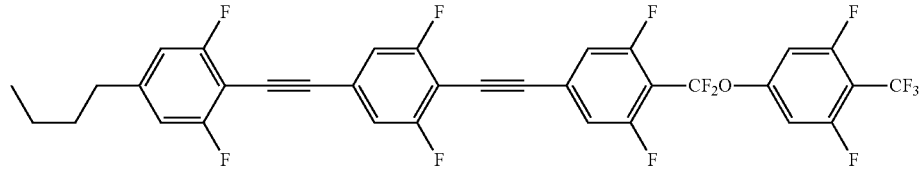
(1-10-5)
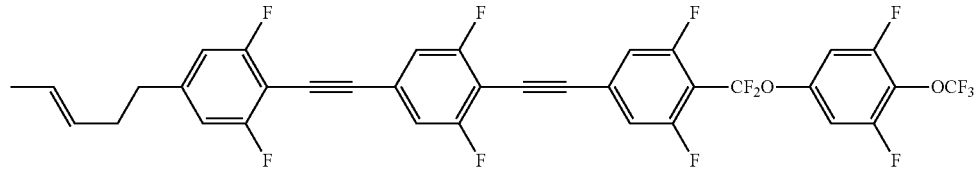
(1-10-6)
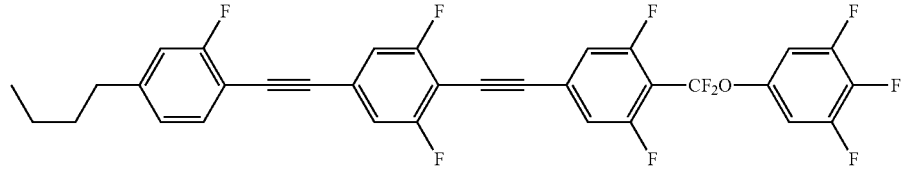
(1-10-7)
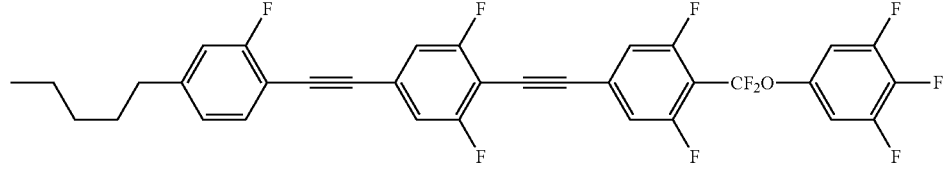
(1-10-8)
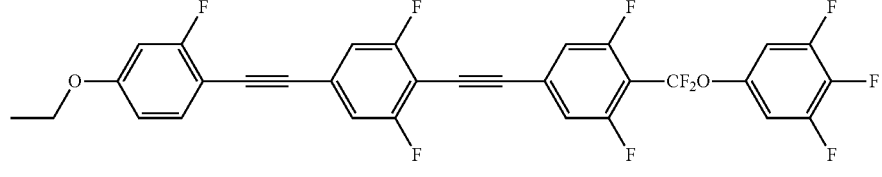
(1-10-9)
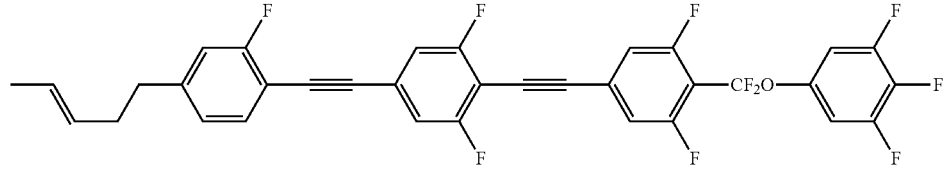
(1-10-10)
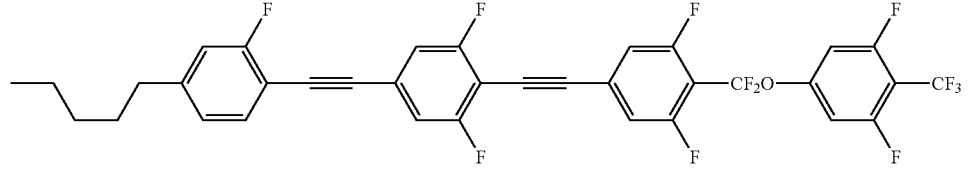
(1-1011)
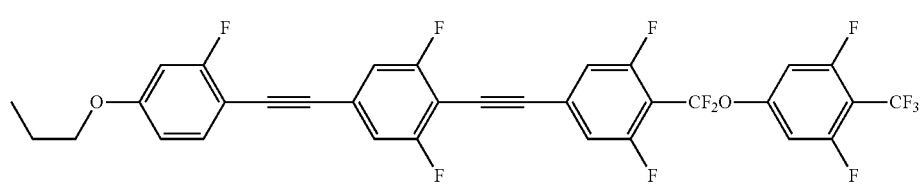
(1-10-12)

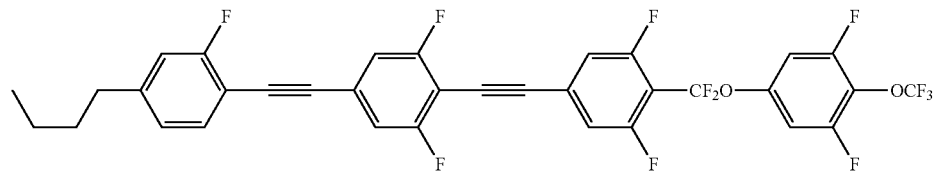
(1-10-13)
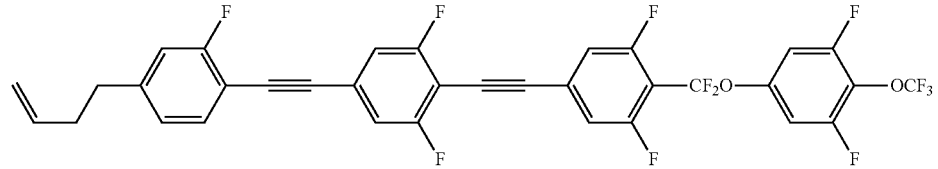
(1-10-14)
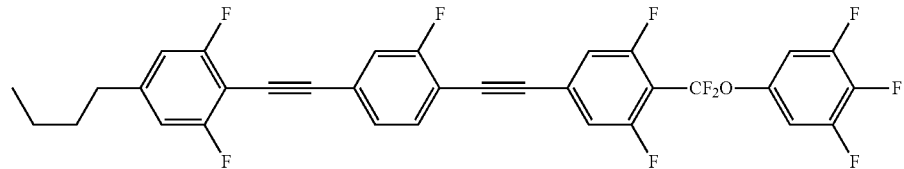
(1-10-15)
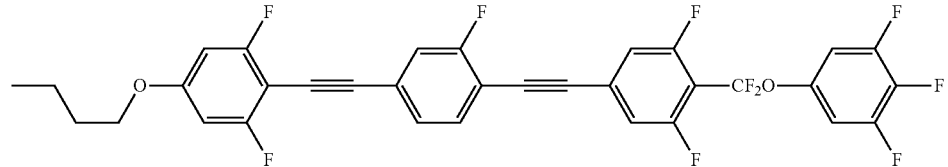
(1-10-16)
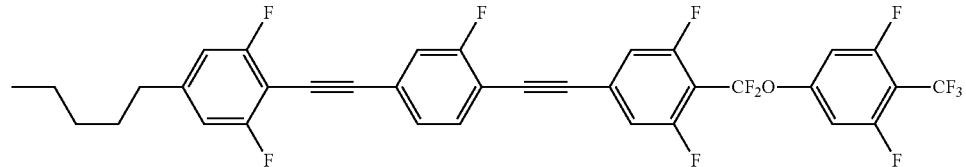
(1-10-17)
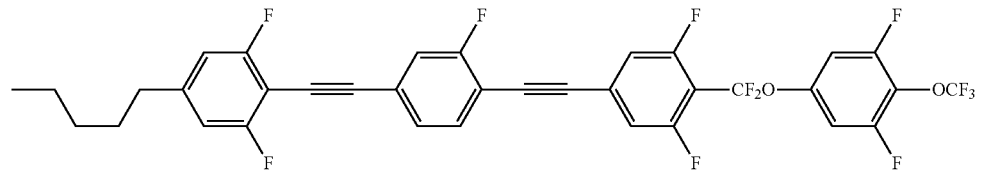
(1-10-18)
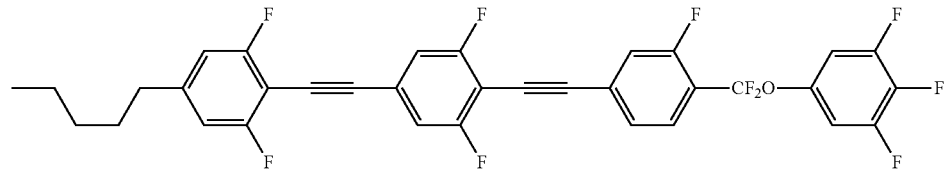
(1-10-19)
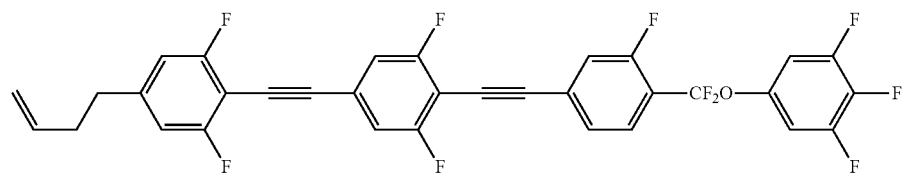
(1-10-20)
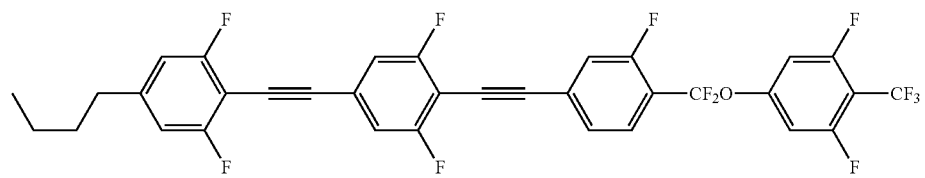
(1-10-21)

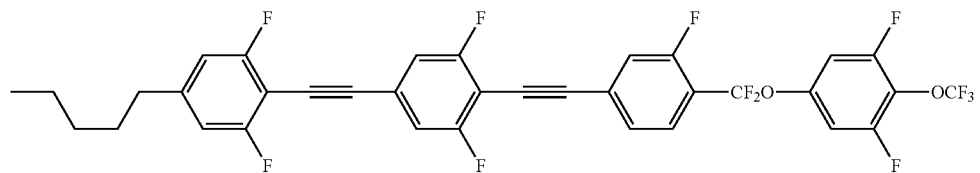
(1-10-22)
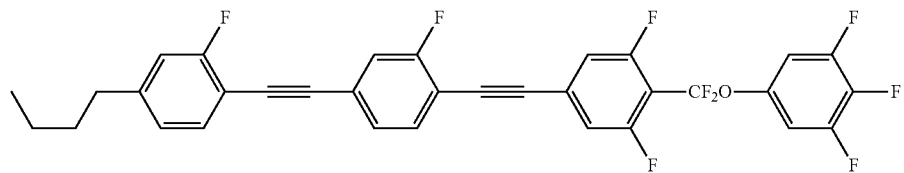
(1-10-23)
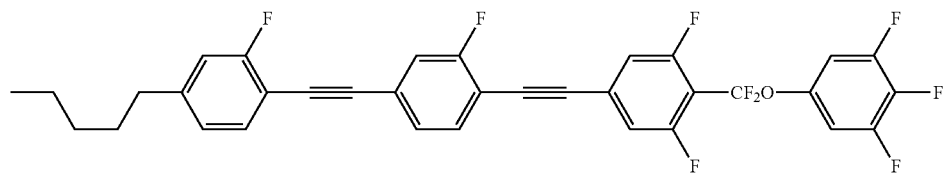
(1-10-24)
92.5 SA 112.5 N 187.4 I
$T_{NI} = 132.4°$ C., $\Delta\varepsilon = 47.9$, $\Delta n = 0.324$
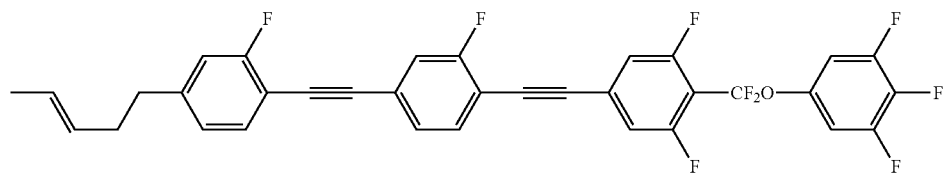
(1-10-25)
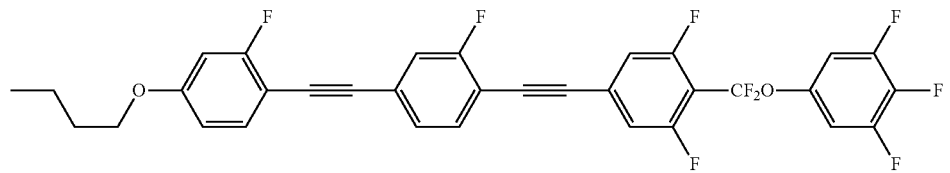
(1-10-26)
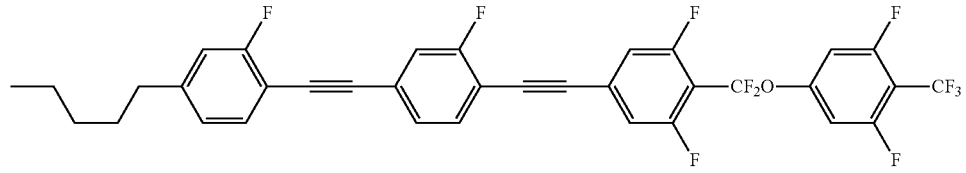
(1-10-27)
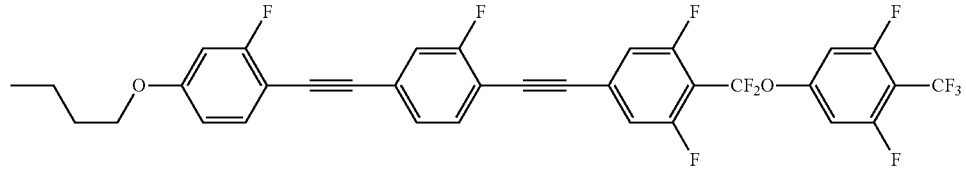
(1-10-28)
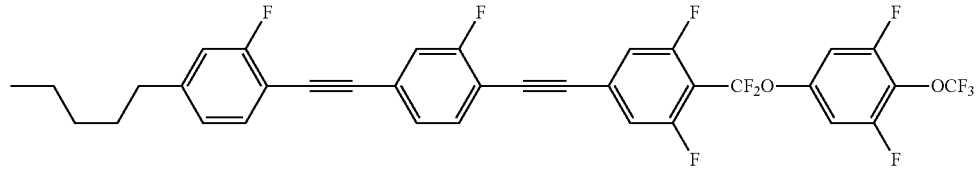
(1-10-29)

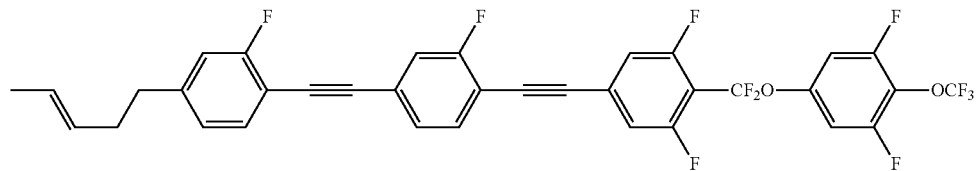
(1-10-30)
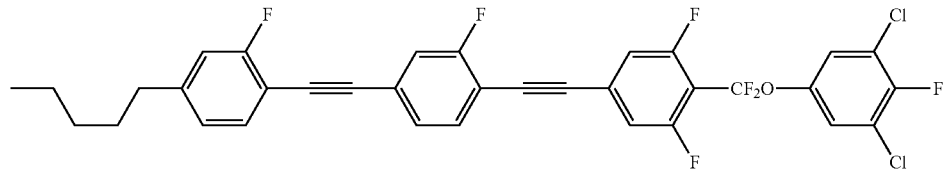
(1-10-31)
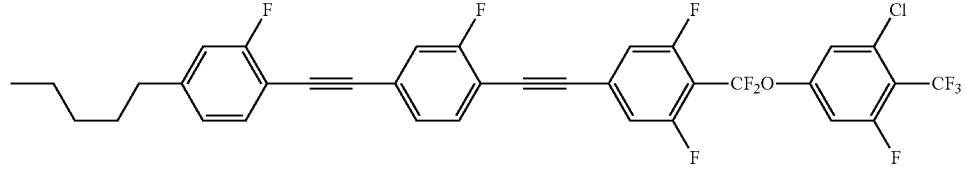
(1-10-32)
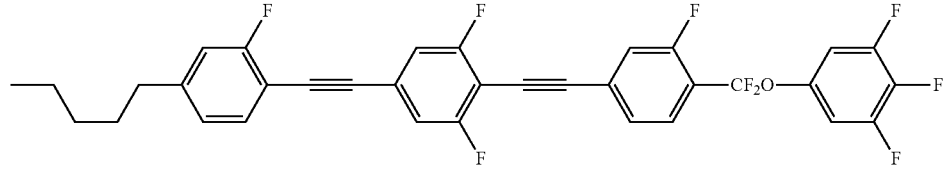
(1-10-33)
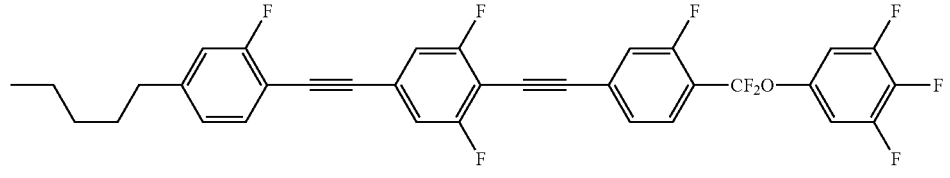
(1-10-34)
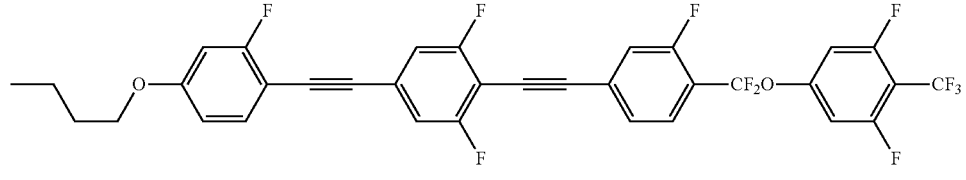
(1-10-35)
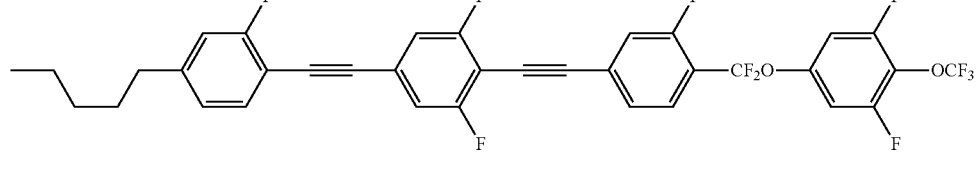
(1-10-36)
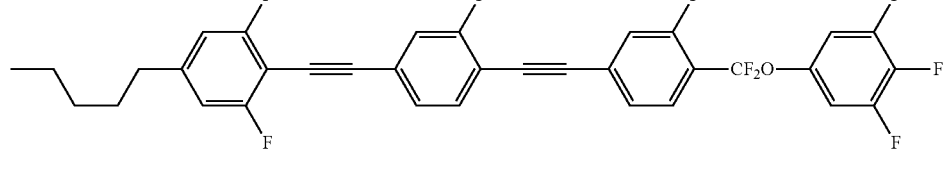
(1-10-37)
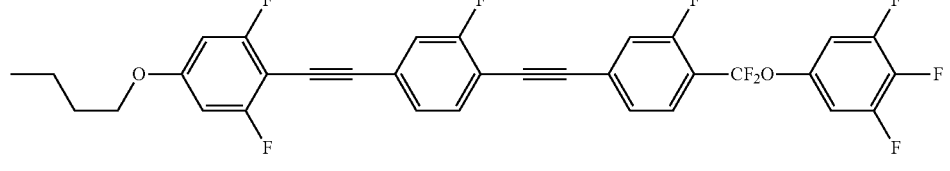
(1-10-38)

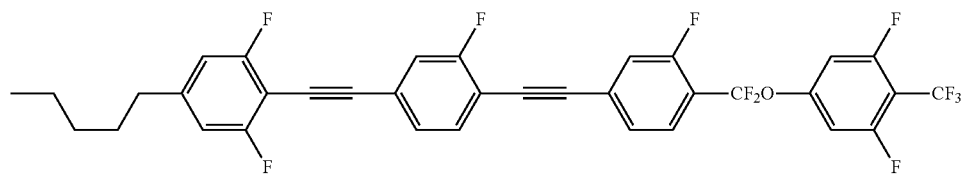
(1-10-39)
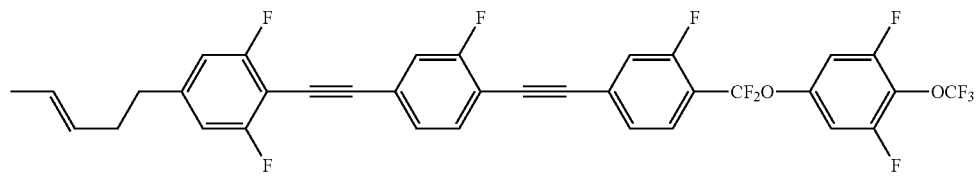
(1-10-40)
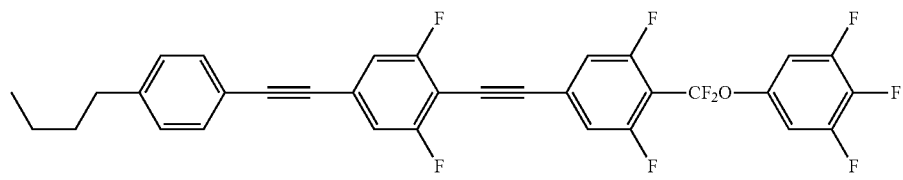
(1-10-41)
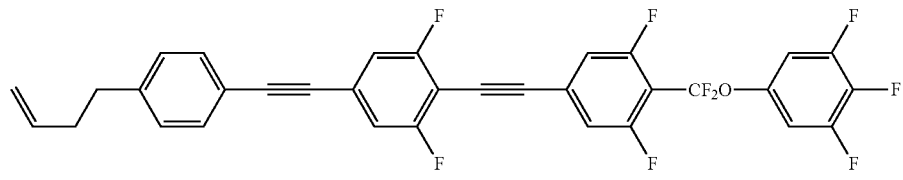
(1-10-42)
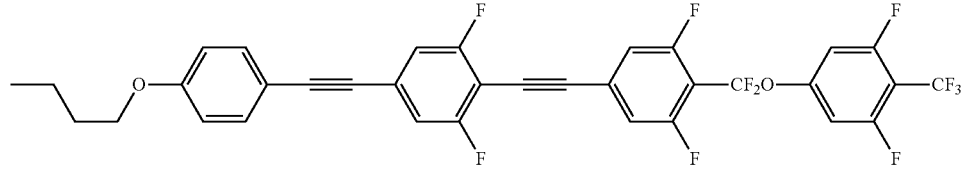
(1-10-43)
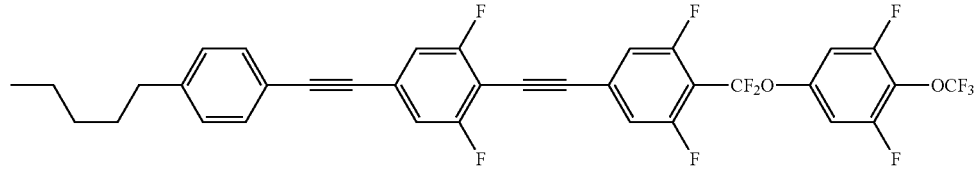
(1-10-44)
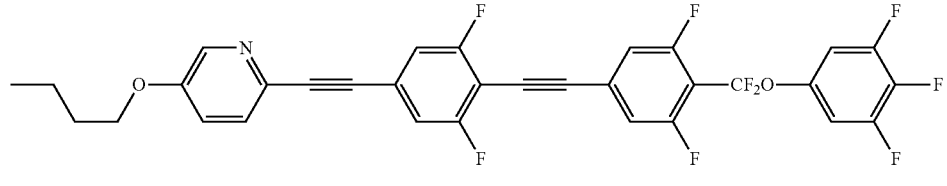
(1-10-45)
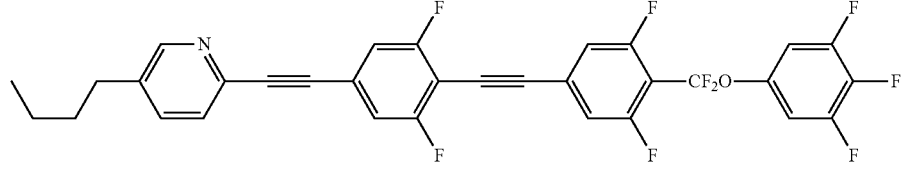
(1-10-46)
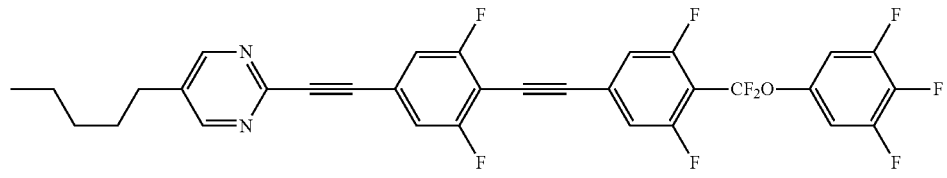
(1-10-47)

-continued
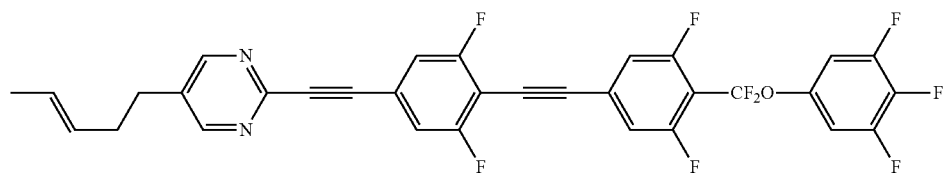 (1-10-48)
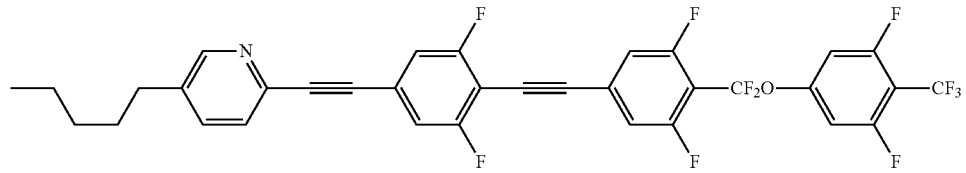 (1-10-49)
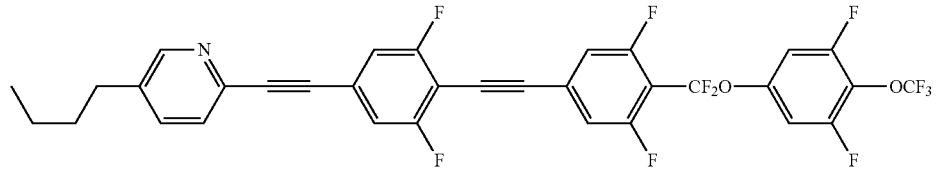 (1-10-50)
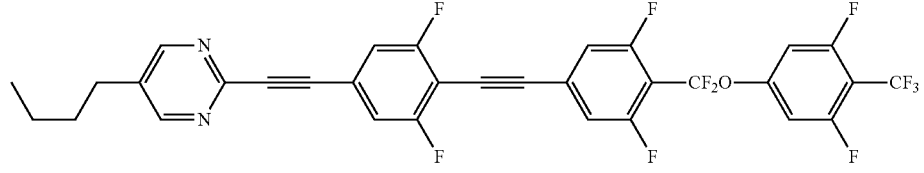 (1-10-51)
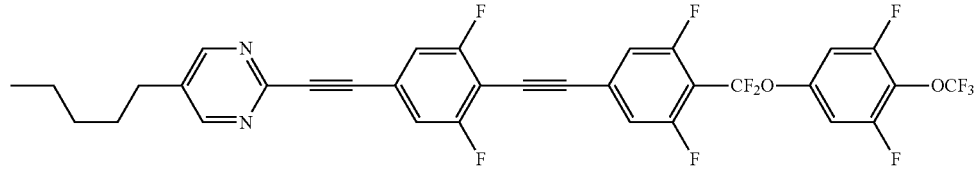 (1-10-52)
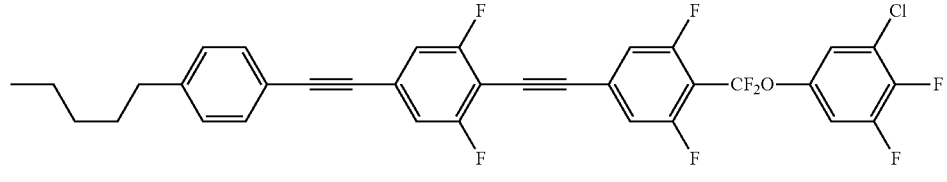 (1-10-53)
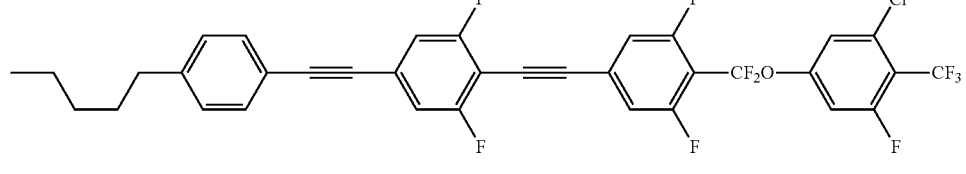 (1-10-54)
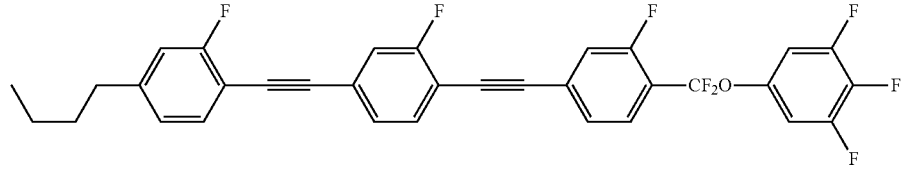 (1-10-55)
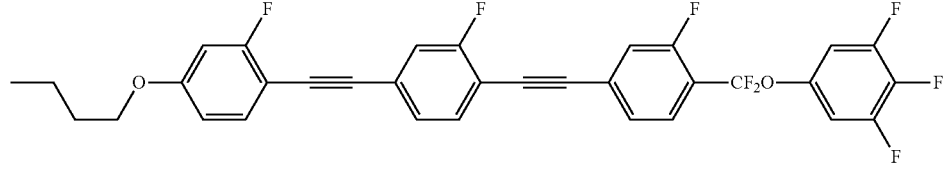 (1-10-56)

-continued
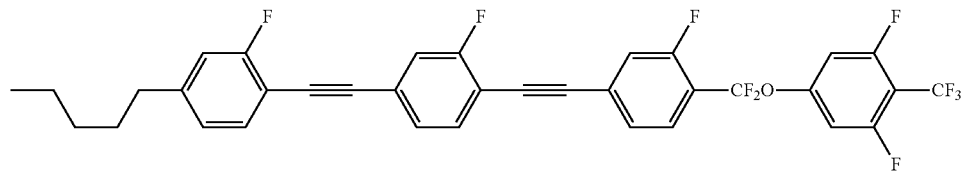
(1-10-57)
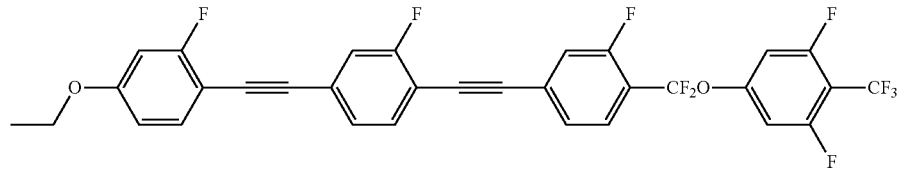
(1-10-58)
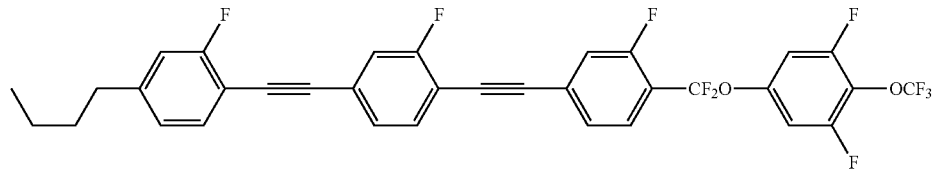
(1-10-59)
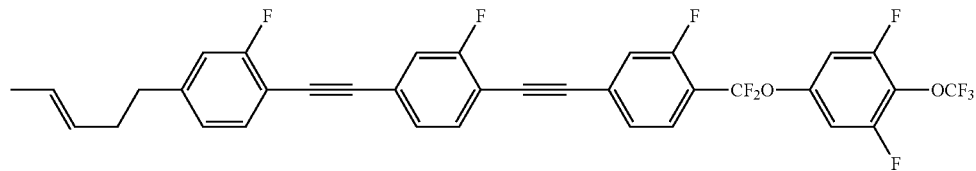
(1-10-60)
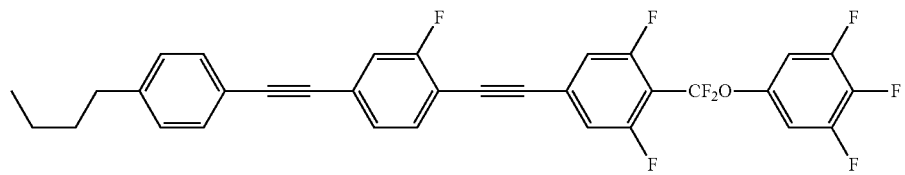
(1-10-61)
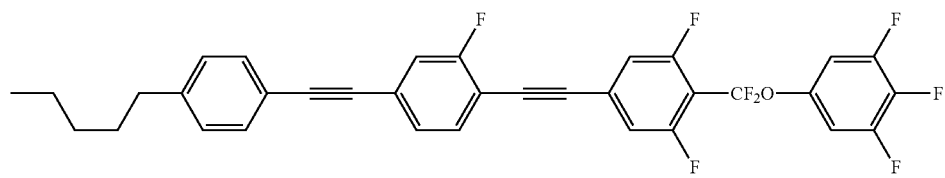
(1-10-62)
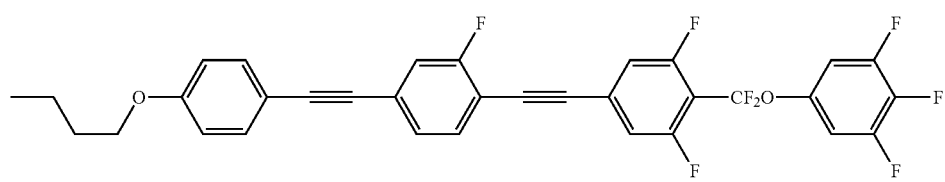
(1-10-63)
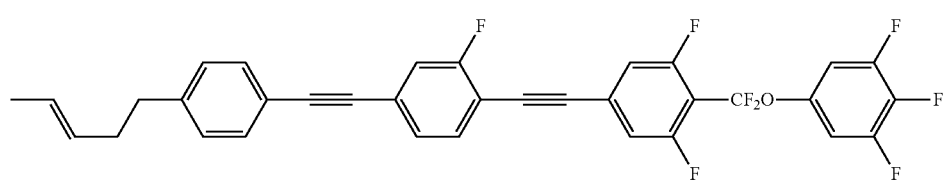
(1-10-64)
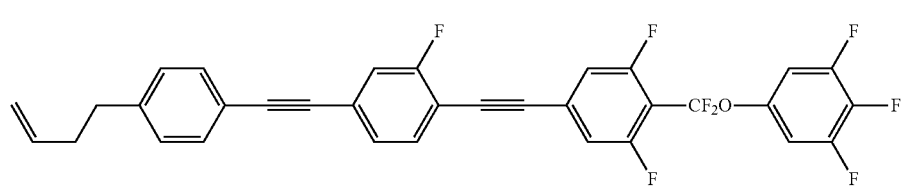
(1-10-65)

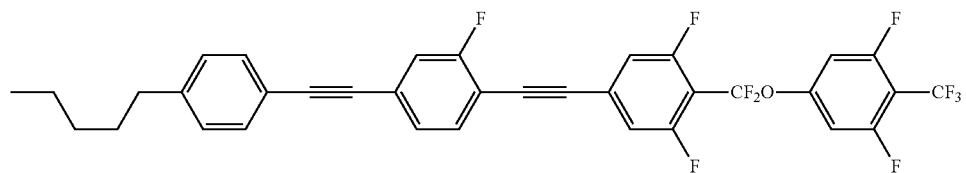 (1-10-66)
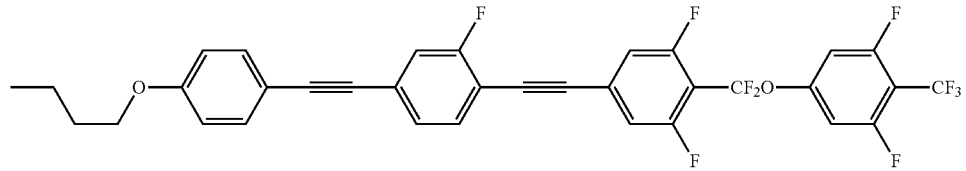 (1-10-67)
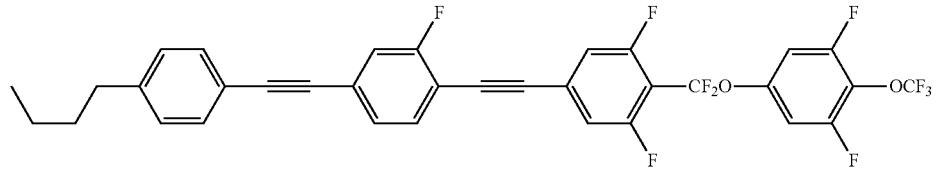 (1-10-68)
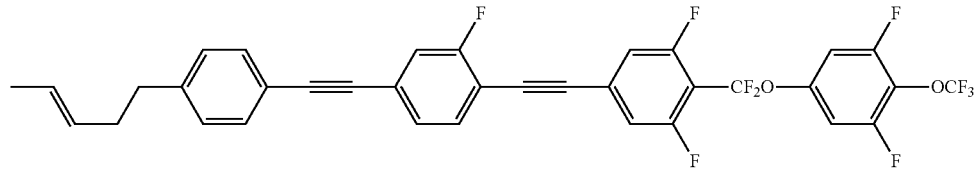 (1-10-69)
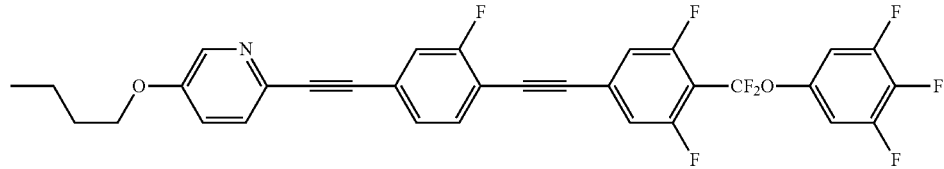 (1-10-70)
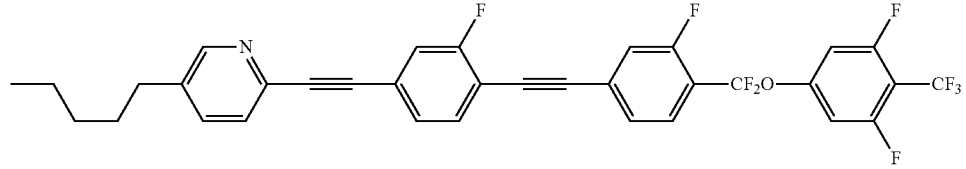 (1-10-71)
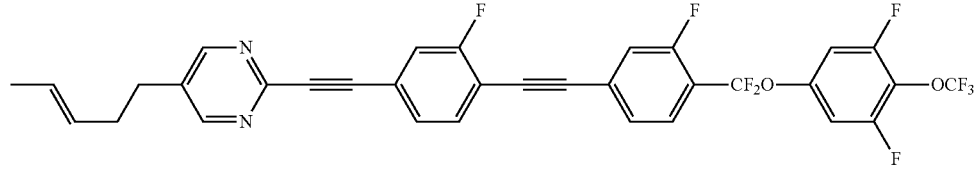 (1-10-72)
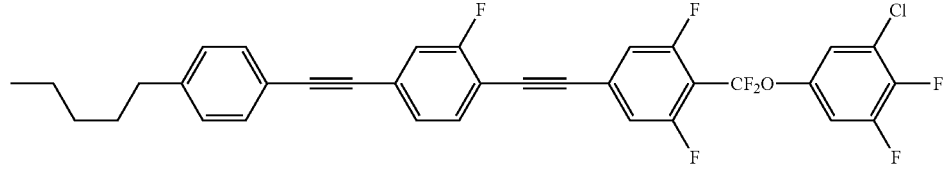 (1-10-73)
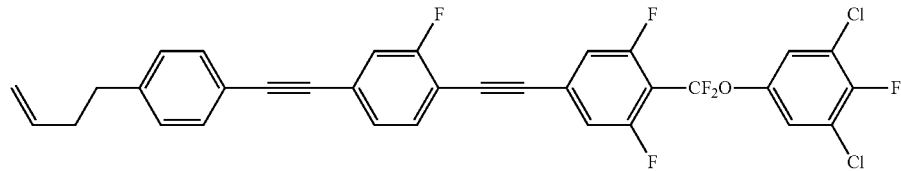 (1-10-74)

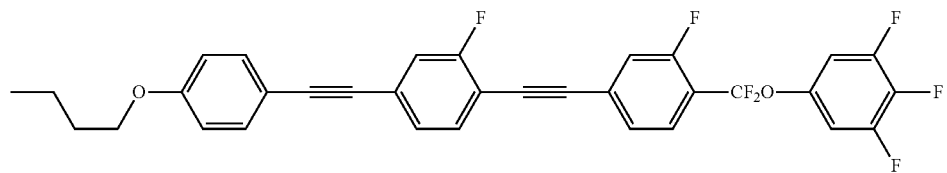
(1-10-75)
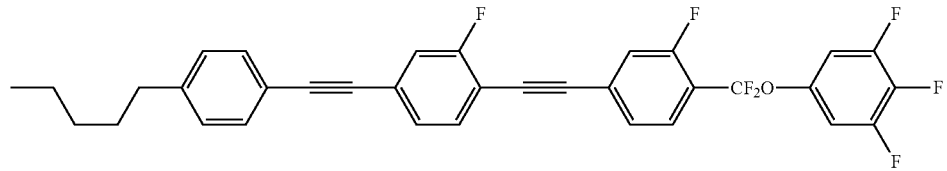
(1-10-76)
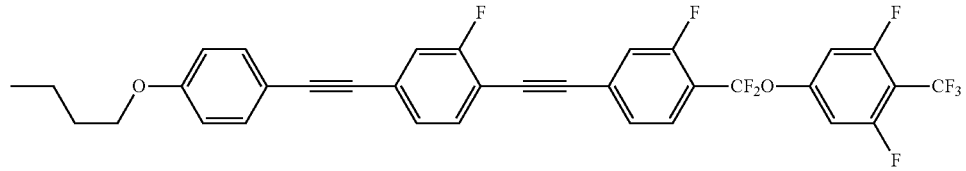
(1-10-77)
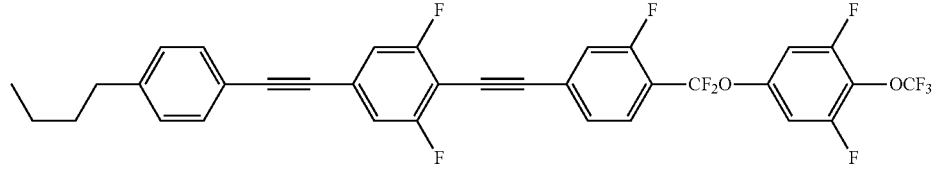
(1-10-78)
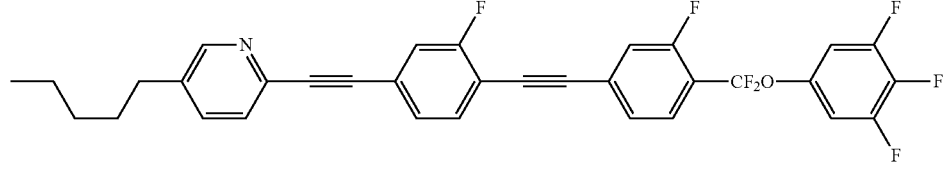
(1-10-79)
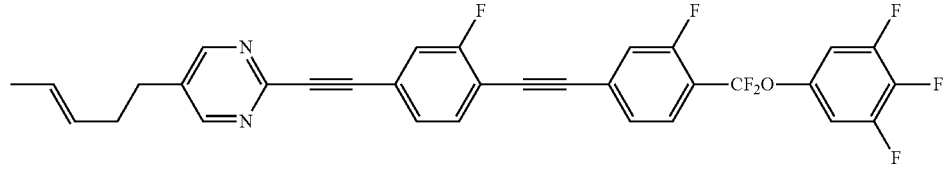
(1-10-80)
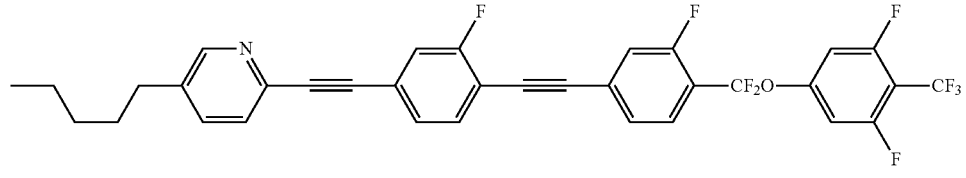
(1-10-81)
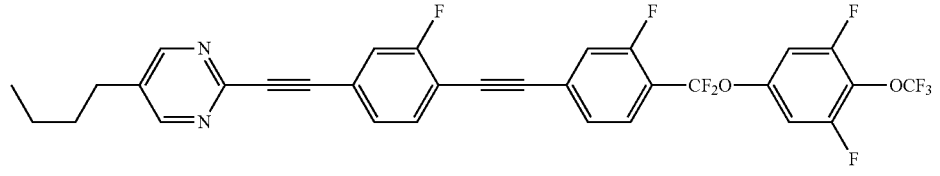
(1-10-82)
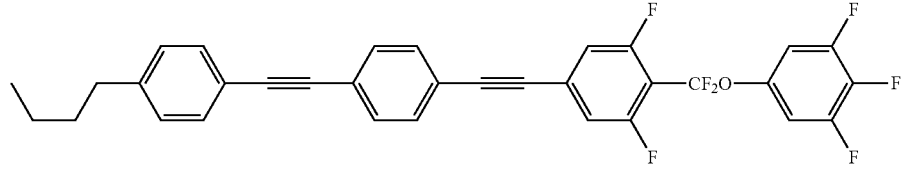
(1-10-83)

-continued
(1-10-84)
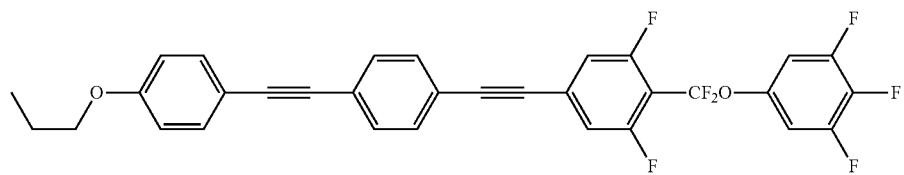
(1-10-85)
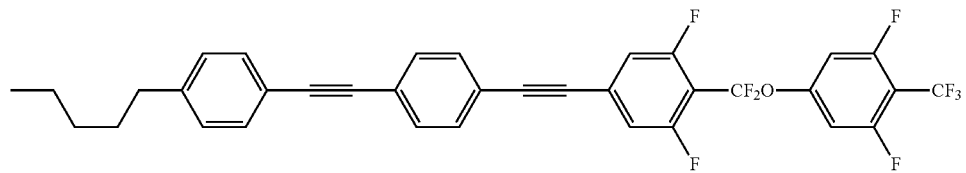
(1-10-86)
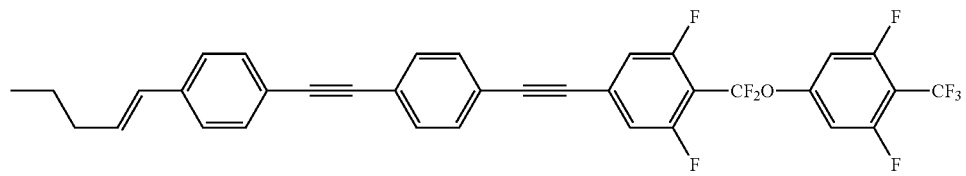
(1-10-87)
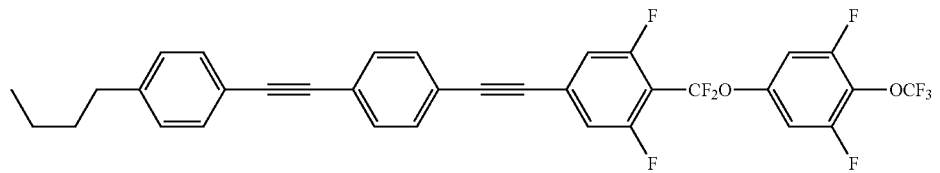
(1-10-88)
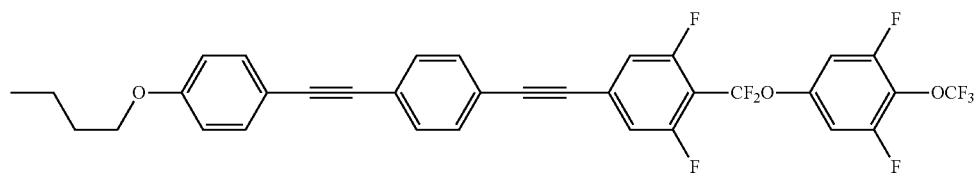
(1-10-89)
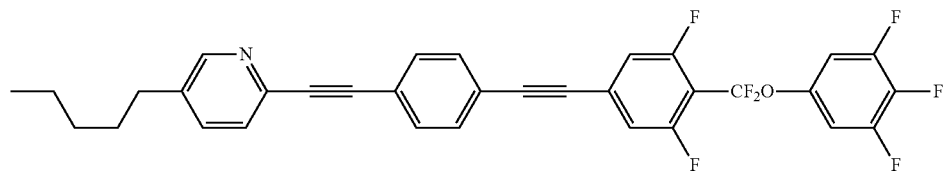
(1-10-90)
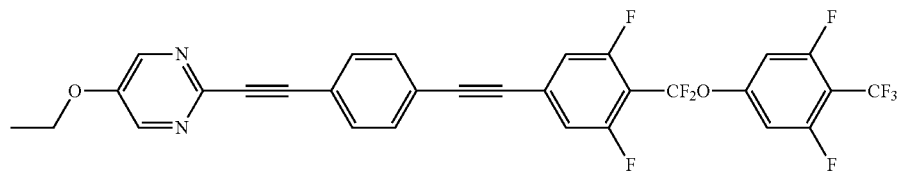
(1-11-1)
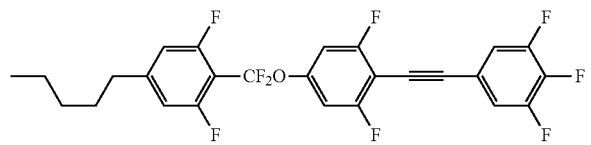
(1-11-2)
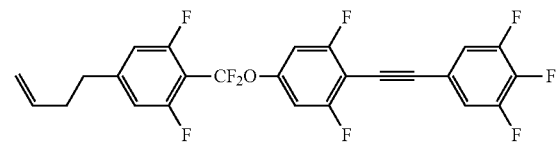
(1-11-3)
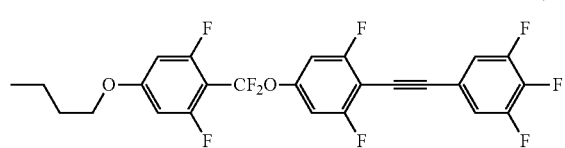
(1-11-4)
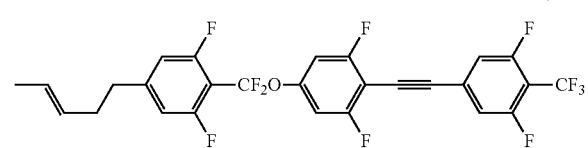

-continued (1-11-5)
(1-11-6)
(1-11-7)
(1-11-8)
(1-11-9)
(1-11-10)
(1-11-11)
(1-11-12)
(1-11-13)
(1-11-14)
(1-11-15)
(1-11-16)
(1-11-17)
(1-11-18)
(1-11-19)
(1-11-20)
(1-11-21)
(1-11-22)

-continued
(1-11-23)
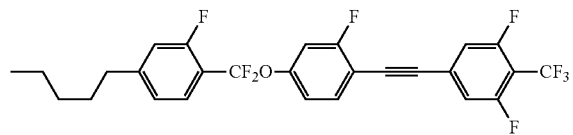
(1-11-24)
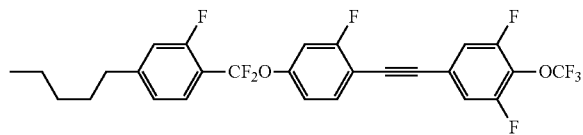
(1-12-1)
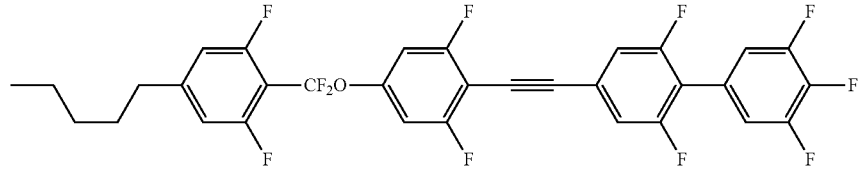
(1-12-2)
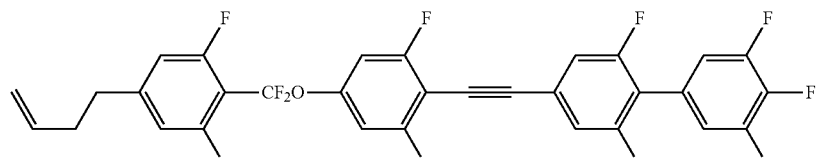
(1-12-3)
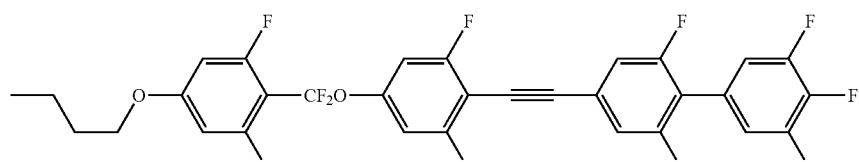
(1-12-)
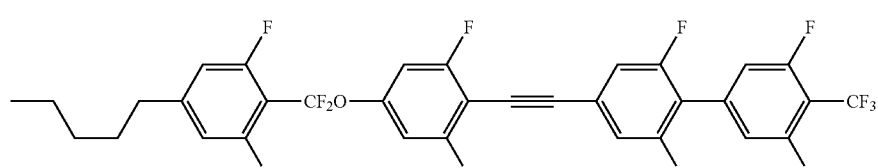
(1-12-5)
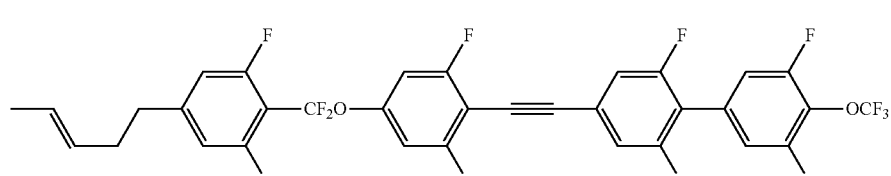
(1-12-6)
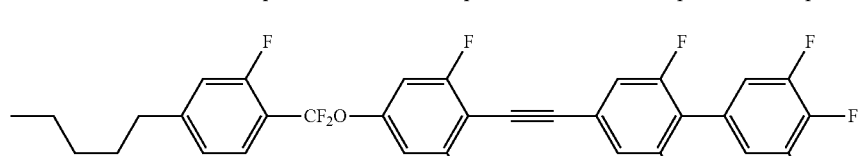
(1-12-7)
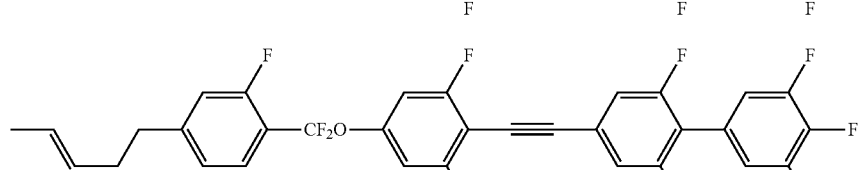
(1-12-8)
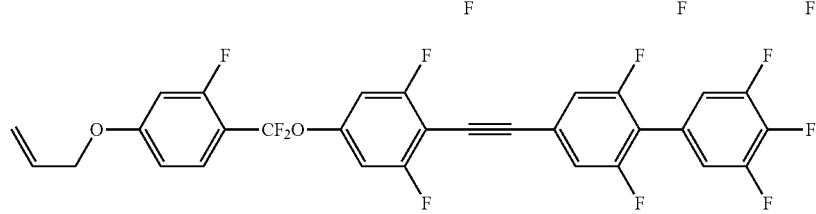

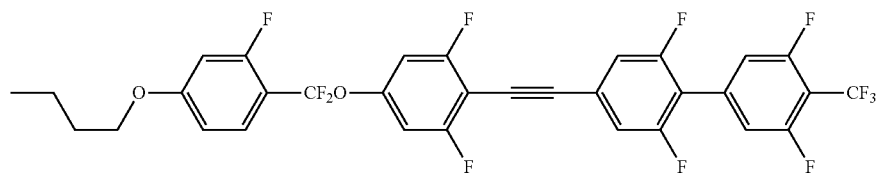
(1-12-9)
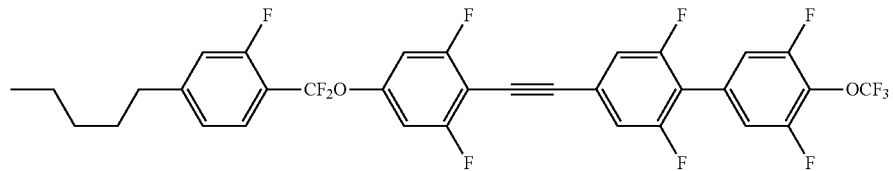
(1-12-10)
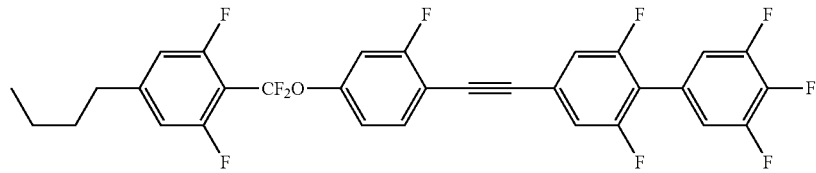
(1-12-11)
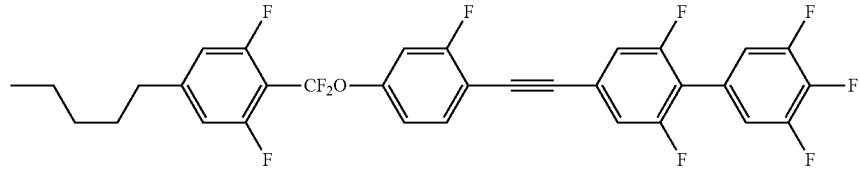
(1-12-12)
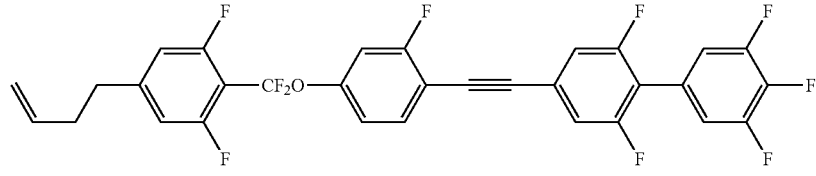
(1-12-13)
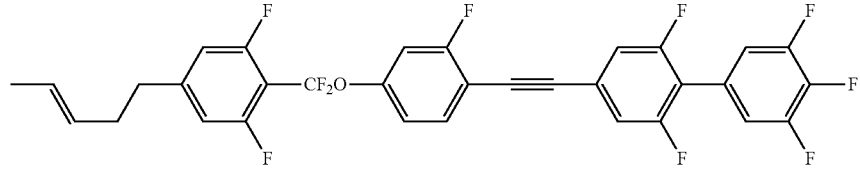
(1-12-14)
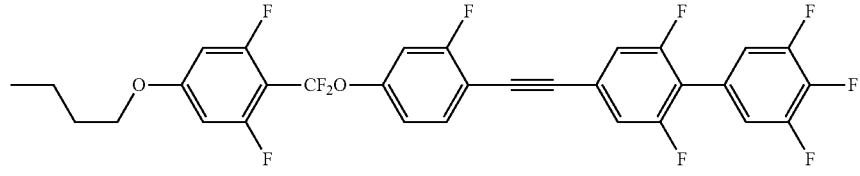
(1-12-15)
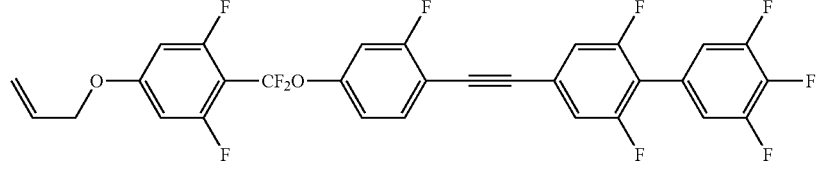
(1-12-16)
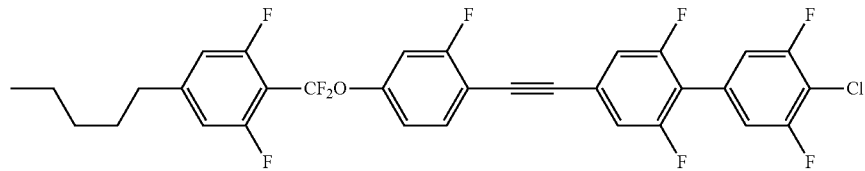
(1-12-17)

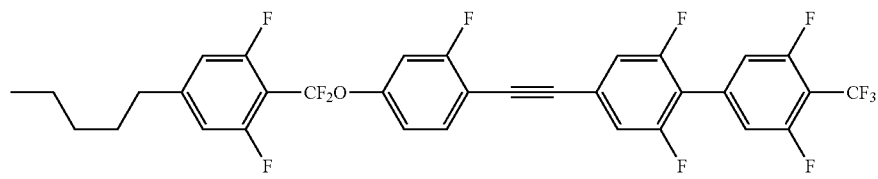
(1-12-18)
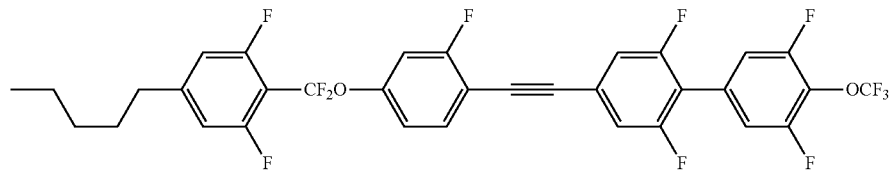
(1-12-19)
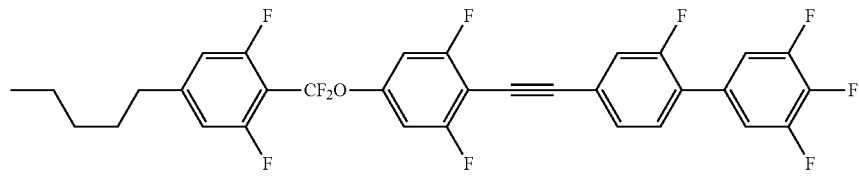
(1-12-20)
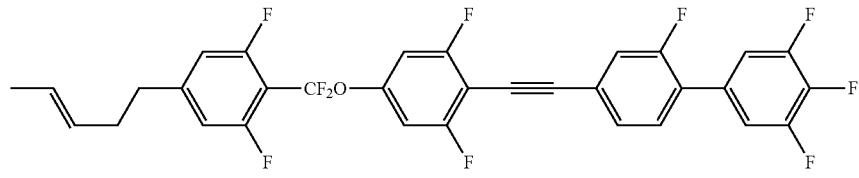
(1-12-21)
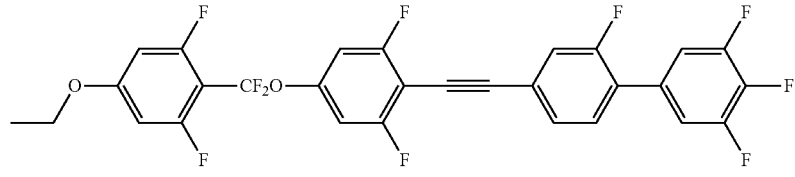
(1-12-22)
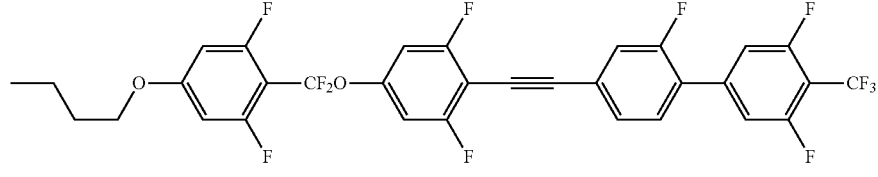
(1-12-23)
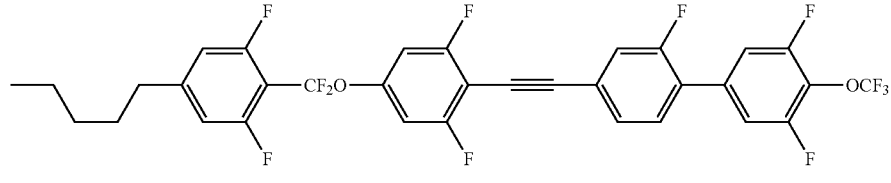
(1-12-24)
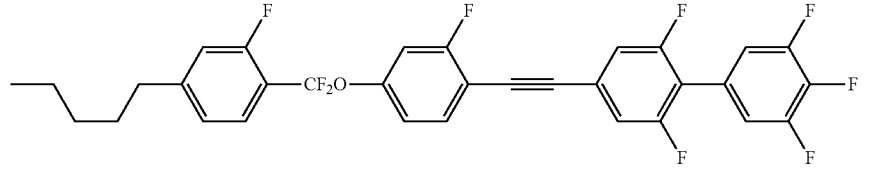
(1-12-25)
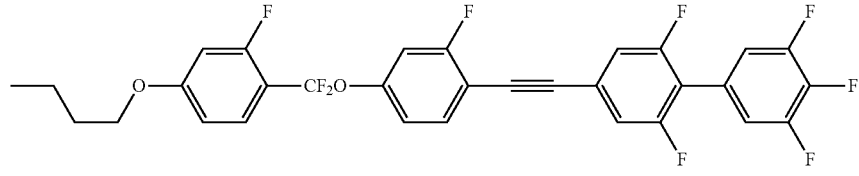
(1-12-26)

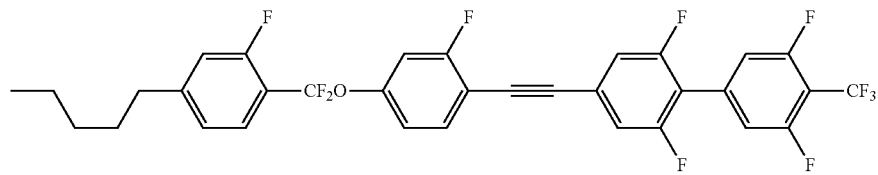 (1-12-27)
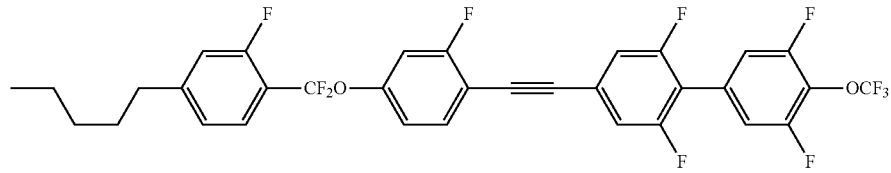 (1-12-28)
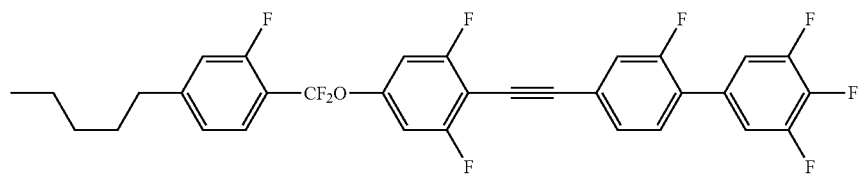 (1-12-29)
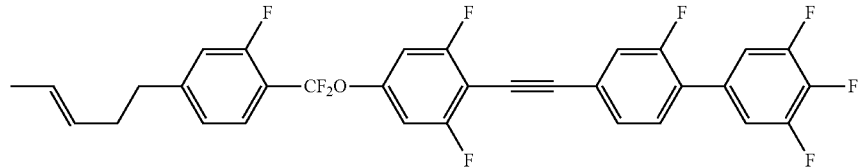 (1-12-30)
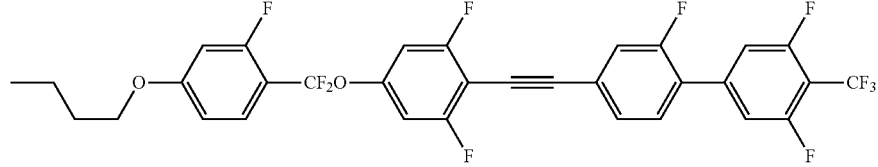 (1-12-31)
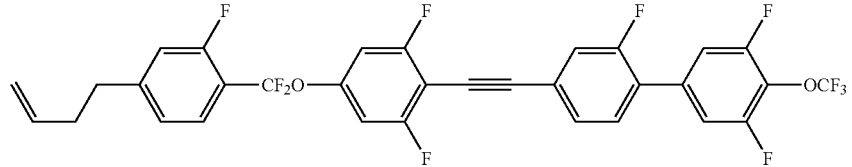 (1-12-32)
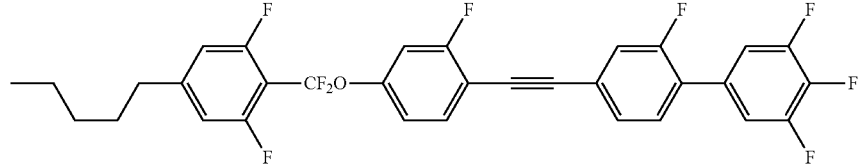 (1-12-33)
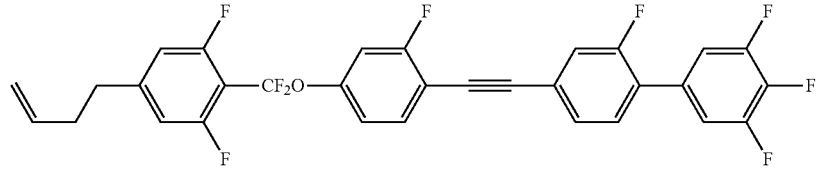 (1-12-34)
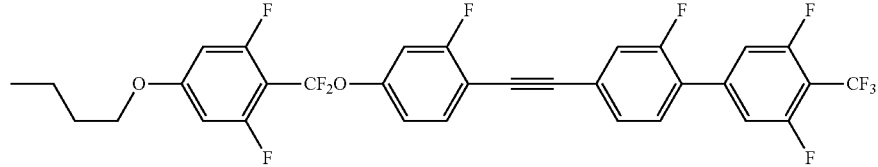 (1-12-35)

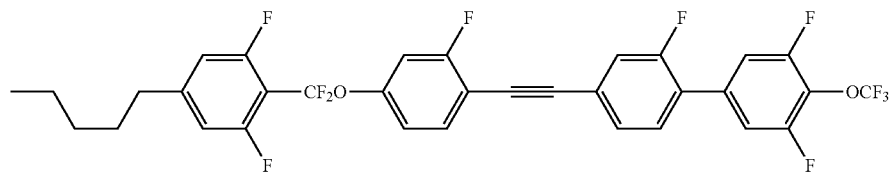
(1-12-36)
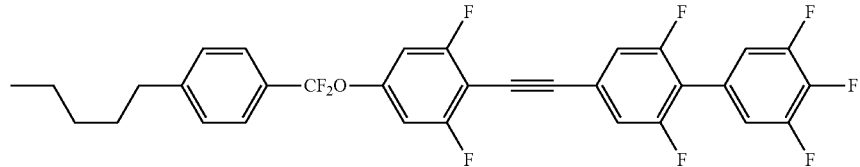
(1-12-37)
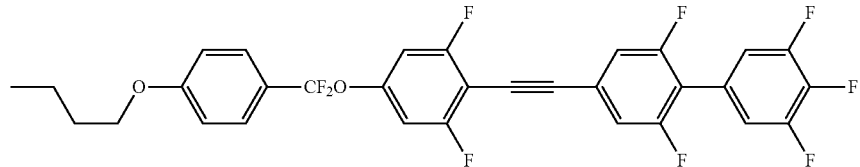
(1-12-38)
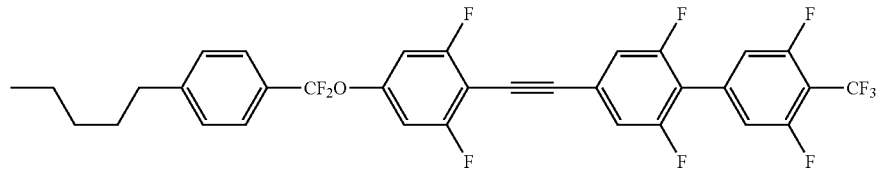
(1-12-39)
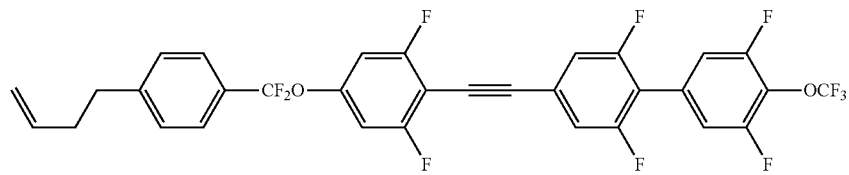
(1-12-40)
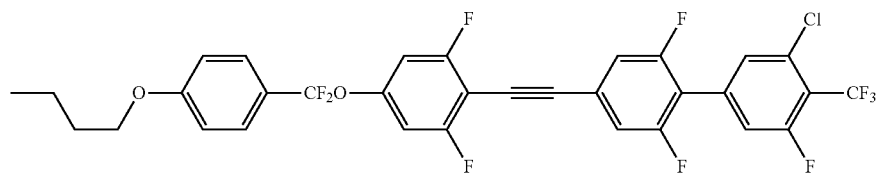
(1-12-41)
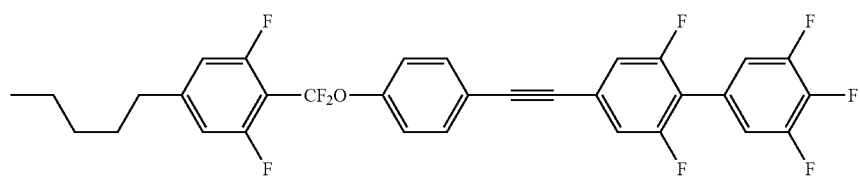
(1-12-42)
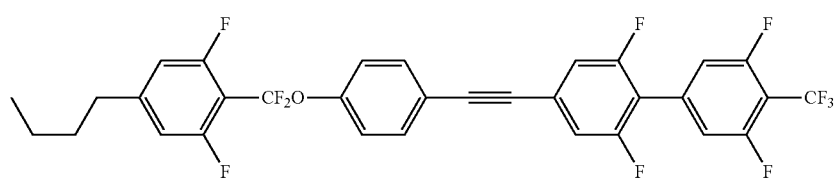
(1-12-43)
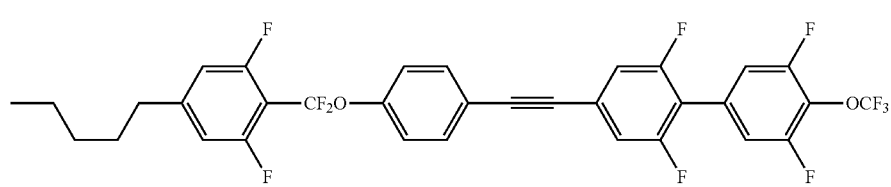
(1-12-44)

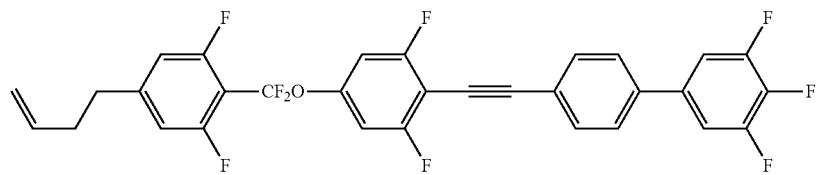 (1-12-45)
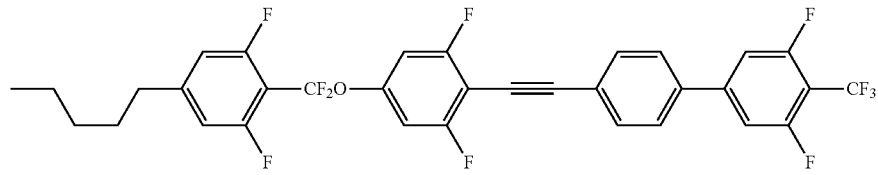 (1-12-46)
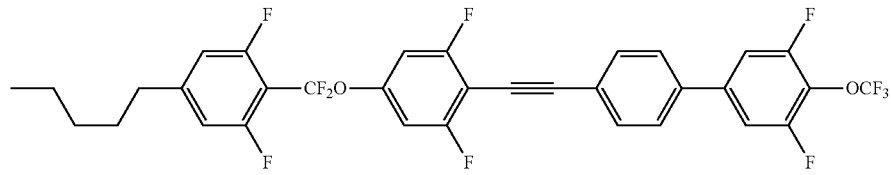 (1-12-47)
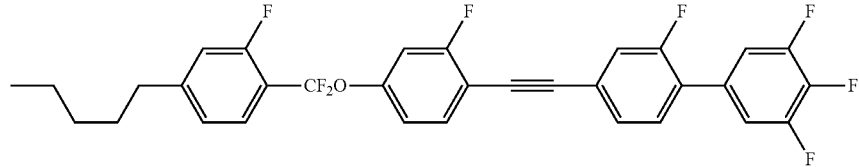 (1-12-48)
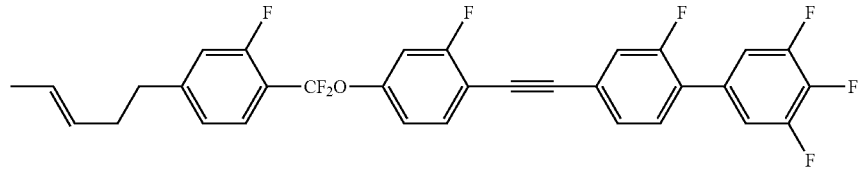 (1-12-49)
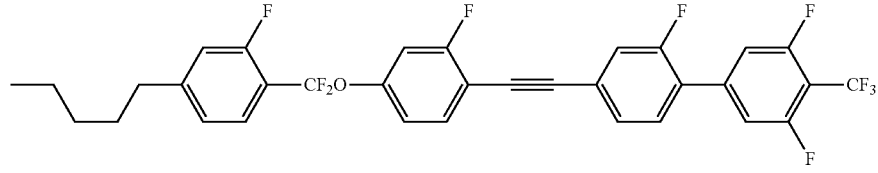 (1-12-50)
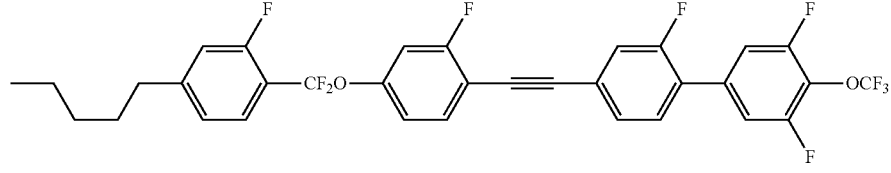 (1-12-51)
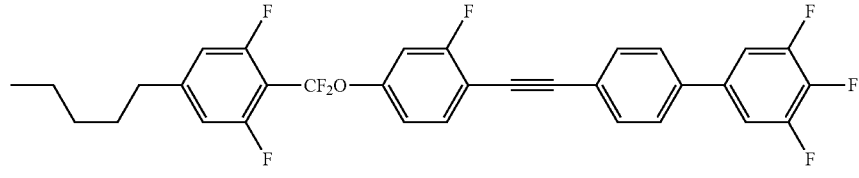 (1-12-52)
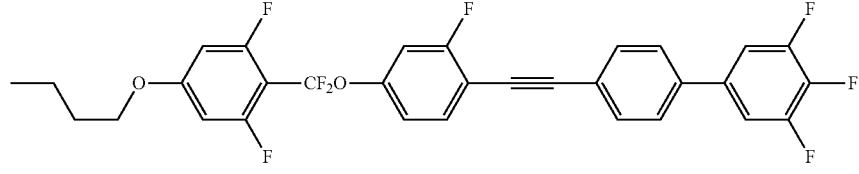 (1-12-53)

-continued
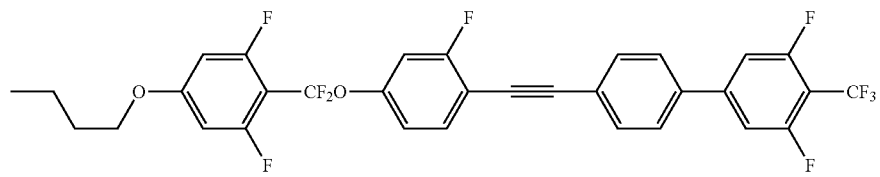
(1-12-54)
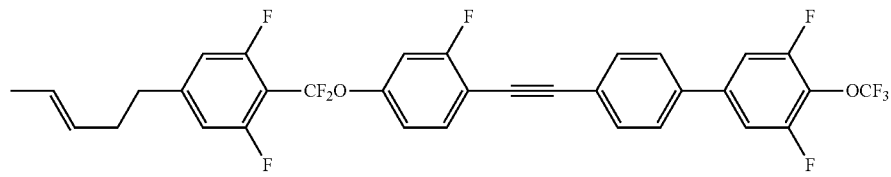
(1-12-55)
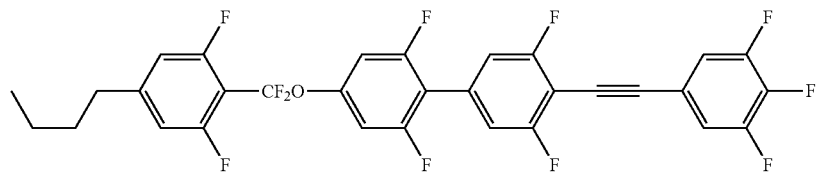
(1-13-1)
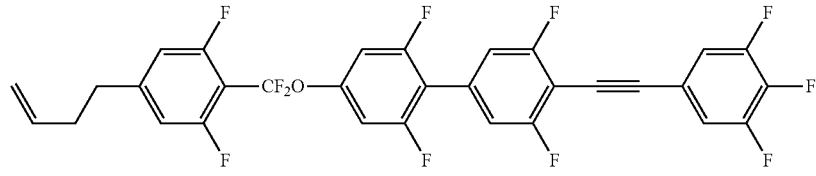
(1-13-2)
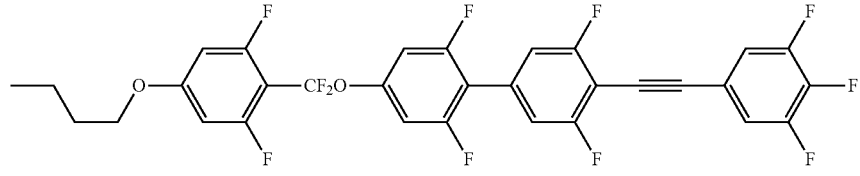
(1-13-3)
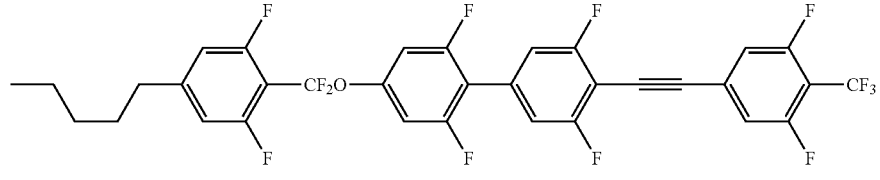
(1-13-4)
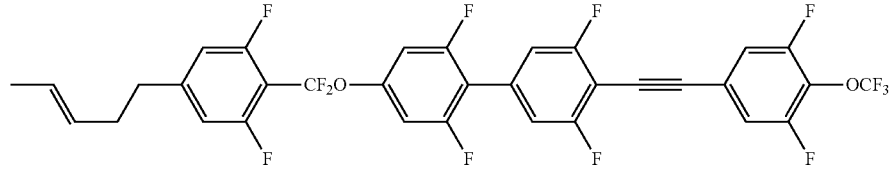
(1-13-5)
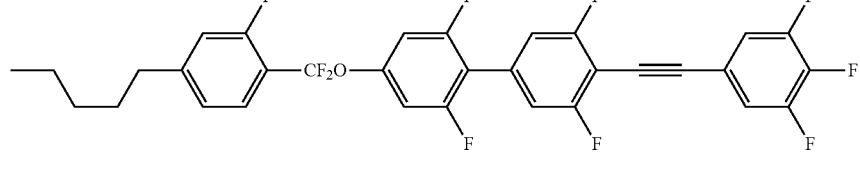
(1-13-6)
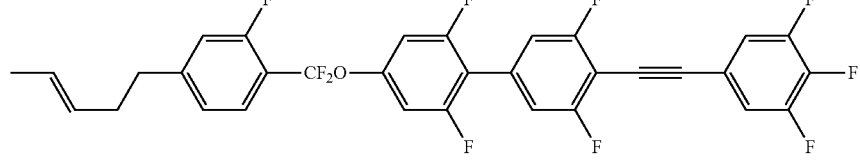
(1-13-7)

-continued
(1-13-8)
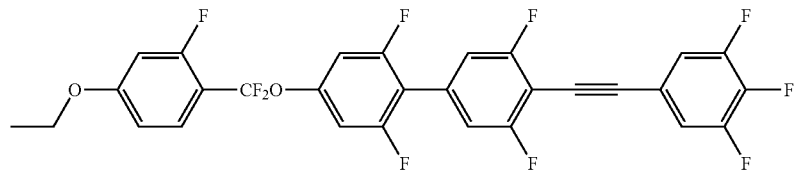
(1-13-9)
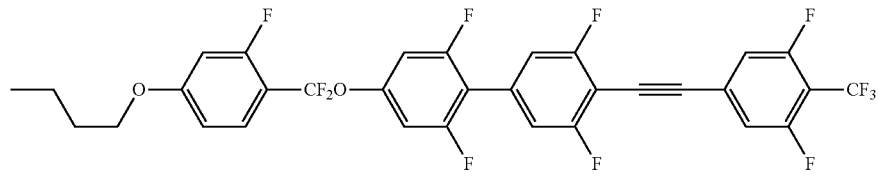
(1-13-10)
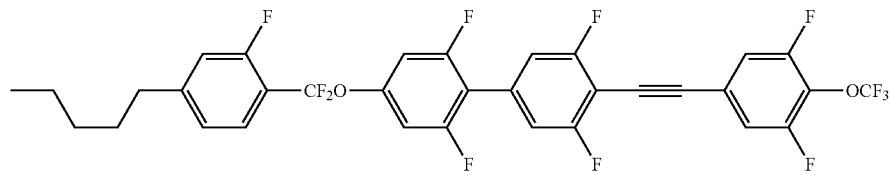
(1-13-11)
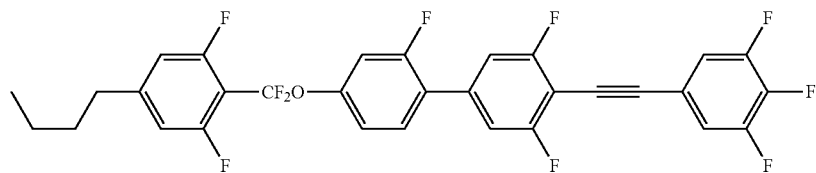
(1-13-12)
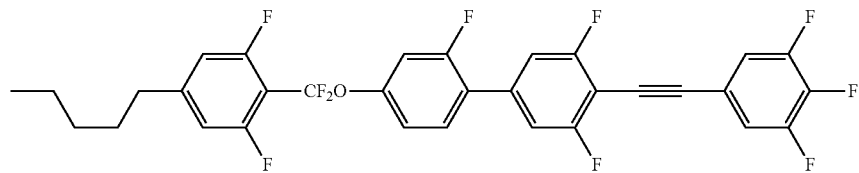
(1-13-13)
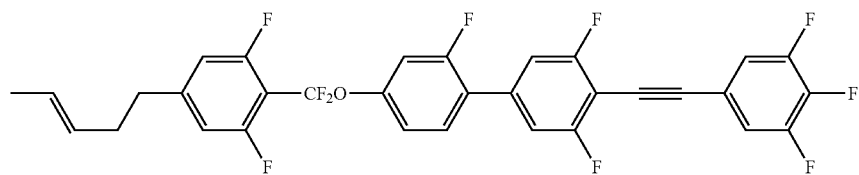
(1-13-14)
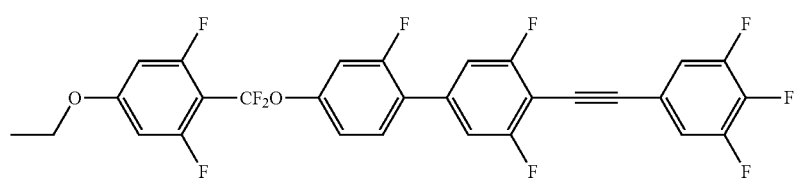
(1-13-15)
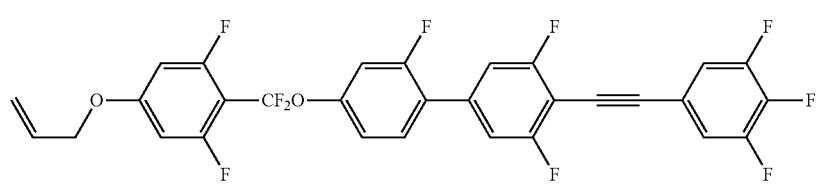
(1-13-16)
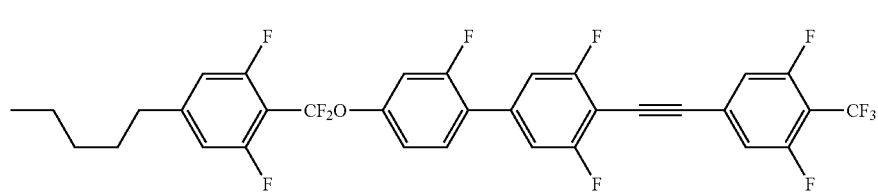

-continued
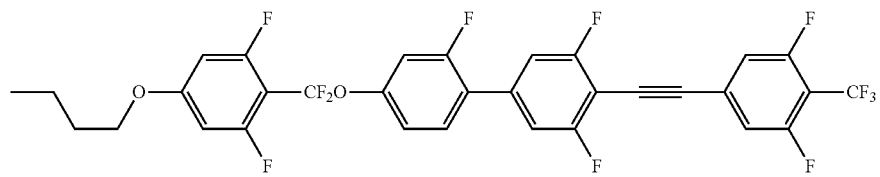
(1-13-17)
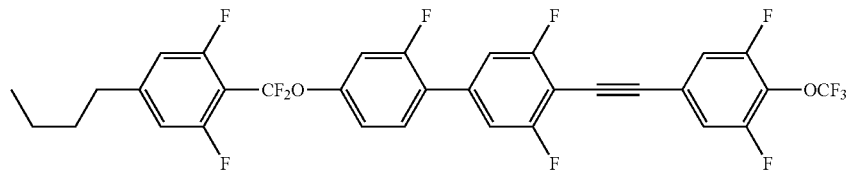
(1-13-18)
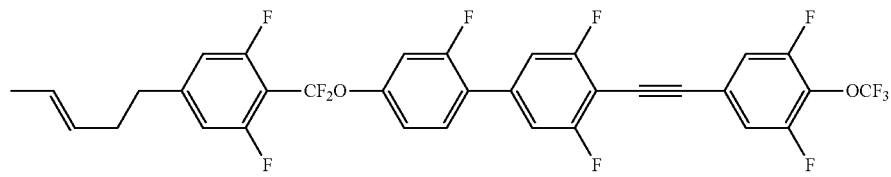
(1-13-19)
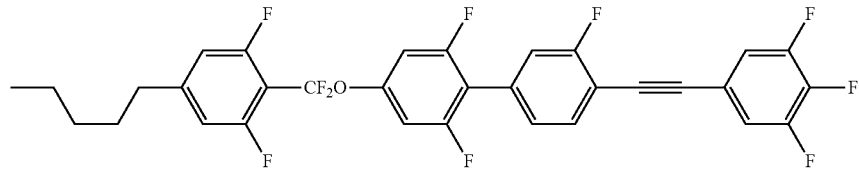
(1-13-20)
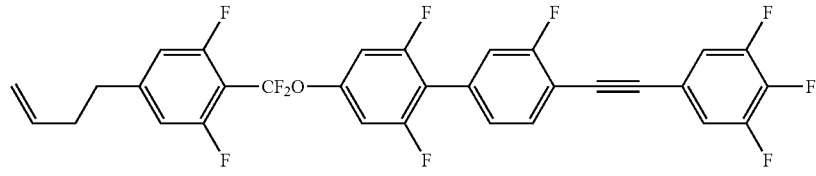
(1-13-21)
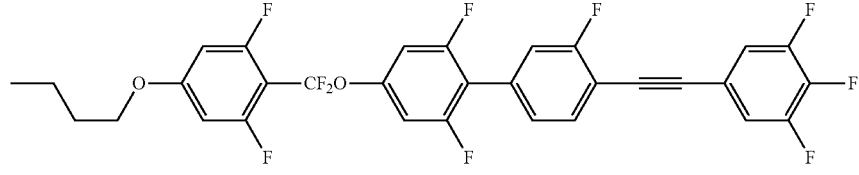
(1-13-22)
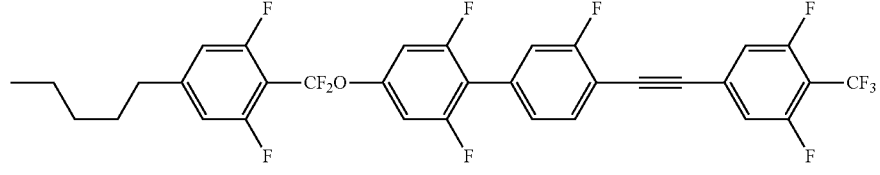
(1-13-23)
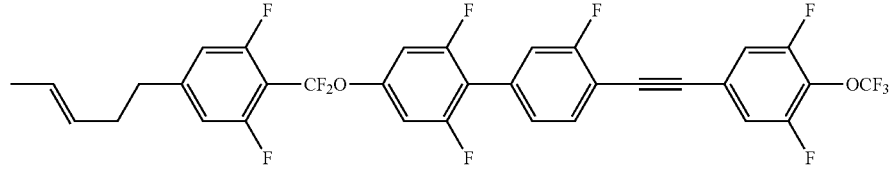
(1-13-24)
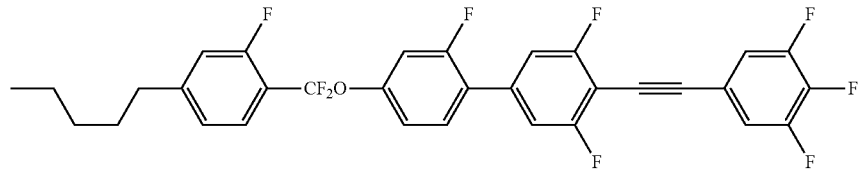
(1-13-25)

-continued
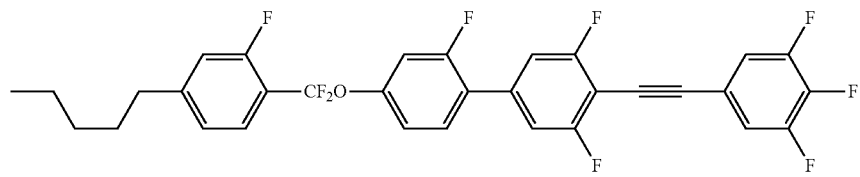
(1-13-26)
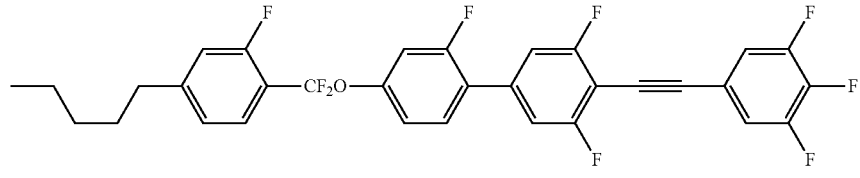
(1-13-27)
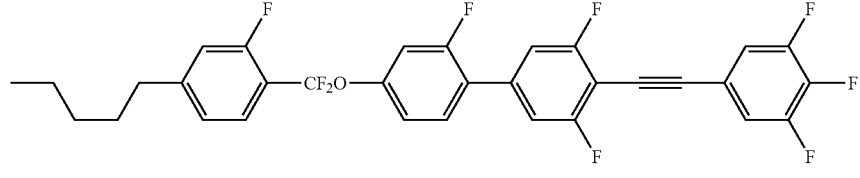
(1-13-28)
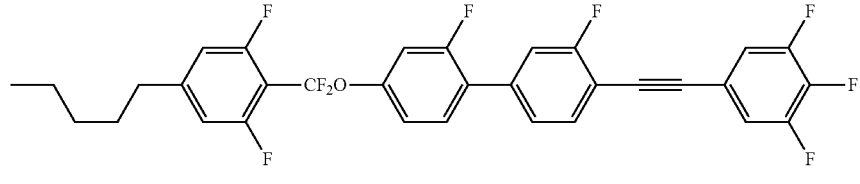
(1-13-29)
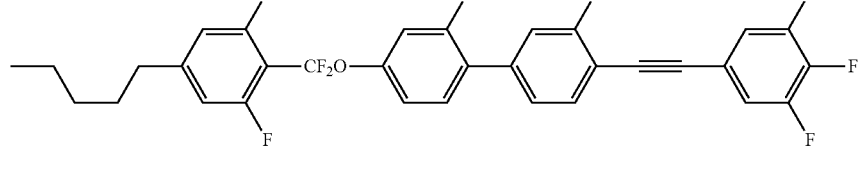
(1-13-30)
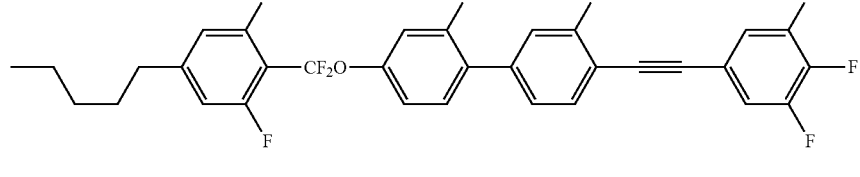
(1-13-31)
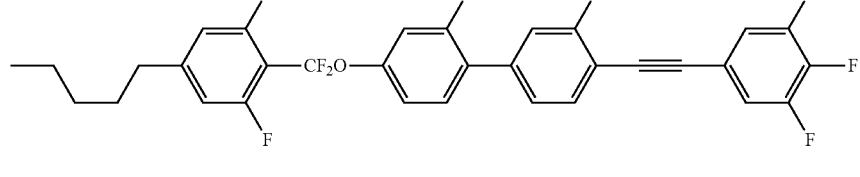
(1-13-32)
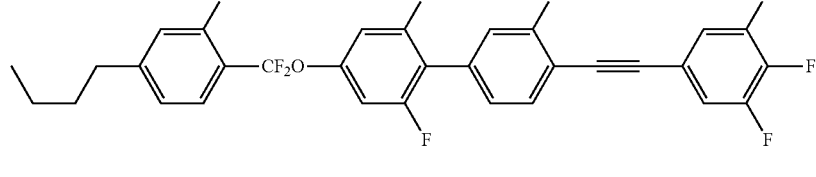
(1-13-33)
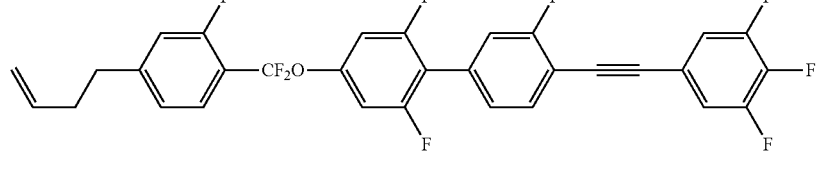
(1-13-34)

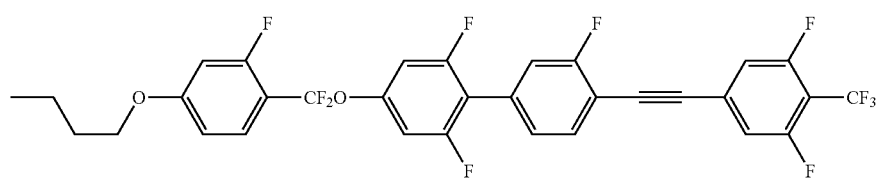 (1-13-35)
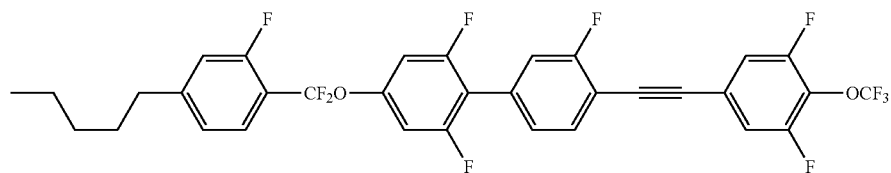 (1-13-36)
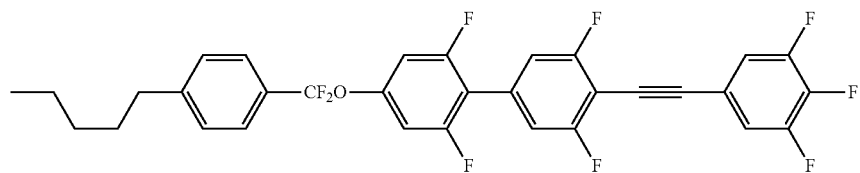 (1-13-37)
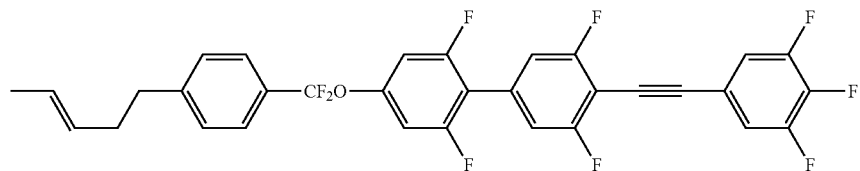 (1-13-38)
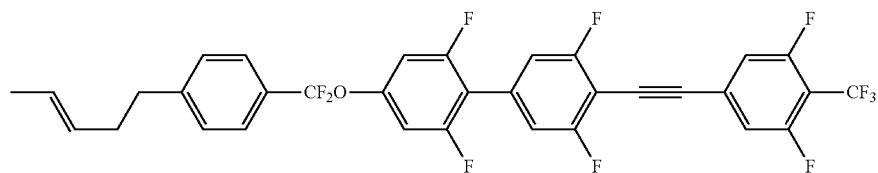 (1-13-39)
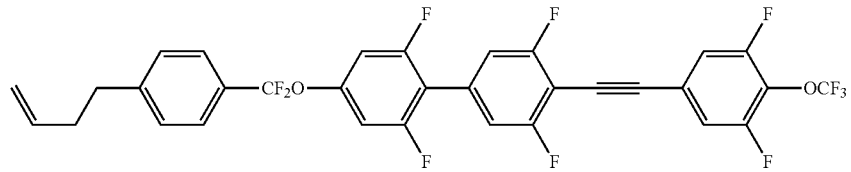 (1-13-40)
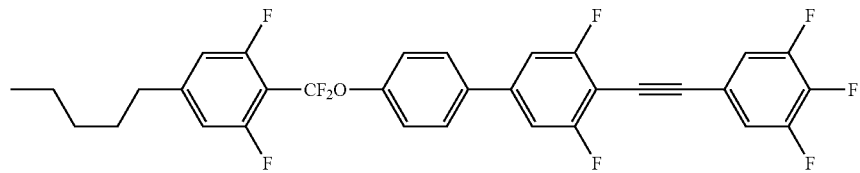 (1-13-41)
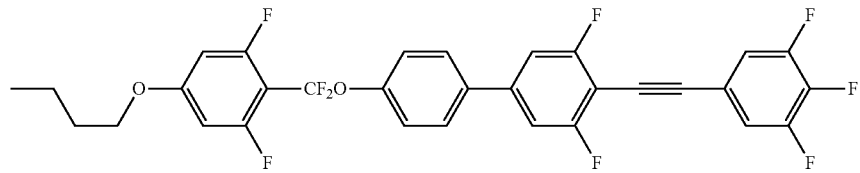 (1-13-42)
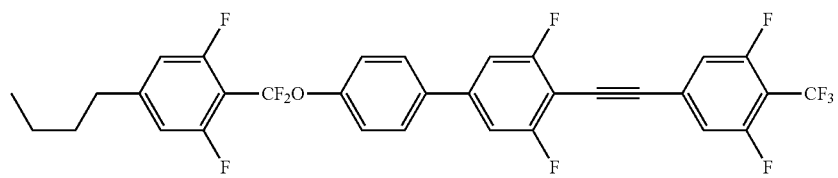 (1-13-43)

-continued
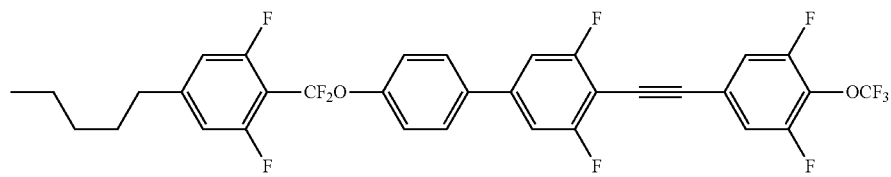
(1-13-44)
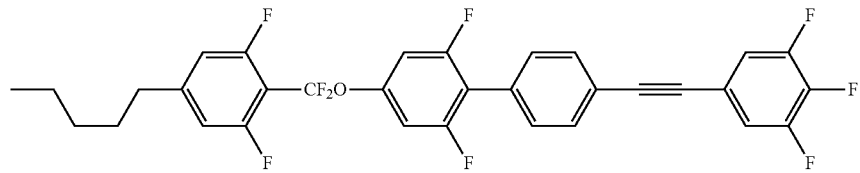
(1-13-45)
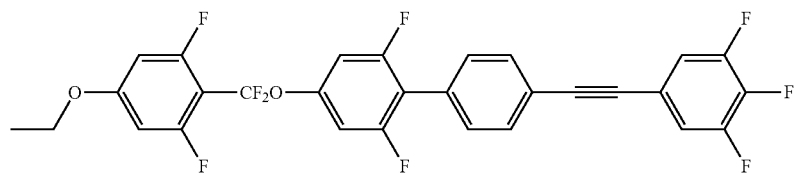
(1-13-46)
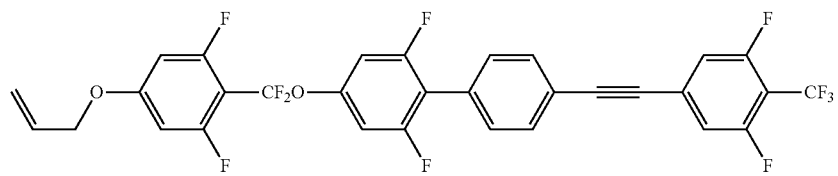
(1-13-47)
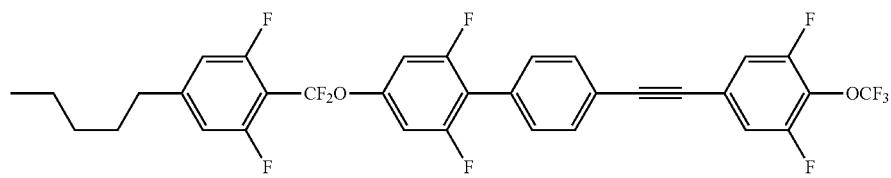
(1-13-48)
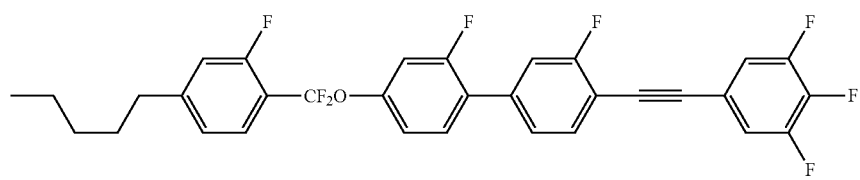
(1-13-49)
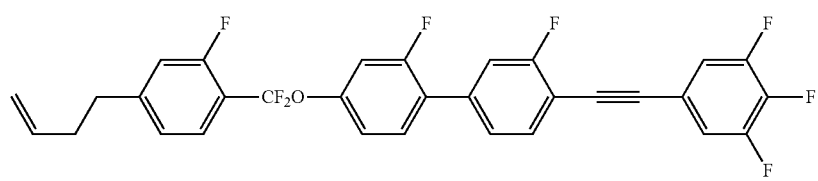
(1-13-50)
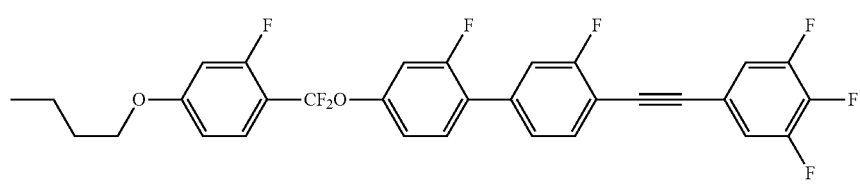
(1-13-51)
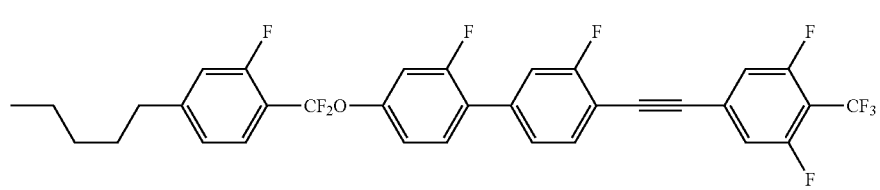
(1-13-52)

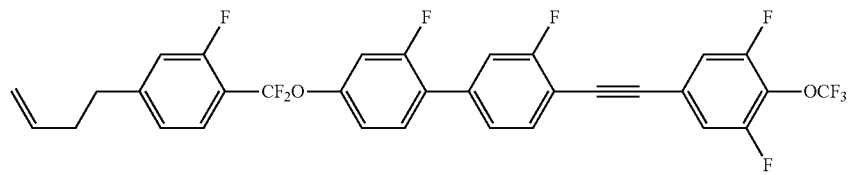
(1-13-53)
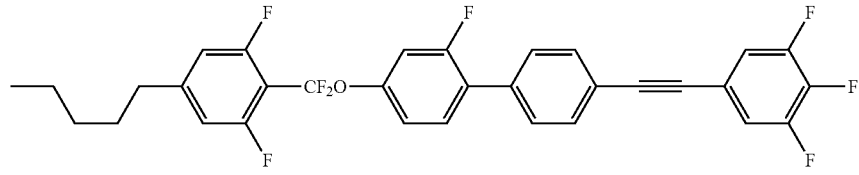
(1-13-54)
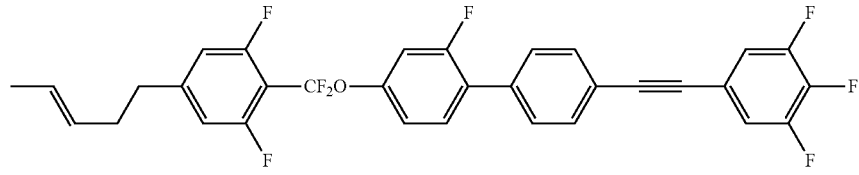
(1-13-55)
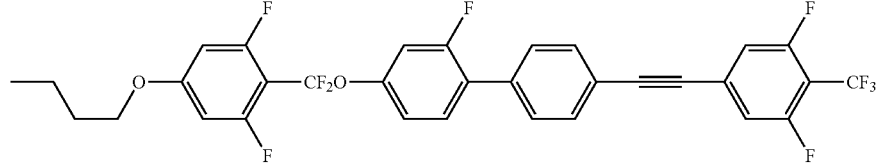
(1-13-56)
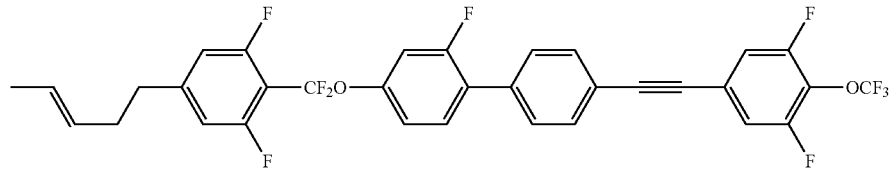
(1-13-57)
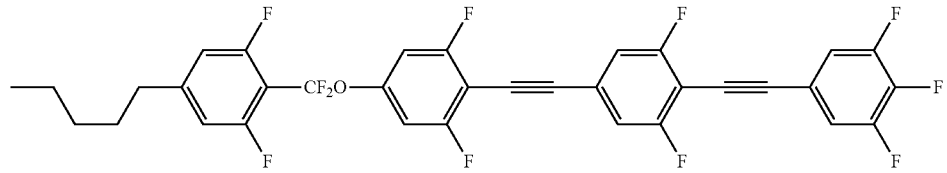
(1-14-1)
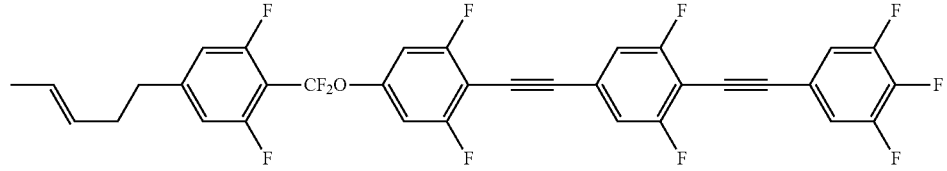
(1-14-2)
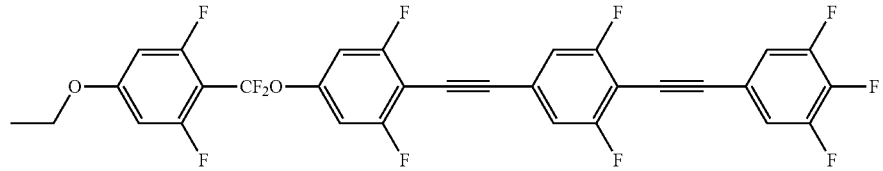
(1-14-3)
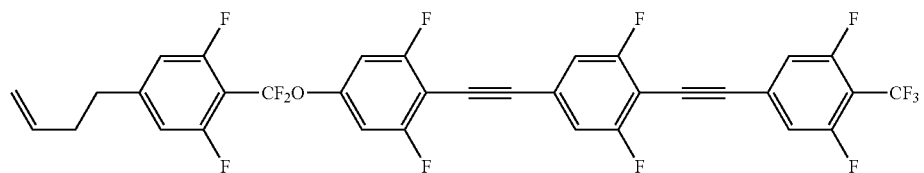
(1-14-4)

-continued
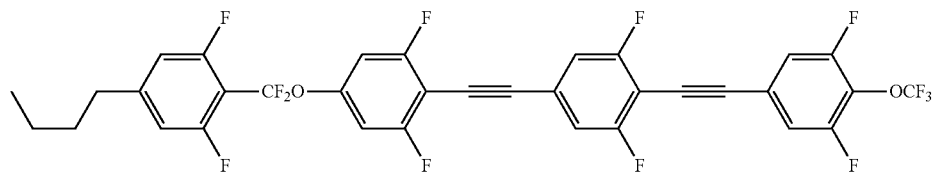
(1-14-5)
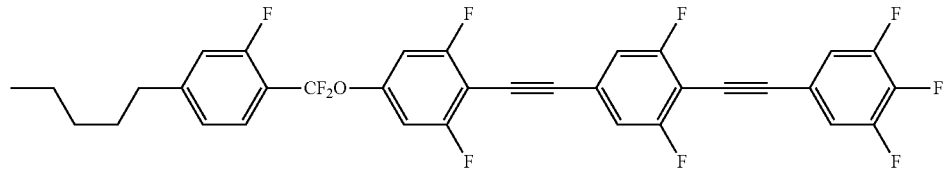
(1-14-6)
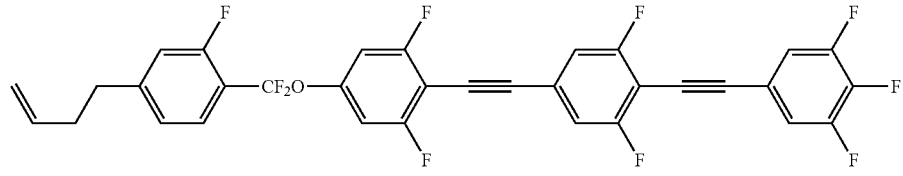
(1-14-7)
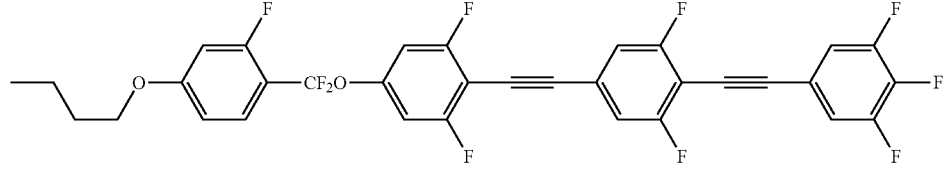
(1-14-8)
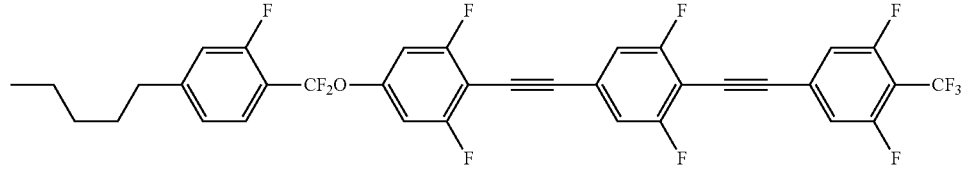
(1-14-9)
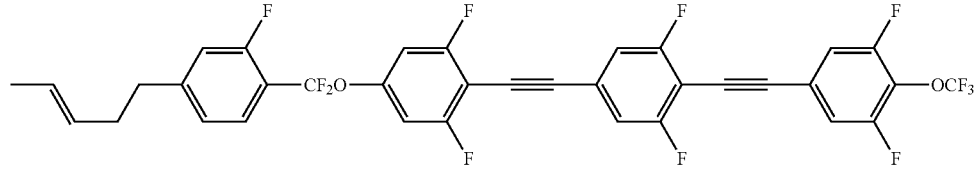
(1-14-10)
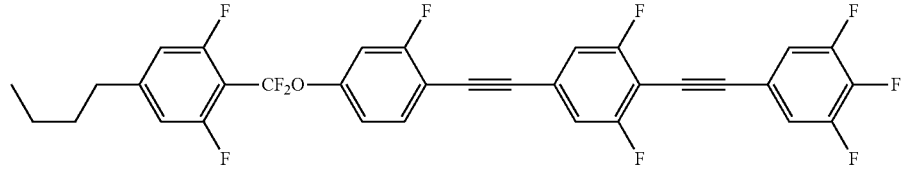
(1-14-11)
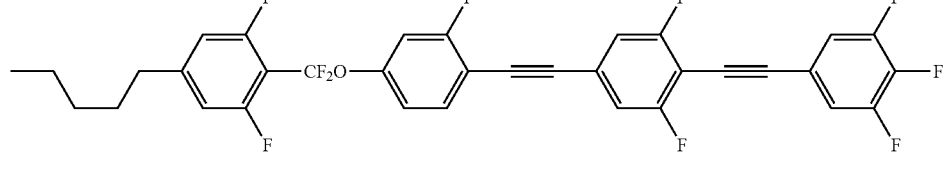
(1-14-12)
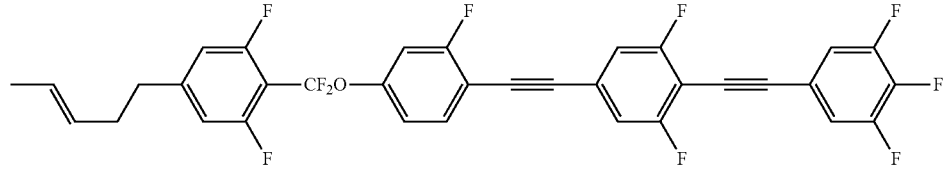
(1-14-13)

-continued
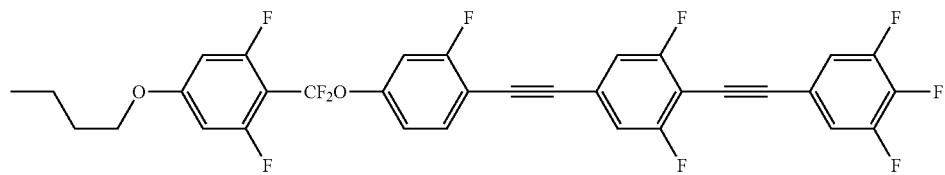
(1-14-14)
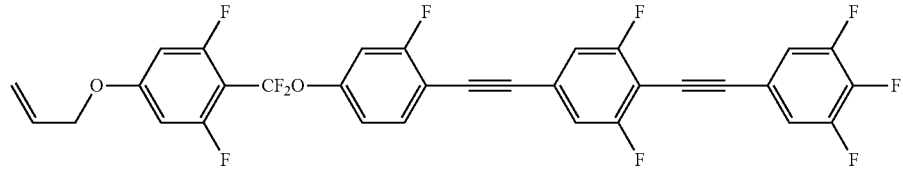
(1-14-15)
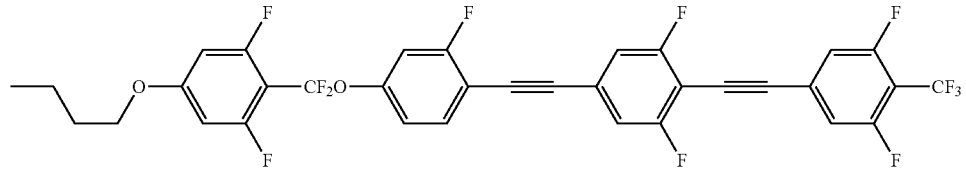
(1-14-16)
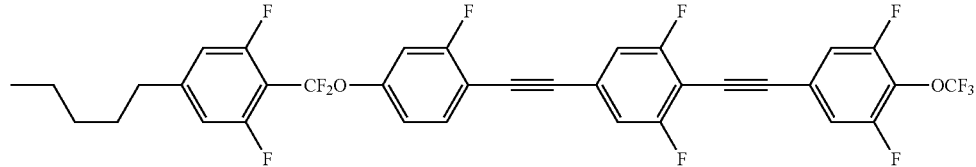
(1-14-17)
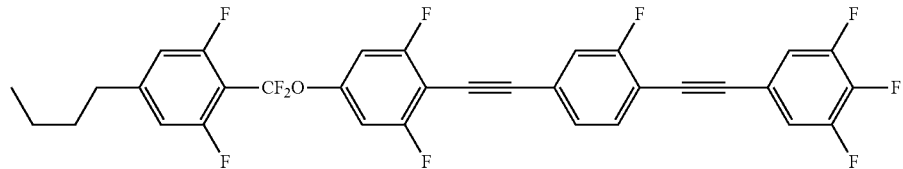
(1-14-18)
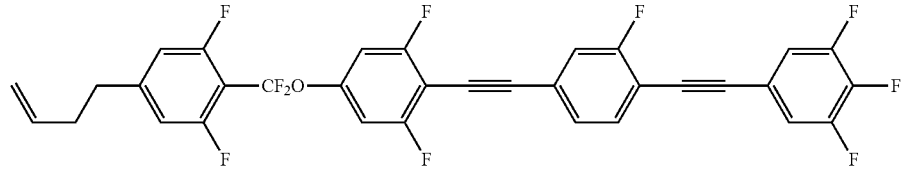
(1-14-19)
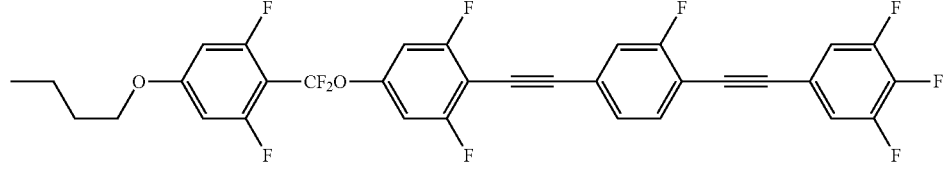
(1-14-20)
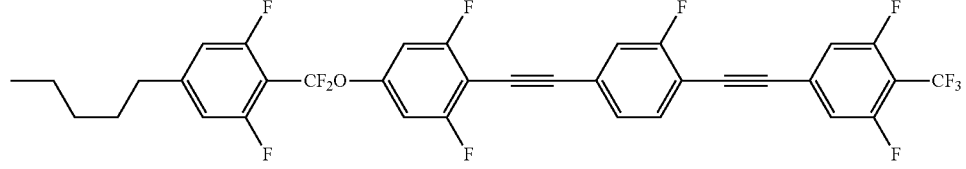
(1-14-21)
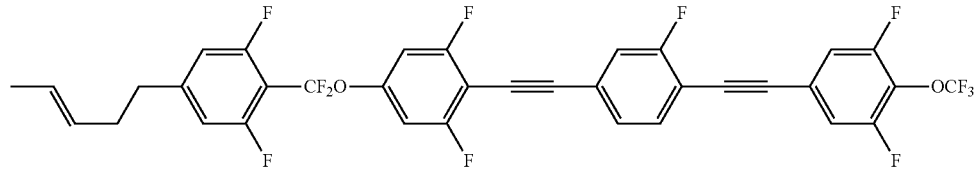
(1-14-22)

-continued
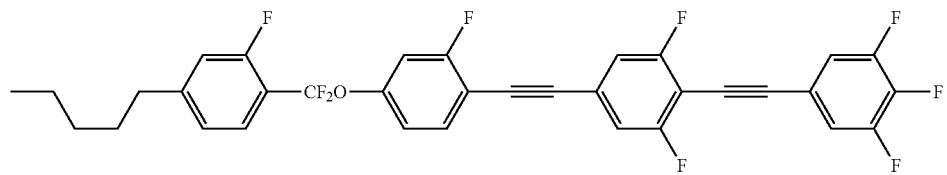
(1-14-23)
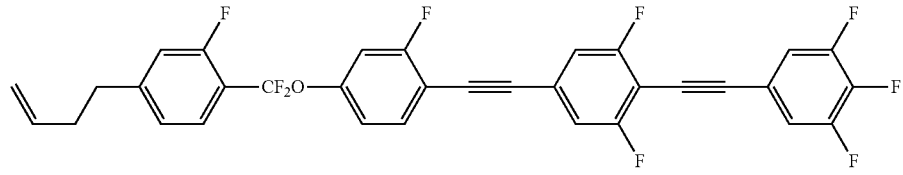
(1-14-24)
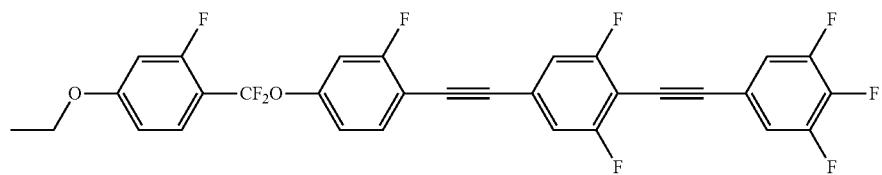
(1-14-25)
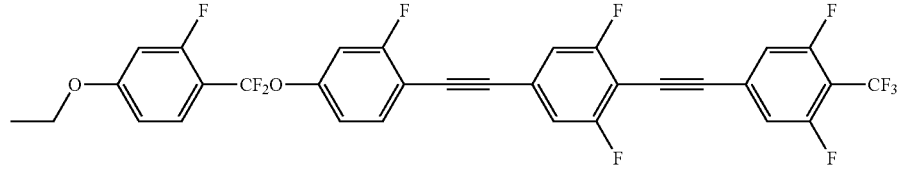
(1-14-26)
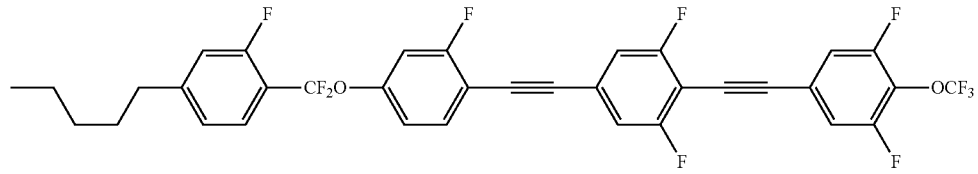
(1-14-27)
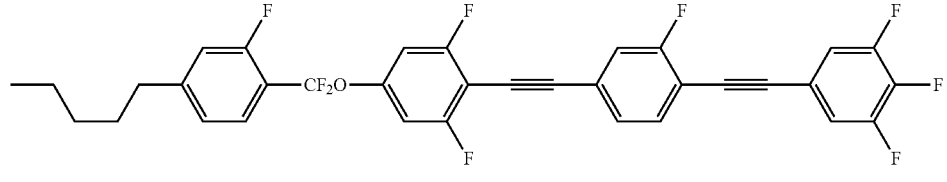
(1-14-28)
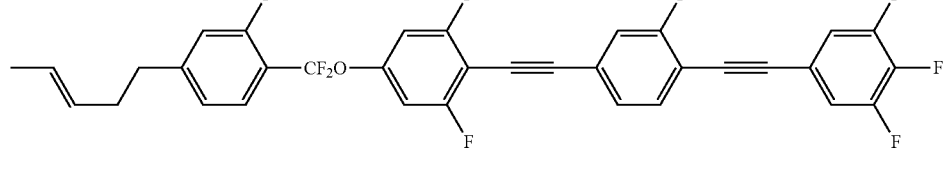
(1-14-29)
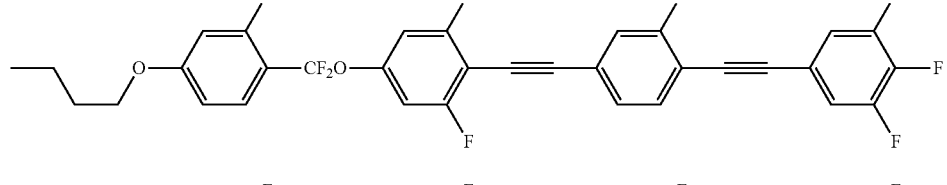
(1-14-30)
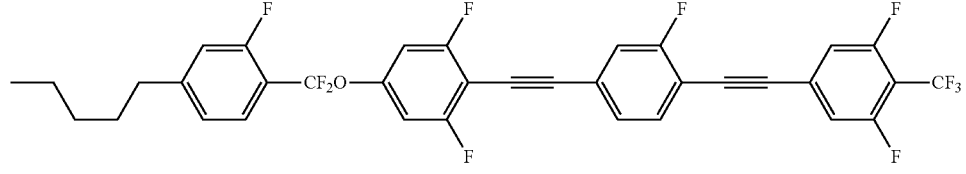
(1-14-31)

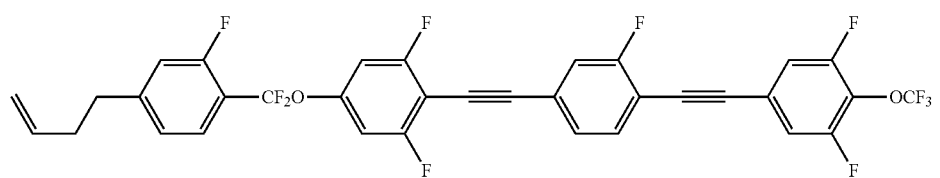
(1-14-32)
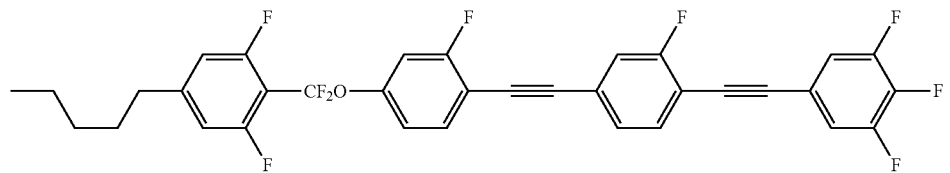
(1-14-33)
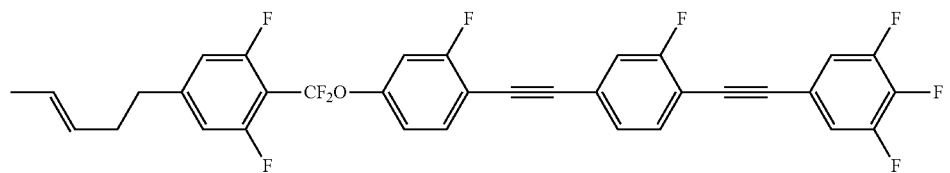
(1-14-34)
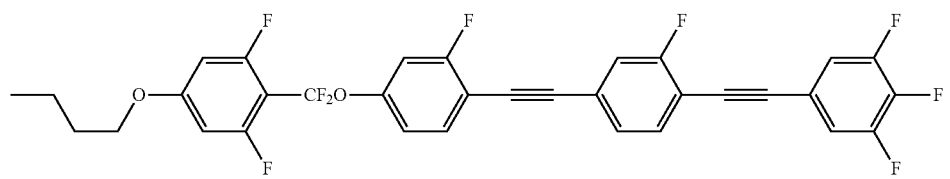
(1-14-35)
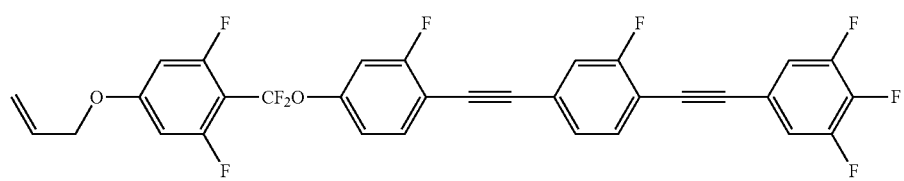
(1-14-36)
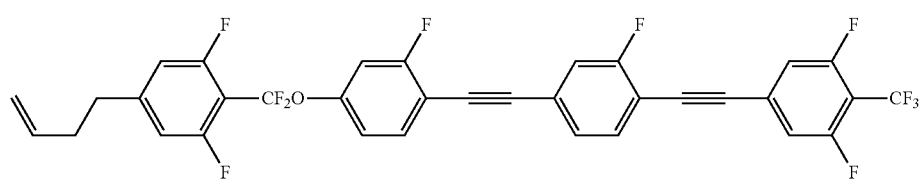
(1-14-37)
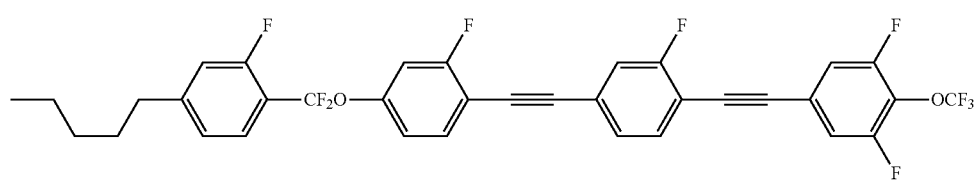
(1-14-38)
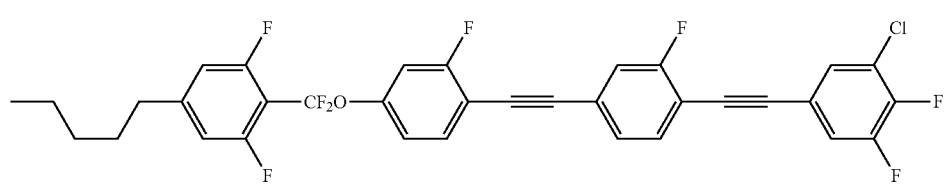
(1-14-39)
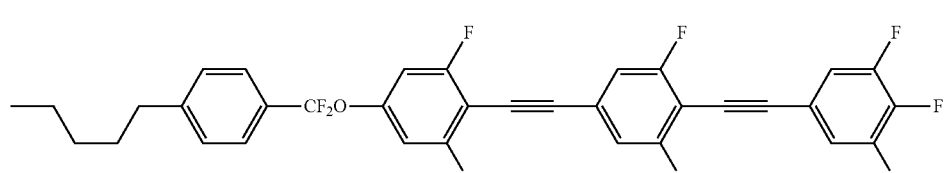
(1-14-40)

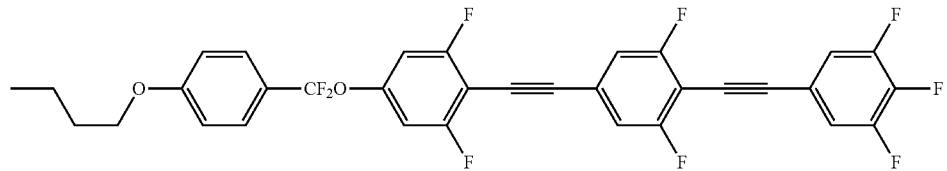
(1-14-41)
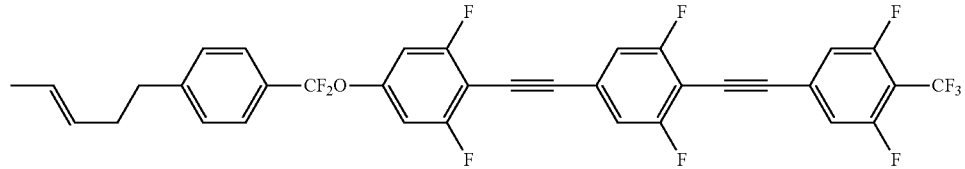
(1-14-42)
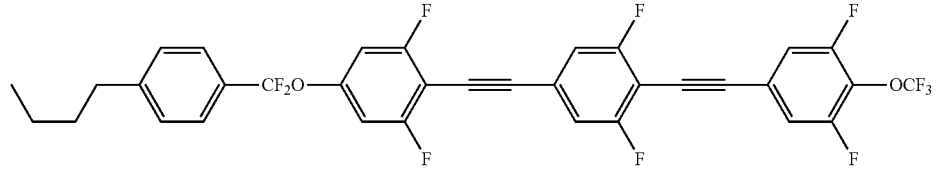
(1-14-43)
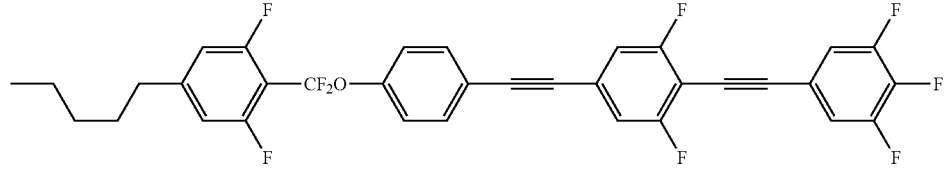
(1-14-44)
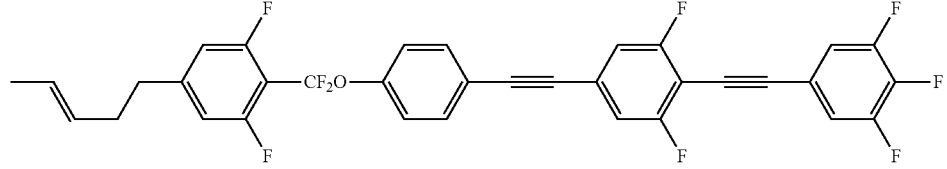
(1-14-45)
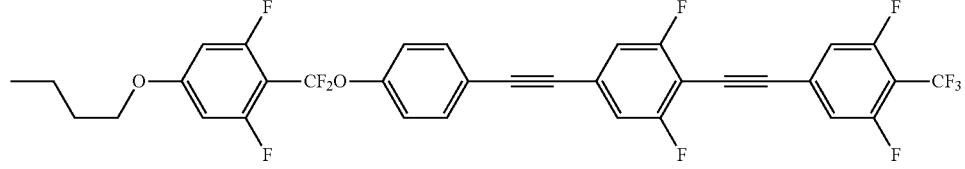
(1-14-46)
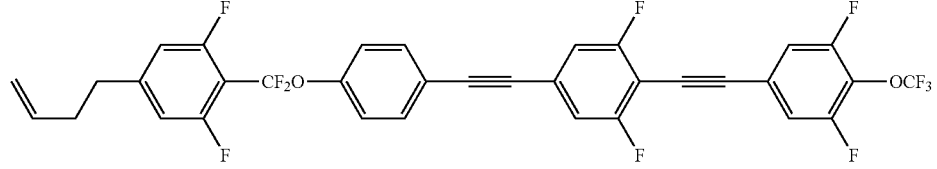
(1-14-47)
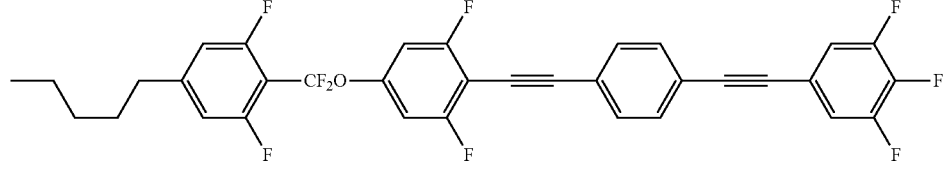
(1-14-48)
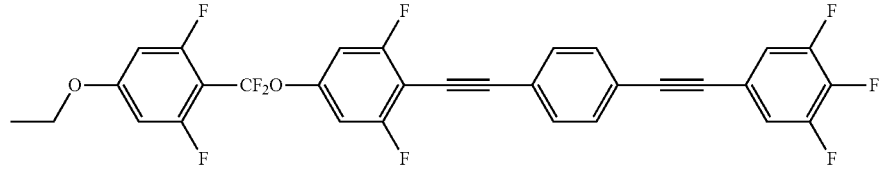
(1-14-49)

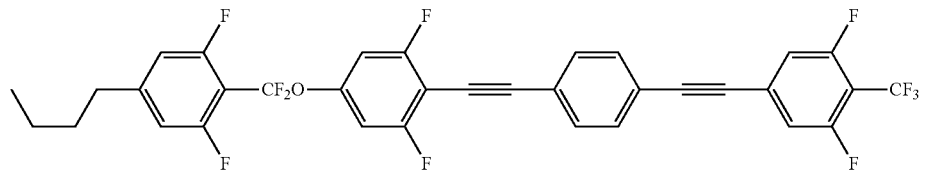 (1-14-50)
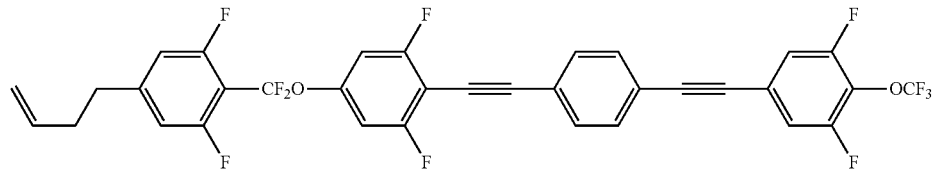 (1-14-51)
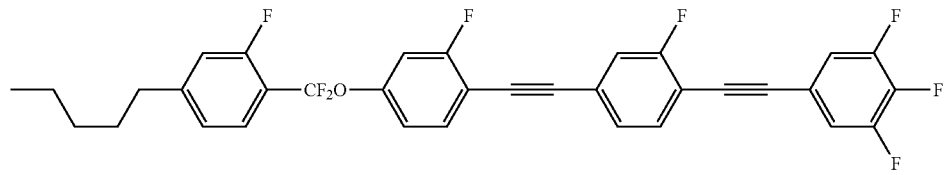 (1-14-52)
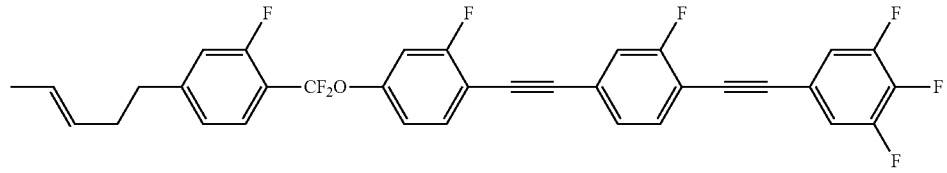 (1-14-53)
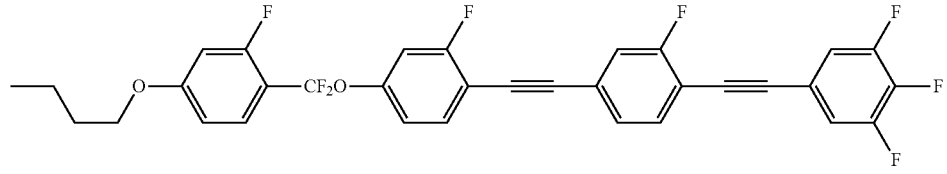 (1-14-54)
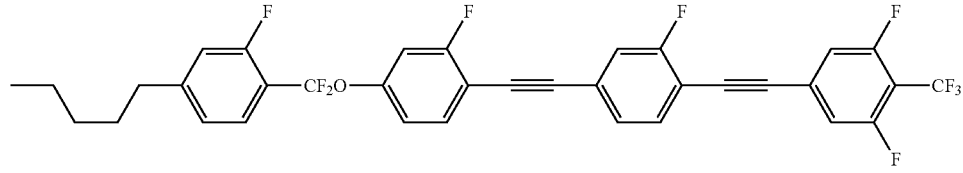 (1-14-55)
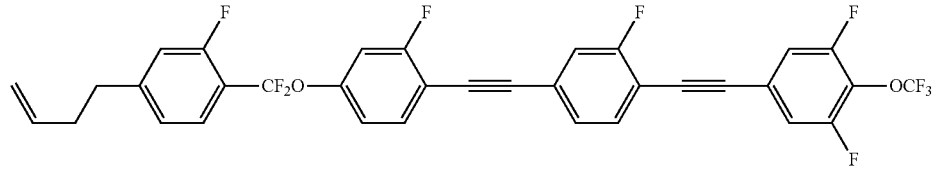 (1-14-56)
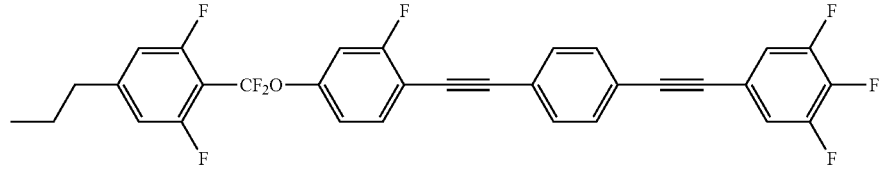 (1-14-57)
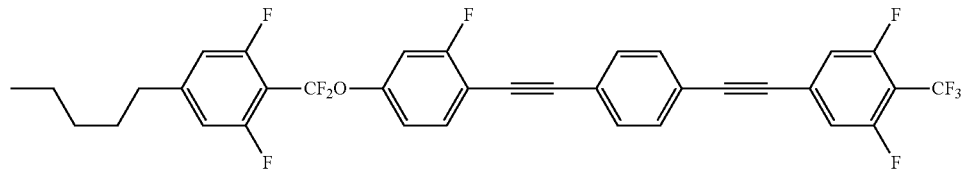 (1-14-58)

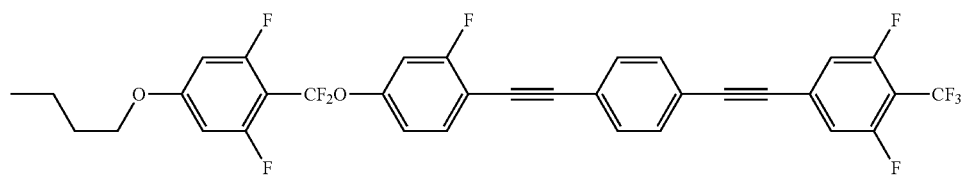

(1-14-59)

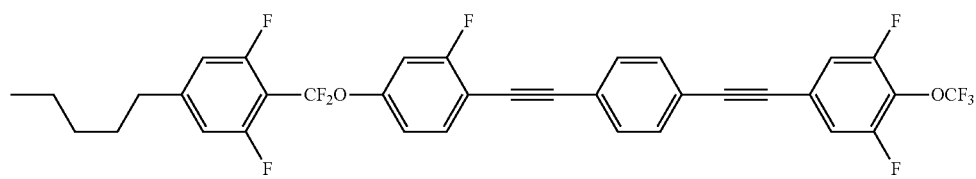

(1-14-60)

2. Example of Composition

The composition of the invention will be described in detail by way of Examples. The invention includes a mixture of a composition in Use Example 1 and a composition in Use Example 2. The invention also includes a mixture of at least two of compositions in Use Examples. Compounds in the Use Examples were represented using symbols according to definitions in Table 2 described below. In Table 2, a configuration of 1,4-cyclohexylene is trans. A parenthesized number next to a symbolized compound in the Use Examples represents a chemical formula to which the compound belongs. A symbol (-) means any other liquid crystal compound. A proportion (percentage) of the liquid crystal compound is expressed in terms of weight percent (% by weight) based on the weight of the liquid crystal composition. Values of the physical properties of the composition are summarized in a last part. The physical properties were measured according to the methods described above, and measured values are directly described (without extrapolation).

TABLE 2

Method of Description of Compounds using Symbols

R—(A$_1$)—Z$_1$— . . . —Z$_n$—(A$_n$)—R'

| | Symbols |
|---|---|
| 1) Left-terminal Group R— | |
| C$_n$H$_{2n+1}$— | n- |
| C$_n$H$_{2n+1}$O— | nO- |
| C$_m$H$_{2m+1}$OC$_n$H$_{2n}$— | mOn- |
| CH$_2$=CH— | V- |
| C$_n$H$_{2n+1}$—CH=CH— | nV- |
| CH$_2$=CH—C$_n$H$_{2n}$— | Vn- |
| C$_m$H$_{2m+1}$—CH=CH—C$_n$H$_{2n}$— | mVn- |
| CF$_2$=CH— | VFF- |
| CF$_2$=CH—C$_n$H$_{2n}$— | VFFn- |
| 2) Right-terminal Group —R' | |
| —C$_n$H$_{2n+1}$ | -n |
| —OC$_n$H$_{2n+1}$ | -On |
| —COOCH$_3$ | -EMe |
| —CH=CH$_2$ | -V |
| —CH=CH—C$_n$H$_{2n+1}$ | -Vn |
| —C$_n$H$_{2n}$—CH=CH$_2$ | -nV |
| —C$_m$H$_{2m}$—CH=CH—C$_n$H$_{2n+1}$ | -mVn |
| —CH=CF$_2$ | -VFF |
| —F | -F |
| —Cl | -CL |
| —OCF$_3$ | -OCF3 |
| —OCF$_2$H | -OCF2H |
| —CF$_3$ | -CF3 |

TABLE 2-continued

Method of Description of Compounds using Symbols

R—(A$_1$)—Z$_1$— . . . —Z$_n$—(A$_n$)—R'

| | Symbols |
|---|---|
| —CF=CH—CF$_3$ | -FVCF3 |
| —C≡N | -C |
| 3) Bonding Group —Z$_n$— | |
| —C$_n$H$_{2n}$— | n |
| —COO— | E |
| —CH=CH— | V |
| —CH$_2$O— | 1O |
| —OCH$_2$— | O1 |
| —CF$_2$O— | X |
| —C≡C— | T |
| 4) Ring Structure —A$_n$— | |
| 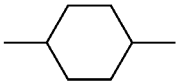 | H |
|  | B |
| 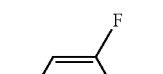 | B(F) |
| 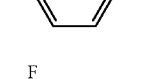 | B(2F) |
| 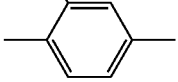 | B(F,F) |

TABLE 2-continued

Method of Description of Compounds using Symbols

R—(A₁)—Z₁—...—Zₙ—(Aₙ)—R'

| | Symbols |
|---|---|
| 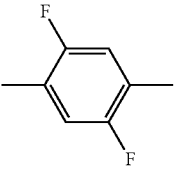 | B(2F,5F) |
| 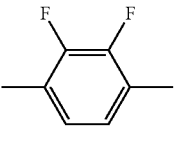 | B(2F,3F) |
| 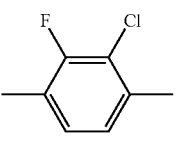 | B(2F,3CL) |
| 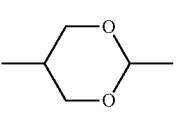 | G |
| 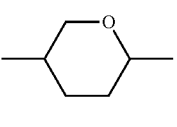 | dh |
| 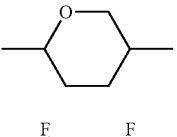 | Dh |
| 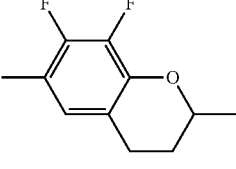 | Cro(7F,8F) |
| 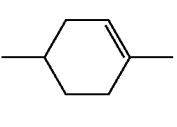 | ch |
| 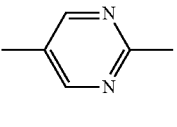 | Py |

5) Examples of Description

Example 1. 5-BTB(F)B(F,F)XB(F,F)-F

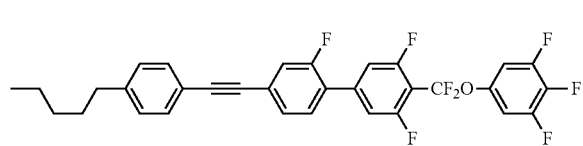

TABLE 2-continued

Method of Description of Compounds using Symbols

R—(A₁)—Z₁—...—Zₙ—(Aₙ)—R'

Symbols

Example 2. 3-HBB(2F,3F)-O2

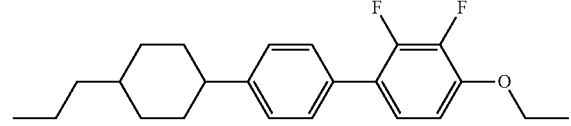 [SMILES: CCCC1CCC(c2ccc(-c3ccc(OCC)c(F)c3F)cc2)CC1]

Use Example 1

| | | |
|---|---|---|
| 5-BTB(F)B(F,F)XB(F,F)-F | (1-5-50) | 5% |
| 5-HB-CL | (2-2) | 11% |
| 3-HH-4 | (13-1) | 8% |
| 3-HHB-1 | (14-1) | 5% |
| 3-HHB(F,F)-F | (3-3) | 8% |
| 3-HBB(F,F)-F | (3-24) | 20% |
| 5-HBB(F,F)-F | (3-24) | 15% |
| 3-HHEB(F,F)-F | (3-12) | 10% |
| 4-HHEB(F,F)-F | (3-12) | 3% |
| 5-HHEB(F,F)-F | (3-12) | 3% |
| 2-HBEB(F,F)-F | (3-39) | 3% |
| 5-HBEB(F,F)-F | (3-39) | 3% |
| 3-HHBB(F,F)-F | (4-6) | 6% |

NI=82.2° C.; Δn=0.110; Δε=9.3; η=23.4 mPa·s.

Use Example 2

| | | |
|---|---|---|
| 5-B(F)B(F,F)TB(F,F)XB(F,F)-F | (1-6-11) | 5% |
| 2-HB-C | (5-1) | 5% |
| 3-HB-C | (5-1) | 12% |
| 3-HB-O2 | (13-5) | 15% |
| 3-HHB-F | (3-1) | 4% |
| 3-HHB-1 | (14-1) | 8% |
| 3-HHB-O1 | (14-1) | 5% |
| 3-HHB-3 | (14-1) | 14% |
| 3-HHEB-F | (3-10) | 4% |
| 5-HHEB-F | (3-10) | 4% |
| 2-HHB(F)-F | (3-2) | 7% |
| 3-HHB(F)-F | (3-2) | 7% |
| 5-HHB(F)-F | (3-2) | 7% |
| 3-HHB(F,F)-F | (3-3) | 3% |

NI=104.2° C.; Δn=0.104; Δε=6.7; η=20.9 mPa·s.

Use Example 3

| | | |
|---|---|---|
| 5-BB(F,F)TB(F,F)XB(F,F)-F | (1-6-42) | 5% |
| 7-HB(F,F)-F | (2-4) | 3% |
| 3-HB-O2 | (13-5) | 7% |
| 2-HHB(F)-F | (3-2) | 10% |
| 3-HHB(F)-F | (3-2) | 10% |
| 5-HHB(F)-F | (3-2) | 10% |
| 2-HBB(F)-F | (3-23) | 8% |
| 3-HBB(F)-F | (3-23) | 8% |
| 5-HBB(F)-F | (3-23) | 14% |
| 2-HBB-F | (3-22) | 4% |
| 3-HBB-F | (3-22) | 4% |

-continued

| | | |
|---|---|---|
| 5-HBB-F | (3-22) | 3% |
| 3-HBB(F,F)-F | (3-24) | 4% |
| 5-HBB(F,F)-F | (3-24) | 10% |

NI=87.3° C.; Δn=0.121; Δε=7.8; η=26.4 mPa·s.

Use Example 4

| | | |
|---|---|---|
| 5-BB(F)TB(F,F)XB(F,F)-F | (1-6-77) | 5% |
| 5-HB-CL | (2-2) | 16% |
| 3-HH-4 | (13-1) | 12% |
| 3-HH-5 | (13-1) | 4% |
| 3-HHB-F | (3-1) | 4% |
| 3-HHB-CL | (3-1) | 3% |
| 4-HHB-CL | (3-1) | 4% |
| 3-HHB(F)-F | (3-2) | 10% |
| 4-HHB(F)-F | (3-2) | 9% |
| 5-HHB(F)-F | (3-2) | 9% |
| 7-HHB(F)-F | (3-2) | 8% |
| 5-HBB(F)-F | (3-23) | 4% |
| 1O1-HBBH-5 | (15-1) | 3% |
| 5-HHBB(F,F)-F | (4-6) | 3% |
| 3-HH2BB(F,F)-F | (4-15) | 3% |
| 4-HH2BB(F,F)-F | (4-15) | 3% |

NI=111.9° C.; Δn=0.097; Δε=5.2; η=18.7 mPa·s.

Use Example 5

| | | |
|---|---|---|
| 5-B(F)TB(F,F)XB(F)B(F,F)-F | (1-7-31) | 5% |
| 5-HB-F | (2-2) | 12% |
| 6-HB-F | (2-2) | 9% |
| 7-HB-F | (2-2) | 7% |
| 2-HHB-OCF3 | (3-1) | 5% |
| 3-HHB-OCF3 | (3-1) | 5% |
| 4-HHB-OCF3 | (3-1) | 6% |
| 5-HHB-OCF3 | (3-1) | 5% |
| 3-HH2B-OCF3 | (3-4) | 4% |
| 5-HH2B-OCF3 | (3-4) | 4% |
| 3-HHB(F,F)-OCF2H | (3-3) | 4% |
| 3-HHB(F,F)-OCF3 | (3-3) | 5% |
| 3-HH2B(F)-F | (3-5) | 3% |
| 3-HBB(F)-F | (3-23) | 10% |
| 5-HBB(F)-F | (3-23) | 10% |
| 5-HBBH-3 | (15-1) | 3% |
| 3-HB(F)BH-3 | (15-1) | 3% |

Use Example 6

| | | |
|---|---|---|
| 5-B(F)TB(F)B(F,F)XB(F,F)-CF3 | (1-5-32) | 5% |
| 5-HB-CL | (2-2) | 17% |
| 7-HB(F,F)-F | (2-4) | 3% |
| 3-HH-4 | (13-1) | 10% |
| 3-HH-5 | (13-1) | 5% |
| 3-HB-O2 | (13-5) | 10% |
| 3-HHB-1 | (14-1) | 8% |
| 3-HHB-O1 | (14-1) | 5% |
| 2-HHB(F)-F | (3-2) | 7% |
| 3-HHB(F)-F | (3-2) | 7% |
| 5-HHB(F)-F | (3-2) | 7% |
| 3-HHB(F,F)-F | (3-3) | 6% |
| 3-H2HB(F,F)-F | (3-15) | 5% |
| 4-H2HB(F,F)-F | (3-15) | 5% |

Use Example 7

| | | |
|---|---|---|
| 5-BB(F)TB(F,F)XB(F,F)-CF3 | (1-6-84) | 5% |
| 5-HB-CL | (2-2) | 3% |
| 7-HB(F)-F | (2-3) | 7% |
| 3-HH-4 | (13-1) | 9% |
| 3-HH-EMe | (13-2) | 20% |
| 3-HHEB-F | (3-10) | 8% |
| 5-HHEB-F | (3-10) | 6% |
| 3-HHEB(F,F)-F | (3-12) | 10% |
| 4-HHEB(F,F)-F | (3-12) | 5% |
| 4-HGB(F,F)-F | (3-103) | 5% |
| 5-HGB(F,F)-F | (3-103) | 6% |
| 2-H2GB(F,F)-F | (3-106) | 4% |
| 3-H2GB(F,F)-F | (3-106) | 5% |
| 5-GHB(F,F)-F | (3-109) | 7% |

Use Example 8

| | | |
|---|---|---|
| 5-B(F)TB(F,F)XB(F)TB(F,F)-F | (1-9-36) | 4% |
| 3-HB-O1 | (13-5) | 13% |
| 3-HH-4 | (13-1) | 5% |
| 3-HB(2F,3F)-O2 | (6-1) | 12% |
| 5-HB(2F,3F)-O2 | (6-1) | 12% |
| 2-HHB(2F,3F)-1 | (7-1) | 12% |
| 3-HHB(2F,3F)-1 | (7-1) | 12% |
| 3-HHB(2F,3F)-O2 | (7-1) | 12% |
| 5-HHB(2F,3F)-O2 | (7-1) | 12% |
| 3-HHB-1 | (14-1) | 6% |

Use Example 9

| | | |
|---|---|---|
| 4O-BB(F)TB(F,F)XB(F,F)-F | (1-6-83) | 5% |
| 3-HB-O1 | (13-5) | 15% |
| 3-HH-4 | (13-1) | 5% |
| 3-HB(2F,3F)-O2 | (6-1) | 12% |
| 5-HB(2F,3F)-O2 | (6-1) | 12% |
| 2-HHB(2F,3F)-1 | (7-1) | 12% |
| 3-HHB(2F,3F)-1 | (7-1) | 10% |
| 3-HHB(2F,3F)-O2 | (7-1) | 10% |
| 5-HHB(2F,3F)-O2 | (7-1) | 13% |
| 6-HEB(2F,3F)-O2 | (5-12) | 6% |

Use Example 10

| | | |
|---|---|---|
| 4O-B(F)TB(F)B(F,F)XB(F,F)-F | (1-5-28) | 5% |
| 2-HH-5 | (13-1) | 3% |
| 3-HH-4 | (13-1) | 15% |
| 3-HH-5 | (13-1) | 4% |
| 3-HB-O2 | (13-5) | 12% |
| 3-H2B(2F,3F)-O2 | (6-4) | 13% |
| 5-H2B(2F,3F)-O2 | (6-4) | 12% |
| 3-HHB(2F,3CL)-O2 | (7-12) | 5% |
| 2-HBB(2F,3F)-O2 | (7-1) | 3% |
| 3-HBB(2F,3F)-O2 | (7-1) | 9% |
| 5-HBB(2F,3F)-O2 | (7-1) | 9% |
| 3-HHB-1 | (14-1) | 3% |
| 3-HHB-3 | (14-1) | 4% |
| 3-HHB-O1 | (14-1) | 3% |

Use Example 11

| | | |
|---|---|---|
| 4O-BB(F)TB(F,F)XB(F,F)-CF3 | (1-6-86) | 5% |
| 2-HH-3 | (13-1) | 21% |
| 3-HH-4 | (13-1) | 9% |
| 1-BB-3 | (13-8) | 9% |
| 3-HB-O2 | (13-5) | 2% |
| 3-BB(2F,3F)-O2 | (6-3) | 9% |
| 5-BB(2F,3F)-O2 | (6-3) | 6% |
| 2-HH1OB(2F,3F)-O2 | (7-5) | 11% |

-continued

| | | |
|---|---|---|
| 3-HH1OB(2F,3F)-O2 | (7-5) | 18% |
| 3-HHB-1 | (14-1) | 5% |
| 3-HHB-O1 | (14-1) | 3% |
| 5-B(F)BB-2 | (14-8) | 2% |

Use Example 12

| | | |
|---|---|---|
| 5-B(F)B(F,F)XB(F)TB(F,F)-F | (1-8-35) | 5% |
| 2-HH-3 | (13-1) | 16% |
| 7-HB-1 | (13-5) | 10% |
| 5-HB-O2 | (13-5) | 8% |
| 3-HB(2F,3F)-O2 | (6-1) | 15% |
| 5-HB(2F,3F)-O2 | (6-1) | 15% |
| 3-HHB(2F,3CL)-O2 | (7-12) | 3% |
| 4-HHB(2F,3CL)-O2 | (7-12) | 3% |
| 3-HH1OCro(7F,8F)-5 | (10-6) | 5% |
| 5-HBB(F)B-2 | (15-5) | 10% |
| 5-HBB(F)B-3 | (15-5) | 10% |

Use Example 13

| | | |
|---|---|---|
| 5-B(F)TB(F,F)XB(F,F)-F | (1-4-10) | 5% |
| 2-HH-3 | (13-1) | 6% |
| 3-HH-V1 | (13-1) | 10% |
| 1V2-HH-1 | (13-1) | 8% |
| 1V2-HH-3 | (13-1) | 7% |
| 3-BB(2F,3F)-O2 | (6-3) | 8% |
| 5-BB(2F,3F)-O2 | (6-3) | 4% |
| 3-H1OB(2F,3F)-O2 | (6-5) | 7% |
| 2-HH1OB(2F,3F)-O2 | (7-5) | 7% |
| 3-HH1OB(2F,3F)-O2 | (7-5) | 17% |
| 3-HDhB(2F,3F)-O2 | (7-3) | 6% |
| 3-HHB-1 | (14-1) | 3% |
| 3-HHB-3 | (14-1) | 2% |
| 2-BB(2F,3F)B-3 | (8-1) | 10% |

Use Example 14

| | | |
|---|---|---|
| 5-BTB(F)B(F,F)XB(F,F)-F | (1-5-50) | 3% |
| 3-GB(F)B(F,F)XB(F,F)-F | (4-57) | 5% |
| 3-BB(F)B(F,F)XB(F,F)-F | (4-47) | 3% |
| 4-BB(F)B(F,F)XB(F,F)-F | (4-47) | 4% |
| 5-BB(F)B(F,F)XB(F,F)-F | (4-47) | 3% |
| 3-HH-V | (13-1) | 41% |
| 3-HH-V1 | (13-1) | 7% |
| 3-HHEH-5 | (14-13) | 3% |
| 3-HHB-1 | (14-1) | 4% |
| V-HHB-1 | (14-1) | 5% |
| V2-BB(F)B-1 | (14-6) | 5% |
| 1V2-BB-F | (2-1) | 3% |
| 3-BB(F,F)XB(F,F)-F | (3-97) | 6% |
| 3-GB(F,F)XB(F,F)-F | (3-113) | 5% |
| 3-HHBB(F,F)-F | (4-6) | 3% |

NI=82.2° C.; Δn=0.105; Δε=7.5; η=12.9 mPa·s.

Use Example 15

| | | |
|---|---|---|
| 5-BTB(F)B(F,F)XB(F,F)-CF3 | (1-5-56) | 5% |
| 2-HB-C | (5-1) | 5% |
| 3-HB-C | (5-1) | 11% |
| 3-HB-O2 | (13-5) | 14% |
| 2-BTB-1 | (13-10) | 3% |
| 3-HHB-F | (3-1) | 4% |
| 3-HHB-1 | (14-1) | 8% |
| 3-HHB-O1 | (14-1) | 4% |
| 3-HHB-3 | (14-1) | 14% |
| 3-HHEB-F | (3-10) | 3% |
| 5-HHEB-F | (3-10) | 4% |
| 2-HHB(F)-F | (3-2) | 7% |

| | | |
|---|---|---|
| 3-HHB(F)-F | (3-2) | 6% |
| 5-HHB(F)-F | (3-2) | 7% |
| 3-HHB(F,F)-F | (3-3) | 5% |

NI=100.2° C.; Δn=0.106; Δε=6.8; η=22.3 mPa·s.

Use Example 16

| | | |
|---|---|---|
| 4-BTB(F)B(F,F)XB(F,F)-F | (1-5-49) | 6% |
| 3-HB-CL | (2-2) | 12% |
| 3-HH-4 | (13-1) | 12% |
| 3-HB-O2 | (13-5) | 8% |
| 3-HHB(F,F)-F | (3-3) | 3% |
| 3-HBB(F,F)-F | (3-24) | 29% |
| 5-HBB(F,F)-F | (3-24) | 22% |
| 5-HBB(F)B-2 | (15-5) | 4% |
| 5-HBB(F)B-3 | (15-5) | 4% |

NI=71.0° C.; Δn=0.122; Δε=7.2; η=21.5 mPa·s.

Use Example 17

| | | |
|---|---|---|
| 4O-BTB(F)B(F,F)XB(F,F)F | (1-5-54) | 4% |
| 7-HB(F,F)-F | (2-4) | 3% |
| 3-HB-O2 | (13-5) | 7% |
| 2-HHB(F)-F | (3-2) | 10% |
| 3-HHB(F)-F | (3-2) | 10% |
| 5-HHB(F)-F | (3-2) | 9% |
| 2-HBB(F)-F | (3-23) | 9% |
| 3-HBB(F)-F | (3-23) | 8% |
| 5-HBB(F)-F | (3-23) | 15% |
| 2-HBB-F | (3-22) | 4% |
| 3-HBB-F | (3-22) | 4% |
| 5-HBB-F | (3-22) | 3% |
| 3-HBB(F,F)-F | (3-24) | 4% |
| 5-HBB(F,F)-F | (3-24) | 10% |

NI=87.4° C.; Δn=0.121; Δε=7.0; η=27.1 mPa·s.

Use Example 18

| | | |
|---|---|---|
| 4O-BTB(F)B(F,F)XB(F,F)-CF3 | (1-5-57) | 5% |
| 5-HB-CL | (2-2) | 16% |
| 3-HH-4 | (13-1) | 12% |
| 3-HH-5 | (13-1) | 3% |
| 3-HHB-F | (3-1) | 3% |
| 3-HHB-CL | (3-1) | 3% |
| 4-HHB-CL | (3-1) | 4% |
| 3-HHB(F)-F | (3-2) | 9% |
| 4-HHB(F)-F | (3-2) | 8% |
| 5-HHB(F)-F | (3-2) | 9% |
| 7-HHB(F)-F | (3-2) | 8% |
| 5-HBB(F)-F | (3-23) | 3% |
| 1O1-HBBH-5 | (15-1) | 3% |
| 3-HHBB(F,F)-F | (4-6) | 2% |
| 4-HHBB(F,F)-F | (4-6) | 3% |
| 5-HHBB(F,F)-F | (4-6) | 3% |
| 3-HH2BB(F,F)-F | (4-15) | 3% |
| 4-HH2BB(F,F)-F | (4-15) | 3% |

NI=115.3° C.; Δn=0.100; Δε=6.0; η=22.3 mPa·s.

Use Example 19

| | | |
|---|---|---|
| 5-B(F,F)TB(F)B(F,F)XB(F,F)-CF3 | (1-5-23) | 3% |
| 5-HB-F | (2-2) | 12% |
| 6-HB-F | (2-2) | 9% |
| 7-HB-F | (2-2) | 7% |
| 2-HHB-OCF3 | (3-1) | 7% |
| 3-HHB-OCF3 | (3-1) | 6% |
| 4-HHB-OCF3 | (3-1) | 7% |
| 5-HHB-OCF3 | (3-1) | 5% |
| 3-HH2B-OCF3 | (3-4) | 3% |

-continued

| | | |
|---|---|---|
| 5-HH2B-OCF3 | (3-4) | 4% |
| 3-HHB(F,F)-OCF2H | (3-3) | 4% |
| 3-HHB(F,F)-OCF3 | (3-3) | 4% |
| 3-HH2B(F)-F | (3-5) | 3% |
| 3-HBB(F)-F | (3-23) | 10% |
| 5-HBB(F)-F | (3-23) | 10% |
| 5-HBBH-3 | (15-1) | 3% |
| 3-HB(F)BH-3 | (15-2) | 3% |

NI=85.2° C.; Δn=0.096; Δε=6.1; η=16.2 mPa·s.

Use Example 20

| | | |
|---|---|---|
| 4O-B(F)TB(F)B(F,F)XB(F,F)-CF3 | (1-5-31) | 5% |
| 5-HB-CL | (2-2) | 11% |
| 3-HH-4 | (13-1) | 7% |
| 3-HHB-1 | (14-1) | 5% |
| 3-HHB(F,F)-F | (3-3) | 7% |
| 3-HBB(F,F)-F | (3-24) | 19% |
| 5-HBB(F,F)-F | (3-24) | 14% |
| 3-HHEB(F,F)-F | (3-12) | 10% |
| 4-HHEB(F,F)-F | (3-12) | 3% |
| 5-HHEB(F,F)-F | (3-12) | 3% |
| 2-HBEB(F,F)-F | (3-39) | 3% |
| 3-HBEB(F,F)-F | (3-39) | 5% |
| 5-HBEB(F,F)-F | (3-39) | 3% |
| 3-HHEB(F,F)-F | (4-6) | 5% |

NI=81.7° C.; Δn=0.111; Δε=11.2; η=26.2 mPa·s.

Use Example 21

| | | |
|---|---|---|
| 5-BB(F,F)TB(F,F)XB(F,F)-CF3 | (1-6-49) | 3% |
| 3-HB-CL | (2-2) | 6% |
| 5-HB-CL | (2-2) | 3% |
| 3-HHB-OCF3 | (3-1) | 5% |
| 3-H2HB-OCF3 | (3-13) | 5% |
| 5-H4HB-OCF3 | (3-19) | 15% |
| V-HHB(F)-F | (3-2) | 5% |
| 3-HHB(F)-F | (3-2) | 4% |
| 5-HHB(F)-F | (3-2) | 4% |
| 3-H4HB(F,F)-CF3 | (3-21) | 8% |
| 5-H4HB(F,F)-CF3 | (3-21) | 10% |
| 5-H2HB(F,F)-F | (3-15) | 5% |
| 5-H4HB(F,F)-F | (3-21) | 7% |
| 2-H2BB(F)-F | (3-26) | 5% |
| 3-H2BB(F)-F | (3-26) | 10% |
| 3-HBEB(F,F)-F | (3-39) | 5% |

NI=70.8° C.; Δn=0.102; Δε=9.9; η=26.6 mPa·s.

Use Example 22

| | | |
|---|---|---|
| 5-B(F)BTB(F,F)XB(F,F)-F | (1-6-62) | 4% |
| 5-HB-CL | (2-2) | 17% |
| 7-HB(F,F)-F | (2-4) | 3% |
| 3-HH-4 | (13-1) | 10% |
| 3-HH-5 | (13-1) | 4% |
| 3-HB-O2 | (13-5) | 14% |
| 3-HHB-1 | (14-1) | 7% |
| 3-HHB-O1 | (14-1) | 5% |
| 2-HHB(F)-F | (3-2) | 7% |
| 3-HHB(F)-F | (3-2) | 6% |
| 5-HHB(F)-F | (3-2) | 7% |

-continued

| | | |
|---|---|---|
| 3-HHB(F,F)-F | (3-3) | 6% |
| 3-H2HB(F,F)-F | (3-15) | 5% |
| 4-H2HB(F,F)-F | (3-15) | 5% |

NI=82.2° C.; Δn=0.105; Δε=7.5; η=12.9 mPa·s.

Use Example 23

| | | |
|---|---|---|
| 5-B(F)BTB(F,F)XB(F,F)-F | (1-6-66) | 3% |
| 5-HB-CL | (2-2) | 3% |
| 7-HB(F)-F | (2-3) | 7% |
| 3-HH-4 | (13-1) | 9% |
| 3-HH-5 | (13-1) | 10% |
| 3-HB-O2 | (13-5) | 13% |
| 3-HHEB-F | (3-10) | 8% |
| 5-HHEB-F | (3-10) | 7% |
| 3-HHEB(F,F)-F | (3-12) | 8% |
| 4-HHEB(F,F)-F | (3-12) | 5% |
| 3-GHB(F,F)-F | (3-109) | 5% |
| 4-GHB(F,F)-F | (3-109) | 6% |
| 5-GHB(F,F)-F | (3-109) | 7% |
| 2-HHB(F,F)-F | (3-3) | 4% |
| 3-HHB(F,F)-F | (3-3) | 5% |

NI=71.1° C.; Δn=0.072; Δε=6.9; η=19.6 mPa·s.

Use Example 24

| | | |
|---|---|---|
| 5-PyB(F)TB(F,F)XB(F,F)-F | (1-6-92) | 5% |
| 3-HB-O1 | (13-5) | 14% |
| 3-HH-4 | (13-1) | 5% |
| 3-HB-O2 | (13-5) | 2% |
| 3-HB(2F,3F)-O2 | (6-1) | 10% |
| 5-HB(2F,3F)-O2 | (6-1) | 12% |
| 2-HHB(2F,3F)-1 | (7-1) | 10% |
| 3-HHB(2F,3F)-1 | (7-1) | 12% |
| 3-HHB(2F,3F)-O2 | (7-1) | 11% |
| 5-HHB(2F,3F)-O2 | (7-1) | 13% |
| 3-HHB-1 | (14-1) | 6% |

NI=88.0° C.; Δn=0.097; Δε=−3.1; η=36.8 mPa·s.

Use Example 25

| | | |
|---|---|---|
| 3-B(F)TB(F,F)XB(F)B(F,F)-F | (1-7-32) | 3% |
| 2-HH-5 | (13-1) | 3% |
| 3-HH-4 | (13-1) | 15% |
| 3-HH-5 | (13-1) | 4% |
| 3-HB-O2 | (13-5) | 12% |
| 3-H2B(2F,3F)-O2 | (6-4) | 14% |
| 5-H2B(2F,3F)-O2 | (6-4) | 14% |
| 3-HHB(2F,3CL)-O2 | (7-12) | 5% |
| 2-HBB(2F,3F)-O2 | (7-7) | 3% |
| 3-HBB(2F,3F)-O2 | (7-7) | 8% |
| 5-HBB(2F,3F)-O2 | (7-7) | 9% |
| 3-HHB-1 | (14-1) | 3% |
| 3-HHB-3 | (14-1) | 4% |
| 3-HHB-O1 | (14-1) | 3% |

NI=76.5° C.; Δn=0.097; Δε=−3.9; η=20.4 mPa·s.

Use Example 26

| | | |
|---|---|---|
| 5-B(F)B(F,F)XB(F,F)TB(F,F)-F | (1-8-9) | 3% |
| 2-HH-3 | (13-1) | 21% |
| 3-HH-4 | (13-1) | 9% |
| 1-BB-3 | (13-8) | 9% |
| 3-HB-O2 | (13-5) | 2% |
| 3-BB(2F,3F)-O2 | (6-3) | 9% |
| 5-BB(2F,3F)-O2 | (6-3) | 6% |
| 2-HH1OB(2F,3F)-O2 | (7-5) | 12% |

-continued

| | | |
|---|---|---|
| 3-HH1OB(2F,3F)-O2 | (7-5) | 20% |
| 3-HHB-1 | (14-1) | 4% |
| 3-HHB-O1 | (14-1) | 3% |
| 5-B(F)BB-2 | (14-6) | 2% |

NI=82.2° C.; Δn=0.105; Δε=7.5; η=12.9 mPa·s.

Use Example 27

| | | |
|---|---|---|
| 5-B(F)TB(F)TB(F,F)XB(F,F)-F | (1-10-24) | 5% |
| 1-BB-3 | (13-8) | 9% |
| 3-HH-V | (13-1) | 29% |
| 3-BB(2F,3F)-O2 | (6-3) | 12% |
| 2-HH1OB(2F,3F)-O2 | (7-5) | 19% |
| 3-HH1OB(2F,3F)-O2 | (7-5) | 13% |
| 3-HHB-1 | (14-1) | 7% |
| 5-B(F)BB-2 | (14-6) | 6% |

NI=77.1° C.; Δn=0.116; Δε=−2.8; η=16.5 mPa·s.

Use Example 28

| | | |
|---|---|---|
| 5-BTB(F,F)XB(F,F)-F | (1-4-32) | 5% |
| 1V2-BEB(F,F)-C | (5-15) | 5% |
| 3-HB-C | (5-1) | 17% |
| 2-BTB-1 | (13-10) | 10% |
| 5-HH-VFF | (13-1) | 29% |
| 3-HHB-1 | (14-1) | 4% |
| VFF-HHB-1 | (14-1) | 8% |
| VFF2-HHB-1 | (14-1) | 10% |
| 3-H2BTB-2 | (14-17) | 5% |
| 3-H2BTB-3 | (14-17) | 3% |
| 3-H2BTB-4 | (14-17) | 4% |

NI=78.9° C.; Δn=0.132; Δε=7.2; η=12.4 mPa·s.

Use Example 29

| | | |
|---|---|---|
| 5-B(F,F)TB(F)B(F,F)XB(F,F)-CF3 | (1-5-23) | 2% |
| 4O-BTB(F,F)XB(F)B(F,F)-F | (1-7-90) | 1% |
| 5-HB(F)B(F,F)XB(F,F)-F | (4-41) | 5% |
| 3-BB(F)B(F,F)XB(F,F)-F | (4-47) | 3% |
| 4-BB(F)B(F,F)XB(F,F)-F | (4-47) | 7% |
| 5-BB(F)B(F,F)XB(F,F)-F | (4-47) | 3% |
| 3-HH-V | (13-1) | 38% |
| 3-HH-V1 | (13-1) | 7% |
| 3-HHEH-5 | (14-13) | 3% |
| 3-HHB-1 | (14-1) | 4% |
| V-HHB-1 | (14-1) | 5% |
| V2-BB(F)B-1 | (14-6) | 5% |
| 1V2-BB-F | (13-8) | 3% |
| 3-BB(F,F)XB(F,F)-F | (3-97) | 11% |
| 3-HHBB(F,F)-F | (4-6) | 3% |

INDUSTRIAL APPLICABILITY

A liquid crystal compound of the invention has excellent physical properties. A liquid crystal composition containing the compound can be widely applied to a liquid crystal display device used for a personal computer, a television and so forth.

What is claimed is:

1. A compound, represented by formula (1):

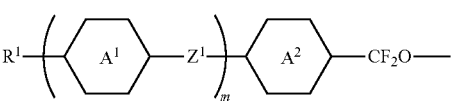

(1)

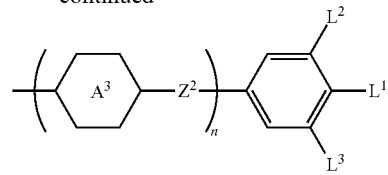

wherein, in formula (1),
$R^1$ is alkyl having 1 to 15 carbons, and in the alkyl, at least one piece of —$CH_2$— may be replaced by —O—, and at least one piece of —$CH_2CH_2$— may be replaced by —CH=CH—, and in the groups, at least one piece of hydrogen may be replaced by halogen;
ring $A^1$, ring $A^2$ and ring $A^3$ are independently 1,4-cyclohexylene, 1,4-cyclohexenylene, 1,4-phenylene, 2-halogeno-1,4-phenylene, 2,6-dihalogeno-1,4-phenylene, pyrimidine-2,5-diyl or pyridine-2,5-diyl;
$Z^1$ and $Z^2$ are independently a single bond or —C≡C—, but at least one is —C≡C—;
$L^1$ is halogen, —$OCF_3$ or —$CF_3$;
$L^2$ and $L^3$ are independently hydrogen or halogen, but at least one is halogen; and
m and n are independently 0, 1 or 2, and a sum of m and n is 1 or 2.

2. The compound according to claim 1, wherein in formula (1)
$R^1$ is alkyl having 1 to 15 carbons, alkenyl having 2 to 15 carbons, alkoxy having 2 to 15 carbons, alkyl having 1 to 15 carbons in which at least one piece of hydrogen is replaced by halogen, alkenyl having 2 to 15 carbons in which at least one piece of hydrogen is replaced by halogen, or alkoxy having 2 to 15 carbons in which at least one piece of hydrogen is replaced by halogen;
ring $A^1$, ring $A^2$ and ring $A^3$ are independently 1,4-cyclohexylene, 1,4-cyclohexenylene, 1,4-phenylene, 2-halogeno-1,4-phenylene, 2,6-dihalogeno-1,4-phenylene, pyrimidine-2,5-diyl or pyridine-2,5-diyl;
$Z^1$ and $Z^2$ are independently a single bond or —C≡C—, and at least one of m pieces of $Z^1$ and n pieces of $Z^2$ is —C≡C—;
$L^1$ is halogen, —$OCF_3$ or —$CF_3$;
$L^2$ and $L^3$ are independently hydrogen or halogen, but at least one is halogen; and
m and n are independently 0, 1 or 2, and a sum of m and n is 1 or 2.

3. The compound according to claim 1, represented by any one of formulas (1-1) to (1-3):

(1-1)

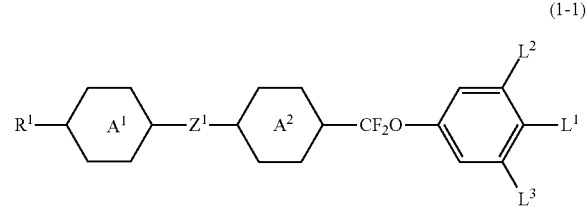

(1-2)

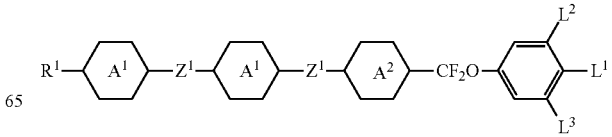

(1-3)

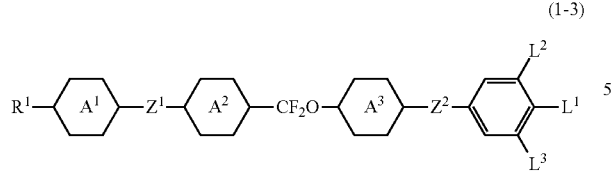

wherein, in formulas (1-1) to (1-3),
R$^1$ is alkyl having 1 to 15 carbons, alkenyl having 2 to 15 carbons, alkoxy having 1 to 14 carbons or alkenyloxy having 2 to 14 carbons;
ring A$^1$, ring A$^2$ and ring A$^3$ are independently 1,4-cyclohexylene, 1,4-cyclohexenylene, 1,4-phenylene, 2-halogeno-1,4-phenylene, 2,6-dihalogeno-1,4-phenylene, pyrimidine-2,5-diyl or pyridine-2,5-diyl;
Z$^1$ and Z$^2$ are independently a single bond or —C≡C—, and at least one of m pieces of Z$^1$ and n pieces of Z$^2$ is —C≡C—;
L$^1$ is halogen, —OCF$_3$ or —CF$_3$; and
L$^2$ and L$^3$ are independently hydrogen or fluorine, and at least one is fluorine.

4. The compound according to claim 3, wherein, in formulas (1-1) to (1-3), ring A$^1$, ring A$^2$ and ring A$^3$ are independently 1,4-phenylene, 2-halogeno-1,4-phenylene, 2,6-dihalogeno-1,4-phenylene, pyrimidine-2,5-diyl or pyridine-2,5-diyl; and L$^1$ is fluorine, —OCF$_3$ or —CF$_3$.

5. The compound according to claim 1, represented by any one of formulas (1-4) to (1-28):

(1-4)

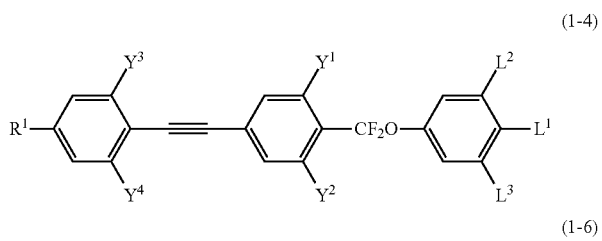

(1-5)

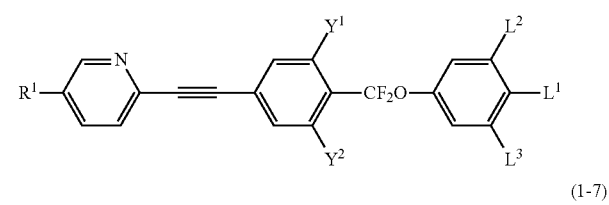

(1-6)

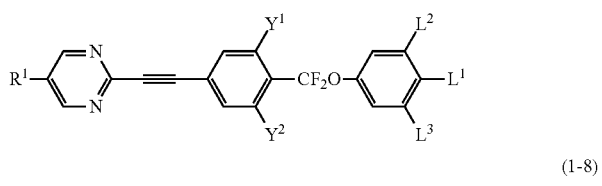

(1-7)

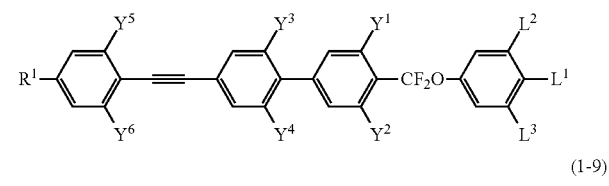

(1-8)

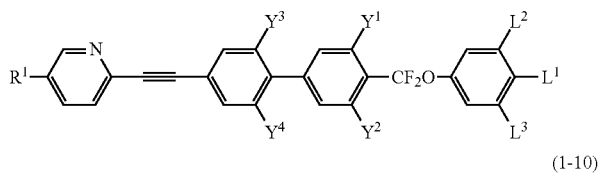

(1-9)

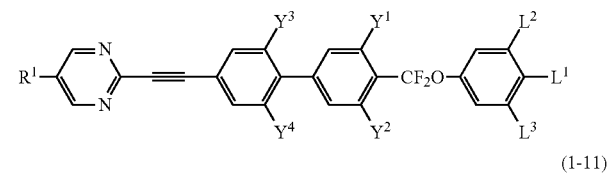

(1-10)

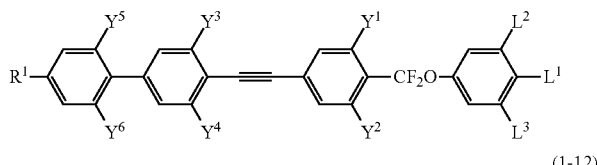

(1-11)

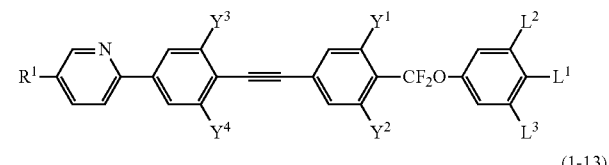

(1-12)

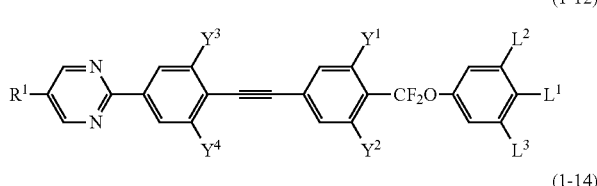

(1-13)

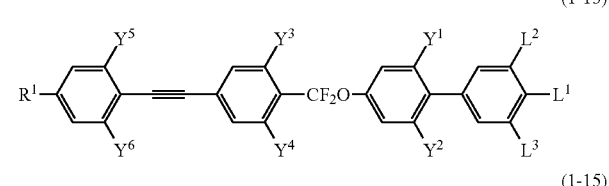

(1-14)

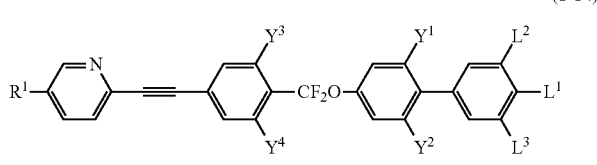

(1-15)

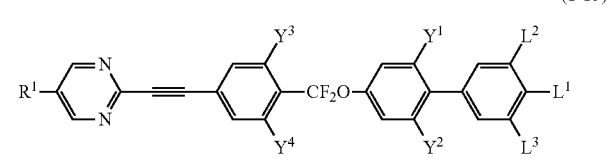

(1-16)

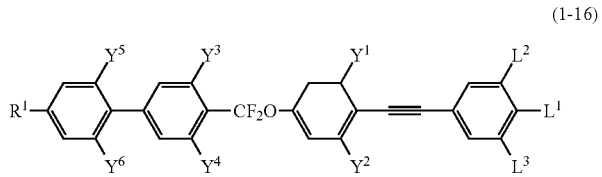

(1-17)

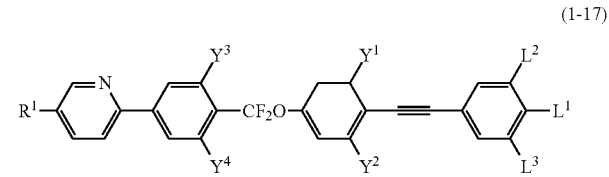

-continued
(1-18)
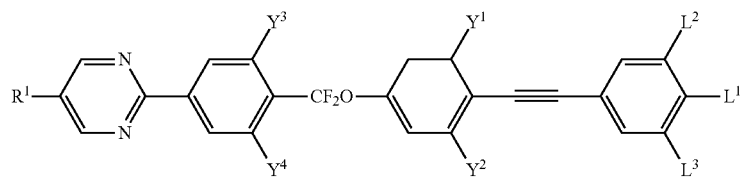
(1-19)
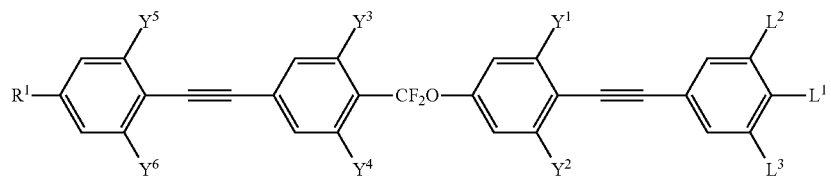
(1-20)
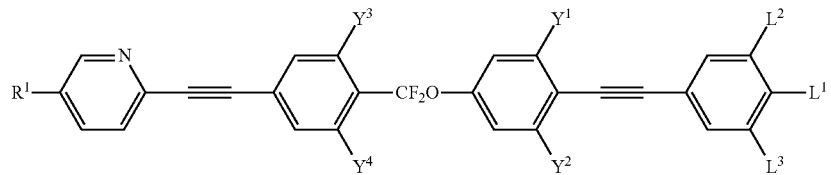
(1-21)
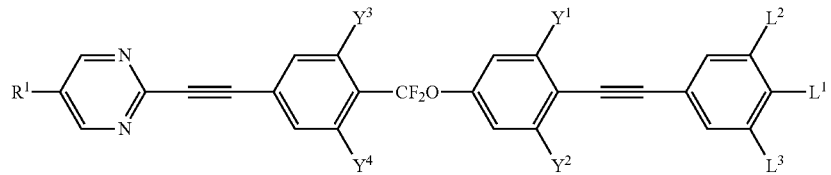
(1-22)
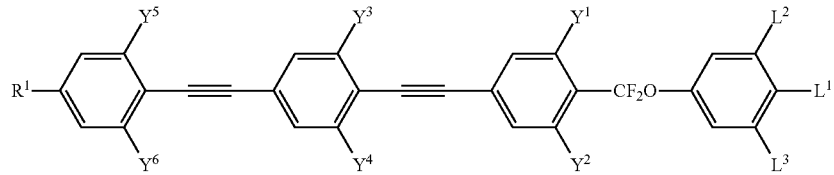
(1-23)
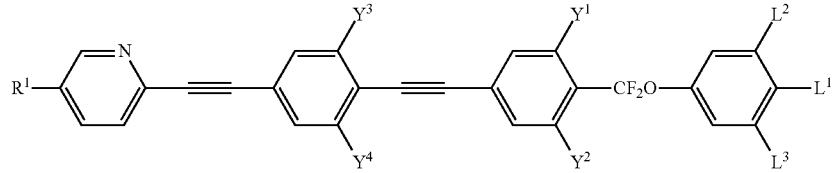
(1-24)
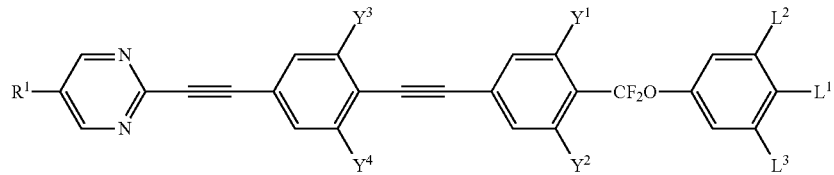
(1-25)
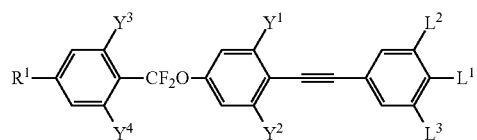
(1-26)
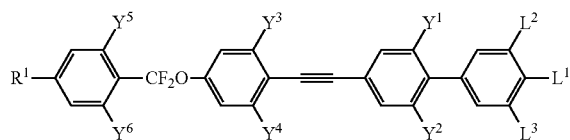

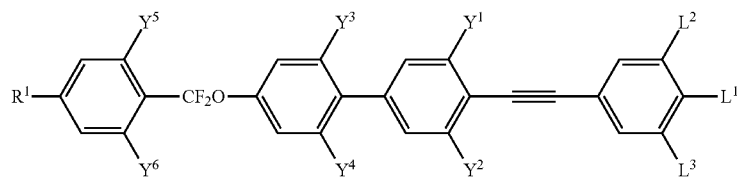
(1-27)

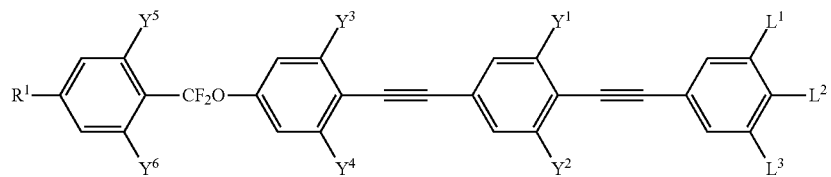
(1-28)

wherein, in formulas (1-4) to (1-28), $R^1$ is alkyl having 1 to 15 carbons, alkenyl having 2 to 15 carbons, alkoxy having 1 to 14 carbons or alkenyloxy having 2 to 14 carbons; $Y^1$, $Y^2$, $Y^3$, $Y^4$, $Y^5$, and $Y^6$ are independently hydrogen, fluorine or chlorine; $L^1$ is fluorine, chlorine, —OCF$_3$ or —CF$_3$; and $L^2$ and $L^3$ are independently hydrogen or fluorine, but at least one is fluorine.

6. The compound according to claim 5, wherein, in formulas (1-4) to (1-28), $L^1$ is fluorine or —CF$_3$.

7. A liquid crystal composition, containing at least one compound according to claim 1.

8. The liquid crystal composition according to claim 7, further containing at least one compound selected from the group of compounds represented by formulas (2) to (4):

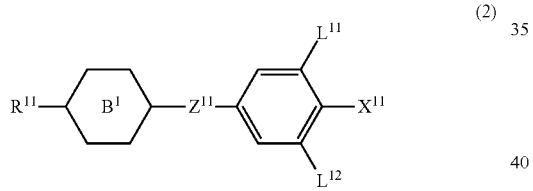
(2)

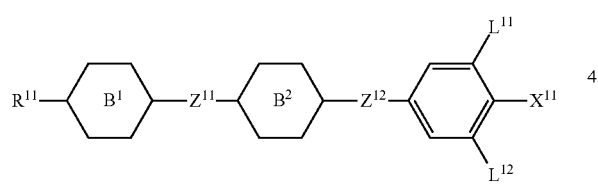
(3)

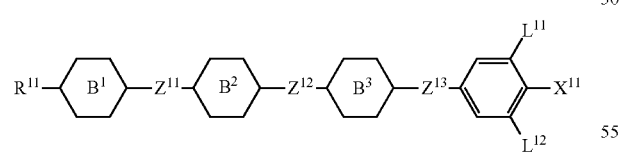
(4)

wherein, in formulas (2) to (4),
$R^{11}$ is alkyl having 1 to 10 carbons or alkenyl having 2 to 10 carbons, and in the alkyl and the alkenyl, at least one piece of hydrogen may be replaced by fluorine, and at least one piece of —CH$_2$— may be replaced by —O—;
$X^{11}$ is fluorine, chlorine, —OCF$_3$, —OCHF$_2$, —CF$_3$, —CHF$_2$, or —OCF$_2$CHFCF$_3$;
ring $B^1$, ring $B^2$ and ring $B^3$ are independently 1,4-cyclohexylene, 1,4-phenylene in which at least one piece of hydrogen may be replaced by fluorine, tetrahydropyran-2,5-diyl, 1,3-dioxane-2,5-diyl or pyrimidine-2,5-diyl;
$Z^{11}$, $Z^{12}$ and $Z^{13}$ are independently a single bond, —CH$_2$CH$_2$—, —CH=CH—, —C≡C—, —COO—, —CF$_2$O—, —OCF$_2$—, —CH$_2$O— or —(CH$_2$)$_4$—, and when any one of $Z^{11}$, $Z^{12}$ and $Z^{13}$ is —CF$_2$O—, others are a single bond, —CH$_2$CH$_2$—, —CH=CH—, —C≡C—, —COO—, —OCF$_2$—, —CH$_2$O— or —(CH$_2$)$_4$—, and when any one of $Z^{11}$, $Z^{12}$ and $Z^{13}$ is —CF$_2$O—, others are a single bond, —CH$_2$CH$_2$—, —CH=CH—, —COO—, —CF$_2$O—, —OCF$_2$—, —CH$_2$O— or —(CH$_2$)$_4$—; and
$L^{11}$ and $L^{12}$ are independently hydrogen or fluorine.

9. The liquid crystal composition according to claim 7, further containing at least one compound selected from the group of compounds represented by formula (5):

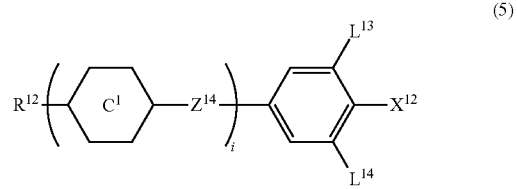
(5)

wherein, in formula (5),
$R^{12}$ is alkyl having 1 to 10 carbons or alkenyl having 2 to 10 carbons, and in the alkyl and the alkenyl, at least one piece of hydrogen may be replaced by fluorine, and at least one piece of —CH$_2$— may be replaced by —O—;
X is —C≡N or —C≡C—C≡N;
ring $C^1$ is 1,4-cyclohexylene, 1,4-phenylene in which at least one piece of hydrogen may be replaced by fluorine, tetrahydropyran-2,5-diyl, 1,3-dioxane-2,5-diyl or pyrimidine-2,5-diyl;
$Z^{14}$ is a single bond, —CH$_2$CH$_2$—, —C≡C—, —COO—, —CF$_2$O—, —OCF$_2$— or —CH$_2$O—;
$L^{13}$ and $L^{14}$ are independently hydrogen or fluorine; and
i is 1, 2, 3 or 4.

10. The liquid crystal composition according to claim 7, further containing at least one compound selected from the group of compounds represented by formulas (6) to (12):

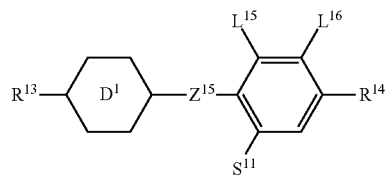
(6)

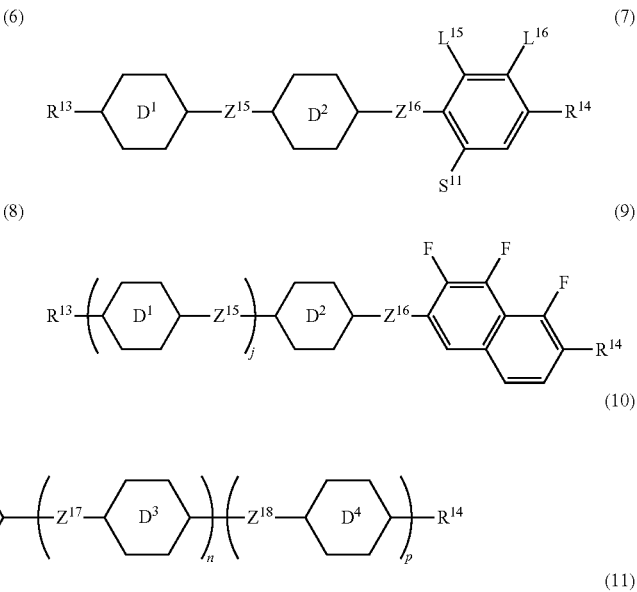
(7)
(8)
(9)

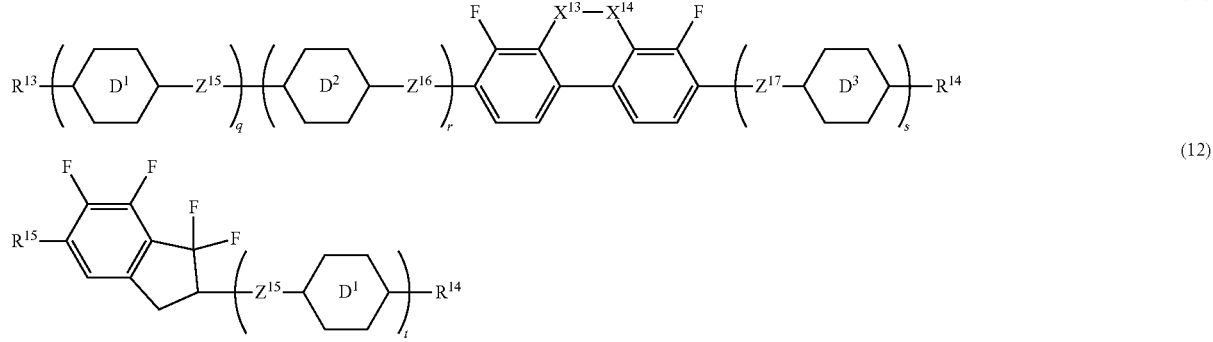
(10)
(11)
(12)

wherein, in formulas (6) to (12), $R^{13}$ and $R^{14}$ are independently alkyl having 1 to 10 carbons or alkenyl having 2 to 10 carbons, and in the alkyl and the alkenyl, at least one piece of —$CH_2$— may be replaced by —O—, and at least one piece of hydrogen may be replaced by fluorine;

$R^{15}$ is hydrogen, fluorine, alkyl having 1 to 10 carbons or alkenyl having 2 to 10 carbons, and in the alkyl and the alkenyl, at least one piece of —$CH_2$— may be replaced by —O—, and at least one piece of hydrogen may be replaced by fluorine;

$S^{11}$ is hydrogen or methyl;

$X^{13}$ and $X^{14}$ are independently —$CF_2$—, —O— or —CHF—;

ring $D^1$, ring $D^2$, ring $D^3$ and ring $D^4$ are independently 1,4-cyclohexylene, 1,4-cyclohexenylene, 1,4-phenylene in which at least one piece of hydrogen may be replaced by fluorine, tetrahydropyran-2,5-diyl or decahydronaphthalene-2,6-diyl;

ring $D^5$ and ring $D^6$ are independently 1,4-cyclohexylene, 1,4-cyclohexenylene, 1,4-phenylene, tetrahydropyran-2,5-diyl or decahydronaphthalene-2,6-diyl;

$Z^{15}$, $Z^{16}$, $Z^{17}$ and $Z^{18}$ are independently a single bond, —$CH_2CH_2$—, —COO—, —$CH_2O$—, —$OCF_2$— or —$OCF_2CH_2CH_2$—;

$L^{15}$ and $L^{16}$ are independently fluorine or chlorine; and j, k, m, n, p, q, r and s are independently 0 or 1, a sum of k, m, n and p is 1 or 2, a sum of q, r and s is 0, 1, 2 or 3, and t is 1, 2 or 3.

11. The liquid crystal composition according to claim 7, further containing at least one compound selected from the group of compounds represented by formulas (13) to (15):

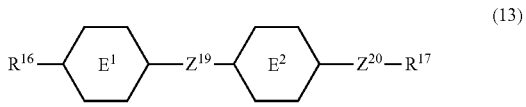
(13)

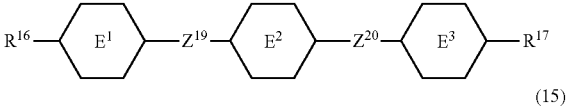
(14)

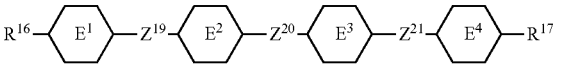
(15)

wherein, in formulas (13) to (15), $R^{16}$ and $R^{17}$ are independently alkyl having 1 to 10 carbons or alkenyl having 2 to 10 carbons, and in the alkyl or the alkenyl, at least one piece of —$CH_2$— may be replaced by —O—, and at least one piece of hydrogen may be replaced by fluorine;

ring $E^1$, ring $E^2$, ring $E^3$ and ring $E^4$ are independently 1,4-cyclohexylene, 1,4-phenylene, 2-fluoro-1,4-phenylene, 2,5-difluoro-1,4-phenylene or pyrimidine-2,5-diyl; and $Z^{19}$, $Z^{20}$ and $Z^{21}$ are independently a single bond, —CH$_2$CH$_2$—, —CH=CH—, —C≡C— or —COO—.

12. The liquid crystal composition according to claim 7, further containing at least one of a polymerizable compound, an optically active compound, an antioxidant, an ultraviolet light absorber, a light stabilizer, a heat stabilizer and an antifoaming agent.

13. A liquid crystal display device, including the liquid crystal composition according to claim 7.

14. The liquid crystal display device according to claim 13, wherein the liquid crystal composition is encapsulated.

15. The liquid crystal display device according to claim 13, wherein the liquid crystal composition is used in a lens to be utilized for switching between 2D and 3D.

* * * * *